(12) United States Patent
Korai et al.

(10) Patent No.: US 12,178,122 B2
(45) Date of Patent: Dec. 24, 2024

(54) COMPOUND, COMPOSITION INCLUDING THE SAME, LIQUID COMPOSITION, AND ORGANIC ELECTROLUMINESCENT DEVICE

(71) Applicant: Samsung Electronics Co., Ltd., Suwon-si (KR)

(72) Inventors: Keisuke Korai, Kanagawa-ken (JP); Atsushi Imamura, Kanagawa-ken (JP); Jhunmo Son, Yongin-si (KR); Masaru Kinoshita, Kanagawa-ken (JP); Mitsunori Ito, Kanagawa-ken (JP); Norifumi Kishi, Kanagawa-ken (JP); Rie Sakurai, Kanagawa-ken (JP); Shiro Irisa, Kanagawa-ken (JP); Masaki Numata, Kanagawa-ken (JP)

(73) Assignee: SAMSUNG ELECTRONICS CO., LTD., Gyeonggi-do (KR)

( * ) Notice: Subject to any disclaimer, the term of this patent is extended or adjusted under 35 U.S.C. 154(b) by 789 days.

(21) Appl. No.: 17/111,641

(22) Filed: Dec. 4, 2020

(65) Prior Publication Data

US 2021/0184132 A1  Jun. 17, 2021

(30) Foreign Application Priority Data

Dec. 4, 2019 (JP) ................................ 2019-219937
Sep. 10, 2020 (KR) ......................... 10-2020-0116216

(51) Int. Cl.
*H10K 85/60* (2023.01)
*C07D 403/14* (2006.01)
(Continued)

(52) U.S. Cl.
CPC ......... *H10K 85/654* (2023.02); *C07D 403/14* (2013.01); *C09K 11/06* (2013.01);
(Continued)

(58) Field of Classification Search
CPC ............... H10K 85/654; H10K 85/342; H10K 85/6572; H10K 85/346; H10K 2101/30;
(Continued)

(56) References Cited

U.S. PATENT DOCUMENTS 9,680,111 B2  6/2017 Feldman et al.
10,547,009 B2  1/2020 Yoshida et al.
(Continued)

FOREIGN PATENT DOCUMENTS

CN  105121595 A  12/2015
CN  107810182 A   3/2018
(Continued)

OTHER PUBLICATIONS

Translation of KR 20160060870 by Bae et al. (Year: 2016).*
(Continued)

*Primary Examiner* — Michael M Dollinger
*Assistant Examiner* — Christina H. W. Rosebach
(74) *Attorney, Agent, or Firm* — CANTOR COLBURN LLP

(57) ABSTRACT

Provided is a compound that has a long pot life of a solution and is able to achieve low driving voltage, high efficiency, and long lifespan of an organic electroluminescent device. The present disclosure relates to a compound having a triphenyl triazine structural moiety and including a group that has a structure in which a substituted or unsubstituted carbazole group and a predetermined number of carbazole rings are directly bonded via a single bond, as described in the specification.

19 Claims, 1 Drawing Sheet

(51) Int. Cl.
  *C09K 11/06* (2006.01)
  *H10K 85/30* (2023.01)
  *H10K 50/11* (2023.01)
  *H10K 101/10* (2023.01)
  *H10K 101/30* (2023.01)

(52) U.S. Cl.
  CPC ......... *H10K 85/342* (2023.02); *H10K 85/346* (2023.02); *H10K 85/6572* (2023.02); *C09K 2211/1018* (2013.01); *C09K 2211/1029* (2013.01); *C09K 2211/185* (2013.01); *H10K 50/11* (2023.02); *H10K 2101/10* (2023.02); *H10K 2101/30* (2023.02)

(58) Field of Classification Search
  CPC .. H10K 2101/10; H10K 50/11; C07D 403/14; C09K 11/06; C09K 2211/1018; C09K 2211/1029; C09K 2211/185; H01K 2101/27
  See application file for complete search history.

(56) References Cited

U.S. PATENT DOCUMENTS

| | | | |
|---|---|---|---|
| 2013/0292654 A1* | 11/2013 | Matsunaga | H10K 85/342 252/301.16 |
| 2015/0249221 A1* | 9/2015 | Zeng | C07D 333/76 548/440 |
| 2015/0357582 A1* | 12/2015 | Hirata | H10K 85/654 257/40 |
| 2016/0172601 A1 | 6/2016 | Kawamura et al. | |
| 2018/0006238 A1 | 1/2018 | Lee et al. | |
| 2018/0037546 A1 | 2/2018 | Sugino et al. | |
| 2018/0166634 A1 | 6/2018 | Numata et al. | |
| 2019/0284174 A1 | 9/2019 | Bergmann et al. | |
| 2020/0207732 A1 | 7/2020 | Numata et al. | |

FOREIGN PATENT DOCUMENTS

| | | |
|---|---|---|
| CN | 107250132 B | 10/2020 |
| EP | 3476915 A1 | 5/2019 |
| JP | 2014509067 A | 4/2014 |
| JP | 2018524797 A | 8/2018 |
| JP | 2019156843 A | 9/2019 |
| JP | 2020105154 A | 7/2020 |
| KR | 20160060870 A | 5/2016 |
| KR | 1020170126812 A | 11/2017 |
| WO | 2012087955 A1 | 6/2012 |
| WO | 2016158540 A1 | 10/2016 |
| WO | 2019086297 A1 | 5/2019 |
| WO | 2019101594 A1 | 5/2019 |
| WO | 2019101746 A1 | 5/2019 |
| WO | 2019162332 A1 | 8/2019 |
| WO | 2019175160 A1 | 9/2019 |

OTHER PUBLICATIONS

X.Yang; C. Yao; G.Zhou. Highly Efficient Phosphorescent Materials Based on Platinum Complexes and Their Application in Organic Light-Emitting Devices (OLEDs). Platinum Metals Rev., 2013, 57, (1), 2-16 (Year: 2013).*
Extended European Search Report issued in EP Patent Application No. 20210232.3 on Jul. 13, 2021.
English Abstract of KR10-2017-0126812.
English Translation of Office Action dated Jul. 18, 2023, issued in corresponding JP Patent Application No. 2019-219937, 7 pp.
Office Action dated Jul. 18, 2023, issued in corresponding JP Patent Application No. 2019-219937, 5 pp.
English Abstract of KR 10-2016-0060870.
English Translation of Office Action dated Mar. 26, 2024, issued in corresponding CN Patent Application No. 202011411958.1, 12 pp.

* cited by examiner

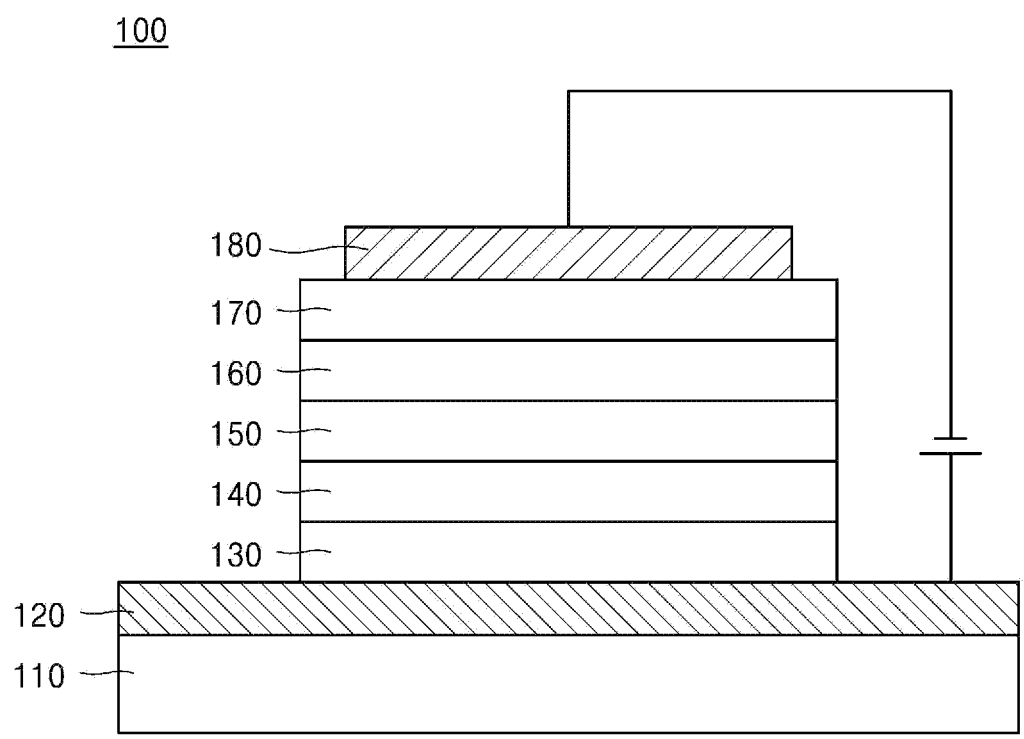

COMPOUND, COMPOSITION INCLUDING THE SAME, LIQUID COMPOSITION, AND ORGANIC ELECTROLUMINESCENT DEVICE

CROSS-REFERENCE TO RELATED APPLICATIONS

This application claims the priority and the benefit of Japanese Patent Application No. 2019-219937, filed on Dec. 4, 2019, in the Japanese Patent Office and Korean Patent Application No. 10-2020-0116216, filed on Sep. 10, 2020, in the Korean Intellectual Property Office, the contents of which are incorporated by reference herein in their entirety.

BACKGROUND

1. Field

The present disclosure relates to compounds, compositions including the same, liquid compositions, and organic electroluminescent devices.

2. Description of Related Art

In recent years, there has been active development of display apparatuses and lighting devices that use an organic electroluminescent device, which is a self-luminescent device. In an example, an organic electroluminescent device includes an organic layer that includes a luminescent material. In the organic layer of the organic electroluminescent device, luminescence occurs when a luminescent material is excited by recombination of electrons and holes and returns from an excited state to a ground state.

In such an organic electroluminescent device, various materials for an organic layer have been developed for the purpose of improving device characteristics such as driving voltage, luminescence efficiency, and lifespan. When excitons are produced by recombination of injected holes and injected electrons, singlet excitons and triplet excitons are generated at a ratio of 1:3 according to the electron spin-statistics theorem. In order to further improve performance of an organic electroluminescent device, an organic electroluminescent device using singlet excitons and triplet excitons has been considered, and as an example thereof, an organic electroluminescent device employing delayed fluorescence, in particular, a thermally activated delayed fluorescence (TADF) mechanism has been proposed and studied. In the TADF mechanism, that reverse intersystem crossing from triplet excitons to the singlet excitons thermally occurs for a material having a small energy difference ($\Delta E_{ST}$) between a singlet state and a triplet state. TADF is described in, for example, ADACHI, Chihaya, ed. (published on Mar. 22, 2012), "Device Physics of Organic Semiconductors", Kodansha, pages 261-262, incorporated herein by reference in its entirety.

US 20160172601 and WO 2016158540 disclose, as a compound exhibiting TADF, a compound of a specific structure having a triphenyltriazine structural moiety and including a group that has a structure in which an unsubstituted carbazole group and two carbazole rings are directly bonded via a single bond. In this compound, the group having a structure in which an unsubstituted carbazole group and two carbazole rings are directly bonded via a single bond is substituted into one same benzene ring constituting the triphenyltriazine structural moiety. In addition, US 20160172601 and WO 2016158540 disclose a compound of a specific structure having a triphenyltriazine structural moiety and including two groups that have a structure in which two carbazole rings are directly bonded via a single bond. In this compound, the two groups having a structure in which two carbazole rings are directly bonded via a single bond are bound to the same phenyl ring of the triphenyltriazine structural moiety.

US 20160172601 and WO 2016158540 also disclose that such compounds of specific structures are available as materials for forming an emission layer of an organic electroluminescent device.

In the manufacture of an organic electroluminescent device, it is common to form an organic film constituting an organic electroluminescent device by a dry film-forming method, such as a vapor deposition method. However, there is a problem in that film formation according to a dry film-forming method, such as a vapor deposition method, is time-consuming and expensive. Therefore, instead of such a dry film-forming method, a wet film-forming method, such as solution coating method (hereinafter, also referred to as a coating method), which can save time and cost, has been reviewed.

SUMMARY

However, an organic electroluminescent device employing the compound of a specific structure disclosed in US 20160172601 and WO 2016158540 fail to provide both sufficiently high efficiency and a long lifespan. Accordingly, the present disclosure provides a compound capable of realizing a sufficiently long pot life of a solution and realizing sufficiently low driving voltage, high efficiency, and long lifespan of an organic electroluminescent device.

Additional aspects will be set forth in part in the description which follows and, in part, will be apparent from the description, or may be learned by practice of the presented embodiments of the disclosure.

The present disclosure has overcome the disadvantages described above with a compound including a triphenyl triazine structural moiety and a group having a structure in which a substituted or unsubstituted carbazole group and a predetermined number of carbazole rings are directly bonded via a single bond, wherein these are bonded at a specific binding site.

A compound represented by Formula (1):

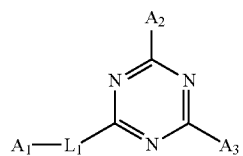

(1)

wherein, in Formula (1), $A_1$ is a substituent represented by Formula (2-1) or (2-2), $A_2$ and $A_3$ are each independently a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, $L_1$ is a single bond, a substituted or unsubstituted divalent aromatic hydrocarbon group having 6 to 30 carbon atoms or a substituted or unsubstituted divalent aromatic heterocyclic group having 5 to 30 ring-forming atoms:

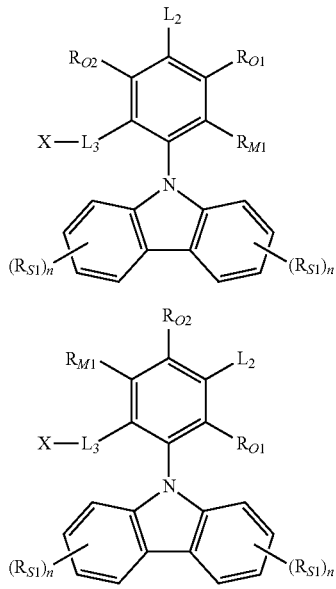

(2-1)

(2-2)

wherein, in Formulae (2-1) and (2-2), $L_2$ is a single bond binding to $L_1$ in Formula (1), a substituted or unsubstituted divalent aromatic hydrocarbon group having 6 to 30 carbon atoms and binding to $L_1$ in Formula (1), or a substituted or unsubstituted divalent aromatic heterocyclic group having 5 to 30 ring-forming atoms and binding to $L_1$ in Formula (1), $R_{O1}$ and $R_{O2}$ are each independently a hydrogen atom, a deuterium atom, a fluoro group, a cyano group, or a substituted or unsubstituted monovalent alkyl group having 1 to 20 carbon atoms, $R_{M1}$ is each independently a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of $R_{S1}$ is independently a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of n is independently 0, 1, 2, 3, or 4, $L_3$ is a single bond, a substituted or unsubstituted divalent aromatic hydrocarbon group having 6 to 30 carbon atoms, or a substituted or unsubstituted divalent aromatic heterocyclic group having 5 to 30 ring-forming atoms and not including a carbazole ring, X is an oligocarbazole group unsubstituted or substituted with a substituent other than a carbazole group, and the oligocarbazole group comprises 2 to 5 carbazole rings that are directly bonded to each other via a single bond, wherein a ring-nitrogen of a carbazole ring of the 2 to 5 carbazole rings binds to $L_3$, a different carbazole ring of the 2 to 5 carbazole rings, an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group (other than a carbazole group) having 5 to 30 ring-forming atoms.

According to the present disclosure, there is provided a compound having a sufficiently long pot life of a solution while realizing sufficiently low driving voltage, high efficiency, and long lifespan of an organic electroluminescent device. In addition, there are provided a composition and a liquid composition that include the compound. Furthermore, there is provided an organic electroluminescent device capable of realizing sufficiently low driving voltage, high efficiency, and long lifespan.

BRIEF DESCRIPTION OF THE DRAWINGS

The above and other aspects, features, and advantages of certain embodiments of the disclosure will be more apparent from the following description taken in conjunction with the accompanying drawings, in which:

FIG. 1 is a schematic diagram showing an organic electroluminescent device according to an embodiment of the present disclosure.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the FIGURES, to explain aspects. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly on the other element or intervening elements may be present therebetween In contrast, when an element is referred to as being "directly on" another element, there are no intervening elements present It will be understood that, although the terms "first," "second," "third" etc. may be used herein to describe various elements, components, regions, layers and/or sections, these elements, components, regions, layers and/or sections should not be limited by these terms These terms are only used to distinguish one element, component, region, layer or section from another element, component, region, layer or section Thus, "a first element," "component," "region," "layer" or "section" discussed below could be termed a second element, component, region, layer or section without departing from the teachings herein.

The terminology used herein is for the purpose of describing particular embodiments only and is not intended to be limiting. As used herein, "a," "an," "the," and "at least one" do not denote a limitation of quantity, and are intended to cover both the singular and plural, unless the context clearly indicates otherwise. For example, "an element" has the same meaning as "at least one element," unless the context clearly indicates otherwise.

"Or" means "and/or." As used herein, the term "and/or" includes any and all combinations of one or more of the associated listed items It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another element as illustrated in the FIGURES It will be understood that relative terms are intended to encompass different orientations of the device in addition to the orientation depicted in the FIGURES For example, if the device in one of the FIGURES is turned over, elements described as being on the "lower" side of other elements would then be oriented on "upper" sides of the other elements The exemplary term "lower," can therefore, encompasses both an orientation of "lower" and "upper," depending on the particular orientation of the FIGURE Similarly, if the device in one of the FIGURES is turned over, elements described as "below" or "beneath" other elements would then be oriented "above" the other elements The exemplary terms "below" or "beneath" can, therefore, encompass both an orientation of above and below.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10% or 5% of the stated value.

Unless otherwise defined, all terms (including technical and scientific terms) used herein have the same meaning as commonly understood by one of ordinary skill in the art to which this disclosure belongs It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments As such, variations from the shapes of the illustrations as a result, for example, of manufacturing techniques and/or tolerances, are to be expected Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features Moreover, sharp angles that are illustrated may be rounded Thus, the regions illustrated in the figures are schematic in nature and their shapes are not intended to illustrate the precise shape of a region and are not intended to limit the scope of the present claims.

Hereinafter, embodiments of the present disclosure will be described. However, the present disclosure is not limited to the following embodiments. In addition, unless otherwise specified, operation and measurement of physical properties are performed under conditions of room temperature (between 20° C. and 25° C.)/relative humidity (RH) between 40% and 50%.

In the present specification, expression 'X and Y are each independently' means that X and Y may be the same or different.

Compound

An aspect of the present disclosure provides a compound represented by Formula (1):

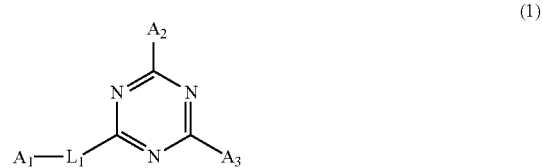

wherein, in Formula (1),
$A_1$ may be a substituent represented by Formula (2-1) or (2-2),
$A_2$ and $A_3$ may each independently be a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms,
$L_1$ may be a single bond, a substituted or unsubstituted divalent aromatic hydrocarbon group having 6 to 30 carbon atoms or a substituted or unsubstituted divalent aromatic heterocyclic group having 5 to 30 ring-forming atoms,

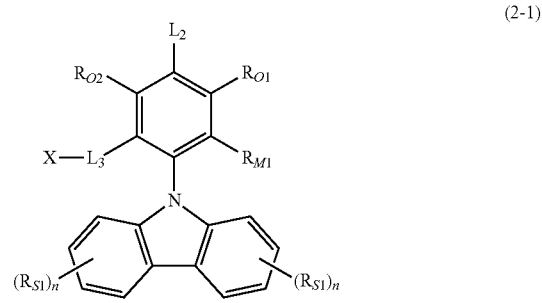

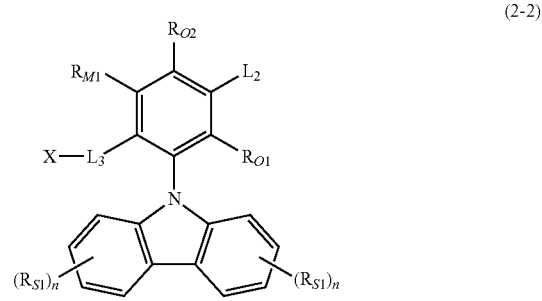

wherein, in Formulae (2-1) and (2-2),
$L_2$ may be a single bond binding to $L_1$ in Formula (1), a substituted or unsubstituted divalent aromatic hydrocarbon group having 6 to 30 carbon atoms and binding to $L_1$ in Formula (1), or a substituted or unsubstituted divalent aromatic heterocyclic group having 5 to 30 ring-forming atoms and binding to $L_1$ in Formula (1), $R_{O1}$ and $R_{O2}$ may each independently be a hydrogen atom, a deuterium atom, a fluoro group, a cyano group, or a substituted or unsubstituted monovalent alkyl group having 1 to 20 carbon atoms, $R_{M1}$ may be a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of $R_{S1}$ may independently be a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of n may independently be 0, 1, 2, 3, or 4, $L_3$ may be a single bond, a substituted or unsubstituted divalent aromatic hydrocarbon group having 6 to 30 carbon atoms, or a substituted or unsubstituted divalent aromatic heterocyclic group having 5 to 30 ring-forming atoms and not including a carbazole ring, X may be an oligocarbazole group unsubstituted or substituted with a substituent other than a carbazole group, and the oligocarbazole group comprises 2 to 5 carbazole rings that are directly bonded via a single bond, wherein a ring-nitrogen of a carbazole ring of the 2 to 5 carbazole rings is bound to $L_3$, a different carbazole ring of the 2 to 5 carbazole rings, an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group (other than a carbazole group) having 5 to 30 ring-forming atoms.

In addition, regarding the compound represented by Formula (1), a substituent of a substituted group comprises a deuterium atom, a fluoro group, a cyano group, an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group having 5 to 30 ring-forming atoms. In addition, regarding the compound represented by Formula (1), the expression "substituted with a substituent other than a carbazole group" means substitution with a substituent comprising a deuterium atom, a fluoro group, a cyano group, an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group (other than a carbazole group) having 5 to 30 ring-forming atoms. Here, the unsubstituted alkyl group having 1 to 20 carbon atoms, the unsubstituted aromatic hydrocarbon group having 6 to 30 carbon atoms, and the unsubstituted aromatic heterocyclic group having 5 to 30 ring-forming atoms are not particularly limited. For example, the substituent may include an unsubstituted monovalent alkyl group having 1 to 20 carbon atoms, an unsubstituted monovalent aromatic hydrocarbon group having 6 to 30 carbon atoms, an unsubstituted monovalent aromatic heterocyclic group having 5 to 30 ring-forming atoms, and the like, which can constitute each of $A_2$ and $A_3$ in Formula (1). In addition, the unsubstituted monovalent aromatic heterocyclic group (other than a carbazole group) having 5 to 30 ring-forming atoms is not particularly limited as long as the group excludes a carbazole group. For example, the substituent may be the same as an unsubstituted monovalent aromatic heterocyclic group having 5 to 30 ring-forming atoms, which can constitute each of $A_2$ and $A_3$ and excludes a carbazole group.

In the compound according to the aspect of the present disclosure, regarding one benzene ring in Formula (2-1) or (2-2), a group (X-$L_3$-group) including an oligocarbazole group unsubstituted or substituted with a substituent other than a carbazole group and an substituted or unsubstituted carbazole group may be bonded to each other at an ortho position. From this, the twist angle between the X-$L_3$-group and the substituted or unsubstituted carbazole group may become large. Such a large twist angle may be due to steric hindrances present in the binding site where the bulky and rigid groups are adjacent to each other. Here, such an X-$L_3$-group may exist so as to have a large twist angle with respect to the plane of the benzene ring to be bonded (preferably, the entire triazine structure portion to which three aromatic groups are directly bonded), thereby effectively suppressing the π-π stacking between molecules. As a result, a solvent may be easily dispersed between molecules. Also, in this regard, aggregation of molecules is unlikely to occur, and precipitation from a solution is also unlikely to occur. Accordingly, a sufficient pot life of a solution for application to a wet process may be obtained.

In addition, in the compound according to the aspect of the present disclosure, as described above, the X-$L_3$-group may have a large twist angle with respect to the plane of the benzene ring (preferably, the entire triazine structure portion to which three aromatic groups are directly bonded). Due to such a structure, the energy difference ($\Delta E_{ST}$) between an excited singlet state and an excited triplet state may be reduced, thereby exhibiting a thermally activated delayed fluorescence (TADF) mechanism. Furthermore, in the case of a conventional compound that does not exhibit the TADF mechanism, the ratio of singlet excitons to all excitons generated therein is 25% (singlet excitons:triplet excitons=1:3). In this regard, in the case of the compound that exhibits the TADF mechanism according to the aspect of the present invention, some triplet excitons are converted into singlet excitons by the TADF mechanism, so that the ratio of singlet excitons occupied in all excitons may exceed 25%.

In general, the Förster-type energy transfer dominates when energy transfers from singlet excitons to a luminescent dopant, whereas the Dexter-type energy transfer dominates when energy transfers from triplet excitons to a luminescent dopant. Here, the Förster-type energy transfer is faster than the Dexter-type energy transfer. In an organic electroluminescent device, since there is also a competitive thermal deactivation process which does not use the exciton energy for luminescence, it may compete with the thermal deactivation process when the energy transfer speed is slow, resulting in low efficiency.

Not wishing to be bound by theory, regarding the compound according to the aspect of the present disclosure, since the ratio of singlet excitons occupied in all excitons becomes greater than 25% by the TADF mechanism, the fast Förster-type energy transfer mechanism predominates, thereby realizing high efficiency of an organic electroluminescent device.

Furthermore, due to the structure having a large twist angle as described above, a difference between highest occupied molecular orbital (HOMO) and lowest unoccupied molecular orbital (LUMO) at singlet levels becomes small, so that an organic electroluminescent device having a driving voltage that is not excessively high, but is sufficiently low may be realized.

In US 20160172601 and WO 2016158540, it is disclosed that a compound of a specific structure emits TADF. Regarding the compound of the specific structure, the triphenyltriazine structural moiety constitutes the LUMO. Regarding one benzene ring constituting the triphenyltriazine structural moiety of the compound of the specific structure, an unsubstituted carbazole group or a group consisting of two carbazole rings that are directly bonded via a single bond may each bind at an ortho position in relation to the binding site to the triazine ring. Here, since the unsubstituted carbazole group or the group consisting of two carbazole rings that are directly bonded via a single bond is present at an adjacent binding position, the twist angle between the benzene ring and the triazine ring in the triphenyltriazine structural moiety becomes large. Such a large twist angle may be due to steric hindrance present in the binding site where the bulky and rigid groups are adjacent to each other. Due to this large twist angle, the LUMO is cut between the triazine ring and the one benzene ring, so that the stability against electron injection is low and the lifespan of an organic electroluminescent device may be shortened.

Also, in the compound according to the aspect of the present disclosure, for the one benzene ring binding to the triazine ring in Formula (1) via $L_1$ and $L_2$ in Formula (2-1) or (2-2), a bulky and rigid group such as an aromatic hydrocarbon group or an aromatic heterocyclic group does not directly bind at the ortho position in relation to the binding position to $L_2$. Accordingly, the twist angle between the aromatic group, such as $L_1$ or $L_2$, and either of the one benzene ring and the triazine may become smaller, thereby providing increased stability against electron injection and a long lifespan of an organic electroluminescent device.

Furthermore, since the mechanism is based on theory, the correctness or difference does not affect the technical scope of the present disclosure. In addition, similarly to other theories set-forth in the present specification, the correctness or difference does not affect the technical scope of the present disclosure.

The substituted or unsubstituted monovalent alkyl group having 1 to 20 carbon atoms that can constitute each of $A_2$ and $A_3$ in Formula (1) is not particularly limited, and may be a linear, branched, or cyclic alkyl group having 1 to 20 carbon atoms.

In detail, examples of the substituted or unsubstituted monovalent alkyl group having 1 to 20 carbon atoms are a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, an neopentyl group, a 1,2-dimethyl propyl group, an n-hexyl group, an isohexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethylhexyl group, a 3-methyl-1-isopropyl butyl group, a 2-methyl-1-isopropyl butyl group, a 1-tert-butyl-2-methyl propyl group, an n-nonyl group, a 3,5,5-trimethyl hexyl group, an n-decyl group, an isodecyl group, an n-undecyl group, a 1-methyl decyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, an n-tetracosyl group, a cyclopropyl group, a cyclopentyl group, a cyclohexyl group, a cycloheptyl group, a cyclooctyl group, a norbornyl group, an adamantyl group, and the like. Among these examples, a linear, branched, or cyclic alkyl group having 1 to 8 carbon atoms may be preferable.

The substituted or unsubstituted monovalent aromatic hydrocarbon group having 6 to 30 carbon atoms that can constitute each of $A_2$ and $A_3$ in Formula (1) is not particularly limited. In addition, monovalent aromatic hydrocarbon group may include a single ring or two or more rings. When the monovalent aromatic hydrocarbon group includes two or more rings, the two or more rings may be linked via a single bond or condensed (i.e., fused) to each other. The monovalent aromatic hydrocarbon group having 6 to 30 carbon atoms is not particularly limited, and examples thereof may include a benzene ring, a pentalene ring, an indene ring, a naphthalene ring, an anthracene ring, an azulene ring, an heptalene ring, an acenaphthylene ring, a phenalene ring, a fluorene ring, a phenanthrene ring, a biphenyl ring, a terphenyl ring, a triphenylene ring, a pyrene ring, a chrysene ring, a picene ring, a perylene ring, a pentaphene ring, a pentacene ring, a tetraphene ring, a hexaphene ring, a hexacene ring, a rubicene ring, a trinaphthylene ring, a heptaphene ring, a pyranthrene ring, and the like.

The substituted or unsubstituted monovalent aromatic heterocyclic group having 5 to 30 ring-forming atoms that can constitute each of $A_2$ and $A_3$ in Formula (1) is not particularly limited. The monovalent aromatic heterocyclic group includes at least one hetero atom, for example, N, O, S, P, Si, B, Se, Ge, and Te, and carbon atoms (C) as the remaining ring-forming atoms. The monovalent aromatic heterocyclic group may include a single ring or two or more rings. In addition, when the monovalent aromatic heterocyclic group includes two or more rings, the two or more rings may be linked via a single bond or condensed to each other (i.e., fused). The monovalent aromatic heterocyclic group is not particularly limited, but examples thereof are a π electron-deficient aromatic hetero ring, a π electron-rich aromatic hetero ring, a π electron-deficient and rich mixed aromatic hetero ring in which a π electron-deficient aromatic hetero ring and a π electron-rich aromatic hetero ring is mixed, and the like.

Non-limiting examples of the π electron-deficient aromatic hetero ring are a pyridine ring, a pyrazine ring, a pyridazine ring, a pyrimidine ring, a triazine ring, a quinoline ring, an isoquinoline ring, a quinoxaline ring, a quinazoline ring, a naphthylidine ring, an acridine ring, a phenazine ring, a benzoquinoline ring, a benzoisoquinoline ring, a phenanthridine ring, a phenanthroline ring, a benzoquinone ring, a coumarin ring, an anthraquinone ring, a fluorenone ring, and the like. Non-limiting examples of the π electron-rich aromatic hetero ring are a furan ring, a thiophene ring, a benzofuran ring, a benzothiophene ring, a dibenzofuran ring, a dibenzothiophene ring, a pyrrole ring, an indole ring, a carbazole ring, an indolocarbazole ring, and the like.

Non-limiting examples of the π electron-deficient and rich mixed aromatic hetero ring are an imidazole ring, a benzimidazole ring, a pyrazole ring, an indazole ring, an oxazole ring, an isoxazole ring, a benzoxazole ring, a benzisoxazole ring, a thiazole ring, an isothiazole ring, a benzothiazole ring, a benzoisothiazole ring, an imidazolinone ring, a benzimidazolinone ring, an imidazopyridine ring, an imidazopyrimidine ring, an imidazophenanthridine ring, a benzimidazophenanthridine ring, an azadibenzofuran ring, an azacarbazole ring, an azadibenzothiophene ring, a diazadibenzofuran ring, a diazacarbazole ring, a diazadibenzothiophene ring, a xanthone ring, a thioxanthone ring, and the like. That is, the monovalent aromatic heterocyclic group having 5 to 30 ring-forming atoms may be a derived from one of the rings above or a combination of the rings above.

Here, as $A_2$ and $A_3$, a substituted or unsubstituted monovalent aromatic hydrocarbon group having 6 to 30 carbon atoms may be preferable. In addition, as $A_2$ and $A_3$, a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, or a substituted or unsubstituted triphenylene group may be more preferable. In addition, as $A_2$ and $A_3$, a substituted or unsubstituted phenyl group may be more preferable. Furthermore, as $A_2$ and $A_3$, a substituted phenyl group may be particularly preferable.

The substituted or unsubstituted divalent aromatic hydrocarbon group having 6 to 30 carbon atoms that can constitute $L_1$ in Formula (1) is not particularly limited. The substituted or unsubstituted divalent aromatic hydrocarbon group having 6 to 30 carbon atoms may include a single ring or two or more rings. In addition, when the divalent aromatic hydrocarbon group includes two or more rings, the two or more rings may be linked via a single bond or condensed to each other. The divalent aromatic hydrocarbon group having 6 to 30 carbon atoms is not particularly limited, and rings included in the divalent aromatic hydrocarbon group may be the same as the rings constituting the monovalent aromatic hydrocarbon group having 6 to 30 carbon atoms as described in connection with $A_2$ and $A_3$.

The substituted or unsubstituted divalent aromatic heterocyclic group having 5 to 30 ring-forming atoms that can constitute $L_1$ in Formula (1) is not particularly limited. The divalent aromatic heterocyclic group having 5 to 30 ring-forming atoms includes at least one heteroatom (for example, N, O, P, S, Si, B, Ge, Se, and Te); and the remaining ring-forming atoms are C. In addition, the divalent aromatic heterocyclic group may include a single ring or two or more rings. When the divalent aromatic heterocyclic group includes two or more rings, the two or more rings may be linked via a single bond or condensed to each other. The divalent aromatic heterocyclic group having 5 to 30 ring-forming atoms is not particularly limited. Non-limiting examples of the rings constituting the divalent aromatic heterocyclic group having 5 to 30 ring-forming atoms may include the same as the rings constituting the monovalent aromatic hydrocarbon group having 5 to 30 ring-forming atoms as described in connection with $A_2$ and $A_3$.

Here, as $L_1$, a substituted or unsubstituted divalent aromatic hydrocarbon group having 6 to 30 carbon atoms or a single bond may be preferable. In addition, $L_1$, may be more preferably an unsubstituted m-phenylene group, an unsubstituted p-phenylene group, or a single bond. In addition, as $L_1$, an unsubstituted p-phenylene group or a single bond may be even more preferable, and a single bond may be particularly preferable.

$A_1$ in Formula (1) may be, as described above, a substituent represented by Formula (2-1) or (2-2).

The substituted or unsubstituted divalent aromatic hydrocarbon group having 6 to 30 carbon atoms that can constitute $L_2$ in Formulae (2-1) and (2-2) is not particularly limited. The substituted or unsubstituted divalent aromatic hydrocarbon group having 6 to 30 carbon atoms that can constitute $L_1$ in Formula (1) is not particularly limited.

The substituted or unsubstituted divalent aromatic heterocyclic group having 5 to 30 ring-forming atoms that can constitute $L_2$ in Formulae (2-1) and (2-2) is not particularly limited. For example, the substituted or unsubstituted divalent aromatic heterocyclic group having 5 to 30 ring-forming atoms that can constitute $L_1$ in Formula (1) is not particularly limited.

Here, as $L_2$, a substituted or unsubstituted divalent aromatic hydrocarbon group having 6 to 30 carbon atoms or a single bond may be preferable. In addition, as $L_2$, an unsubstituted m-phenylene group, an unsubstituted p-phenylene group, or a single bond may be more preferable. In addition, as $L_2$, an unsubstituted p-phenylene group or a single bond may be still more preferable, and a single bond may be particularly preferable.

The relationship between $L_1$ in Formula (1) and $L_2$ in Formula (2-1) or (2-2) is not particularly limited. However, it is preferable that $L_1$ does not include an aromatic hydrocarbon or heterocyclic group at the ortho position in relation to the triazine ring of Formula (1) binding to $L_1$. Similarly, it is preferable that $L_2$ does not include an aromatic hydrocarbon or heterocyclic group at the ortho position in relation to the benzene ring of Formula (2-1) or (2-2) binding to $L_2$. $L_1$ and $L_2$ do not include an aromatic hydrocarbon or heterocyclic group at the ortho position in relation to $L_1$ and $L_2$.

By having such a structure, stability against electron injection is further improved, so that a new long-term lifespan of an organic electroluminescent device may be realized. Not wishing to be bound by theory, it is believed that in this structure, between the triazine ring in Formula (1) and the one benzene ring bonded by insertion of $L_1$ and $L_2$ in Formula (2-1) or (2-2), there is no occasion in any of binding positions that a bulky and rigid group, such as an aromatic hydrocarbon group or an aromatic heterocyclic group, directly binds at the ortho position. As a result, the twist angle between the triazine ring in Formula (1) and the one benzene ring bonded by insertion of $L_1$ and $L_2$ in Formula (2-1) or (2-2), becomes small. Here, regarding the compound according to the aspect of the present disclosure, the structural moiety from $A_2$, $A_3$, and the triazine ring in Formula (1) to the one benzene ring binding to the triazine ring via $L_1$ and $L_2$ in Formula (2-1) or (2-2) may constitute the LUMO. Thus, in the case of having this structure, the LUMO is not cut within the structural moiety, and a wide LUMO may be rather obtained. As a result, stability against electron injection is further improved, so that a new long-term lifespan of an organic electroluminescent device may be realized. Here, from the same point of view, a case where both $L_1$ and $L_2$ are single bonds or a case where one of them is a single bond and the other is an unsubstituted p-phenylene group is more preferable. For example, the case where one of them is a single bond and the other is an unsubstituted p-phenylene group is further preferable.

The substituted or unsubstituted monovalent alkyl group having 1 to 20 carbon atoms that can constitute each of $R_{O1}$, $R_{O2}$, $R_{M1}$, and $R_{S1}$ in Formulae (2-1) and (2-2) is not particularly limited. For example, the substituted or unsubstituted monovalent alkyl group having 1 to 20 carbon atoms may be the same as the substituted or unsubstituted monovalent alkyl group having 1 to 20 carbon atoms that can constitute each of $A_2$ and $A_3$ in Formula (1).

The substituted or unsubstituted monovalent aromatic hydrocarbon group having 6 to 30 carbon atoms that can constitute each of $R_{M1}$ and $R_{S1}$ in Formulae (2-1) and (2-2)

is not particularly limited. For example, the substituted or unsubstituted monovalent aromatic hydrocarbon group having 6 to 30 carbon atoms may be the same as the substituted or unsubstituted monovalent aromatic hydrocarbon group having 6 to 30 carbon atoms that can constitute each of $A_2$ and $A_3$ in Formula (1).

The substituted or unsubstituted monovalent aromatic heterocyclic group having 5 to 30 ring-forming atoms that can constitute each of $R_{M1}$ and $R_{S1}$ in Formulae (2-1) and (2-2) is not particularly limited. For example, the substituted or unsubstituted monovalent aromatic heterocyclic group having 5 to 30 ring-forming atoms may be the same as the substituted or unsubstituted monovalent aromatic heterocyclic group having 5 to 30 ring-forming atoms that can constitute each of $A_2$ and $A_3$ in Formula (1).

Here, as $R_{O1}$ and $R_{O2}$, a hydrogen atom may be preferable.

As $R_{M1}$, a hydrogen atom or a substituted or unsubstituted monovalent aromatic heterocyclic group having 5 to 30 ring-forming atoms may be preferable. Also, as $R_{M1}$, a hydrogen atom or an unsubstituted monovalent aromatic heterocyclic group having 5 to 30 ring-forming atoms may be more preferable, and a hydrogen atom or an unsubstituted carbazole group may be also more preferable. In addition, as $R_{M1}$, a hydrogen atom or an N-carbazole group may be still more preferable, and a hydrogen atom may be particularly preferable.

In addition, it is preferable that only one of n(s) is 1, 2, 3, or 4, and the other n is 0, or that all n(s) are 0. In addition, it is more preferable that only one of n(s) is 1, and the other n is 0, or that all n(s) are 0. In addition, it is more preferable that all n(s) are 0. That is, a case where each $R_{S1}$ corresponding to each n does not exist may be more preferable. Therefore, it is more preferable that the ring-forming carbon atoms of the carbazole group in Formulae (2-1) and (2-2) are bound to a hydrogen atoms.

Regarding a case where n indicates 1, 2, 3, or 4, as $R_{S1}$, a substituted or unsubstituted monovalent aromatic hydrocarbon group having 6 to 30 carbon atoms may be preferable. In addition, as $R_{S1}$, a substituted or unsubstituted phenyl group, a substituted or unsubstituted biphenyl group, a substituted or unsubstituted terphenyl group, a substituted or unsubstituted naphthyl group, a substituted or unsubstituted phenanthrenyl group, or a substituted or unsubstituted triphenylene group may be more preferable. In addition, as $R_{S1}$, a substituted or unsubstituted phenyl group may be still more preferable, and an unsubstituted phenyl group may be particularly preferable.

The substituted or unsubstituted divalent aromatic hydrocarbon group having 6 to 30 carbon atoms that can constitute $L_3$ in Formulae (2-1) and (2-2) is not particularly limited. For example, the substituted or unsubstituted divalent aromatic hydrocarbon group having 6 to 30 carbon atoms may be the same as the substituted or unsubstituted divalent aromatic hydrocarbon group having 6 to 30 carbon atoms that can constitute $L_1$ in Formula (1).

The substituted or unsubstituted divalent aromatic heterocyclic group having 5 to 30 ring-forming atoms that does not include a carbazole group and can constitute $L_3$ in Formulae (2-1) and (2-2) is not particularly limited.

For example, the unsubstituted divalent aromatic heterocyclic group having 5 to 30 ring-forming atoms may be the same as the unsubstituted divalent aromatic heterocyclic group having 5 to 30 ring-forming atoms that can constitute $L_1$ in Formula (1), wherein the unsubstituted divalent aromatic heterocyclic group having 5 to 30 ring-forming atoms may not include a carbazole group. In addition, the divalent aromatic heterocyclic group having 5 to 30 ring-forming atoms and not including a carbazole ring may be substituted. Furthermore, when $L_3$ is a substituted divalent aromatic heterocyclic group having 5 to 30 ring-forming atoms, $L_3$ may include, only as a substituent, a carbazole group or a group containing a carbazole ring.

Here, as $L_3$, a substituted or unsubstituted divalent aromatic hydrocarbon group having 6 to 30 carbon atoms or a single bond may be more preferable, and an unsubstituted divalent aromatic hydrocarbon group having 6 to 30 carbon atoms or a single bond may be more preferable. In addition, as $L_3$, an unsubstituted m-phenylene group, an unsubstituted p-phenylene group, or a single bond may be preferable, and an unsubstituted p-phenylene group or a single bond may be more preferable. In addition, as $L_3$, a single bond may be still more preferable.

In Formulae (2-1) and (2-2), X indicates an oligocarbazole group unsubstituted or substituted with a substituent other than a carbazole group as described above.

The term "oligocarbazole group" (i.e., an unsubstituted oligocarbazole group in terms of defining the oligocarbazole group) as used herein refers to a group having a structure in which 2 to 5 carbazole rings are directly bonded to each other via a single bond, wherein a ring-nitrogen of a carbazole ring of the 2 to 5 carbazole rings binds to $L_3$, a different carbazole ring of the 2 to 5 carbazole rings, an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group (other than a carbazole group) having 5 to 30 ring-forming atoms.

In addition, in the compound represented by Formula (1), $L_3$ may bind to a ring-forming atom that is a nitrogen atom or a carbon atom of one of carbazole rings in the oligocarbazole group unsubstituted or substituted with a substituent other than a carbazole group.

In the "oligocarbazole group", the unsubstituted monovalent alkyl group having 1 to 20 carbon atoms that can bind to a nitrogen atom of the carbazole ring is not particularly limited. For example, the unsubstituted monovalent alkyl group having 1 to 20 carbon atoms may be the same as the unsubstituted monovalent alkyl group having 1 to 20 carbon atoms that can constitute each of $A_2$ and $A_3$ in Formula (1).

In the "oligocarbazole group", the unsubstituted monovalent aromatic hydrocarbon group having 6 to 30 carbon atoms that can bind to a nitrogen atom of the carbazole ring is not particularly limited. For example, the unsubstituted monovalent aromatic hydrocarbon group having 6 to 30 carbon atoms may be the same as the unsubstituted monovalent aromatic hydrocarbon group having 6 to 30 carbon atoms that can constitute each of $A_2$ and $A_3$ in Formula (1).

In the "oligocarbazole group", the unsubstituted monovalent aromatic heterocyclic group (other than a carbazole group) having 5 to 30 ring-forming atoms that can bind to a nitrogen atom of the carbazole ring is not particularly limited. For example, the unsubstituted monovalent aromatic heterocyclic group (other than a carbazole group) having 5 to 30 ring-forming atoms may be the same as the unsubstituted monovalent aromatic heterocyclic group having 5 to 30 ring-forming atoms that can constitute each of $A_2$ and $A_3$ and excludes a carbazole group.

Here, it is preferable that the nitrogen atom of the carbazole ring in the "oligocarbazole group" binds to a different carbazole ring or an unsubstituted monovalent aromatic hydrocarbon group having 6 to 30 carbon atoms. In addition, it is more preferable that the nitrogen atom of the carbazole ring in the "oligocarbazole group" binds to a different carbazole ring or an unsubstituted phenyl group.

Furthermore, when the oligocarbazole group is substituted with a substituent other than a carbazole group, the substituent may bind to a ring-forming atom (i.e., a carbon atom or a nitrogen atom) of a carbazole ring of the oligocarbazole group. In addition, the substituent may include an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group (other than a carbazole group) having 5 to 30 ring-forming atoms, which binds to the nitrogen atom of a carbazole ring of the oligocarbazole group.

When the oligocarbazole group is substituted with a substituent other than a carbazole group, as the substituent, an unsubstituted monovalent aromatic hydrocarbon group having 6 to 30 carbon atoms may be preferable.

In addition, when the oligocarbazole group is substituted with a substituent other than a carbazole group, as the substituent, an unsubstituted phenyl group, an unsubstituted biphenyl group, an unsubstituted terphenyl group, an unsubstituted naphthyl group, an unsubstituted phenanthrenyl group, or an unsubstituted triphenylene group may be more preferable. In addition, when the oligocarbazole group is substituted with a substituent other than a carbazole group, as the substituent, an unsubstituted phenyl group may be particularly preferable.

In the "oligocarbazole group", the number of the carbazole rings linked by a single bond may be 2 or more and 5 or less as described above. When the number of the carbazole ring is 1, the HOMO level is not shallow as in the oligocarbazole group, and thus there may be insufficient hole injection capability and/or the hole transport capability. In this regard, the probability of direct recombination on the compound becomes insufficient. In addition, since the energy difference ($\Delta E_{ST}$) between the excited singlet state and the excited triplet state is not sufficiently small, the TADF mechanism is not exhibited. Accordingly, the energy transfer is not efficient by the TADF mechanism. In addition, when the number of the carbazole ring is 6 or more, the volume ratio of the oligocarbazole group occupied by one molecule becomes too large, and the charge balance is biased toward the hole excess, leading to a decrease in efficiency of an organic electroluminescent device. In the oligocarbazole group, when the number of carbazole rings present is not particularly limited as long as it is within the ranges above. However, from the viewpoint of simplicity of synthesis and simplicity of purification, two or more and three or less carbazole rings may be preferable, and two carbazole rings may be more preferable.

In the oligocarbazole group, when the number of the carbazole rings is 2 or more, the oligocarbazole group unsubstituted or substituted with a substituent other than a carbazole group may be preferably one represented by Formulae (3a) to (3g):

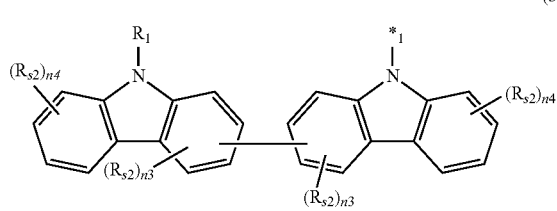
(3a)

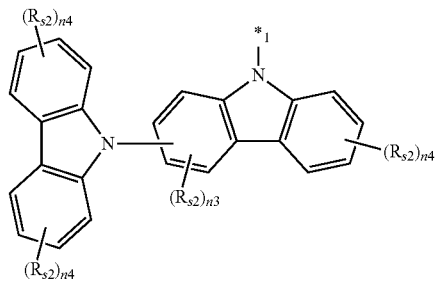
(3b)

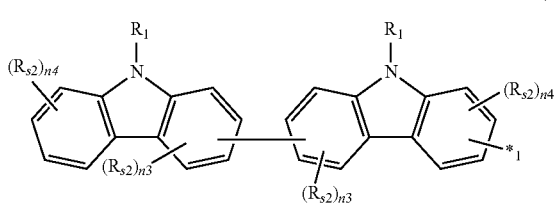
(3c)

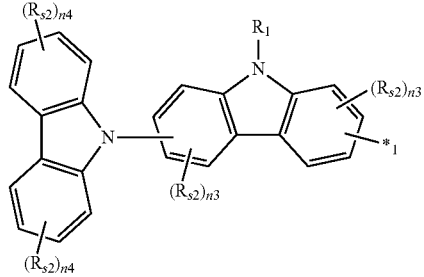
(3d)

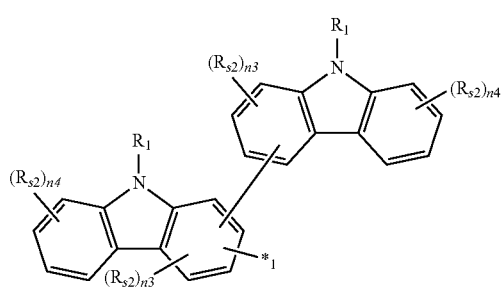
(3e)

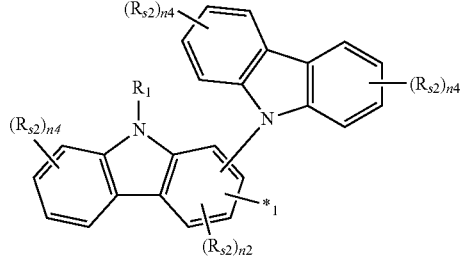
(3f)

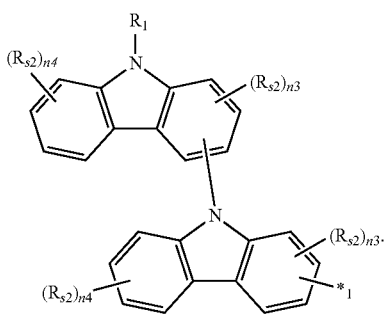

(3g)

In Formulae (3a) to (3g),

*1 indicates a binding site to Lin Formula (2-1) or (2-2), each occurrence of $R_1$ may independently be a monovalent alkyl group having 1 to 20 carbon atoms and being unsubstituted or substituted with a substituent other than a carbazole group, a monovalent aromatic hydrocarbon group having 6 to 30 carbon atoms unsubstituted or substituted with a substituent other than a carbazole group, or a monovalent aromatic heterocyclic group (other than a carbazole group) having 5 to 30 ring-forming atoms and being unsubstituted or substituted with a substituent other than a carbazole group, each occurrence of $R_{S2}$ may independently be a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group (other than a carbazole group) having 5 to 30 ring-forming atoms, each occurrence of n4 may independently be 0, 1, 2, 3, or 4, each occurrence of n3 may independently be 0, 1, 2, or 3, and each occurrence of n2 may independently be 0, 1, or 2.

The substituted or unsubstituted monovalent alkyl group having 1 to 20 carbon atoms that can constitute each of $R_1$ and $R_{S2}$ in Formulae (3a) to (3g) is not particularly limited. For example, the substituted or unsubstituted monovalent alkyl group having 1 to 20 carbon atoms may be the same as the substituted or unsubstituted monovalent alkyl group having 1 to 20 carbon atoms that can constitute each of $A_2$ and $A_3$ in Formula (1).

The substituted or unsubstituted monovalent aromatic hydrocarbon group having 6 to 30 carbon atoms that can constitute each of $R_1$ and $R_{S2}$ in Formulae (3a) to (3g) is not particularly limited. For example, the substituted or unsubstituted monovalent aromatic hydrocarbon group having 6 to 30 carbon atoms may be the same as the substituted or unsubstituted monovalent aromatic hydrocarbon group having 6 to 30 carbon atoms that can constitute each of $A_2$ and $A_3$ in Formula (1).

The substituted or unsubstituted monovalent aromatic heterocyclic group (other than a carbazole group) having 5 to 30 ring-forming atoms that can constitute each of $R_1$ and $R_{S2}$ in Formulae (3a) to (3g) is not particularly limited as long as a substituted or unsubstituted carbazole group is excluded. For example, the substituted of unsubstituted monovalent aromatic heterocyclic group (other than a carbazole group) having 5 to 30 ring-forming atoms may be the same as the substituted or unsubstituted monovalent aromatic heterocyclic group having 5 to 30 ring-forming atoms that can constitute each of $A_2$ and $A_3$ and excludes a substituted or unsubstituted carbazole group.

Here, as $R_1$, a monovalent aromatic hydrocarbon group having 6 to 30 carbon atoms and being unsubstituted or substituted with a substituent other than a carbazole group may be preferable. In addition, as $R_1$, a phenyl group unsubstituted or substituted with a substituent other than a carbazole group, a biphenyl group unsubstituted or substituted with a substituent other than a carbazole group, a terphenyl group unsubstituted or substituted with a substituent other than a carbazole group, a naphthyl group unsubstituted or substituted with a substituent other than a carbazole group, a phenanthrenyl group unsubstituted or substituted with a substituent other than a carbazole group, or a triphenylene group unsubstituted or substituted with a substituent other than a carbazole group may be more preferable. In addition, as $R_1$, a phenyl group unsubstituted or substituted with a substituent other than a carbazole group may be more preferable. In addition, as $R_1$, a phenyl group unsubstituted or substituted with a phenyl group may be more preferable.

In addition, it is preferable that n4(s), n3(s), and n2(s) may each independently be 0, and it is more preferable that n4(s), n3(s), and n2(s) may all be 0. That is, it is preferable that $R_{S2}$(s) corresponding to each of n4(s), each of n3(s), and each of n2(s) do not exist.

Also in the groups represented by Formulae (3a) to (3g), the oligocarbazole group unsubstituted or substituted with a substituent other than a carbazole group may be preferably one represented by Formulae (3a) to (3d) and (3g). In addition, the oligocarbazole group unsubstituted or substituted with a substituent other than a carbazole group may be more preferably one represented by Formulae (3a-1) to (3a-6), (3b-1), (3b-2), (3c-1) to (3c-6), (3d-1), (3d-2), (3g-1), and (3g-2). In addition, the oligocarbazole group unsubstituted or substituted with a substituent other than a carbazole group may be further preferably one represented by Formulae (3a-1), (3a-2), (3b-1), (3c-2), (3d-1), (3d-2), and (3g-2). Furthermore, the oligocarbazole group unsubstituted or substituted with a substituent other than the carbazole group may be still more preferably a group represented by Formula (3a-1) or (3b-1). In addition, the oligocarbazole group unsubstituted or substituted with a substituent other than the carbazole group may be particularly preferably a group represented by Formula (3a-1):

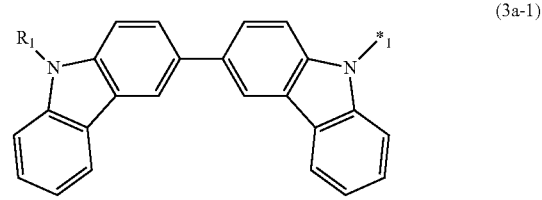

(3a-1)

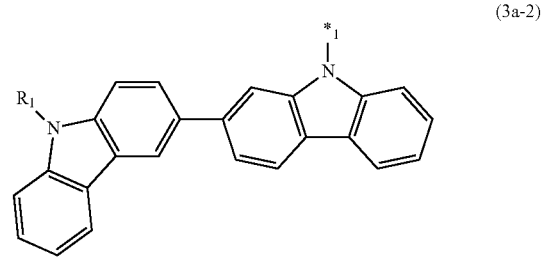

(3a-2)

-continued
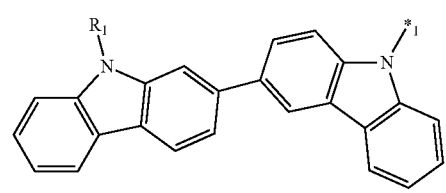
(3a-3)
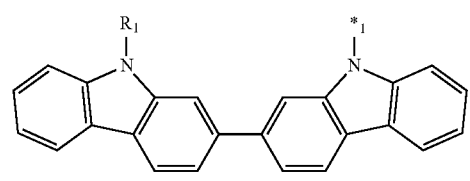
(3a-4)
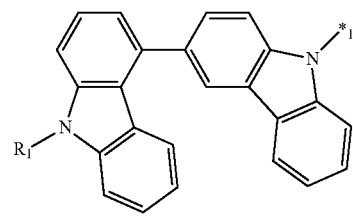
(3a-5)
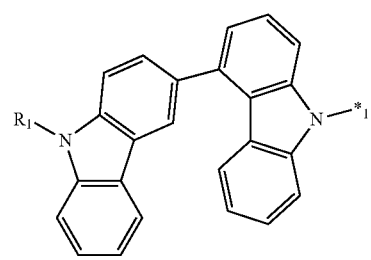
(3a-6)
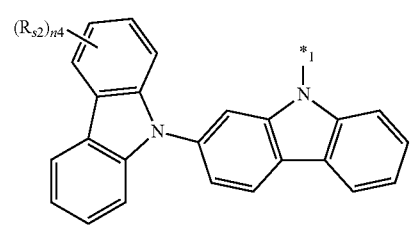
(3b-1)
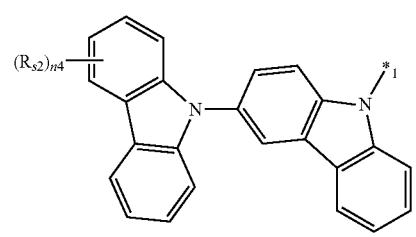
(3b-2)
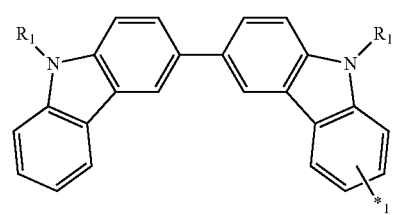
(3c-1)
-continued
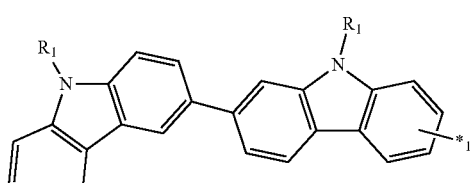
(3c-2)
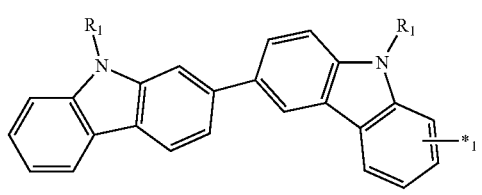
(3c-3)
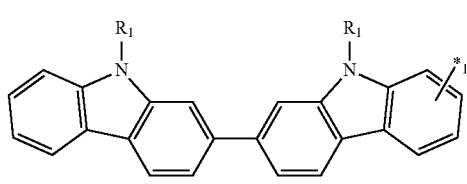
(3c-4)
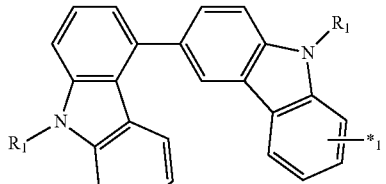
(3c-5)
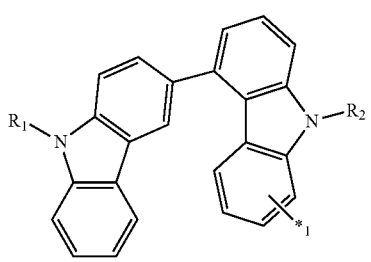
(3c-6)
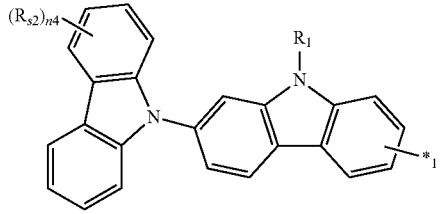
(3d-1)
(3d-2)

-continued

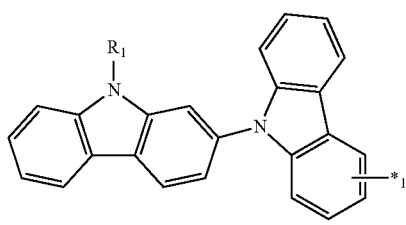
(3g-1)

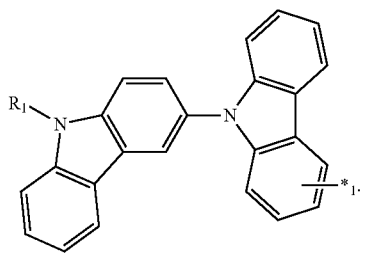
(3g-2)

In Formulae (3a-1) to (3a-6), (3b-1), (3b-2), (3c-1) to (3c-6), (3d-1), (3d-2), (3g-1), and (3g-2), *1, each $R_1$, each $R_{S2}$, and each n4 may each independently be the same as those described in connection with Formulae (3a) to (3g).

Here, n4 may be preferably 0. That is, it is preferable that each $R_{S2}$ corresponding to n4 does not exist.

When the number of the carbazole group in the oligocarbazole group is 3, the oligocarbazole group unsubstituted or substituted with a substituent other than a carbazole group may be preferably one selected from groups represented by Formulae (4a-1) to (4a-9), (4b-1) to (4b-4), (4c-1) to (4c-10), (4d-1) to (4d-6), (4e-1) to (4e-8), (4f-1) to (4f-4), and (4g-1) to (4g-5). In addition, the oligocarbazole group unsubstituted or substituted with a substituent other than a carbazole group may be more preferably one selected from groups represented by Formulae (4a-1), (4a-7), (4b-3), and (4b-4). In addition, the oligocarbazole group unsubstituted or substituted with a substituent other than the carbazole group may be more preferably a group represented by Formula (4b-4):

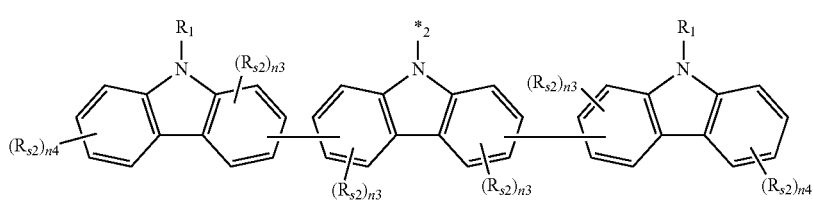
(4a-1)

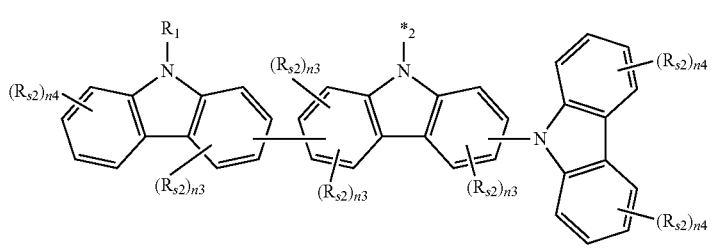
(4a-2)

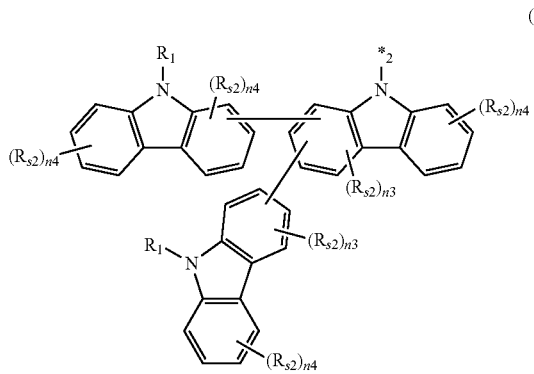
(4a-3)

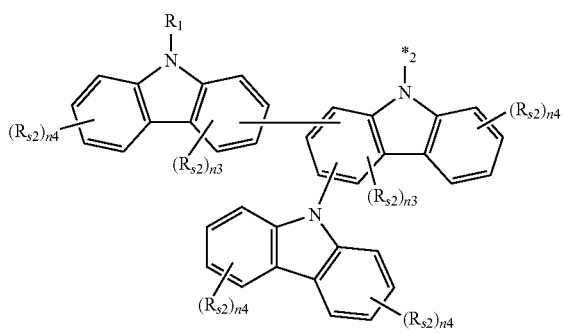
(4a-4)

-continued
(4a-5)
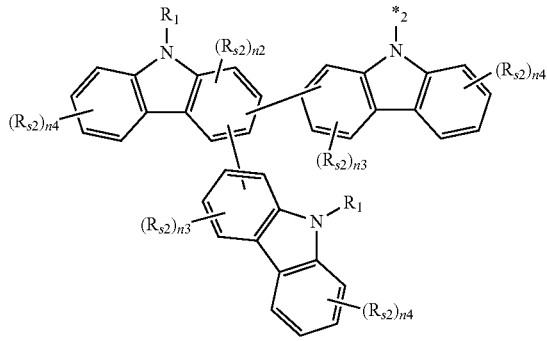
(4a-6)
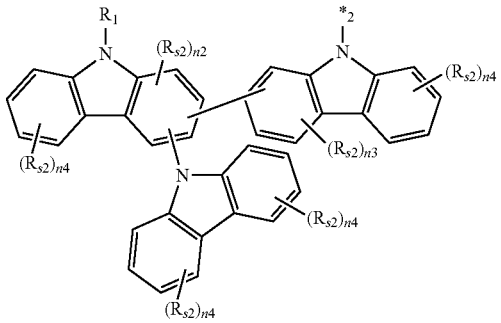
(4a-7)
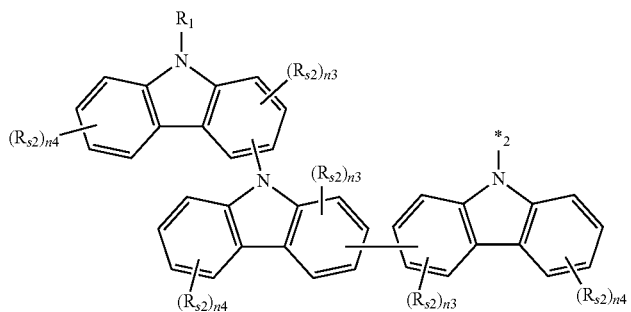
(4a-8)
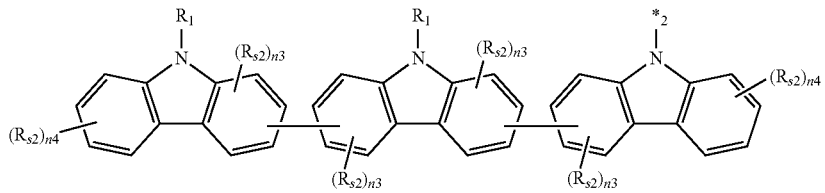
(4a-9)
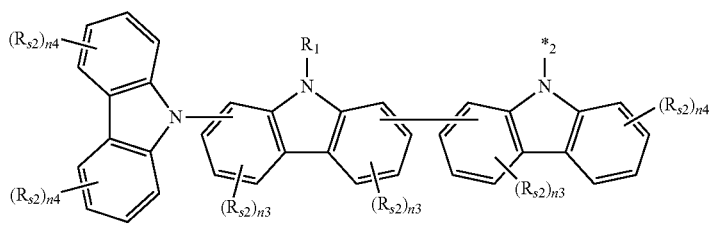
(4b-1)
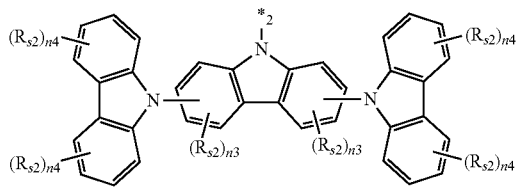
(4b-2)
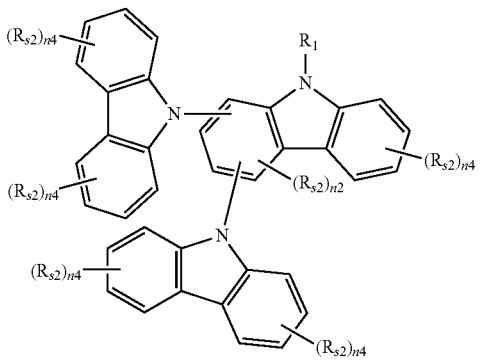

-continued
(4b-3)
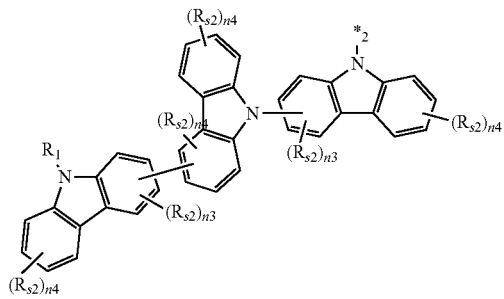
(4b-4)
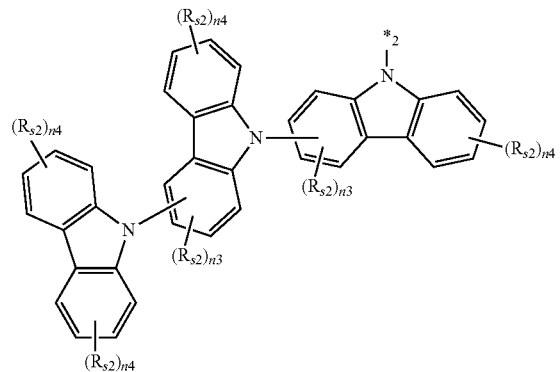
(4c-1)
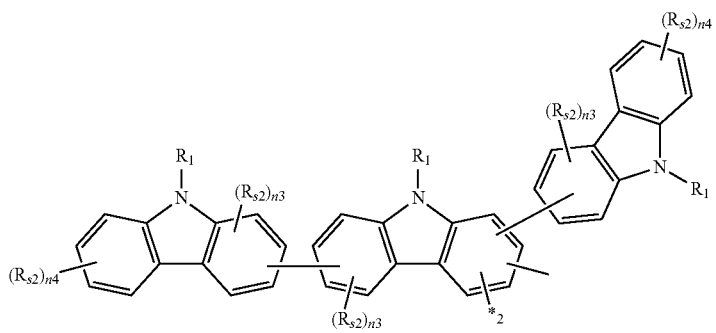
(4c-2)
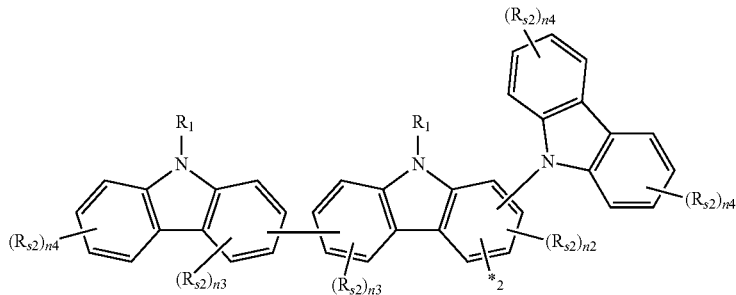
(4c-3)
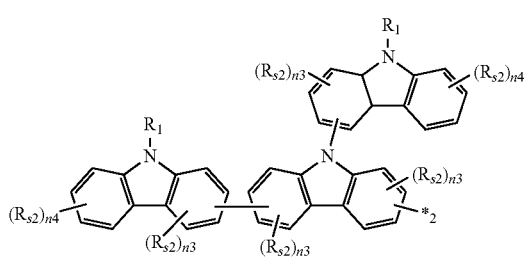
(4c-4)
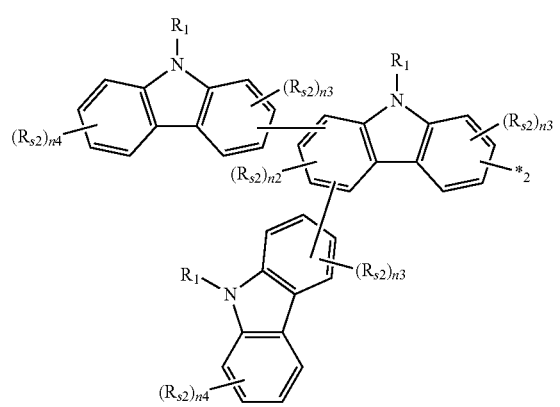

(4c-5)
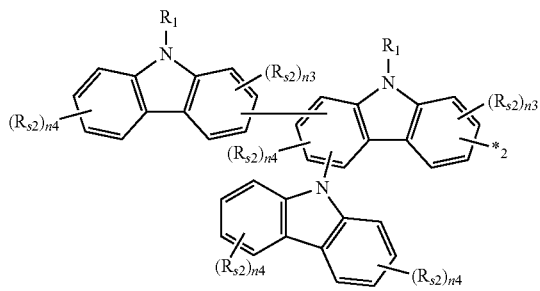
(4c-6)
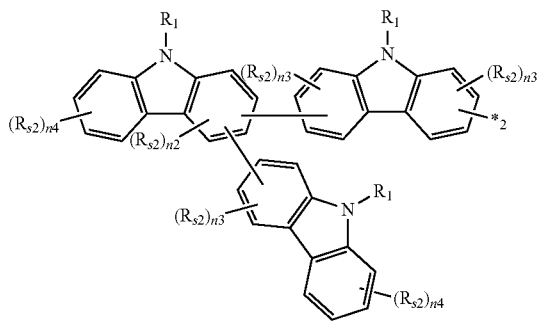
(4c-7)
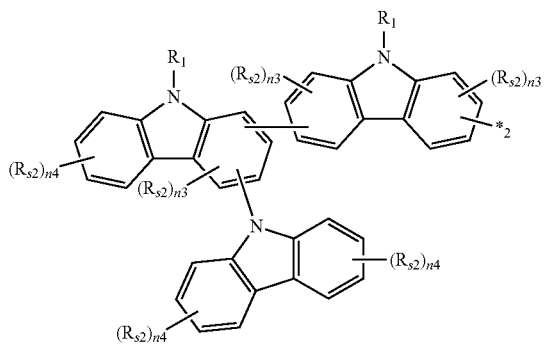
(4c-8)
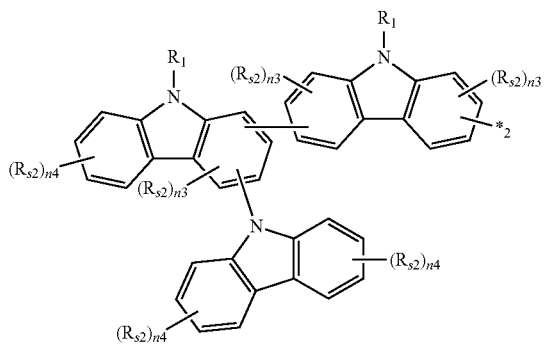
(4c-9)
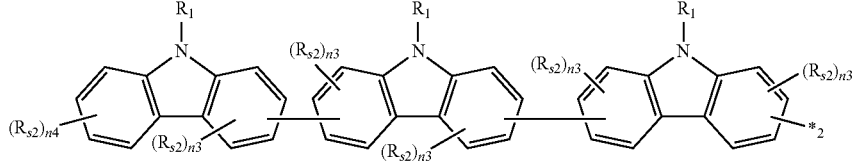
(4c-10)
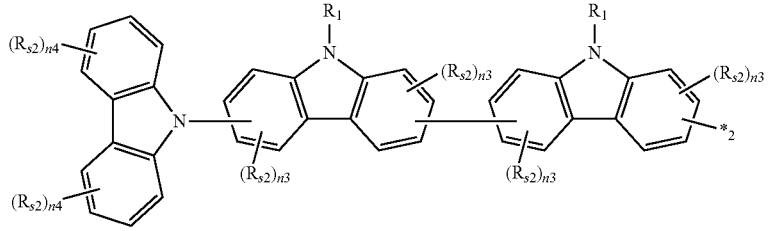
(4d-1)
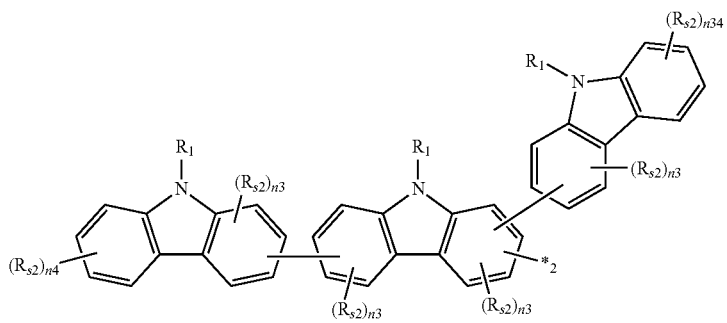

-continued
(4d-2)
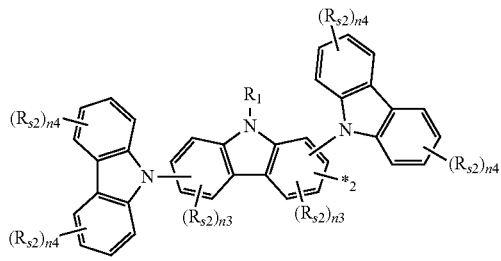
(4d-3)
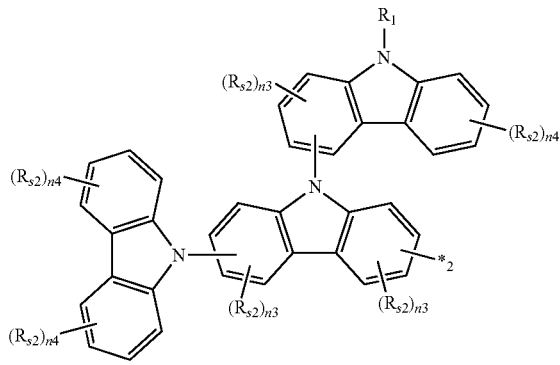
(4d-4)
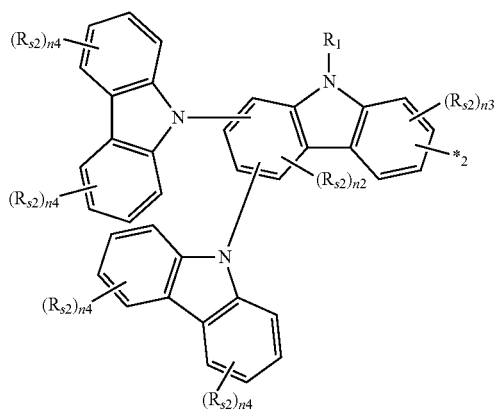
(4d-5)
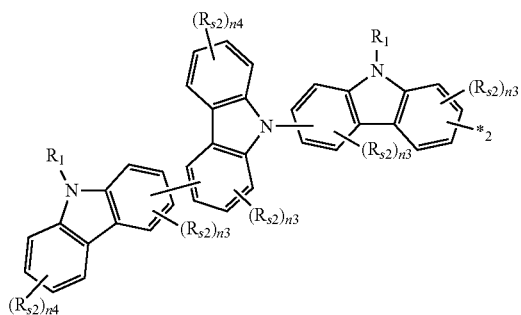
(4d-6)
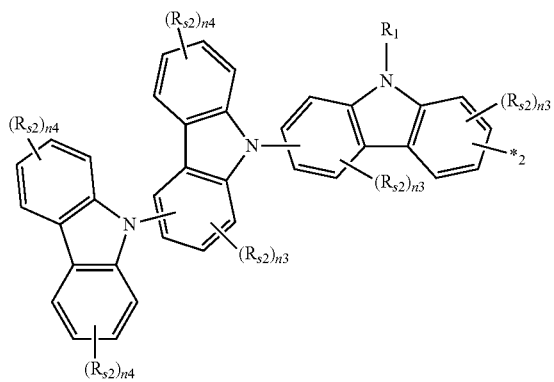
(4e-1)
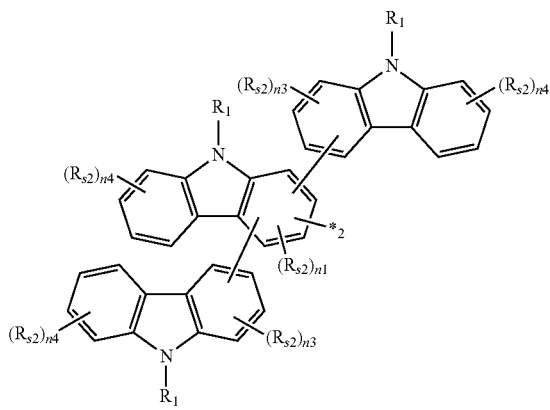
(4e-2)
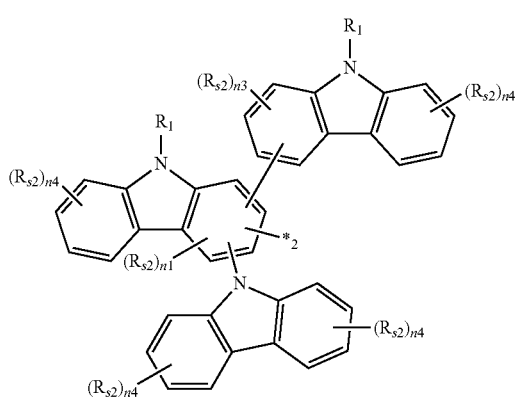
(4e-3)
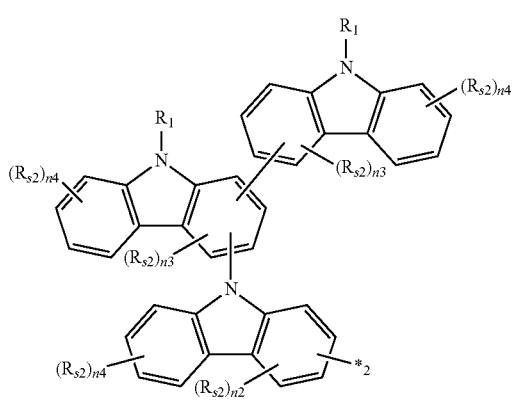

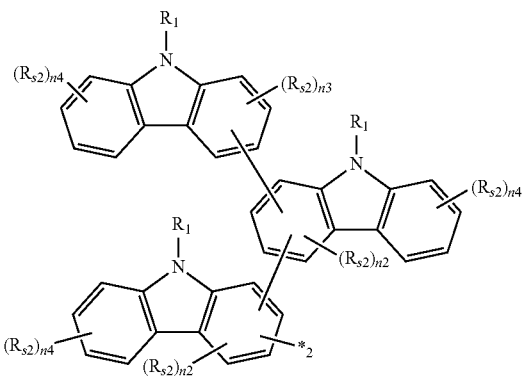
(4e-4)
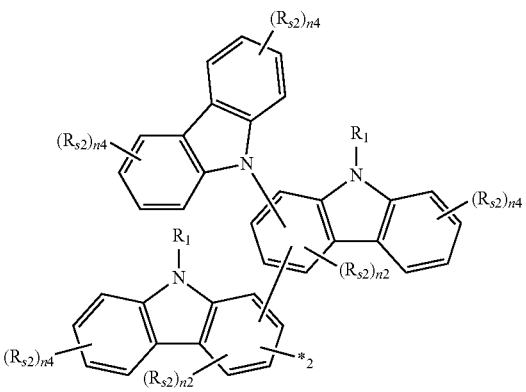
(4e-5)
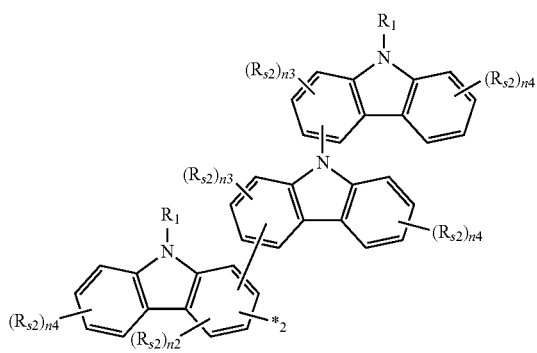
(4e-6)
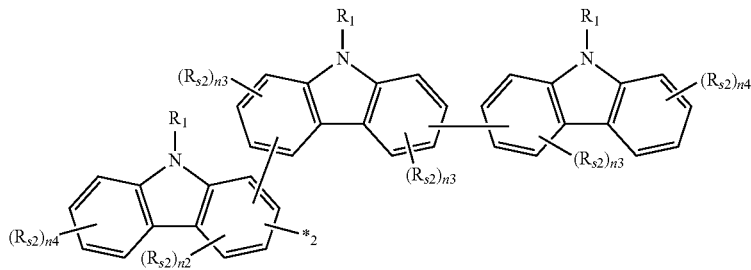
(4e-7)
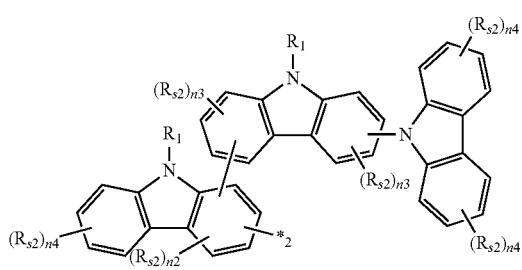
(4e-8)
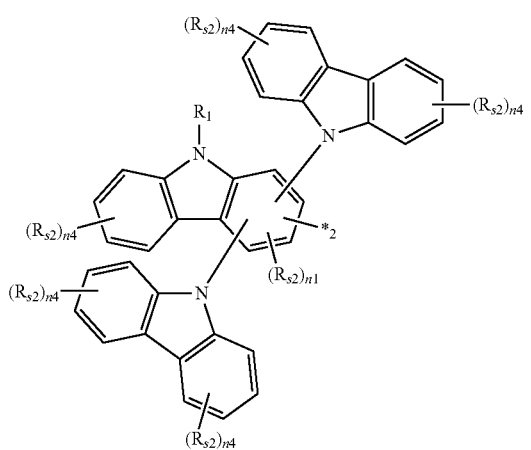
(4f-1)

-continued
(4f-2)
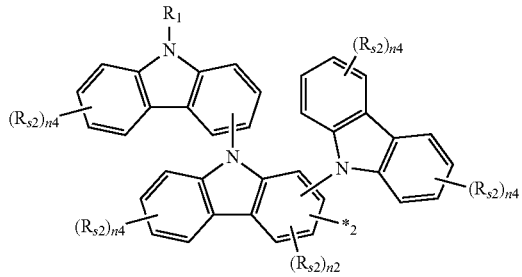
(4f-3)
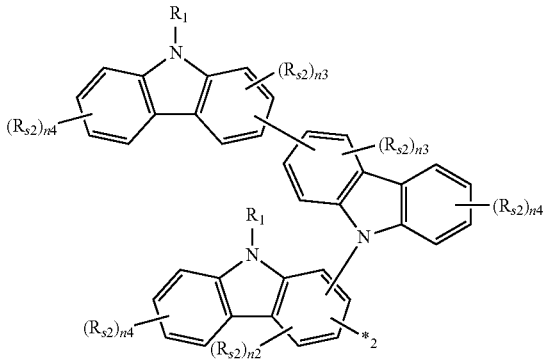
(4f-4)
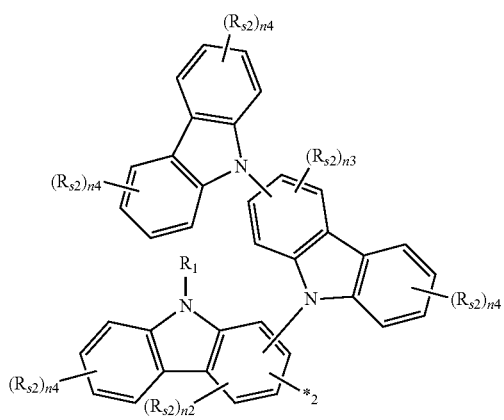
(4g-1)
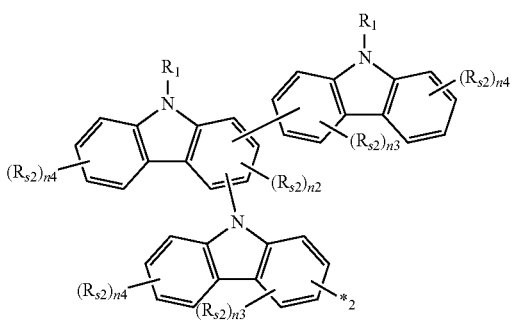
(4g-2)
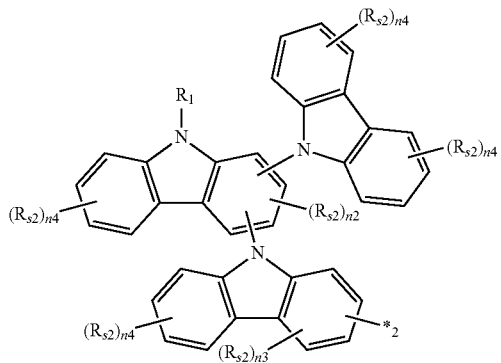
(4g-3)
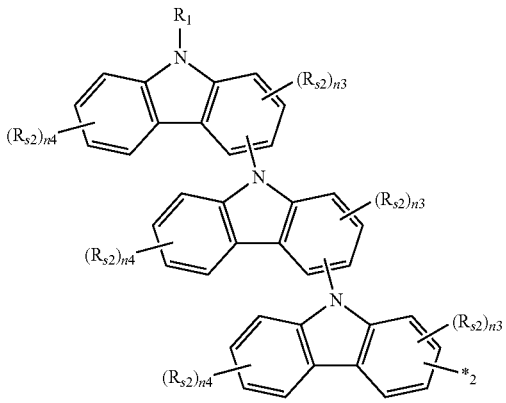
(4g-4)
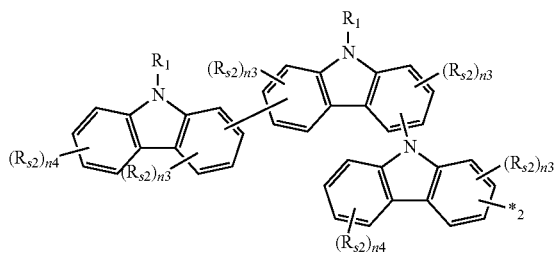
(4g-5)
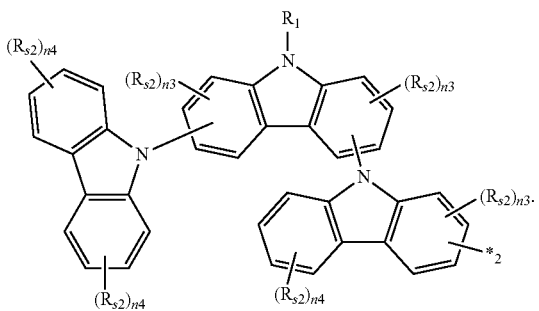

In Formulae (4a-1) to (4a-9), (4b-1) to (4b-4), (4c-1) to (4c-10), (4d-1) to (4d-6), (4e-1) to (4e-8), (4f-1) to (4f-4), and (4g-1) to (4g-5), 2 indicates a binding site to $L_3$ in Formula (2-1) or (2-2), each occurrence of n1 may independently be 0 or 1, and $R_1(s)$, $R_{S2}(s)$, n4(s), n3(s), and n2(s) may each independently be the same as those described in connection with Formulae (3a) to (3g), each occurrence of $R_1$ may independently be a monovalent alkyl group having 1 to 20 carbon atoms and being unsubstituted or substituted with a substituent other than a carbazole group, a monovalent aromatic hydrocarbon group having 6 to 30 carbon atoms unsubstituted or substituted with a substituent other than a carbazole group, or a monovalent aromatic heterocyclic group (other than a carbazole group) having 5 to 30 ring-forming atoms and being unsubstituted or substituted with a substituent other than a carbazole group, each occurrence of $R_{S2}$ may independently be a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group (other than a carbazole group) having 5 to 30 ring-forming atoms, each occurrence of n4 may independently be 0, 1, 2, 3, or 4, each occurrence of n3 may independently be 0, 1, 2, or 3, and each occurrence of n2 (may each independently be 0, 1, or 2.

Here, it is preferable that n4(s), n3(s), n2(s), and n1(s) may each independently be 0, and it is more preferable that n4(s), n3(s), n2(s), and n1(s) may all be 0. That is, it is preferable that $R_{S2}(s)$ corresponding to each n4, each n3, each n2, and each n1 do not exist.

Furthermore, as described above, in Formulae (3a) to (3g), (3a-1) to (3a-6), (3b-1), (3b-2), (3c-1) to (3c-6), (3d-1), (3d-2), (3g-1), (3g-2), (4a-1) to (4a-9), (4b-1) to (4b-4), (4c-1) to (4c-10), (4d-1) to (4d-6), (4e-1) to (4e-8), (4f-1) to (4f-4), and (4g-1) to (4g-5), a more preferable example of $R_1$ is a phenyl group unsubstituted or substituted with a phenyl group. Here, as $R_1$ in in Formulae (3a) to (3g), (3a-1) to (3a-6), (3b-1), (3b-2), (3c-1) to (3c-6), (3d-1), (3d-2), (3g-1), and (3g-2), an unsubstituted phenyl group may be particularly preferable. In addition, as $R_1$ in Formulae (4a-1) to (4a-9), (4b-1) to (4b-4), (4c-1) to (4c-10), (4d-1) to (4d-6), (4e-1) to (4e-8), (4f-1) to (4f-4), and (4g-1) to (4g-5), a phenyl group substituted with a phenyl group may be particularly preferable.

Specific examples of the compound represented by Formula (1) are provided below. However, the present disclosure is not limited to these specific examples:

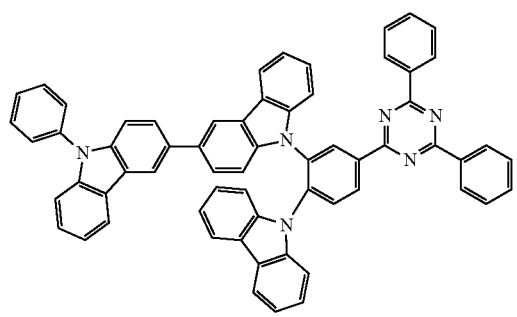

1

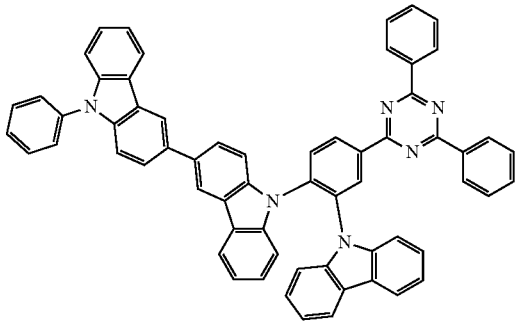

2

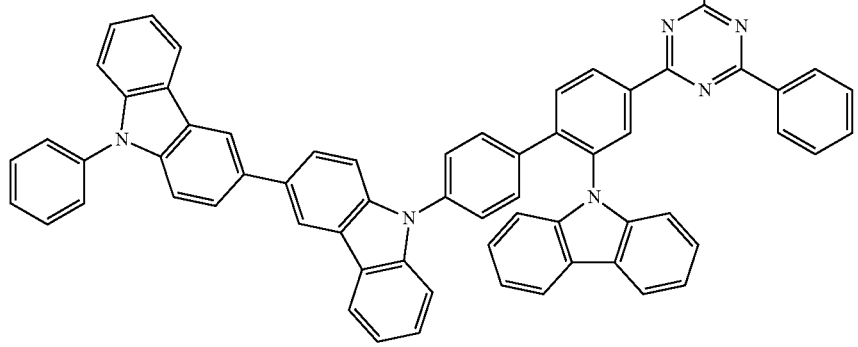

3

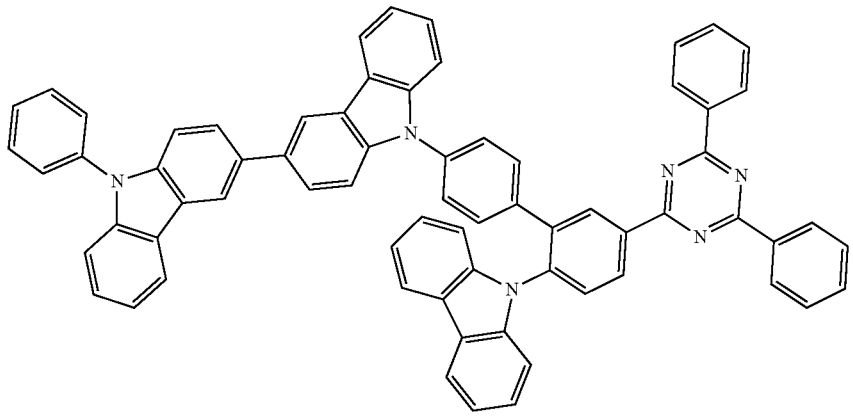
4
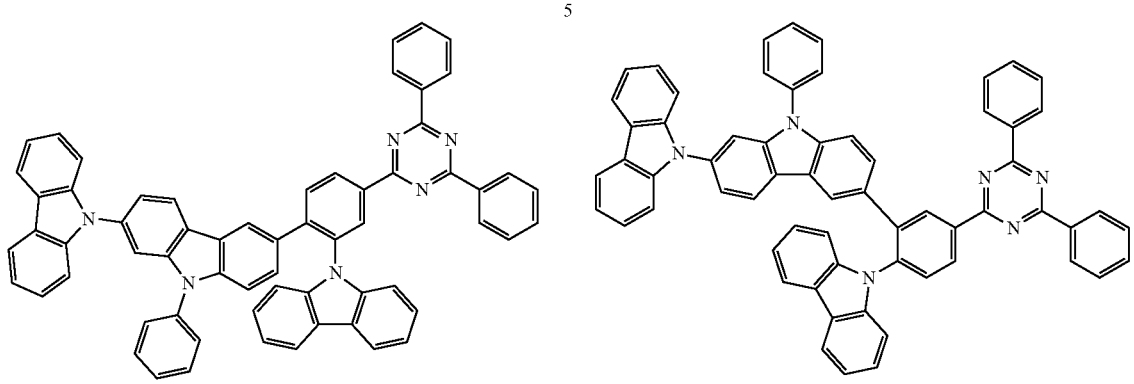
5 6
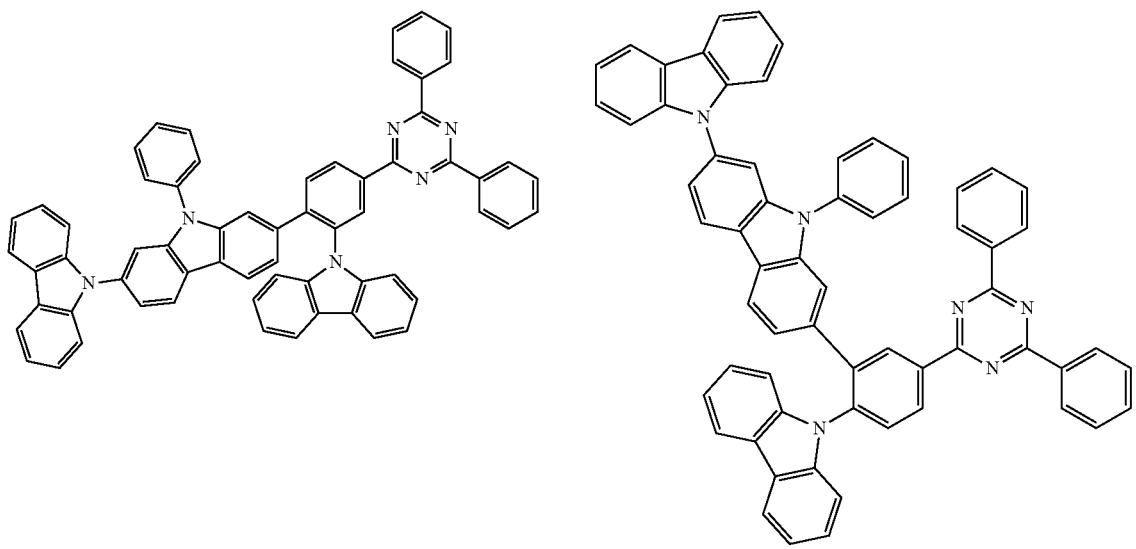
7 8

9
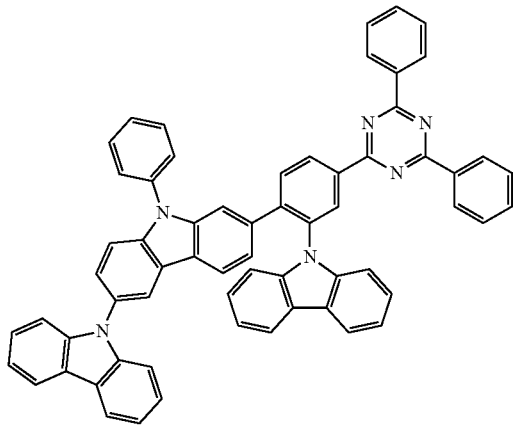
10
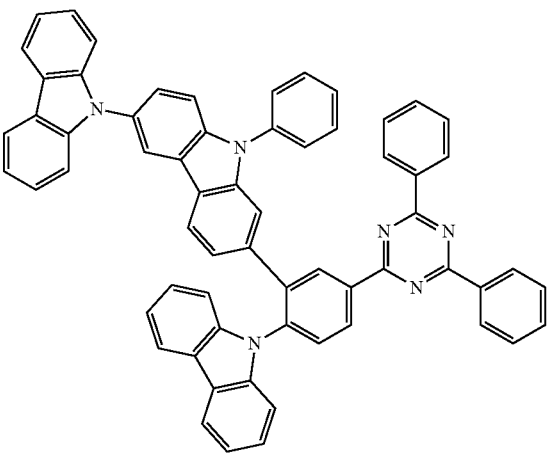
11
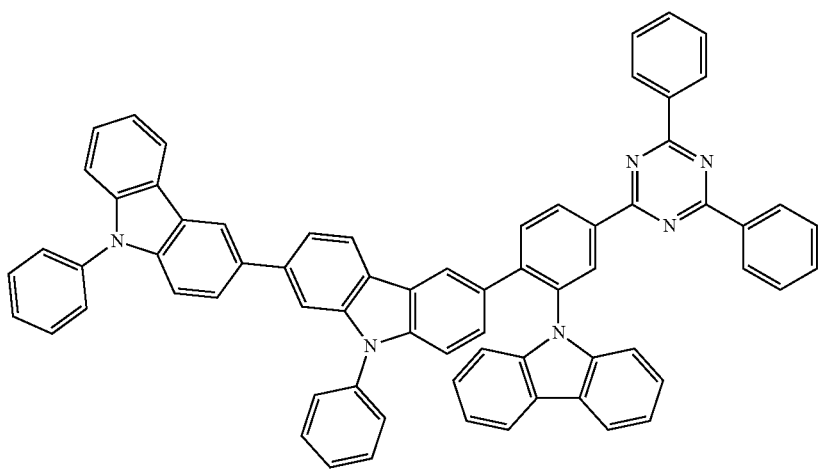
12
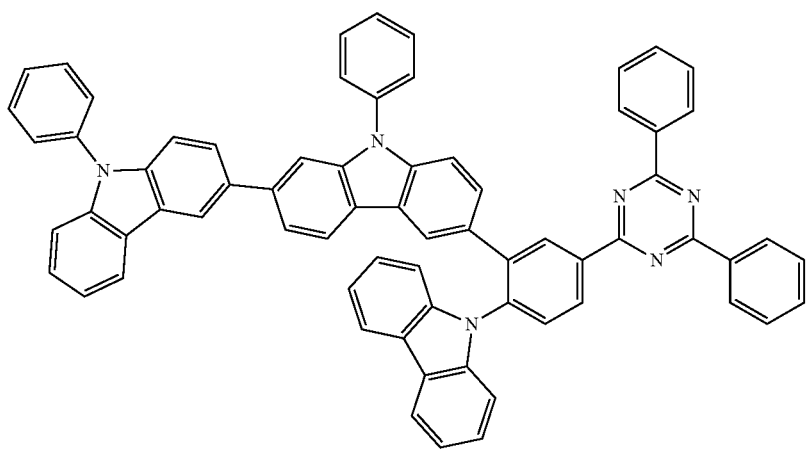

13
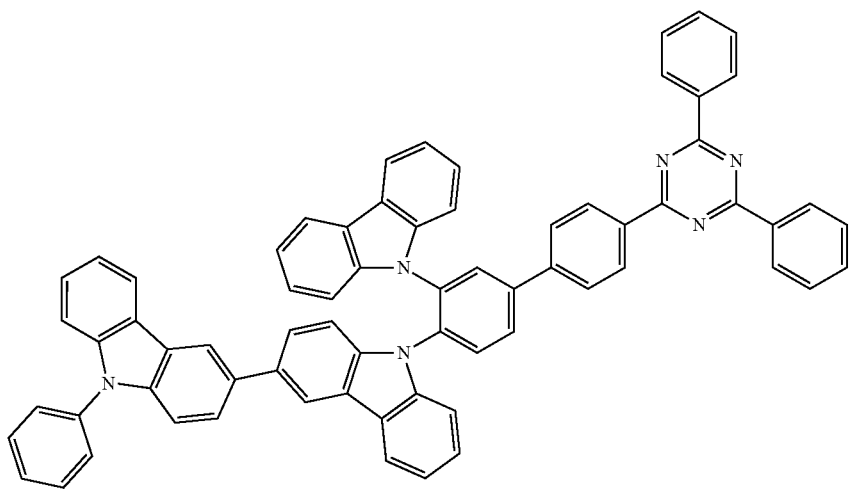
14
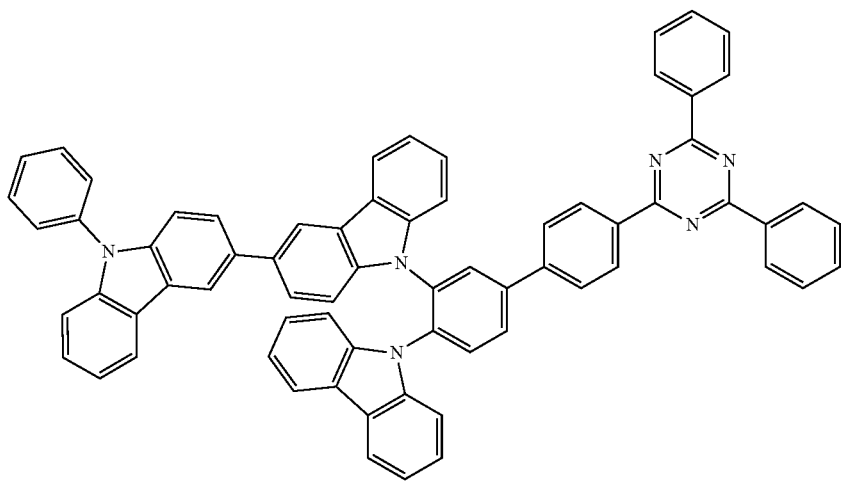
15
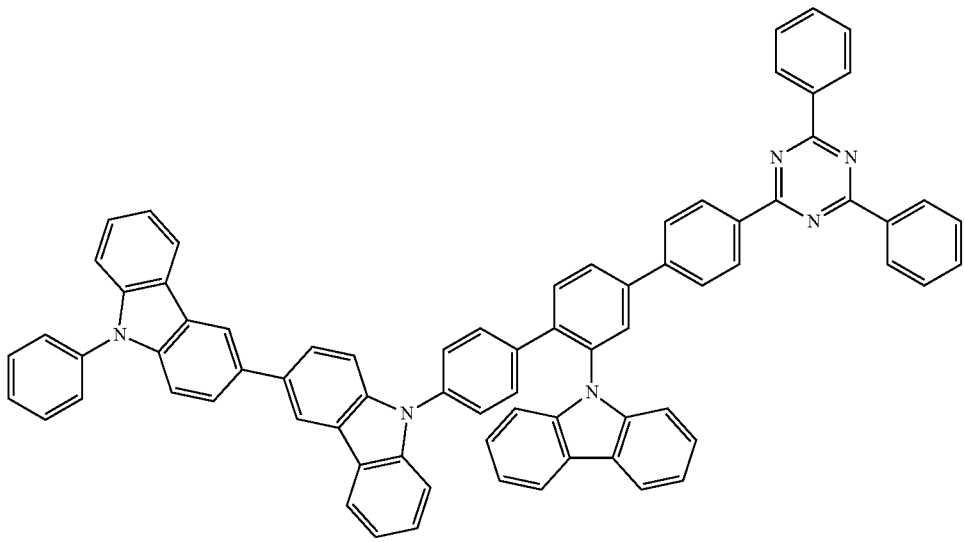

16
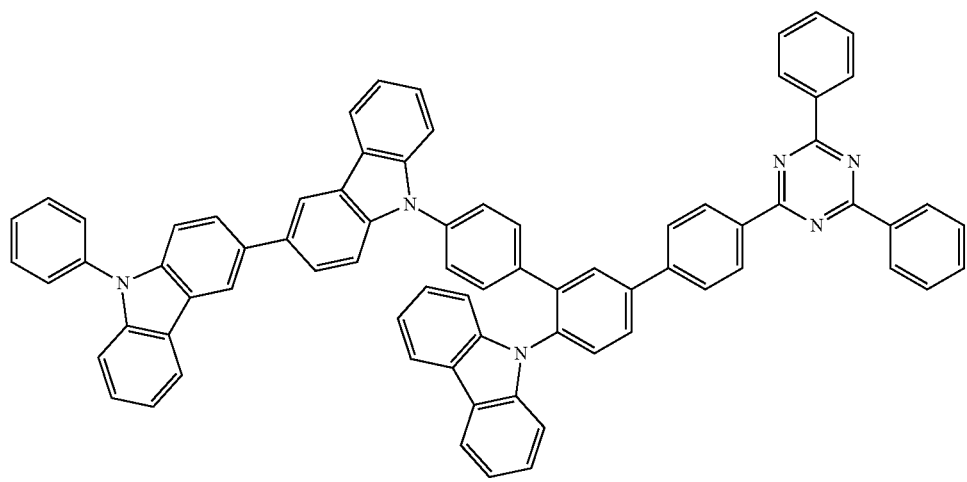
17
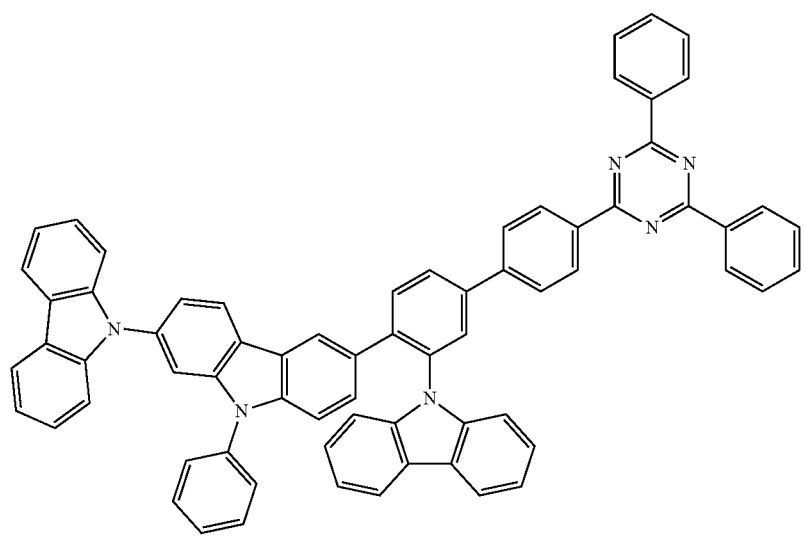
18
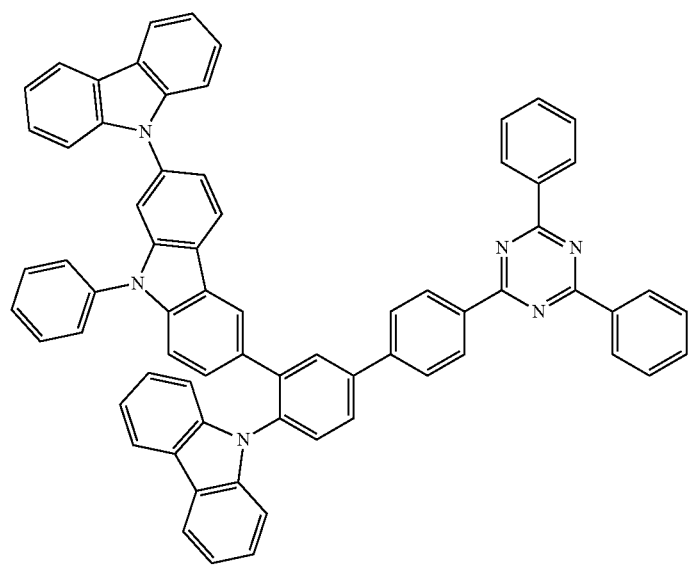

-continued
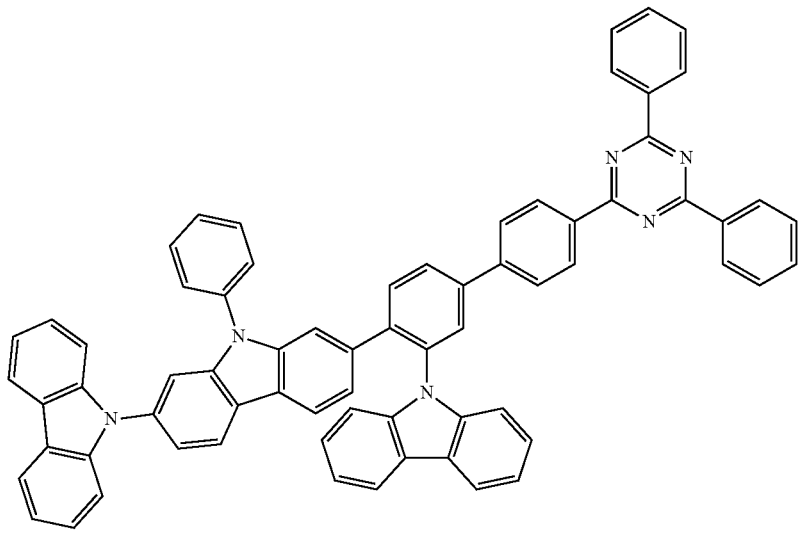
19
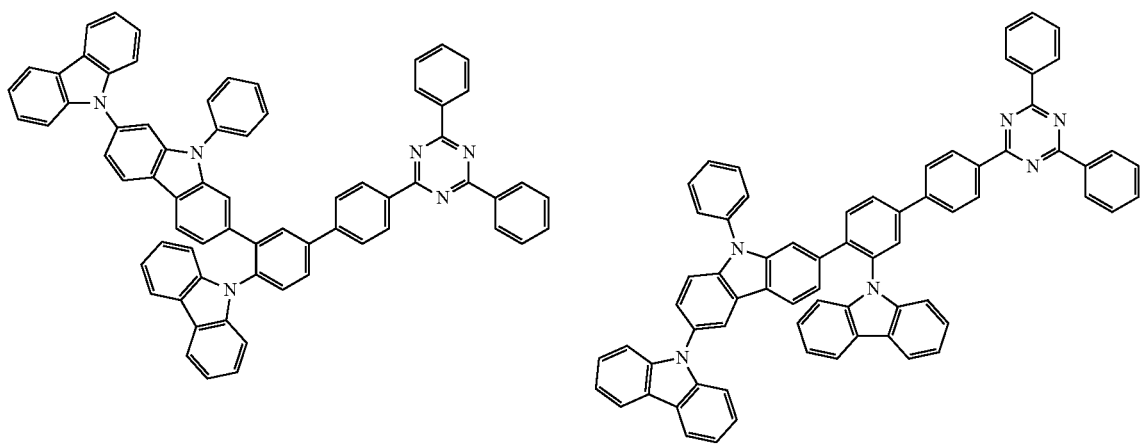
20
21
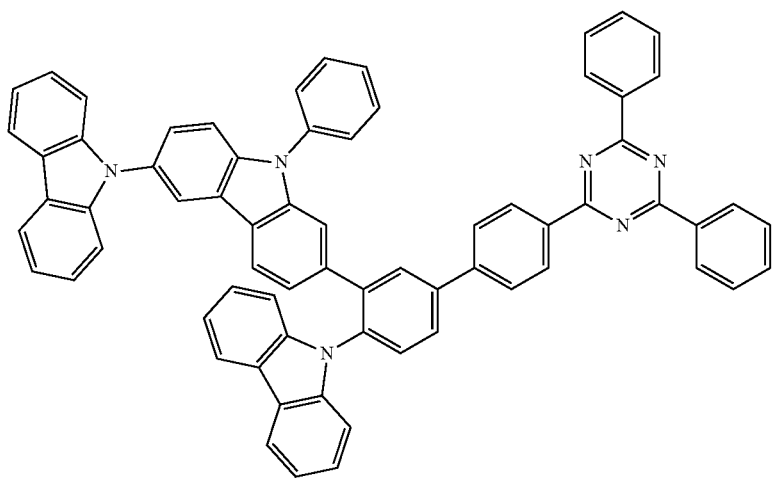
22

23
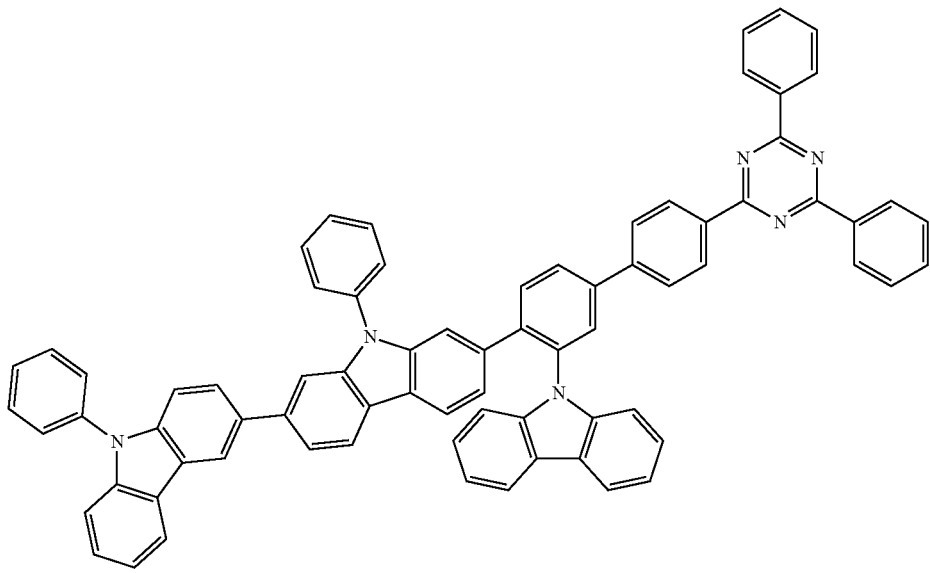
24
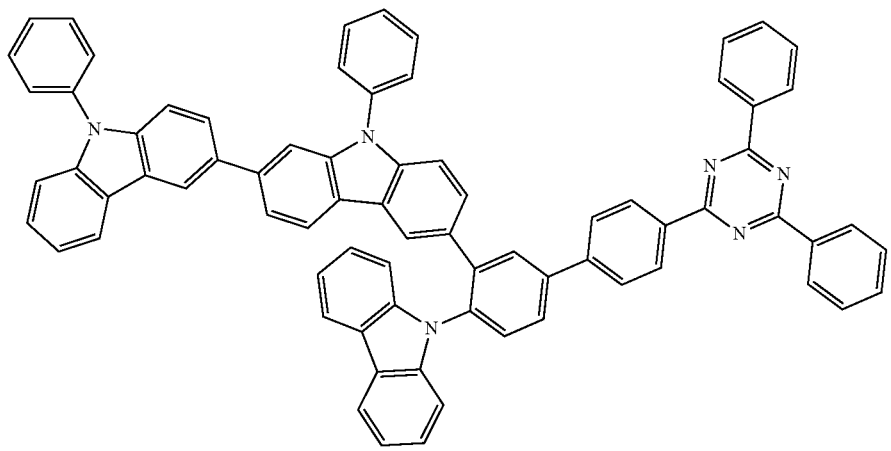
25
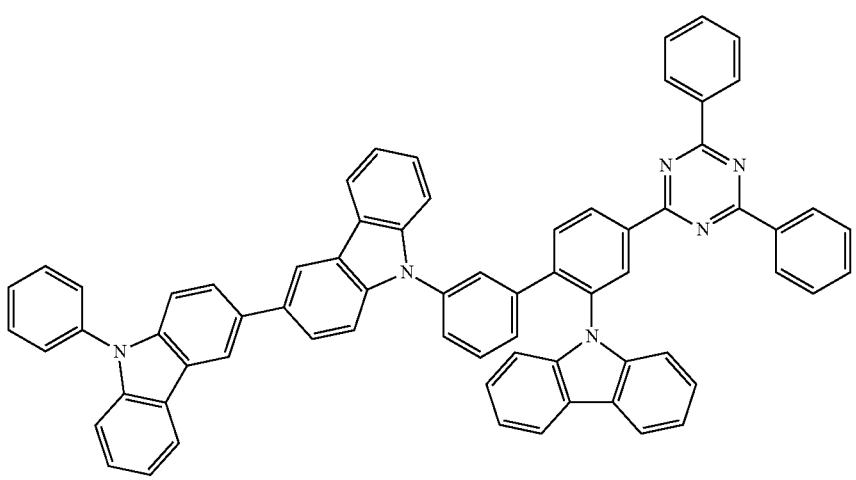

-continued
26
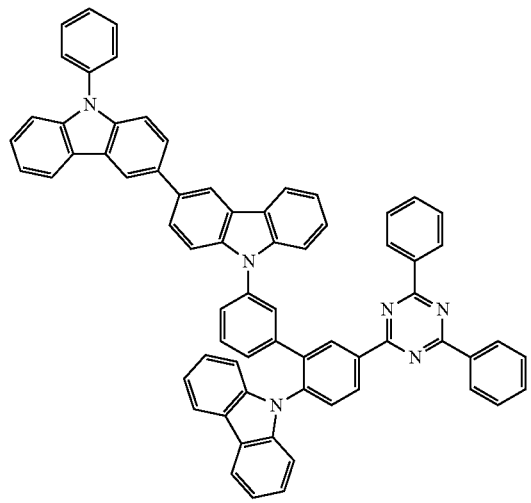
27
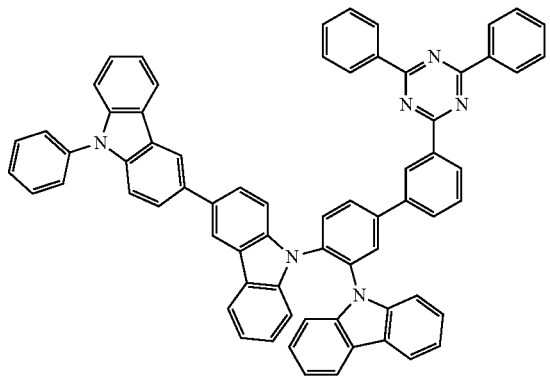
28
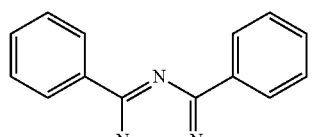
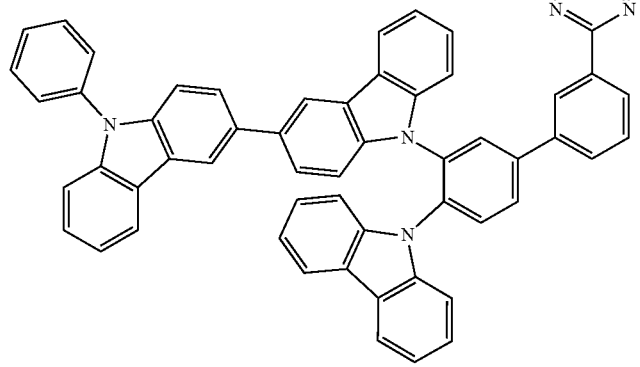
29
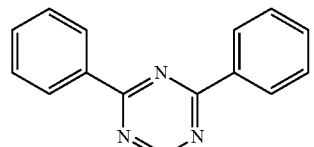
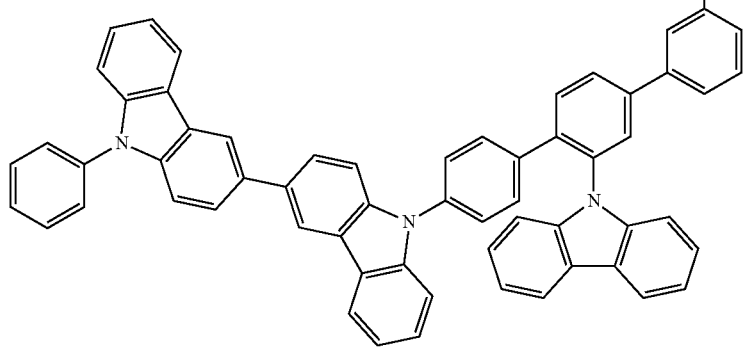

-continued
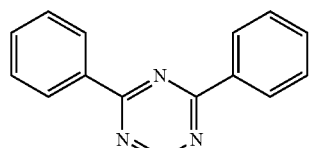
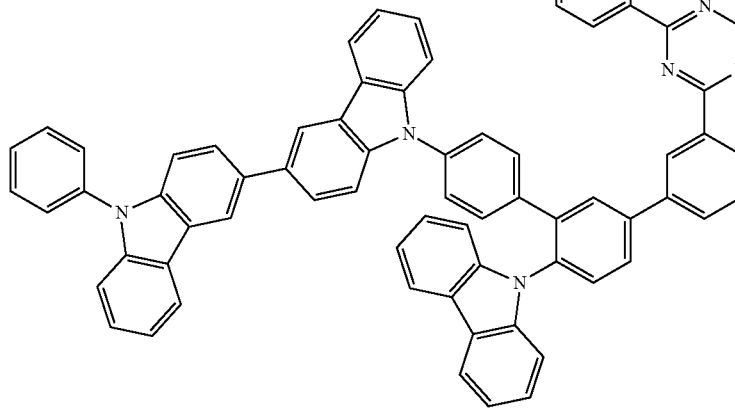
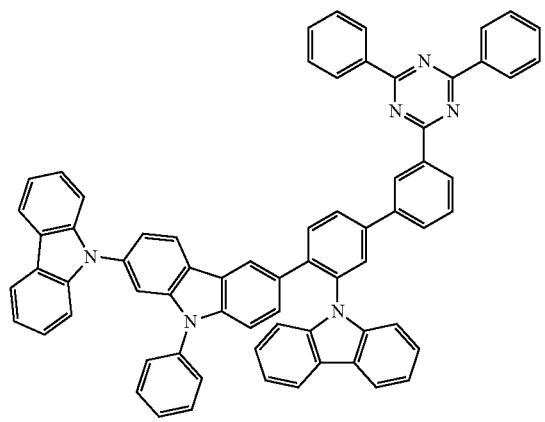
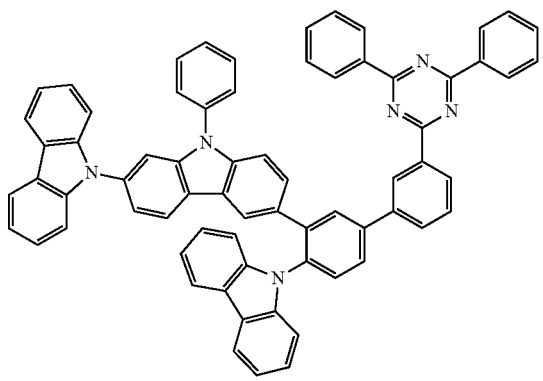
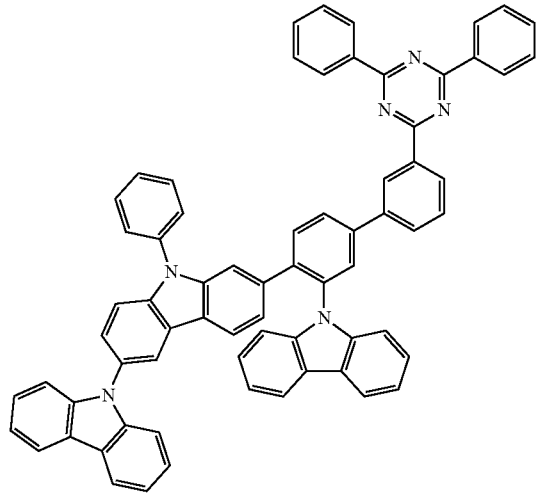
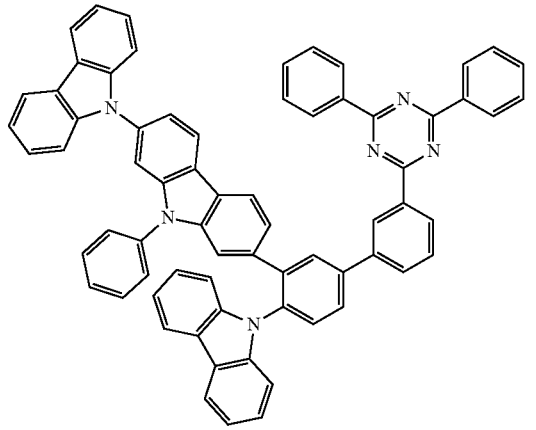

-continued
35
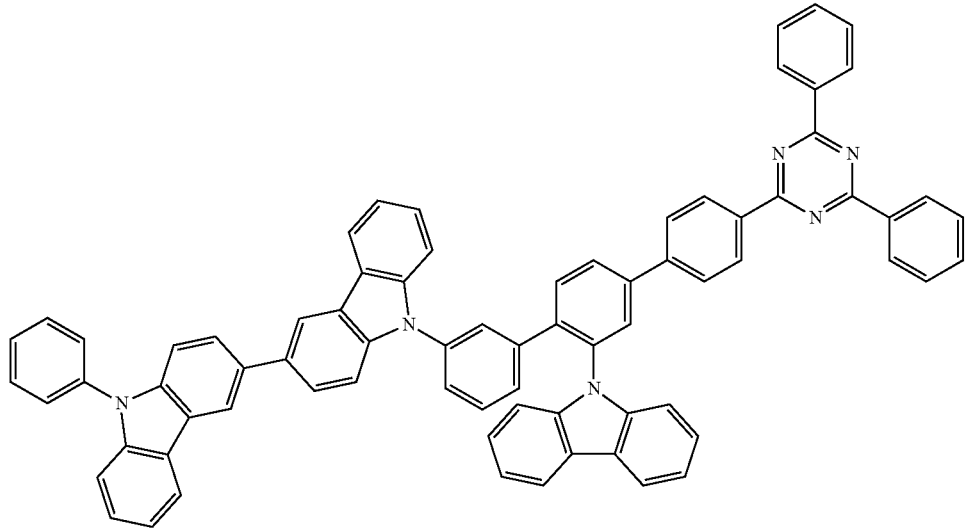
36
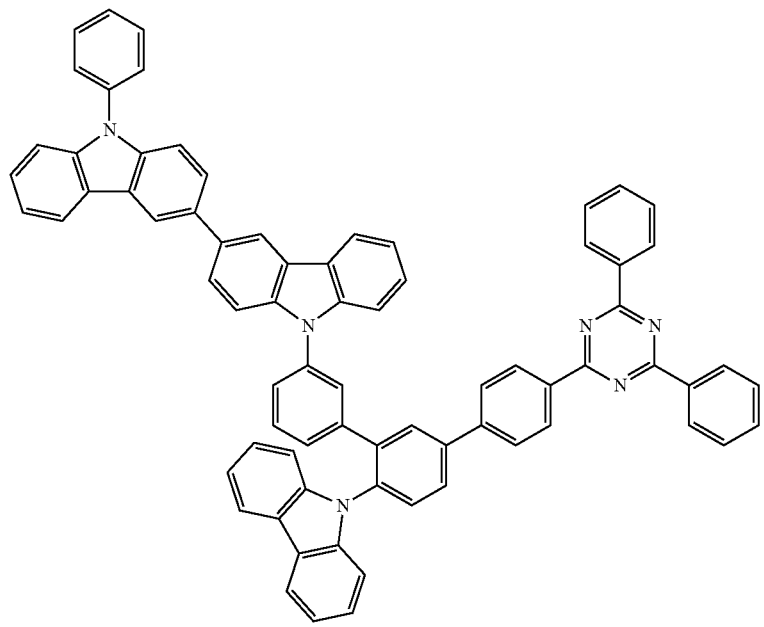
37
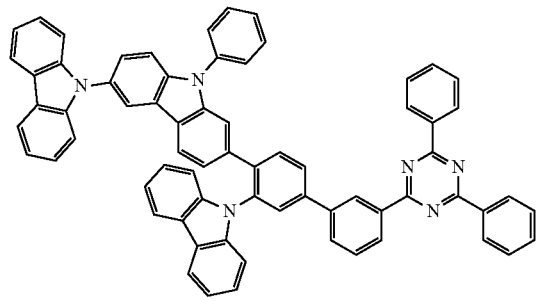
38
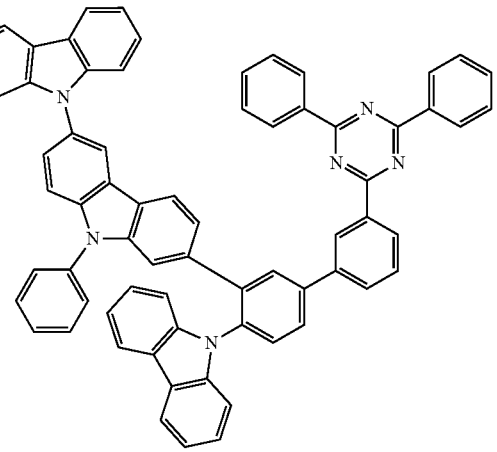

-continued
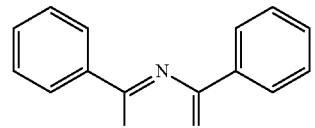
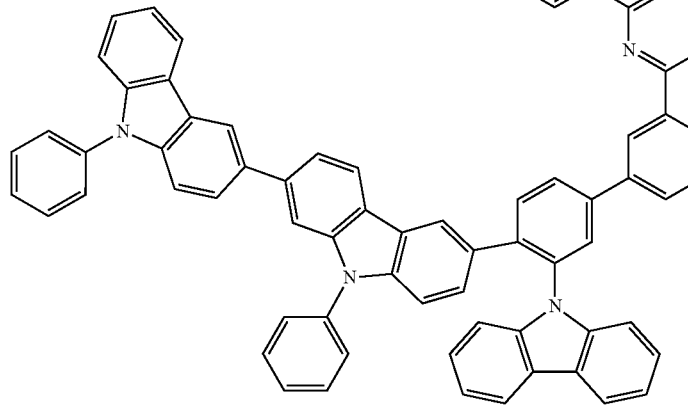
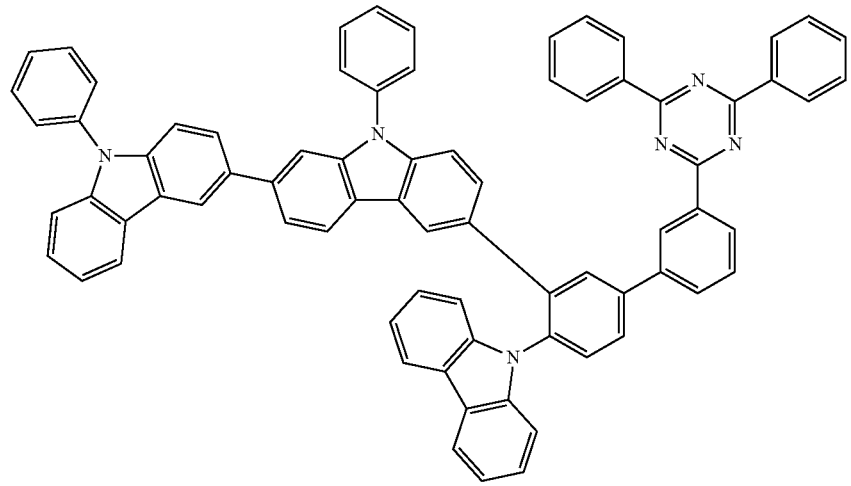
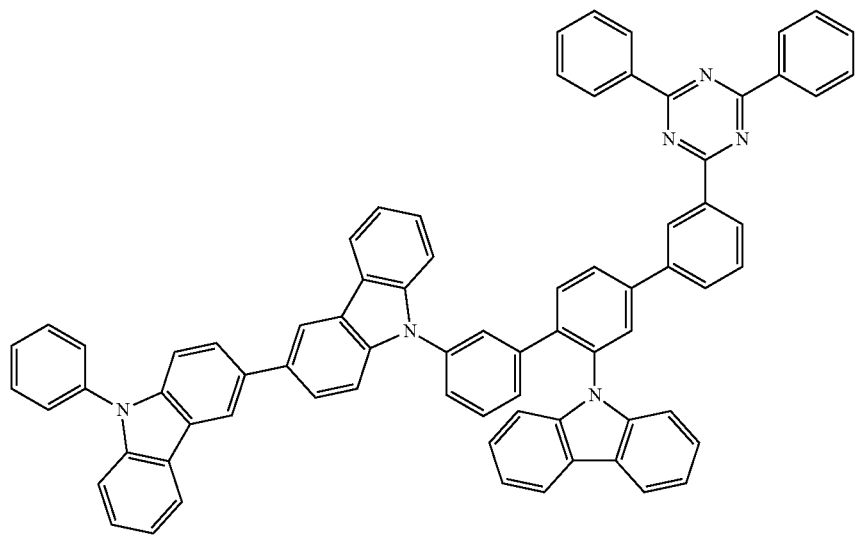

42
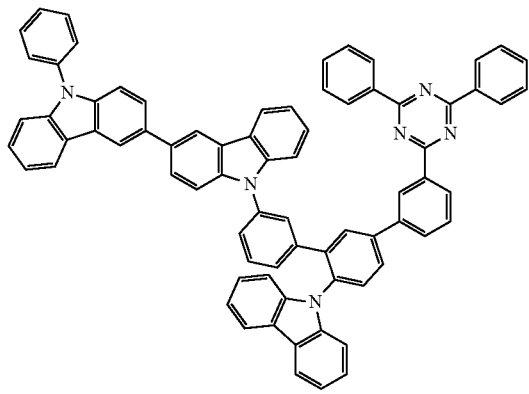
43
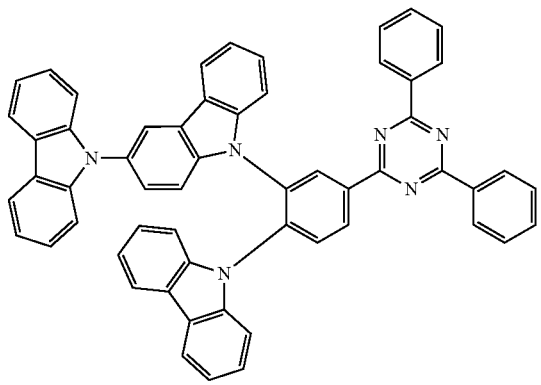
44
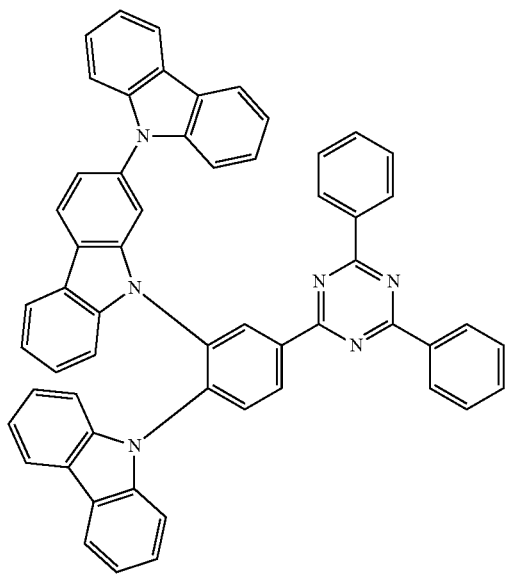
45
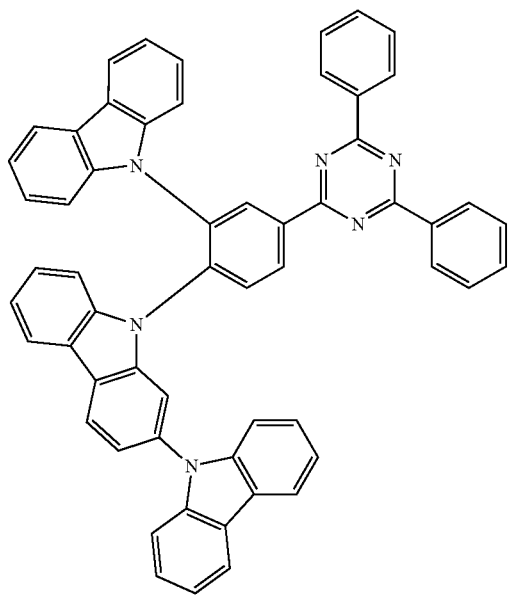
46
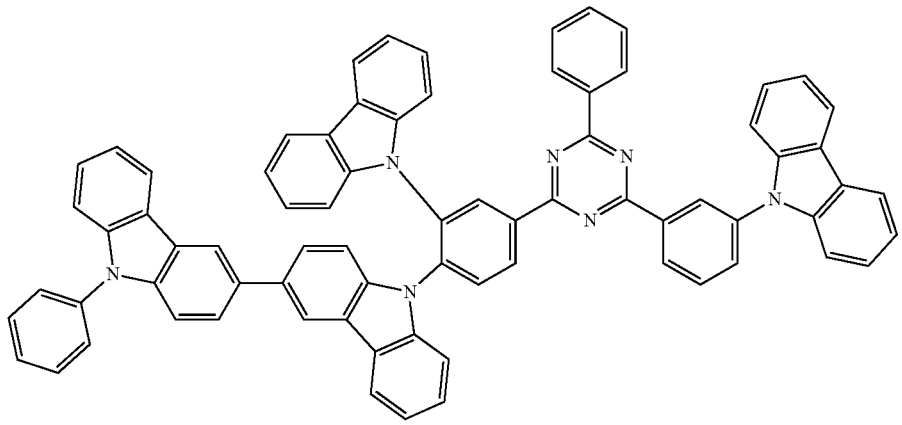

47
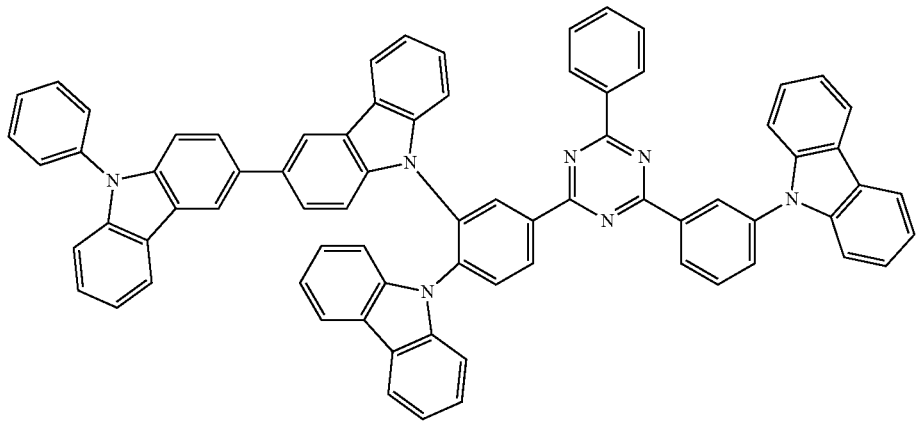
48
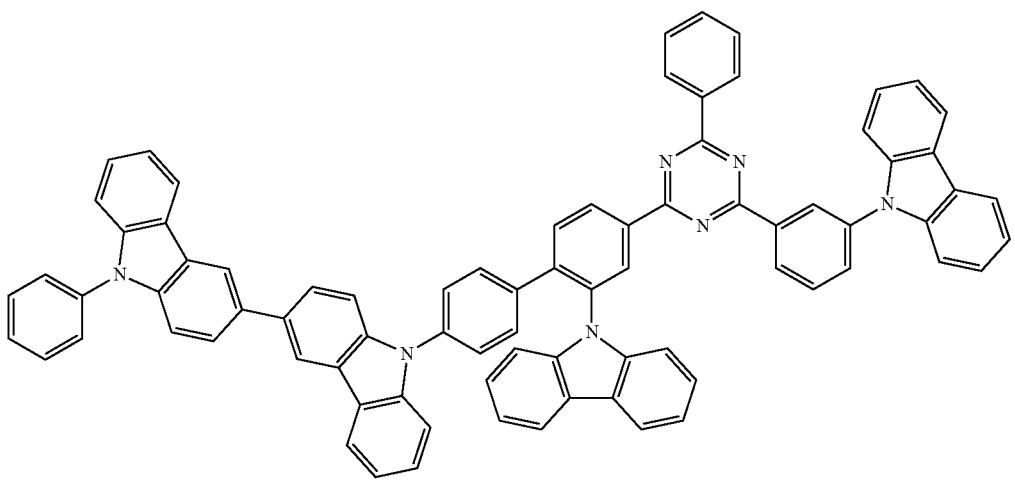
49
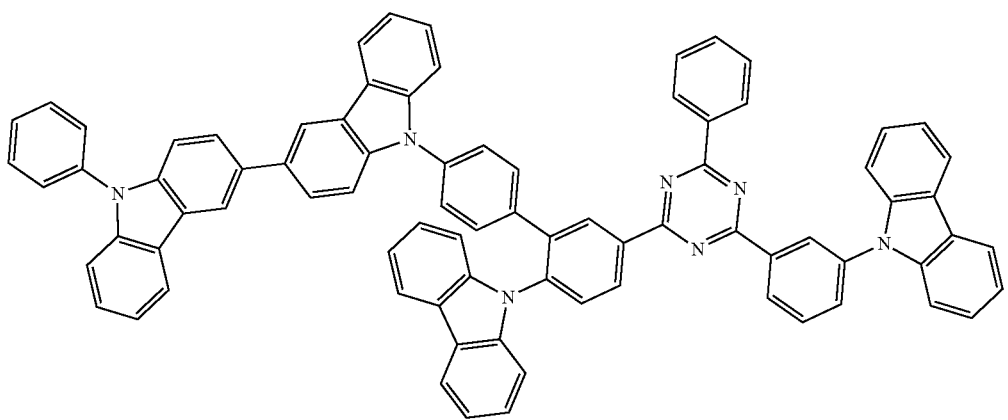

50
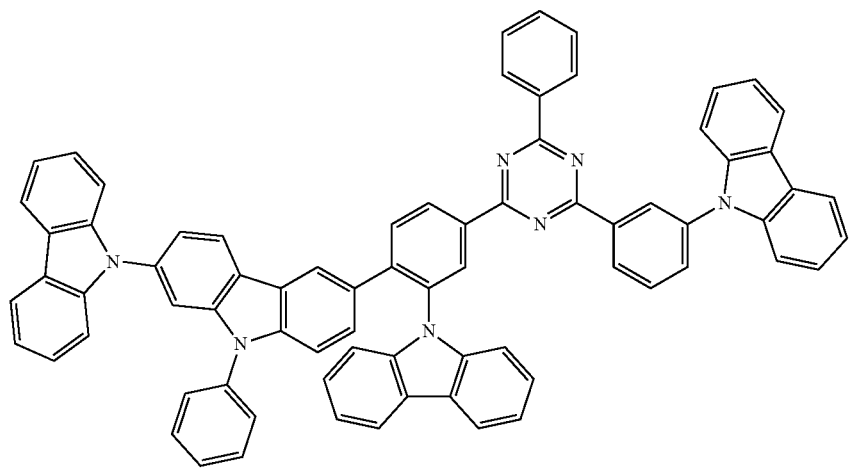
51
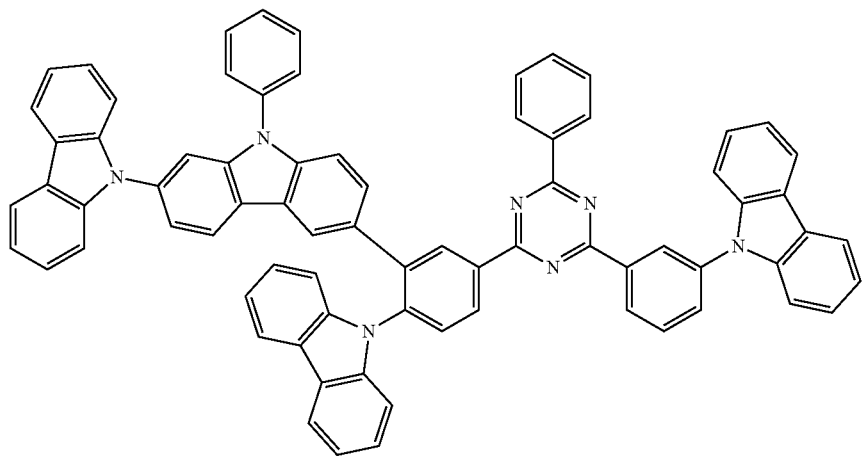
52
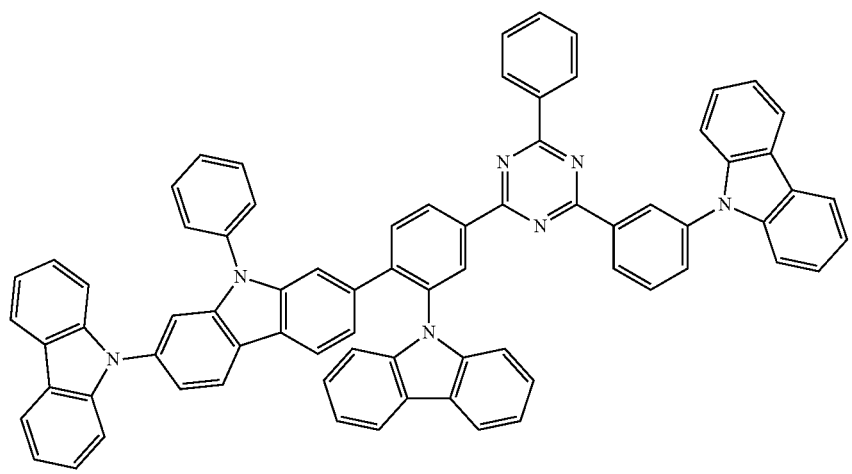

53
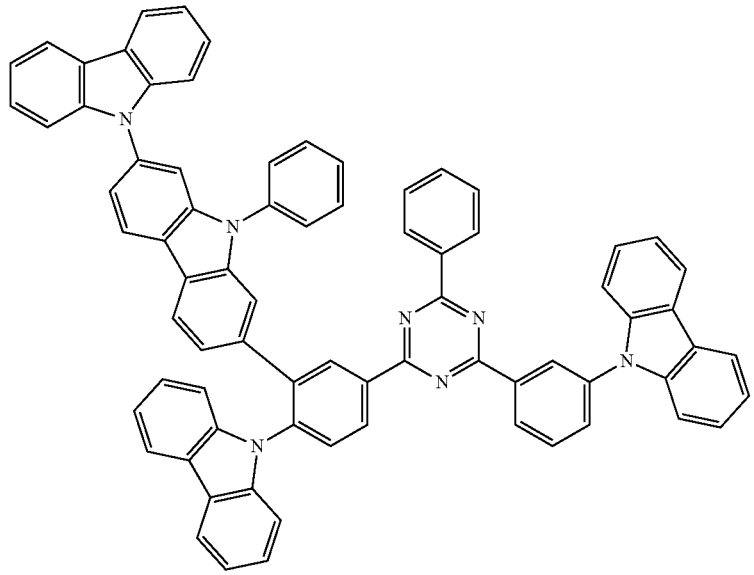
54
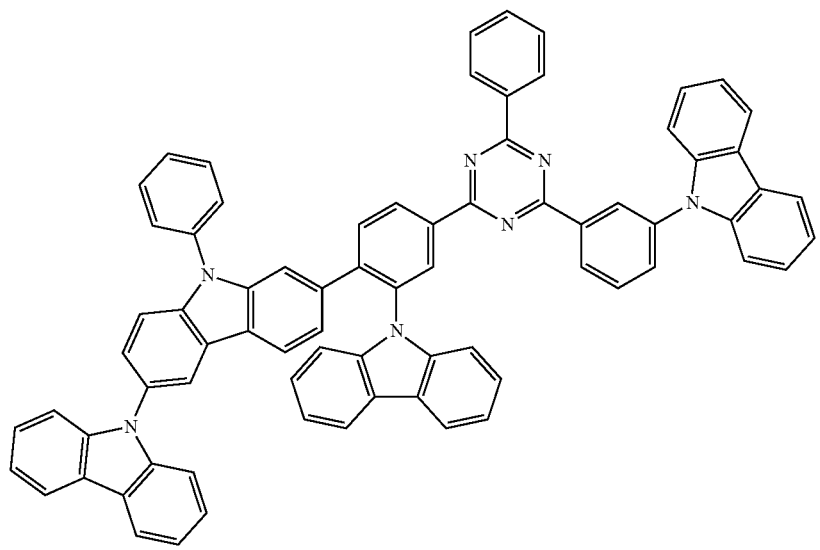
55
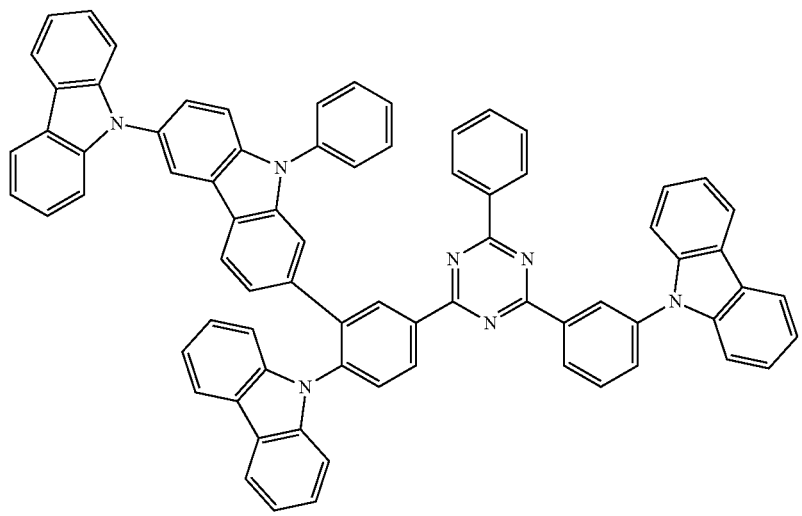

56
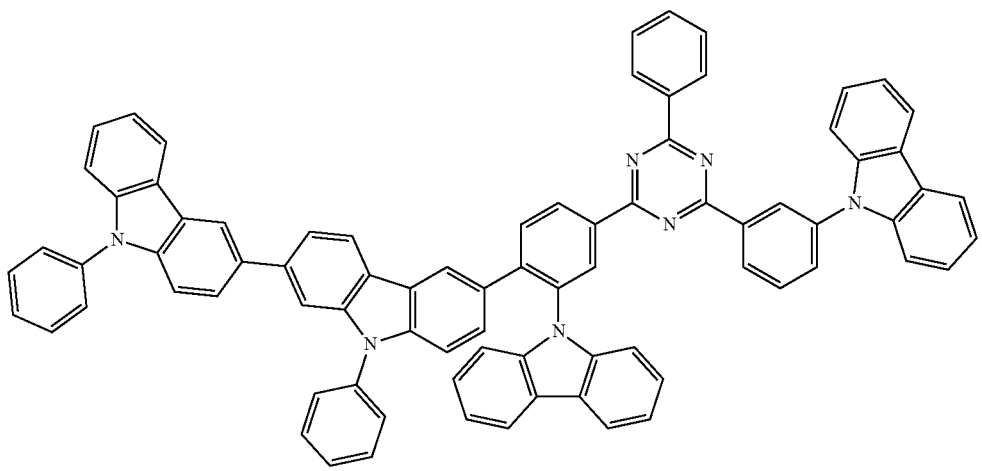
57
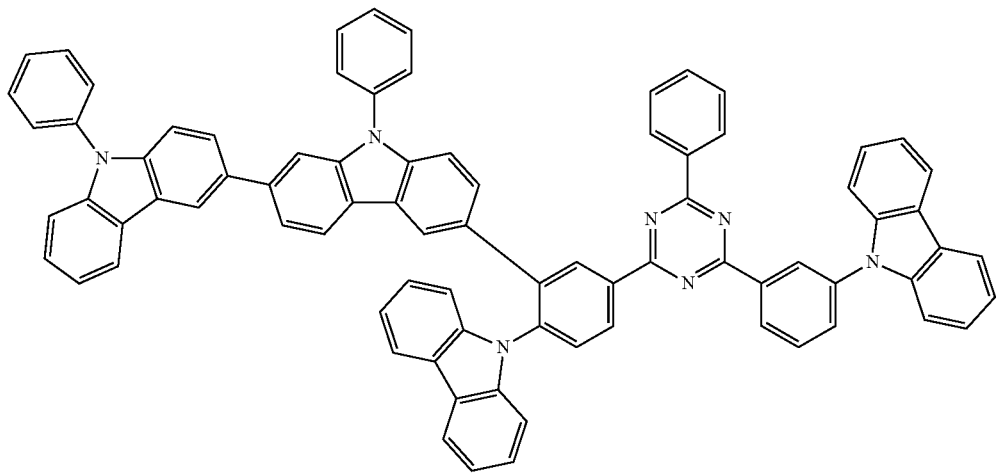
58
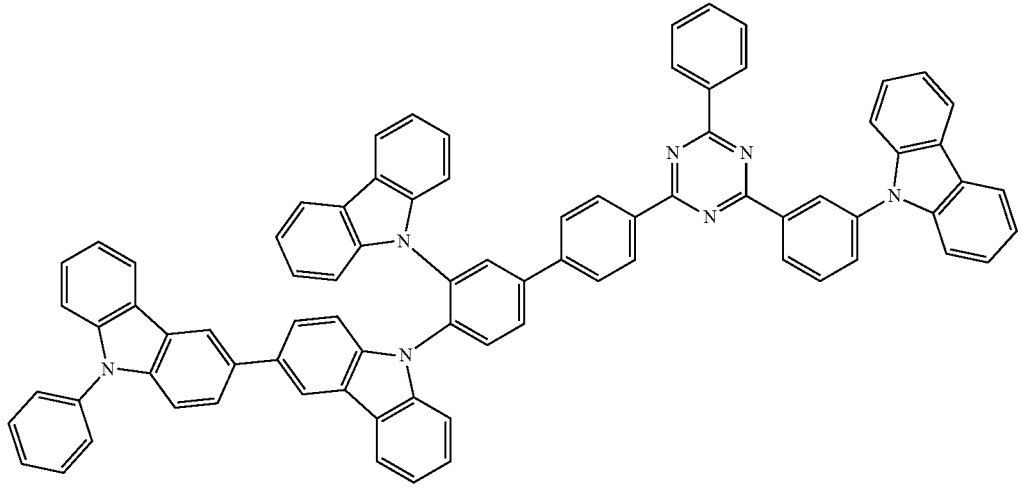

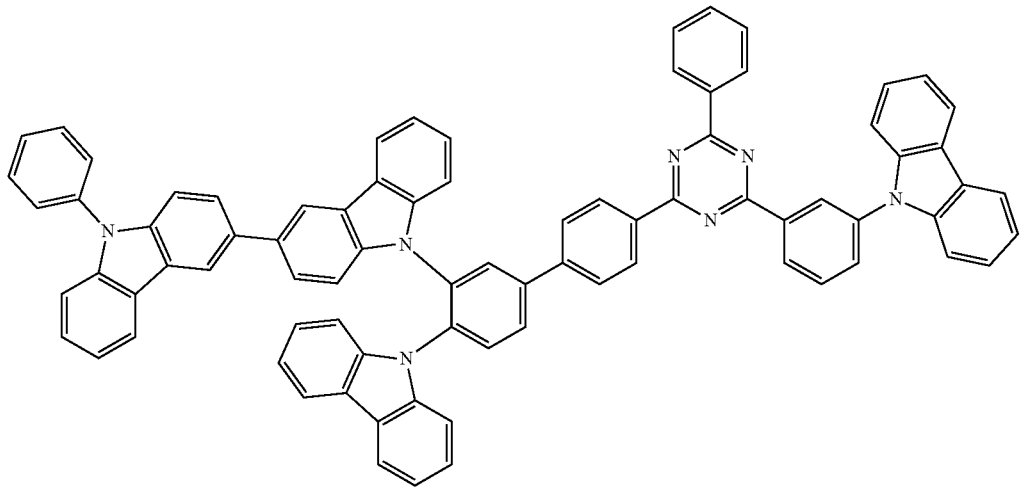
59
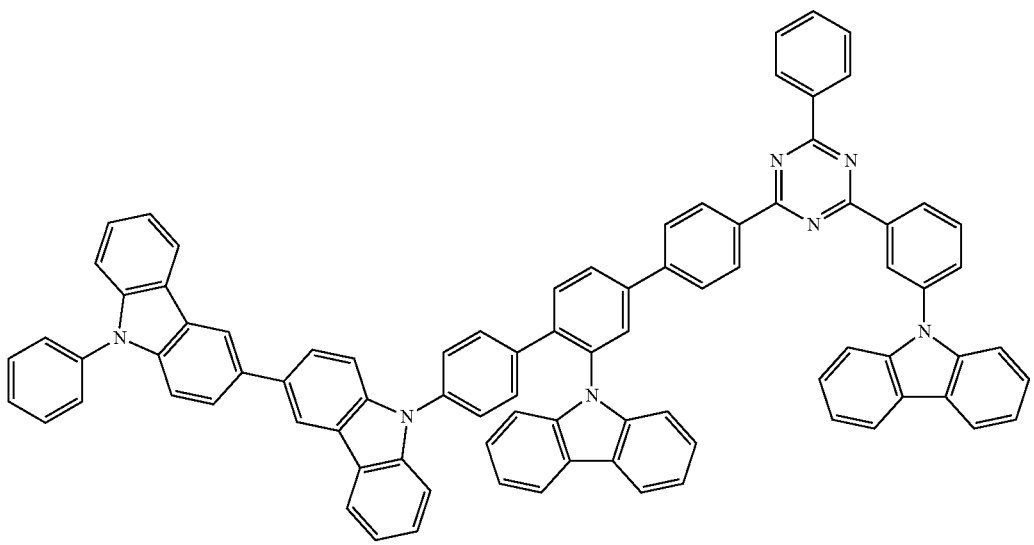
60
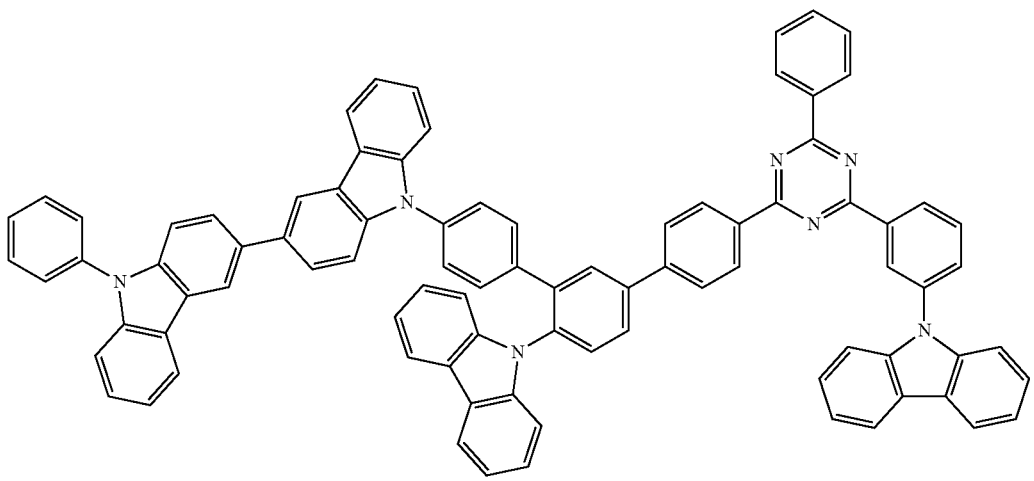
61

-continued
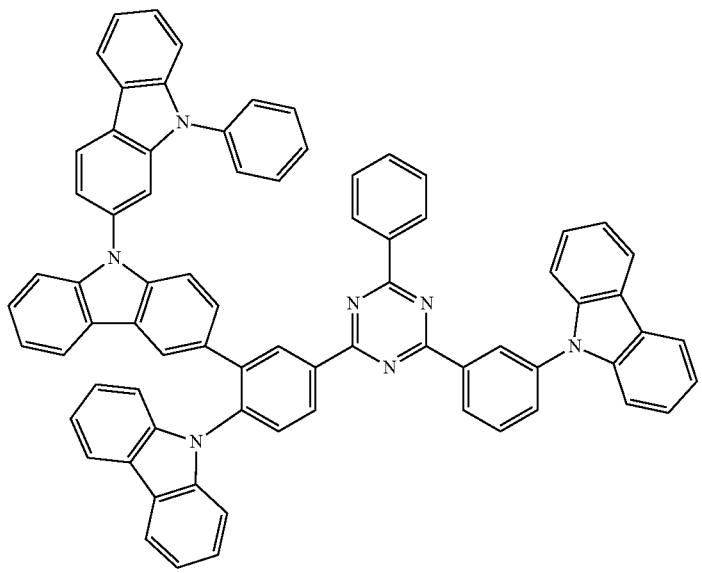
62
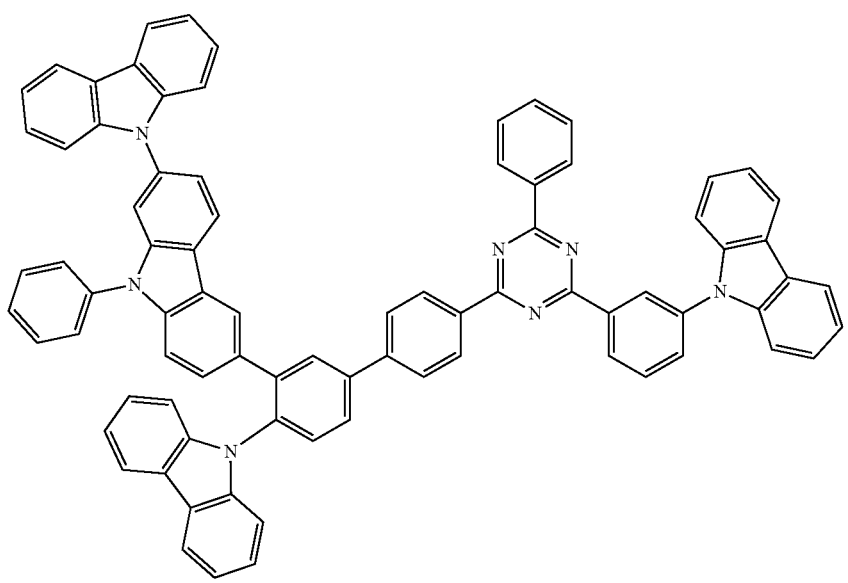
63
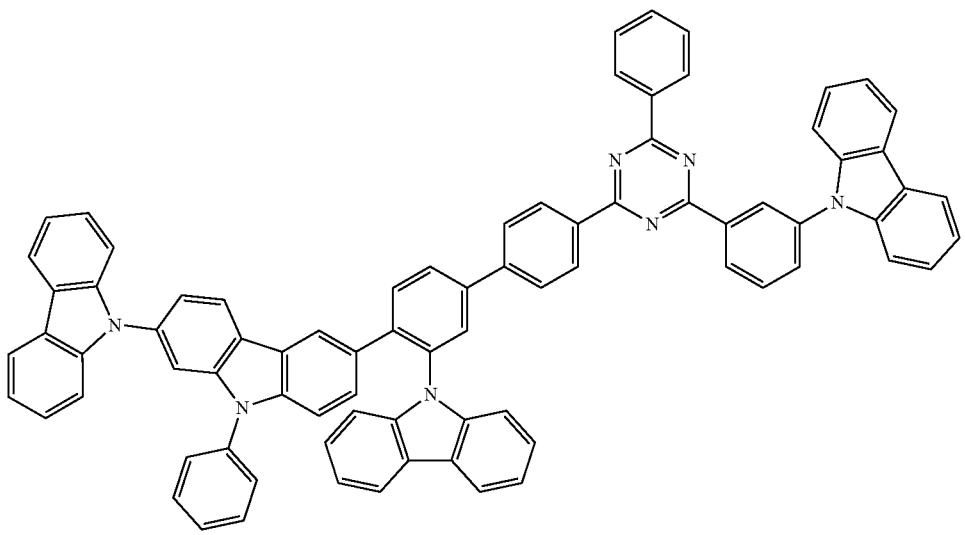
64

65
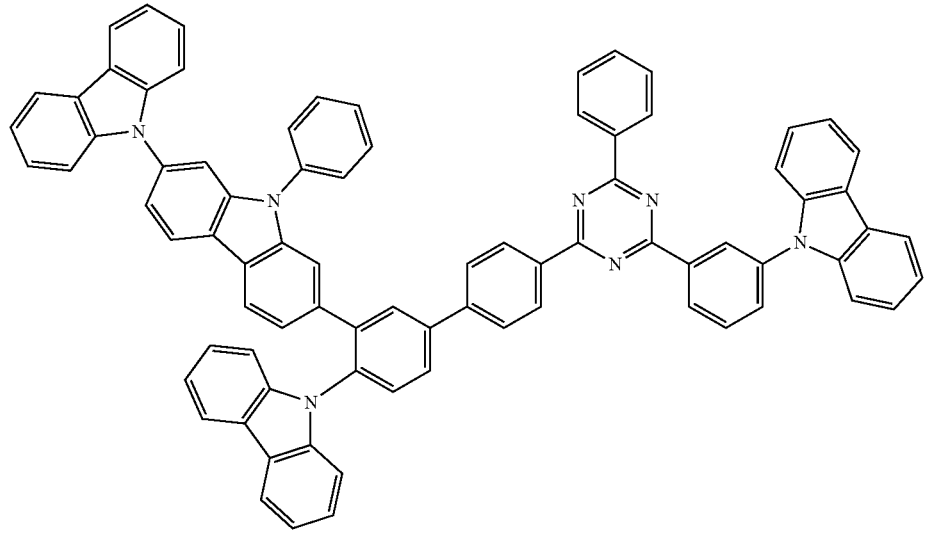
66 67
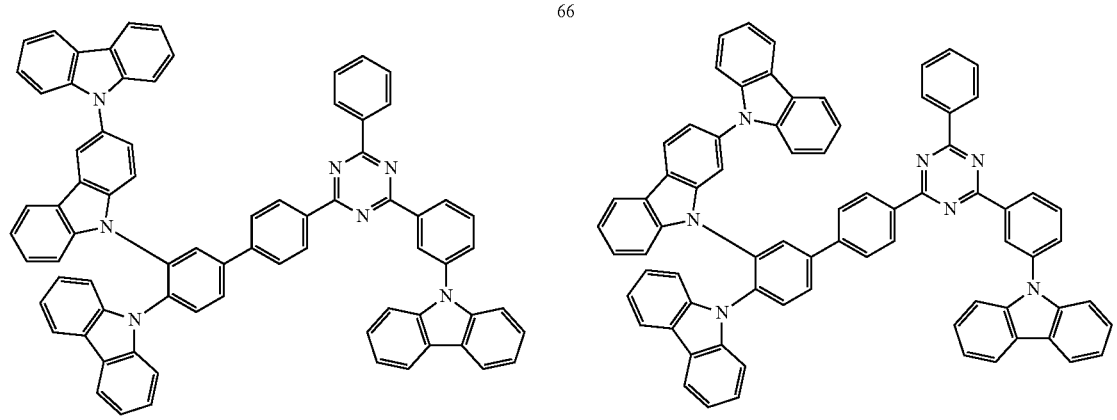
68
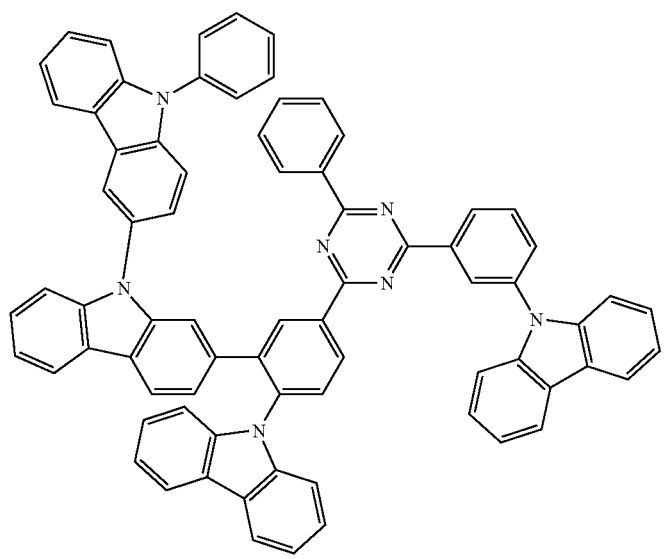

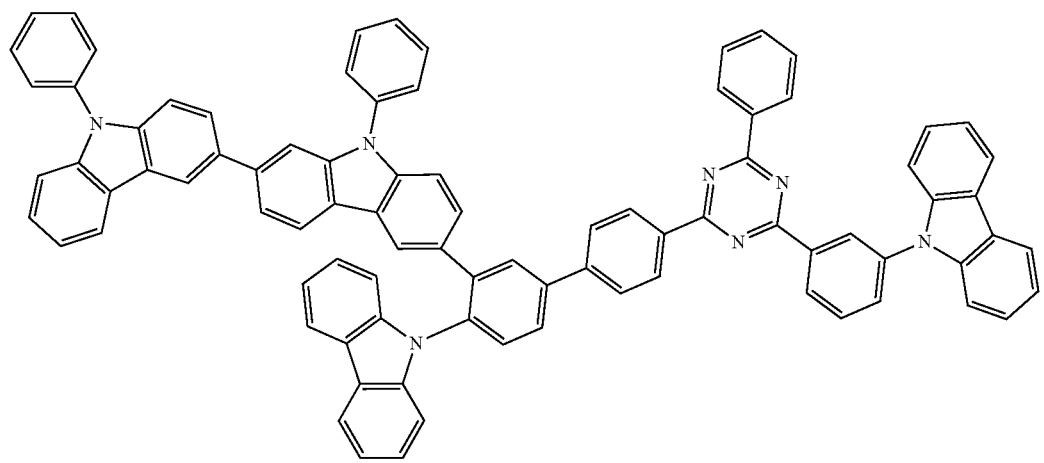
69
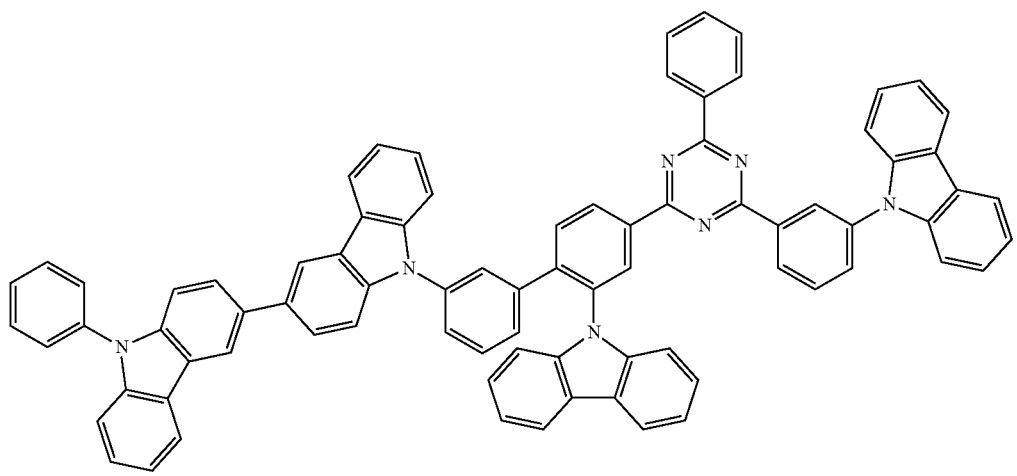
70
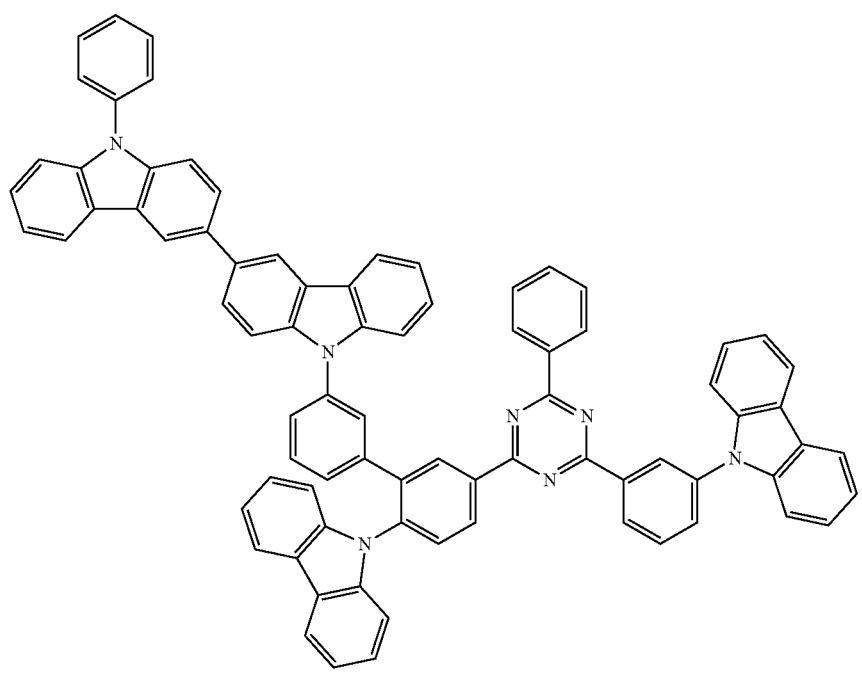
71

72
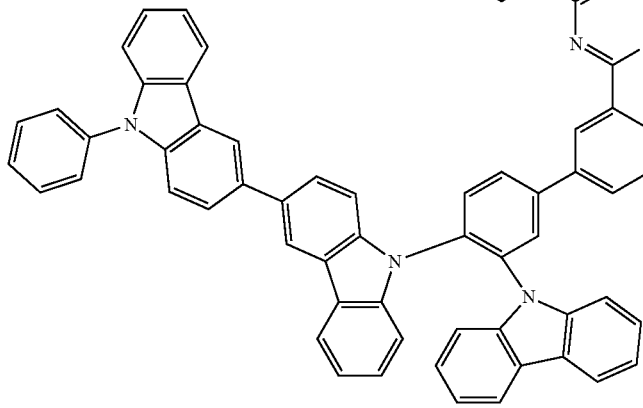
73
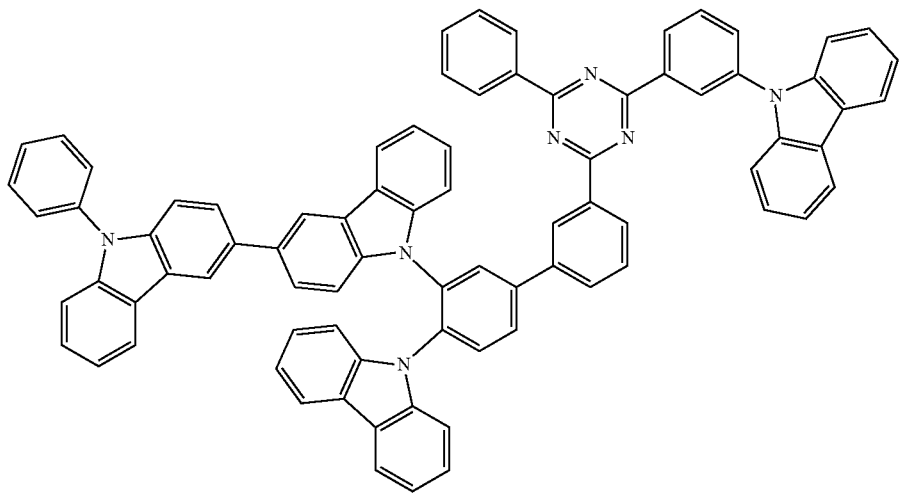
74
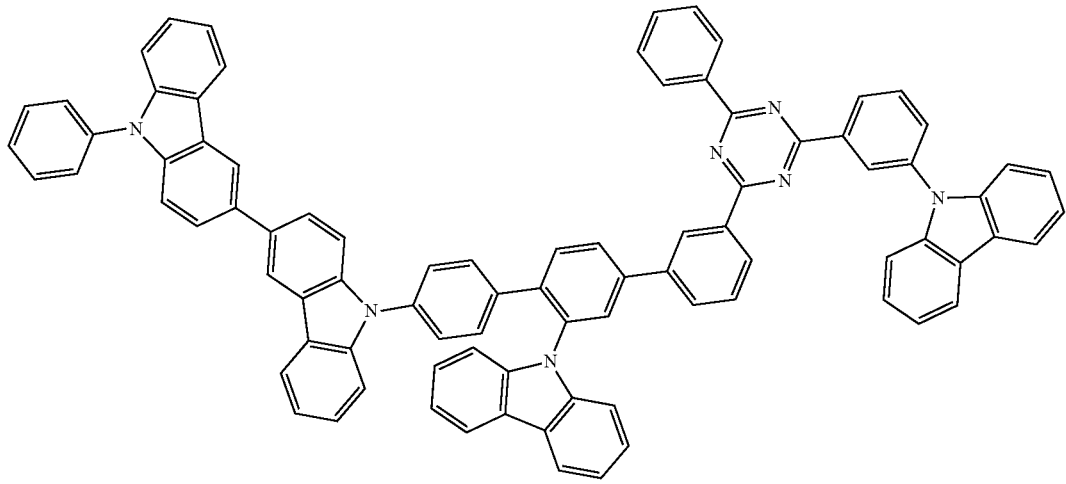

-continued
75
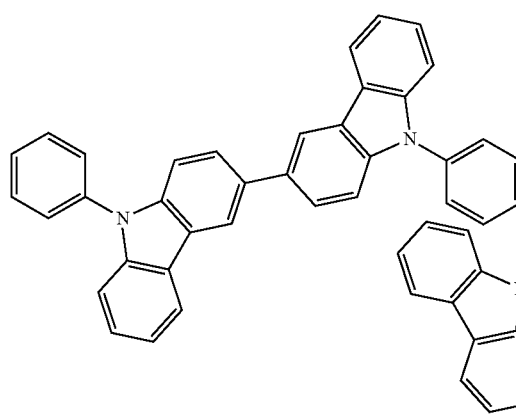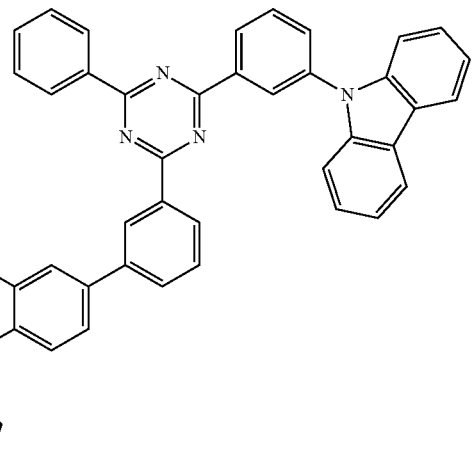
76
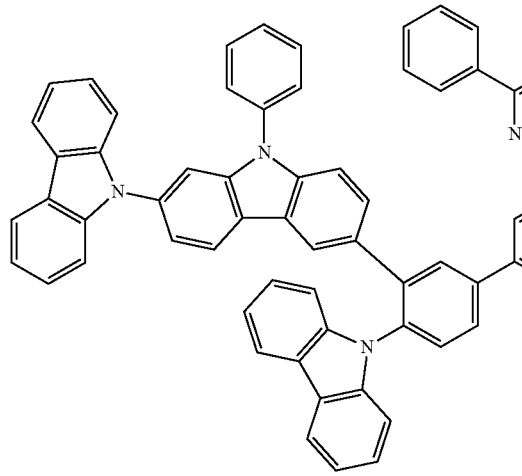
77
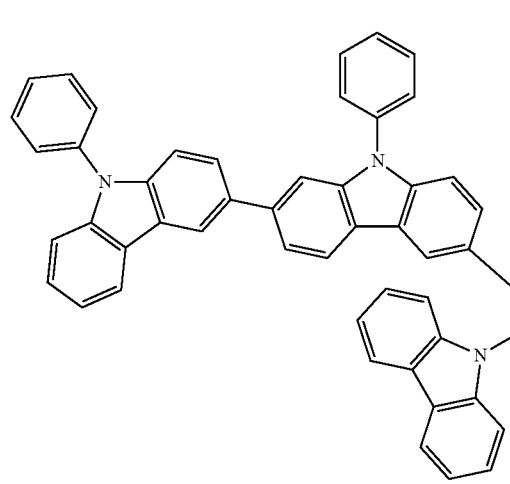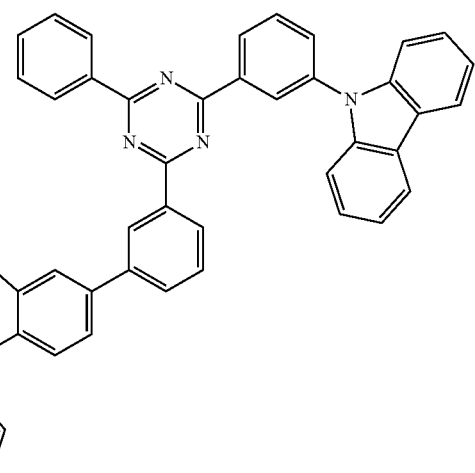

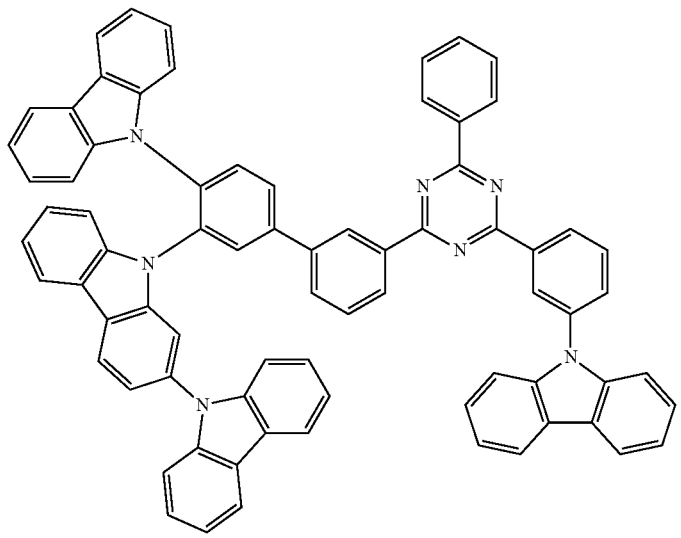
78
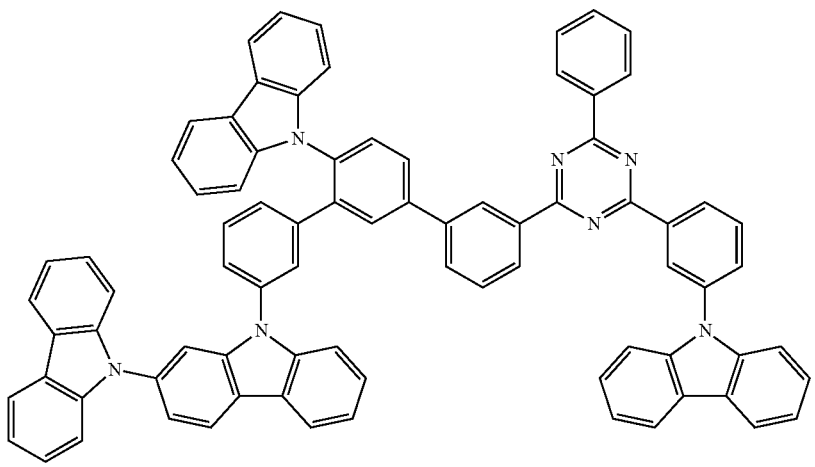
79
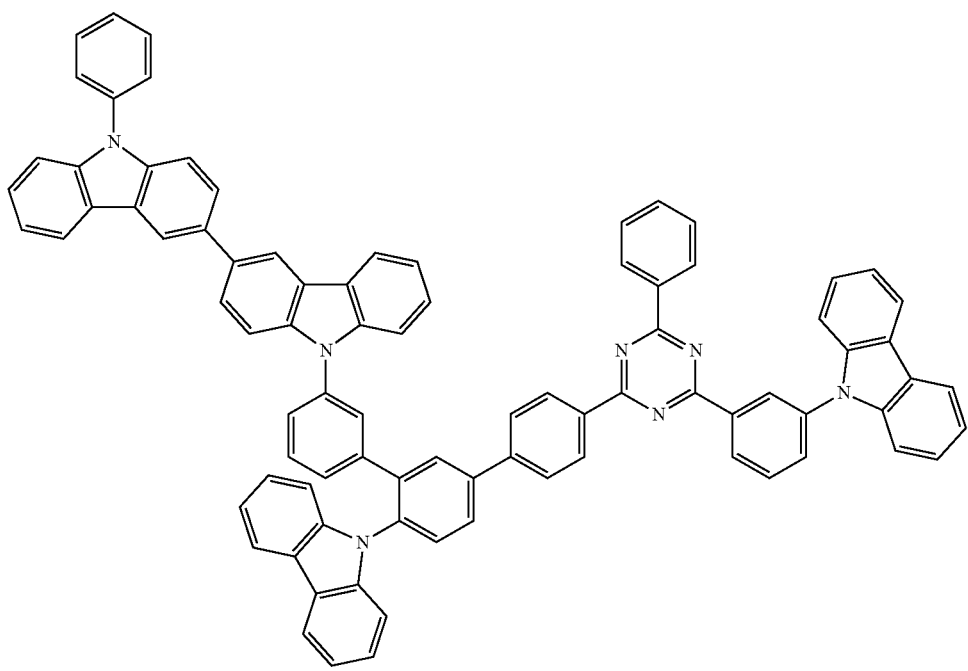
80

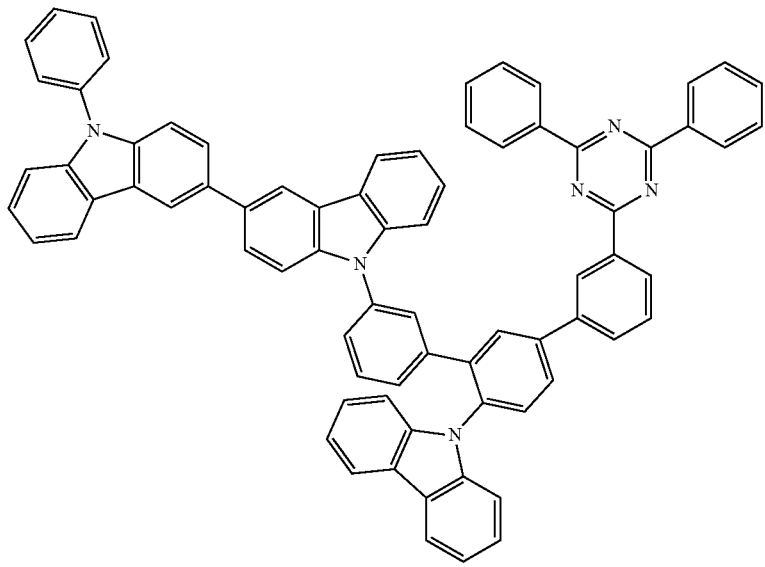
81
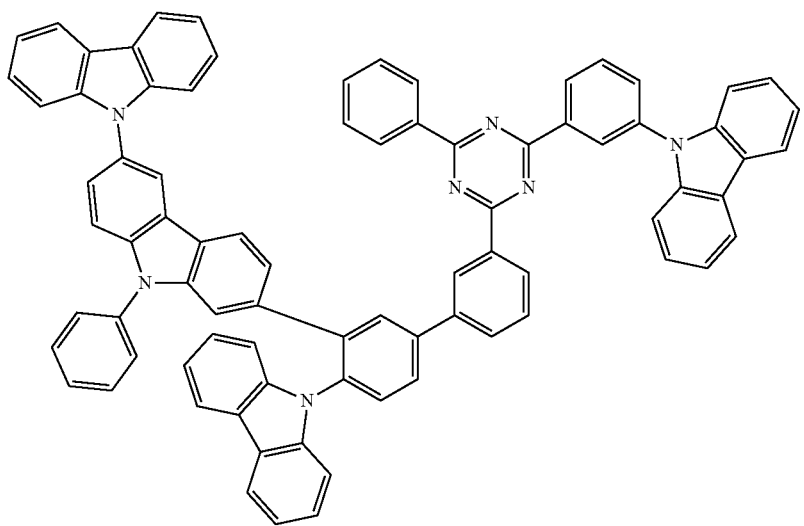
82
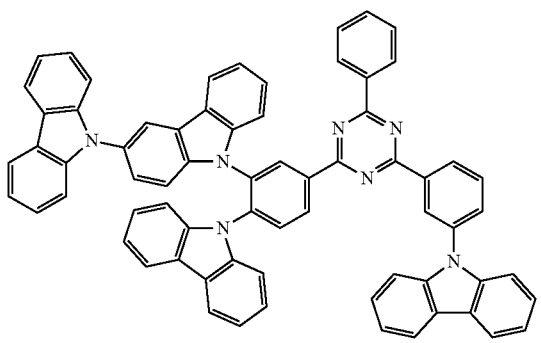
83
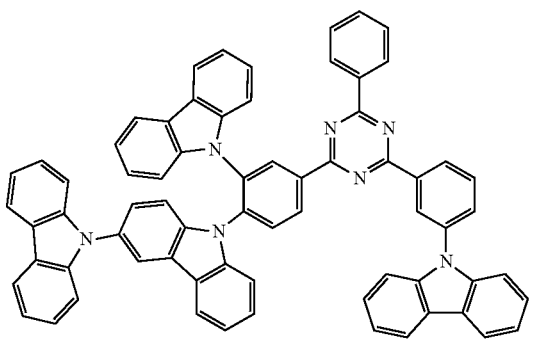
84

85
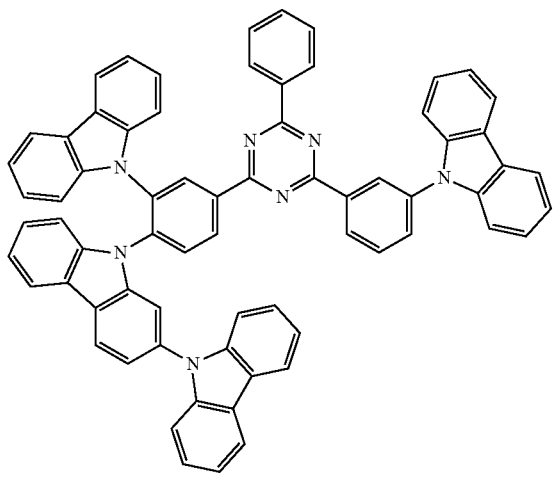
86
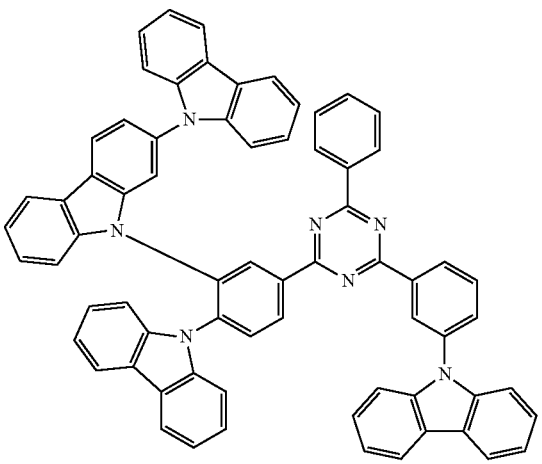
87
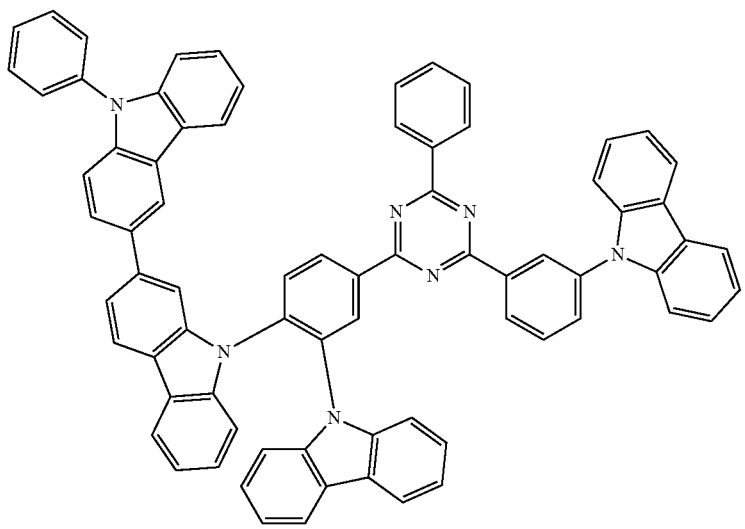
88
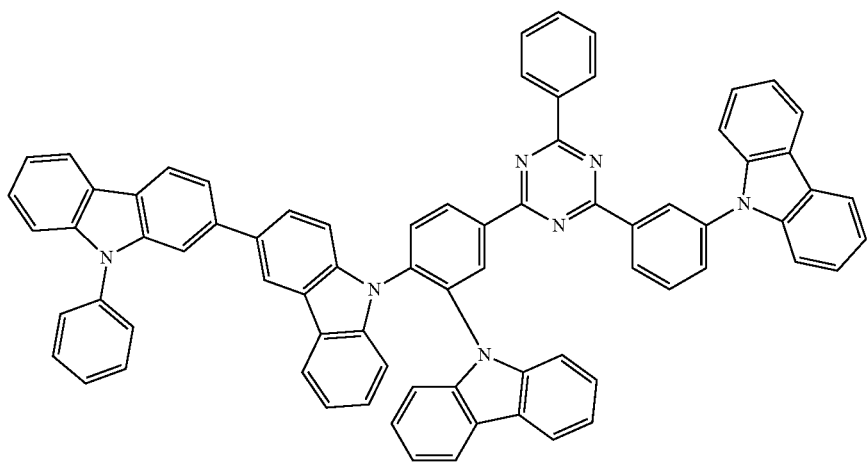

89
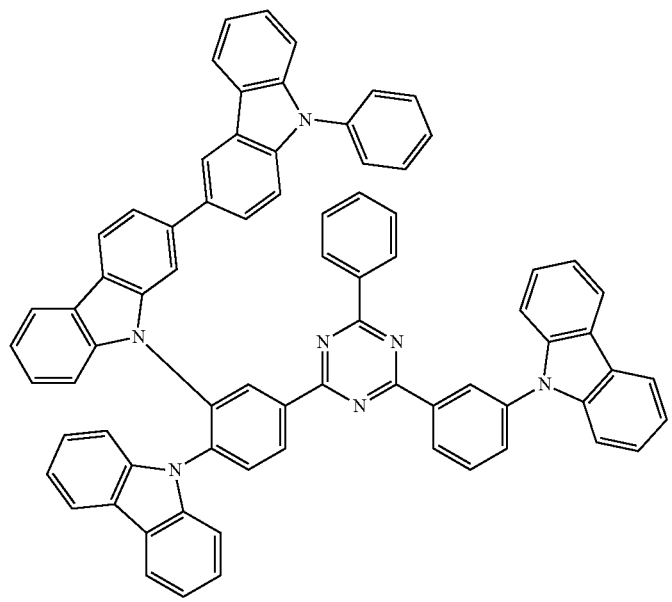
90
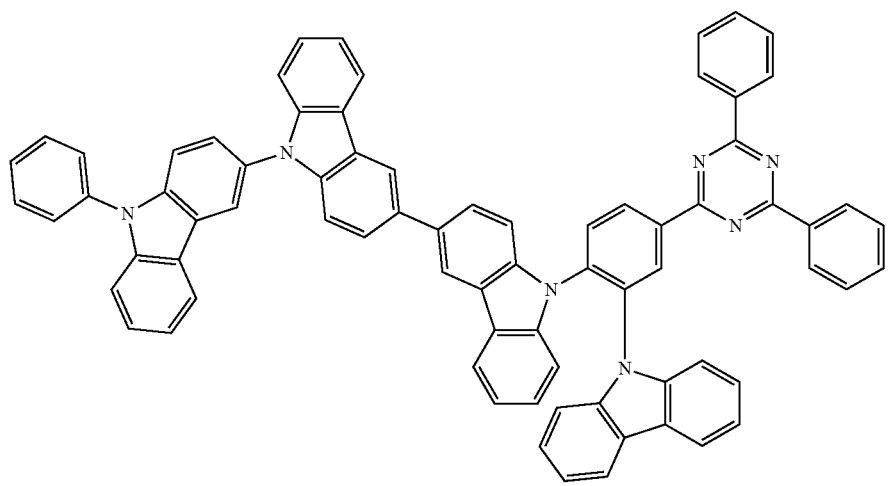
91
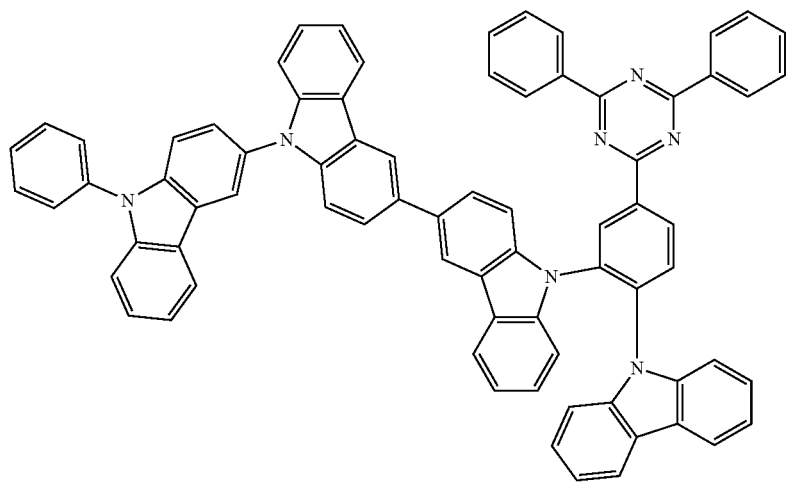

92
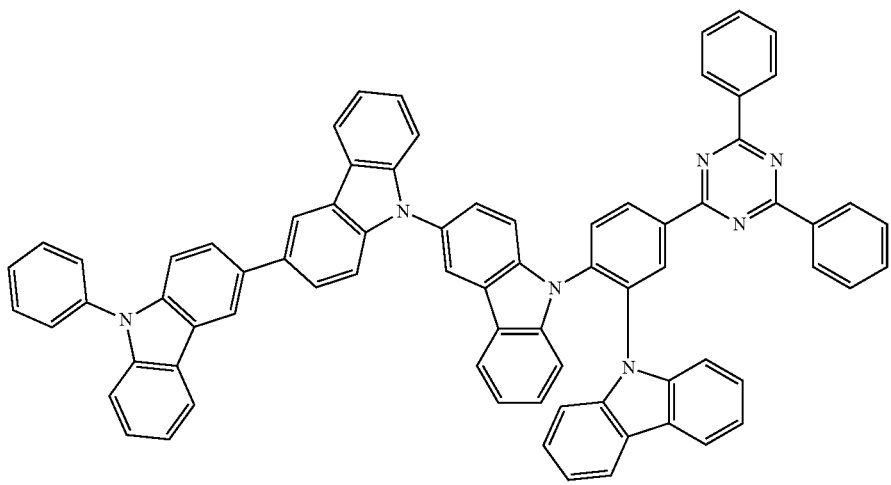
93
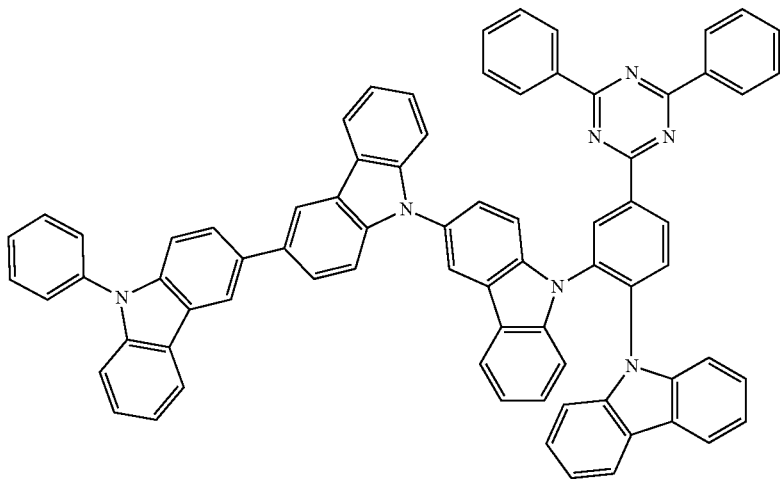
94
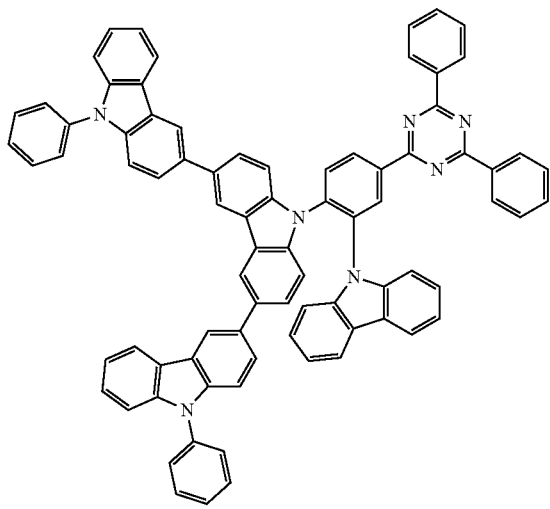
95
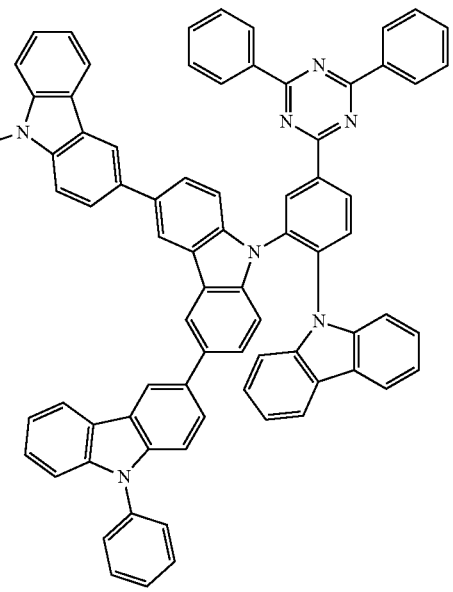

96
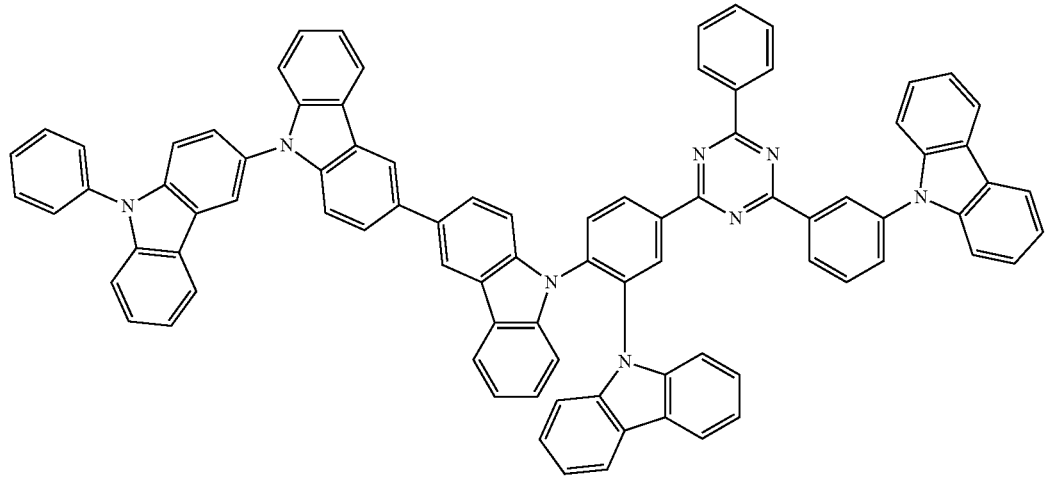
97
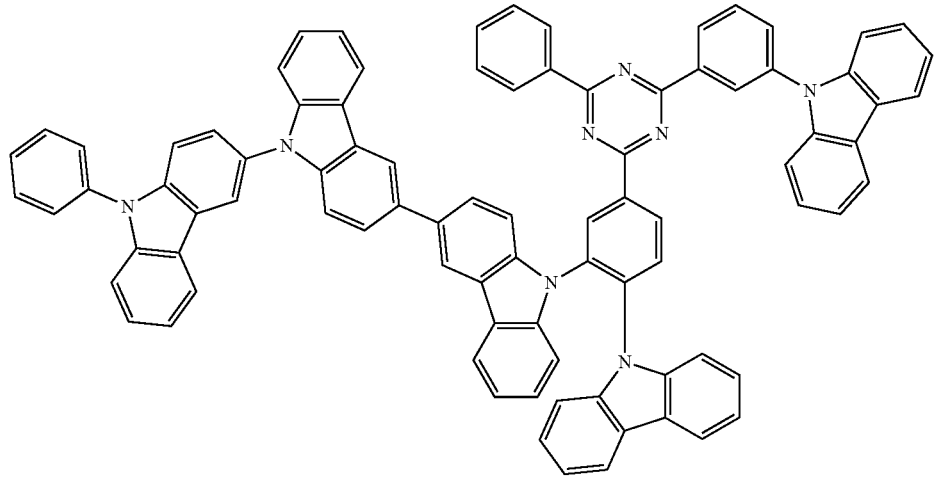
98
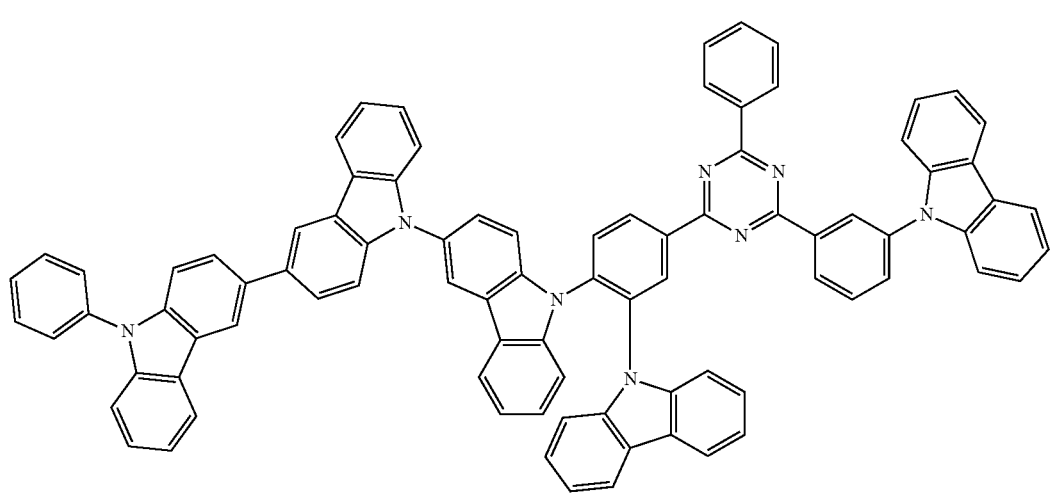

-continued
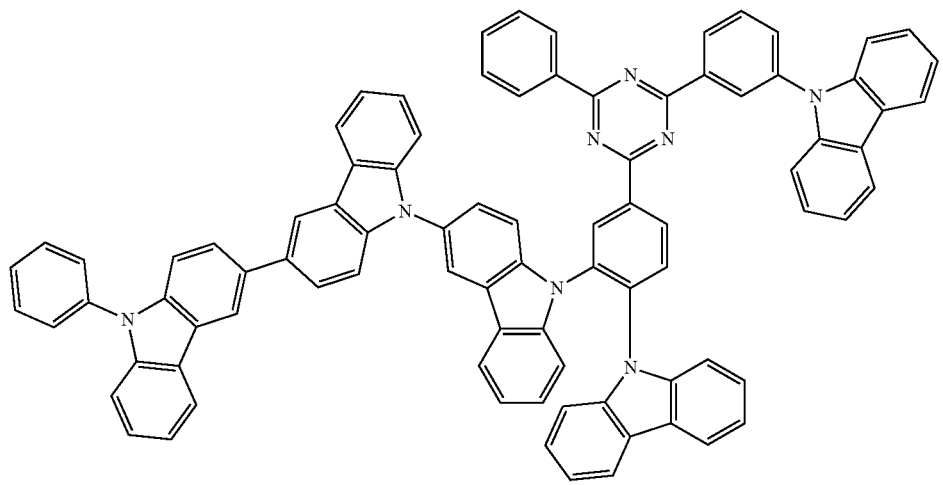
99
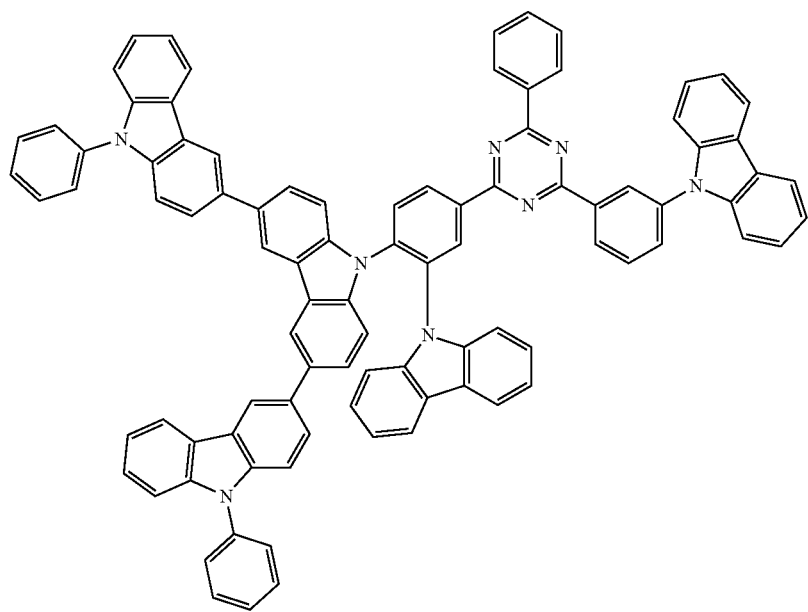
100

101
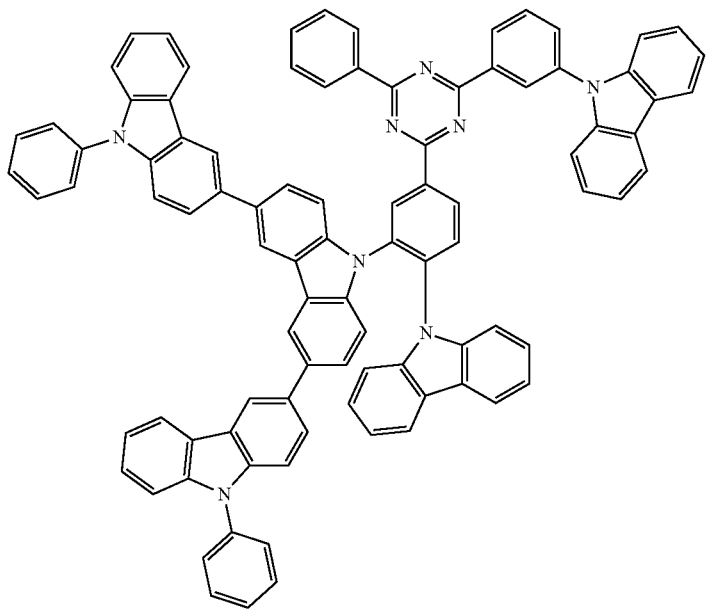
102
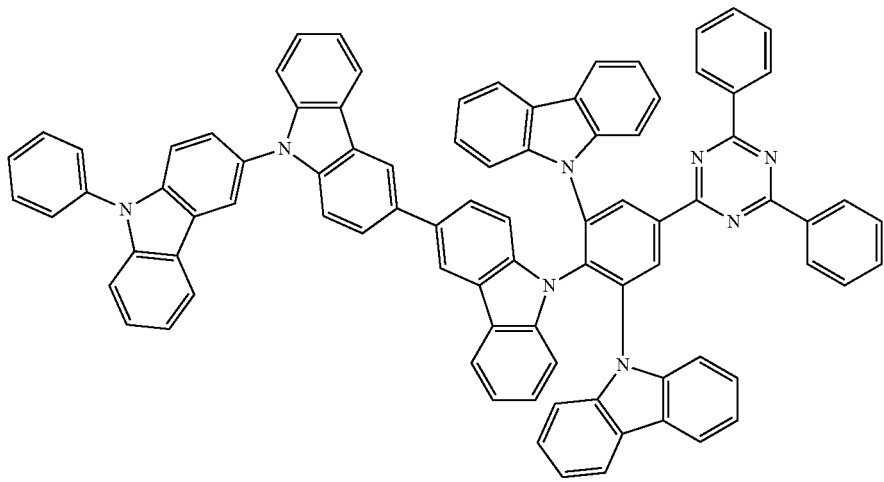
103
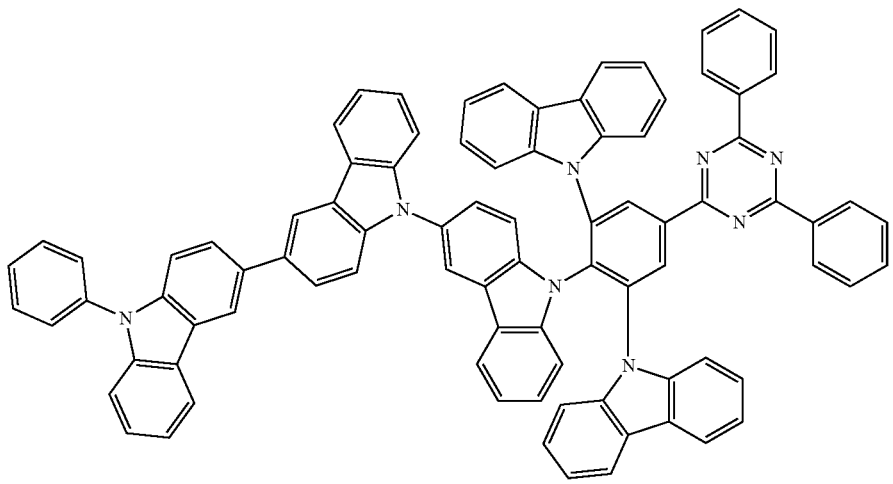

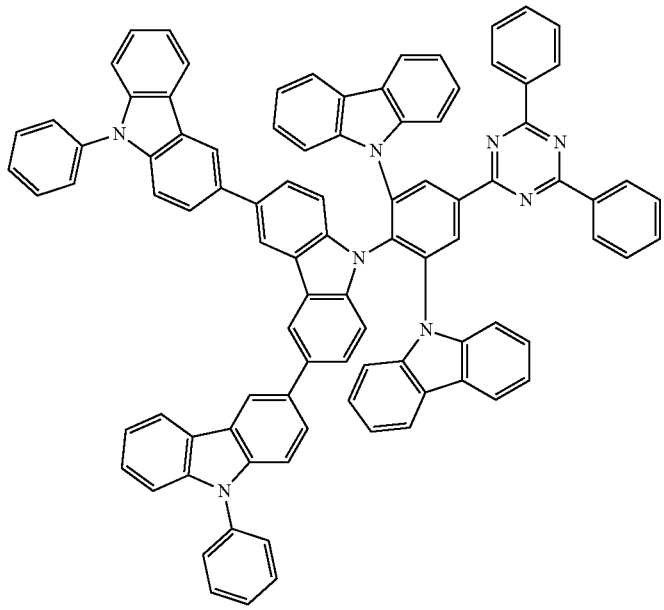
104
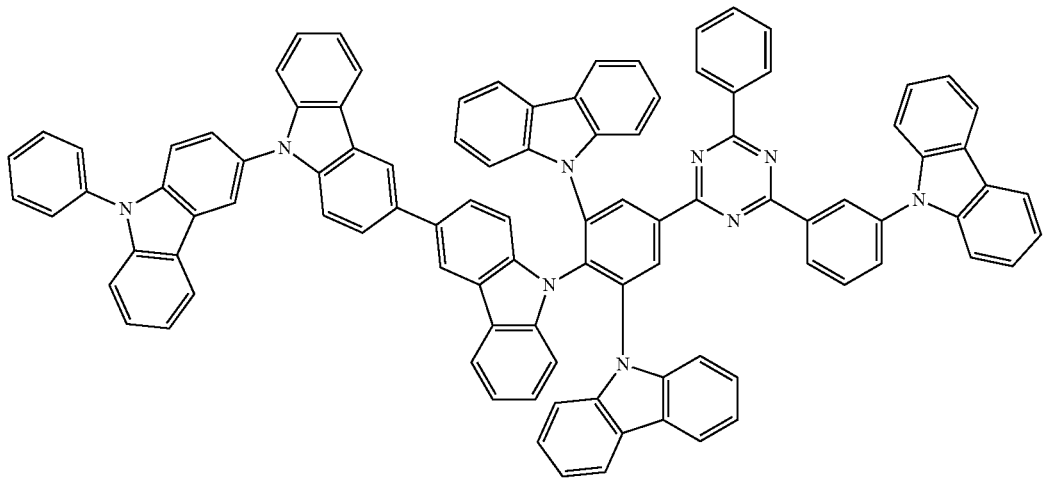
105
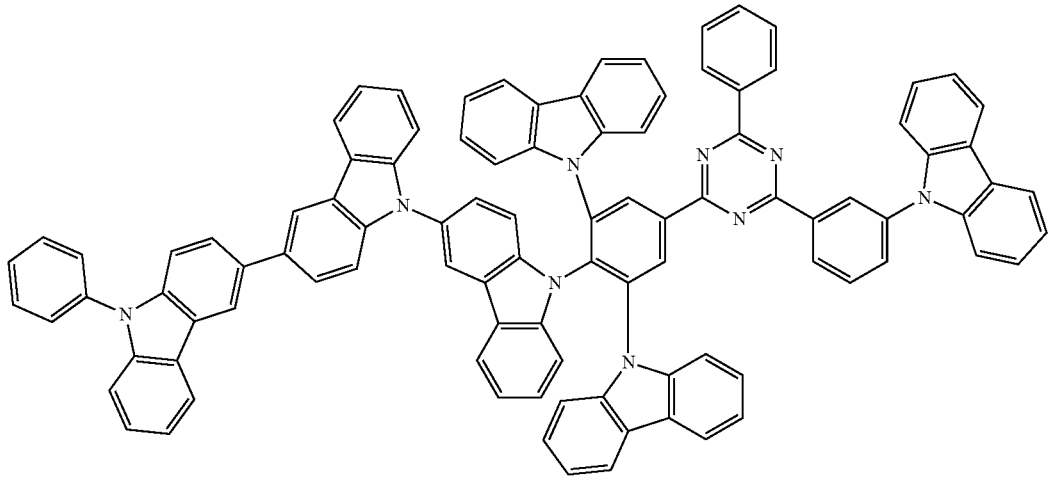
106

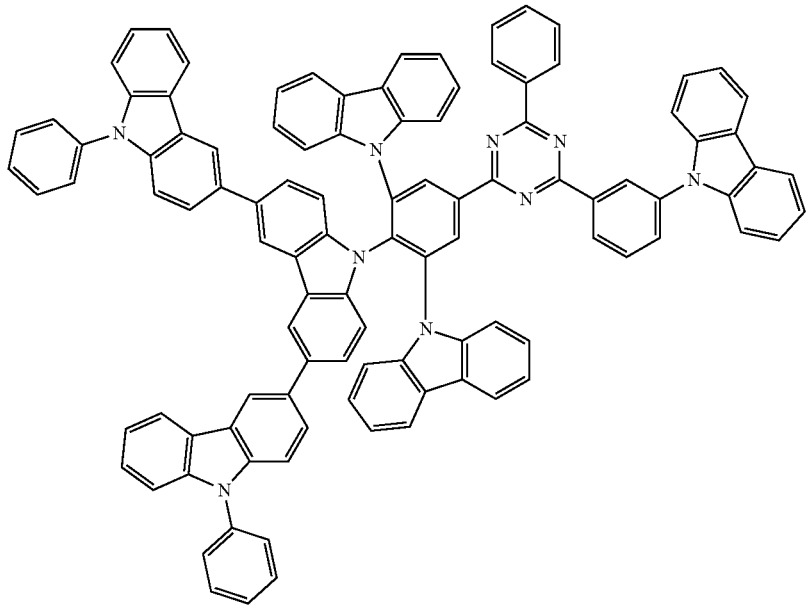
107
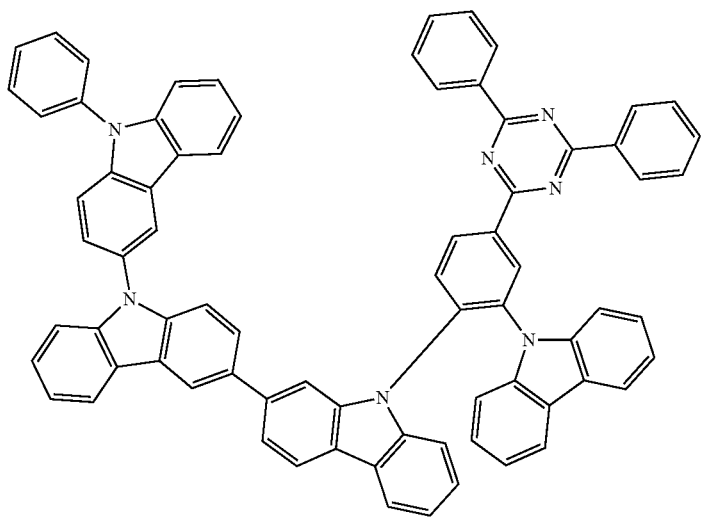
108
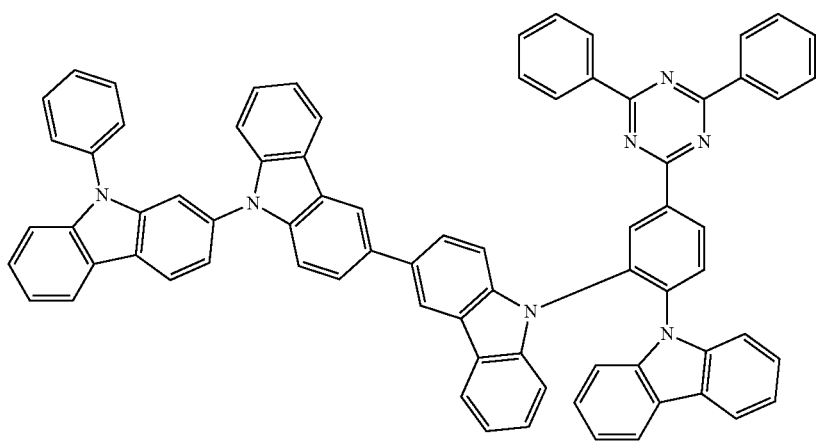
109

-continued
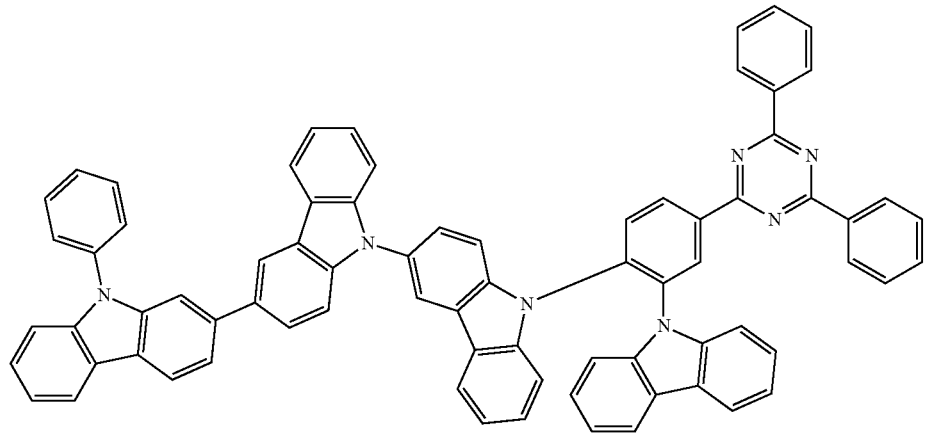
110
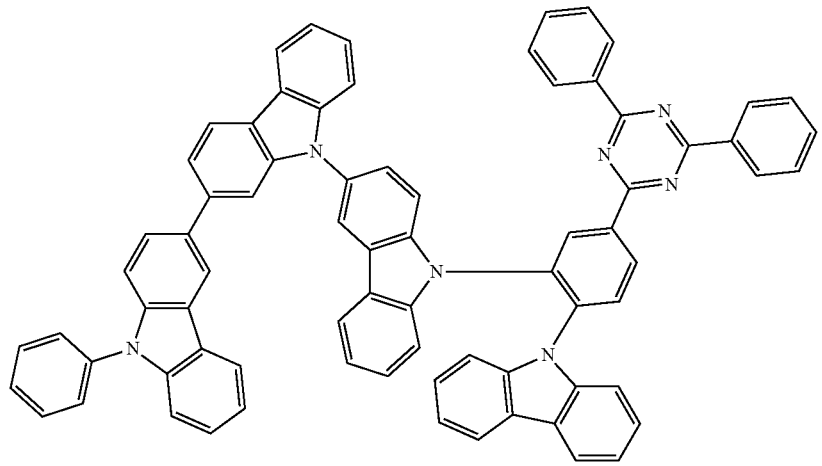
111
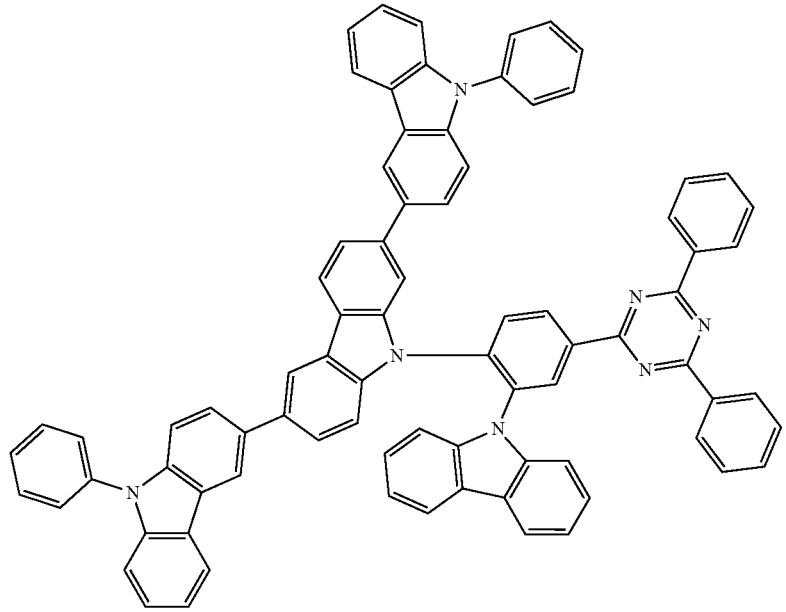
112

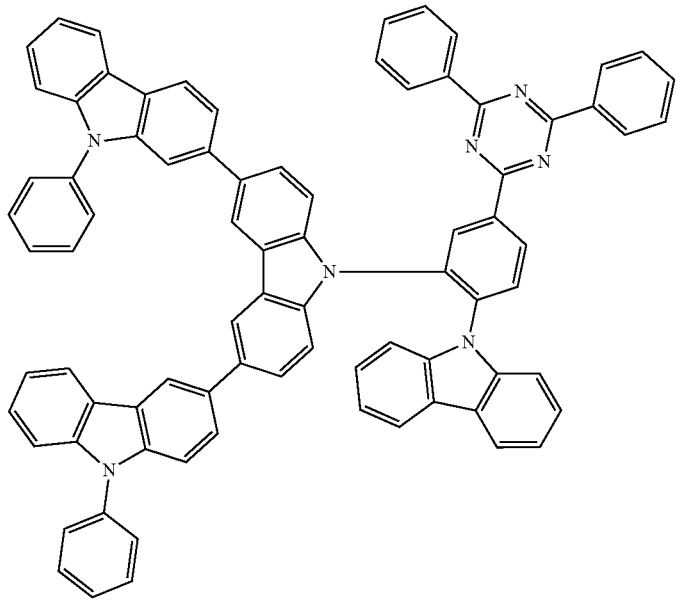
113
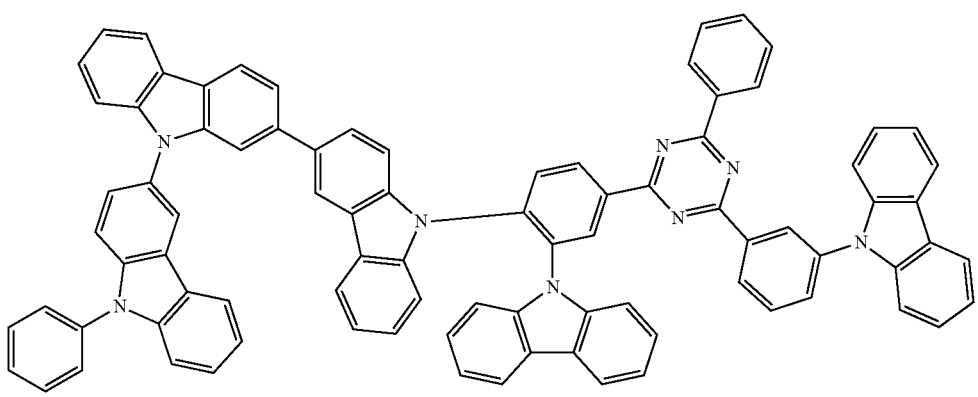
114
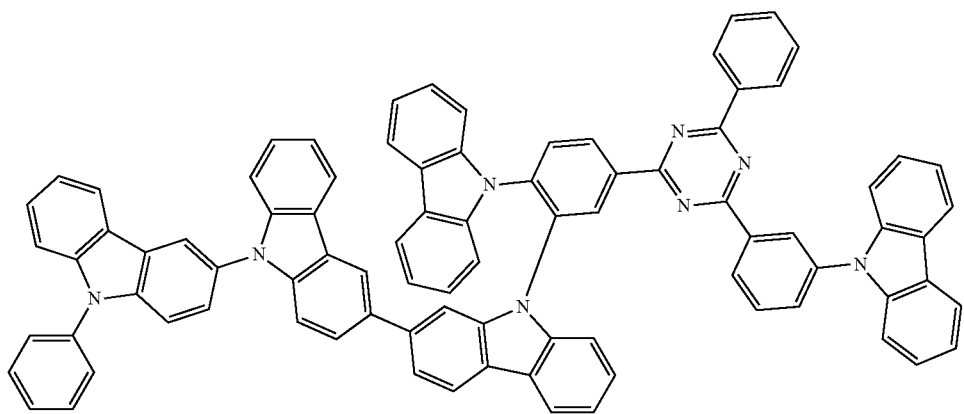
115

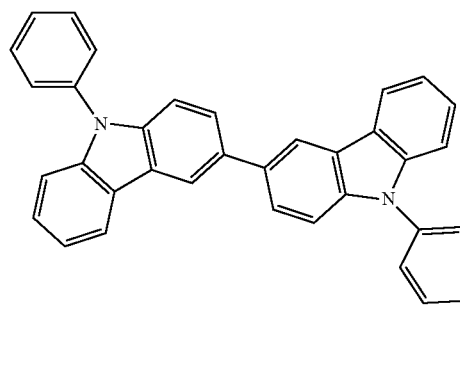
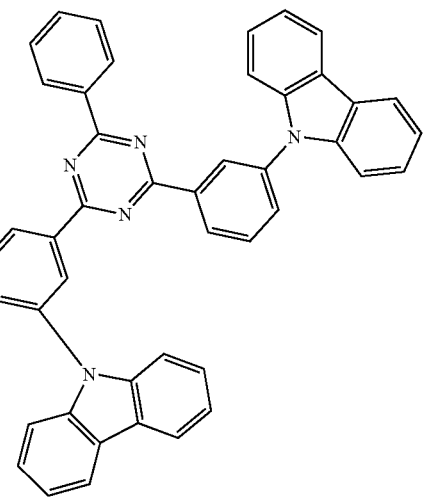
116
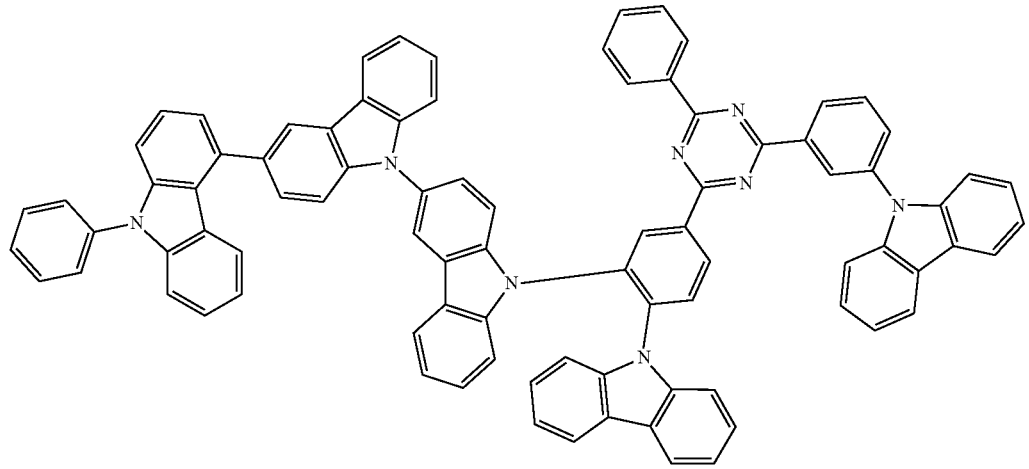
117
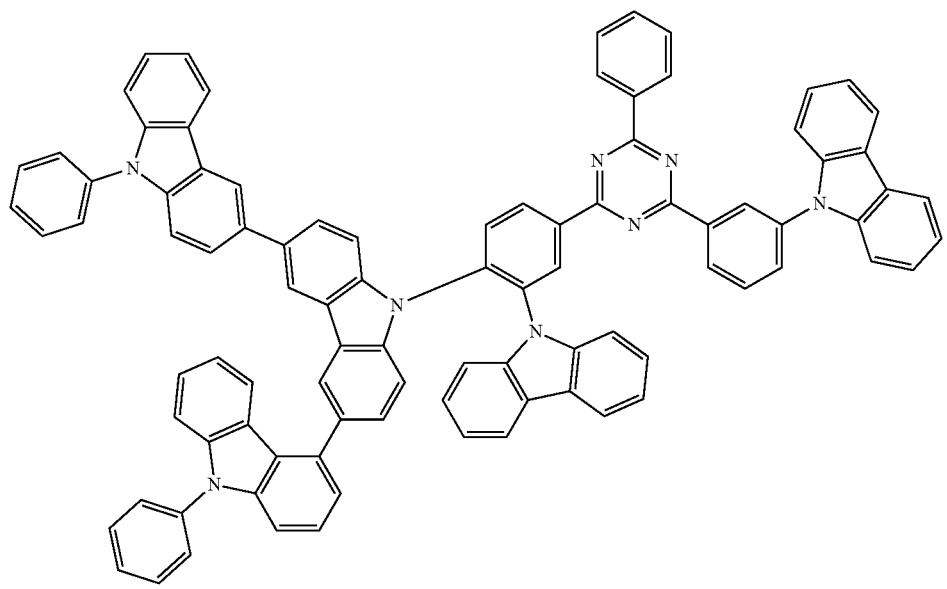
118

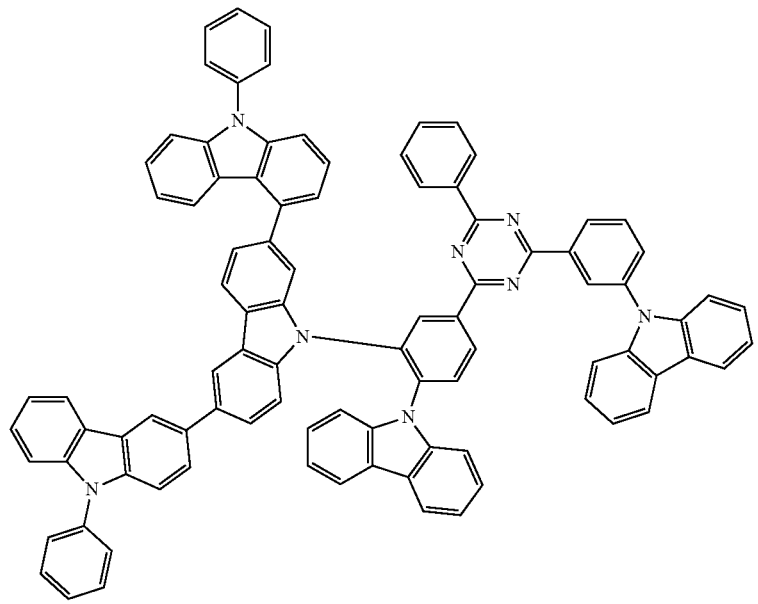
119
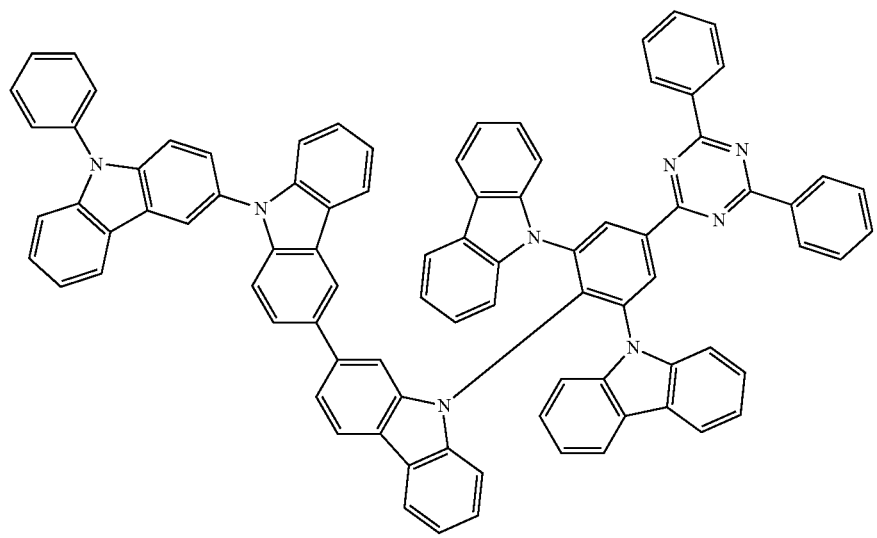
120

121
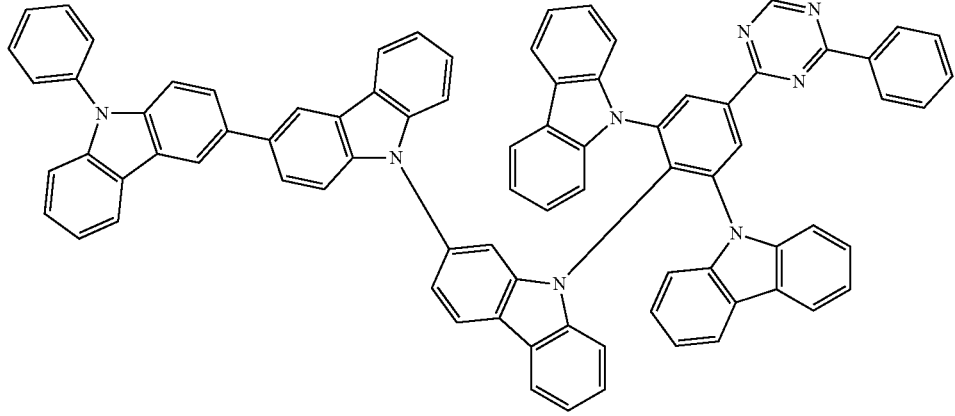
122
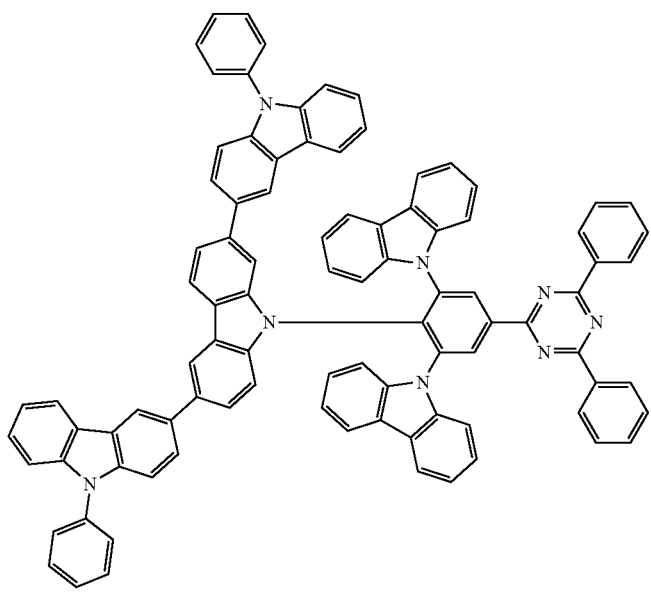
123
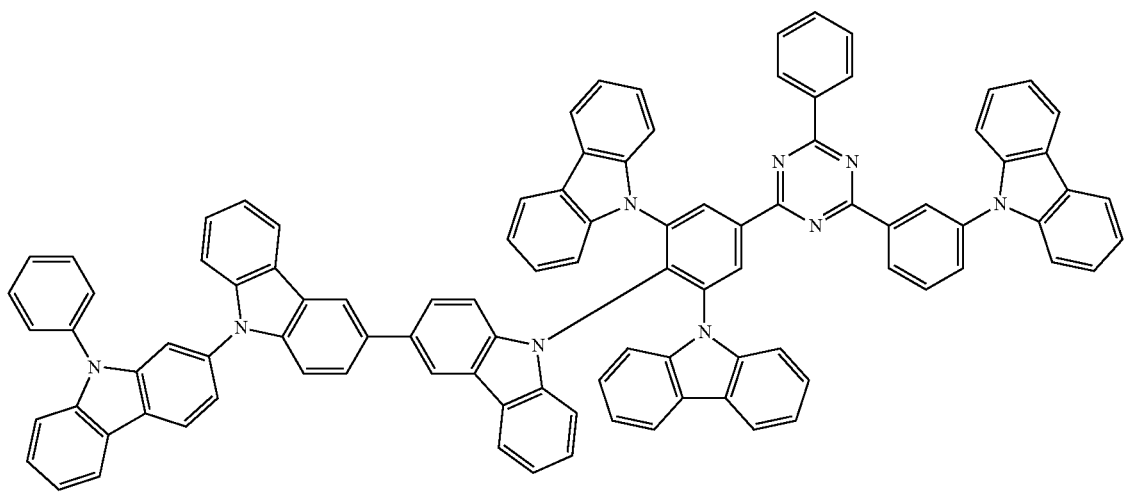

124
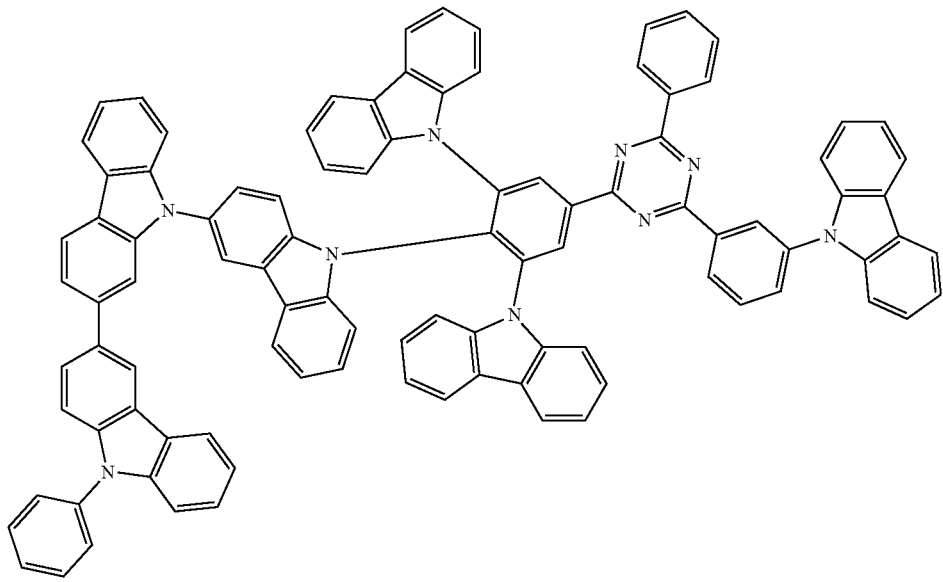
125
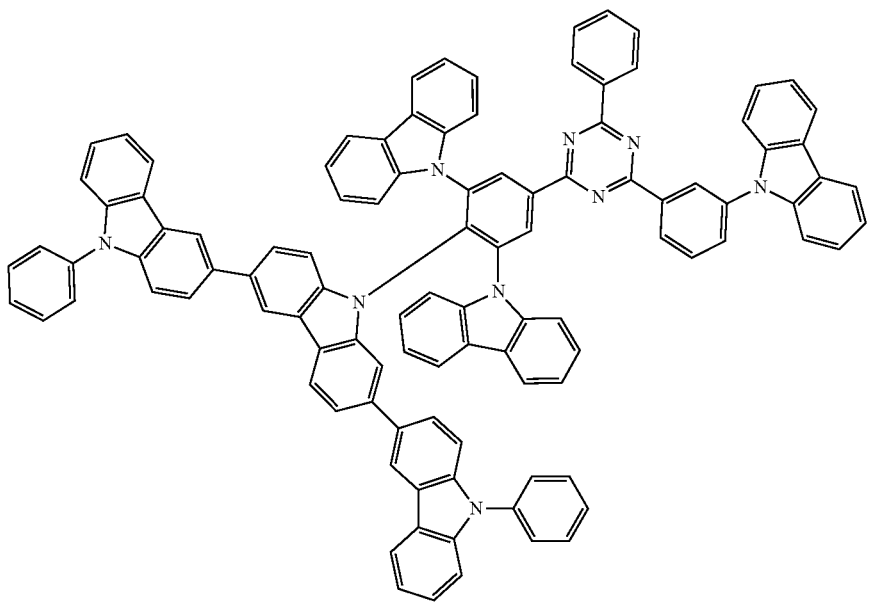

-continued
126
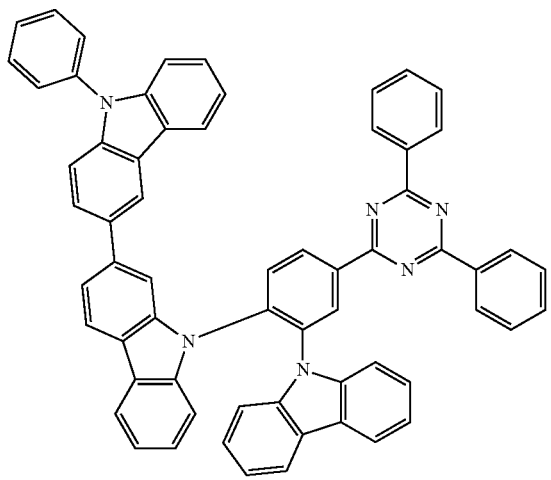
127
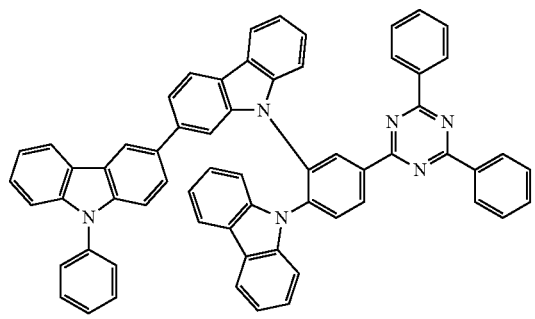
128
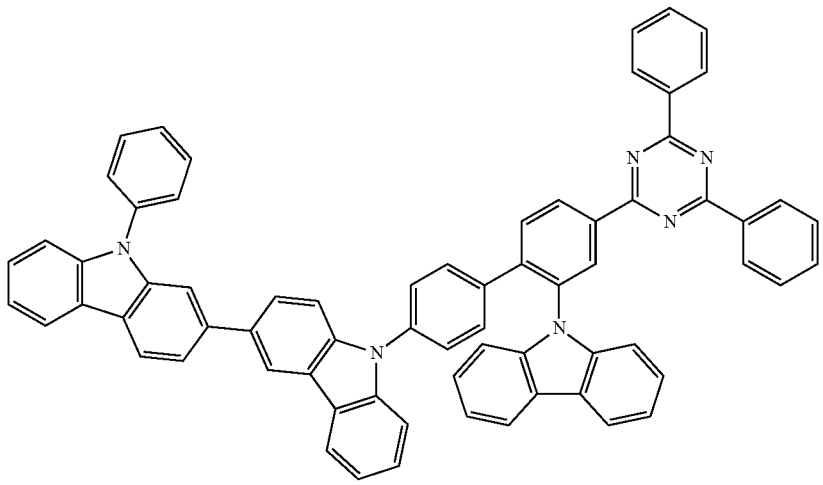
129
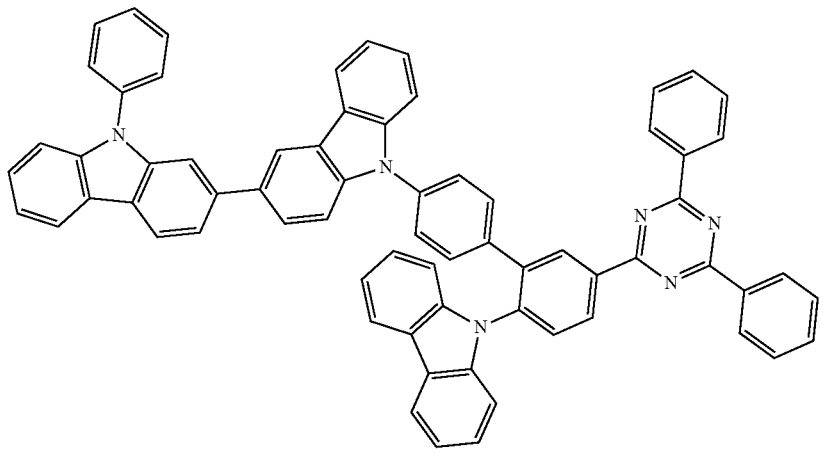

130
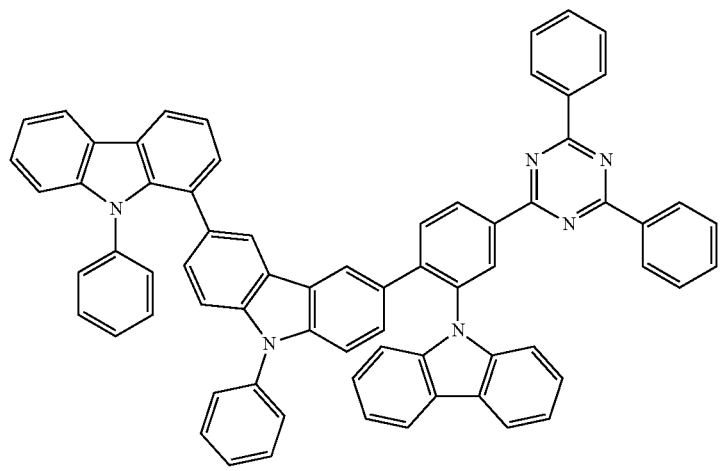
131
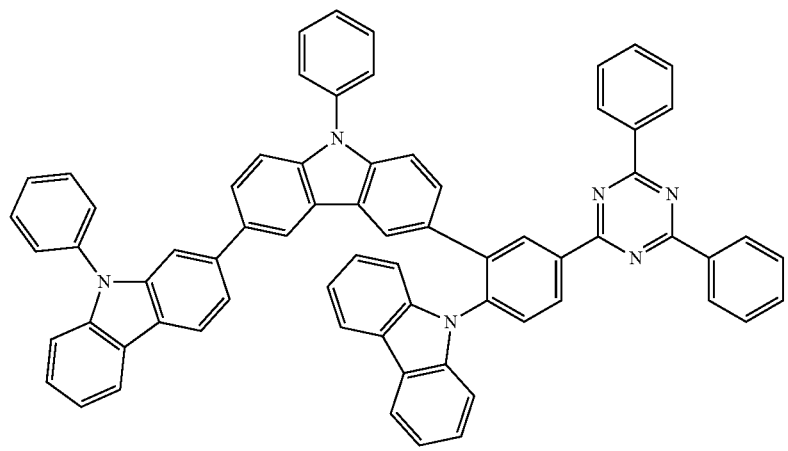
132 133
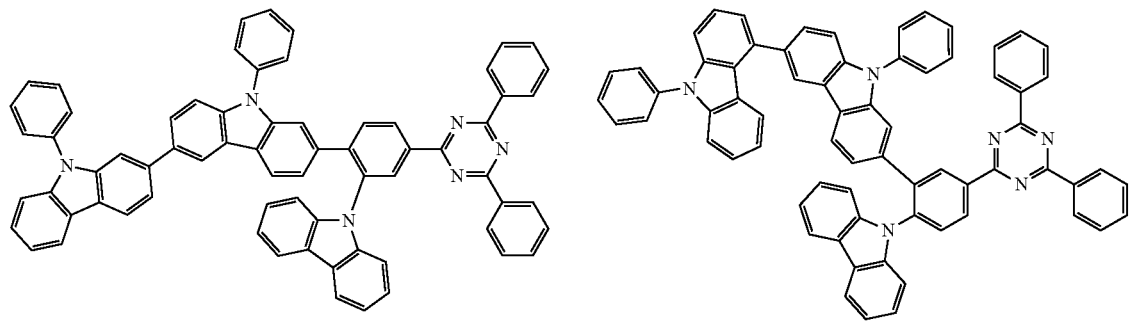
134 135
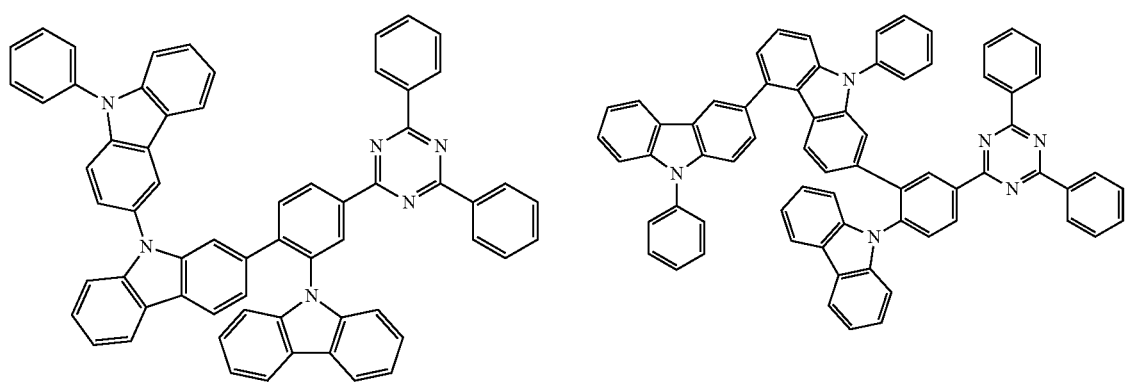

136
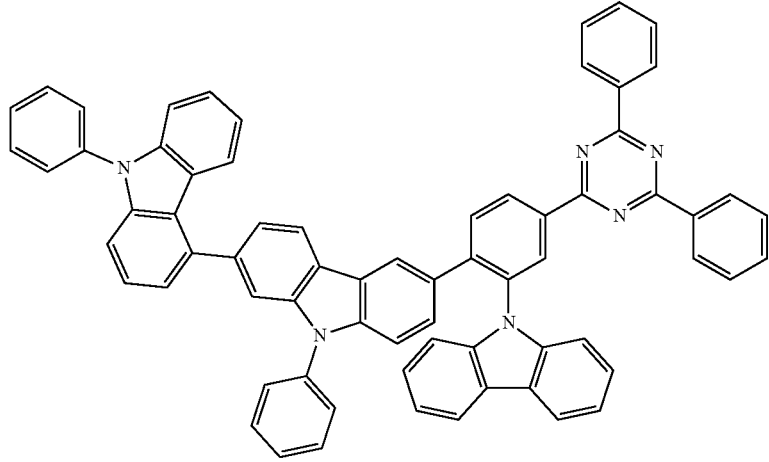
137
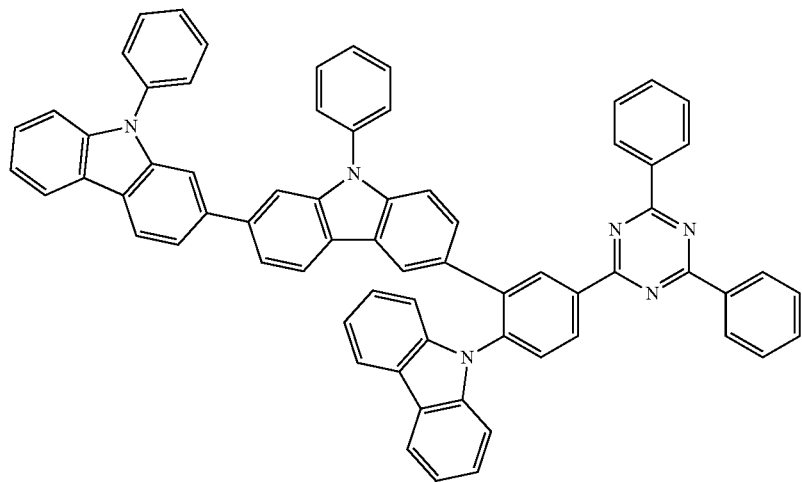
138
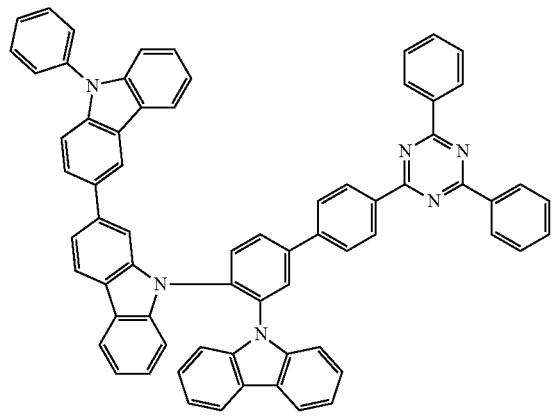
139
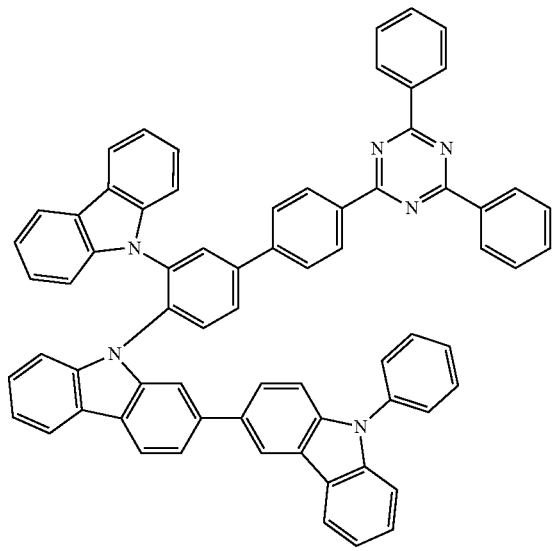

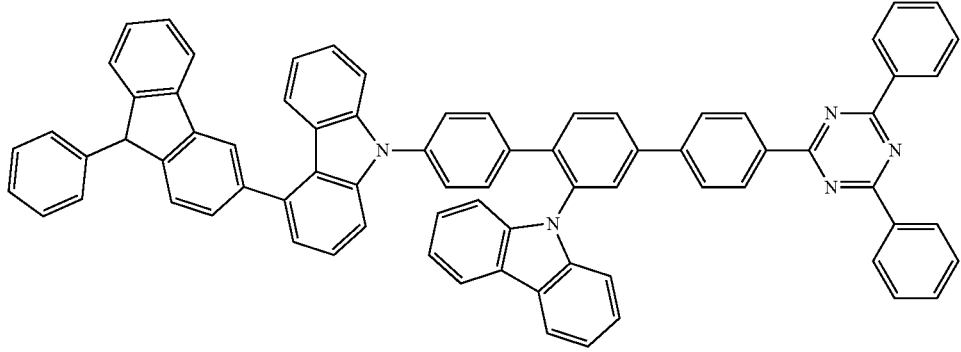

143
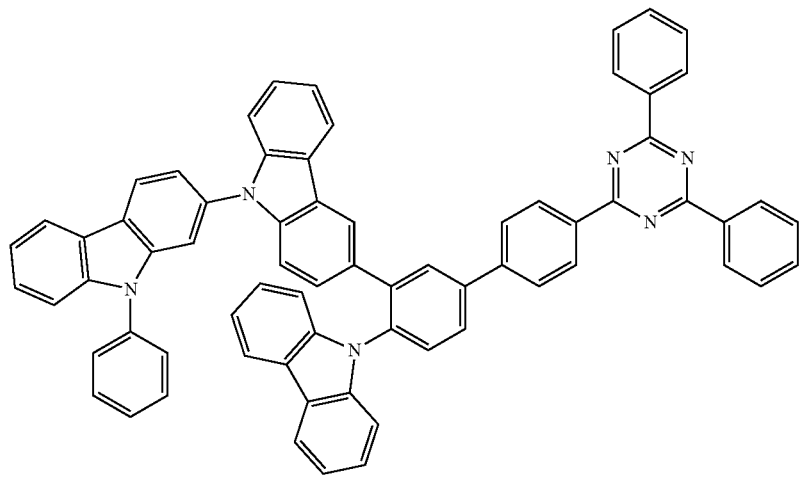
144
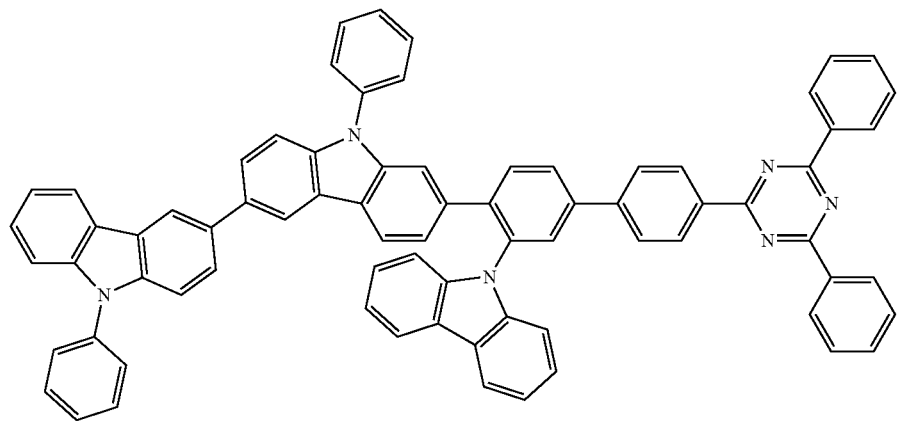
145
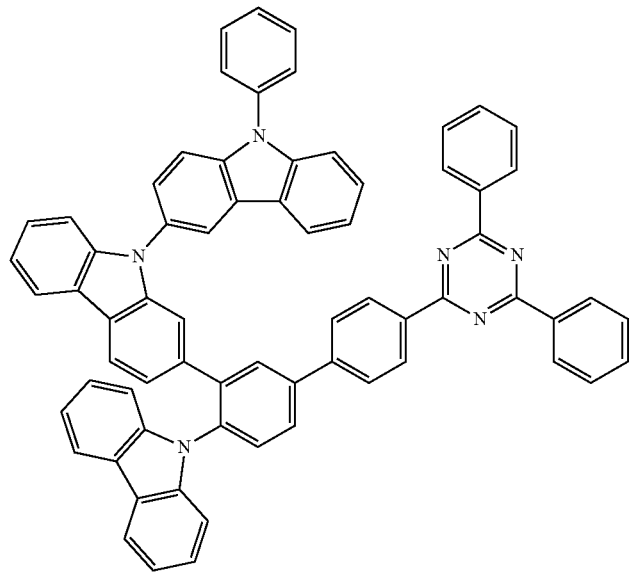

146
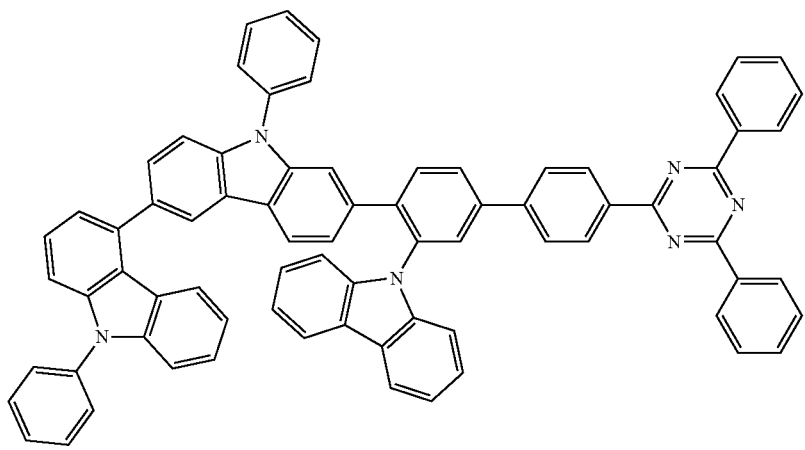
147
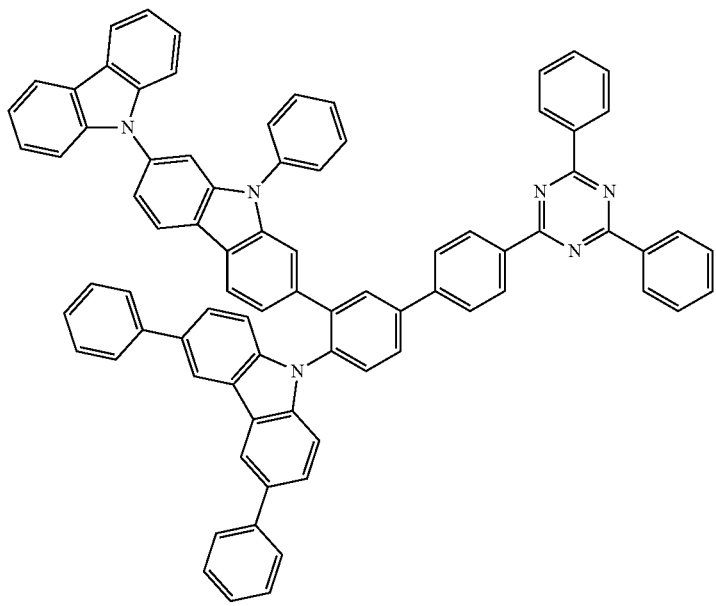
148
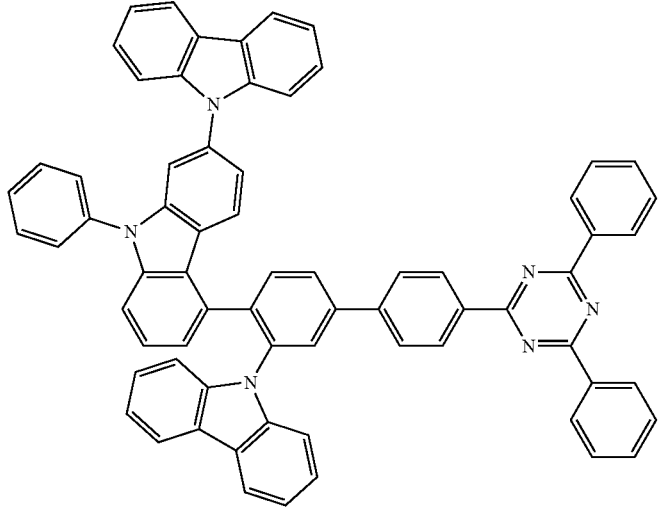

-continued
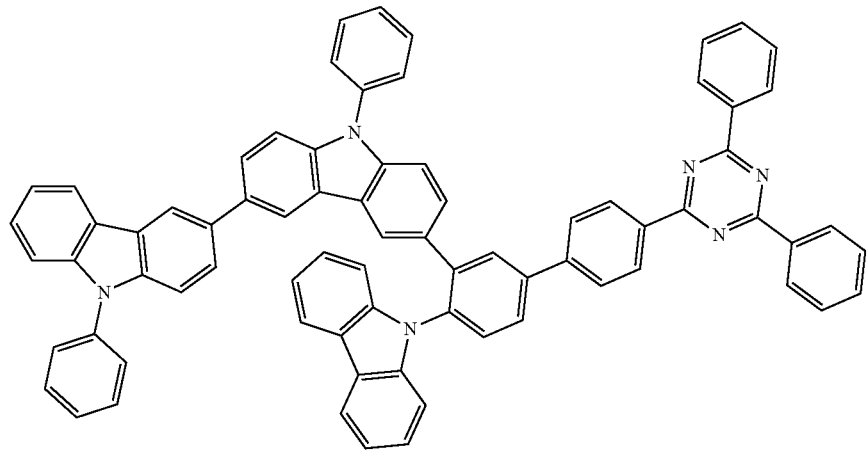
149
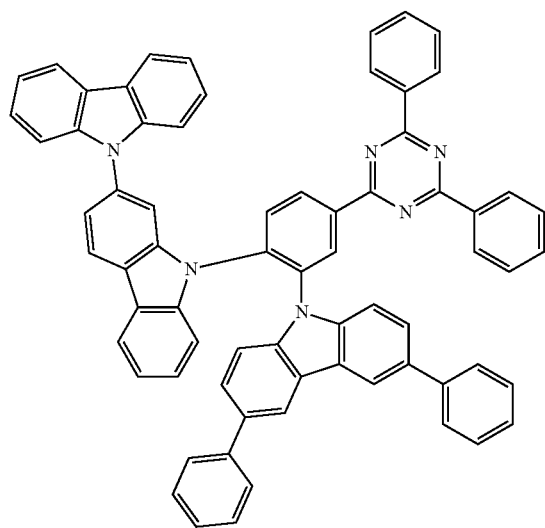
150
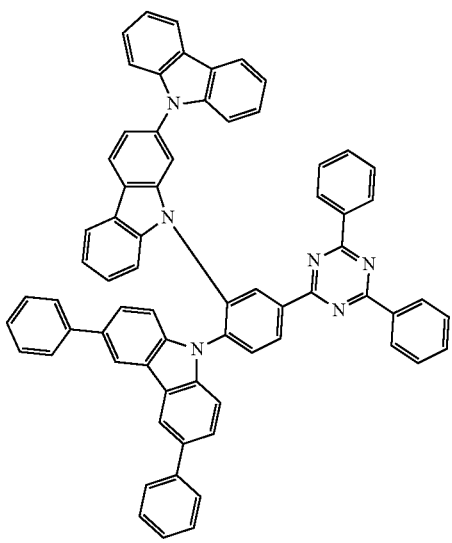
151
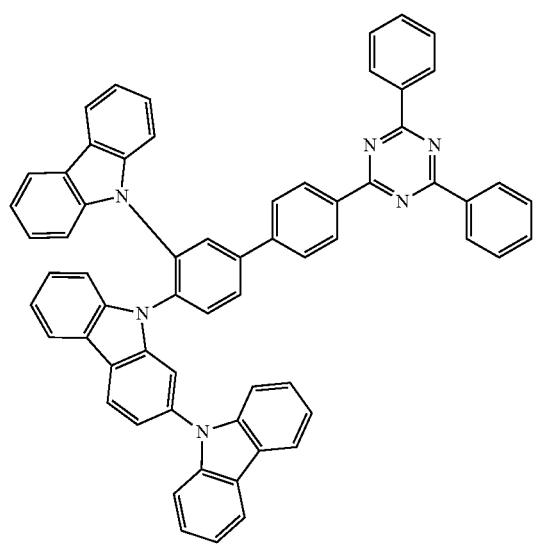
152
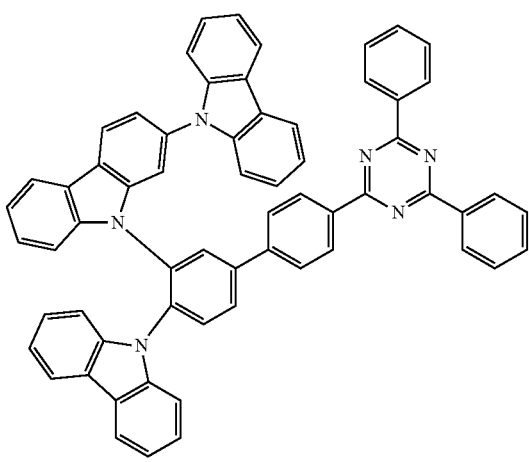
153

-continued
154
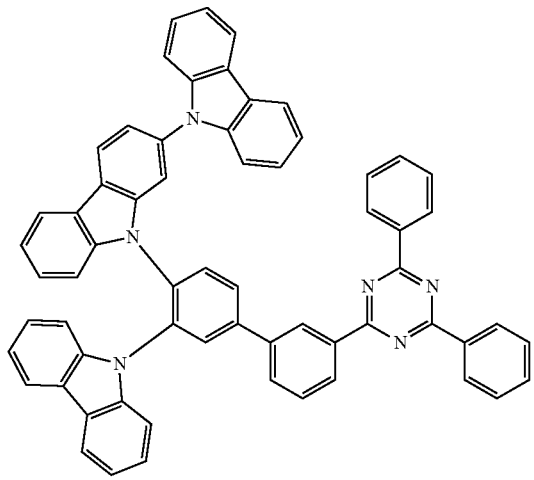
155
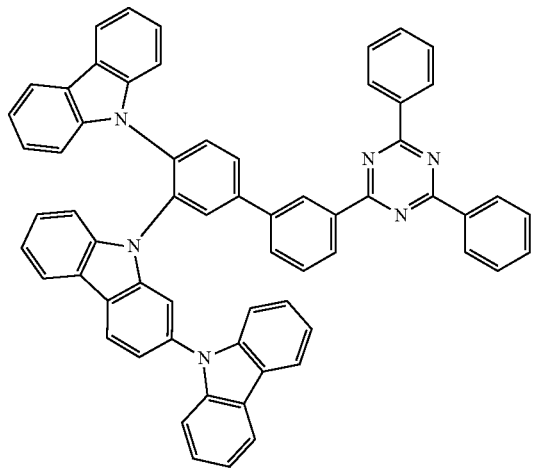
156
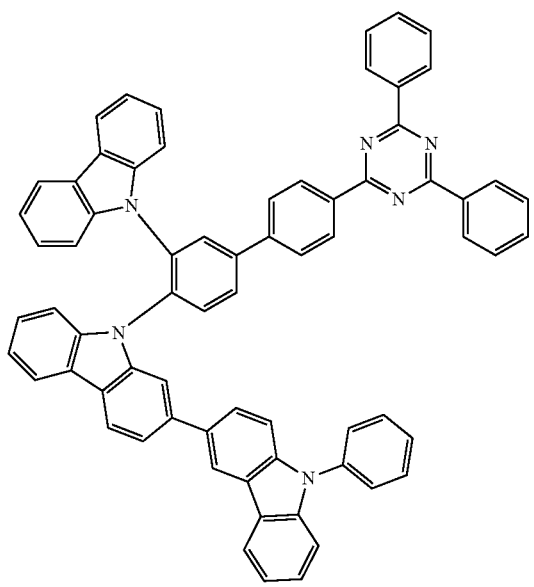
157
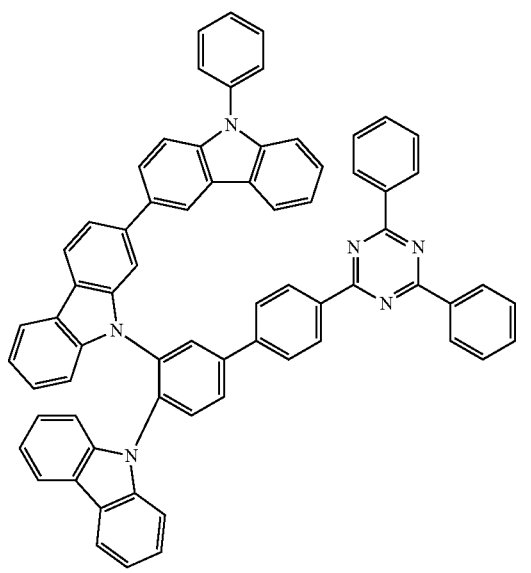

-continued
158 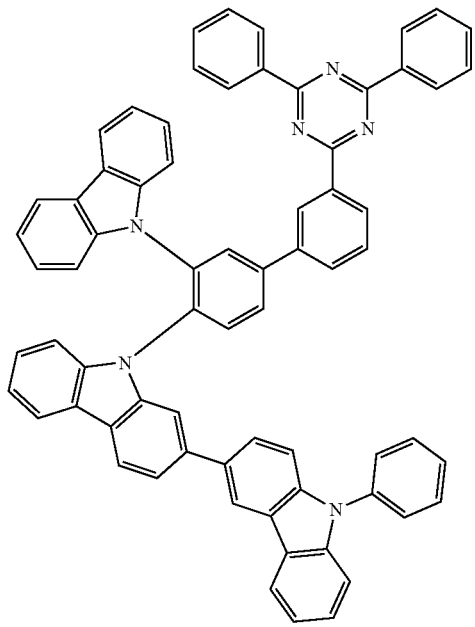
159 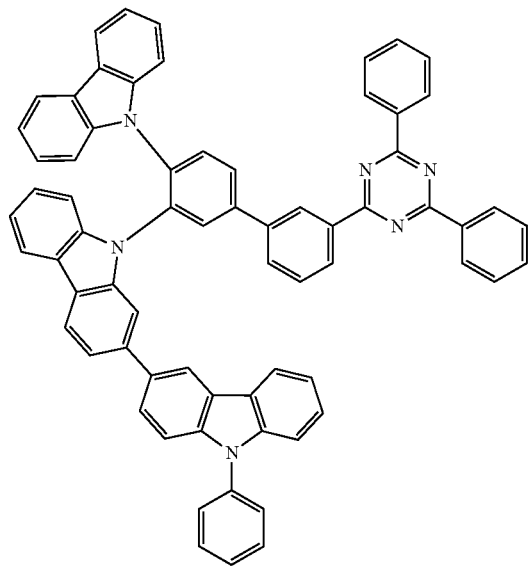
160 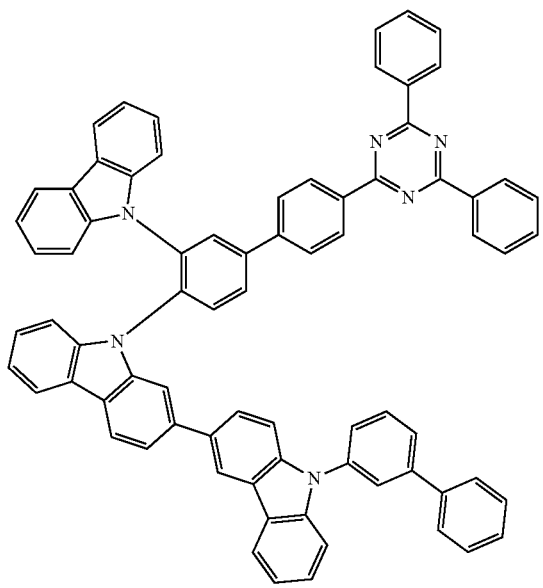
161 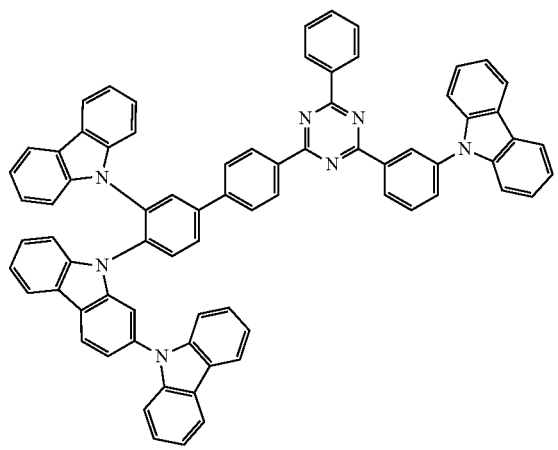
162 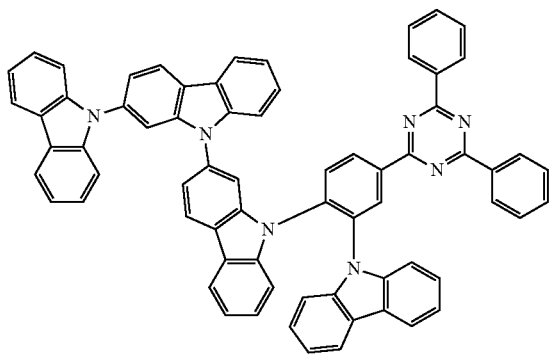
163 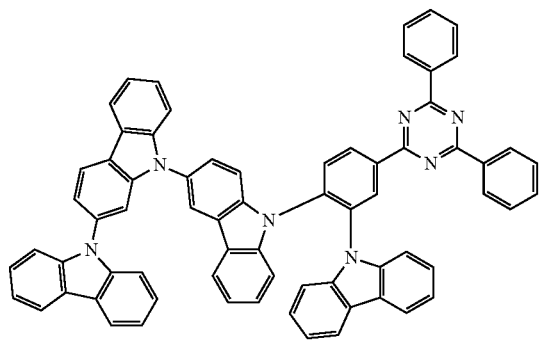

-continued
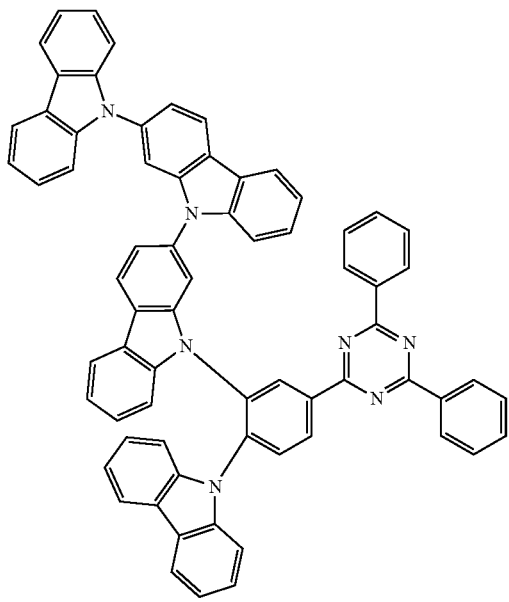
164
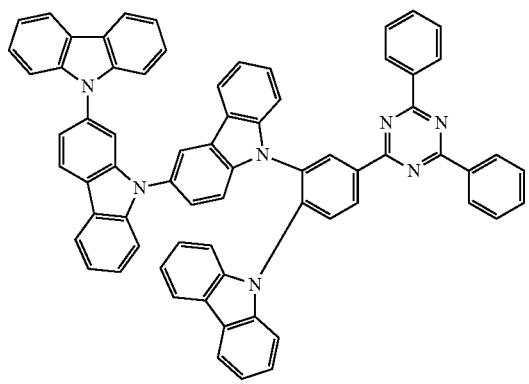
165
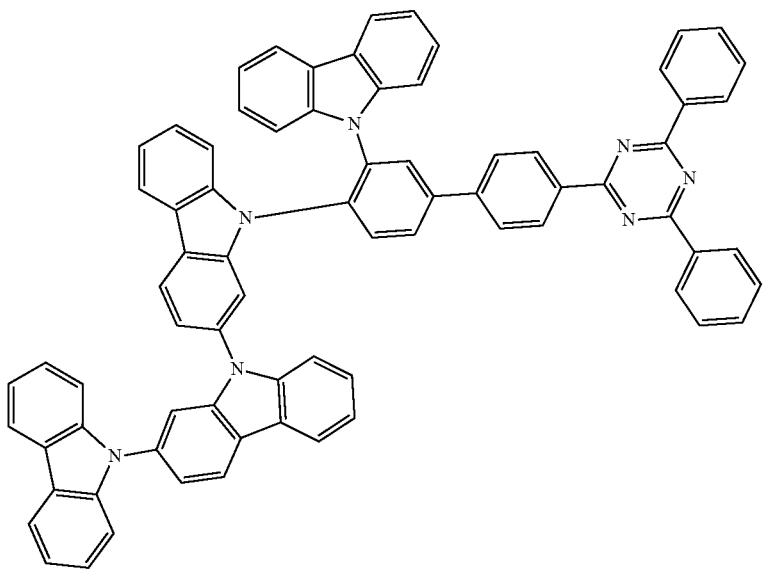
166
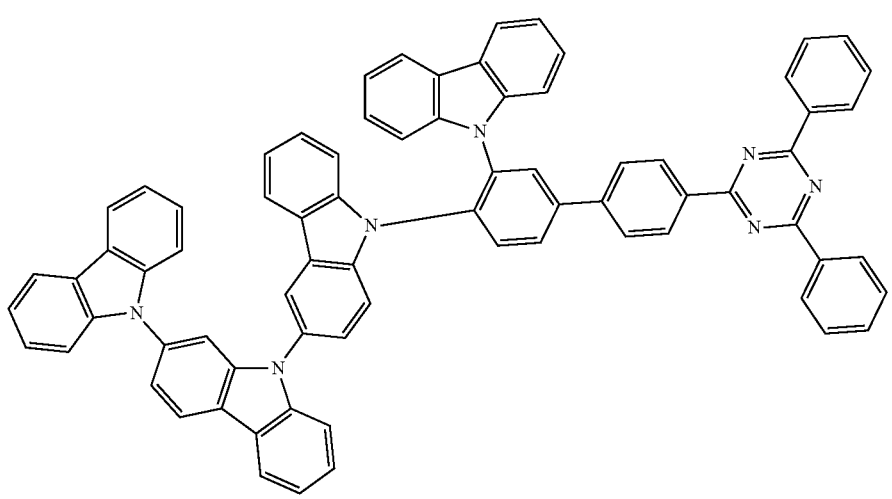
167

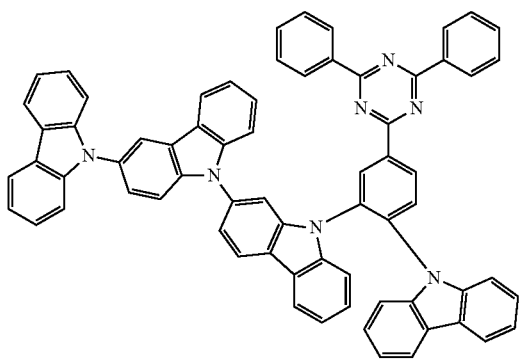

168

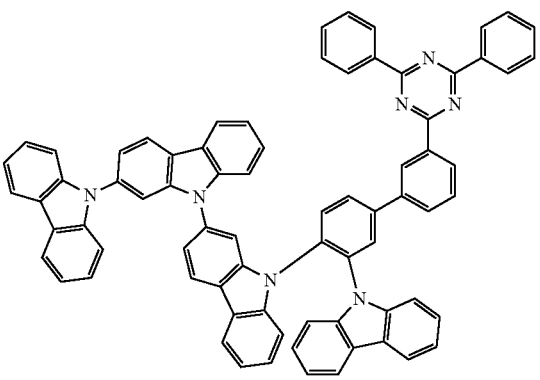

169

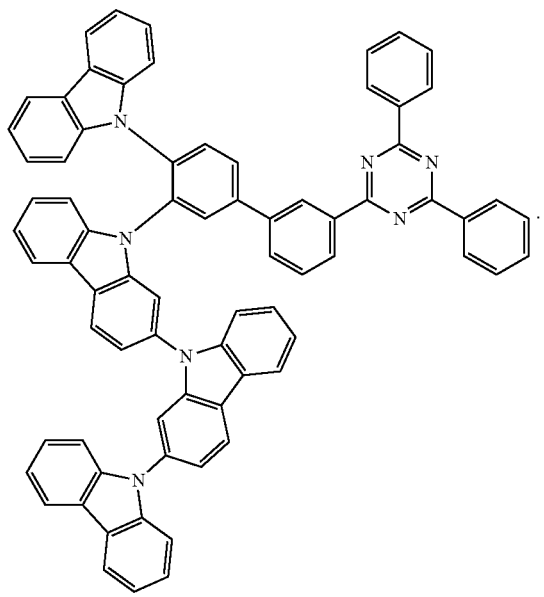

170

As examples of the compound disclosed herein, Compounds 1 to 4, 6, 8, 10, 12 to 14, 16, 18, 22, 24, 25, 27 to 30, 33, 36, 39, 44 to 47, 58, 59, 86, 89, 90, 92, 93, 100, 102, 103, 126, 127, 151 to 155, 157 to 161, 164, and 168 may be preferable. In addition, as examples of the compound disclosed herein, Compounds 59, 8, 10, 8, 10, 2 to 14, 16, 18, 22, 24, 27 to 30, 33, 36, 39, 44, 45, 47, 58, 59, 86, 89, 90, 92, 93, 100, 102, 103, 126, 127, 151 to 155, 157 to 161, 164, and 168 may be more preferable. In addition, as examples of the compound disclosed herein, Compound 16, 59, 86, 103, 153, 160, 161, and 164 may be still more preferable. Furthermore, as examples of the compound disclosed herein, Compounds 86 and 160 may be more preferable, and Compound 160 may be particularly preferable.

The compound represented by Formula (1) may be preferably a material having a narrow gap. Here, the material having a narrow gap refers to a material having a HOMO-LUMO energy gap of about 3.0 eV or less. The HOMO-LUMO energy gap is not particularly limited, but may be preferably about 3.0 eV or less. In addition, the HOMO-LUMO energy gap may be more preferably about 2.9 eV or less. Within these ranges above, the driving voltage of an organic electroluminescent device may be lowered. Furthermore, the HOMO-LUMO energy gap may be preferably about 2.4 eV or less.

The HOMO level of the compound represented by Formula (1) is not particularly limited, but may be preferably about −6.0 eV or more. In addition, the HOMO level may be more preferably about −5.8 eV or more. Within these ranges above, the driving voltage of an organic electroluminescent device may be lowered. Furthermore, from the viewpoint of matching with the energy diagram of a general phosphorescent dopant and stability in the atmosphere, the HOMO level may be preferably about −5.0 eV or less.

The LUMO level of the compound represented by Formula (1) is not particularly limited, but may be preferably about −2.5 eV or less. In addition, the LUMO level may be more preferably about −2.6 eV or less. Within these ranges above, the driving voltage of an organic electroluminescent device may be lowered. Furthermore, from the viewpoint of matching with the energy diagram of a general phosphorescent dopant, the LUMO level may be preferably about −3.5 eV or more.

The HOMO level may be measured and calculated by using an atmospheric photoelectron spectroscopic device, and the LUMO level may be measured and calculated by using an atmospheric photoelectron spectroscopic device and a spectrophotometer. Details of the measurement and calculation will be described in Examples below.

The compound represented by Formula (1) may be preferably used as a material for an organic electroluminescent device (also referred to as an organic EL device material in the present specification). Accordingly, the organic EL device material may preferably include the compound represented by Formula (1).

An organic electroluminescent device including the compound represented by Formula (1) may be able to provide low driving voltage, high efficiency, and long lifespan. The organic EL device material including the compound of the present disclosure may be available as a material for forming a hole injection layer, a hole transport layer, an emission layer, an electron transport layer, or an electron injection layer. In particular, the organic EL device material including the compound of the present disclosure may be preferably used as a material for forming an emission layer, and may be more preferably used as a host material in an emission layer.

In addition, the compound represented by Formula (1) may be difficult to precipitate from a solution, and may have a long pot life of a solution. Therefore, the compound represented by Formula (1) may be able to achieve low driving voltage, high efficiency, and long lifespan of an organic electroluminescent device, even when a wet film-forming method is used.

Furthermore, a preparation method of the compound represented by Formula (1) is not particularly limited, and various preparation methods including synthesis methods known in the art may be used. An example of the preparation method of the compound represented by Formula (1) is described below, but is not limited thereto.

In the compound represented by Formula (1) according to the aspect of the present disclosure, a compound having a structure in which a carbon atom of the carbazole ring of the oligocarbazole group X is directly bonded to the benzene ring of Formula (2-1) or (2-2) may be synthesized by, for example, a synthesis method represented by Reaction Scheme (1-I) or (1-II). The compound having such a structure may be, for example, a compound in which, in Formula (2-1) or (2-2), $L_3$ is a single bond and X is represented by Formula (3a) or (3b).

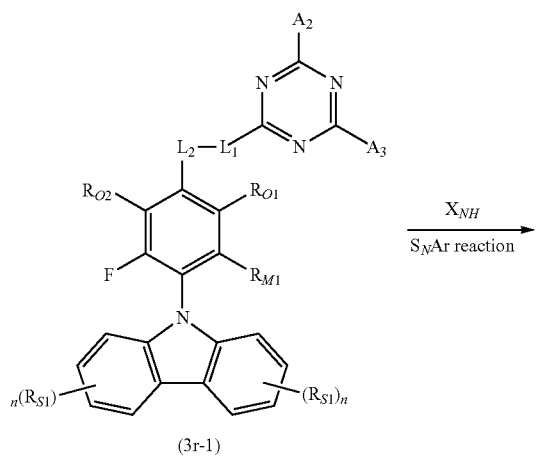

(3r-1)

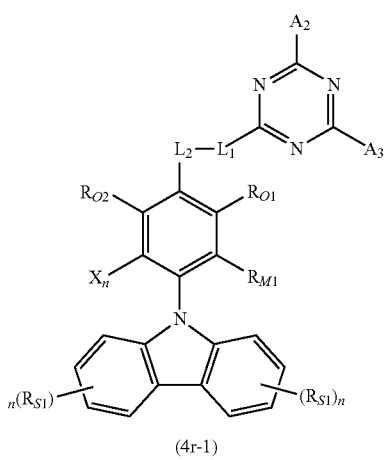

(4r-1)

(Reaction Schme 1-I)

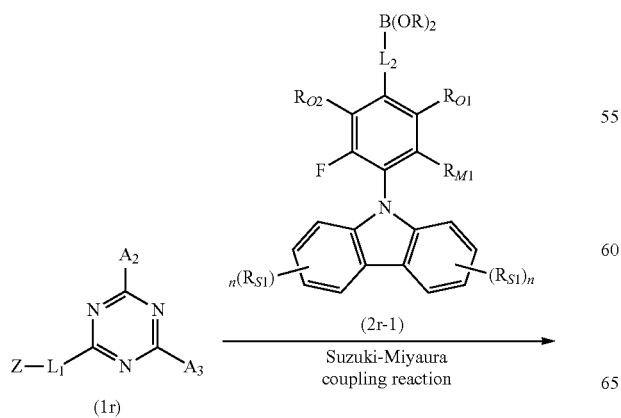

(Reaction Scheme 1-II)

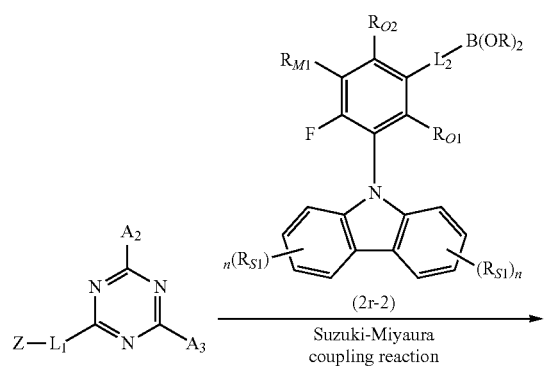

-continued

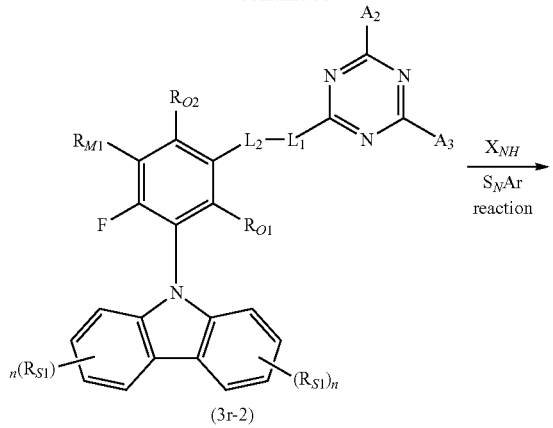

(3r-2)

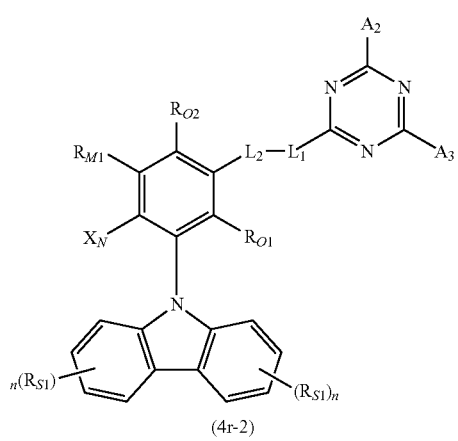

(4r-2)

In Reaction Schemes (1-I) and (1-II), $A_2$, $A_3$, and $L_1$ may each be the same as described in Formula (1), $L_2$, $R_{O1}$, $R_{O2}$, $R_{M1}$, each $R_{S1}$, and each n may each be the same as described in Formulae (2-1) and (2-2), Z indicates a halogen atom selected from a chlorine atom, a bromine atom, and an iodine atom, each occurrence of R may independently be a hydrogen atom, an alkyl group, an aromatic hydrocarbon group, or an aromatic heterocyclic group, wherein two R(s) may be linked to each other, $X_{NH}$ indicates a compound in which at least one nitrogen atom of a carbazole ring of the oligocarbazole group X is NH (secondary nitrogen atom), and $X_N$ indicates a substituted or unsubstituted oligocarbazole group bound to the benzene ring specified in Formulae (2-1) and (2-2) via a nitrogen atom of a carbazole ring of the oligocarbazole group.

Here, B is a boron atom, O is an oxygen atom, and F is a fluorine atom.

In addition, regarding the compound represented by Formula (1) according to the aspect of the present disclosure, a compound having a structure in which the benzene ring in Formula (2-1) or (2-2) and a carbon atom of a carbazole ring of the oligocarbazole group X are bonded via $L_3$ may be synthesized by, for example, by a synthesis method represented by Reaction Scheme (2-I) or (2-II). The compound having such a structure may be, for example, a compound in which, in Formula (2-1) or (2-2), $L_3$ is a single bond and X is represented by one of Formulae (3c) to (3g). In addition, in Formula (2-1) or (2-2), $L_3$ may be the aromatic hydrocarbon group or the aromatic heterocyclic group described in this formula, or may be a compound having a structure formed by directly binding the benzene ring specified in Formula (2-1) or (2-2) and a carbon atom of the aromatic hydrocarbon group or the aromatic heterocyclic group:

(Reaction Schme 2-I)

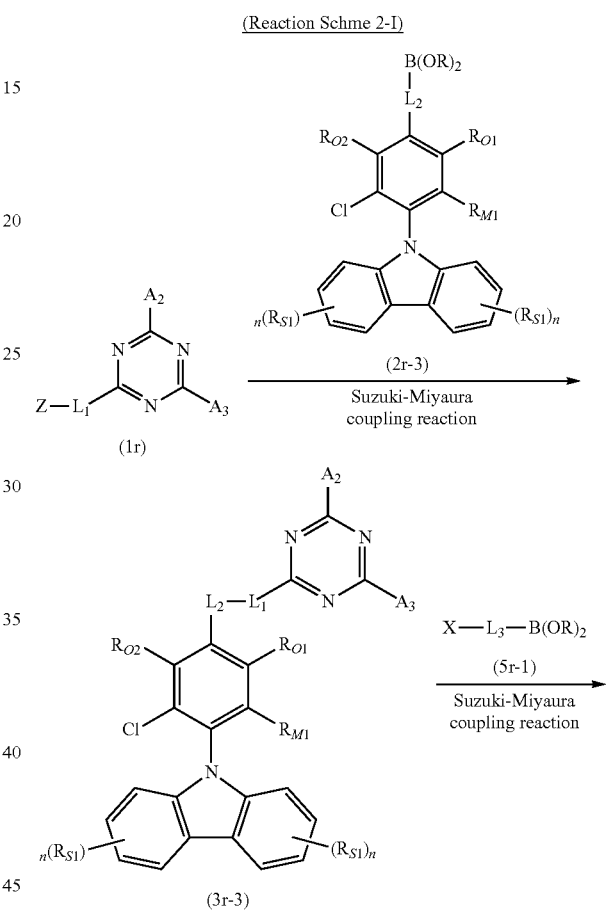

(3r-3)

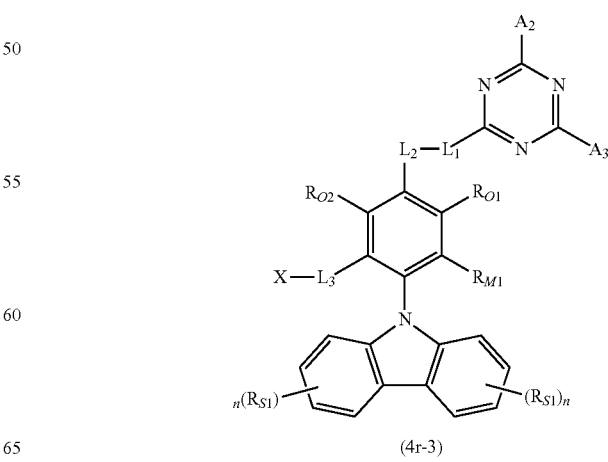

(4r-3)

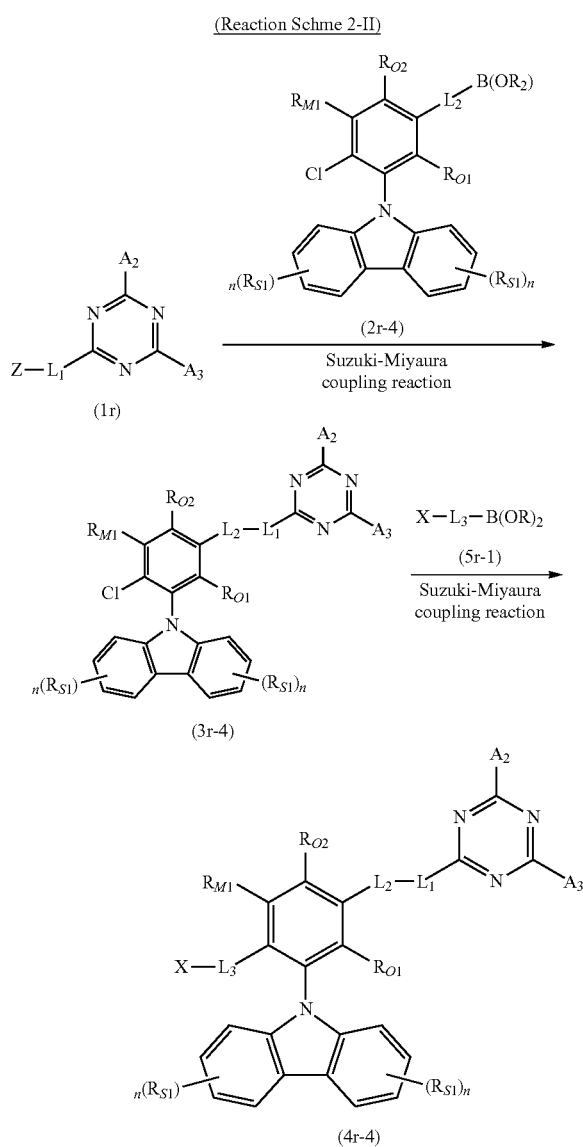

(Reaction Schme 2-II)

In Reaction Schemes (2-I) and (2-II), $A_2$, $A_3$, and L may each be the same as described in Formula (1), $L_2$, $R_{O1}$, $R_{O2}$, $R_{M1}$, each $R_{S1}$ each n, $L_3$, and X may each be the same as described in Formulae (2-1) and (2-2), Z indicates a halogen atom selected from a chlorine atom, a bromine atom, and an iodine atom, and each occurrence of R may independently be a hydrogen atom, an alkyl group, an aromatic hydrocarbon group, or an aromatic heterocyclic group, wherein two R(s) may be linked to each other.

Here, B is a boron atom, O is an oxygen atom, and Cl is a chlorine atom.

In addition, the compound represented by Formula (1) may be synthesized by, in addition to the Reaction Schemes above, a combination of reactions known to those skilled in the art.

Composition

Another aspect of the present disclosure provides a composition including other compounds in addition to the compound represented by Formula (1). The other compounds are not particularly limited, and compounds known in the art may be appropriately employed as materials for forming an organic layer of an organic electroluminescent device. Among these compounds, a luminescent material, a compound represented by Formula (B1) to be described later, a carbazole derivative (other than the compound represented by Formula (1)) to be described later, or an azine derivative (other than the compound represented by Formula (1)) to be described may be preferable.

Hereinafter, the carbazole derivative (other than the compound represented by Formula (1)) is also simply referred to as the "carbazole derivative". Hereinafter, the azine ring derivative (other than the compound represented by Formula (1)) is also simply referred to as the "azine ring derivative".

In the composition according to the another aspect of the present disclosure, an amount of the compound represented by Formula (1) may be preferably in a range of about 5 weight % to about 95 weight % based on 100 weight % of the composition. In addition, the amount of the compound represented by Formula (1) may be preferably in a range of about 10 weight % to about 90 weight %, and more preferably in a range of about 20 weight % to about 80 weight %. In this range, the solubility may be further improved so that precipitation from the solution becomes difficult, and the pot life of the solution becomes longer. In addition, the driving voltage of an organic electroluminescent device is lowered, thereby further improving luminescence efficiency and luminescence lifespan.

Hereinafter, a luminescent material which is another preferable compound, a compound represented by Formula (B1), a carbazole derivative, and an azine ring derivative will be described in detail.

Luminescent Material

The composition according to another aspect of the present disclosure may preferably further include a luminescent material. That is, the composition including the compound represented by Formula (1) and the luminescent material may be preferable.

As the luminescent material, any material having high luminescence function may be used, and for example, an organic fluorescent molecule, a phosphorescent luminescent material consisting of an organic metal complex that includes a metal element of the platinum family (hereinafter, also referred to as a phosphorescent metal complex of the platinum family), a quantum dot, and the like may be used.

The luminescent material may be preferably a phosphorescent metal complex of the platinum family from the viewpoint of luminescence efficiency. The metal element of the platinum family represents the generic term for ruthenium (Ru), rhodium (Rh), palladium (Pd), osmium (Os), iridium (Ir), and platinum (Pt). Among these metals, a phosphorescent Ir complex and a phosphorescent Pt complex may be more preferable, and a phosphorescent Ir complex may be more preferable.

The phosphorescent metal complex of the platinum family is not particularly limited, and any known material may be appropriately used. For example, the known phosphorescent metal complex of the platinum family described in paragraphs [0105] to [0113] in the specification of US2016/0093808 and JP2014-509067, which are each incorporated by reference in their entirety, may also be included. In addition, the phosphorescent metal complex of the platinum family described in such reference documents may be used as a basis for correction in the specification of the present application.

Hereinafter, specific examples of the phosphorescent Ir complex, which is a preferable example of the phosphorescent metal complex of the platinum family, will be shown below. However, the phosphorescent metal complex of the platinum family is not limited thereto:

D1
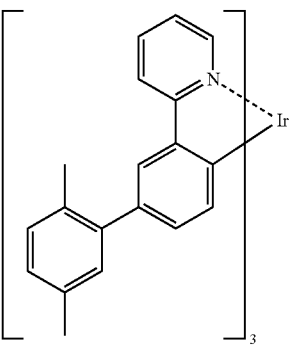

D2
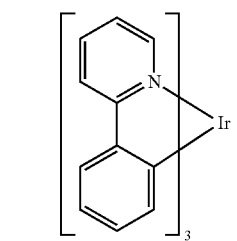

D3
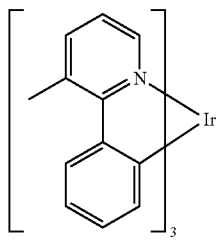

D4
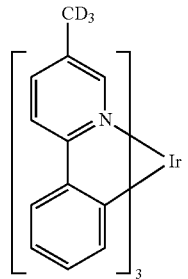

D5
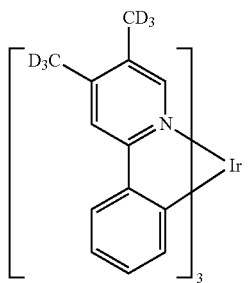

D6
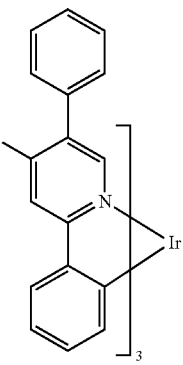

D7
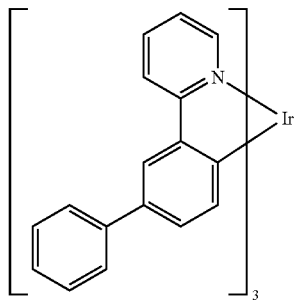

D8
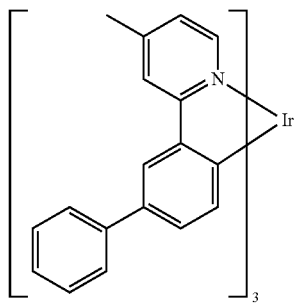

D9
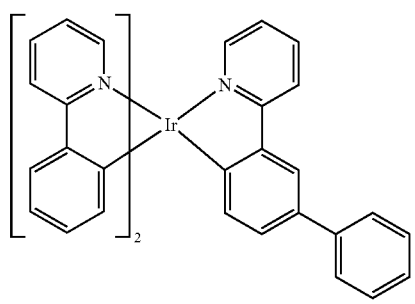

D10
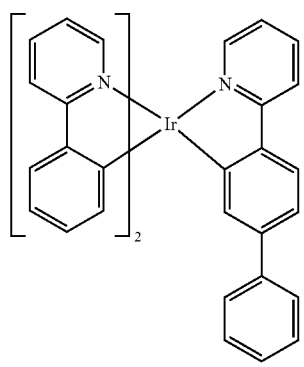

D11 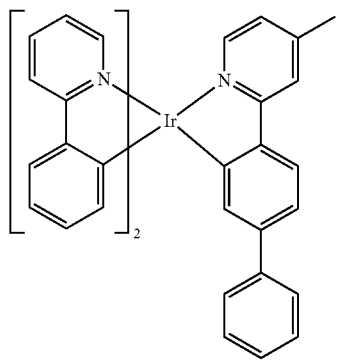
D12 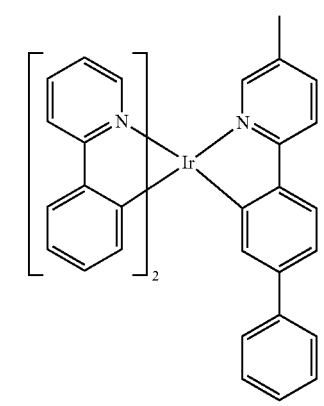
D13 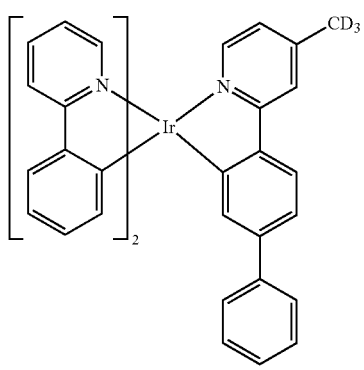
D14 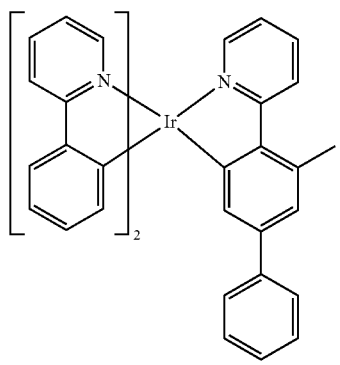
D15 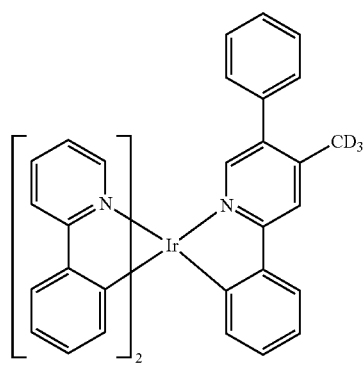
D16 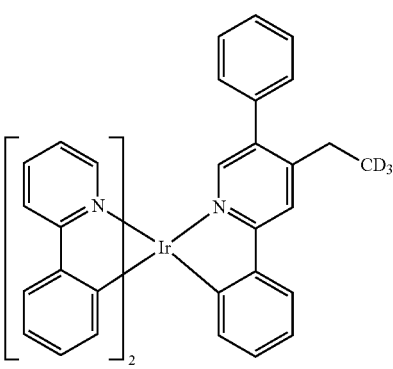
D17 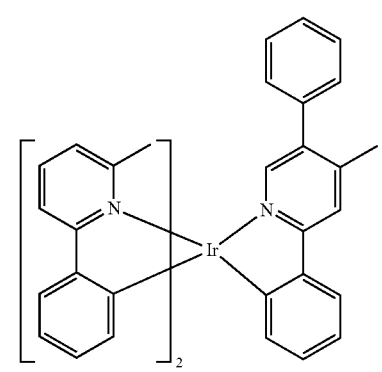
D18 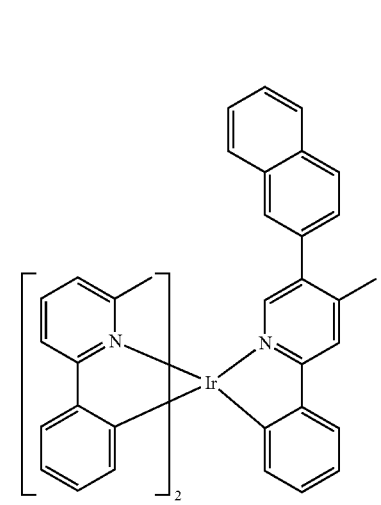

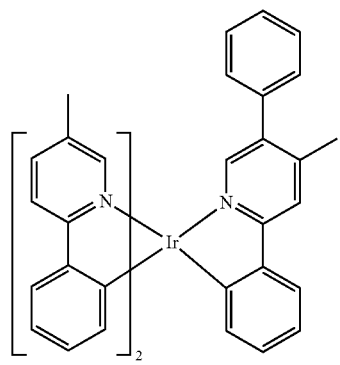 D19
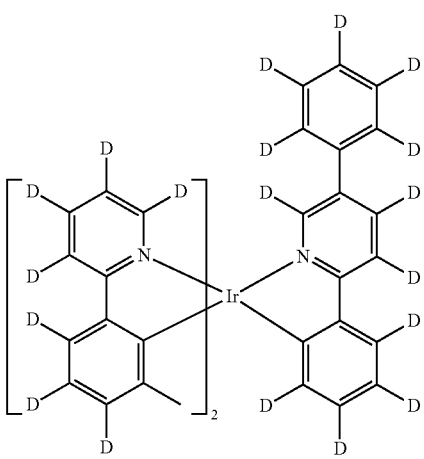 D20
D21
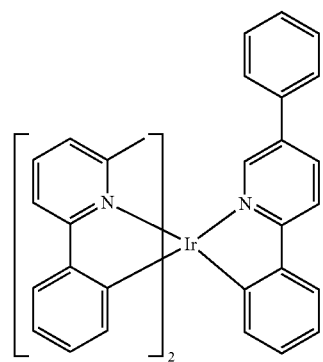 D22
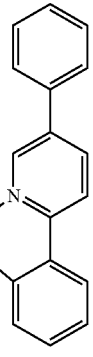 D23
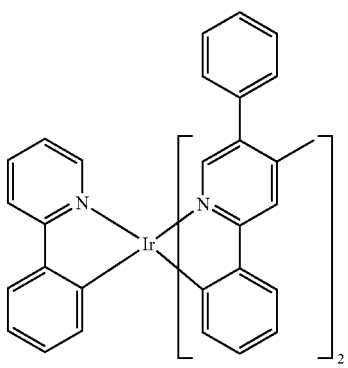 D24
D25
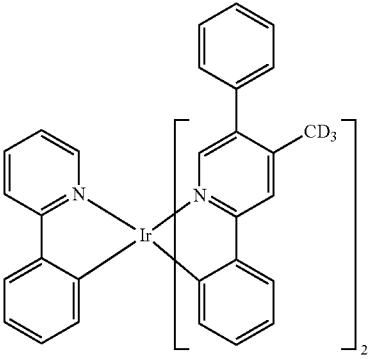 D26

-continued
D27
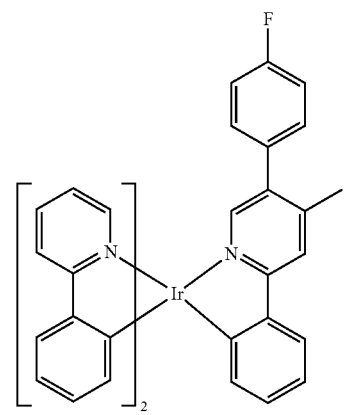
D28
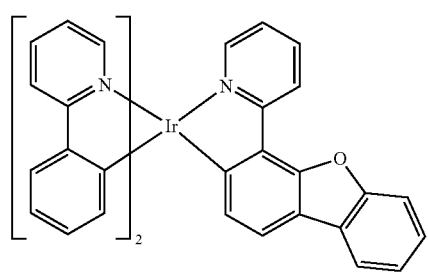
D29
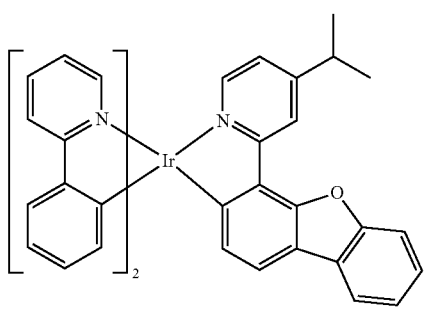
D30
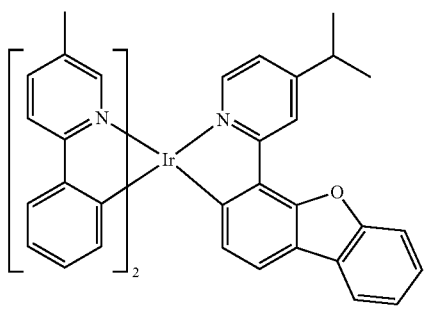
D31
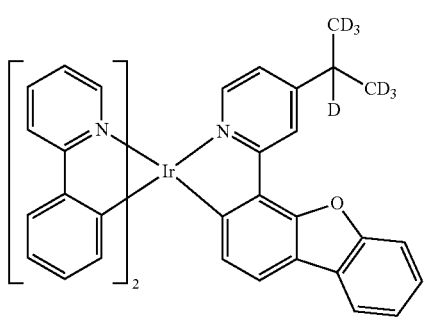
D32
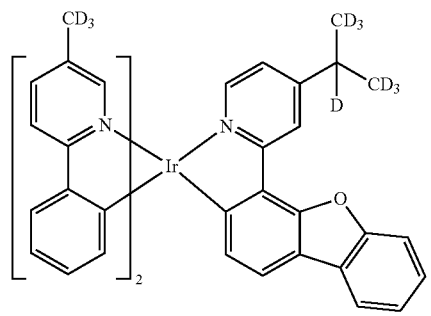
D33
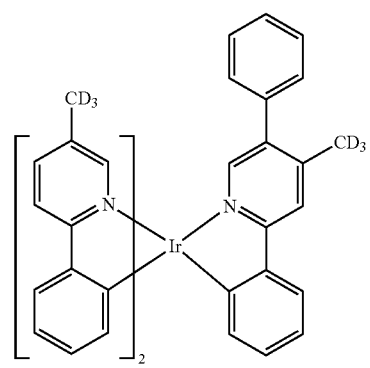
D34
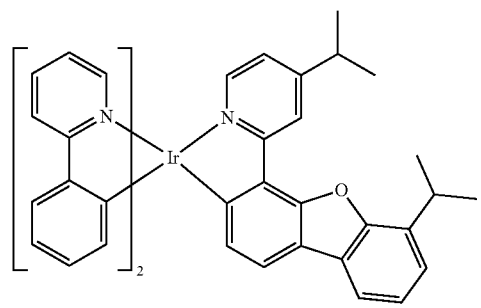
D35
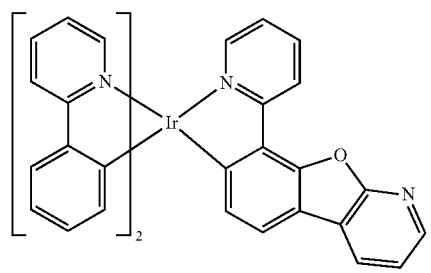
D36
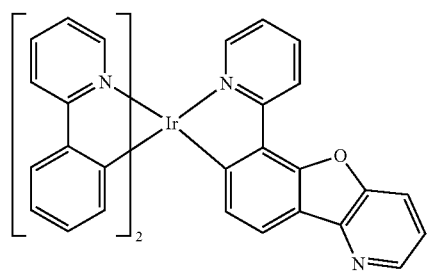

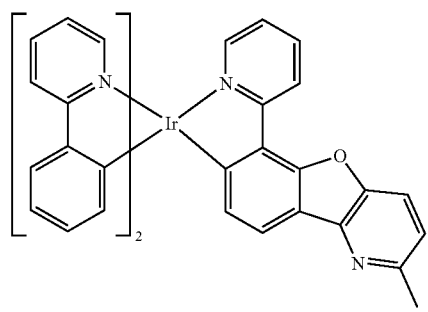 D37
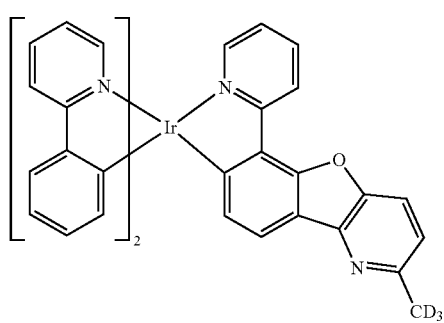 D38
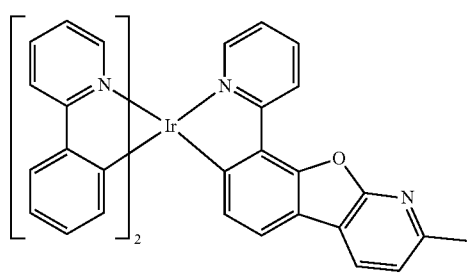 D39
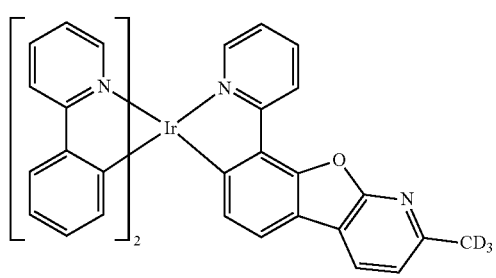 D40
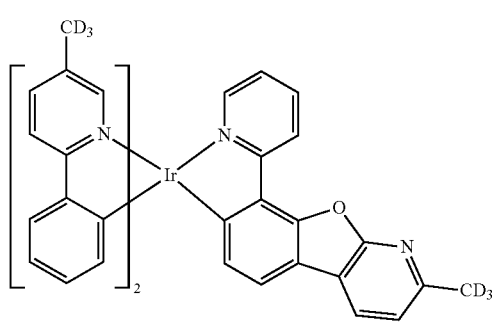 D41
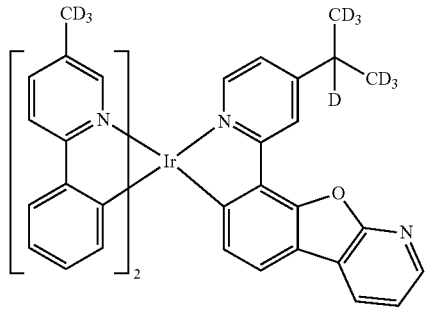 D42
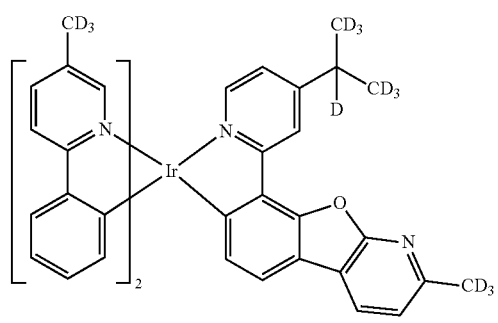 D43
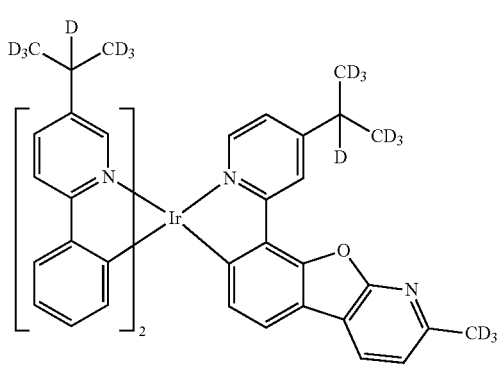 D44
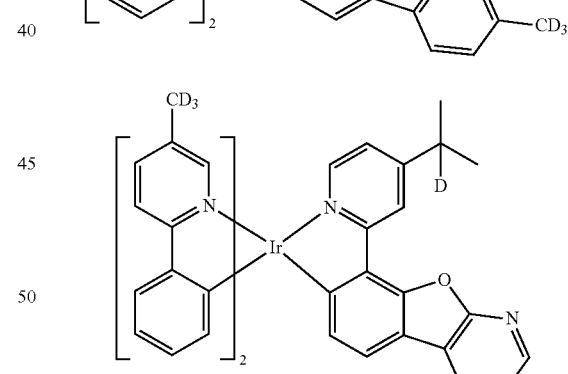 D45
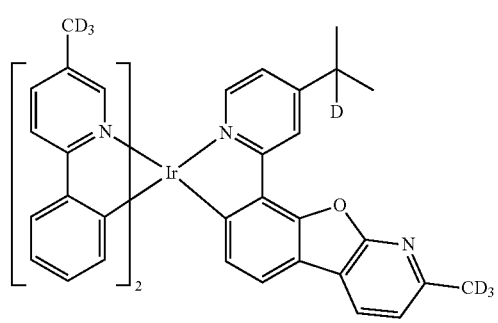 D46

D47
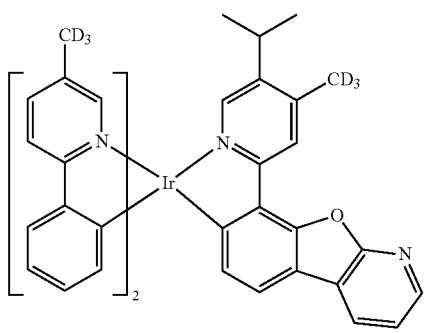
D48
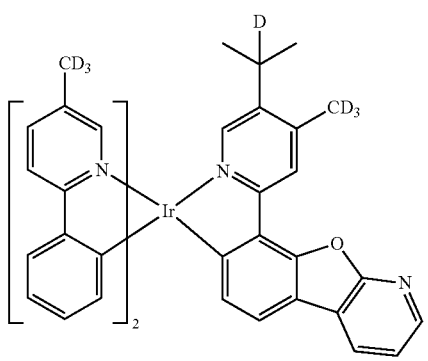
D49
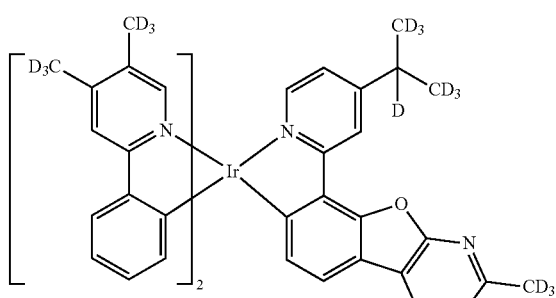
D50
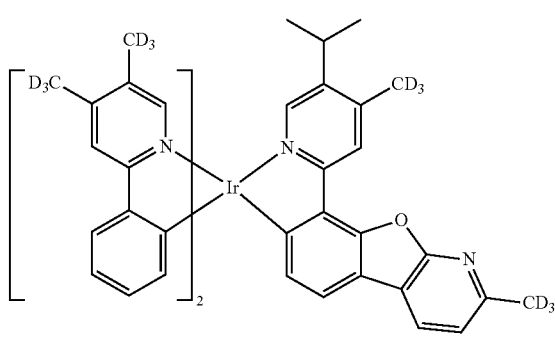
D51
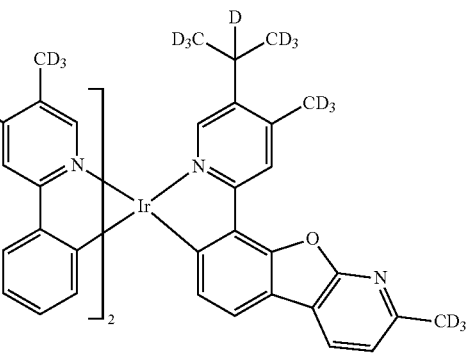
D52
D53
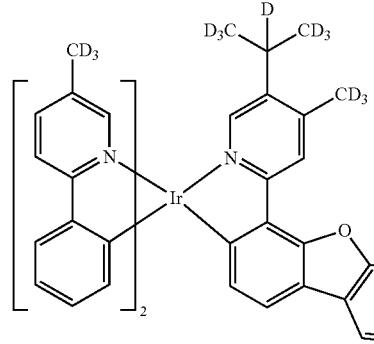
D54
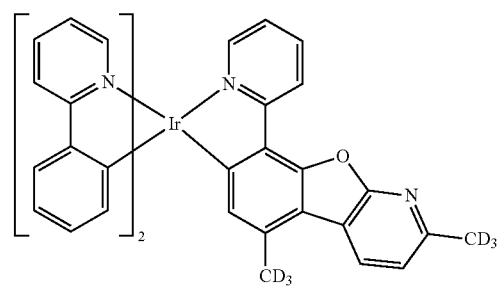

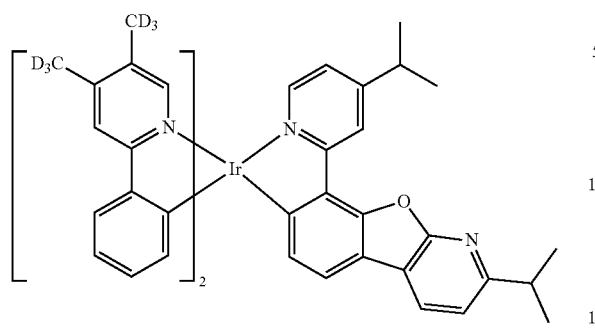
D55
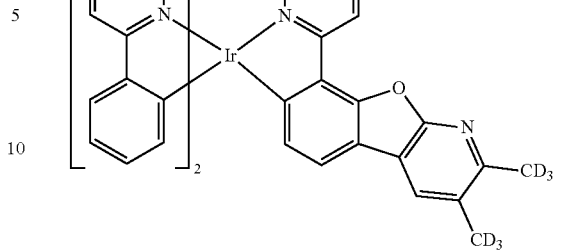
D59
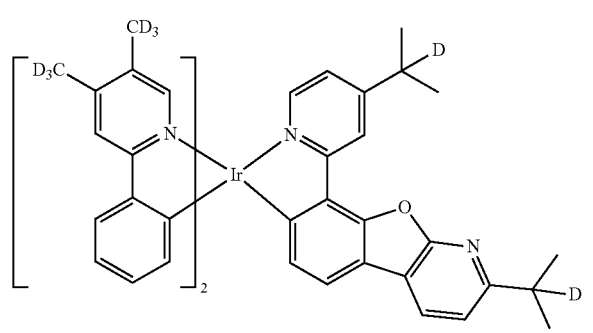
D56
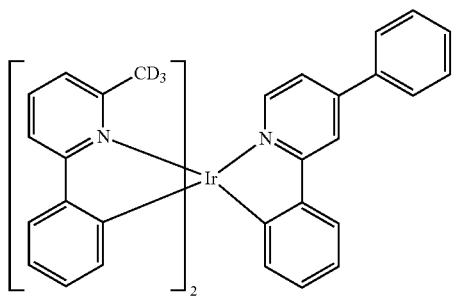
D60
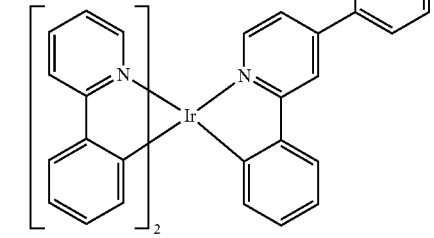
D61
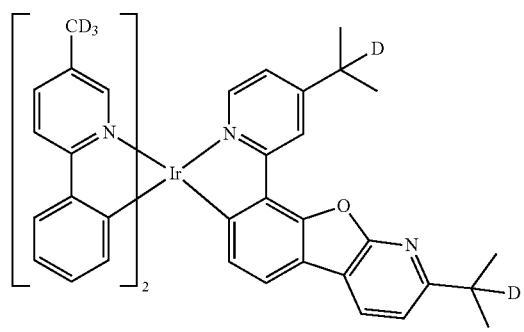
D57
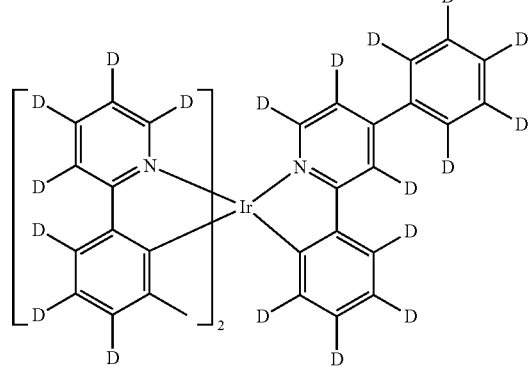
D62
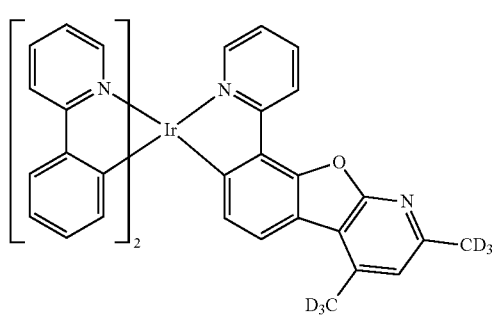
D58
D63

D64 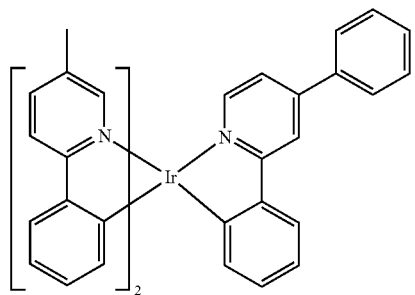
D65 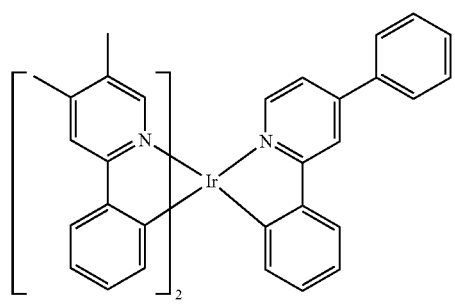
D66 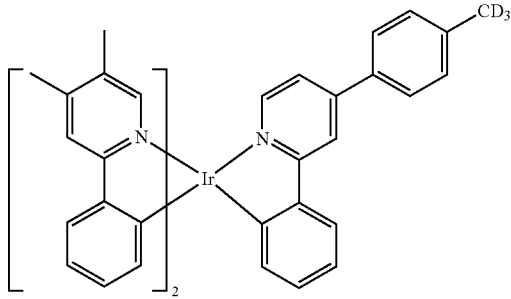
D67 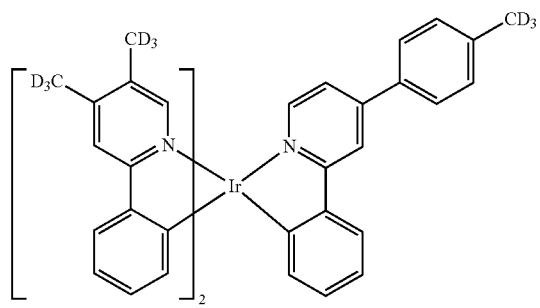
D68 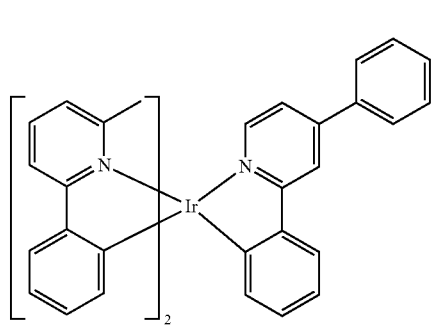
D69 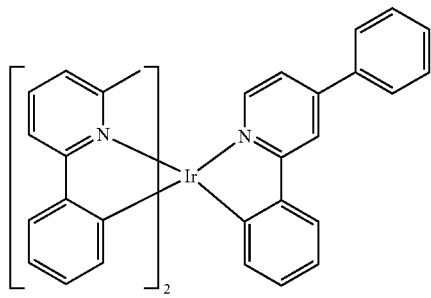
D70 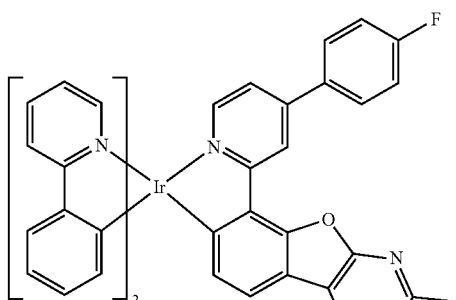
D71 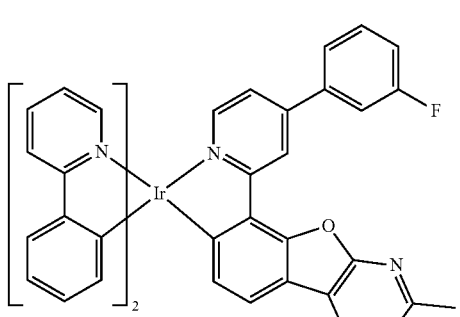
D72 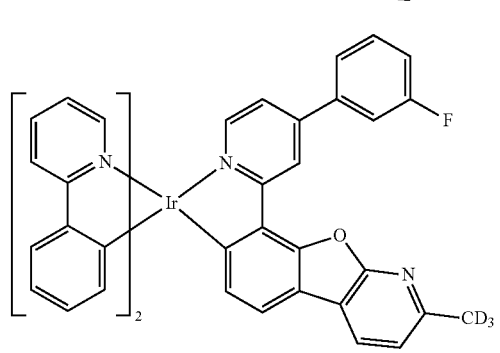
D73 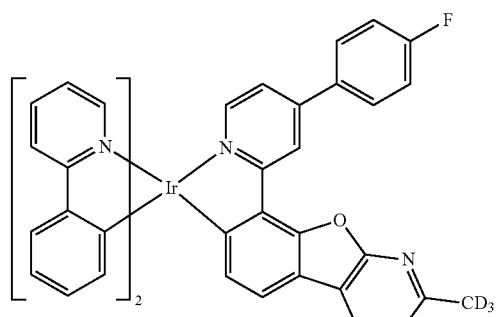

D74
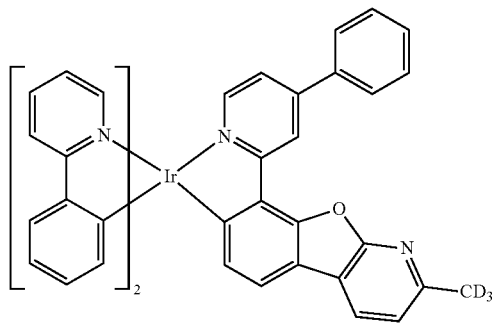
D75
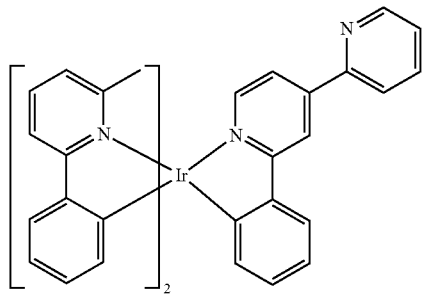
D76
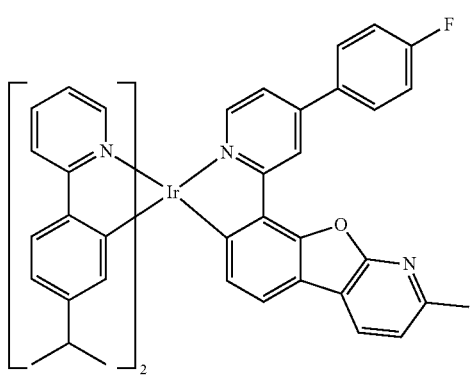
D77
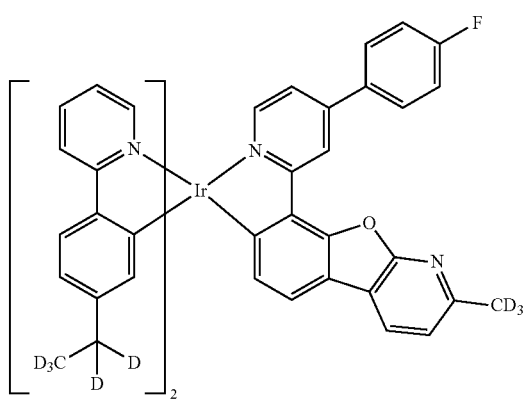
D78
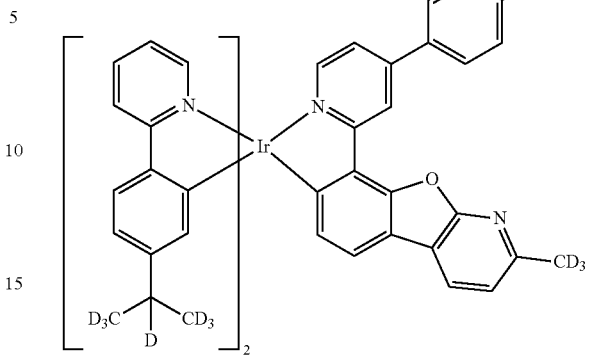
D79
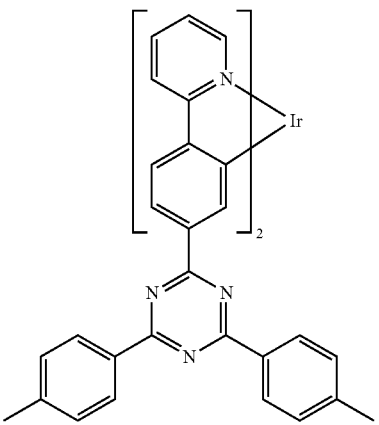
D80
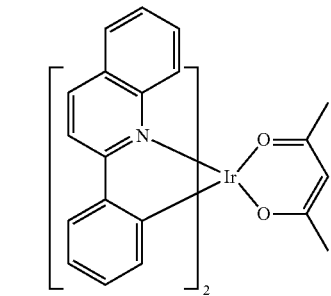
D81
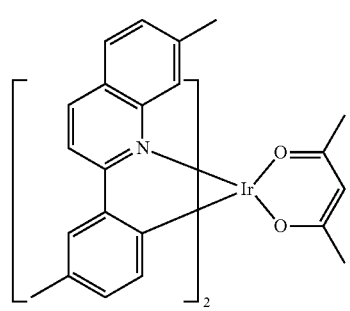

D82
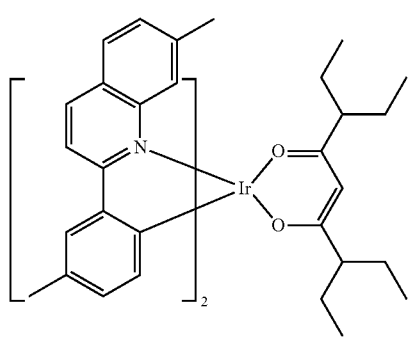
D83
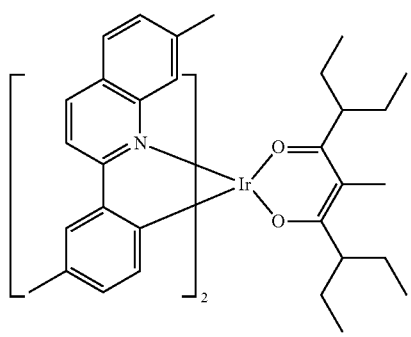
D84
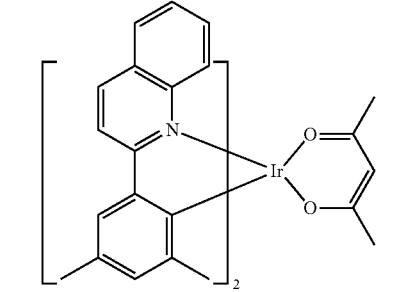
D85
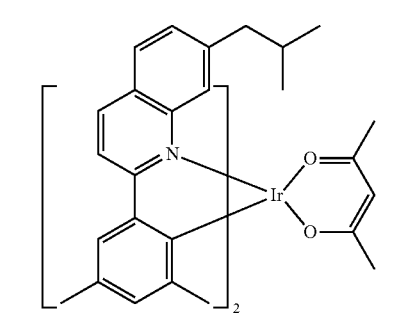
D86
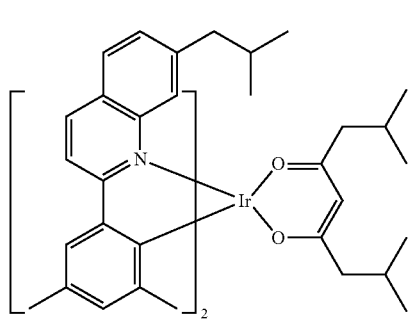
D87
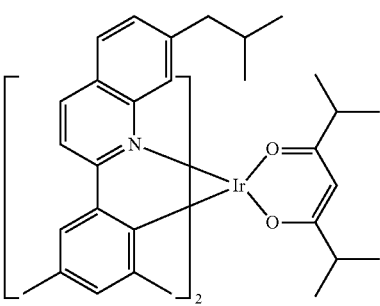
D88
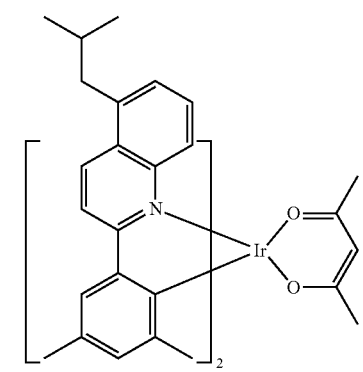
D89
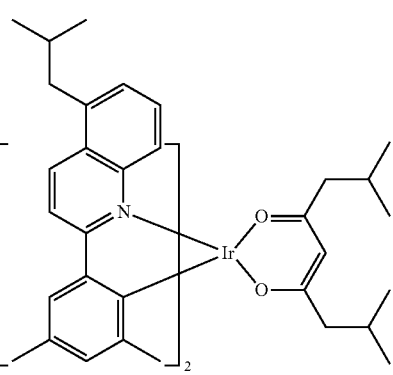
D90
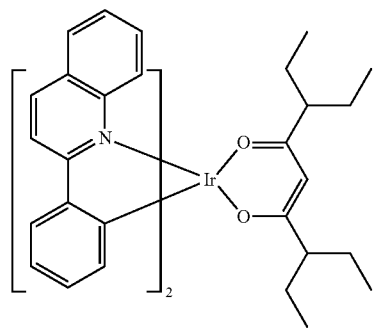

-continued
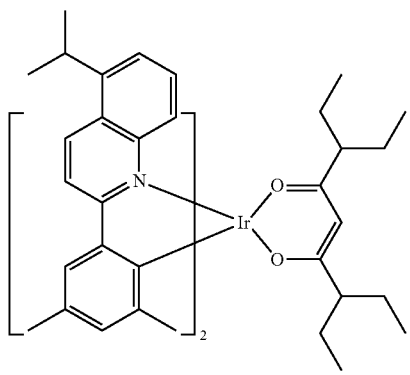
D91

D92
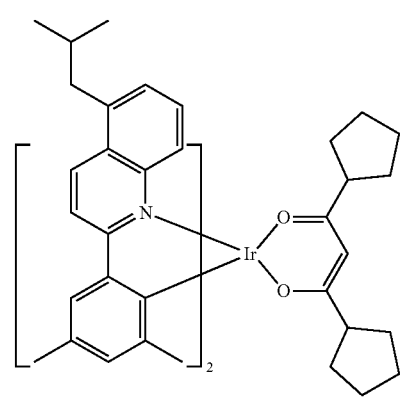
D93
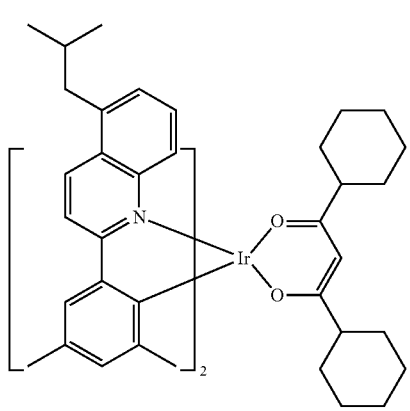
D94
-continued
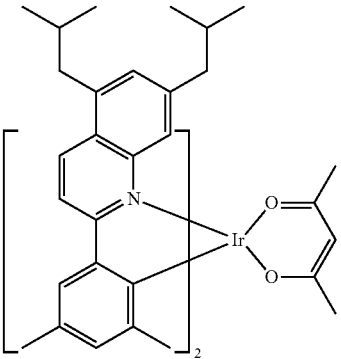
D95
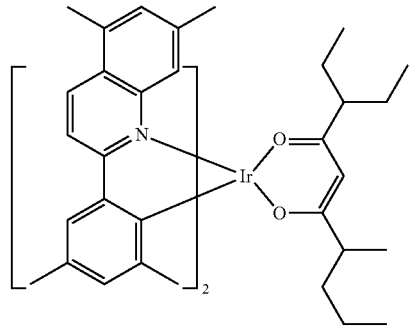
D96
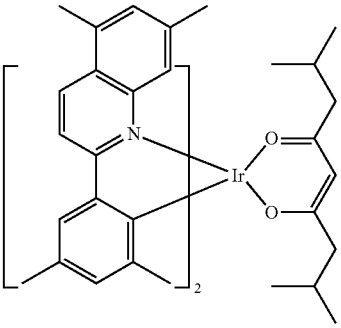
D97
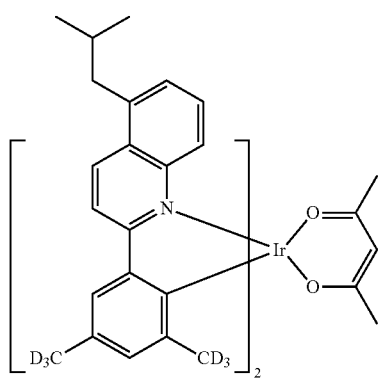
D98

-continued
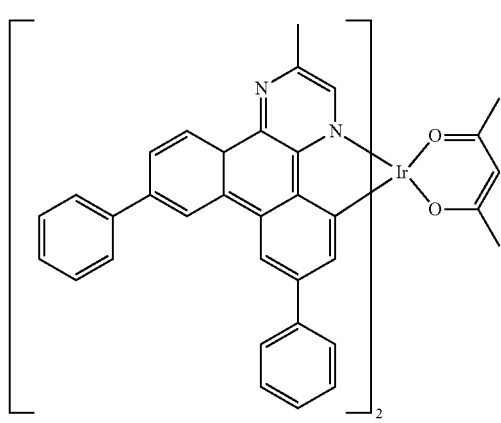
D99
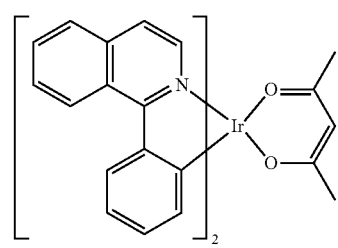
D100
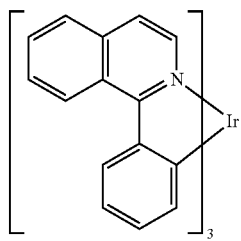
D101
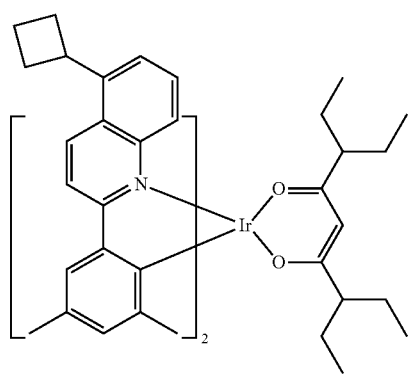
D102
-continued
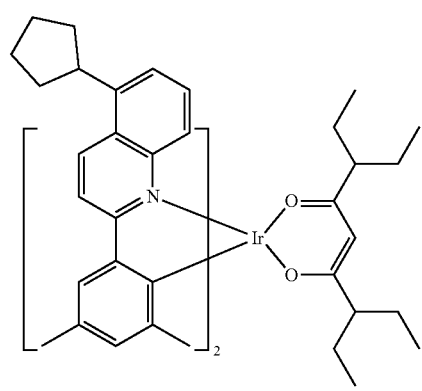
D103
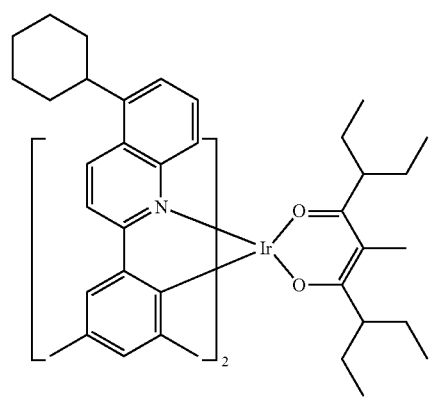
D104
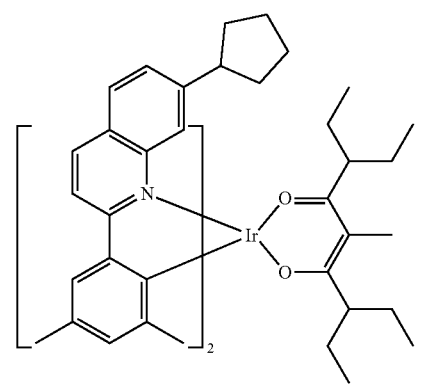
D105
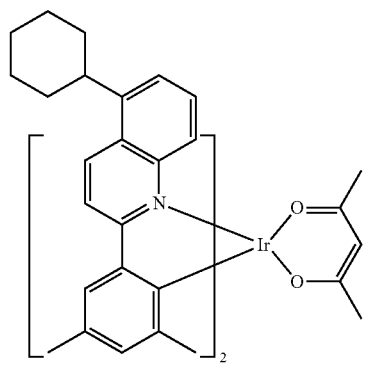
D106

D107
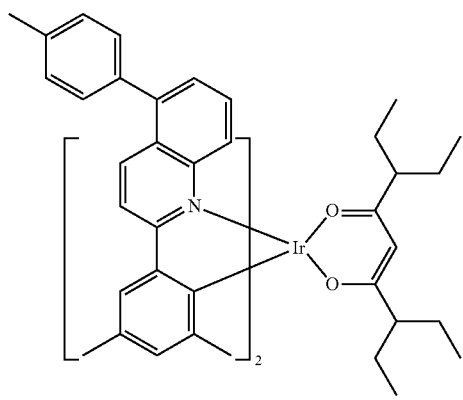
D108
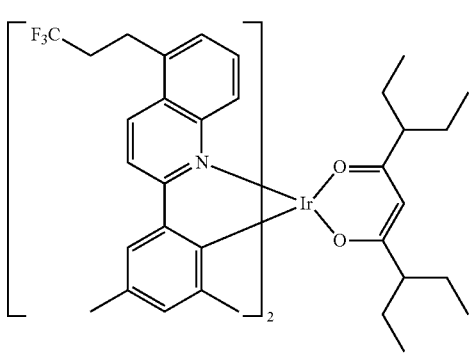
D109
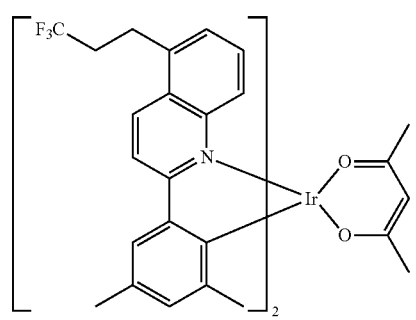
D110
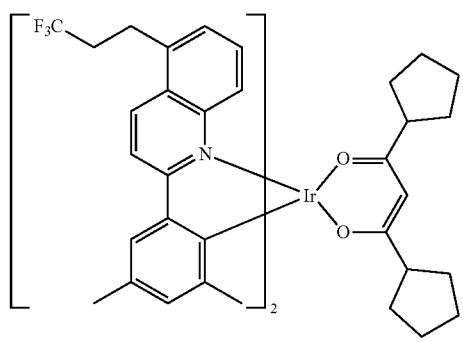
D111
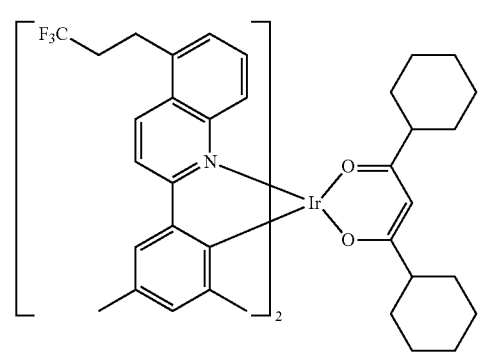
D112
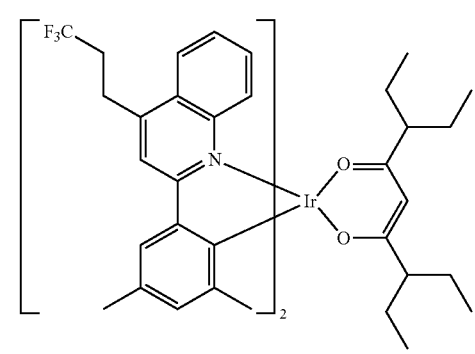
D113
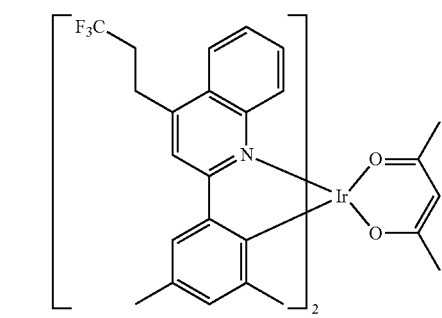
D114
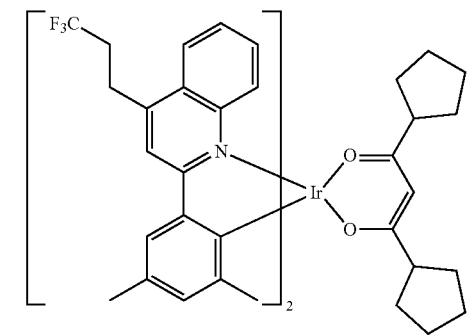

-continued
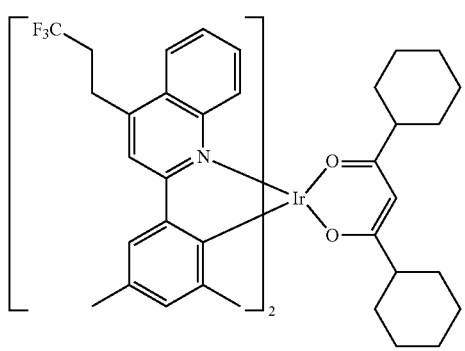
D115
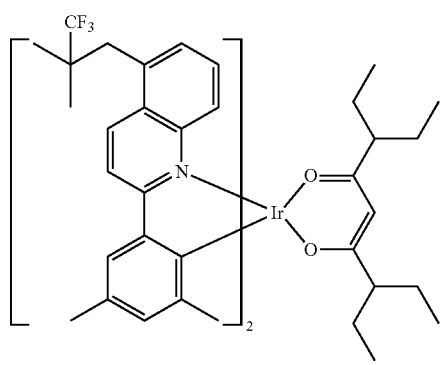
D116
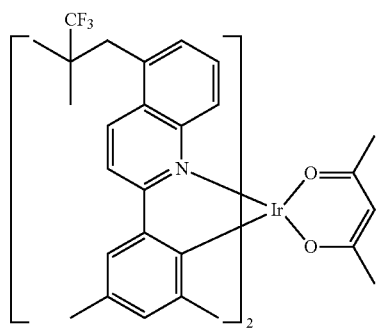
D117
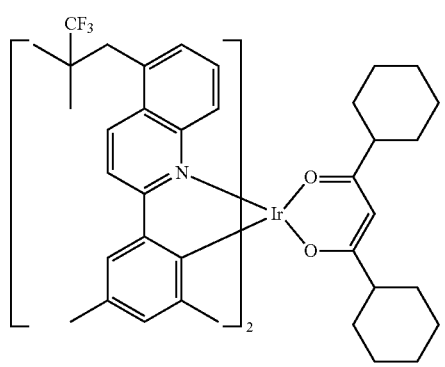
D118
-continued
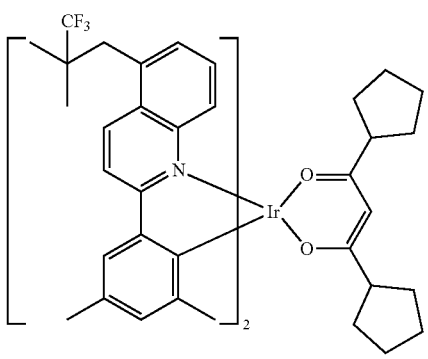
D119
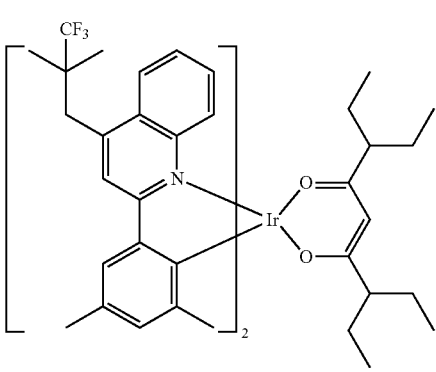
D120
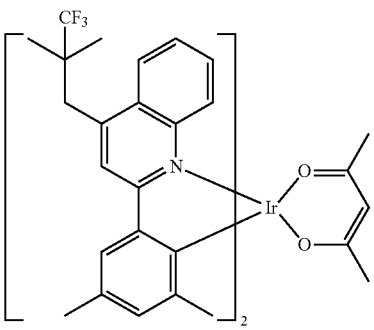
D121
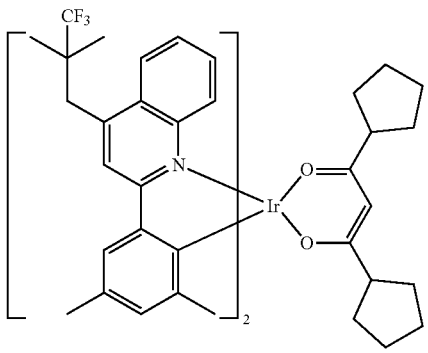
D122

D123
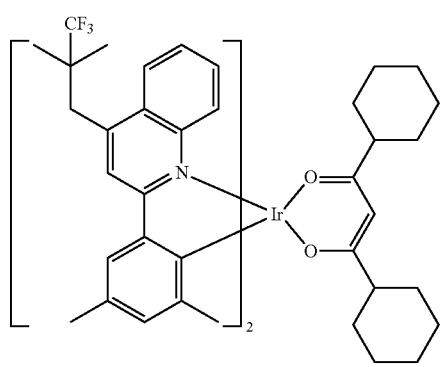
D124
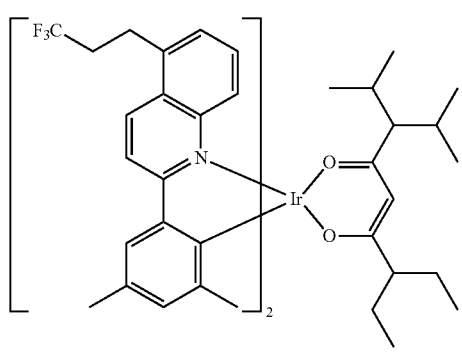
D125
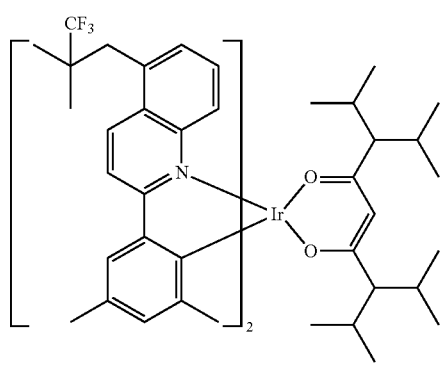
D126
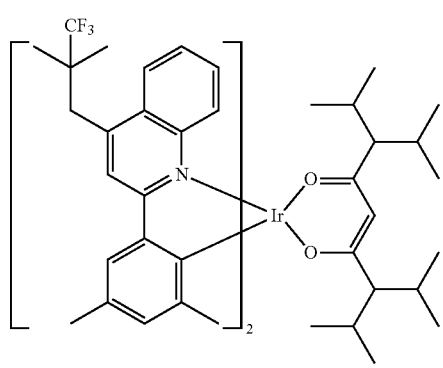
D127
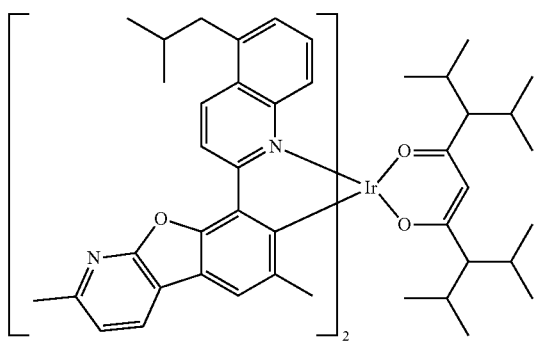
D128
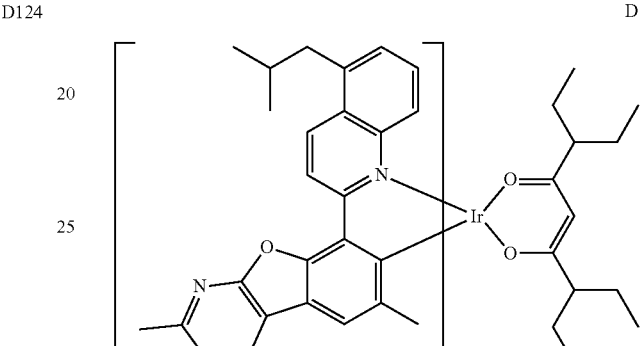
D129
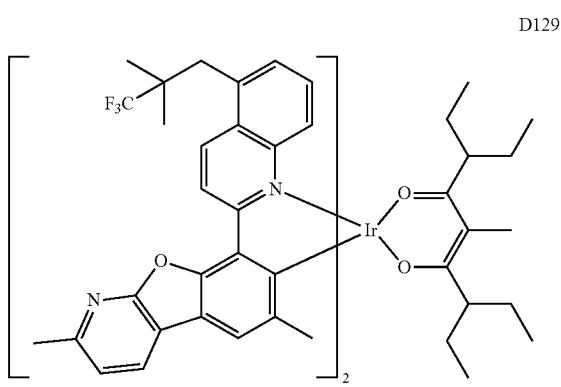
D130
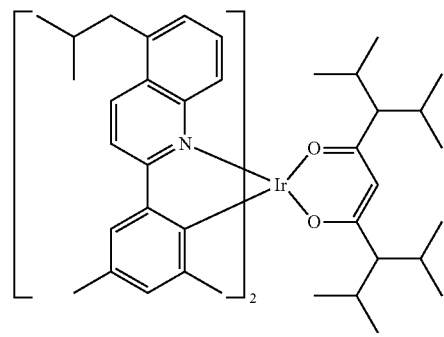

D131
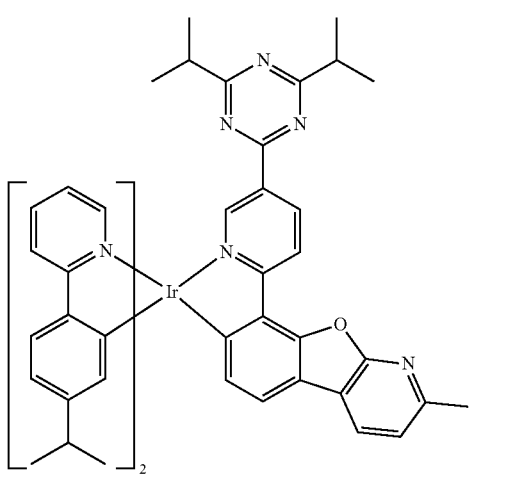
D132
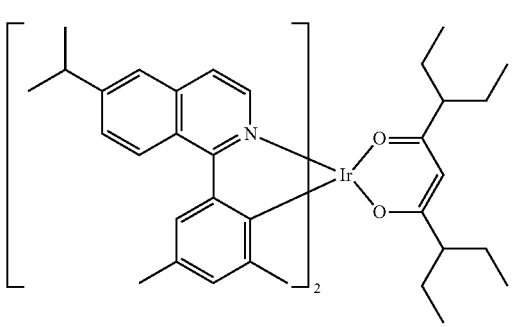
D133
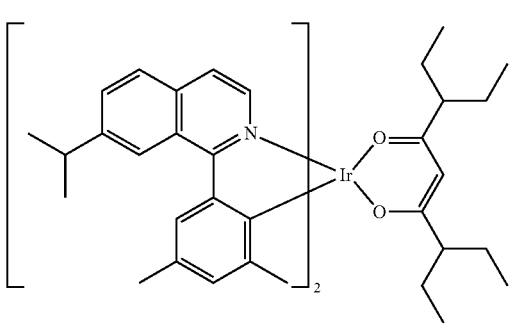
D134
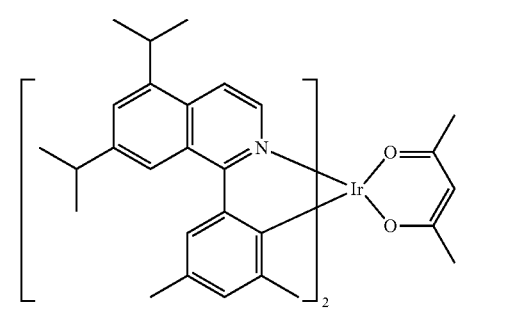
D135
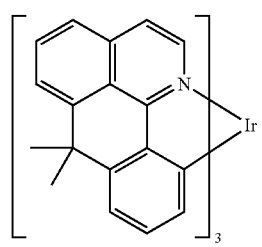
D136
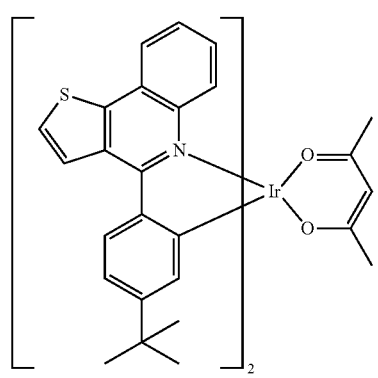
D137
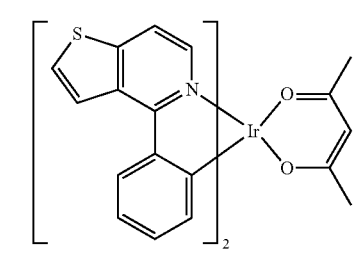
D138
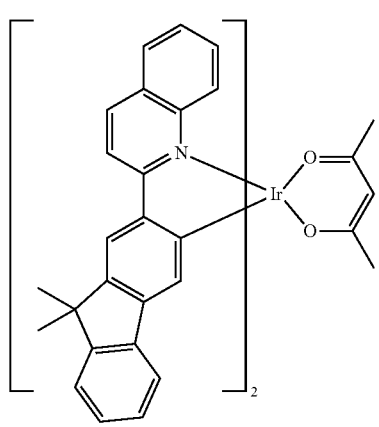
D139
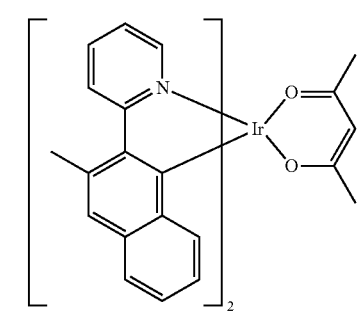

-continued

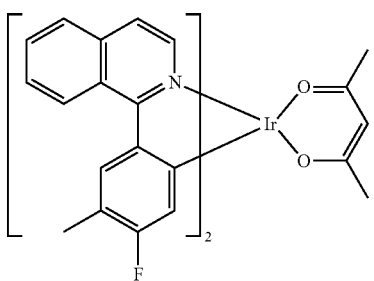
D140

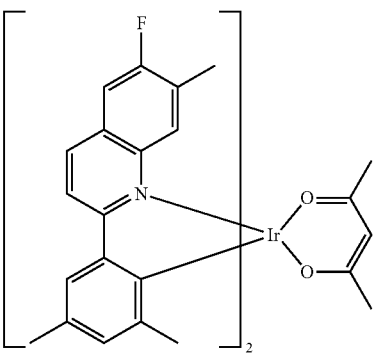
D141

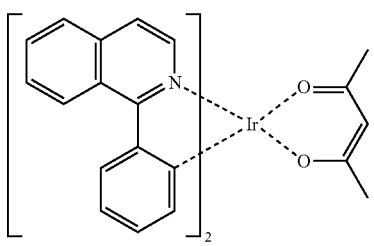
D142

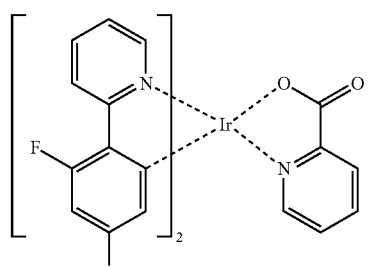
D143

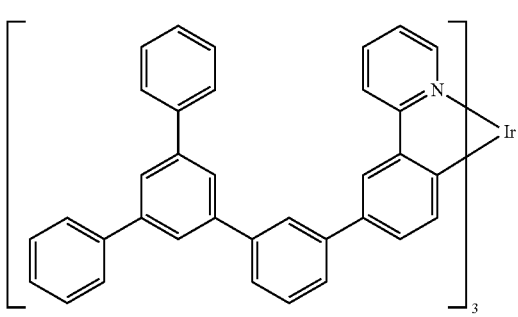
D144

Among these examples of the phosphorescent metal complex of the platinum family, Complex D144 may be preferable.

In the composition, the amount of the luminescent material may be preferably in a range of about 0.5 parts by weight to about 50 parts by weight based on 100 parts by weight of the compound represented by Formula (1) which functions as a host material. In addition, the amount of the luminescent material may be preferably in a range of about 1 parts by weight to about 30 parts by weight, and more preferably in a range of about 2 parts by weight to about 25 parts by weight.

In addition, the amount of the luminescent material in the composition may be preferably in a range of about 0.5 parts by weight to about 50 parts by weight based on 100 parts by weight of the total weight of the compound represented by Formula (1) which functions as a host material, the compound represented by Formula (B1) which functions as a host material, the carbazole derivative which functions as a host material as described below, and the azine ring derivative which functions as a host material as described below. In addition, the amount of the luminescent material may be preferably in a range of about 1 parts by weight to about 30 parts by weight, and more preferably in a range of about 2 parts by weight to about 25 parts by weight. When the amount of the luminescent material is within these ranges above, the solubility of the composition may be further improved so that precipitation from a solution becomes difficult to occur, and the pot life of a solution becomes longer. In addition, the driving voltage of an organic electroluminescent device is lowered, thereby further improving luminescence efficiency and luminescence lifespan.

Compound Represented by Formula (B1)

The composition according to another aspect of the present disclosure may further preferably include the compound represented by Formula (B1). The composition may preferably include the compound represented by Formula (1) and compound represented by Formula (B1):

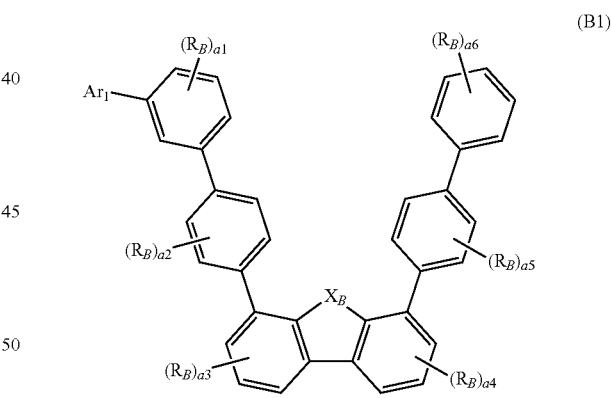

(B1)

wherein, in Formula (B1), $X_B$ is O, S, or Se, $Ar_1$ is a substituted or unsubstituted phenyl group, a substituted or unsubstituted naphthyl group, or a monovalent aromatic hydrocarbon ring aggregation group comprising two or more substituted or unsubstituted benzene rings directly bonded to one another, two or more substituted or unsubstituted naphthalene rings directly bonded to one another, or at least one substituted or unsubstituted benzene ring and at least one substituted or unsubstituted naphthalene ring directly bonded to each other (wherein a ring is not further condensed in the benzene ring and the naphthalene ring), each occurrence of $R_B$ is independently a deuterium atom, a cyano group, a fluoro group, a substituted or unsubstituted alkyl group having 1 to 20 carbon atoms, a substituted or unsubstituted phenyl group, a substituted or unsubstituted naphthyl group, or a monovalent aromatic hydrocarbon ring aggregation group in which two or more substituted or unsubstituted benzene rings, two or more substituted or unsubstituted naphthalene rings or at least one substituted or unsubstituted benzene ring and at least one substituted or unsubstituted naphthalene ring are directly bonded to each other via a single bond (wherein a ring is not further condensed in the benzene ring and the naphthalene ring), a1, a2, and a5 are each independently 0, 1, 2, 3, or 4, a3 and a4 are each independently 0, 1, 2, or 3, and a6 is 0, 1, 2, 3, 4, or 5.

Also, regarding the compound according to the aspect of the present disclosure, in the monovalent aromatic hydrocarbon ring aggregation group, the binding positions between the respective benzene rings or the respective naphthalene rings are not particularly limited. That is, the compound according to the aspect of the present disclosure may include those having a structure in which the respective benzene rings or the respective naphthalene rings are bonded at various binding positions.

The compound represented by Formula (B1) may be able to realize high efficiency and a long lifespan of an organic electroluminescent device. This is presumed to be because the compound represented by Formula (B1) has a low glass transition temperature, a good LUMO level, and a balanced charged electron mobility between electrons and holes. In addition, the compound represented by Formula (B1) is difficult to precipitate from a solution, and has a long pot life of a solution. Not wishing to be bound by theory, the reason for this is presumed to be that the compound represented by Formula (B1) has a great number of conformations, so that the compound is highly conformationally unstable and the crystallization thereof is difficult.

In Formula (B1), a phenyl group, a naphthyl group, or a monovalent aromatic hydrocarbon ring aggregation group, which can constitute $Ar_1$, is not particularly limited. In detail, examples of substituents that can constitute $Ar_1$ are a phenyl group, a terphenyl group, a quaterphenyl group, a quinquephenyl group, a sexyphenyl group, a naphthyl group, a binaphthyl group, a ternaphthyl group, a quaternaphthyl group, a phenylnaphthyl group, a biphenylnaphthyl group, a diphenylnaphthyl group, a phenylbiphenylnaphthyl group, and the like.

In addition, a ring is not further condensed with the benzene ring and the naphthalene ring that form the aromatic hydrocarbon ring aggregation group. In other words, a condensed ring that the aromatic hydrocarbon ring aggregation group can have is only the naphthalene ring in which two rings of the naphthalene ring are condensed. Not wishing to be bound by theory, this is because, when a condensed ring formed by condensation of three or more rings is additionally included, the glass transition temperature becomes high as described above, making it difficult to remove volatile impurity molecules.

In Formula (B1), the alkyl group having 1 to 20 carbon atoms that can constitute $R_B$ is not particularly limited, and may be a linear, branched, or cyclic alkyl group having 1 to 20 carbon atoms. In detail, examples of the substituted or unsubstituted monovalent alkyl group having 1 to 20 carbon atoms are a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, an neopentyl group, a 1,2-dimethyl propyl group, an n-hexyl group, an isohexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethylhexyl group, a 3-methyl-1-isopropyl butyl group, a 2-methyl-1-isopropyl butyl group, a 1-tert-butyl-2-methyl propyl group, an n-nonyl group, a 3,5,5-trimethyl hexyl group, an n-decyl group, an isodecyl group, an n-undecyl group, a 1-methyl decyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, an n-tetracosyl group, a cyclopropyl group, a cyclopentyl group, a cyclohexyl group, a cycloheptyl group, a cyclooctyl group, a norbornyl group, an adamantyl group, and the like. Among these examples, a linear, branched, or cyclic alkyl group having 1 to 8 carbon atoms may be preferable.

The monovalent aromatic hydrocarbon ring aggregation group capable of constituting $R_B$ is the same as described in connection with $Ar_1$ in Formula (B1), and thus a description thereof is omitted.

In Formula (B1), a phenyl group, a naphthyl group, or a monovalent aromatic hydrocarbon ring aggregation group, which can constitute $Ar_1$, may be substituted with other substituents.

Examples of the other substituents capable of substituting a phenyl group, a naphthyl group, or a monovalent aromatic hydrocarbon ring aggregation group, which can constitute $Ar_1$, are a deuterium atom, a cyano group, a fluoro group, a substituted or unsubstituted alkyl group having 1 to 20 carbon atoms, and the like. Among these examples, a cyano group, a fluoro group, or a substituted or unsubstituted alkyl group having 1 to 20 carbon atoms may be preferable. Here, the other substituents do not form a ring through any condensation or binding.

In Formula (B1), the alkyl group having 1 to 20 carbon atoms, a phenyl group, a naphthyl group, or a monovalent aromatic hydrocarbon ring aggregation group, which can constitute $R_B$, may be substituted with other substituents.

Examples of the other substituents capable of substituting a phenyl group, a naphthyl group, or a monovalent aromatic hydrocarbon ring aggregation group, which can constitute $R_B$, are a deuterium atom, a cyano group, a fluoro group, a substituted or unsubstituted alkyl group having 1 to 20 carbon atoms, and the like. Among these examples, a cyano group, a fluoro group, or a substituted or unsubstituted alkyl group having 1 to 20 carbon atoms may be preferable. Here, the other substituents do not form a ring through any condensation or binding.

Examples of other substituents capable of substituting the alkyl group having 1 to 20 carbon atoms that can constitute $R_B$ are a deuterium atom, a cyano group, a fluoro group, and the like. Among these examples, a cyano group and a fluoro group may be preferable.

The alkyl group having 1 to 20 carbon atoms capable of constituting other substituents is the same as described in connection with $R_B$ in Formula (B1), and thus a description thereof is omitted.

In addition, the monovalent aromatic hydrocarbon ring aggregation group capable of constituting other substituents is the same as described in connection with $Ar_1$, and thus a description thereof is omitted.

In addition, examples of other new substituents capable of further substituting the alkyl group having 1 to 20 carbon atoms are a deuterium atom, a cyano group, a fluoro group, and the like. Among these examples, a cyano group and a fluoro group may be preferable.

Specific examples of the compound represented by Formula (B1) are provided below. However, the present disclosure is not limited to these specific examples:

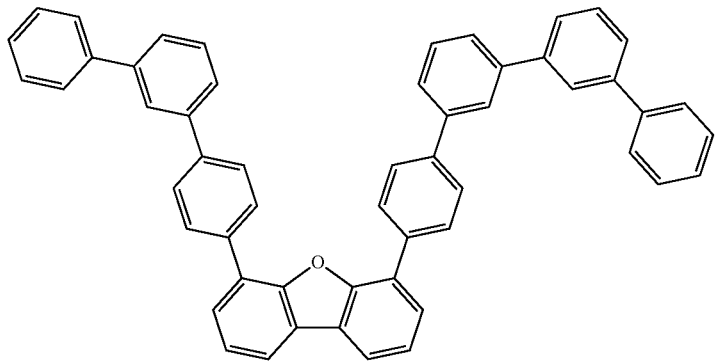

W1

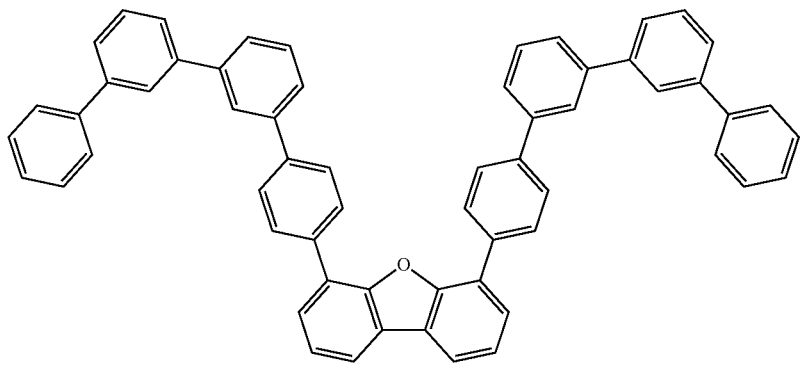

W2

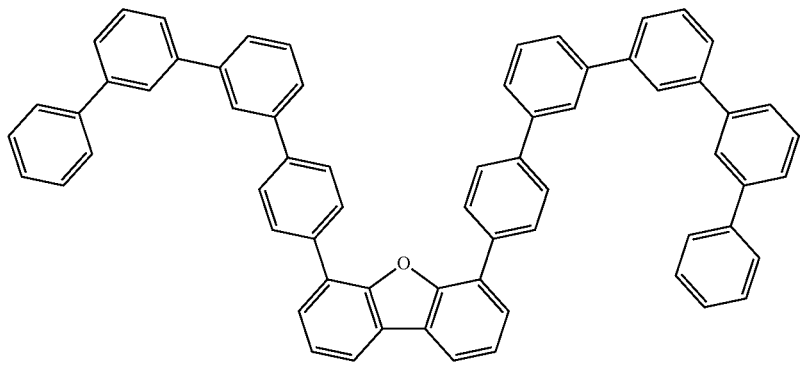

W3

-continued
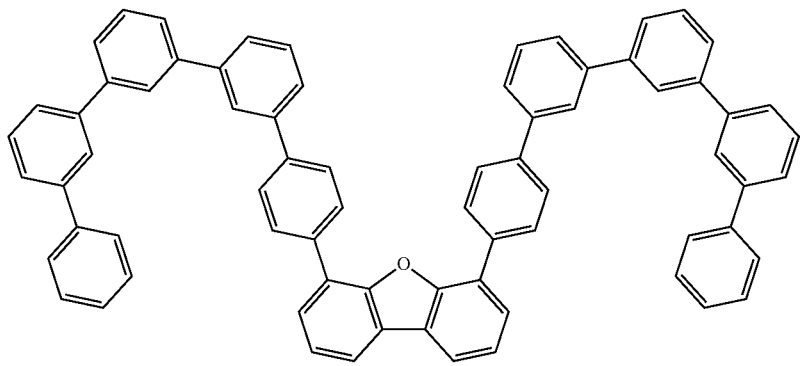
W4
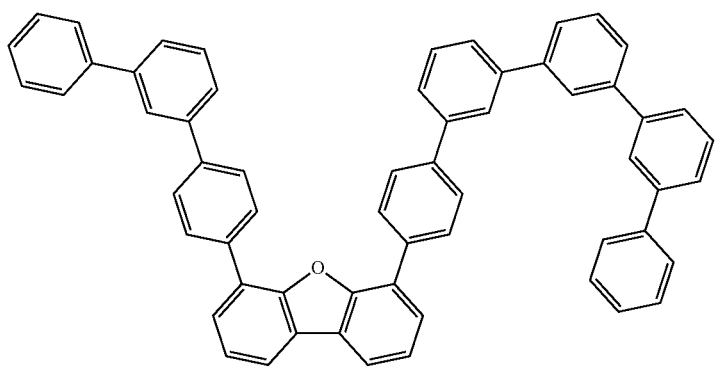
W5
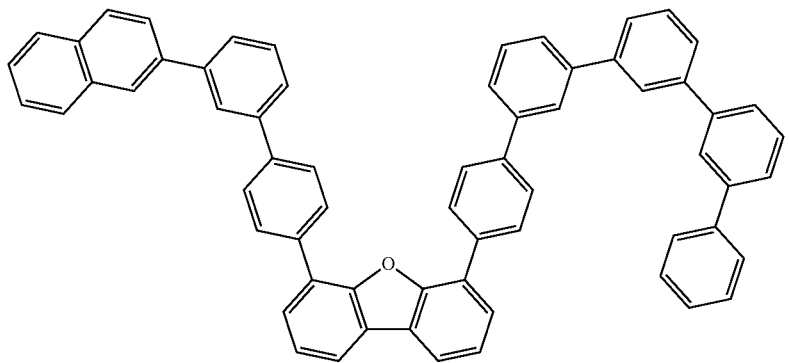
W6
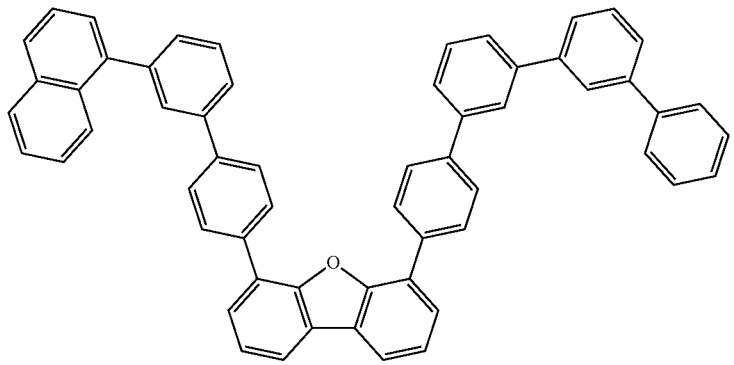
W7

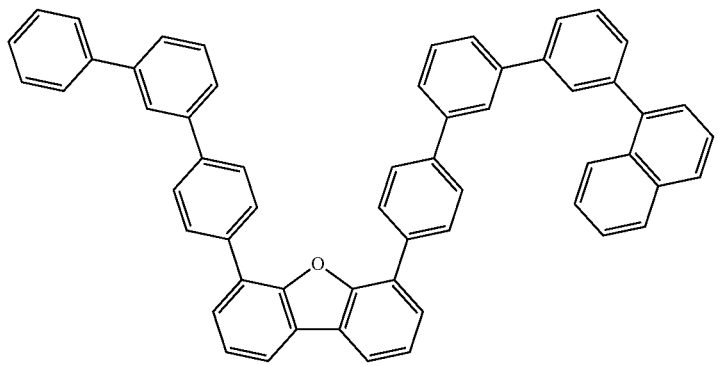
W8
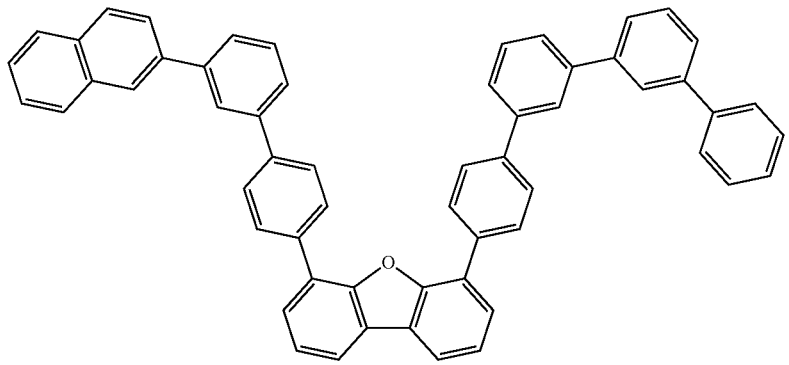
W9
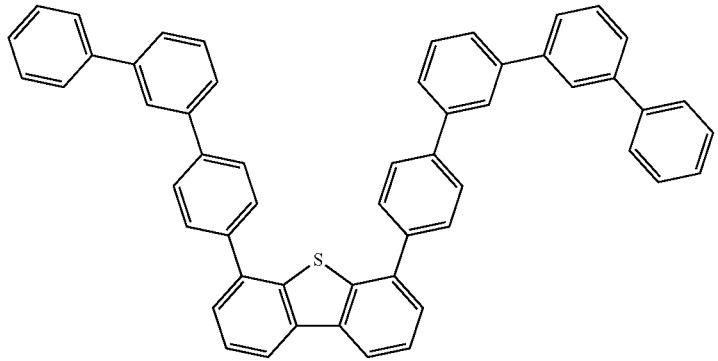
W10
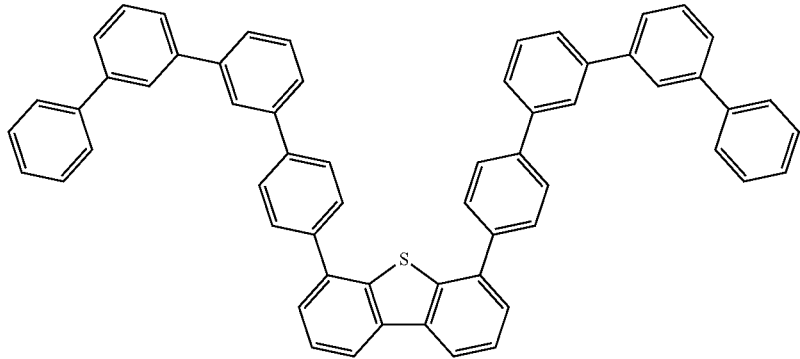
W11

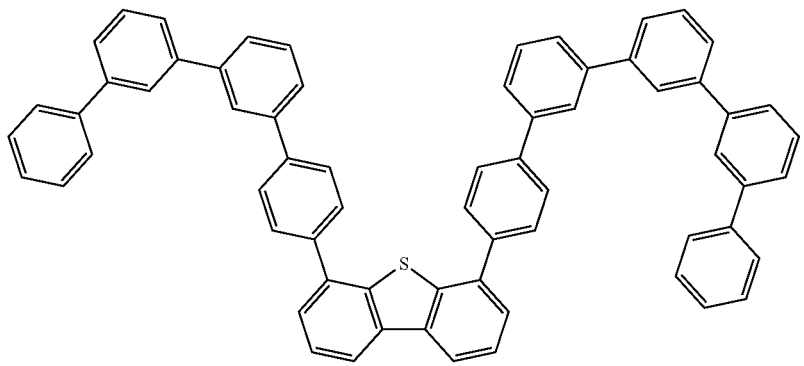
W12
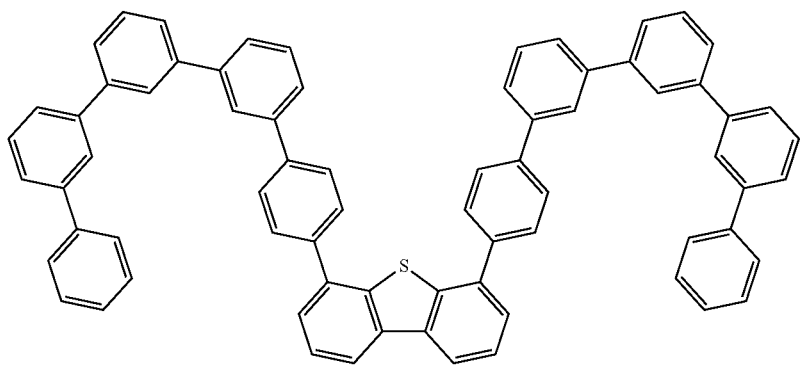
W13
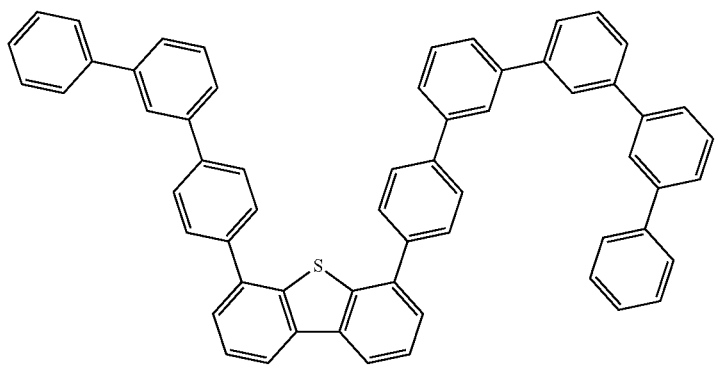
W14
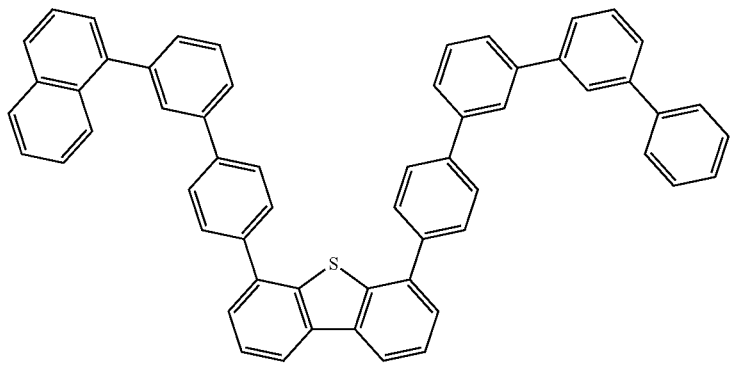
W15

-continued
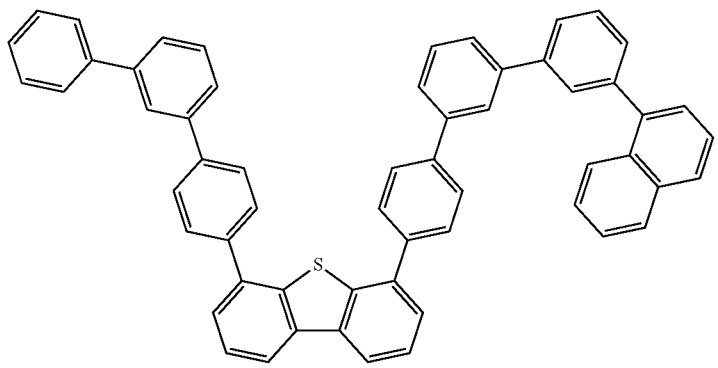

W21

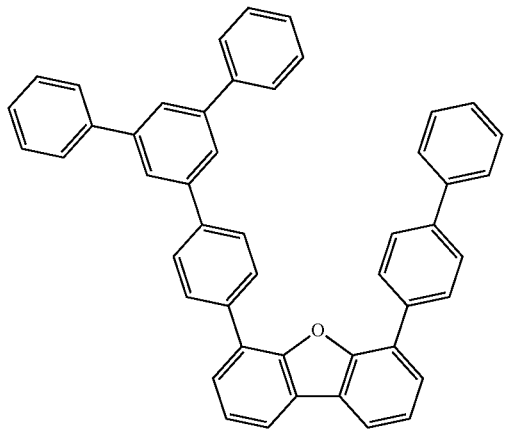

W22

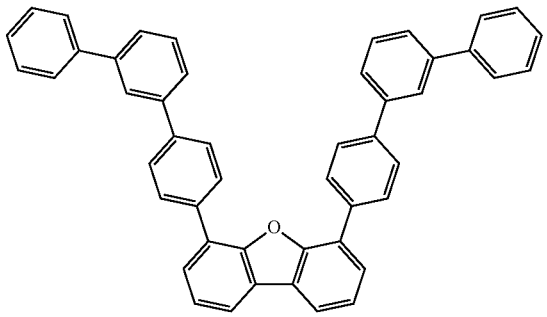

W23

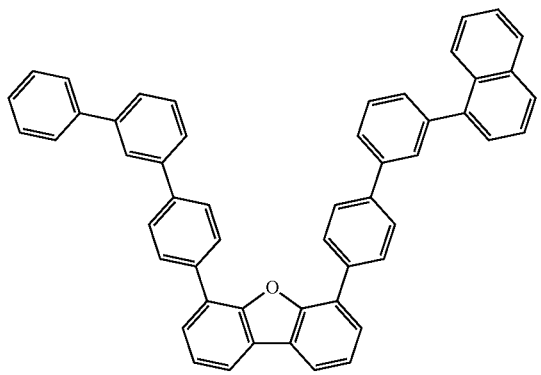

W24

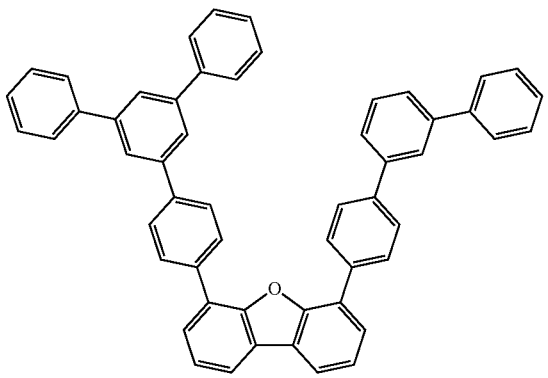

Among these compounds, Compound W1 may be particularly preferable.

Furthermore, a preparation method of the compound represented by Formula (B1) is not particularly limited, and various preparation methods including synthesis methods known in the art may be used.

In the composition, an amount of the compound represented by Formula (B1) may be preferably in a range of about 5 weight % to about 90 weight % based on 100 weight % of the total weight of the compound represented by Formula (B1) which functions as a host material and the compound represented by Formula (1) which functions as a host material. In addition, the amount of the compound represented by Formula (B1) may be preferably in a range of about 10 weight % to about 80 weight %, and more preferably in a range of about 15 weight % to about 70 weight %.

In the composition, the amount of the compound represented by Formula (B1) may be preferably in a range of about 5 weight % to about 90 weight % based on 100 weight % of the total weight of the compound represented by Formula (B1) which functions as a host material, the compound represented by Formula (1) which functions as a host material, the carbazole derivative which functions as a host material as described below, and the azine ring derivative which functions as a host material as described below. In addition, the amount of the compound represented by Formula (B1) may be preferably in a range of about 10 weight % to about 80 weight %, and more preferably in a range of about 15 weight % to about 70 weight %. When the amount of the compound represented by Formula (B1) is within these ranges above, the solubility of the composition may be further improved so that precipitation from a solution becomes difficult, and the pot life of a solution becomes longer. In addition, the driving voltage of an organic electroluminescent device is lowered, thereby further improving luminescence efficiency and luminescence lifespan.

Carbazole Derivative

The composition according to another aspect of the present disclosure may further preferably include a carbazole derivative (other than the compound represented by Formula (1)). That is, the composition including the compound represented by Formula (1) and the carbazole derivative may be preferable.

The composition according to the another aspect of the present disclosure may further increase the effect of inhibiting aggregation of molecules by including the carbazole derivative, and may also improve the balance of charge mobility between electrons and holes. In this regard, the solubility of the composition may be further improved so that precipitation from a solution becomes difficult to occur, and the pot life of a solution becomes longer. In addition, the driving voltage of an organic electroluminescent device is lowered, thereby further improving luminescence efficiency and luminescence lifespan.

The carbazole derivative may be preferably a compound represented by Formula (C1). The compound represented by Formula (C1) may have a structure (skeletal structure) in which $R_{21}$ is bonded to N at position 9 of a hetero ring (a nitrogen-containing heterocyclic compound) including a nitrogen atom (N):

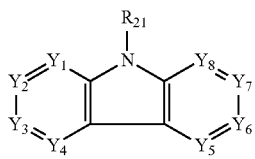
(C1)

In Formula (C1), $R_{21}$ does not include an azine ring structure. In addition, $R_{21}$ may be a monovalent aromatic hydrocarbon group consisting of at least one unsubstituted or substituted aromatic hydrocarbon ring, a monovalent aromatic heterocyclic group consisting of at least one unsubstituted or substituted aromatic hetero ring (wherein the azine ring structure is not included), or a monovalent ring aggregation group consisting of at least one substituted or unsubstituted aromatic hydrocarbon ring and at least one substituted or unsubstituted aromatic hetero ring (hereinafter also referred to as "monovalent aromatic hydrocarbon ring-aromatic hetero ring aggregation group" with respect to the description of the carbazole derivative) (wherein the azine ring structure is not included).

The term "azine ring structure" as used herein refers to a 6-membered ring structure, such as an azine ring, a diazine ring, or a triazine ring, or a condensed cyclic structure including the 6-membered ring in part.

The monovalent aromatic hydrocarbon group capable of constituting $R_{21}$ is not particularly limited and may include a single ring or two or more rings. In addition, when the aromatic hydrocarbon ring includes two or more rings, the two or more rings may be linked via a single bond or condensed to each other.

The rings of the monovalent aromatic hydrocarbon group are not particularly limited, and examples thereof include a benzene ring, a pentalene ring, an indene ring, a naphthalene ring, an anthracene ring, an azulene ring, a heptalene ring, an acenaphthylene ring, a phenalene ring, a fluorene ring a phenanthrene ring, a biphenyl ring, a triphenylene ring, a pyrene ring, a chrysene ring, a picene ring, a perylene ring, a pentaphene ring, a pentacene ring, a tetraphene ring, a hexaphene ring, a hexacene ring a rubicene ring, a trinaphthylene ring, a heptaphene ring, a pyranthrene ring, a fluorene ring, and the like.

In addition, the monovalent aromatic heterocyclic group capable of constituting $R_{21}$ is not particularly limited as long as it does not include the azine ring structure. For example, the monovalent aromatic heterocyclic group includes at least one aromatic ring that includes at least one hetero atom (for example, N, O, P, B, Si, Ge, Te, Se, and S) and carbon atoms as the remaining ring-forming atoms (wherein a group including the azine ring structure is excluded). In addition, when the aromatic heterocyclic group includes two or more rings, the two or more rings may be condensed or linked to each other via a single bond.

Here, the number of ring-forming atoms refers to the number of atoms constituting the ring itself (for example, a monocyclic ring, a condensed ring, or a ring group). An atom that does not constitute a ring (for example, a hydrogen atom terminating a binding site of a ring-forming atom) or an atom included in a substituent used to substitute a ring is not counted as the number of the ring-forming atom. For example, the number of ring-forming atoms in a carbazolyl group (i.e., carbazole group) is 13.

The aromatic hetero rings constituting the monovalent aromatic heterocyclic group is not particularly limited, but examples thereof are a π electron-deficient aromatic hetero ring, a π electron-rich aromatic hetero ring, a π electron-deficient and rich mixed aromatic hetero ring in which a π electron-deficient aromatic hetero ring and a π electron-rich aromatic hetero ring is mixed, and the like.

Examples of the π electron-rich aromatic hetero ring include a furan ring, a thiophene ring, a benzofuran ring, a benzothiophene ring, a dibenzofuran ring, a dibenzothiophene ring, a pyrrole ring, an indole ring, a carbazole ring, an indolocarbazole ring, and the like.

Examples of the π electron-deficient and rich mixed aromatic hetero ring include an imidazole ring, an indazole ring, an oxazole ring, an isoxazole ring, a benzoxazole ring, a benzoisoxazole ring, a thiazole ring, an isothiazole ring, a benzothiazole ring, a benzoisothiazole ring, an imidazolinone ring, a benzimidazolinone ring, a diazadibenzothiophene ring, a xanthone ring, a thioxanthone ring, and the like.

That is, the monovalent aromatic heterocyclic group may include one of the rings above or a combination of such rings above.

The monovalent aggregation group of aromatic hydrocarbon rings and aromatic hetero rings is not particularly limited. For example, the monovalent aggregation group may include at least one aromatic hydrocarbon ring having 6 to 60 carbon atoms and at least one aromatic hetero ring having 3 to 60 ring-forming atoms are bonded together via a single bond. Here, at least one hydrogen atom included in the aromatic hydrocarbon ring or the aromatic hetero ring may be substituted with other substituents. In addition, the aromatic hydrocarbon ring and the aromatic hetero ring that constitute the monovalent aggregation group of aromatic hydrocarbon rings and aromatic hetero rings are the same as the monovalent aromatic hydrocarbon ring group and the monovalent aromatic heterocyclic group described above, respectively, and thus descriptions thereof are omitted. That is, the monovalent aggregation group of aromatic hydrocarbon rings and aromatic hetero rings may include a group derived such rings above or a group derived from a combination of such rings above.

$Y_1$ to $Y_8$ may each independently be $C(R_{22})$. C in $C(R_{22})$ indicates a carbon atom. In addition, $R_{22}$ in $C(R_{22})$ is a group not including the azine ring structure. In addition, $R_{22}$ is not particularly limited and may include a hydrogen atom, a deuterium atom, or an organic group not including the azine ring structure. Among these examples, $R_{22}$ may be preferably a hydrogen atom, a deuterium atom, a cyano group, a substituted or unsubstituted alkyl group, a substituted or unsubstituted alkoxy group, a substituted or unsubstituted aryloxy group (other than a group including the azine ring structure), a substituted or unsubstituted alkylamino group, a substituted or unsubstituted arylamino group (other than a group including the azine ring structure), a substituted or unsubstituted monovalent aromatic hydrocarbon ring group, a substituted or unsubstituted monovalent aromatic heterocyclic group (other than a group including the azine ring structure), or a substituted or unsubstituted monovalent aromatic aggregation group of hydrocarbon rings and aromatic hetero rings (other than a group including the azine ring structure).

In $Y_1$ to $Y_8$, the alkyl group capable of constituting $R_{22}$ in $C(R_{22})$ is not particularly limited. For example, the alkyl group may be a linear or branched alkyl group having 1 to 30 carbon atoms. In detail, examples of the alkyl group are a methyl group, an ethyl group, an n-propyl group, an isopropyl group, an n-butyl group, an isobutyl group, a sec-butyl group, a tert-butyl group, an n-pentyl group, an isopentyl group, a tert-pentyl group, an neopentyl group, a 1,2-dimethyl propyl group, an n-hexyl group, an isohexyl group, a 1,3-dimethyl butyl group, a 1-isopropyl propyl group, a 1,2-dimethyl butyl group, an n-heptyl group, a 1,4-dimethyl pentyl group, a 3-ethyl pentyl group, a 2-methyl-1-isopropyl propyl group, a 1-ethyl-3-methyl butyl group, an n-octyl group, a 2-ethylhexyl group, a 3-methyl-1-isopropyl butyl group, a 2-methyl-1-isopropyl group, a 1-tert-butyl-2-methyl propyl group, an n-nonyl group, a 3,5,5-trimethyl hexyl group, an n-decyl group, an isodecyl group, an n-undecyl group, a 1-methyl decyl group, an n-dodecyl group, an n-tridecyl group, an n-tetradecyl group, an n-pentadecyl group, an n-hexadecyl group, an n-heptadecyl group, an n-octadecyl group, an n-nonadecyl group, an n-eicosyl group, an n-heneicosyl group, an n-docosyl group, an n-tricosyl group, an n-tetracosyl group, and the like.

In $Y_1$ to $Y_8$, the alkoxy group capable of constituting $R_{22}$ in $C(R_{22})$ is not particularly limited. For example, the alkoxy group may be a linear or branched alkoxy group having 1 to 30 carbon atoms. In detail, examples of the alkoxy group are a methoxy group, an ethoxy group, a propoxy group, an iso propoxy group, a butoxy group, a pentyloxy group, a hexyloxy group, a heptyloxy group, an octyloxy group, a nonyloxy group, a decyloxy group, an undecyloxy group, a dodecyl oxy group, a tridecyloxy group, a tetradecyloxy group, a pentadecyloxy group, a hexadecyloxy group, a heptadecyloxy group, an octadecyloxy group, a 2-ethylhexyloxy group, a 3-ethylpentyloxy group, and the like. Among these examples, the alkoxy group may be preferably a linear or branched alkoxy group having 1 to 8 carbon atoms.

In $Y_1$ to $Y_8$, the aryloxy group capable of constituting $R_{22}$ in $C(R_{22})$ is not particularly limited as long as it does not include the azine ring structure. For example, the aryloxy group may be an aryloxy group (other than the azine ring structure) having 6 to 30 ring-forming atoms. Here, the aryloxy group may include a hetero atom. That is, the aryloxy group may be a heteroaryloxy group. In detail, examples of the heteroaryloxy group are a phenoxy group, a 1-naphthyloxy group, a 2-naphthyloxy group, a 2-azulenyloxy group, a 2-furanyloxy group, a 2-thienyloxy group, a 2-indolyloxy group, a 3-indolyloxy group, a 2-benzofuryloxy group, a 2-benzothienyloxy group, and the like.

In $Y_1$ to $Y_8$, the arylamino group capable of constituting $R_{22}$ in $C(R_{22})$ is not particularly limited as long as it does not include the azine ring structure. For example, the arylamino group may be an arylamino group (other than the azine ring structure) having 6 to 60 ring-forming atoms. Here, the arylamino group may include a hetero atom. That is, the arylamino group may be a heteroarylamino group. In detail, an example of the arylamino group is an N-arylamino group, such as an N-phenylamino group, an N-biphenylamino group, an N-terphenylamino group, and the like. In addition, an example of the arylamino group is an N, N-diarylamino group, such as an N, N-diphenylamino group, an N, N-dibiphenylamino group, an N, N-diterphenylamino group, an N-biphenyl N-phenylamino group, an N-biphenyl N-terphenylamino group, an N-phenyl N-terphenyl amino group, and the like.

In $Y_1$ to $Y_8$, the alkylamino group capable of constituting $R_{22}$ in $C(R_{22})$ is not particularly limited. For example, the alkylamino group may be a linear or branched alkylamino group having 1 to 30 carbon atoms. In detail, an example of the alkylamino is an N-alkylamino group, such as an N-methylamino group, an N-ethylamino group, an N-propylamino group, an N-isopropylamino group, an N-butylamino group, an N-isobutylamino group, an N-sec-butylamino group, an N-tert-butylamino group, an N-pentylamino group, an N-hexylamino group, and the like. In detail, an example of the alkylamino is an N, N-dialkylamino group, such as an N, N-dimethylamino group, an N-methyl-N-ethylamino group, an N, N-diethylamino group, an N, N-dipropylamino group, an N, N-diisopropylamino group, an N, N-dibutylamino group, an N, N-diisobutylamino group, an N, N-dipentylamino group, an N, N-dihexylamino group, and the like.

In addition, in $Y_1$ to $Y_8$, the monovalent aromatic hydrocarbon group, the monovalent aromatic heterocyclic group, and the monovalent aggregation group of aromatic hydrocarbon rings and aromatic hetero rings, which can constitute $R_{22}$ in $C(R_{22})$, are the same as the monovalent aromatic hydrocarbon group, the monovalent aromatic heterocyclic group, and the monovalent aggregation group of aromatic hydrocarbon rings and aromatic hetero rings, which can constitute $R_{21}$ as described above, and thus descriptions thereof are omitted.

The monovalent aromatic hydrocarbon group, the monovalent aromatic heterocyclic group, and the monovalent aggregation group that can constitute $R_{21}$, may be substituted with other substituents.

The alkyl group, the alkoxy group, the aryloxy group (other than a group having the azine ring structure), the alkylamino group, the arylamino group (other than a group having the azine ring structure), the monovalent aromatic hydrocarbon group, the monovalent aromatic heterocyclic group, the monovalent aggregation group of aromatic hydrocarbon rings and aromatic hetero rings, which can constitute $R_{22}$, may be substituted with other substituents.

The other substituents are not particularly limited as long as they are each a deuterium atom or an organic group not including the azine ring structure.

Examples of other substituents capable of substituting the monovalent aromatic hydrocarbon group, the monovalent aromatic heterocyclic group, the monovalent aggregation group of aromatic hydrocarbon rings and aromatic hetero rings, which can constitute $R_{21}$ and $R_{22}$, are a deuterium atom, a cyano group, a substituted or unsubstituted alkyl group, a substituted or unsubstituted alkoxy group, a substituted or unsubstituted aryloxy group (other than a group having the azine ring structure), a substituted or unsubstituted alkylamino group, a substituted or unsubstituted arylamino group (other than a group having the azine ring structure), and the like.

Examples of other substituents capable of substituting the alkyl group, the alkoxy group, the aryloxy group (other than a group having the azine ring structure), the alkylamino group, and the arylamino group (other than a group having the azine ring structure), which can constitute $R_{22}$, are a deuterium atom, a cyano group, an unsubstituted alkyl group, an unsubstituted alkoxy group, an unsubstituted aryloxy group (other than a group having the azine ring structure), an unsubstituted alkylamino group, an unsubstituted arylamino group (other than a group having the azine ring structure), and the like.

Regarding $R_{21}$ and $R_{22}$, the alkyl group, the alkoxy group, the aryloxy group, and the alkylamino group, which can constitute other substituents, are each the same as described in connection with the group capable of constituting $R_{22}$ in $C(R_{22})$, and thus descriptions thereof are omitted.

Regarding $R_{21}$ and $R_{22}$, the monovalent aromatic hydrocarbon group, the monovalent aromatic heterocyclic group (other than a group having the azine ring structure), and the monovalent aggregation group of aromatic hydrocarbon rings and aromatic hetero rings, which can constitute other substituents, are each the same as described in connection with the aromatic hydrocarbon group, the aromatic heterocyclic group and the monovalent aggregation group of aromatic hydrocarbon rings and aromatic hetero rings that can constitute $R_{21}$, and thus descriptions thereof are omitted.

Furthermore, examples of other substituents of the monovalent aromatic hydrocarbon group, the monovalent aromatic heterocyclic group, the monovalent aggregation group of aromatic hydrocarbon rings and aromatic hetero rings include a deuterium atom, a cyano group, an unsubstituted alkyl group, an unsubstituted alkoxy group, an unsubstituted aryloxy group (other than a group having the azine ring structure), an unsubstituted alkylamino group, an unsubstituted arylamino group (other than a group having the azine ring structure), and the like.

The monovalent aromatic hydrocarbon group capable of constituting $R_{21}$ and $R_{22}$ may be preferably a monovalent aromatic hydrocarbon group having 6 to 60 carbon atoms. In addition, the monovalent aromatic hydrocarbon group may be more preferably a monovalent hydrocarbon group having 6 to 30 carbon atoms.

The monovalent aromatic heterocyclic group capable of constituting $R_{21}$ and $R_{22}$ may be preferably a monovalent aromatic heterocyclic group having 3 to 60 carbon atoms. In addition, monovalent aromatic heterocyclic group may be more preferably a monovalent heterocyclic group having 3 to 30 carbon atoms.

The monovalent aggregation group of aromatic hydrocarbon rings and aromatic hetero rings, which can constitute $R_{21}$ and $R_{22}$, may be preferably a group in which at least one aromatic hydrocarbon ring having 6 to 60 carbon atoms and at least one aromatic hetero ring having 3 to 60 ring-forming atoms are bonded together via a single bond. In addition, the monovalent aggregation group of aromatic hydrocarbon rings and aromatic hetero rings may be preferably a group in which at least one aromatic hydrocarbon ring having 6 to 60 carbon atoms and at least one aromatic hetero ring having 3 to 60 ring-forming atoms are bonded together via a single bond.

In addition, the monovalent aggregation group of aromatic hydrocarbon rings and aromatic hetero rings may be a group having a ring structure in which $R_{21}$ and at least one $R_{22}$ or at least two $R_{22}(s)$ are each independently condensed or bonded to each other.

In addition, the compound represented by Formula (C1) may be a multimer in which at least one of $R_{21}$ and $R_{22}$ is a carbazole group.

The compound represented by Formula (C1) is not particularly limited, but may be preferably a compound represented by Formula (C3). The compound represented by Formula (C3) may be preferably a compound represented by Formula (C4):

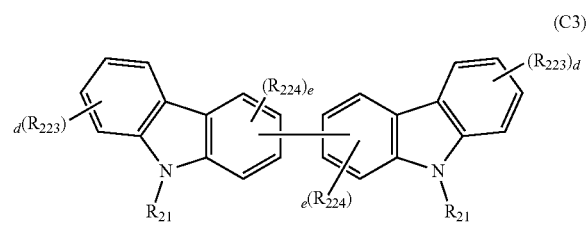

(C3)

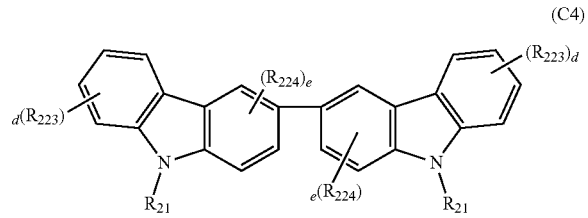

(C4)

In Formulae (C3) and (C4), each occurrence of $R_{21}$ may independently be the same as described in connection with Formula (C1), each occurrence of $R_{223}(s)$ and $R_{224}(s)$ may each independently be a deuterium atom, a cyano group, a substituted or unsubstituted alkyl group, a substituted or unsubstituted alkoxy group, a substituted or unsubstituted aryloxy group (other than a group having the azine ring structure), a substituted or unsubstituted alkylamino group, a substituted or unsubstituted arylamino group (other than a group having the azine ring structure), a substituted or unsubstituted monovalent aromatic hydrocarbon group, a substituted or unsubstituted monovalent aromatic heterocyclic group (other than a group having the azine ring structure), or a substituted or unsubstituted monovalent aggregation group of aromatic hydrocarbon rings and aromatic hetero rings (other than a group having the azine ring structure), d(s) may each independently be 0, 1, 2, 3, or 4, and e(s) may each independently be 0, 1, 2, or 3.

Here, each substituent capable of constituting $R_{223}$ and $R_{224}$ may be the same as described in connection with the each substituent capable of constituting $R_{22}$ in Formula (C1), and thus descriptions thereof are omitted.

Here, it is more preferable when both d and e in Formula (C4) are 0 and each $R_{21}$ is an unsubstituted monovalent aromatic hydrocarbon group having 6 to 30 carbon atoms. In addition, it is more preferable when both d and e are 0 and each $R_{21}$ is an unsubstituted biphenyl group.

In Formula (C4), at least two groups of at least one $R_{21}$, at least one $R_{223}$, and at least one $R_{224}$ may be condensed or bonded together to form a ring structure.

Specific examples of the compound represented by Formula (C3) are provided below. However, the carbazole derivative is not limited thereto:

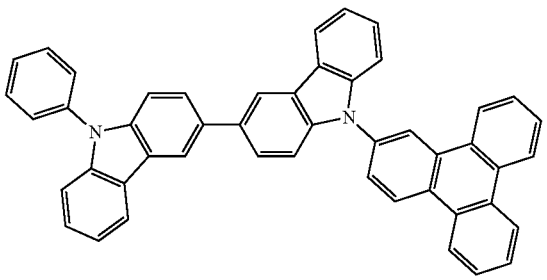

(H2-1)

(H2-2)
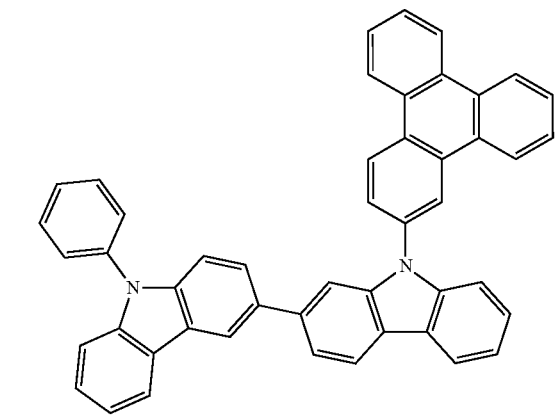
(H2-3)
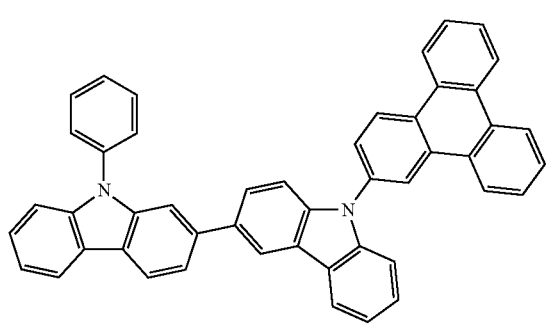
(H2-4)
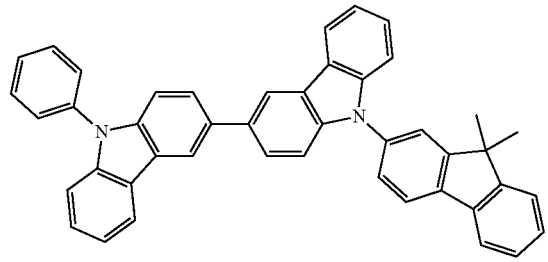
(H2-5)
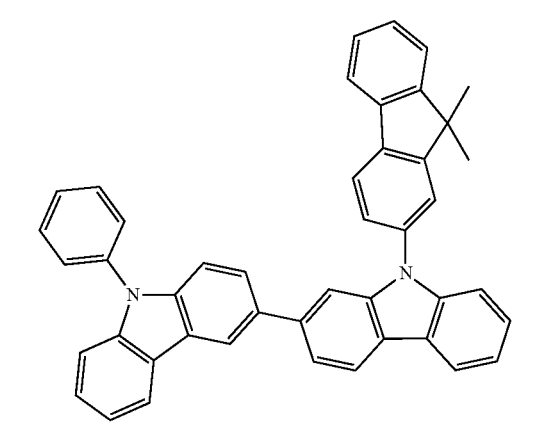
(H2-6)
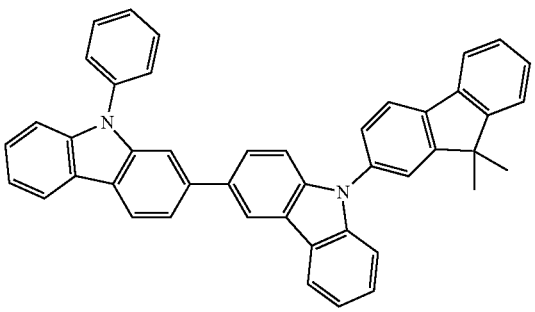
(H2-7)
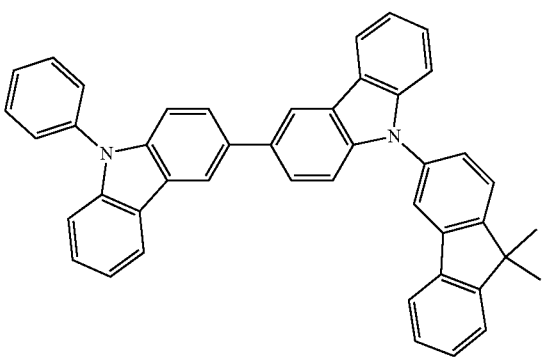
(H2-8)
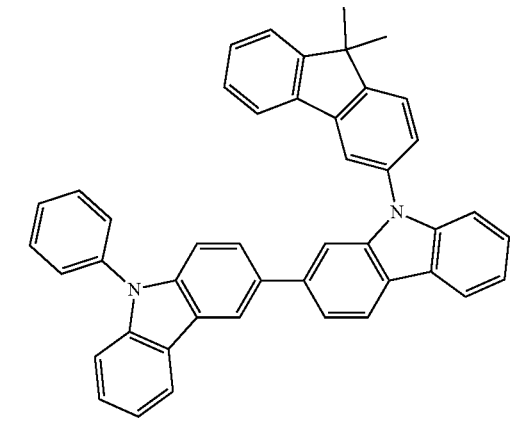
(H2-9)
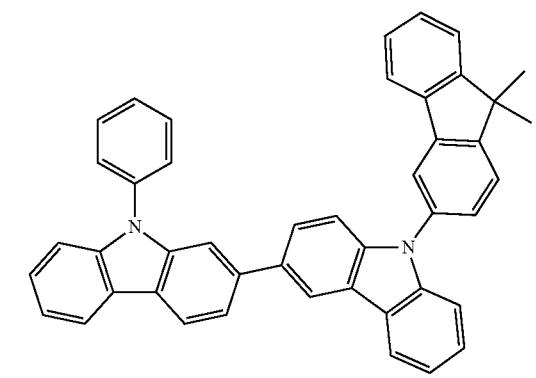

(H2-10)
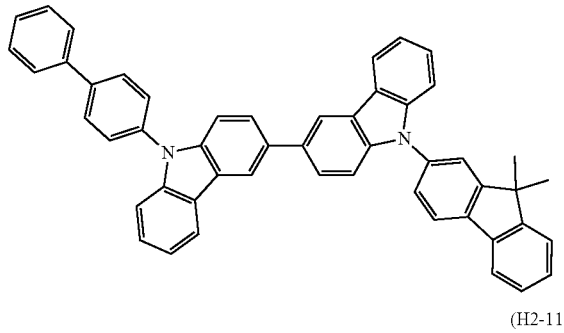
(H2-11)
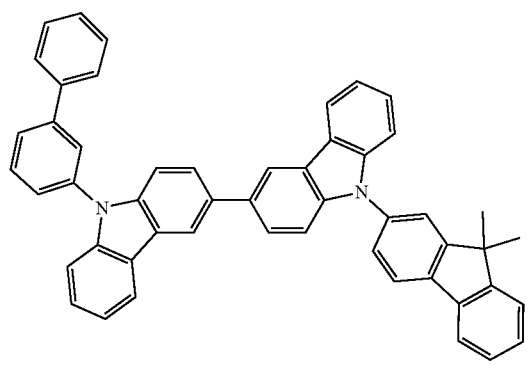
(H2-12)
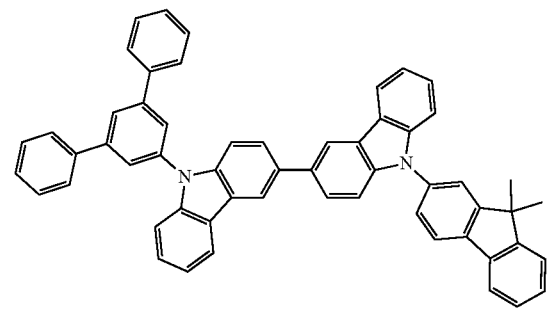
(H2-13)
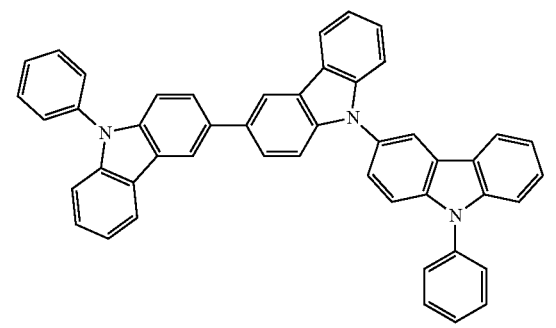
(H2-14)
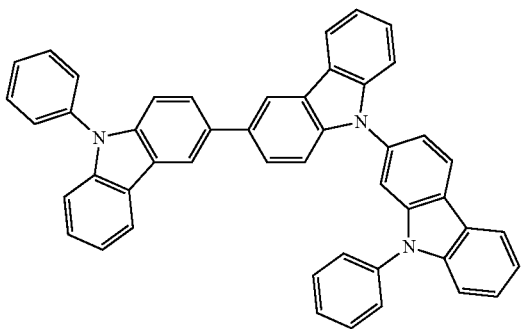
(H2-14-2)
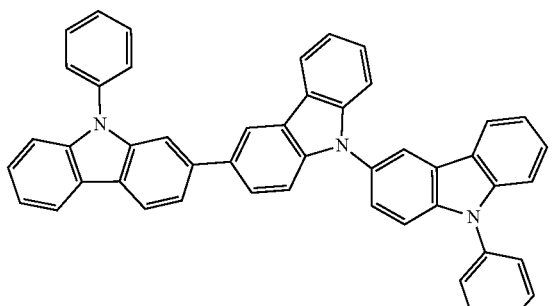
(H2-15)
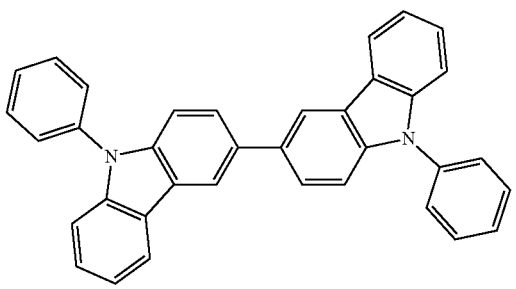
(H2-16)
(H2-17)
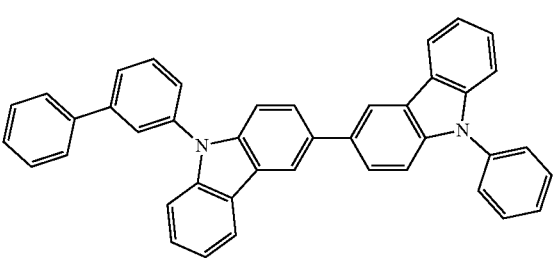

(H2-18) 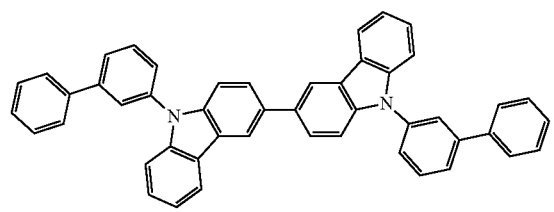
(H2-19) 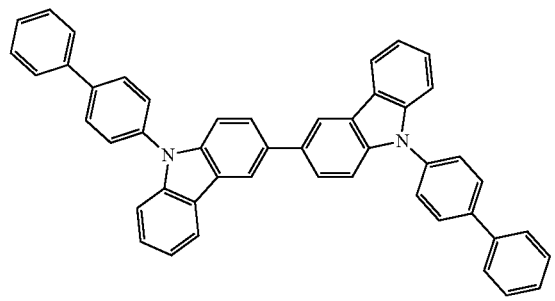
(H2-20) 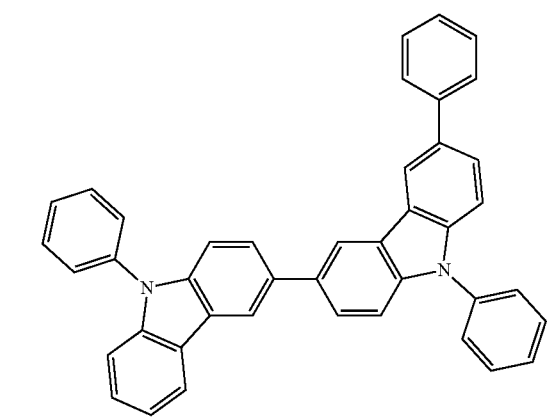
(H2-21) 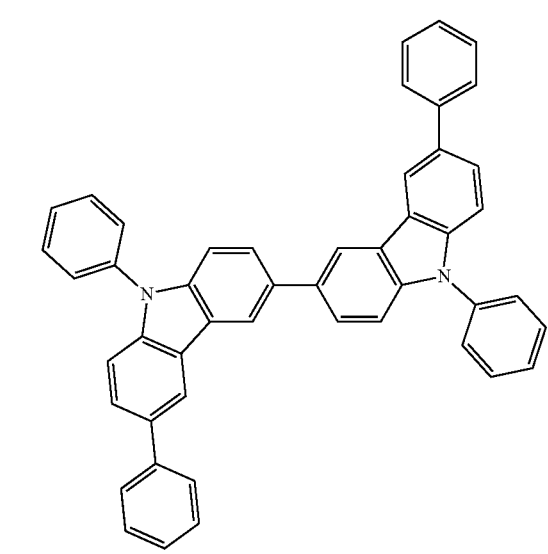
(H2-22) 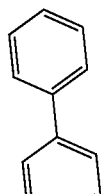
(H2-23) 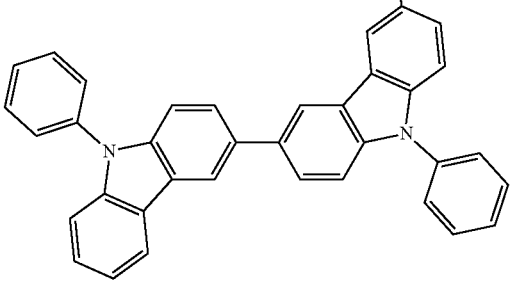
(H2-24) 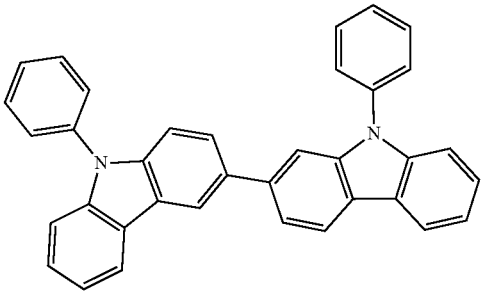
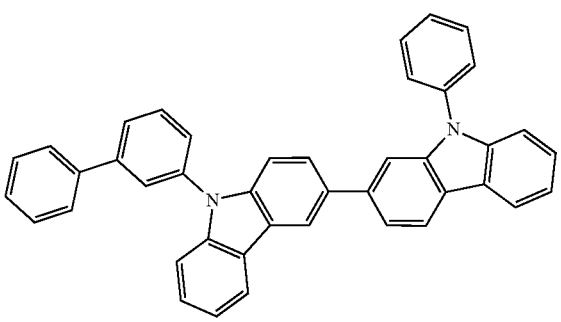
(H2-25) 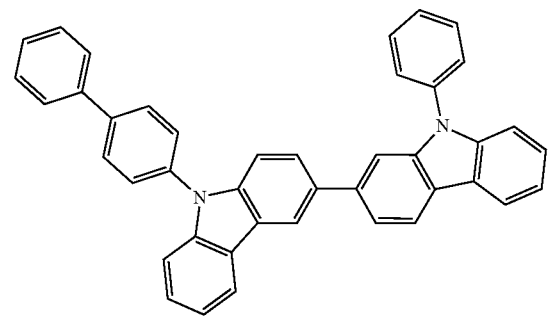

-continued
(H2-26)
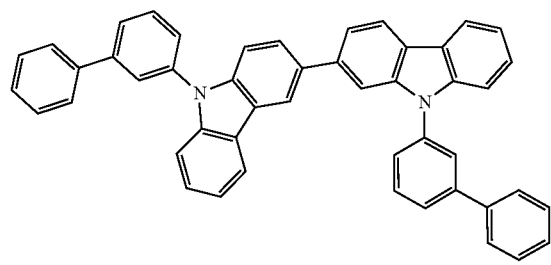
(H2-27)
(H2-28)
(H2-29)
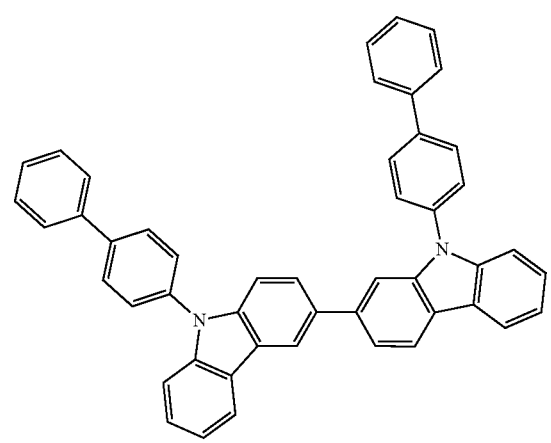
-continued
(H2-30)
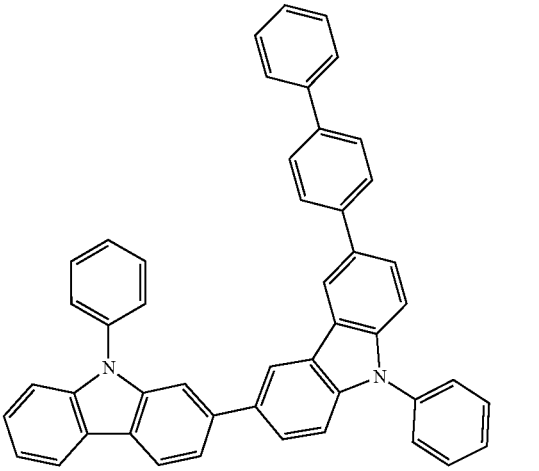
(H2-31)
(H2-32)
(H2-33)
(H2-34)
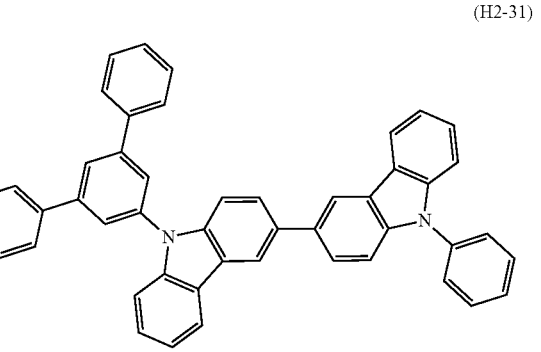

Among these examples of the carbazole derivative, Compound H2-34 may be preferable.

However, the carbazole derivative is not limited to the examples shown above. For example, the known carbazole derivative described in paragraphs [0095] to [0104] in the specification of US2016/009388 and JP2014-509067, each of which are incorporated by reference in their entirety, may also be included in the present compositions. In addition, the carbazole derivative described in such reference documents may be used as a basis for correction in the specification of the present application.

In the composition, an amount of the carbazole derivative may be preferably in a range of about 5 weight % to about 90 weight % based on 100 weight % of the total weight of the carbazole derivative which functions as a host material and the compound represented by Formula (1) which functions as a host material. In addition, the amount of the carbazole derivative may be preferably in a range of about 10 weight % to about 80 weight %, and more preferably in a range of about 15 weight % to about 70 weight %.

In addition, the amount of the carbazole derivative in the composition may be preferably in a range of about 5 weight % to about 90 weight % based on 100 weight % of the total weight of the carbazole derivative which functions as a host material, the compound represented by Formula (1) which functions as a host material, the compound represented by Formula (B1) which functions as a host material, and the azine ring derivative which functions as a host material as described below. In addition, the amount of the carbazole derivative may be preferably in a range of about 10 weight % to about 80 weight %, and more preferably, in a range of about 15 weight % to about 70 weight %. When the amount of the carbazole derivative is within these ranges above, the solubility of the composition may be further improved so that precipitation from a solution becomes difficult to occur, and the pot life of a solution becomes longer. In addition, the driving voltage of an organic electroluminescent device is lowered, thereby further improving luminescence efficiency and luminescence lifespan.

Azine Ring Derivative

The composition according to another aspect of the present disclosure may further preferably include an azine ring derivative (other than the compound represented by Formula (1)). That is, the composition including the compound represented by Formula (1) and the azine ring derivative may be preferable.

The term "azine ring derivative" as used herein refers to a compound having a 6-membered ring structure, such as an azine ring, a diazine ring, or a triazine ring, or a condensed cyclic structure including the 6-membered ring in part.

The composition according to the another aspect of the present disclosure may further increase the effect of inhibiting aggregation of molecules by including the azine ring derivative, and may also improve the balance of charge mobility between electrons and holes. In this regard, the solubility of the composition may be further improved so that precipitation from a solution becomes difficult, and the pot life of a solution is increased. In addition, the luminescence efficiency and luminescence lifespan of an organic electroluminescent device may be further improved.

The azine ring derivative may be preferably a compound represented by Formula (A1):

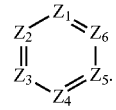

(A1)

In Formula (A1), $Z_1$ to $Z_6$ may each independently be $C(R_{31})$ or N. In addition, at least one of $Z_1$ to $Z_6$ may be N. That is, the compound represented by Formula (A1) may be a 6-membered heterocyclic compound including N (i.e., a nitrogen-containing heterocyclic compound).

Regarding $Z_1$ to $Z_6$, C in $C(R_{31})$ is carbon.

Here, $R_{31}$ in $C(R_{31})$ is not particularly limited as long as it is a hydrogen atom, a deuterium atom, or an organic group. Among these examples, $R_{31}$ in $C(R_{31})$ may be preferably a hydrogen atom, a deuterium atom, a substituted or unsubstituted alkyl group, a substituted or unsubstituted monovalent aromatic hydrocarbon group consisting of at least one aromatic hydrocarbon ring, a substituted or unsubstituted monovalent aromatic heterocyclic group consisting of at least one aromatic hetero ring, or a substituted or unsubstituted monovalent ring aggregation group consisting of at least one aromatic hydrocarbon group and at least one aromatic hetero ring (hereinafter also referred to as "monovalent aggregation group of aromatic hydrocarbon rings and aromatic hetero rings with respect to the description of the azine ring derivative".

The alkyl group capable of constituting $R_{31}$ in $C(R_{31})$ is the same as described in connection with $R_{22}$ in Formula (C1), and thus a description thereof is omitted.

The monovalent aromatic hydrocarbon group capable of constituting $R_{31}$ in $C(R_{31})$ is the same as described in connection with $R_{21}$ in Formula (C1), and thus a description thereof is omitted.

In addition, the monovalent aromatic heterocyclic group capable of constituting $R_{31}$ in $C(R_{31})$ is not particularly limited. For example, the monovalent aromatic heterocyclic group may be a monovalent aromatic heterocyclic group having 3 to 60 ring-forming atoms. The monovalent aromatic heterocyclic group includes at least one hetero atom (for example, N, O, P, B, Si, Se, Ge, Te, or S) and carbon atoms as the remaining ring-forming atoms. The monovalent aromatic heterocyclic group capable of constituting $R_{31}$ may be preferably a monovalent aromatic heterocyclic group having 3 to 30 carbon atoms. The aromatic heterocyclic group may include a single ring or two or more rings. In addition, when the aromatic heterocyclic group includes two or more rings, the two or more rings may be linked via a single bond or condensed to each other.

The aromatic hetero ring constituting the monovalent aromatic heterocyclic group is not particularly limited, but examples thereof are a π electron-deficient aromatic hetero ring, a π electron-rich aromatic hetero ring, a π electron-deficient and rich mixed aromatic hetero ring in which a π electron-deficient aromatic hetero ring and a π electron-rich aromatic hetero ring is mixed, and the like.

Examples of the π electron-deficient aromatic hetero ring include a pyridine ring, a pyrazine ring, a pyridazine ring, a pyrimidine ring, a triazine ring, a quinoline ring, an isoquinoline ring, a quinoxaline ring, a quinazoline ring, a naphthylidine ring, an acridine ring, a phenazine ring, a benzoquinoline ring, a benzoisoquinoline ring, a phenanthridine ring, a phenanthroline ring, a benzoquinone ring, a coumarin ring, an anthraquinone ring, a fluorenone ring, and the like.

Examples of the π electron-rich aromatic hetero ring include a furan ring, a thiophene ring, a benzofuran ring, a benzothiophene ring, a dibenzofuran ring, a dibenzothiophene ring, a pyrrole ring, an indole ring, a carbazole ring, an indolocarbazole ring, and the like.

Examples of the π electron-deficient and rich mixed aromatic hetero ring are an imidazole ring, a benzimidazole ring, a pyrazole ring, an indazole ring, an oxazole ring, an isoxazole ring, a benzoxazole ring, a benzisoxazole ring, a thiazole ring, an isothiazole ring, a benzothiazole ring, a benzoisothiazole ring, an imidazolinone ring, a benzimidazolinone ring, an imidazopyridine ring, an imidazopyrimidine ring, an imidazophenanthridine ring, a benzimidazophenanthridine ring, an azadibenzofuran ring, an azacarbazole ring, an azadibenzothiophene ring, a diazadibenzofuran ring, a diazacarbazole ring, a diazadibenzothiophene ring, a xanthone ring, a thioxanthone ring, and the like.

That is, the monovalent aromatic heterocyclic group may include a single ring as described above or a combination of such rings above.

The monovalent aggregation group of aromatic hydrocarbon rings and aromatic hetero rings is not particularly limited. For example, the monovalent aggregation group of aromatic hydrocarbon rings and aromatic hetero rings may include a group in which at least one aromatic hydrocarbon ring having 6 to 60 carbon atoms and at least one aromatic hetero ring having 3 to 60 ring-forming atoms are bonded together via a single bond. Here, at least one hydrogen atom included in the aromatic hydrocarbon ring or the aromatic hetero ring may be substituted with other substituents. In addition, the aromatic hydrocarbon ring and the aromatic hetero ring that constitute the monovalent aggregation group of aromatic hydrocarbon rings and aromatic hetero rings are the same as the monovalent aromatic hydrocarbon ring group and the monovalent aromatic heterocyclic group described above, respectively, and thus descriptions thereof are omitted. That is, the monovalent aggregation group of aromatic hydrocarbon rings and aromatic hetero rings may include a ring described above or a combination of such rings above.

The monovalent aromatic hydrocarbon group, the monovalent aromatic heterocyclic group, the monovalent aggregation group of aromatic hydrocarbon rings and aromatic hetero rings, which can constitute $R_{31}$, may be substituted with other substituents.

The alkyl group capable of constituting $R_{31}$ may be substituted with other substituents.

The other substituents are not particularly limited as long as they are each a deuterium atom or an organic group.

Examples of other substituents capable of substituting the monovalent aromatic hydrocarbon group, the monovalent aromatic heterocyclic group, and the monovalent aggregation group of aromatic hydrocarbon rings and aromatic hetero rings, which can constitute $R_{31}$, are a deuterium atom, a cyano group, a substituted or unsubstituted alkyl group, a substituted or unsubstituted alkoxy group, a substituted or unsubstituted aryloxy group, a substituted or unsubstituted alkylamino group, a substituted or unsubstituted arylamino group, and the like.

Examples of the other substituents capable of substituting the alkyl group that can constitute $R_{31}$ are a deuterium atom, a cyano group, an unsubstituted alkoxy group, an unsubstituted aryloxy group, an unsubstituted alkylamino group, an unsubstituted arylamino group, and the like.

Here, the alkyl group, the alkoxy group, and the alkylamino group, which can constitute other substituents in $R_{31}$ may each be the same as described in connection with the group capable of constituting $R_{22}$ in Formula (C1), and thus descriptions thereof are omitted.

The aryloxy group capable of constituting other substituents in $R_{31}$ is not particularly limited. For example, the aryloxy group may be an aryloxy group having 6 to 30 ring-forming atoms. Here, the aryloxy group may include a hetero atom. That is, the aryloxy group may be a heteroaryloxy group. The aryloxy group may be a monocyclic or condensed polycyclic aryloxy group having 6 to 30 ring-forming atoms. In detail, examples of the aryloxy group are a phenoxy group, a 1-naphthyloxy group, a 2-naphthyloxy group, a 2-azulenyloxy group, a 2-furanyloxy group, a 2-thienyloxy group, a 2-indolyloxy group, a 3-indolyloxy group, a 2-benzofuryloxy group, a 2-benzothienyloxy group, and the like.

The arylamino group capable of constituting other substituents in $R_{31}$ is not particularly limited. For example, the arylamino group may be an arylamino group (other than the azine ring structure) having 6 to 60 ring-forming atoms. Here, the arylamino group may include a hetero atom. That is, the arylamino group may be a heteroarylamino group.

In detail, an example of the arylamino group is an N-arylamino group, such as an N-phenylamino group, an N-biphenylamino group, an N-terphenylamino group, and the like. In addition, an example of the arylamino group is an N, N-diarylamino group, such as an N, N-diphenylamino group, an N, N-dibiphenylamino group, an N, N-diterphenylamino group, an N-biphenyl N-phenylamino group, an N-biphenyl N-terphenylamino group, an N-phenyl N-terphenyl amino group, and the like.

The monovalent aromatic hydrocarbon group, the monovalent aromatic heterocyclic group, and the monovalent aggregation group of aromatic hydrocarbon rings and aromatic hetero rings, which can constitute other substituents in $R_{31}$, may each be the same as the monovalent aromatic hydrocarbon group, the monovalent aromatic heterocyclic group, and the monovalent aggregation group of aromatic hydrocarbon rings and aromatic hetero rings, which can constitute $R_{31}$ as described above, respectively, and thus descriptions thereof are omitted.

Furthermore, examples of other new substituents capable of further substituting the monovalent aromatic hydrocarbon group, the monovalent aromatic heterocyclic group, the monovalent aggregation group of aromatic hydrocarbon rings and aromatic hetero rings are a deuterium atom, a cyano group, an unsubstituted alkyl group, an unsubstituted alkoxy group, an unsubstituted aryloxy group, an unsubstituted alkylamino group, an unsubstituted arylamino group, and the like.

In addition, two or more $R_{31}$(s) may be bonded or condensed together via a single bond to form a ring structure.

In addition, the compound represented by Formula (A1) may be a multimer in which the structure represented by Formula (A1) is bonded through each $R_{31}$.

Preferable examples of the azine ring derivative are compounds represented by Formulae (A2-1) to (A2-5):

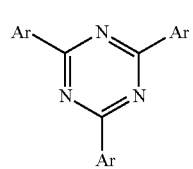

(A2-1)

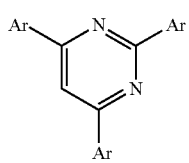 (A2-2)

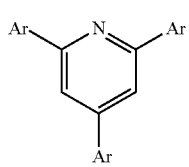 (A2-3)

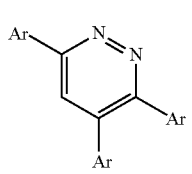 (A2-4)

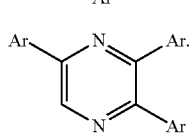 (A2-5)

In Formulae (A2-1) to (A2-5), Ar(s) may each independently be a substituted or unsubstituted monovalent aromatic hydrocarbon group, a substituted or unsubstituted monovalent aromatic heterocyclic group, or a substituted or unsubstituted monovalent aggregation group of aromatic hydrocarbon rings and aromatic hetero rings.

In Formulae (A2-1) to (A2-5), the monovalent aromatic hydrocarbon group, the monovalent aromatic heterocyclic group, and the monovalent aggregation group of aromatic hydrocarbon rings and aromatic hetero rings, which can constitute Ar, may each be the same as described in connection with the group capable of constituting $R_{31}$ in Formula (A1), and thus descriptions thereof are omitted.

Regarding Ar in Formulae (A2-1) to (A2-5), the monovalent aromatic hydrocarbon group, the monovalent aromatic heterocyclic group, and the monovalent aggregation group of aromatic hydrocarbon rings and aromatic hetero rings may each independently be substituted with other substituents. Here, the other substituents in Ar may be the same as the other substituents capable of substituting the monovalent aromatic hydrocarbon group, the monovalent aromatic heterocyclic group, and the monovalent aggregation group of aromatic hydrocarbon rings and aromatic hetero rings regarding $R_{31}$ in Formula (A1), and thus descriptions thereof are omitted.

In Formulae (A2-1) to (A2-5), two or more substituents may be condensed or bonded together via a single bond to form a ring structure.

Among these examples, the azine ring derivative may preferable a compound represented by Formula (A2-1). In addition, Ar in Formula (A2-1) may be preferably a substituted or unsubstituted monovalent aromatic hydrocarbon group or a substituted or unsubstituted monovalent aggregation group of aromatic hydrocarbon rings and aromatic hetero rings. In addition, one of three Ar(s) in Formula (A2-1) may be more preferably a substituted or unsubstituted monovalent aromatic hydrocarbon group, and two Ar(s) in Formula (A2-1) may each be more preferably a substituted or unsubstituted monovalent aggregation group of aromatic hydrocarbon rings and aromatic hetero rings. In addition, one of three Ar(s) in Formula (A2-1) may be more preferably an unsubstituted monovalent aromatic hydrocarbon group, and two Ar(s) in Formula (A2-1) may each be more preferably an unsubstituted monovalent aggregation group of aromatic hydrocarbon rings and aromatic hetero rings. The monovalent aromatic hydrocarbon group in Formula (A2-1) may be preferably a phenyl group. In addition, the monovalent aggregation group of aromatic hydrocarbon rings and aromatic hetero rings may be preferable a group consisting of at least one benzene ring and at least one carbazole ring. Such a group may be more preferably a group consisting of one to three benzene rings and one carbazole ring. In addition, it is more preferable when one of two monovalent aggregation groups of aromatic hydrocarbon rings and aromatic hetero rings is a group consisting of one benzene ring and one carbazole ring, and the other is a group consisting of three benzene rings and one carbazole ring.

In addition, a preferable example of the azine ring derivative is a compound represented by Formula (A3):

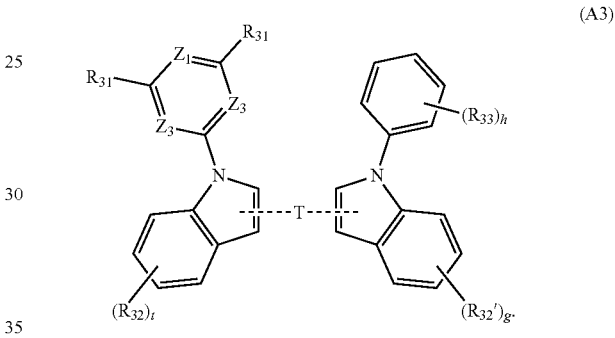 (A3)

In Formula (A3), T indicates a ring structure represented by the following formula condensed with each of the indole rings of Formula (A3),

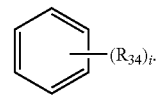

$Z_1$, $Z_3$, and $Z_5$ may each independently be CH or N, and at least one of $Z_1$, $Z_3$, and $Z_5$ may be N, each occurrence of $R_{31}$ may e independently be the same as described in connection with Formula (A1), $R_{32}(s)$, $R_{32}'(s)$, $R_{33}(s)$, and $R_{34}(s)$ may each independently be deuterium atom, a cyano group, a substituted or unsubstituted alkyl group, a substituted or unsubstituted alkoxy group, a substituted or unsubstituted aryloxy group, a substituted or unsubstituted alkylamino group, a substituted or unsubstituted arylamino group, a substituted or unsubstituted monovalent aromatic hydrocarbon group, a substituted or unsubstituted monovalent aromatic heterocyclic group, or a substituted or unsubstituted monovalent aggregation group of aromatic hydrocarbon rings and aromatic hetero rings, f and g may each independently be 0, 1, 2, 3, or 4, h may be 0, 1, 2, 3, 4, or 5, and i may be 0, 1, or 2.

Here, each substituent capable of constituting $R_{32}$, $R_{32}'$, $R_{33}$, and $R_{34}$ in Formula (A3) may be the same as described in connection with the each substituent capable of constituting the other substituents in $R_{31}$ in Formula (A1), and thus descriptions thereof are omitted.

For example, in Formula (A3), it is preferable when $Z_1$, $Z_3$, and $Z_5$ are all N.

In addition, in Formula (A3), it is preferable when both f and g are 0, h is 1, i is 0, and $R_{31}(s)$ and $R_{33}(s)$ are each an unsubstituted monovalent aromatic hydrocarbon group. In addition, in Formula (A3), it is preferable when both f and g are 0, h is 1, i is 0, $R_{31}(s)$ are each an unsubstituted monovalent aromatic hydrocarbon group, and $R_{33}(s)$ are each an unsubstituted biphenyl group.

In Formula (A3), two or more groups selected from at least one $R_{31}$, at least one $R_{32}$, at least one $R_{32}'$, at least one $R_{33}$, and at least one $R_{34}$ may be bonded or condensed together via a single bond to form a ring structure.

Examples of the azine ring derivative are as follows:

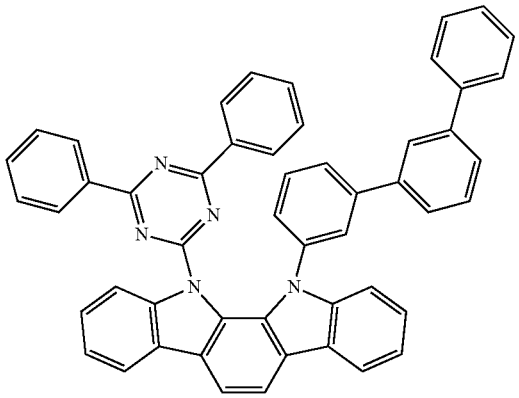

Az1

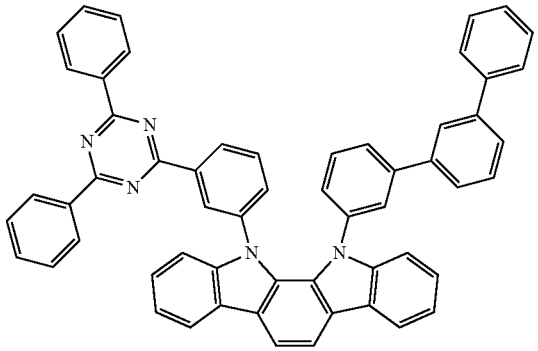

Az2

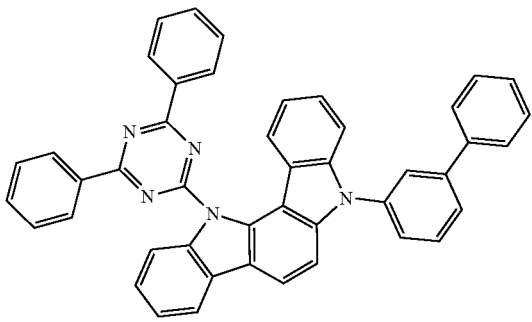

Az3

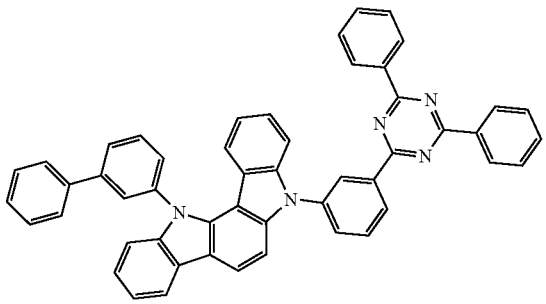

Az4

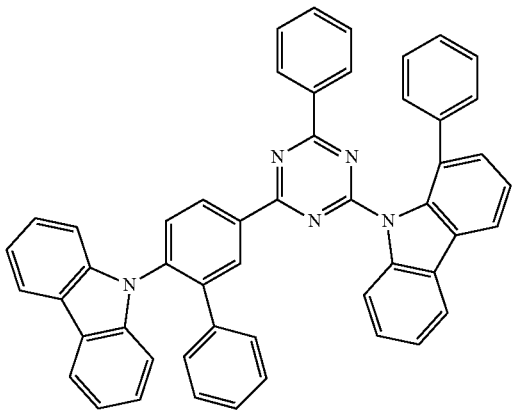

Az5

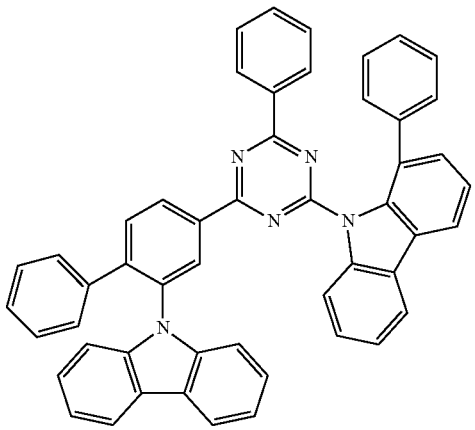

Az6

-continued
Az7
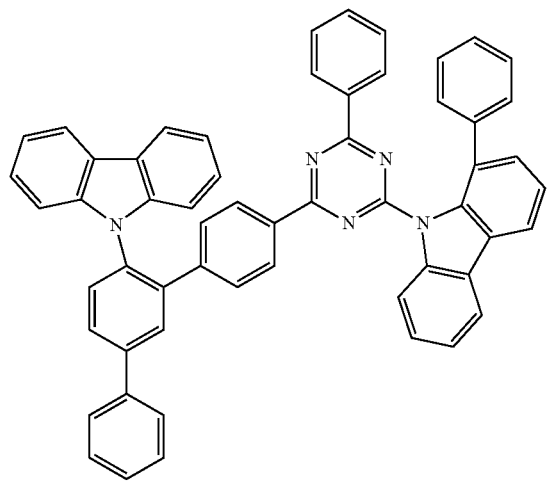
Az8
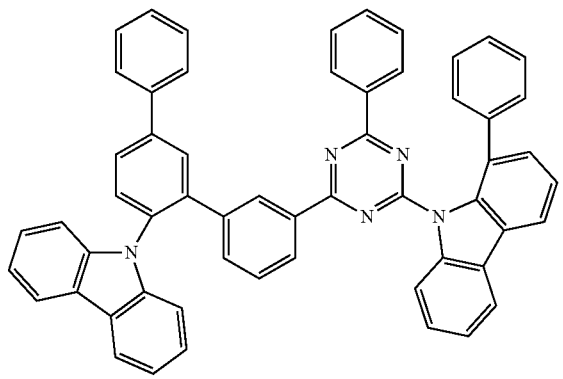
Az9
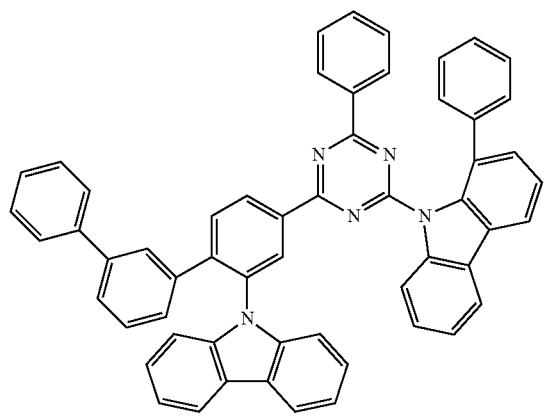
Az10
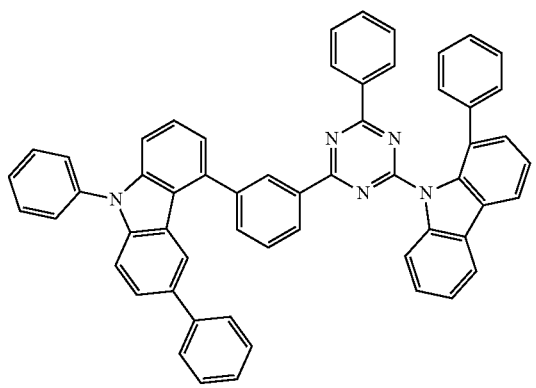
Az11
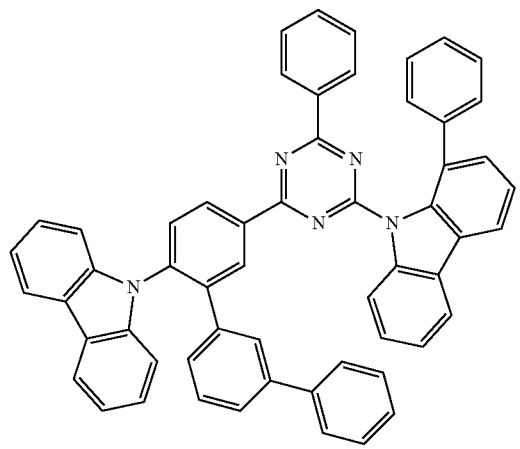
Az12
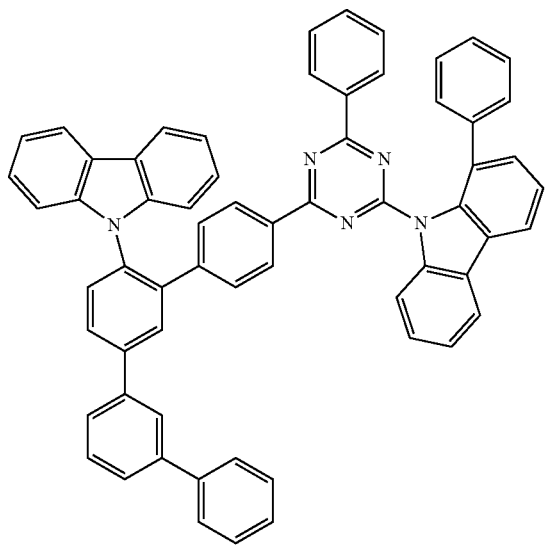

-continued
Az13
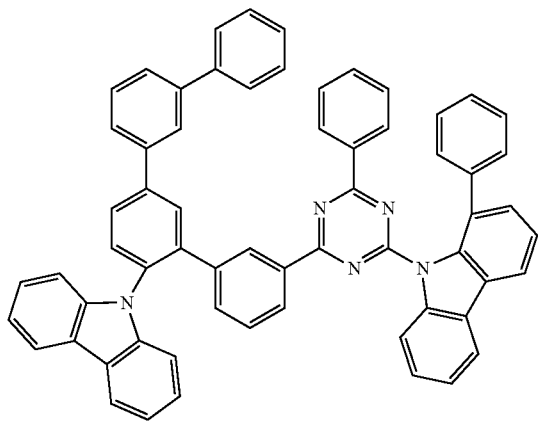
Az14
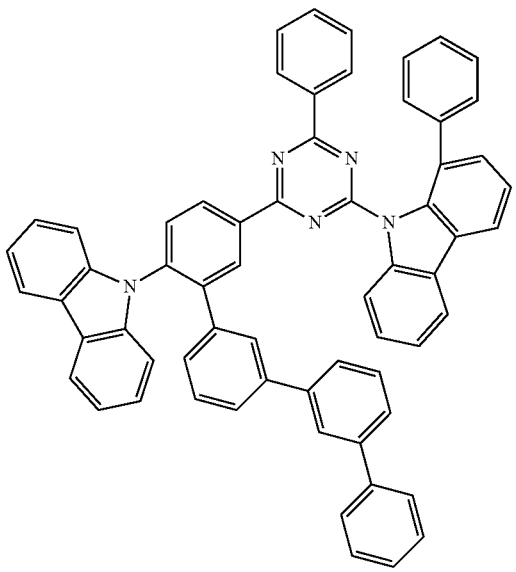
Az15
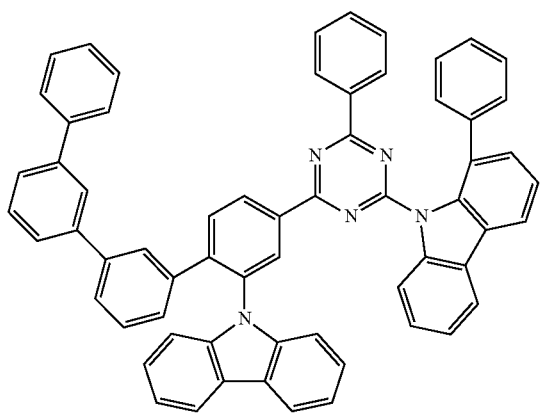
Az16
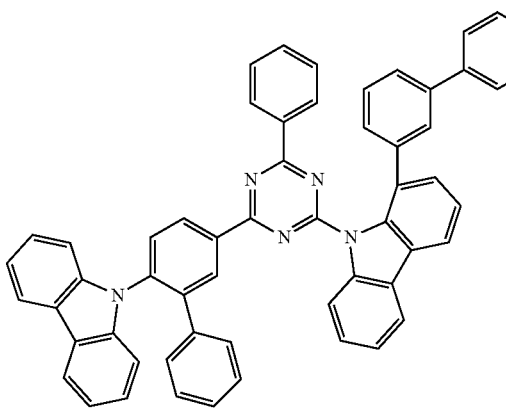
Az17
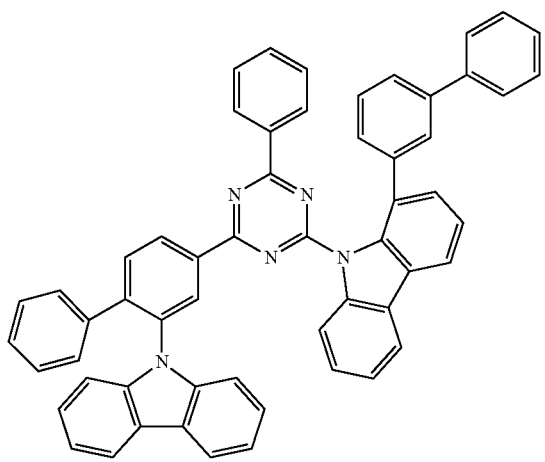
Az18
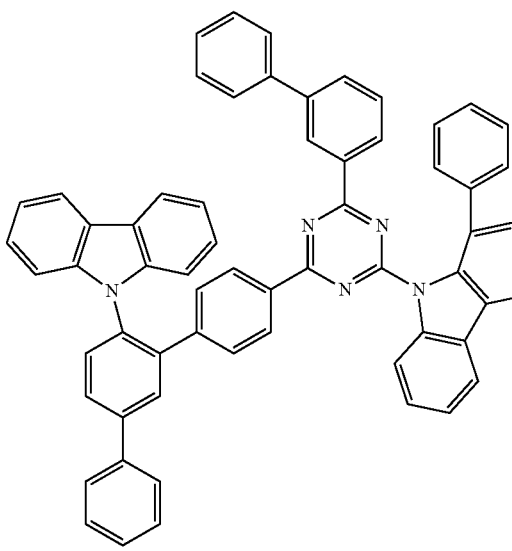

-continued
Az19
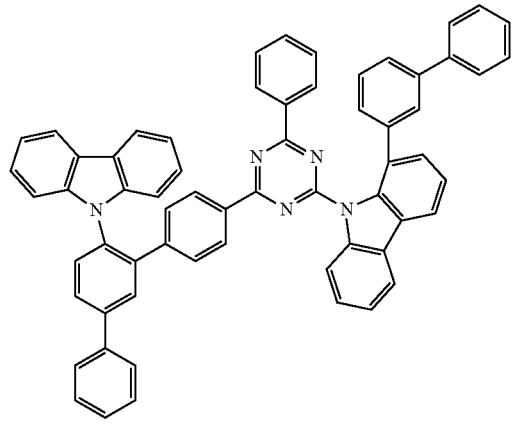
Az20
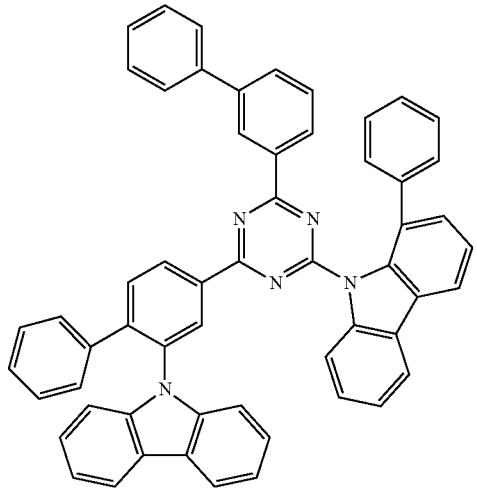
Az21
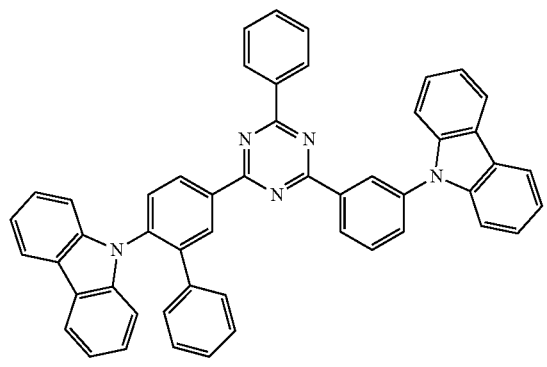
Az22
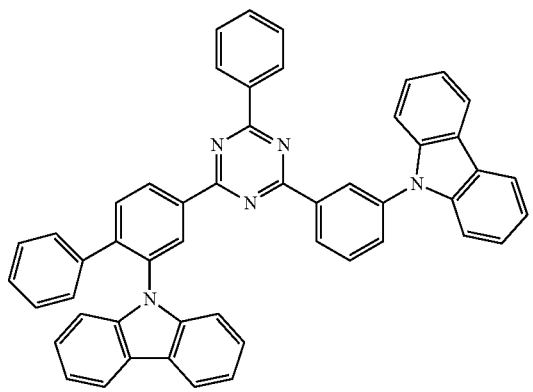
Az23
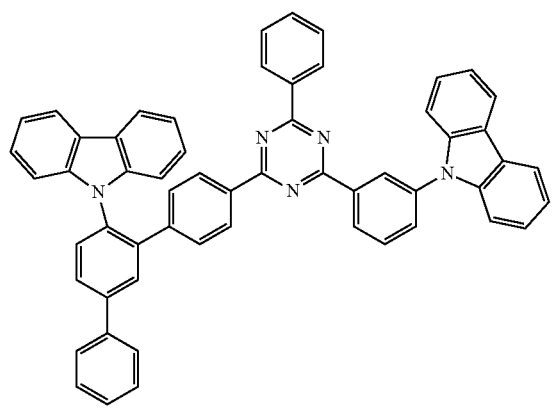
Az24
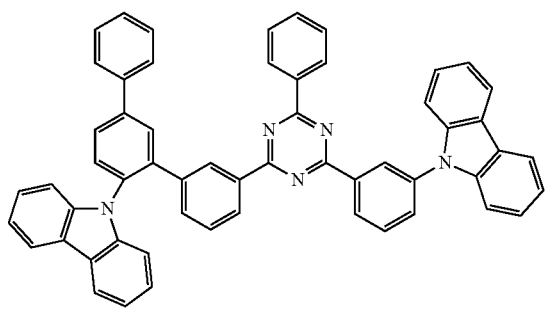

-continued
Az25
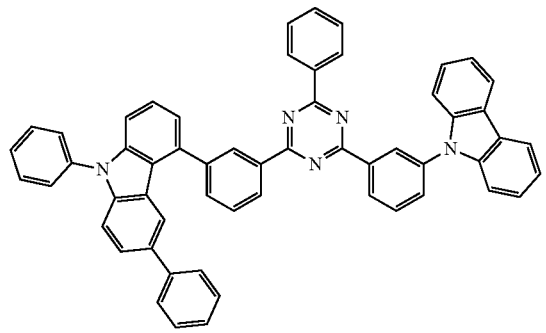
Az26
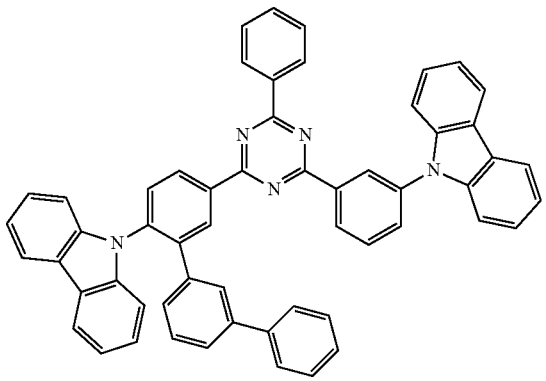
Az27
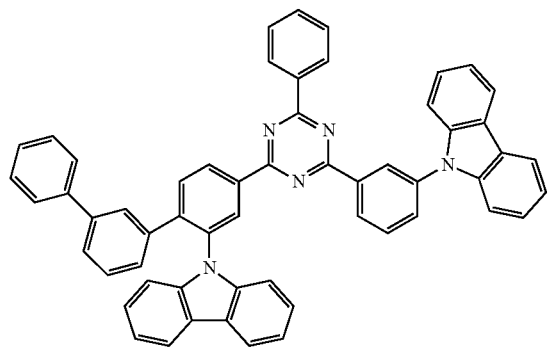
Az28
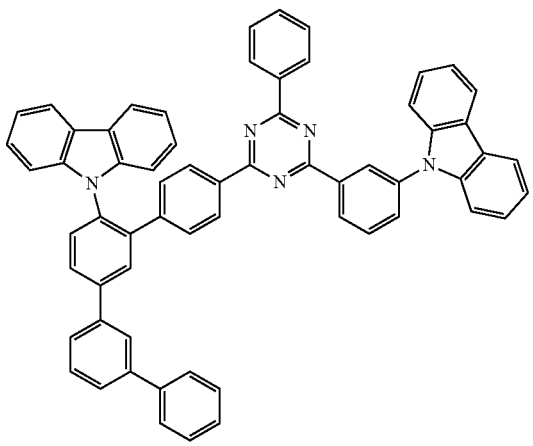
Az29
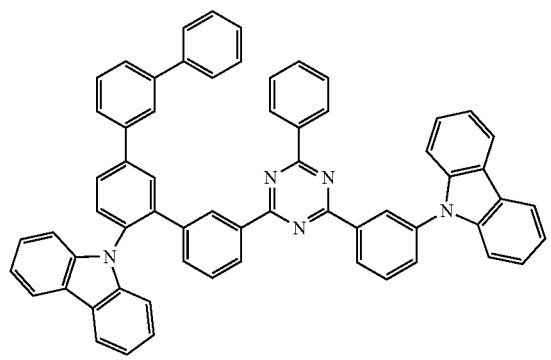
Az30
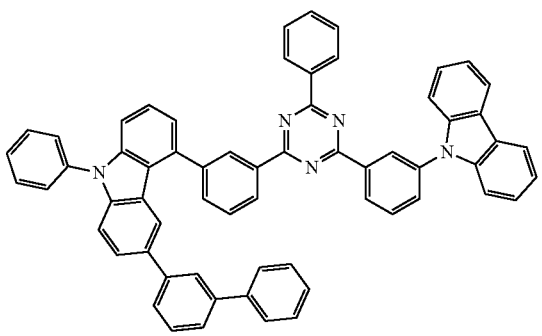

-continued
Az31
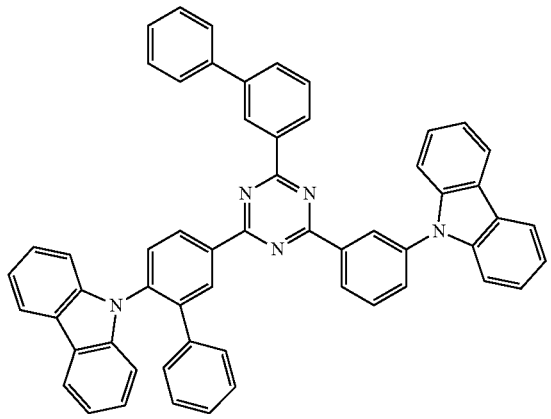
Az32
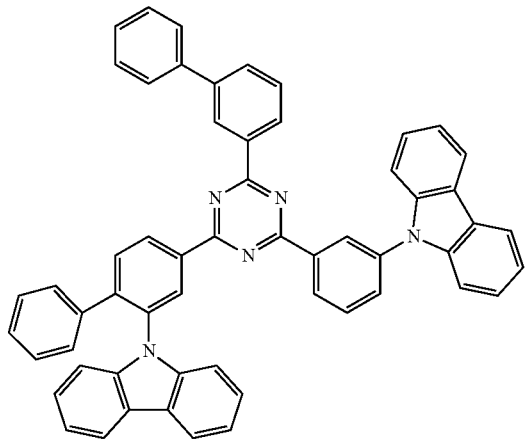
Az33
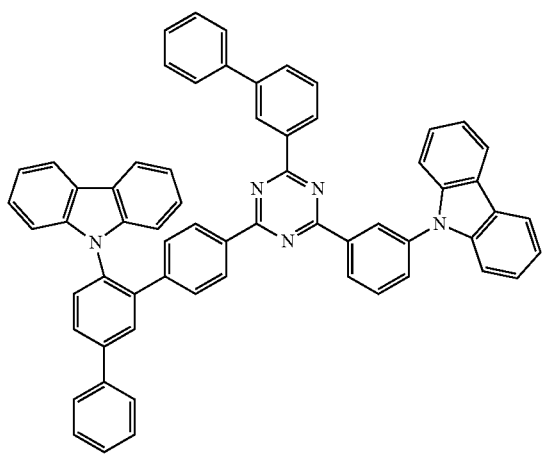
Az34
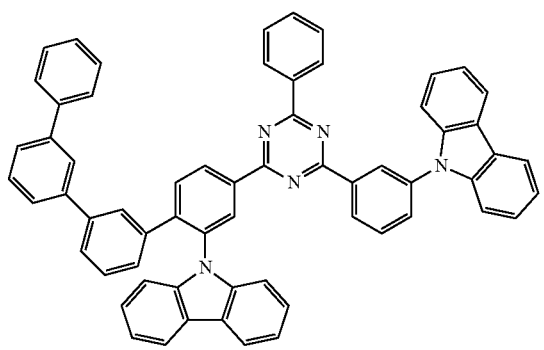
Az35
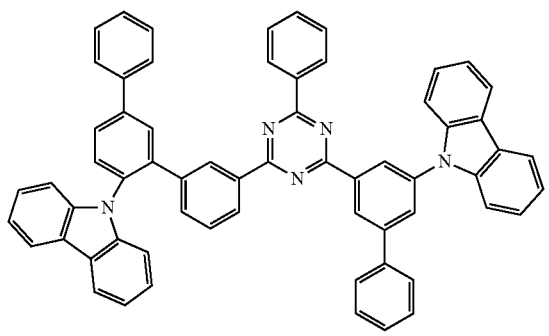
Az36
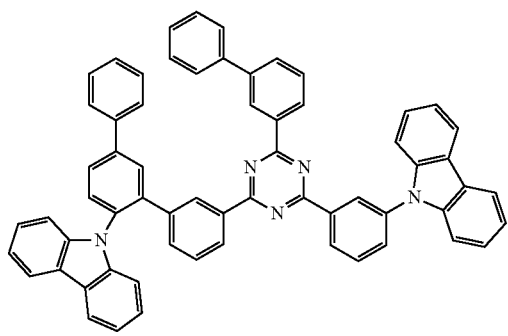

-continued

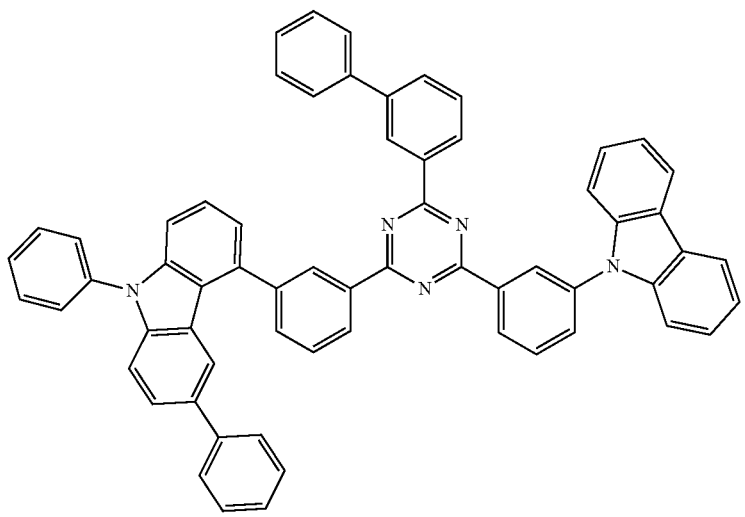
Az37

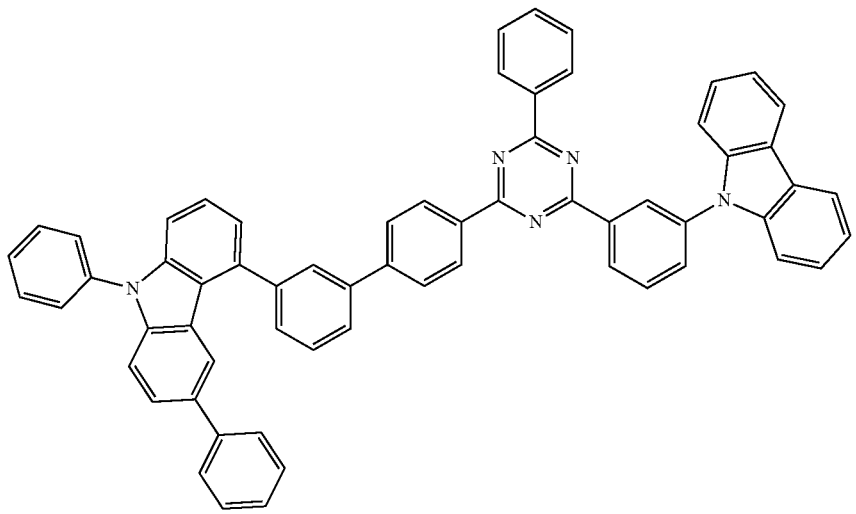
Az38

Among these examples of the azine ring derivative, Compound AZ27 may be preferable.

However, the azine ring derivative is not limited to the examples above. For example, the known azine ring derivative described in paragraphs [0078] to [0094] in the specification of US2016/0093808, JP2013-535830, JP2018-524797, US2017/0346020, US2017/0309829, and JP2014-509067, each of which is incorporated by reference in their entirety may also be included in the present disclosure by reference. In addition, the azine ring derivative described in such reference documents may be used as a basis for correction in the specification of the present application.

In the composition, an amount of the azine ring derivative may be preferably in a range of about 5 weight % to about 90 weight % based on 100 weight % of the total weight of the azine ring derivative which functions as a host material and the compound represented by Formula (1) which functions as a host material. In addition, the amount of the azine ring derivative may be preferably in a range of about 10 weight % to about 80 weight %, and more preferably in a range of about 15 weight % to about 70 weight %.

In addition, the amount of the azine ring derivative in the composition may be preferably in a range of about 5 weight % to about 90 weight % based on 100 weight % of the total weight of the azine ring derivative which functions as a host material, the compound represented by Formula (1) which functions as a host material, the compound represented by Formula (B1) which functions as a host material, and the carbazole derivative which functions as a host material. In addition, the amount of the azine ring derivative may be preferably in a range of about 10 weight % to about 80 weight %, and more preferably in a range of about 15 weight % to about 70 weight %. When the amount of the azine ring derivative is within these ranges above, the solubility of the composition may be further improved so that precipitation from a solution becomes difficult to occur, and the pot life of a solution becomes longer. In addition, the driving voltage of an organic electroluminescent device is lowered, thereby further improving luminescence efficiency and luminescence lifespan.

Examples of Preferred Composition

The composition according to another aspect of the present disclosure may preferably include the compound represented by Formula (1) and the compound represented by Formula (B1).

In addition, the composition according to another aspect of the present disclosure may preferably include the compound represented by Formula (1) and at least one of the carbazole derivative and the azine ring derivative. In addition, the composition according to another aspect of the present disclosure may preferably include the compound represented by Formula (1), the carbazole derivative, and the azine ring derivative. In addition, the composition according to another aspect of the present disclosure may preferably include the compound represented by Formula (B1).

Accordingly, the solubility may be further improved based on the composition. In addition, precipitation from a solution is more difficult, so that the pot life of a solution becomes longer. In addition, the driving voltage of an organic electroluminescent device is lowered, thereby further improving luminescence efficiency and luminescence lifespan. In addition, the composition according to another aspect of the present disclosure may further preferably include the phosphorescent metal complex of the platinum family. By including the phosphorescent metal complex of the platinum family, the driving voltage of an organic electroluminescent device may be lowered, thereby further improving luminescence efficiency and luminescence lifespan. In addition, embodiments of the compound represented by Formula (1), the compound represented by Formula (B1), the carbazole derivative, the azine ring derivative, and the phosphorescent metal complex of the platinum family are the same as described in connection with each compound above. When these compounds are used in combination with the preferred compounds according to the preferred embodiments in the description, the effects of the present disclosure may be enhanced.

In addition, a preparation method of each composition is not particularly limited. For example, such a composition may be prepared by mixing the compound represented by Formula (1) and any other compositions. Here, the mixing order is not particularly limited, and mixing methods and mixing conditions are not particularly limited. Various preparation methods including known preparation methods may be used.

The composition according to another aspect of the present disclosure may be preferably used as a material for an organic electroluminescent device (also referred to as an organic EL device material in the present specification). That is, the organic EL device material may preferably include the composition according to another aspect of the present disclosure.

Liquid Composition

Another aspect of the present disclosure provides a liquid composition including: a compound represented by Formula (1) or a compound represented by Formula (1) and a different compound from the compound represented by Formula (1); and a solvent. As the liquid composition, it is preferable to include the composition exemplified by the preferred example above and a solvent.

In addition, the solvent is not particularly limited, but a solvent having a boiling point in a range of about 100° C. to about 350° C. at atmospheric pressure (101.3 kPa 1 atm) may be preferable. That is, a preferred embodiment of the present disclosure is a liquid composition including: a composition including the compound represented by Formula (1) or a different compound from the compound represented by Formula (1); or a solvent having a boiling point in a range of about 100° C. to about 350° C. at atmospheric pressure. The boiling point of the solvent at atmospheric pressure may be preferably in a range of about 150° C. to about 320° C., and more preferably in a range of about 180° C. to about 300° C. When the boiling point of the solvent at atmospheric pressure is within these ranges above, the film formation property and processability of a wet film-forming method, such as an inkjet printing method, may be improved. As a result, the driving voltage of an organic electroluminescent device may be lowered, so that luminescence efficiency and luminescence lifespan may be further improved. In addition, at least one effect capable of improving the convenience (operation efficiency or yield) of the preparation process may be obtained.

The solvent having a boiling point at atmospheric pressure in a range of about 100° C. to about 350° C. is not particularly limited, and a known solvent may be appropriately used. Specific examples of the solvent having a boiling point at atmospheric pressure in a range of about 100° C. to about 350° C. are provided below, but the present disclosure is not limited thereto.

Examples of a hydrocarbon-based solvent are octane, nonane, decane, undecane, dodecane, and the like. Examples of an aromatic hydrocarbon-based solvent are toluene, xylene, ethylbenzene, n-propylbenzene, iso-propylbenzene, mesitylene, n-butylbenzene, sec-butylbenzene, 1-phenylpentane, 2-phenylpentane, 3-phenylpentane, phenylcyclopentane, phenylcyclohexane, 2-ethylbiphenyl, 3-ethylbiphenyl, and the like. Examples of an ether-based solvent are 1,4-dioxane, 1,2-diethoxyethane, diethylene glycol dimethylether, diethylene glycol diethylether, anisole, ethoxybenzene, 3-methylanisole, m-dimethoxybenzene, and the like. Examples of a ketone-based solvent are 2-hexanone, 3-hexanone, cyclohexanone, 2-heptanone, 3-heptanone, 4-heptanone, cycloheptanone, and the like. Examples of an ester-based solvent are butylacetate, butylpropionate, heptylbutyrate, propylenecarbonate, methylbenzoate, ethylbenzoate, 1-propylbenzoate, 1-butylbenzoate, and the like. Examples of a nitrile-based solvent are benzonitrile, 3-methylbenzonitrile, and the like. Examples of an amide-based solvent are dimethylformamide, dimethylacetamide, N-methylpyrrolidone, and the like. Among these examples, the ester-based solvent may be preferable, and the methyl benzoate may be more preferable. Such a solvent may be used alone or in combination of two or more materials.

When the liquid composition includes the composition including the compound represented by Formula (1) and the solvent, an amount of the composition in the liquid composition is not particularly limited, and may be appropriately adjusted depending on the application. However, from the viewpoint of applicability and the like, a concentration of the composition in the liquid composition may be adjusted to be preferably in a range of about 0.05 parts by weight to about 10 parts by weight based on 100 parts by weight of the solvent. In addition, the concentration of the composition in the liquid composition may be adjusted to be more preferably in a range of about 0.1 parts by weight to about 6 parts by weight based on 100 parts by weight of the solvent. When the concentration of the composition is within these ranges above, precipitation from a solution is more difficult to occur, so that the pot life of a solution becomes longer. In addition, the driving voltage of an organic electroluminescent device is lowered, thereby further improving luminescence efficiency and luminescence lifespan. In addition, when the liquid composition includes only the compound represented by Formula (1) and the solvent, a preferable concentration of the compound is also within the same ranges as described above.

In addition, a preparation method of the liquid composition is not particularly limited. For example, such a liquid composition may be prepared by mixing the compound represented by Formula (1), and any other compounds, and the solvent. Here, the mixing order is not particularly limited, and mixing methods and mixing conditions are not particularly limited. Various preparation methods including known preparation methods may be used.

Organic Electroluminescent Device

Another aspect of the present disclosure provides an organic electroluminescent device including the compound represented by Formula (1). In an embodiment, the organic electroluminescent device may be an organic light-emitting diode device including a pair of electrodes and an organic layer arranged between the pair of electrodes, wherein the organic layer includes the compound represented by Formula (1) or the composition including the compound represented by Formula (1).

Hereinafter, embodiments of the present disclosure will be described in detail with reference to the attached drawings. In addition, dimensional ratios in the drawings may be exaggerated for convenience of description, and thus may be different from actual ratios.

FIG. 1 is a schematic diagram showing an organic electroluminescent device according to an embodiment of the present disclosure. Hereinafter, the organic electroluminescent device according to an embodiment of the present disclosure will be described in detail by referring to the FIG. 1.

As shown in the FIG. 1, the organic electroluminescent device (also referred to as organic EL device) 100 according to an embodiment of the present disclosure includes a substrate 110, a first electrode 120 arranged on the substrate 110, a hole injection layer 130 arranged on the first electrode 120, a hole transport layer 140 arranged on the hole injection layer 130, an emission layer 150 arranged on the hole transport layer 140, an electron transport layer 160 arranged on the emission layer 150, an electron injection layer 170 arranged on the electron transport layer 160, and a second electrode 180 arranged on the electron injection layer 170.

Here, the compound represented by Formula (1) may be included in one organic layer arranged between the first electrode 120 and the second electrode 180. The composition including the compound represented by Formula (1) and the different compound from the compound represented by Formula (1) may be included in, for example, one organic layer arranged between the first electrode 120 and the second electrode 180.

In detail, considering that the compound represented by Formula (1) exhibits excellent hole transport capability and electron transport capability, it is preferable to include the compound represented by Formula (1) in the emission layer 150. It is more preferable to include the compound represented by Formula (1) as a host material in the emission layer 150. Considering that the composition including the compound represented by Formula (1) and the different compound from the compound represented by Formula (1) exhibits excellent hole transport capability and electron transport capability, it is preferable to include the composition in the emission layer 150. It is more preferable to include the composition as a host material in the emission layer 150.

In addition, it is preferable to form the organic layer including the compound represented by Formula (1) by a wet film-forming method. It is more preferable to form the organic layer by a coating method. In detail, examples of the coating method are spin coating, casting, micro-gravure coating, gravure coating, bar coating, roll coating, wire bar coating, dip coating, spray coating, screen printing, flexographic printing, offset printing, ink jet printing, and the like. Among these examples, ink jet printing may be preferable from the viewpoint of productivity.

As a coating liquid used in the coating method, the liquid composition described above may be preferable. Thus, details of the coating liquid are the same as those described in connection with the liquid composition.

In addition, procedures, conditions, and equipment for the wet film-forming method or the coating method are not particularly limited, and procedures, conditions, and equipment that are similar to those used for known wet film-forming methods and known coating methods may be appropriately employed.

In addition, a method of depositing a layer other than the organic layer including the compound represented by Formula (1) is not particularly limited. Such a layer other than the organic layer may be, for example, formed by a dry film-forming method, such as a vacuum deposition method, or a wet film-forming method, such as a coating method.

For the substrate 100, any substrate used in a general organic EL device may be used. For example, the substrate 110 may be a glass substrate, a semiconductor substrate, such as a silicon substrate, or a transparent plastic substrate.

The first electrode 120 may be formed on the substrate 100. The first electrode 120 may be preferably a cathode. The first electrode 120 may be preferably formed of a material, such as metal, alloy, or a conductive compound, having a large work function (i.e., minimum energy required to take out one electron in a material). For example, the first electrode 120 may be formed as a transmissive electrode, formed of a transparent conductive layer such as indium tin oxide ($In_2O_3$—$SnO_2$:ITO), indium zinc oxide ($In_2O_3$—ZnO), tin oxide ($SnO_2$), and zinc oxide (ZnO), each having excellent transparency and conductivity. In addition, the first electrode 120 may be formed as a reflective electrode by stacking magnesium (Mg), aluminum (Al), or the like on the transparent conductive layer.

Accordingly, a hole injection layer 130 may be formed on the first electrode 120. The hole injection layer 130 is a layer that facilitates injection of holes from the first electrode 120. A thickness of the hole injection layer 130 is not particularly limited, but may be preferably in a range of about 10 nm to about 1,000 nm. In addition, the thickness of the hole injection layer 130 may be preferably in a range of about 10 nm to about 100 nm.

The hole injection layer 130 may include a known material, such as a known hole injection material.

The hole injection material is not particularly limited, but examples thereof include poly(ether ketone)-containing triphenylamine (TPAPEK), 4-isopropyl-4'-methyldiphenyliodonium tetrakis(pentafluorophenyl) borate (PPBI), N, N'-diphenyl-N, N'-bis-[4-(phenyl-m-tolyl-amino-phenyl]-biphenyl-4,4'-diamine (DNTPD), copper phthalocyanine, 4,4',4"-tris(3-methylphenylphenylamino) triphenylamine (m-MTDATA), N, N'-di(1-naphthyl)-N, N'-diphenylbenzidine (NPB), 4,4',4"-tris(diphenyamino) triphenylamine (TDATA), 4,4',4"-tris(N,N-2-naphthylphenylamino) triphenylamine (2-TNATA), polyaniline/dodecylbenzenesulphonic acid, poly(3,4-ethylenedioxythiophene)/poly(4-styrenesulfonate) (PEDOT/PSS), polyaniline/10-camphorsulfonic acid, and the like.

Then, a hole transport layer 140 may be formed on the hole injection layer 130. The hole transport layer 140 is a functional layer that transports holes. A thickness of the hole transport layer 140 is not particularly limited, but may be preferably in a range of about 10 nm to about 150 nm.

The hole transport layer 140 may include a known material, such as a known hole transport material.

The hole transport material is not particularly limited, but examples thereof include: a carbazole derivative, such as 1,1-bis [(di-4-tolylamino) phenyl] cyclohexane (TAPC), N-phenylcarbazole, and polyvinylcarbazole; N,N'-bis(3-methylphenyl)-N, N'-diphenyl-[1,1-biphenyl]-4,4'-diamine (TPD); 4,4',4''-tris(N-carbazolyl) triphenylamine (TCTA); N,N'-di(1-naphthyl)-N,N'-diphenylbenzidine (NPB); and the like. In addition, the hole transport materials disclosed in WO2011/159872 and US2016/0315259 may be used. A preferred hole transport material may be, for example, Compound HTP1 or Compound AD1 used in Examples below.

Next, an emission layer 150 may be formed on the hole transport layer 140. The emission layer 150 is a layer emitting fluorescence or phosphorescence. A thickness of the emission layer 150 is not particularly limited, but may be preferably in a range of about 10 nm to about 60 nm.

A luminescent material included in the emission layer 150 may be preferably a luminescent material capable of emitting light from triplet excitons (i.e., phosphorescence). In this case, the luminescence efficiency and luminescence lifetime of the organic EL device 100 may be further improved.

The emission layer 150 may particularly preferably include the compound represented by Formula (1), and may more preferably include the composition including the compound represented by Formula (1). As a host material in the emission layer 150, the emission layer 150 may particularly preferably include the compound represented by Formula (1), and may more preferably include the composition including the compound represented by Formula (1).

The emission layer 150 may further include, in addition to the compound represented by Formula (1), other materials including a known luminescent material. In addition, when the organic layer other than the emission layer 150 includes the compound represented by Formula (1), the emission layer 150 does not include the compound represented by Formula (1), but may include other materials including a known luminescent material.

The host material in the emission layer 150 (also referred to as emission layer host material) is not particularly limited, but examples thereof are known materials, such as (tris(8-quinolinato) aluminium ($Alq_3$), 4,4'-bis(carbazol-9-yl)biphenyl (CBP), poly(N-vinyl carbazole) (PVK), 9,10-di (naphthyl)anthracene (ADN), 4,4', 4''-tris(N-carbazolyl) triphenylamine (TCTA), 1,3,5-tris(N-phenyl-benzimidazol-2-yl)benzene (TPBI), 3-tert-butyl-9,10-di(naphth-2-yl)anthracene (TBADN), distyrylanthracene (DSA), 4,4'-bis(9-carbazolyl)2,2'-dimethyl-biphenyl (dmCBP), and the like. In addition, a preferred host material (emission layer host material) other than the compound represented by Formula (1) in the emission layer 150 may be the compound represented by Formula (B1), the carbazole derivative, or the azine ring derivative.

A dopant material in the emission layer 150 is not particularly limited, but examples thereof are known materials, such as perylene and a derivative thereof, rubrene and a derivative thereof, coumarin and a derivative thereof, 4-dicyanomethylene-2-(p-dimethylaminostyryl)-6-methyl-4H-pyran (DCM) and a derivative thereof, Ir complex, Os complex, Pt complex, and the like. In addition, a preferred dopant material in the emission layer 150 may be the phosphorescent metal complex of the platinum family described, and for example, a phosphorescent Ir complex and a phosphorescent Pt complex may be preferable.

The emission layer 150 may include, as the luminescent material, nanoparticles including quantum dots. The quantum dots are nanoparticles consisting of Groups II-VI semiconductor, Groups III-V semiconductor, or Groups IV-IV semiconductor. Examples of the semiconductor are CdS, CdSe, CdTe, ZnSe, ZnS, PbS, PbSe, HgS, HgSe, HgTe, CdHgTe, $CdSe_xTe_{1-x}$, GaAs, InAs, InP, and the like. However, the semiconductor is not limited thereto. A diameter of the nanoparticles including quantum dots is not particularly limited, but may be preferably in a range of about 1 nm to about 20 nm. The nanoparticles including quantum dots may have a single core structure or a core/shell structure in which a shell is coated on the surface of the core.

Then, an electron transport layer 160 may be formed on the emission layer 150. The electron transport layer 160 is a functional layer that transports electrons. A thickness of the electron transport layer 160 is not particularly limited, but may be preferably in a range of about 15 nm to about 50 nm.

The electron transport layer 160 may include a known material, such as a known electron transport material.

The electron transport material is not particularly limited, but may be $Alq_3$ and a compound including a nitrogen-containing aromatic ring. Examples of the compound including a nitrogen-containing aromatic ring are: a compound including a pyridine ring, such as 1,3,5-tri [(3-pyridyl)-phen-3-yl]benzene; a compound including a triazine ring, such as 2,4,6-tris(3'-(pyridin-3-yl)biphenyl-3-yl)-1,3,5-triazine; a compound including an imidazole ring, such as 2-(4-(N-phenylbenzoimidazol-1-yl-phenyl)-9,10-di-naphthylanthracene; and the like. In addition, the compound including a nitrogen-containing aromatic ring may be a mixture of (8-quinolinato)lithium (Liq) and KLET-03 (a product of Chemipro Chemical Corporation).

Then, an electron injection layer 170 may be formed on the electron transport layer 160. The electron injection layer 130 is a functional layer that facilitates injection of electrons from the second electrode 180. A thickness of the electron injection layer 170 is not particularly limited, but may be preferably in a range of about 0.3 nm to about 20 nm.

The electron injection layer 170 may include a known material, such as a known electron injection material.

The material of electron injection layer 170 is not particularly limited, but examples thereof are known materials, such as a Li compound including Liq and lithium fluoride (LiF), sodium chloride (NaCl), cesium fluoride (CsF), lithium oxide ($Li_2O$), barium oxide (BaO), and the like.

Then, a second electrode 180 may be formed on the electron injection layer 170. The second electrode 180 may be preferably an anode. The second electrode 180 is not particularly limited, but may be preferably formed of, for example, a material, such as metal, alloy, or a conductive compound, having a small work function. The second electrode 180 may be formed as a reflective electrode using metal, such as lithium (Li), magnesium (Mg), aluminum (Al), or calcium (Ca), or alloy, such as aluminum-lithium (Al—Li), magnesium-indium (Mg—In), or magnesium-silver (Mg—Ag). In addition, the second electrode 180 may be formed as a transparent electrode using a transparent conductive film having a thickness of 20 nm or less and consisting of a metal oxide, such as indium tin oxide ($In_2O_3$—$SnO_2$) and indium zinc oxide ($In_2O_3$—ZnO).

As such, the organic EL device 100 according to another aspect of the present disclosure may include the organic layer including the compound represented by Formula (1). Accordingly, an organic EL device having a low driving voltage, excellent current efficiency, and a long luminescence lifespan may be prepared by a wet film-forming method.

Here, a preferable combination of each compound to form the organic layer may be the same as the combination of each compound to form the preferred composition described above.

Here, a preferable amount of each component in the organic layer may be the same as described in connection with the composition.

In addition, the stacking structure of the organic EL device 100 according to an embodiment of the present disclosure is not limited to the embodiments above. The organic EL device 100 according to an embodiment of the present disclosure may be formed in a different stacking structure known in the art. For example, in the organic EL device 100 of the FIGURE, at least one layer of the hole injection layer 130, the hole transport layer 140, the electron transport layer 160, and the electron injection layer 170 may be omitted, or other layers may be further provided. In addition, each layer of the organic EL device 100 may be formed of a single layer or several layers.

For example, the organic EL device 100 may further include, to prevent excitons or holes from diffusing into the electron transport layer 160, a hole blocking layer between the emission layer 150 and the electron transport layer 160. In addition, such a hole blocking layer may be formed of, for example, an oxadiazole derivative, a triazole derivative, or a phenanthroline derivative.

EXAMPLES

Although the present disclosure will be described in more detail using Examples and Comparative Examples below, the technical scope of the present disclosure is not limited to Examples below.

<Synthesis of Compound Represented by Formula (1)>

Each compound represented by Formula (1) used in Examples (i.e., each Example Compound) was synthesized by a reaction described in Reaction Scheme (1-I), (1-II), (2-I), or (2-II) regarding the compound represented by Formula (1) or by a combination of these reactions and other known reactions.

Among the synthesis methods of compounds of each Example, specific synthesis methods of Compounds 1, 2, 6, 14, 25, 28, 46, 47, 59, 90, and 103 of Examples are as follows. In addition, compounds of other Examples were also synthesized by a method Such as Synthesis Methods Described Herein.

Synthesis Method of Compound 1

Synthesis of IM-1

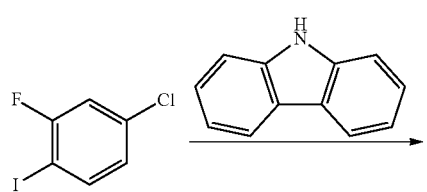

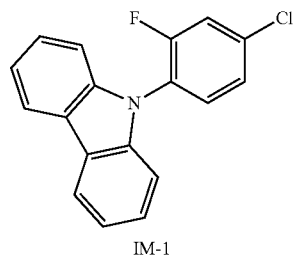

IM-1

4-chloro-2-fluoro-1-iodine benzene (300 mmol, 76.9 g), carbazole (1.1 eq., 330 mmol, 55.2 g), K$_3$PO$_4$ (1.5 eq., 450 mmol, 95.5 g), and 1,4-dioxane (60 ml) were added to a three neck-flask, and the reaction system was purged with nitrogen (N$_2$). Then, CuI (4 mol %, 12 mmol, 2.29 g) and trans-1,2-diamino cyclohexane (10 mol %, 30 mmol, 3.61 ml) were added to the three neck-flask, and the mixed solution was heated and stirred at a temperature of 100° C. for 40 hours. Subsequently, the reaction mixture solution thus obtained was diluted with toluene (1 L), filtered through Celite, filtered again through a silica gel pad, and then concentrated. The crude thus obtained was purified by silica gel chromatography (developing solvent was hexane:toluene=1:1), and recrystallized using ethyl acetate (3 ml): MeOH (10 ml)/filtrate (1 g), so as to obtain IM-1. Here, IM-1 had a yield of 38.4 g and a yield rate of 43%.

Synthesis of IM-2

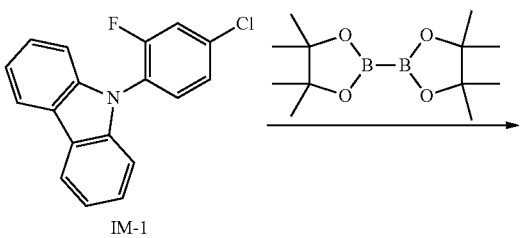

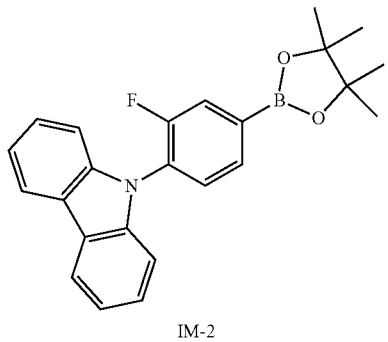

IM-2

IM-1 (1.0 eq., 130 mmol, 38.4 g), bis(pinacolato)diboron (1.1 eq., 143 mmol, 36.3 g), potassium acetate (2.0 eq., 260 mmol, 25.5 g), and 1, 4-dioxane (520 ml) were added to a three neck-flask, and the reaction system was purged with nitrogen ($N_2$). Then, palladium acetate (2 mol %, 2.6 mmol, 0.58 g) and 2-dicyclohexyl phosphino-2', 4', 6'-triisopropyl biphenyl (XPhos) (4 mol %, 5.2 mmol, 2.48 g) were added to the three neck-flask. The mixed solution was heated and stirred at a temperature of 100° C. for 6 hours in the nitrogen atmosphere. After completion of the reaction, the reaction mixture solution thus obtained was diluted with toluene (500 ml), filtered through Celite, repeatedly water-rinsed three times, dried using anhydrous magnesium sulfate, filtered by passing through a short silica gel column. The precipitated solid was dispersed in hexane (200 ml), ultrasonically washed for 10 minutes, and then filtered. In addition, the sample thus obtained was recrystallized using hexane (10 ml)/sample (1 g), so as to obtain IM-2. Here IM-2 had a yield of 39.8 g and a yield rate of 79%.

Synthesis of IM-3

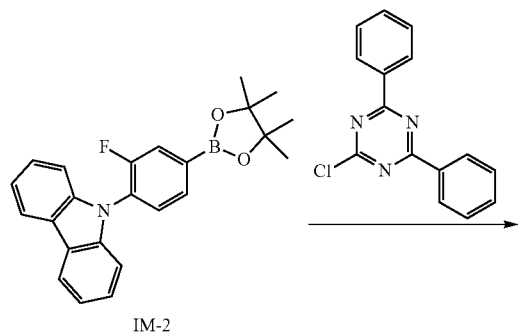

IM-2

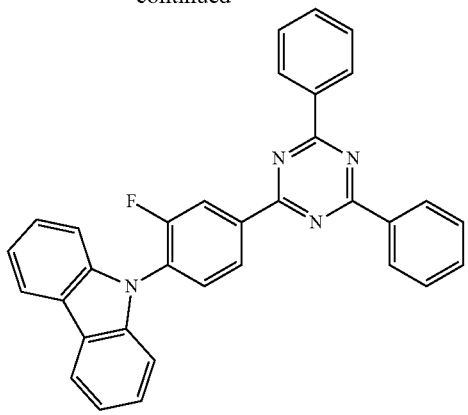

IM-3

IM-2 (1.05 eq., 105 mmol, 40.7 g), 2-chloro-4,6-diphenyl-1,3,5-triazine (1.0 eq., 100 mmol, 26.8 g), an aqueous potassium carbonate solution (2.0 M, 100 ml), and tetrahydrofuran (300 ml) were added to a three neck-flask, and the reaction system was purged with nitrogen. Then, palladium acetate (4 mol %, 4 mmol, 0.90 g) and tri(o-tolyl) phosphine (6 mol %, 6 mmol 1.83 g) were added to the three neck-flask, and the mixed solution was heated and stirred at a temperature of 60° C. for 2 hours in the nitrogen atmosphere. After completion of the reaction, the reaction mixture solution thus obtained was diluted with water (500 ml) and methanol (500 ml), and the precipitated solid was collected by filtration, water-washed, washed with methanol, and dried in a vacuum condition (50° C., 16 h). The crude thus obtained was dissolved in chloroform and concentrated by passing through a short silica gel column. The precipitated solid was dispersed in ethyl acetate (500 ml), ultrasonically washed for 10 minutes, and then filtered. In addition, the crude thus obtained was recrystallized using toluene (15 ml):ethyl acetate (30 ml)/sample (1 g), so as to obtain IM-3. Here, IM-3 had a yield of 34.5 g and a yield rate of 70%.

Synthesis of Compound 1

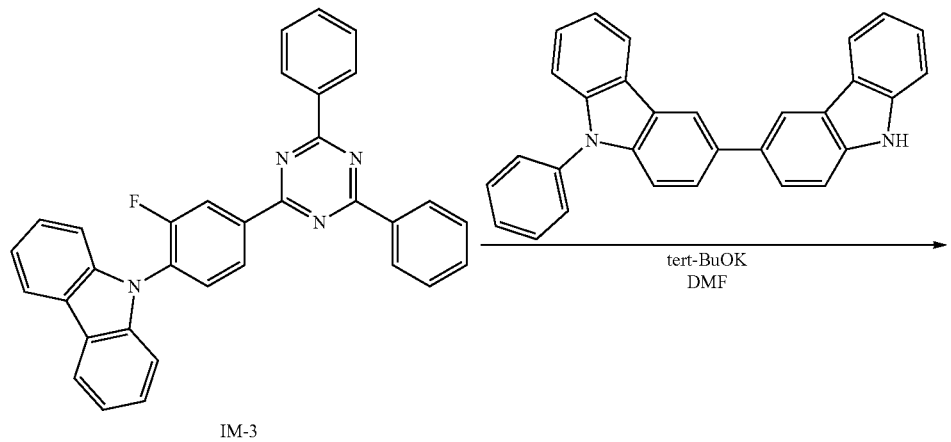

IM-3

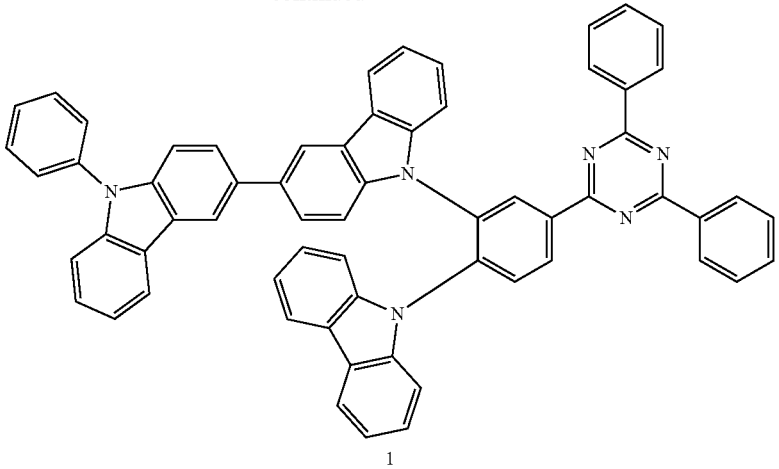

1

IM-3 (1.0 eq., 15 mmol, 7.39 g), 9-phenyl-9H, 9'H-3,3'-bicarbazole (1.3 eq., 19.5 mmol, 7.97 g), and N, N-dimethyl formamide (30 ml) were added to a three neck-flask, and the reaction system was replaced with nitrogen. Then, tert-BuOK (potassium tert-butoxide) (1.2 eq., 18 mmol, 2.02 g) was added to the three neck-flask, and the mixed solution was heated and stirred at a temperature of 140° C. for 8 hours in the nitrogen atmosphere. After completion of the reaction, the reaction mixture solution thus obtained was diluted with toluene (500 ml), filtered through Celite, and filtered again through a silica gel pad. Subsequently, the resultant solution thus obtained was repeatedly water-rinsed three times, dried using anhydrous magnesium sulfate, and concentrated by passing through a short silica gel column. The crude thus obtained was purified by silica gel chromatography (developing solvent was hexane:toluene=1:1), and recrystallized twice using toluene (10 ml):ethyl acetate (20 ml)/filtrate (1 g), so as to obtain Compound 1. Here, Compound 1 had a yield of 7.0 g and a yield rate of 53%.

Synthesis Method of Compound 2

Synthesis of IM-4

IM-4 was synthesized in the same manner as used to synthesize IM-1 according to the following materials and scheme. Here, IM-4 had a yield rate of 73%.

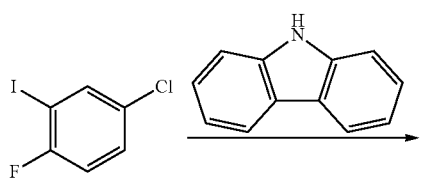

Synthesis of IM-5

IM-5 was synthesized in the same manner as used to synthesize IM-2 according to the following materials and scheme. Here, IM-5 had a yield rate of 54%.

Synthesis of IM-6

IM-6 was synthesized in the same manner as used to synthesize IM-3 according to the following materials and scheme. Here, IM-6 had a yield rate of 81%.

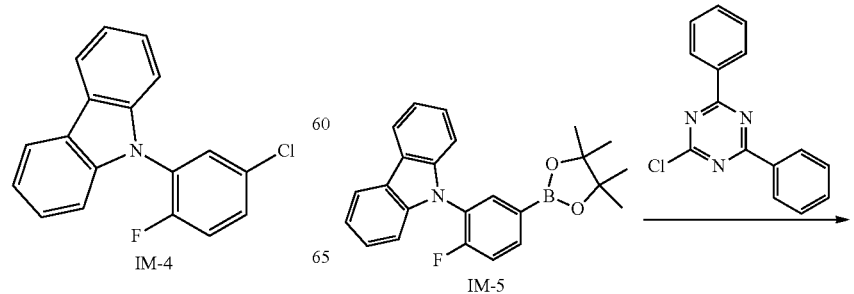

233
-continued
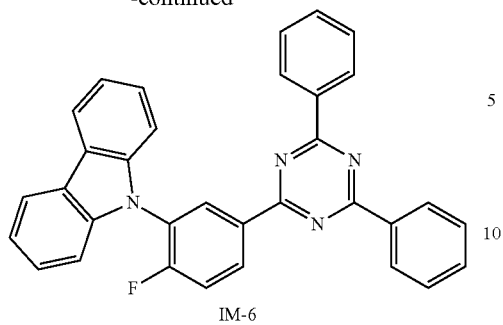
IM-6
Synthesis of Compound 2
Compound 2 was synthesized in the same manner as used to synthesize Compound 1 according to the following materials and scheme. Here, Compound 2 had a yield rate of 55%.
234
Synthesis Method of Compound 47
Synthesis of IM-7
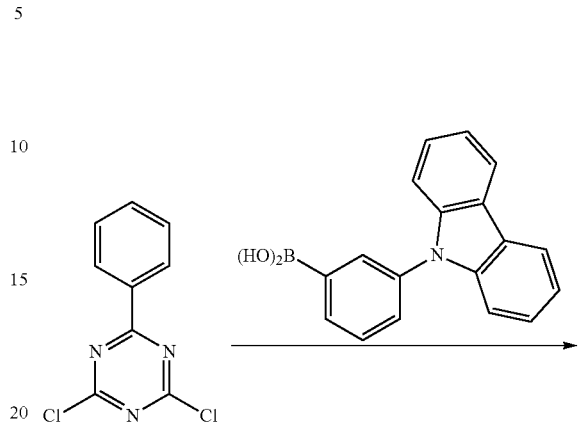
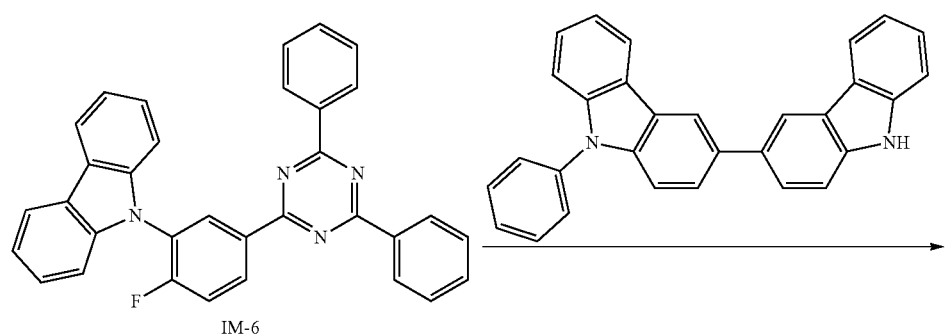
IM-6
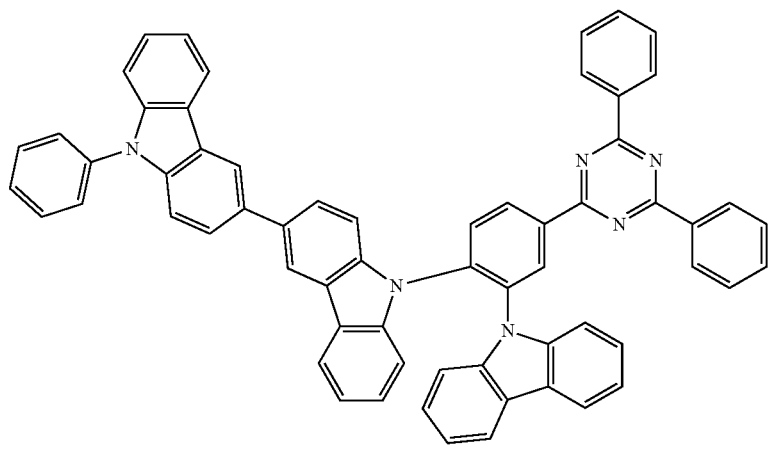
2

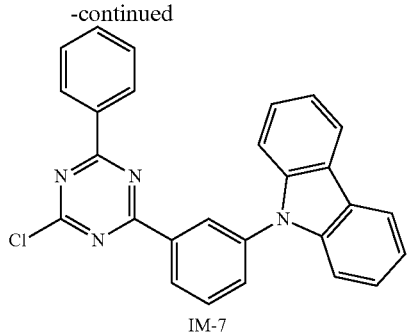

IM-7

2,4-dichloro-6-phenyl-1,3,5-triazine (1.05 eq., 210 mmol, 47.5 g), 3-(9H-carbazole-9-yl) phenylboronic acid (1.0 eq., 200 mmol, 57.4 g), an aqueous potassium carbonate solution (2.0 M, 200 ml), and tetrahydrofuran (800 ml) were added to a three neck-flask, and dissolved uniformly. After the reaction system was purged with nitrogen, palladium acetate (4 mol %, 8 mmol, 1.80 g) and tri(o-tolyl)phosphine (6 mol %, 12 mmol, 3.65 g) were added to the three neck-flask, and the mixed solution was heated and stirred at a temperature of 50° C. for 2 hours in the nitrogen atmosphere. After completion of the reaction, the reaction mixture solution thus obtained was diluted with toluene (1 L), filtered through Celite, repeatedly water-rinsed three times, dried using anhydrous magnesium sulfate, and concentrated by passing through a short silica gel column. The crude thus obtained was purified by silica gel chromatography (developing solvent was hexane:toluene=1:1), and recrystallized using toluene (5 ml):ethyl acetate (15 ml)/filtrate (1 g), so as to obtain IM-7. Here, IM-7 had a yield of 57.1 g and a yield rate of 66%.

Synthesis of IM-8

IM-8 was synthesized in the same manner as used to synthesize IM-3 according to the following materials and scheme. Here, IM-8 had a yield rate of 75%.

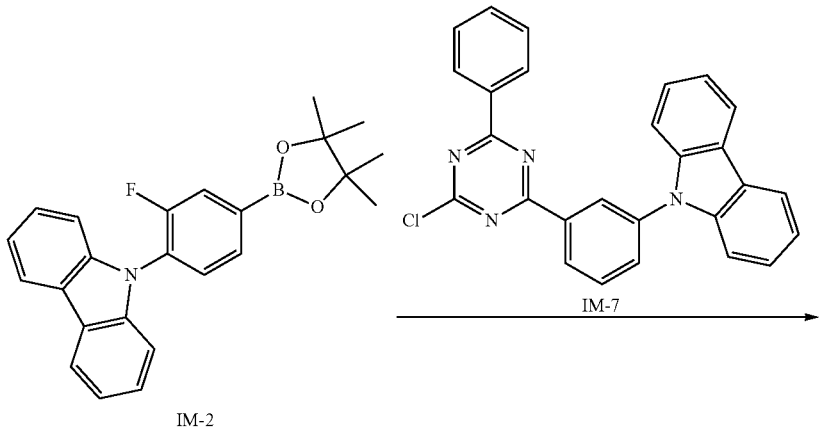

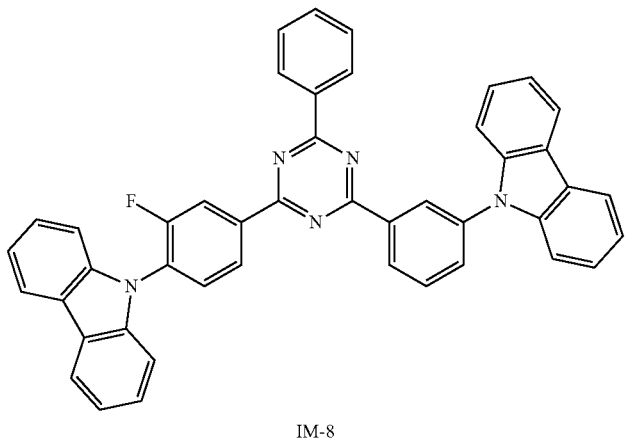

IM-8

Synthesis of Compound 47

Compound 47 was synthesized in the same manner as used to synthesize Compound 1 according to the following materials and scheme. Here, Compound 47 had a yield rate of 52%

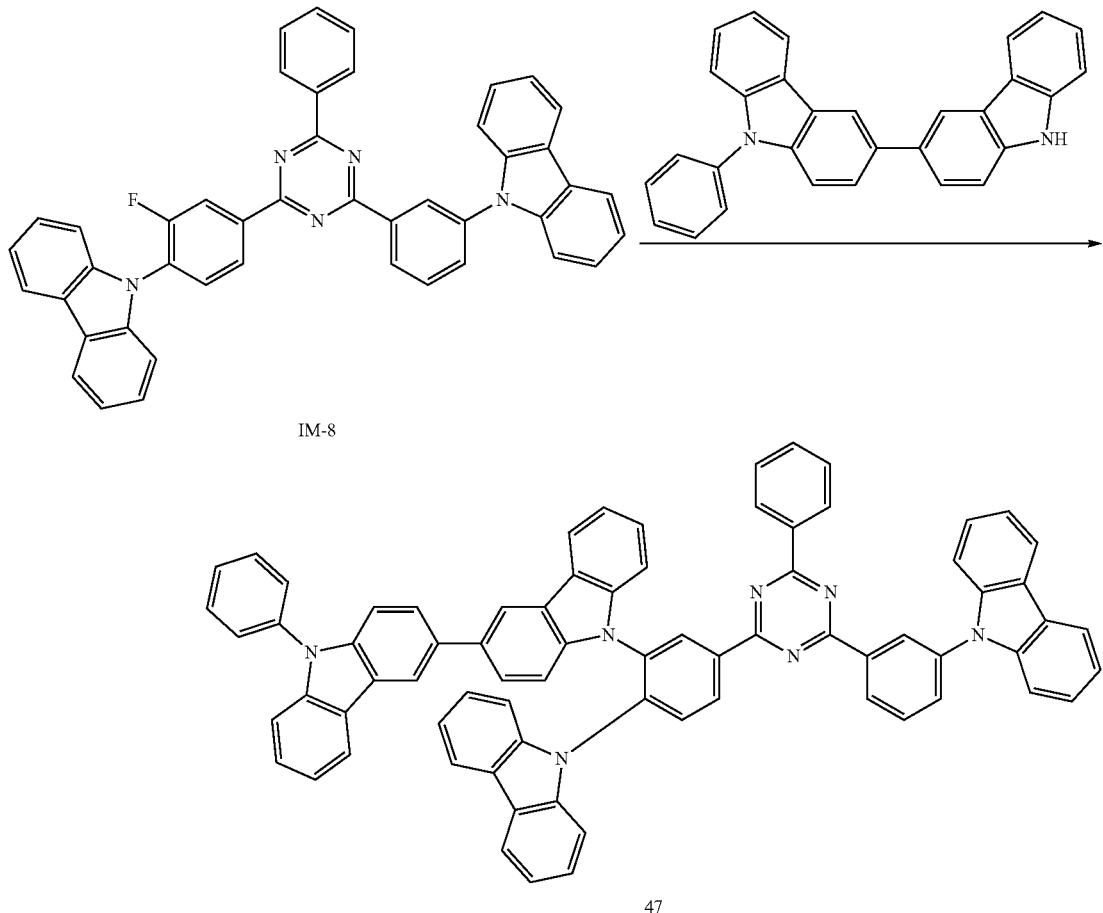

Synthesis Method of Compound 46

Synthesis of IM-9

IM-9 was synthesized in the same manner as used to synthesize IM-3 according to the following materials and scheme. Here, IM-9 had a yield rate of 70%.

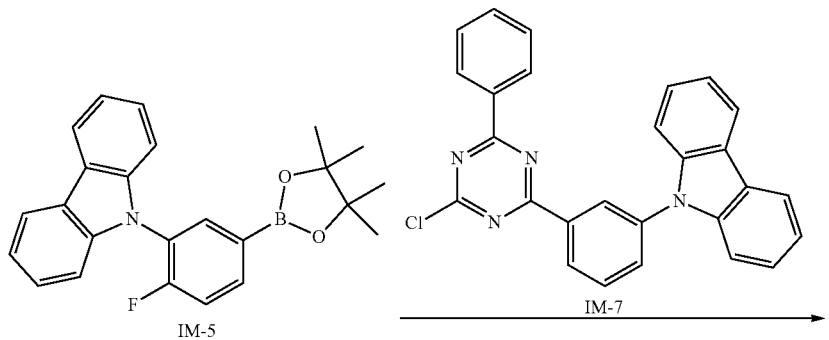

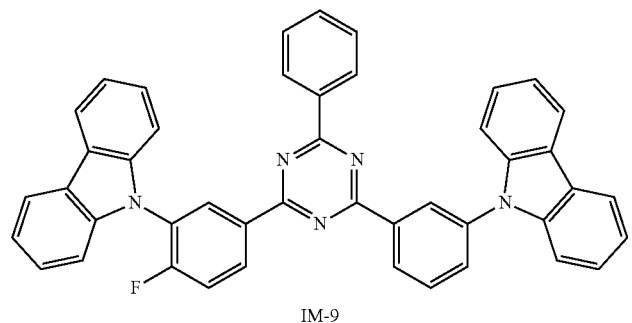
IM-9
Synthesis of Compound 46
Compound 46 was synthesized in the same manner as used to synthesize Compound 1 according to the following materials and scheme. Here, Compound 46 had a yield rate of 59%.
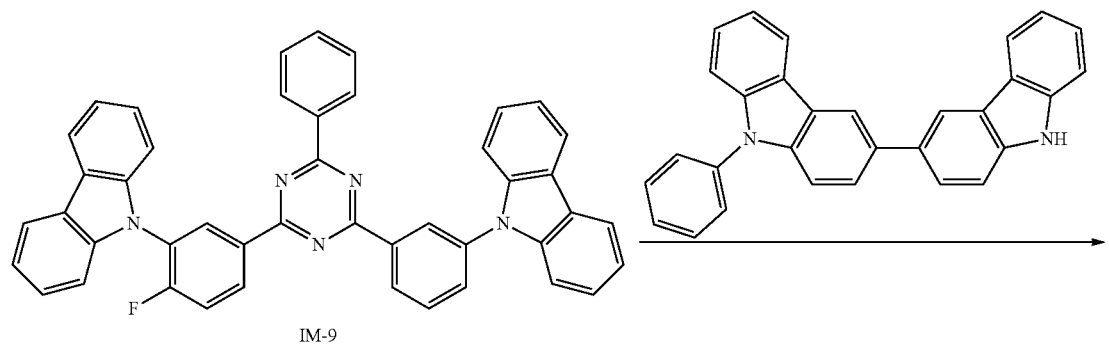
IM-9
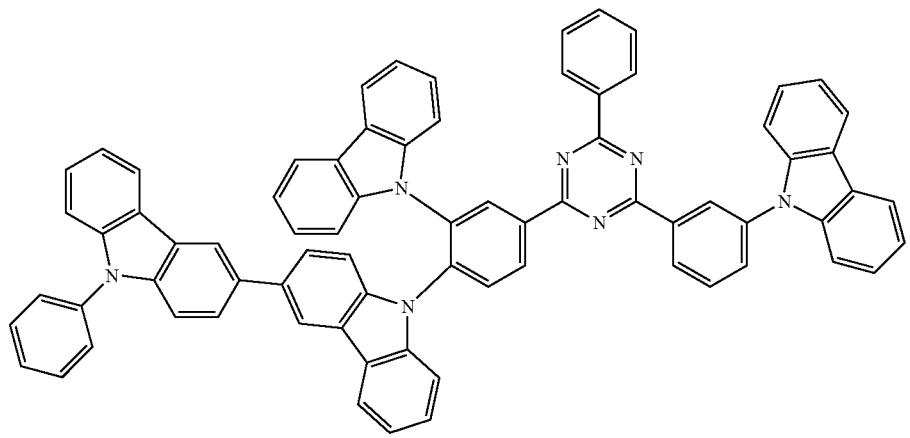
46

Synthesis Method of Compound 14

Synthesis of IM-10

IM-10 was synthesized in the same manner as used to synthesize IM-3 according to the following materials and scheme. Here, IM-10 had a yield rate of 80%.

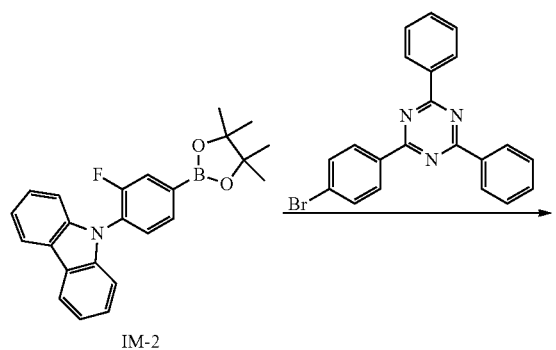

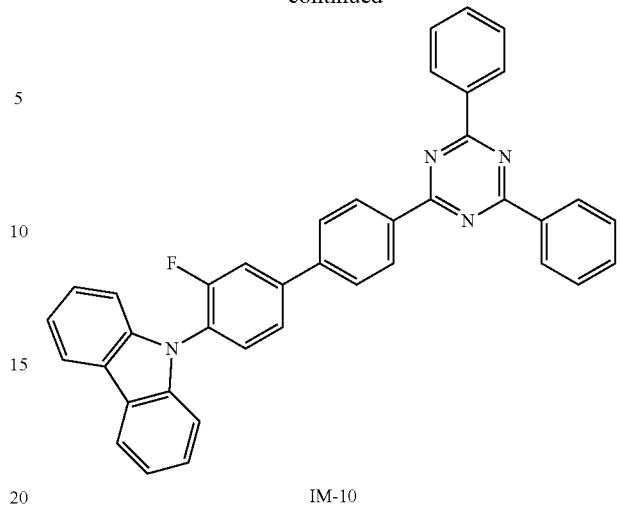

Synthesis of Compound 14

Compound 14 was synthesized in the same manner as used to synthesize Compound 1 according to the following materials and scheme. Here, Compound 14 had a yield rate of 54%.

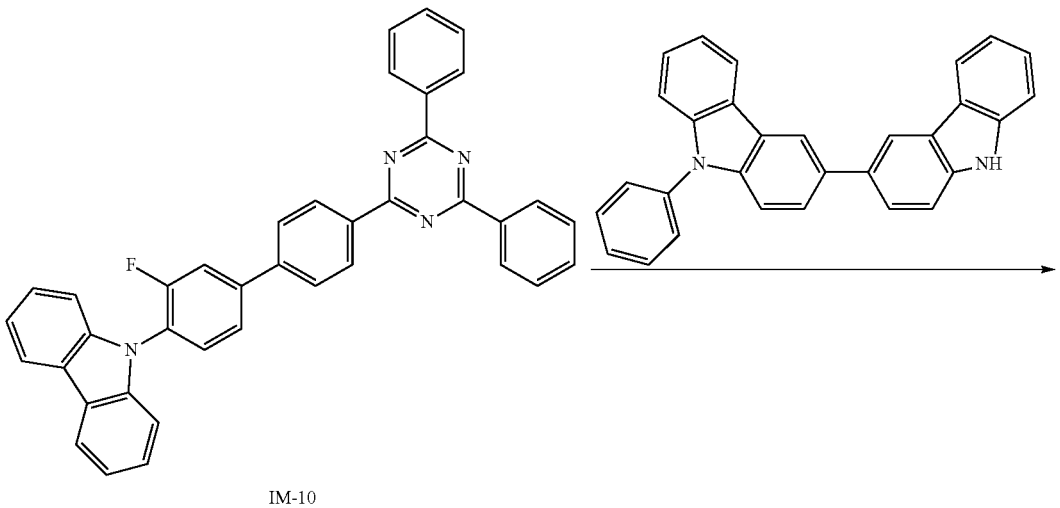

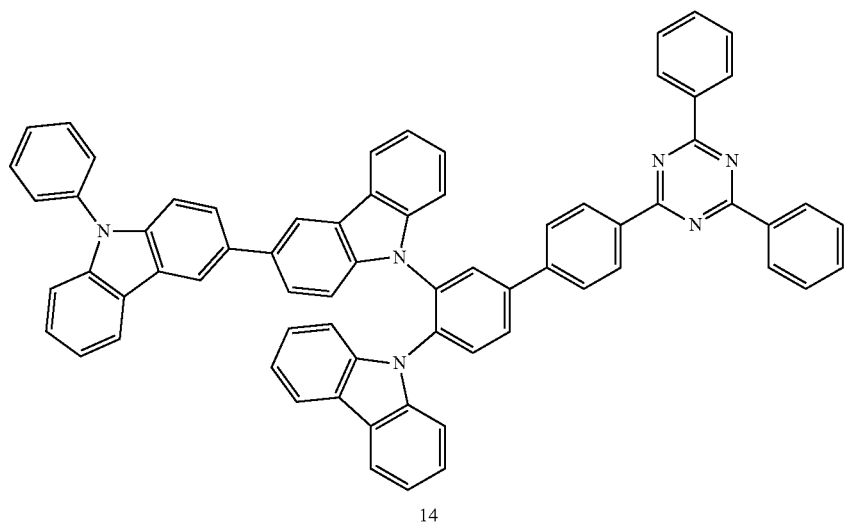

14

Synthesis Method of Compound 28

Synthesis of IM-11

IM-11 was synthesized in the same manner as used to synthesize IM-3 according to the following materials and scheme. Here, IM-11 had a yield rate of 76%.

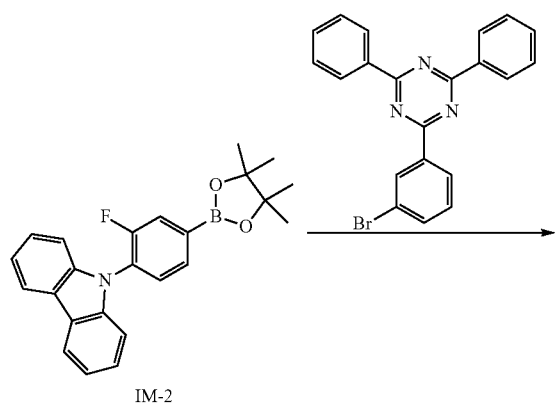

IM-2

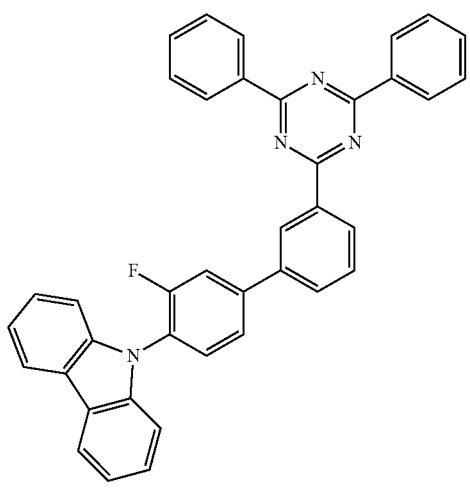

IM-11

Synthesis of Compound 28

Compound 28 was synthesized in the same manner as used to synthesize Compound 1 according to the following materials and scheme. Here, Compound 28 had a yield rate of 61%.

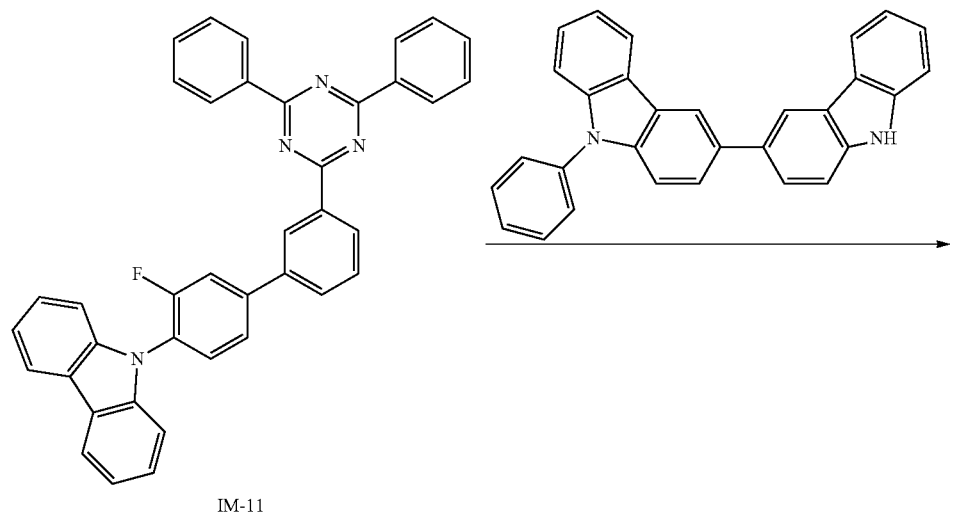
IM-11
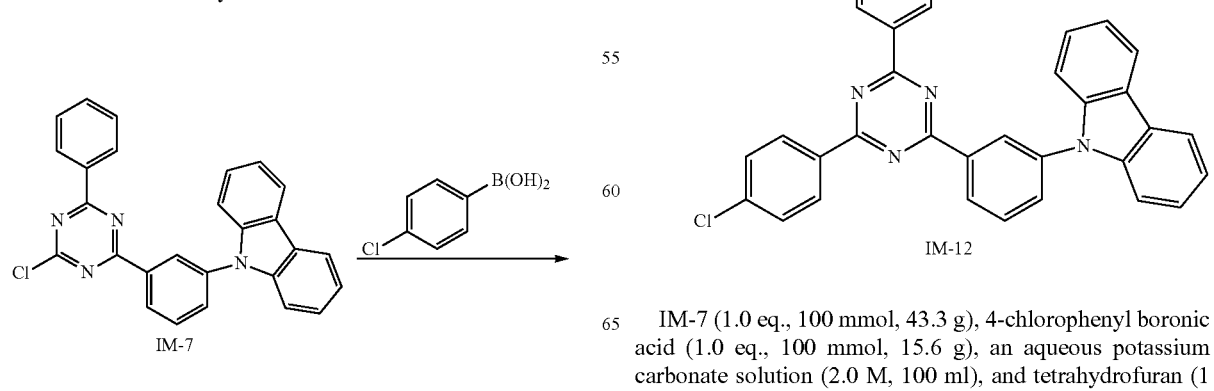
28
Synthesis Method of Compound 59
Synthesis of IM-12
IM-7 (1.0 eq., 100 mmol, 43.3 g), 4-chlorophenyl boronic acid (1.0 eq., 100 mmol, 15.6 g), an aqueous potassium carbonate solution (2.0 M, 100 ml), and tetrahydrofuran (1

L) were added to a three neck-flask, and dissolved uniformly. After the reaction system was purged with nitrogen, palladium acetate (4 mol %, 4 mmol, 0.90 g) and tri(o-tolyl) phosphine (6 mol %, 6 mmol, 1.83 g) were added to the three neck-flask, and the mixed solution was heated and stirred at a temperature of 50° C. for 4 hours in the nitrogen atmosphere. After completion of the reaction, the reaction mixture solution thus obtained was diluted with toluene (1 L), filtered through Celite, repeatedly water-rinsed three times, dried using anhydrous magnesium sulfate, and concentrated by passing through a short silica gel column. The crude thus obtained was recrystallized twice using toluene (5 ml):ethyl acetate (20 ml)/filtrate (1 g), so as to obtain IM-12. Here, IM-12 had a yield of 36.1 g and a yield rate of 71%.

IM-12 (1.0 eq., 40 mmol, 20.4 g), IM-2 (1.05 eq., 42 mmol, 16.3 g), an aqueous potassium carbonate solution (2.0 M, 40 ml), toluene (400 ml), and ethanol (40 ml) were added to a three neck-flask, and dispersed uniformly. After the reaction system was purged with nitrogen, palladium acetate (4 mol %, 1.6 mmol, 0.36 g) and 2-dicyclohexyl phosphino-2', 6'-dimethoxy biphenyl (SPhos)(6 mol %, 2.4 mmol, 0.99 g) were added to the three neck-flask, and the mixed solution was heated and stirred at a temperature of 70° C. for 6 hours in the nitrogen atmosphere. After completion of the reaction, the reaction mixture solution thus obtained was diluted with chloroform (2 L), filtered through Celite, repeatedly water-rinsed three times, dried using anhydrous magnesium sulfate, and concentrated by passing through a short silica gel column. The crude thus obtained was recrystallized twice using toluene (10 ml):ethyl acetate (20 ml)/filtrate (1 g), so as to obtain IM-13. Here, IM-13 had a yield of 23.5 g and a yield rate of 80%.

Synthesis of IM-13

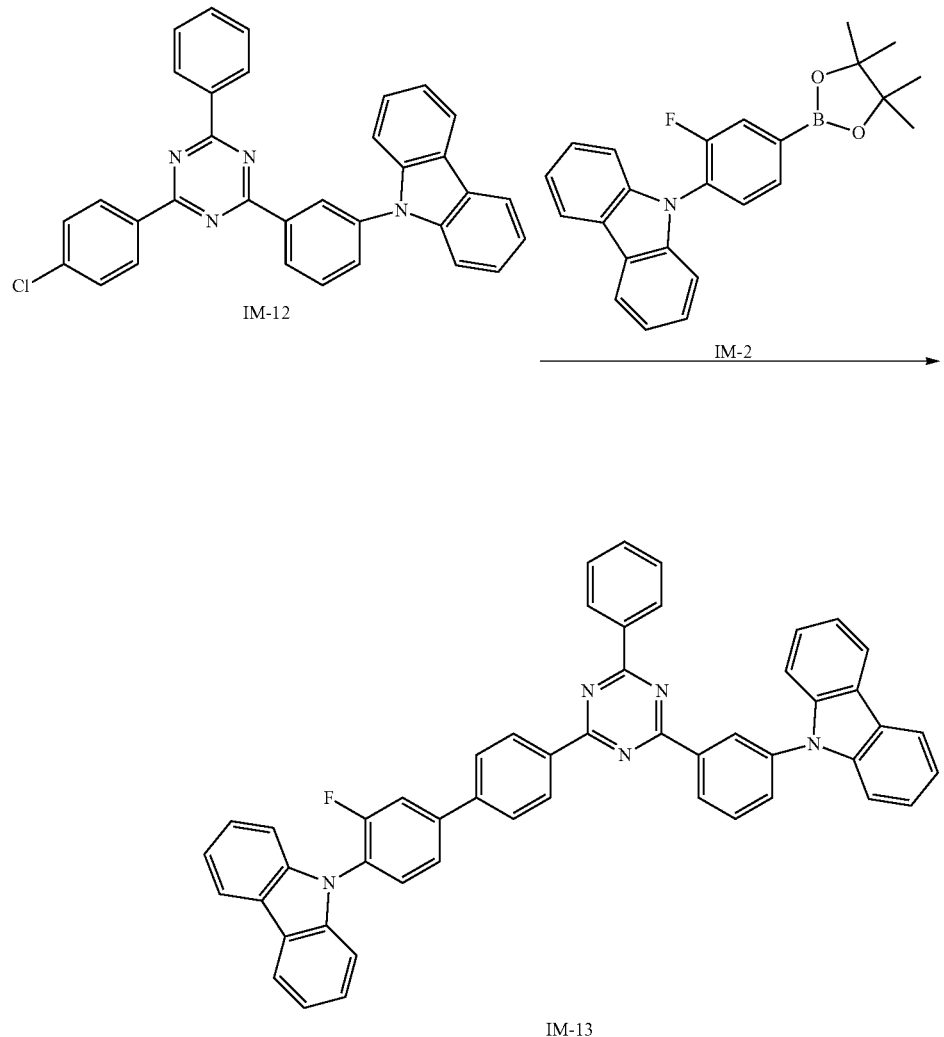

Synthesis of Compound 59

Compound 59 was synthesized in the same manner as used to synthesize Compound 1 according to the following materials and scheme. Here, Compound 59 had a yield rate of 45%.

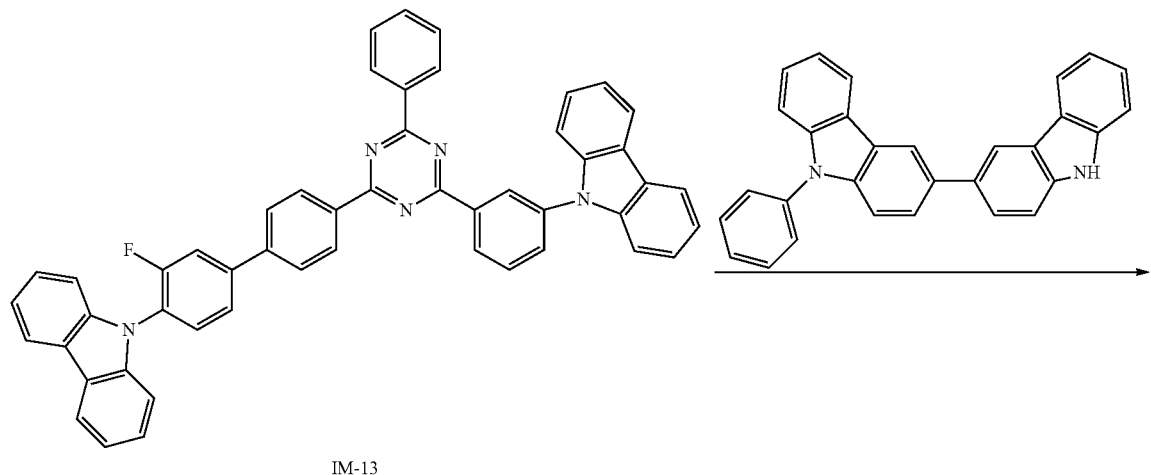

IM-13

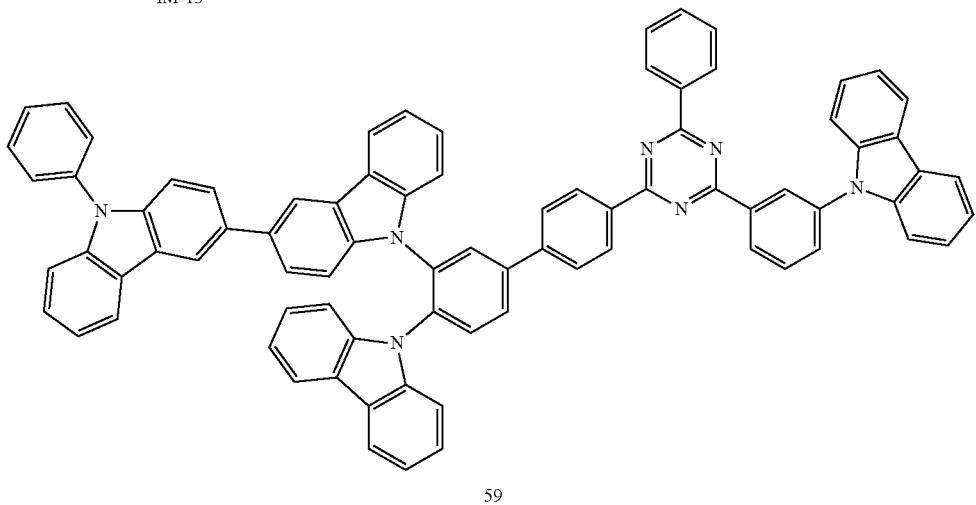

59

Synthesis Method of Compound 103

Synthesis of IM-14

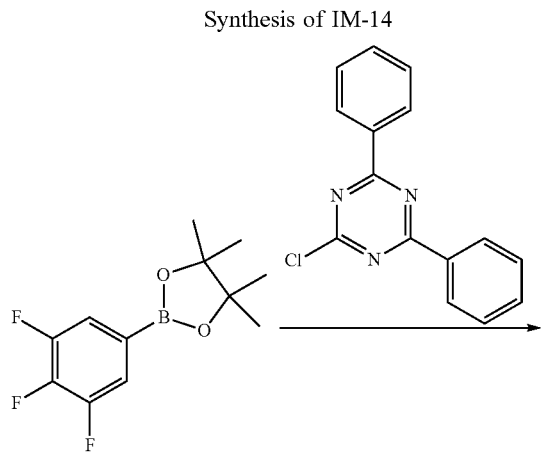

IM-14

4,4,5,5-tetramethyl-2-(3,4,5-trifluorophenyl)-1,3,2-dioxaborolane (1.05 eq., 84 mmol, 21.7 g), 2-chloro-4 6-diphenyl-1,3,5-triazine (1.0 eq., 80 mmol, 21.4 g), an aqueous potassium carbonate solution (2.0 M, 80 ml), and tetrahydrofuran (400 ml) were added to a three neck-flask, and dissolved uniformly. After the reaction system was purged with nitrogen, palladium acetate (4 mol %, 3.2 mmol, 0.72 g) and tri(o-tolyl)phosphine (6 mol %, 4.8 mmol, 1.46 g) were added to the three neck-flask, and the mixed solution was heated and stirred at a temperature of 50° C. for 4 hours in the nitrogen atmosphere. After completion of the reaction, the reaction mixture solution thus obtained was diluted with chloroform (1 L), filtered through Celite, repeatedly water-rinsed three times, dried using anhydrous magnesium sulfate, and concentrated by passing through a short silica gel column. The crude thus obtained was recrystallized using toluene (5 ml):hexane (20 ml)/filtrate (1 g), so as to obtain IM-14. Here, IM-14 had a yield of 15.1 g and a yield rate of 52%.

Synthesis of IM-15

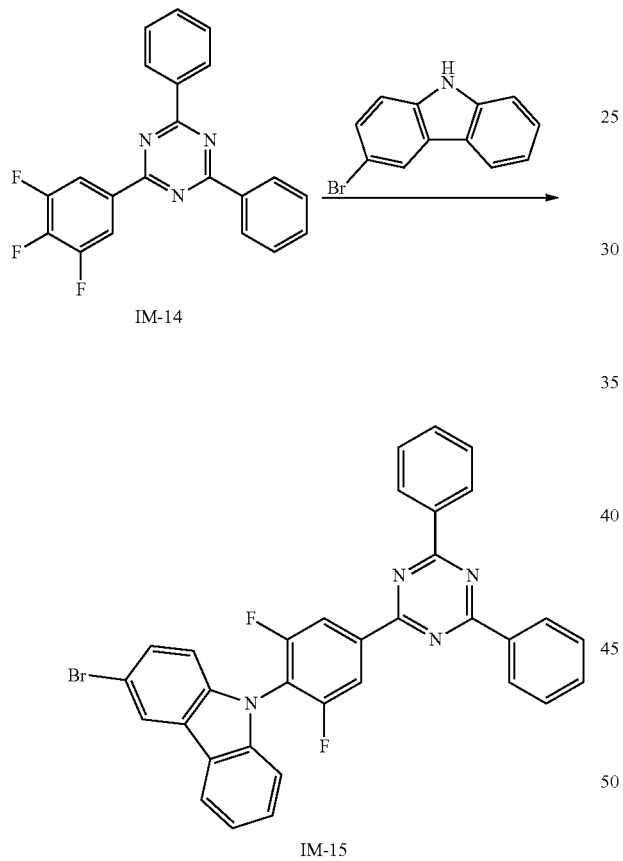

3-bromo carbazole (1.2 eq., 24 mmol, 5.90 g), N, N-dimethyl formamide (20 ml), and tert-BuOK (1.0 eq., 20 mmol, 2.24 g) were added to a three neck-flask, and completely dissolved. After the reaction system was purged with nitrogen, IM-14 (1.0 eq., 20 mmol, 7.27 g) was added to the three neck-flask, and the mixed solution was heated and stirred at a temperature of 120° C. for 8 hours in the nitrogen atmosphere. After completion of the reaction, the reaction mixture solution thus obtained was cooled to room temperature, and methanol (300 ml) was added thereto to precipitate a solid. The precipitated solid was dispersed by irradiating with ultrasonic waves, filtered, washed with methanol, and dried in a vacuum condition (50° C., 14 h). The crude thus obtained was dissolved in toluene (500 ml) by heating, filtered through a silica gel pad, and then concentrated. The resultant concentrate was recrystallized twice using toluene (10 ml):ethyl acetate (20 ml)/filtrate (1 g), so as to obtain IM-15. Here, IM-15 had a yield of 5.7 g and a yield rate of 48%.

Synthesis of IM-16

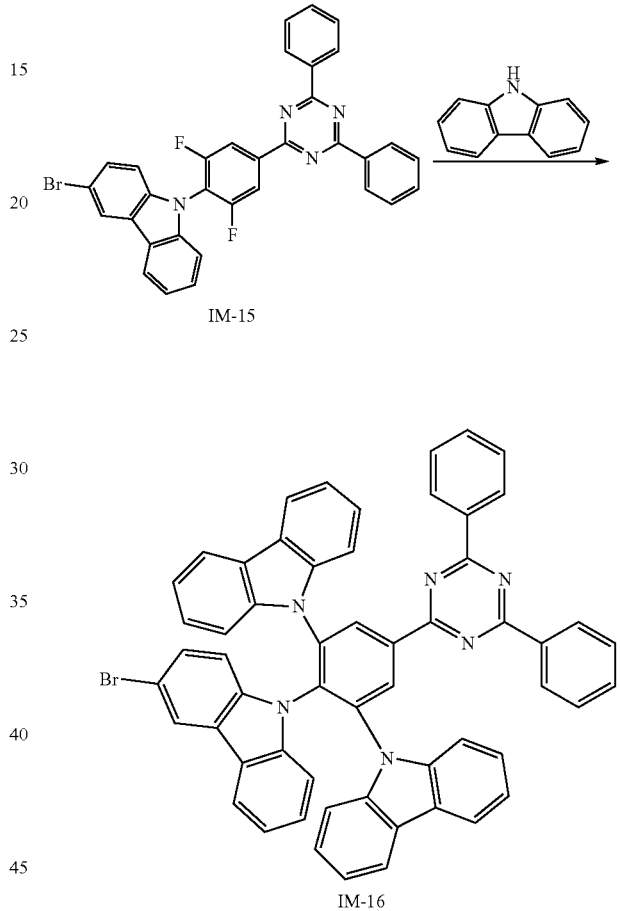

IM-15 (1.0 eq., 9.5 mmol, 5.60 g), carbazole (3.6 eq., 34.2 mmol, 5.72 g), N, N-dimethyl formamide (19 ml), and tert-BuOK (3 eq., 28.5 mmol, 3.20 g) were added to a three neck-flask, and the mixed solution was heated and stirred at a temperature of 140° C. for 8 hours in the nitrogen atmosphere. After completion of the reaction, the reaction mixture solution thus obtained was cooled to room temperature, and methanol (300 ml) was added thereto to precipitate a solid. The precipitated solid was dispersed by irradiating with ultrasonic waves, filtered, washed with methanol, and dried in a vacuum condition (50° C. 14 h). The crude thus obtained was dissolved in toluene (500 ml) by heating, filtered through a silica gel pad, and then concentrated. The resultant concentrate was recrystallized twice using toluene (10 ml):ethyl acetate (20 ml)/filtrate (1 g), so as to obtain IM-16. Here, IM-16 had a yield of 5.6 g and a yield rate of 67%.

Synthesis of Compound 103

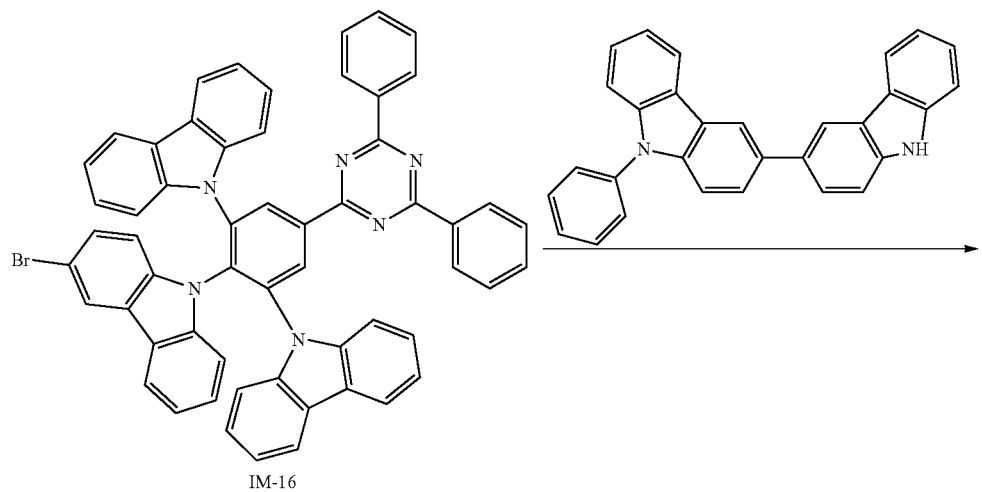

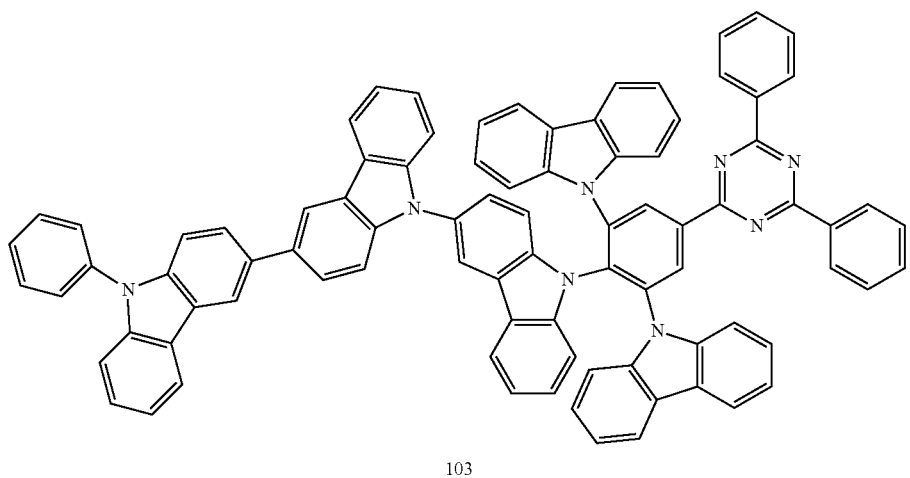

IM-16 (1.0 eq., 6 mmol, 5.30 g), 9-phenyl-9H, 9'H-3,3'-bicarbazole (1.2 eq., 7.2 mmol, 2.94 g), sodium tert-butoxide (tert-BuONa) (2 eq., 12 mmol, 1.35 g), and toluene (120 ml) were added to a three neck-flask, and the reaction system was replaced with nitrogen. Then, palladium acetate (6 mol %, 0.36 mmol, 81 mg) and tri-tert-butyl phosphonium tetrafluoroborate (6 mol %, 0.36 mmol, 104 mg) were added to the three neck-flask, and the mixed solution was heated and stirred at a temperature of 110° C. for 16 hours in the nitrogen atmosphere. After completion of the reaction, the reaction mixture solution thus obtained was diluted with toluene (200 ml), filtered through Celite, and then concentrated. The crude thus obtained was purified by silica gel chromatography (developing solvent was hexane:toluene=3:7), and recrystallized twice using toluene (10 ml):ethyl acetate (40 ml)/filtrate (1 g), so as to obtain Compound 103. Here, Compound 103 had a yield of 4.07 g and a yield rate of 56%.

Synthesis Method of Compound 90

Synthesis of IM-17

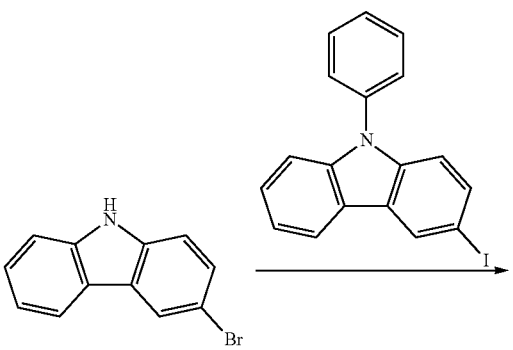

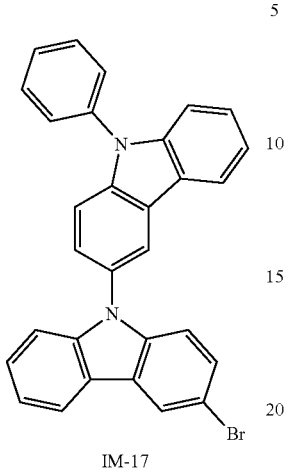

IM-17

3-bromo carbazole (1.0 eq., 100 mmol, 24.6 g), 3-iodine-9-phenyl carbazole (1.1 eq., 110 mmol, 40.6 g), K$_3$PO$_4$ (1.5 eq., 150 mmol, 31.8 g), and 1,4-dioxane (100 ml) were added to a three neck-flask, and the reaction system was purged with nitrogen. Then, CuI (4 mol %, 4 mmol, 0.76 g) and trans-1,2-diamino cyclohexane (20 mol %, 20 mmol, 2.4 ml) were added to the three neck-flask, and the mixed solution was heated and stirred at a temperature of 100° C. for 20 hours. Subsequently, the reaction mixture solution thus obtained was diluted with toluene (500 ml), filtered through Celite, filtered again through a silica gel pad, and then concentrated. The crude thus obtained was purified by silica gel chromatography (developing solvent was hexane:toluene=9:1), so as to obtain IM-17. Here, IM-17 had a yield of 43.4 g and a yield rate of 89%.

Synthesis of IM-18

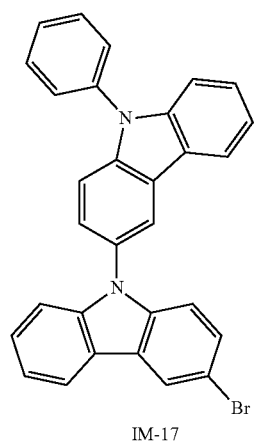

IM-17

→

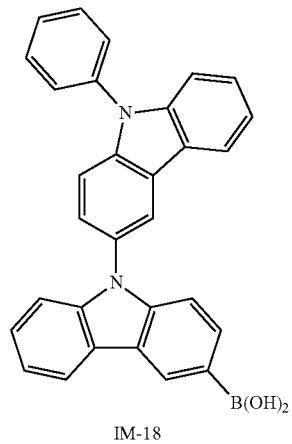

IM-18

IM-17 (1.0 eq., 89 mmol, 43.3 g) and tetrahydrofuran (445 ml) were added to a three neck-flask, and dissolved. Then, the reaction system was purged with nitrogen, and the mixed solution was cooled to a temperature of −80° C. To the cooled solution, n-butyl lithium (2.64 M, 1.1 eq., 97.9 mmol, 37.1 ml) was added dropwise. Afterwards, trimethyl borate (1.5 eq., 133.5 mmol, 13.9 g, 14.9 ml) was added to the mixture solution, and the resultant solution was stirred at a temperature of −80° C. for 30 minutes, and was allowed to warm to room temperature. Then, the solution thus obtained was stirred at room temperature for 2 hours. Next, the reaction was inactivated using a small amount of methanol, and the solution was concentrated to about half with an evaporator. The resultant solution was cooled to a temperature of 0° C., and an aqueous hydrochloric acid solution (1 N, 200 ml) was added thereto. The mixed solution was then stirred at room temperature for 1 hour. The solution thus obtained was transferred to a separatory funnel, and an organic phase was extracted twice using ethyl acetate. The organic phase collected therefrom was water-rinsed three times, dried using anhydrous magnesium sulfate, filtered, and then concentrated. The crude thus obtained was dried in a vacuum condition (70° C., 14 h) and dissolved in toluene (300 ml), and hexane (800 ml) was gradually added thereto while stirring the mixed solution to precipitate a solid. The resultant slurry solution was stirred under reflux for 6 hours and cooled to room temperature. Then, a solid sample was collected therefrom by filtration and dried in a vacuum condition (50° C., 14 h), so as to obtain IM-18. Here, IM-18 had a yield of 30.2 g and a yield rate of 75%.

Synthesis of IM-19

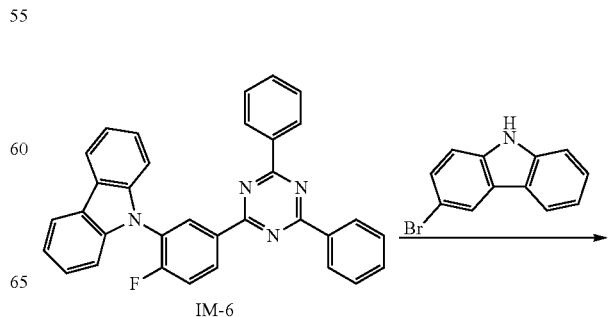

IM-6

-continued

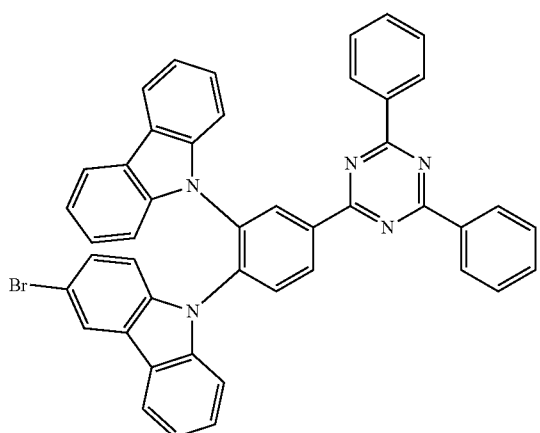
IM-19

IM-6 (1.0 eq., 30 mmol, 14.8 g), 3-bromo carbazole (1.5 eq., 45 mmol, 11.1 g), N, N-dimethyl formamide (19 ml), and tert-BuOK (1.4 eq., 42 mmol, 4.71g) were added to a three neck-flask, and the mixed solution was heated and stirred at a temperature of 140° C. for 8 hours in the nitrogen atmosphere. After completion of the reaction, the reaction mixture solution thus obtained was cooled to room temperature, and methanol (300 ml) was added thereto to precipitate a solid. The precipitated solid was dispersed by irradiating with ultrasonic waves, filtered, washed with methanol, and dried in a vacuum condition (50° C., 14 h). The crude thus obtained was dissolved in toluene (500 ml) by heating, filtered through a silica gel pad, and then concentrated. The resultant concentrate was recrystallized twice using toluene (10 ml):ethyl acetate (20 ml)/filtrate (1 g), so as to obtain IM-19. Here, IM-19 had a yield of 13.4 g and a yield rate of 62%.

Synthesis of Compound 90

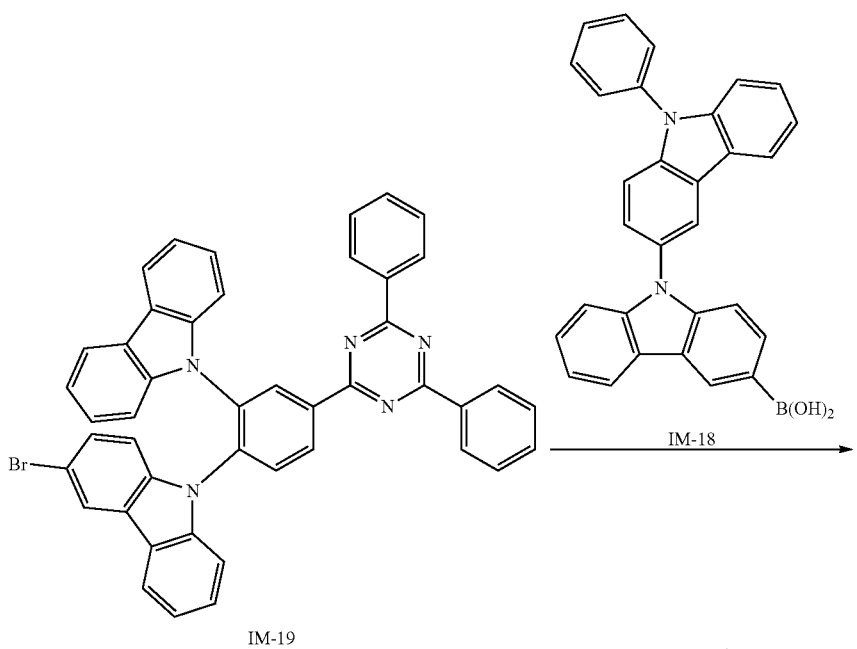

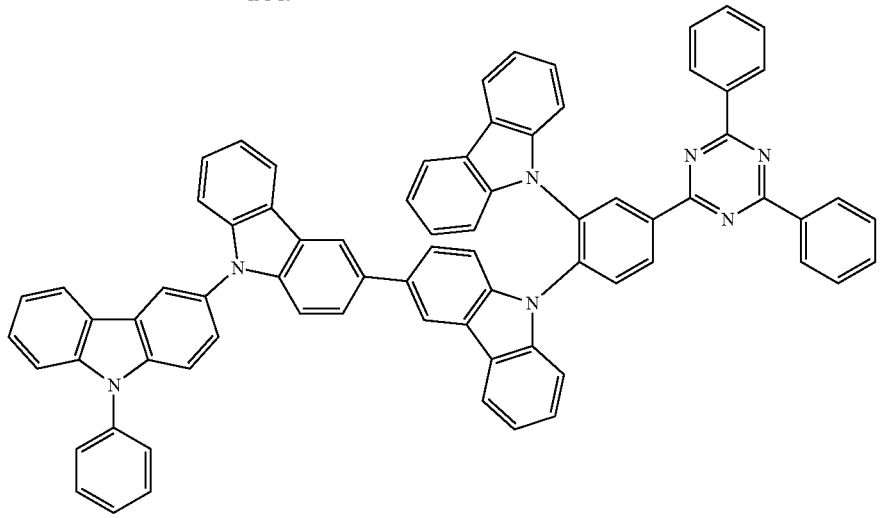

90

IM-19 (1.0 eq., 9 mmol, 6.47 g), IM-18 (1.05 eq., 9.45 mmol, 4.27 g), an aqueous potassium carbonate solution (2.0 M, 9 ml), toluene (180 ml), and ethanol (9 ml) were added to a three neck-flask, and dispersed uniformly. After the reaction system was purged with nitrogen, palladium acetate (4 mol %, 0.36 mmol, 81 mg) and tri(o-tolyl)phosphine (6 mol %, 0.54 mmol, 164 mg) were added to the three neck-flask, and the mixed solution was heated and stirred at a temperature of 70° C. for 6 hours in the nitrogen atmosphere. After completion of the reaction, the reaction mixture solution thus obtained was diluted with toluene (200 ml), filtered through Celite, repeatedly water-rinsed three times, dried using anhydrous magnesium sulfate, and concentrated by passing through a short silica gel column. The crude thus obtained was purified by silica gel chromatography (developing solvent was hexane:toluene=3:7), and recrystallized twice using toluene (10 ml):ethyl acetate (40 ml)/filtrate (1 g), so as to obtain Compound 90. Here, Compound 90 had a yield of 4.52 g and a yield rate of 48%.

Synthesis Method of Compound 25

Synthesis of IM-20

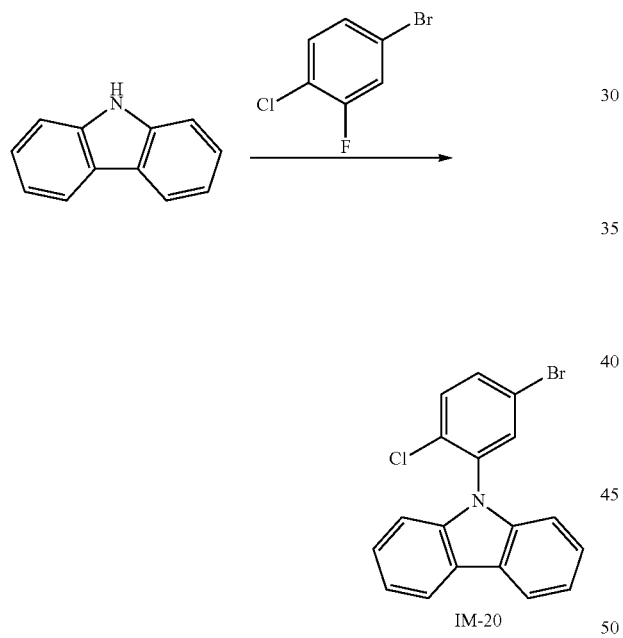

To a three neck-flask, carbazole (1.2 eq., 960 mmol, 160.5 g), 4-bromo-1-chloro-2-fluorobenzene (1.0 eq., 800 mmol, 167.6 g), and dimethyl formamide (200 ml) were added. Then, the reaction system was purged with nitrogen, and sodium hydride (62% paraffin dispersion) (1.1 eq., 880 mmol, 34.1 g) was added thereto portion-wise in consideration of the amount of generated hydrogen gas. The reaction solution thus obtained was then heated and stirred at a temperature of 150° C. for 12 hours. After cooling to room temperature, the reaction mixture solution thus obtained was diluted with toluene (1 L), filtered through Celite, filtered again through a silica gel pad, and then water-rinsed three times using a separatory funnel. The organic phase solution thus obtained was dried using anhydrous magnesium sulfate, filtered through a silica gel pad, and then concentrated. The crude thus obtained was purified by silica gel chromatography (developing solvent was hexane:toluene=8:2), and recrystallized using toluene (2 ml):ethanol (10 ml)/filtrate (1 g), so as to obtain IM-20. Here, IM-20 had a yield of 199.7 g and a yield rate of 70%.

Synthesis of IM-21

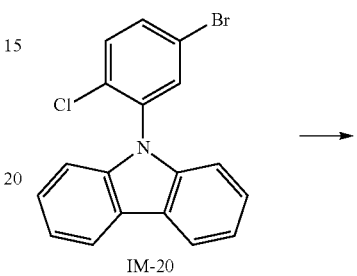

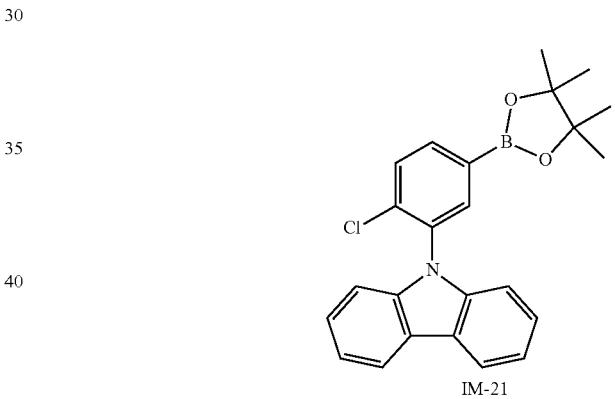

To a three neck-flask, IM-20 (1.0 eq., 200 mmol, 71.3 g), bis(pinacolato) diboron (1.1 eq., 220 mmol, 55.9 g), potassium acetate (3.0 eq., 600 mmol, 58.9 g), and dimethylformamide (400 ml) were added, and the reaction system was purged with nitrogen. Then, [1,1'-bis(diphenylphosphino) ferrocene]dichloro palladium(I) (Pd(dppf)Cl$_2$) (5 mol %, 10 mmol, 7.31 g) was added thereto, and the mixed solution was heated and stirred at a temperature of 80° C. for 6 hours. After cooling to room temperature, the reaction mixture solution thus obtained was diluted with toluene (1 L), filtered through Celite, filtered again through a silica gel pad, repeatedly water-rinsed three times, dried using anhydrous magnesium sulfate, filtered again through a silica gel pad, and then concentrated. The crude thus obtained was purified by silica gel chromatography (developing solvent was hexane:toluene=2:8), and recrystallized using hexane (5 ml)/filtrate (1 g), so as to obtain IM-21. Here, IM-21 had a yield of 37.1 g and a yield rate of 46%.

Synthesis of IM-22

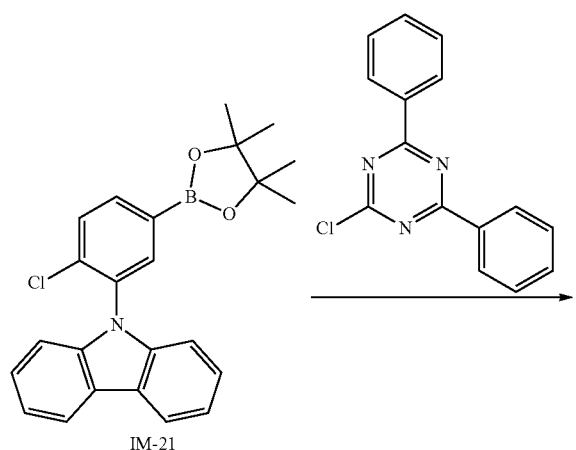

IM-21

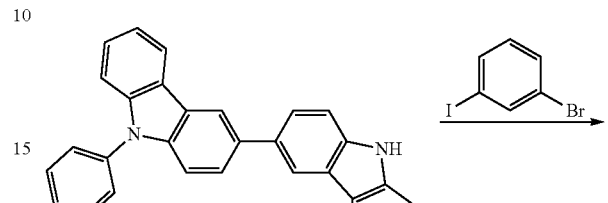

Synthesis of IM-23

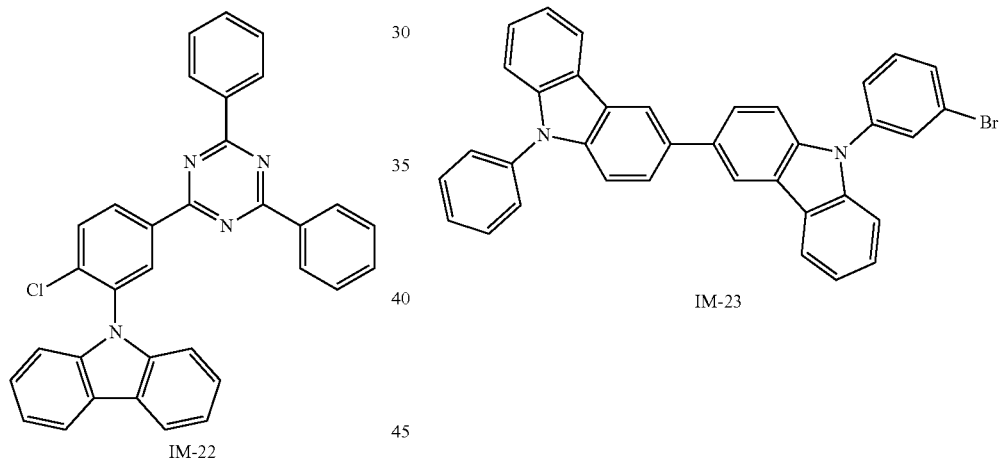

IM-22

IM-23

IM-21 (1.0 eq., 90 mmol, 36.3 g), 2-chloro-4,6-diphenyl-1,3,5-triazine (1.05 eq., 94.5 mmol, 25.3 g), an aqueous potassium carbonate solution (2.0 M, 90 ml), and tetrahydrofuran (400 ml) were added to a three neck-flask, and dissolved uniformly. After the reaction system was replaced with nitrogen, palladium acetate (4 mol %, 3.6 mmol, 0.81 g) and tri(o-tolyl) phosphine (6 mol %, 5.4 mmol, 1.64 g) were added to the three neck-flask, and the mixed solution was heated and stirred at a temperature of 50° C. for 4 hours in the nitrogen atmosphere. After completion of the reaction, the reaction mixture solution thus obtained was diluted with chloroform (1 L), filtered through Celite, repeatedly water-rinsed three times, dried using anhydrous magnesium sulfate, and concentrated by passing through a short silica gel column. The crude thus obtained was recrystallized using toluene (5 ml):ethyl acetate (20 ml)/filtrate (1 g), so as to obtain IM-22. Here, IM-22 had a yield of 27.9 g and a yield rate of 61%.

9-phenyl-9H, 9'H-3,3'-bicarbazole (1.0 eq., 100 mmol, 40.9 g), 1-bromo-3-iodine benzene (1.2 eq, 120 mmol, 33.9 g) tert-BuONa (1.5 eq., 150 mmol, 14.4 g), and 1,4-dioxane (100 ml) were added to a three neck-flask, and the reaction system was purged with nitrogen. Then, CuI (4 mol %, 4 mmol, 0.76 g) and trans-1,2-diamino cyclohexane (20 mol %, 20 mmol, 2.28 g) were added to the three neck-flask, and the mixed solution was heated and stirred at a temperature of 100° C. for 20 hours. Subsequently, the reaction mixture solution thus obtained was diluted with toluene (300 ml), filtered through Celite, filtered again through a silica gel pad, and then concentrated. The crude thus obtained was purified by silica gel chromatography (developing solvent was hexane:toluene=8:2), and recrystallized using hexane (20 ml)/filtrate (1 g), so as to obtain IM-23. Here, IM-23 had a yield of 38.3 g and a yield rate of 68%.

263
Synthesis of IM-24
IM-24 was synthesized in the same manner as used to synthesize IM-2 according to the following materials and scheme. Here, IM-24 had a yield rate of 60%.
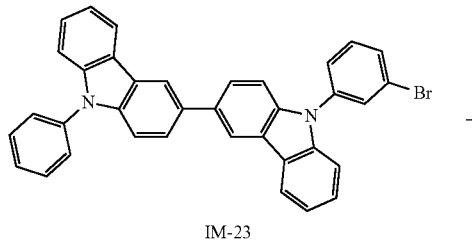
IM-23
264
-continued
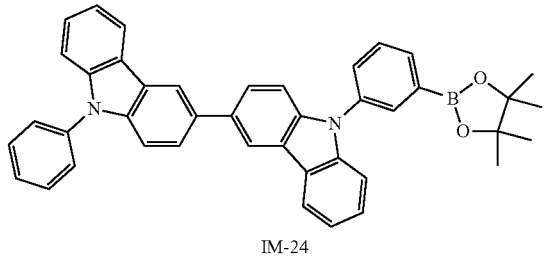
IM-24
Synthesis of Compound 25
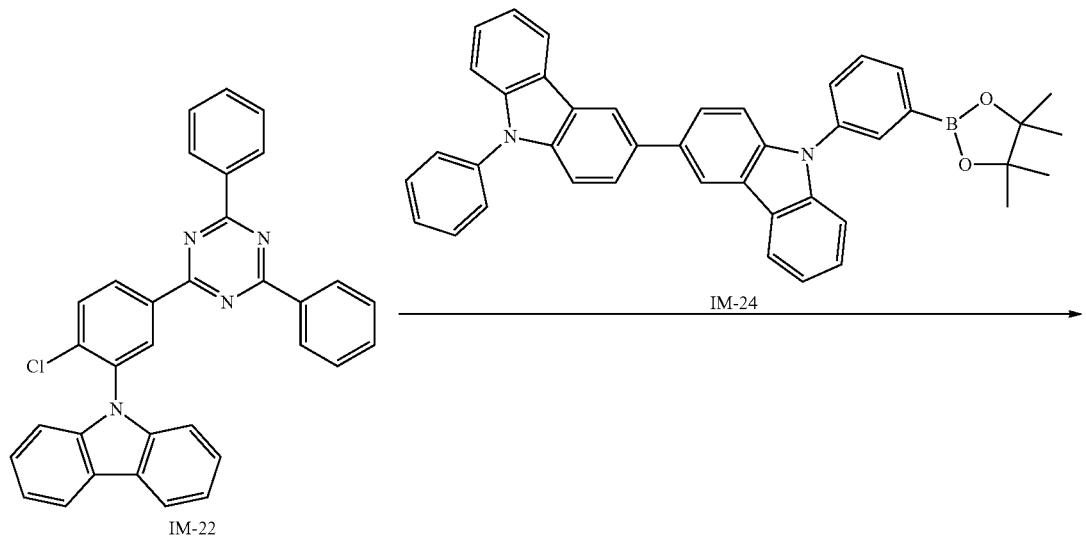
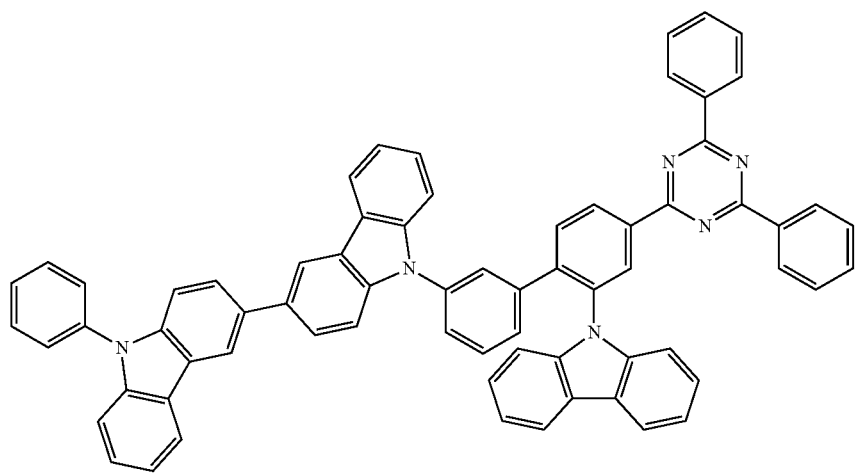
25

IM-22 (1.0 eq., 15 mmol, 7.64 g), IM-24 (1.1 eq., 16.5 mmol, 10.1 g), K₃PO₄ (3.0 eq., 45 mmol, 9.55 g), and 1,4-dioxane (60 ml) were added to a three neck-flask, and dispersed. After the reaction system was purged with nitrogen, bis(dibenzylidene acetone)palladium (Pd(dba)₂) (6 mol %, 0.9 mmol, 0.52 g) and tricyclohexyl phosphonium tetrafluoroborate (6 mol %, 0.9 mmol, 0.33 g) were added to the three neck-flask, and the mixed solution was heated and stirred at a temperature of 100° C. for 2 hours in the nitrogen atmosphere. After completion of the reaction, the reaction mixture solution thus obtained was diluted with toluene (200 ml), filtered through Celite, repeatedly water-rinsed three times, dried using anhydrous magnesium sulfate, and concentrated by passing through a short silica gel column. The crude thus obtained was purified by silica gel chromatography (developing solvent was hexane:toluene=4:6), and recrystallized twice using toluene (5 ml):ethyl acetate (25 ml)/filtrate (1 g), so as to obtain Compound 25. Here, Compound 25 had a yield of 8.04 g and a yield rate of 56%.

Synthesis Method of Compound 6

Synthesis of IM-25

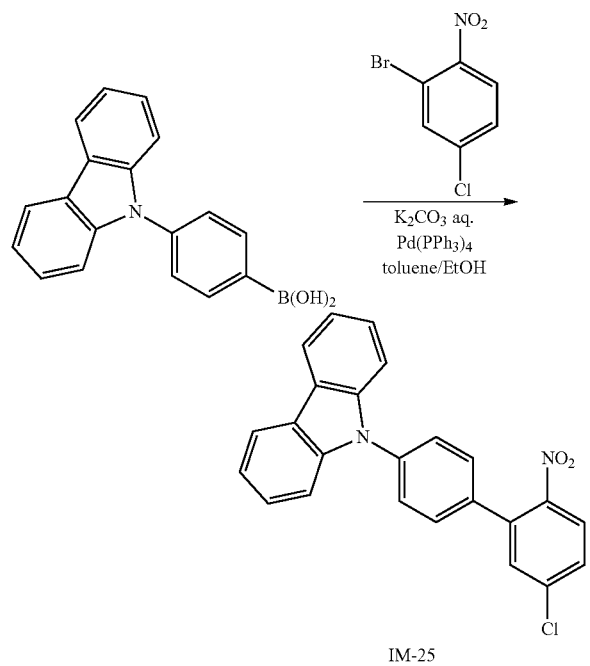

IM-25

4-(9H-carbazole-9-yl)phenylboroic acid (1.05 eq., 315 mmol, 90.4 g), 1-bromo-5-chloro-2-nitrobenzene (1.0 eq., 300 mmol, 70.9 g), an aqueous potassium carbonate solution (2.0 M, 300 ml), toluene (600 ml), and ethanol (150 ml) were added to a three neck-flask, and dissolved uniformly. After the reaction system was replaced with nitrogen, tetrakis triphenyl phosphine palladium (6 mol %, 18 mmol 20.8 g) was added to the three neck-flask, and the mixed solution was heated and stirred at a temperature of 70° C. for 8 hours in the nitrogen atmosphere. After completion of the reaction, the reaction mixture solution thus obtained was diluted with toluene (1 L), filtered through Celite, repeatedly water-rinsed three times, dried using anhydrous magnesium sulfate, and concentrated by passing through a short silica gel column. The crude thus obtained was purified by silica gel chromatography (developing solvent was hexane:toluene=6:4), and recrystallized using hexane (15 ml)/filtrate (1 g), so as to obtain IM-25. Here, IM-25 had a yield of 104.1 g and a yield rate of 87%.

Synthesis of IM-26

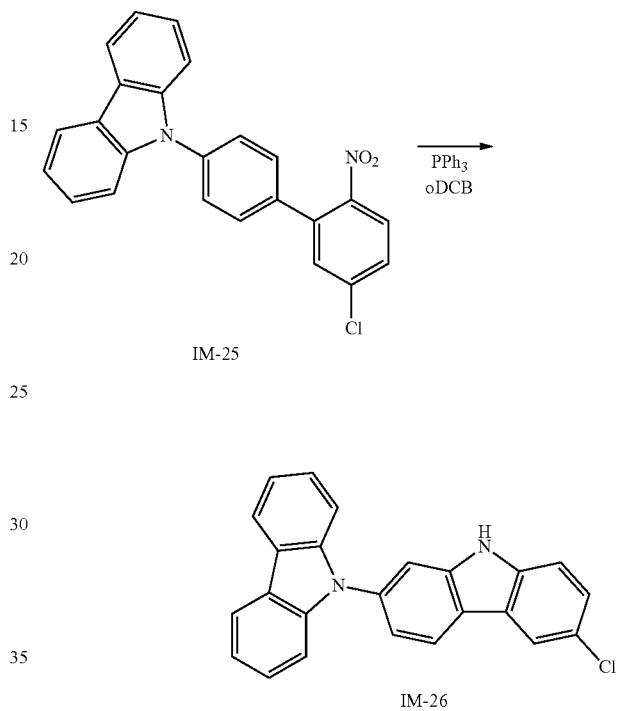

IM-25

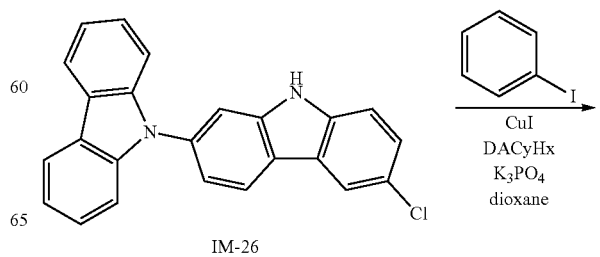

IM-26

IM-25 (1.0 eq., 260 mmol, 103.7 g), o-dichloro benzene (oDCB) (520 ml), and triphenyl phosphine (PPh₃) (3.0 eq., 780 mmol, 204.6 g) were added to a three neck-flask, and the reaction system was purged with nitrogen. Then, the mixed solution was heated and stirred at a temperature of 150° C. for 8 hours in the nitrogen atmosphere. After completion of the reaction, the reaction mixture solution thus obtained was diluted with toluene (500 ml) and concentrated by passing through a short silica gel column. The crude thus obtained was recrystallized twice using toluene (15 ml):hexane (15 ml)/filtrate (1 g), so as to obtain IM-26. Here, IM-26 had a yield of 66.8 g and a yield rate of 70%.

Synthesis of IM-27

IM-26

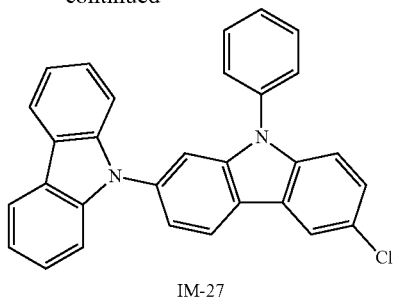

IM-27

IM-26 (1.0 eq., 180 mmol, 66.0 g), iodine benzene (1.2 eq., 216 mmol, 44.1 g), K₃PO₄ (1.5 eq., 270 mmol, 57.3 g), and 1,4-dioxane (180 ml) were added to a three neck-flask, and the reaction system was purged with nitrogen. Then, CuI (4 mol %, 7.2 mmol, 1.37 g and trans-1,2-diamino cyclohexane (DAC$_y$H$_x$) (20 mol %, 36 mmol, 4.11 g) were added to the three neck-flask, and the mixed solution was heated and stirred at a temperature of 100° C. for 20 hours. Subsequently, the reaction mixture solution thus obtained was diluted with toluene (300 ml), filtered through Celite, filtered again through a silica gel pad, and then concentrated. The crude thus obtained was purified by silica gel chromatography (developing solvent was hexane:toluene=8:2), and recrystallized using toluene (5 ml):ethanol (10 ml)/filtrate (1 g), so as to obtain IM-27. Here, IM-27 had a yield of 51.8 g and a yield rate of 65%.

Synthesis of IM-28

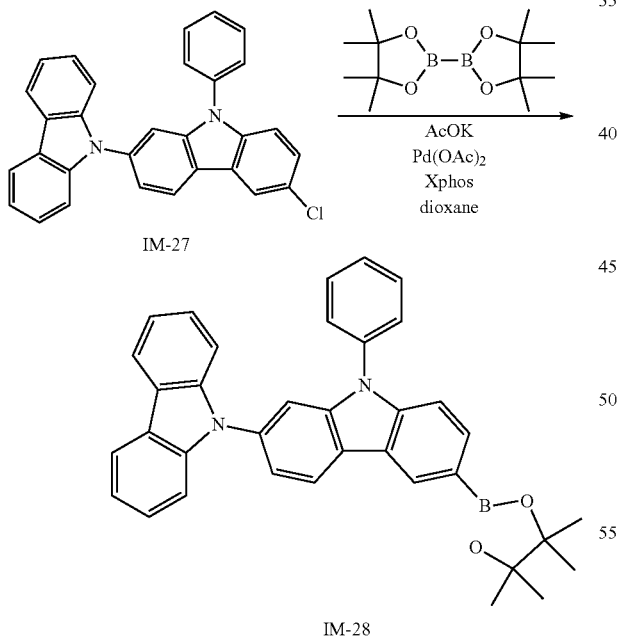

To a three neck-flask, IM-27 (1.0 eq., 115 mmol, 50.9 g), bis(pinacolato)diboron (1.1 eq., 126.5 mmol, 32.1 g), potassium acetate (AcOK) (2.0 eq., 230 mmol, 22.6 g), and 1,4-dioxane (460 ml) were added, and the reaction system was purged with nitrogen. Then, palladium acetate (2 mol %, 2.3 mmol, 0.52 g) and 2-dicyclohexyl phosphino-2',4',6'-triisopropyl biphenyl (XPhos) (4 mol %, 4.6 mmol, 2.19 g) were added to the three neck-flask, and the mixed solution was heated and stirred at a temperature of 100° C. for 6 hours. After cooling to room temperature, the reaction mixture solution thus obtained was diluted with toluene (1 L), filtered through Celite, filtered again through a silica gel pad, repeatedly water-rinsed three times, dried using anhydrous magnesium sulfate, filtered again through a silica gel pad, and then concentrated. The crude thus obtained was purified by silica gel chromatography (developing solvent was hexane:toluene=2:8), and recrystallized using hexane (5 ml)/filtrate (1 g), so as to obtain IM-28. Here, IM-28 had a yield of 36.3 g and a yield rate of 59%.

Synthesis of IM-29

IM-29 was synthesized in the same manner as used to synthesize IM-20 to IM-22 according to the following scheme.

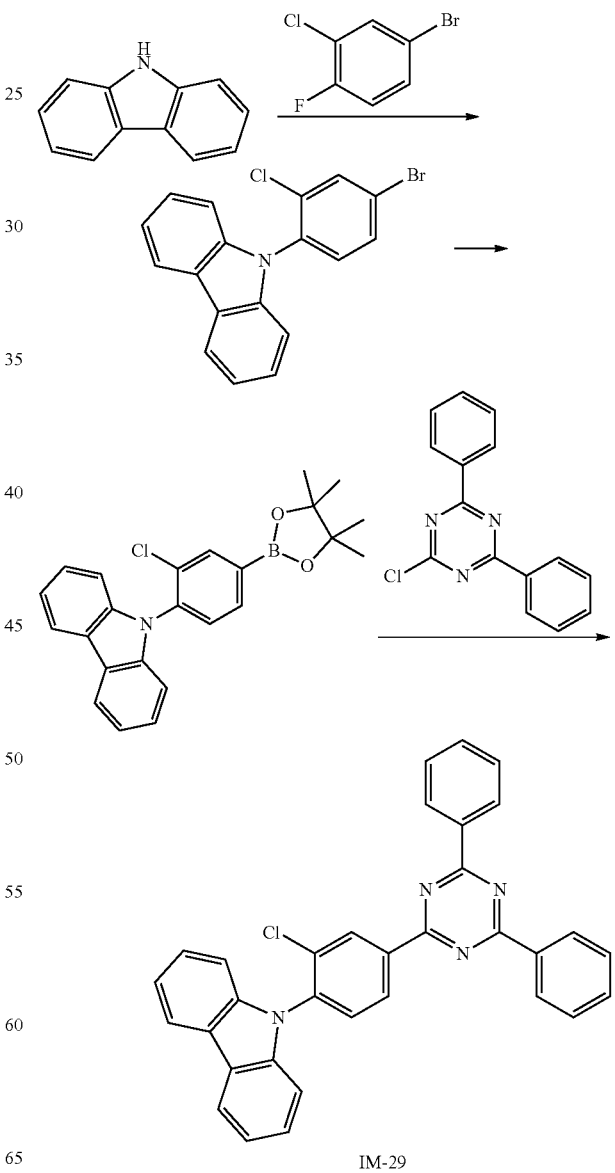

Synthesis of Compound 6
Compound 6 was synthesized in the same manner as used to synthesize Compound 25 according to the following materials and scheme.
Here, Compound 6 had a yield rate of 40%.
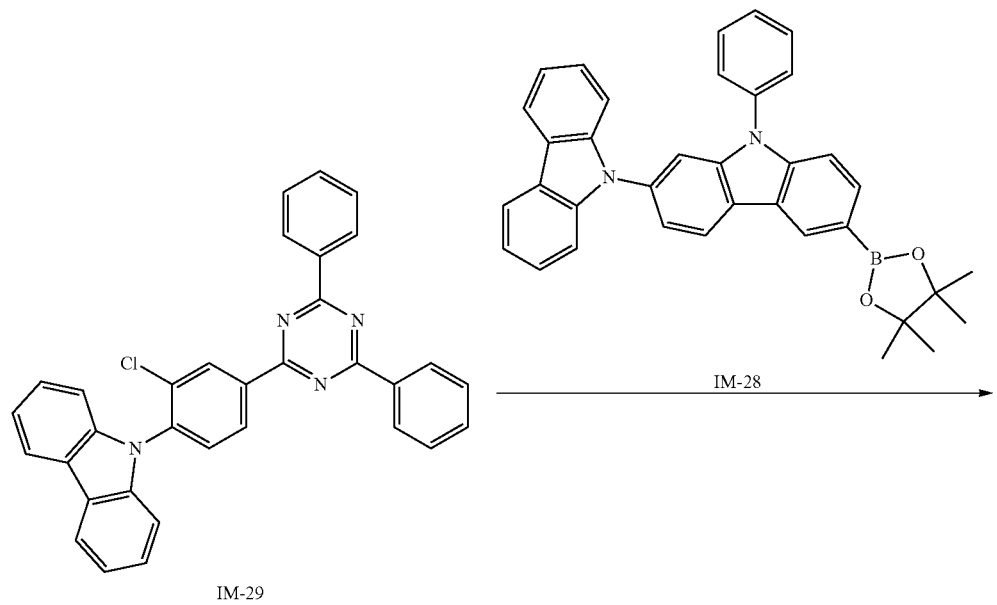

Synthesis Methods of Compounds of Other Examples
Compounds of other Examples were also synthesized according to the methods described in Synthesis Examples 5 above.
Compounds of each Example used in this experiment are as follows:
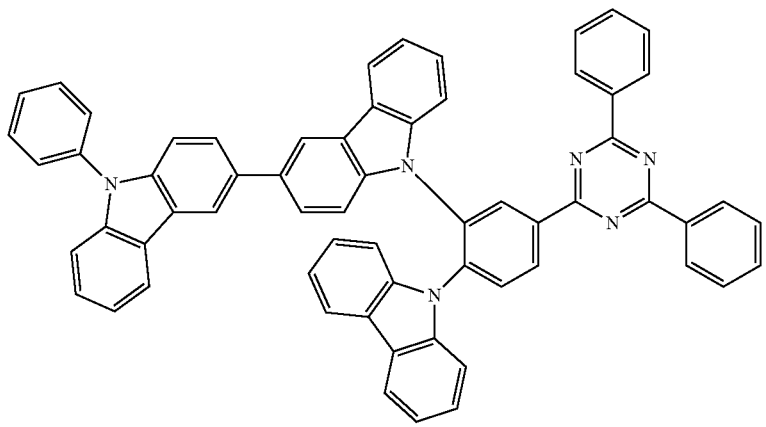
1
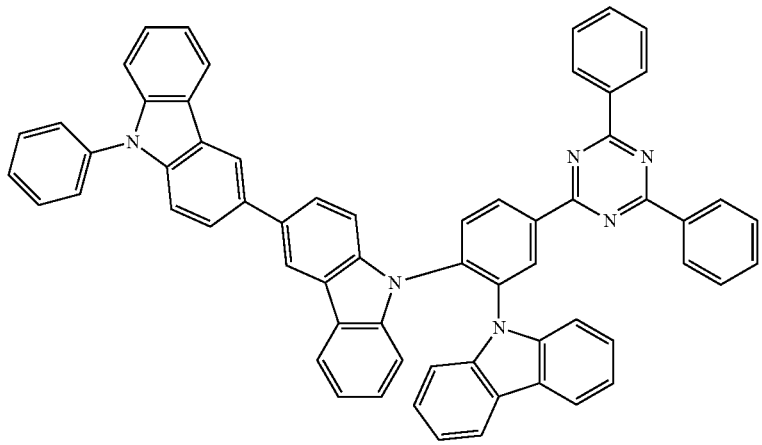
2
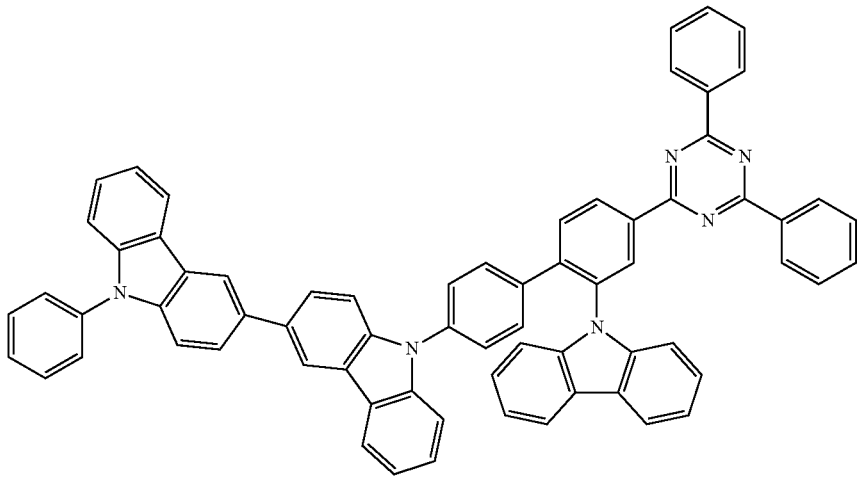
3

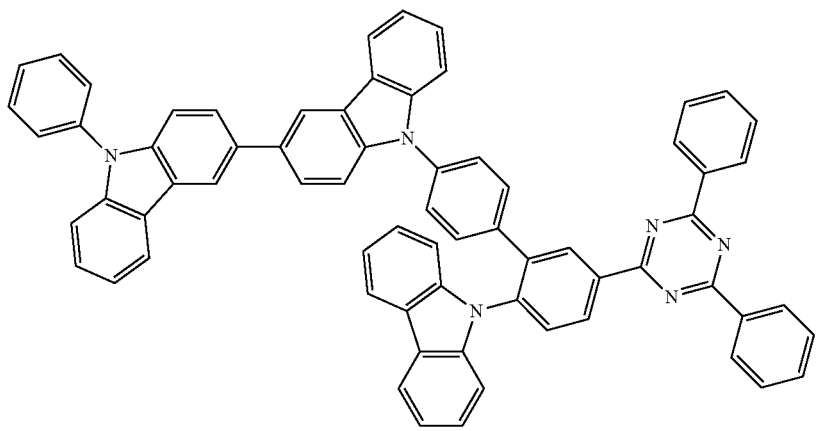
4
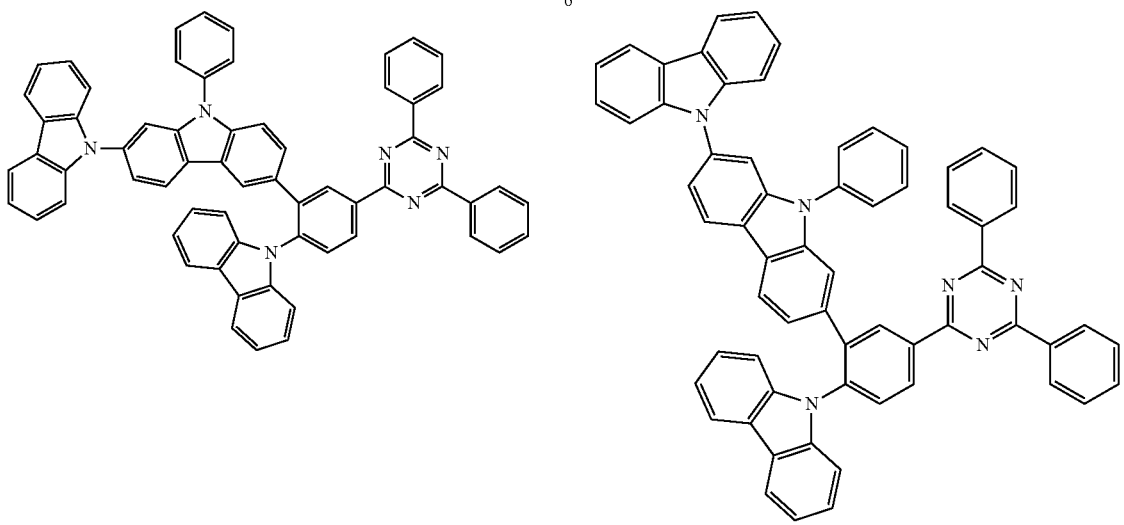
6
8
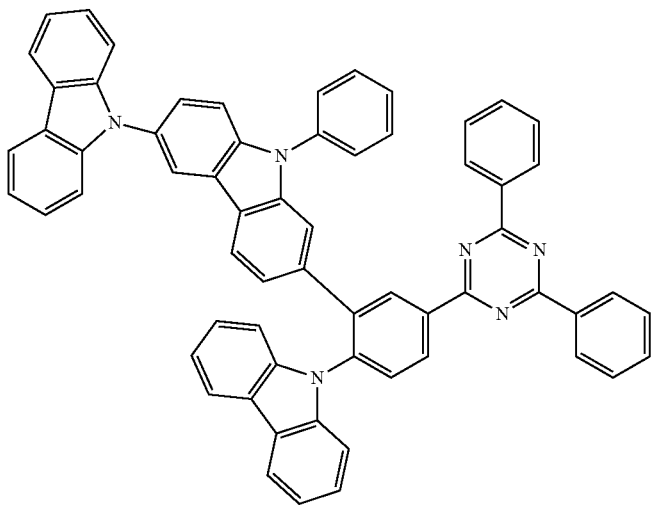
10

12
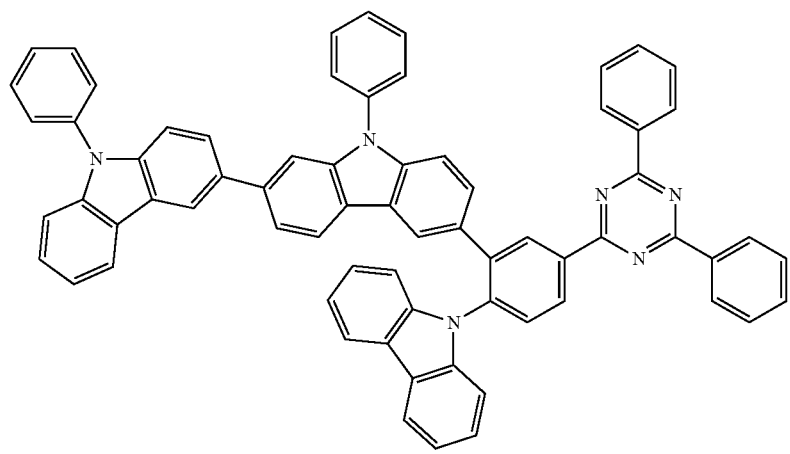
13
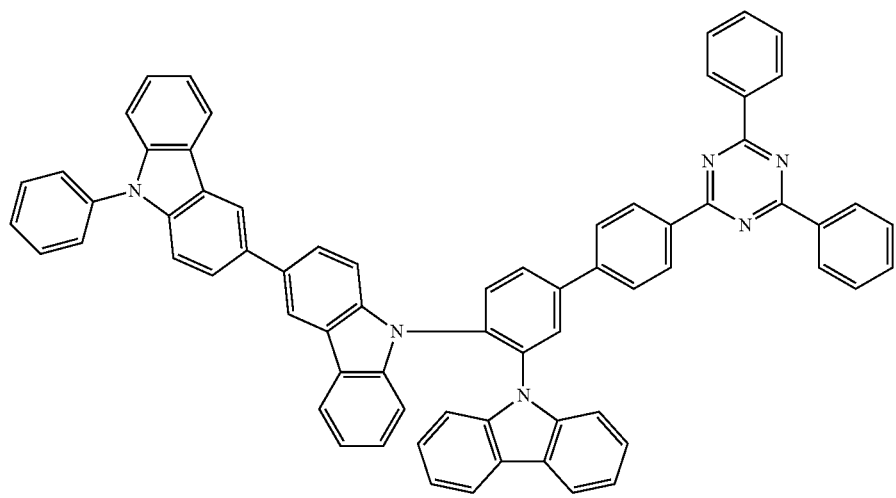
14
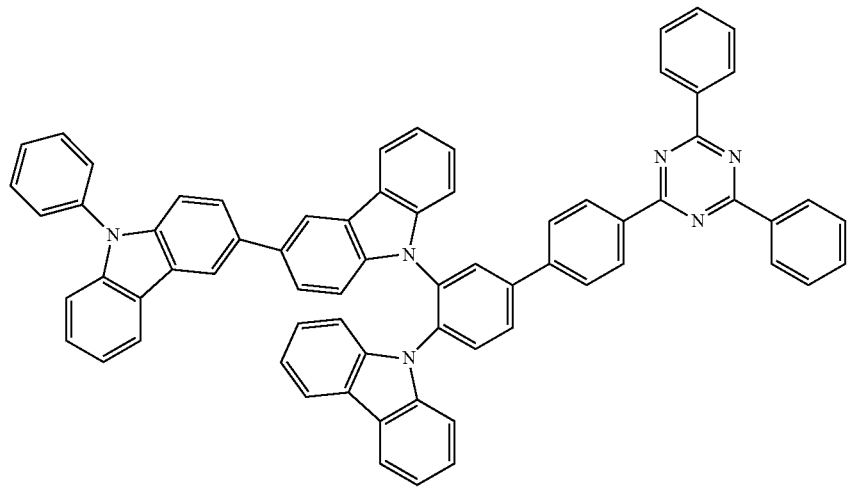

16
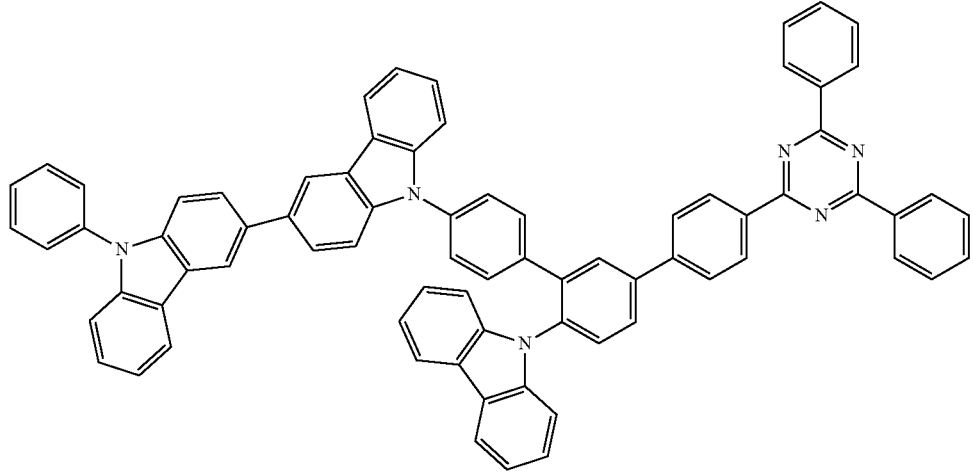
18
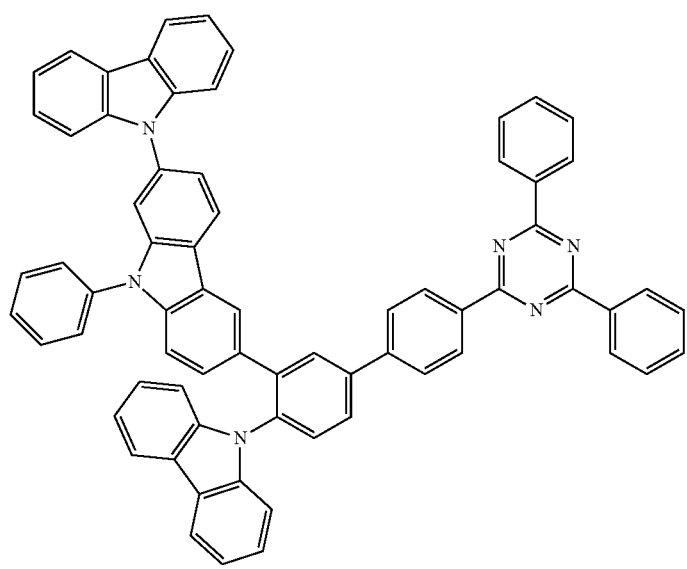
22
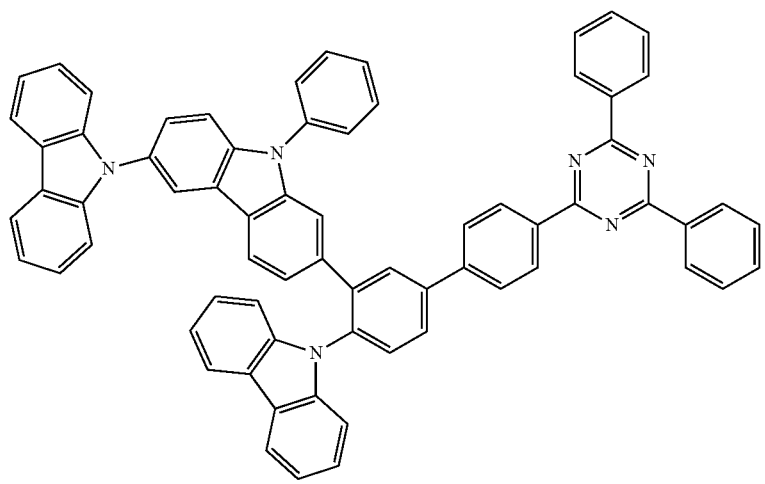

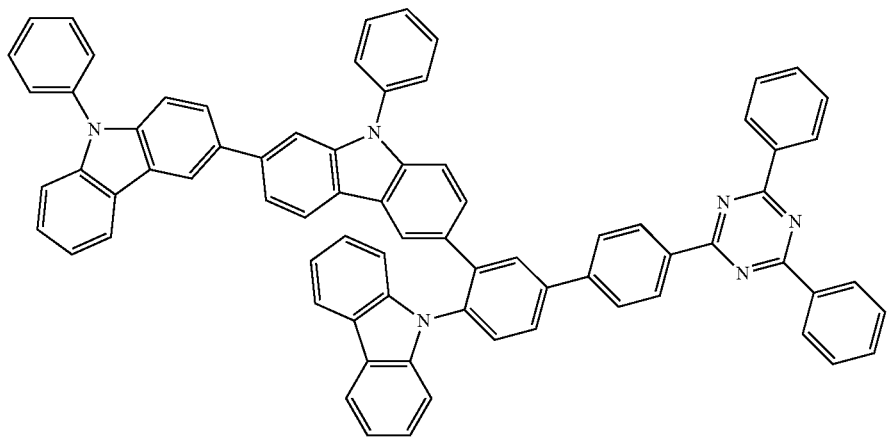
24
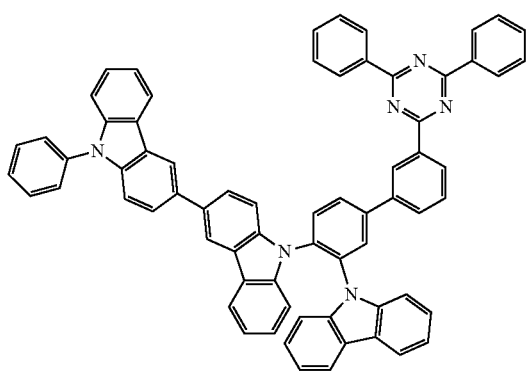
27
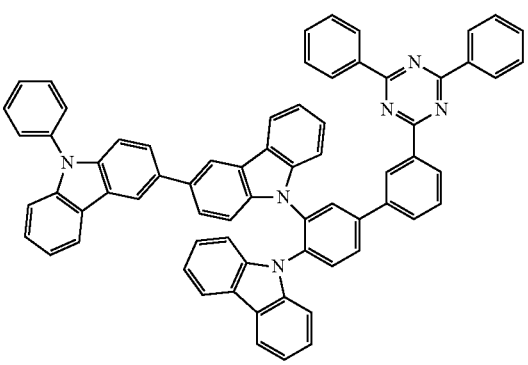
28
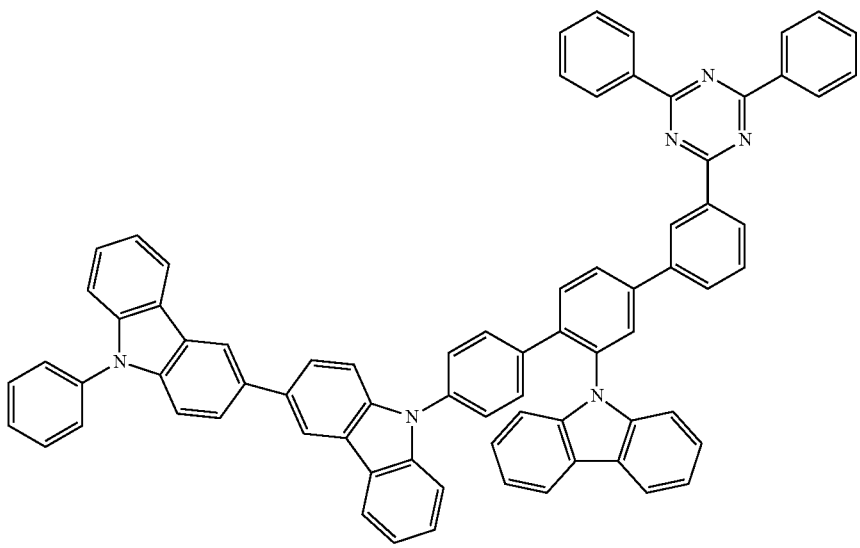
29

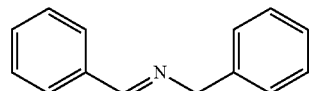
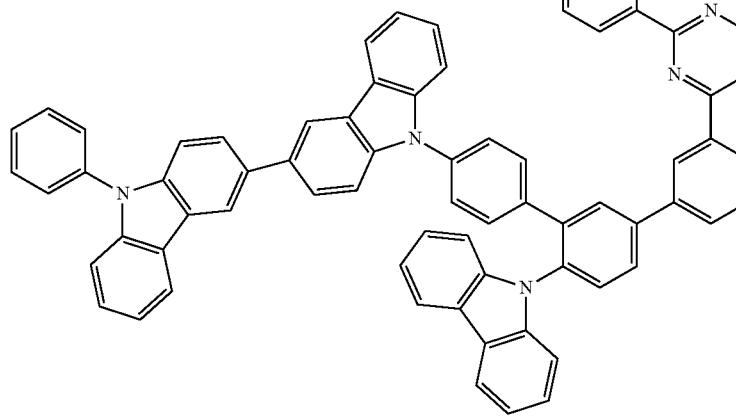
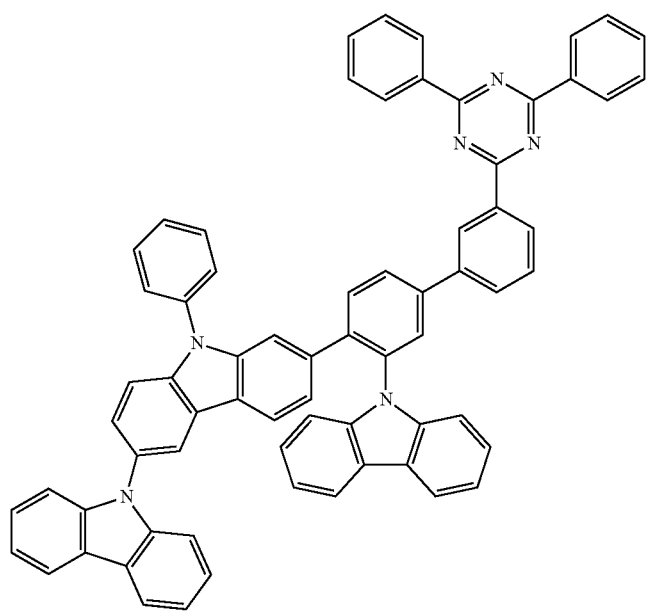

-continued
36
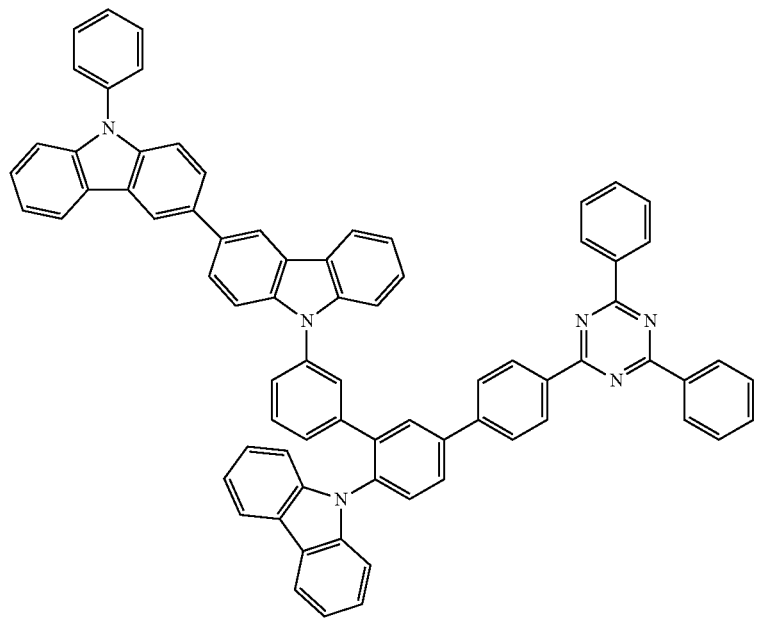
39
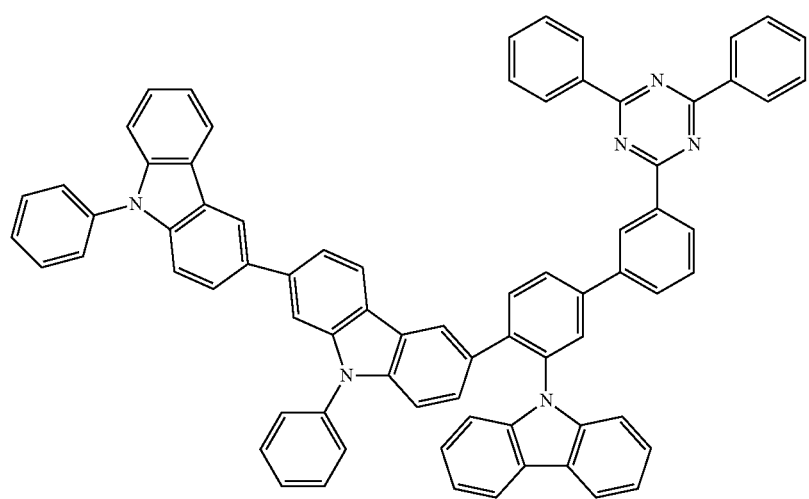

44
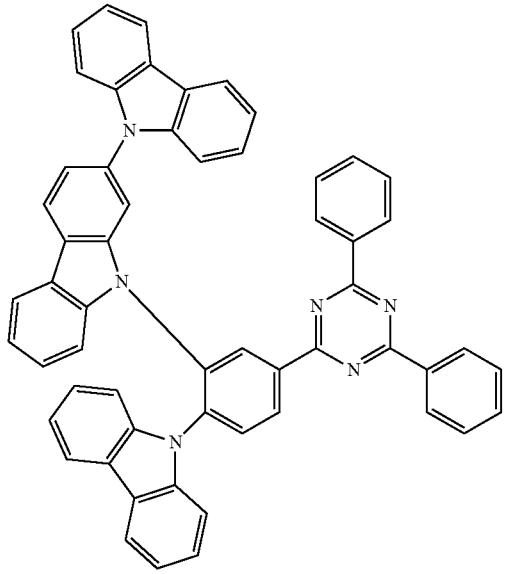
45
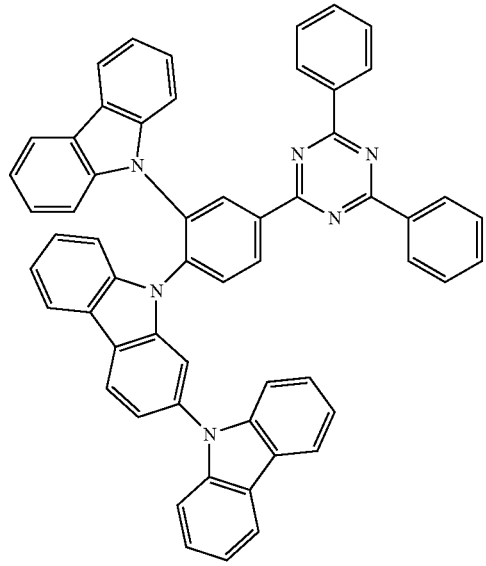
47
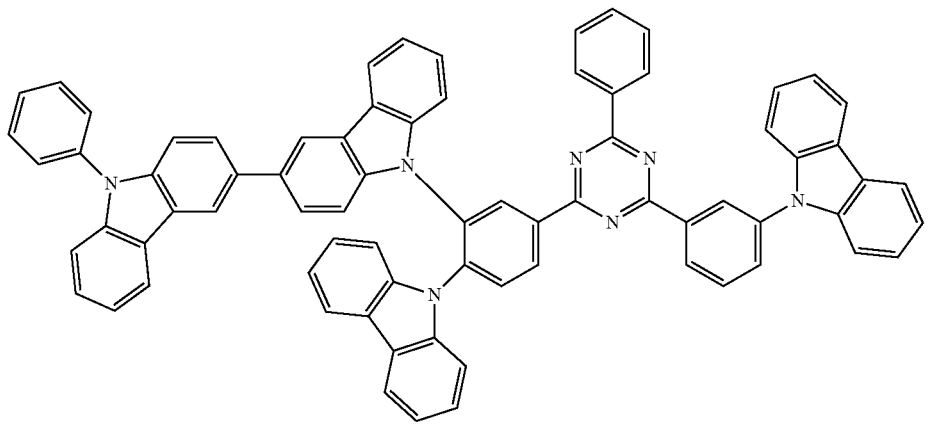
58
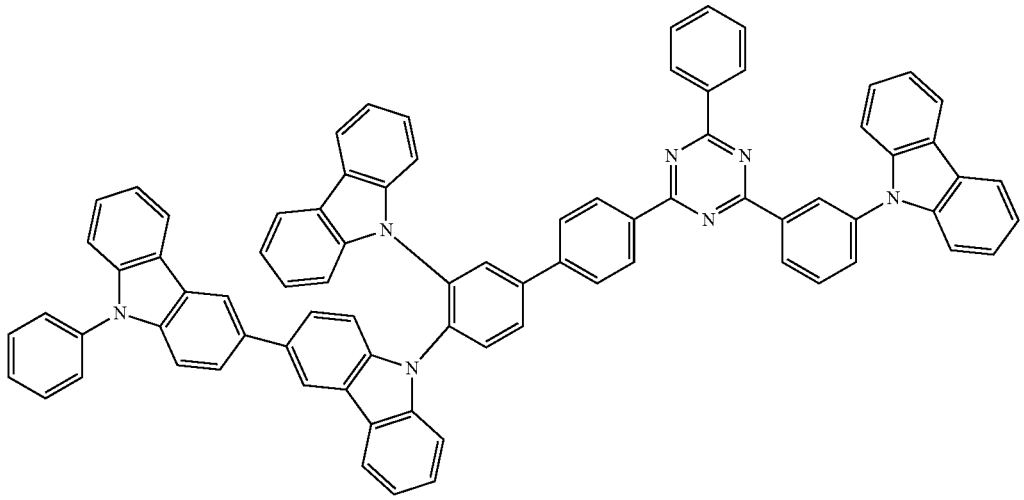

59
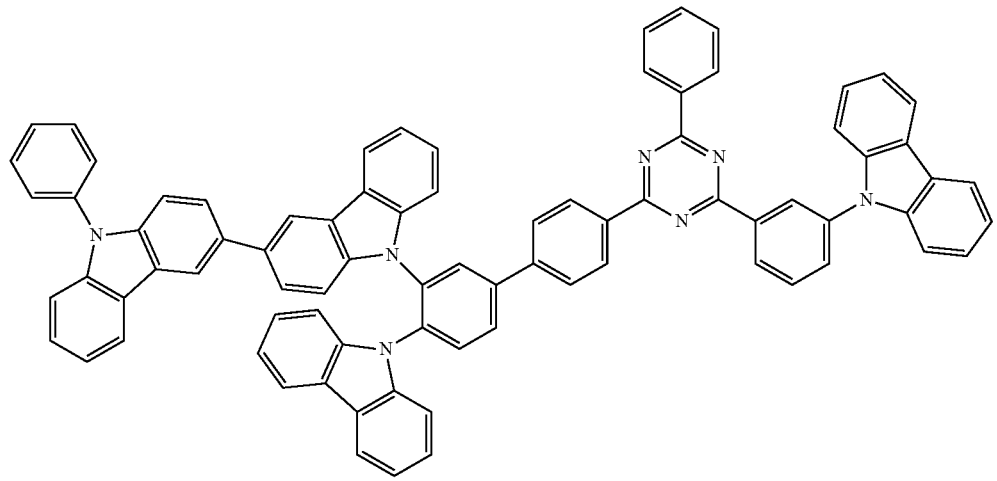
86
89
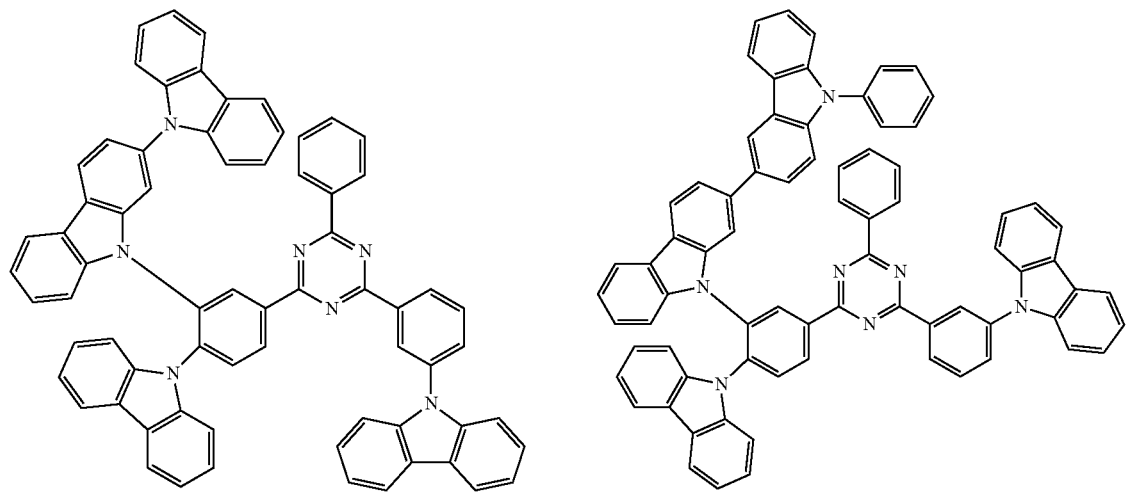
90
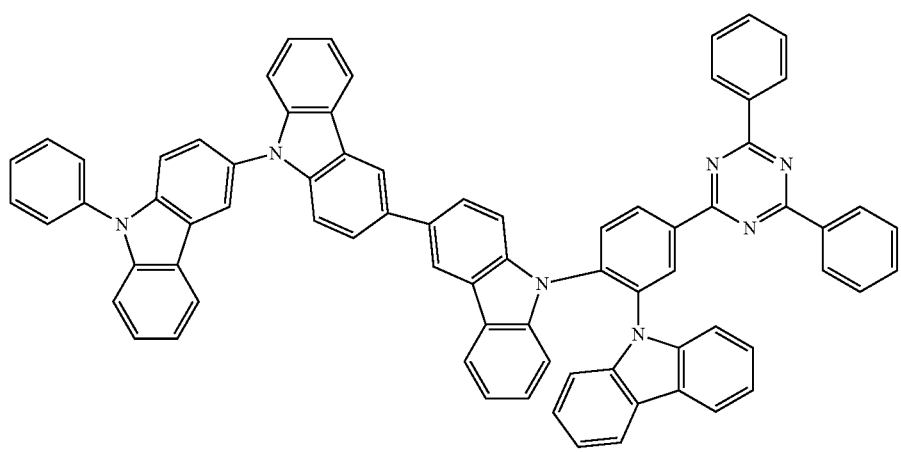

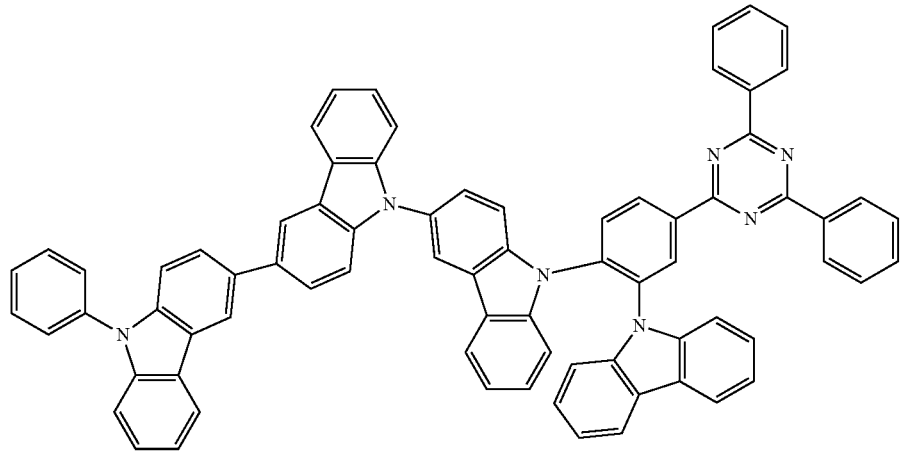
92
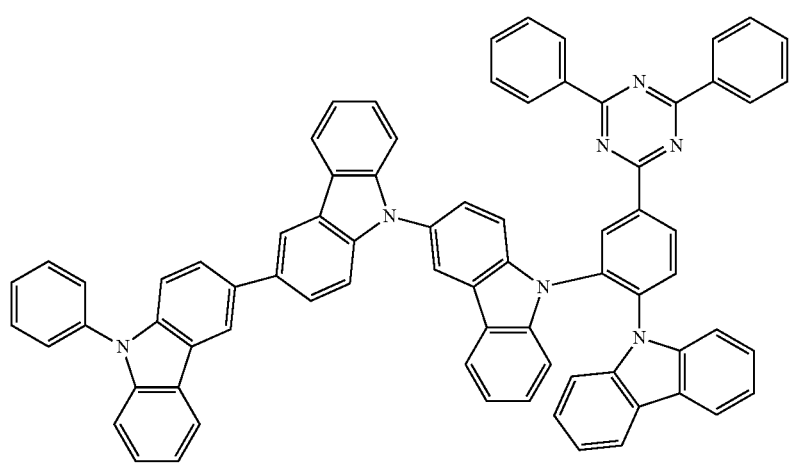
93
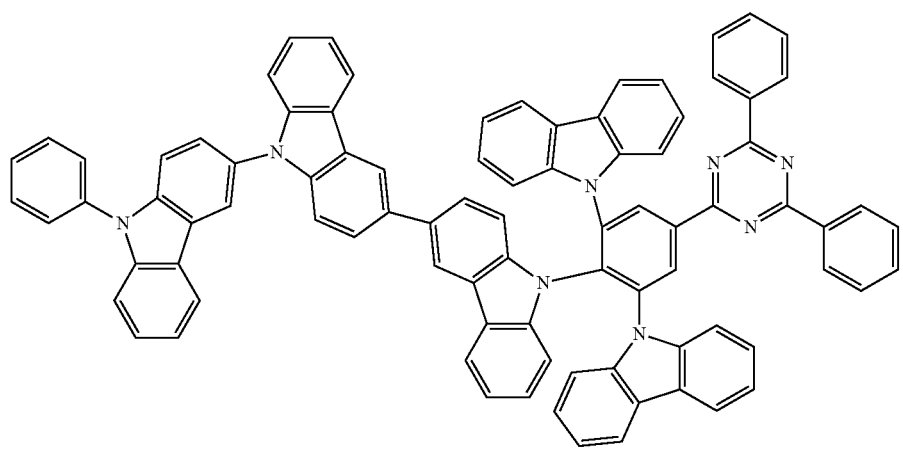
102

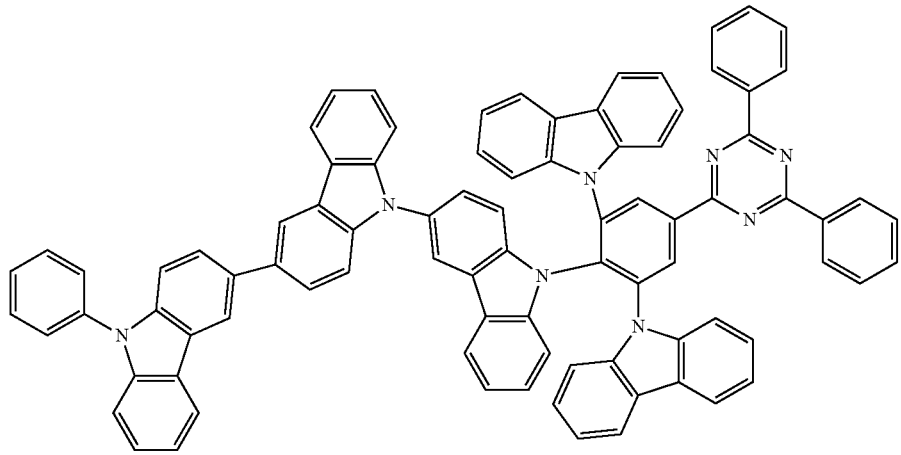
103
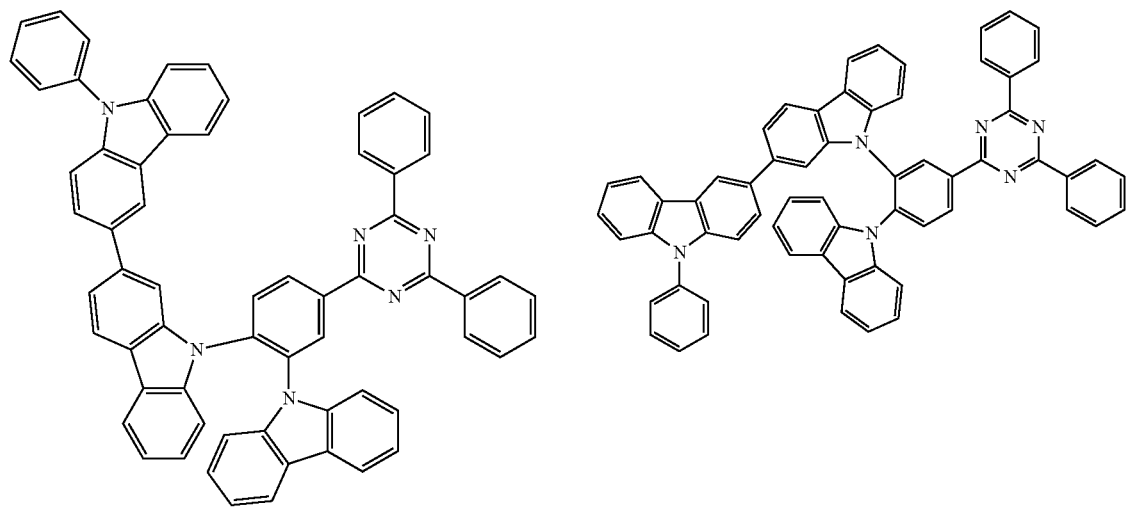
126
127
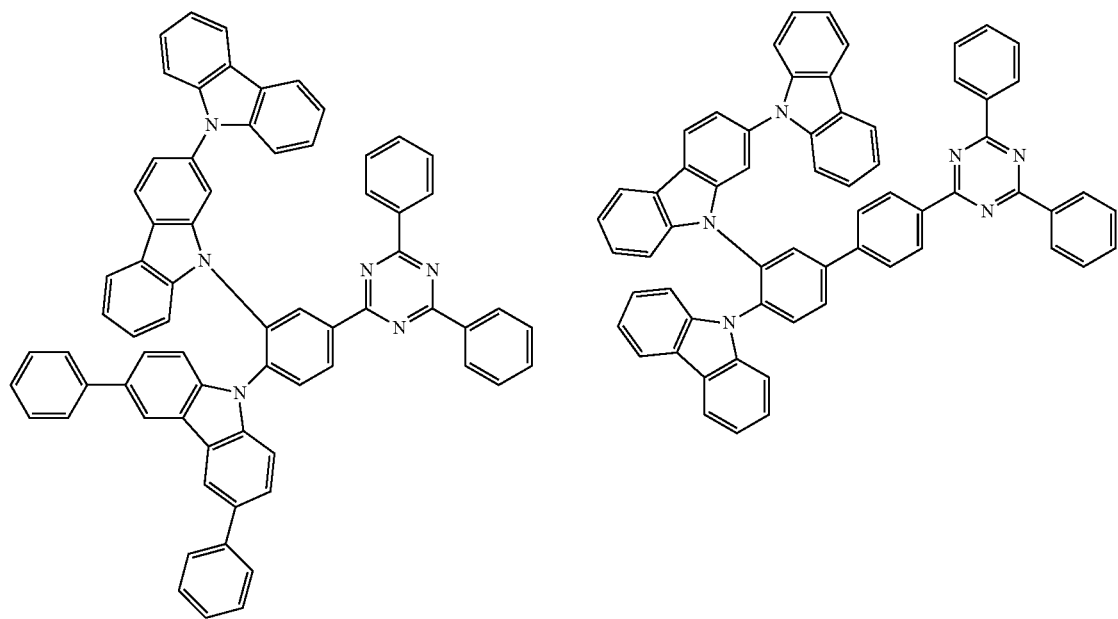
151
153

154
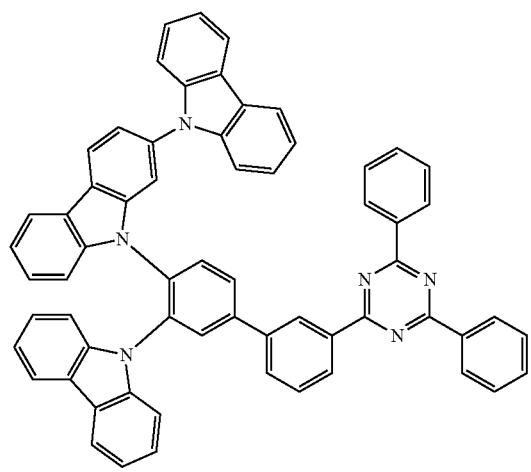
155
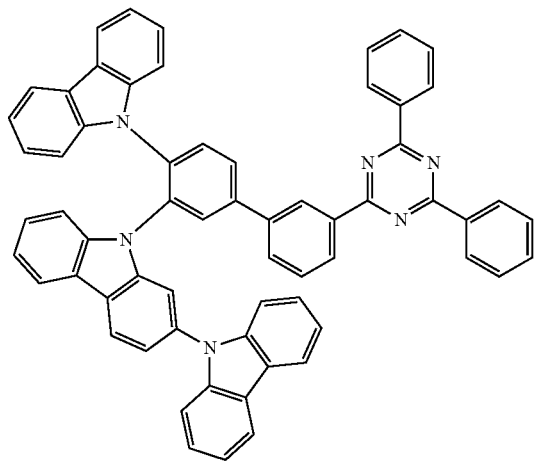
157
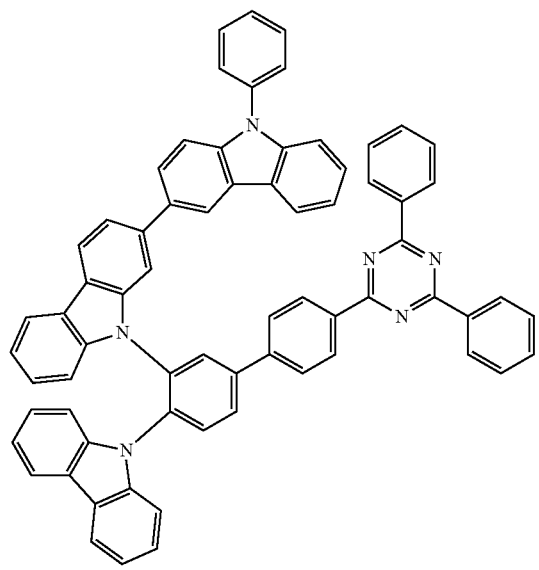
158
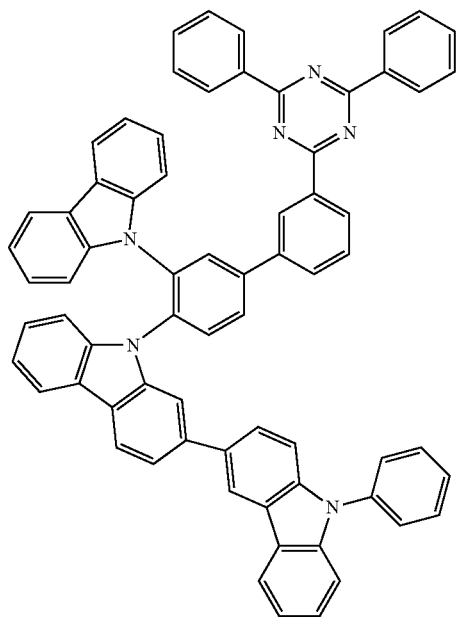

159
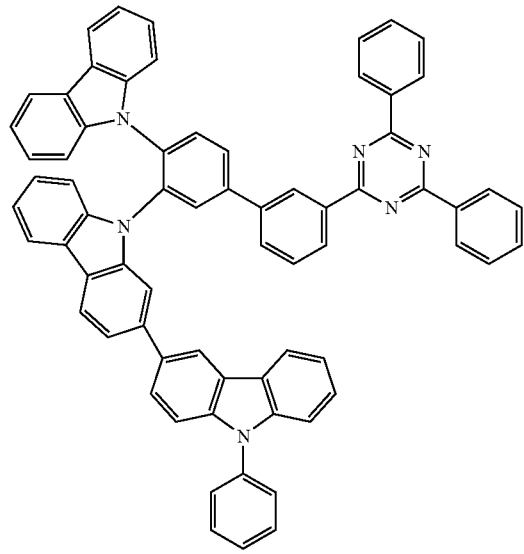
160
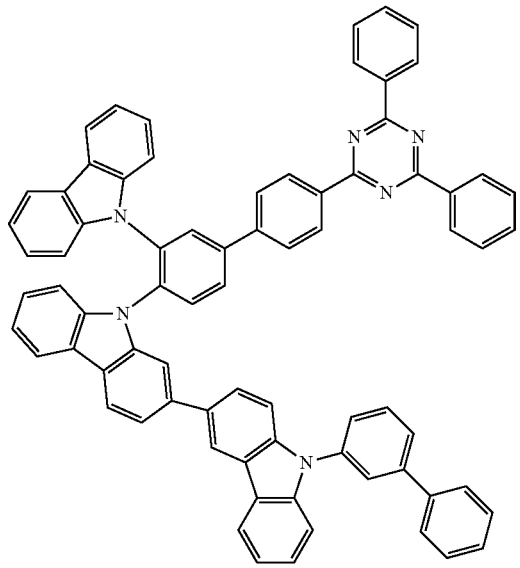
161
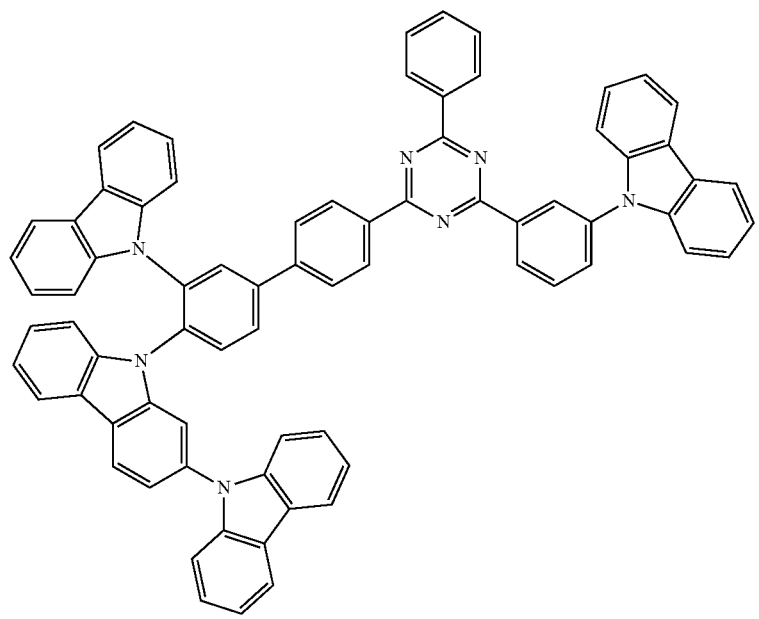

164

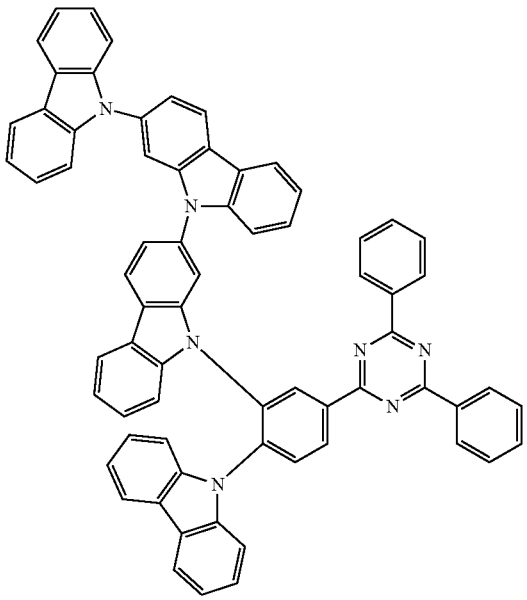

168

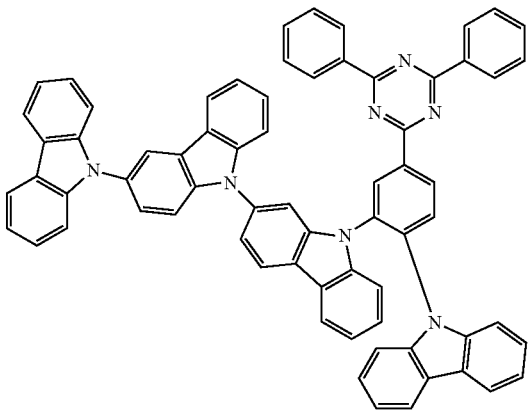

In addition, in this experiment, compounds of each Comparative Example used to compare the effects of the compounds of each Example above are as follows:

C1

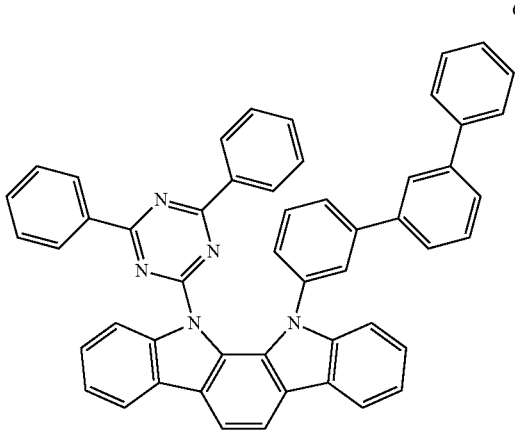

-continued

C3

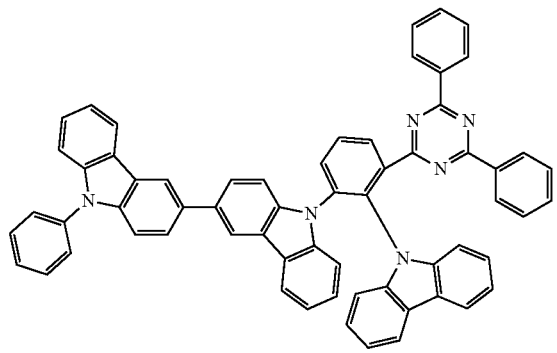

Evaluation of Compounds

Evaluation of Solution Pot Life

Each of the compounds obtained according to Examples and Comparative Example was prepared as an individual solid sample.

50 mg of the solid sample was added to a colorless sample bottle, and 1.0 g of methyl benzoate was added thereto as solvent. Then, the mixed solution was heated at a temperature of 150° C. to completely dissolve the solid sample therein, so as to prepare a 5 weight % solution. Afterwards, the solution thus obtained was cooled to room temperature and its observation was started. The time (h) until a precipitated solid such as a crystal was visually confirmed was measured as a pot life. Here, a long pot life indicates difficult crystallization of the solution. In this evaluation, it was determined that, when the pot life was 1 hour or longer, the solution had a long pot life so that it is suitable for a wet process. It was also determined that, as the pot life was longer, the solution was excellent to apply for the wet process. The results are shown in Table 1 below.

C2

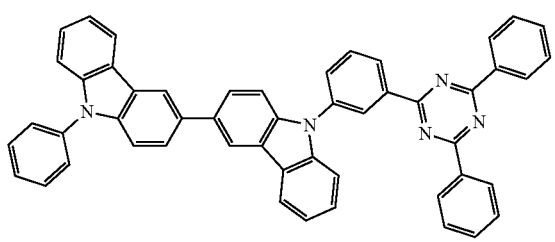

TABLE 1

Solution pot life for each compound of Examples and Comparative Compounds

| Compound | Pot life (h) for 5 weight % methyl benzoate solution |
|---|---|
| 1 | 40 |
| 2 | 5 |
| 3 | 40 |
| 4 | 20 |
| 6 | 70 |
| 8 | 50 |
| 10 | 50 |
| 12 | >100 |
| 13 | 10 |
| 14 | 50 |
| 16 | 50 |
| 18 | 60 |
| 22 | 80 |
| 24 | 50 |
| 27 | >100 |
| 28 | 40 |
| 29 | >100 |
| 30 | >100 |
| 33 | 20 |
| 36 | 40 |
| 39 | 40 |
| 44 | 30 |
| 45 | 10 |
| 47 | >100 |
| 58 | >100 |
| 59 | >100 |
| 86 | >100 |
| 89 | >100 |
| 90 | >100 |
| 92 | >100 |
| 93 | >100 |
| 102 | 70 |
| 103 | 50 |
| 126 | 40 |
| 127 | 30 |
| 151 | 10 |
| 153 | 10 |
| 154 | 5 |
| 155 | 20 |
| 157 | 5 |
| 158 | >100 |
| 159 | 50 |
| 160 | 80 |
| 161 | >100 |
| 164 | >100 |
| 168 | >100 |
| C1 | >100 |
| C2 | <1 |
| C3 | 60 |

Measurement of HOMO and LUMO Values

Each of the compounds obtained according to Examples and Comparative Example was prepared as an individual solid sample. Then, HOMO and LUMO values of the solid samples were measured according to the following steps.

1. Preparation of Measurement Sample (1) A sample solution was prepared to contain 4 parts by weight of the solid sample based on 100 parts by weight of the solvent (methyl benzoate).

(2) The sample solution of (1) was applied to each of an ITO substrate and a quartz substrate via spin-coating method to form a dried coating film having a thickness of 50 nm. The dried coating film was heated at a temperature of 120° C. under a vacuum of $10^{-1}$ Pa or less, and cooled to room temperature under a vacuum of $10^{-1}$ Pa or less, so as to form a thin-film layer (thin-film sample).

2. Measurement of HOMO Value

Regarding the thin-film sample formed on the ITO substrate of 1. (2), the HOMO value was measured using a photoelectron spectroscopy apparatus AC-3 (a product of RIKEN KEIKI Co, Ltd.) in the art.

3. Measurement of LUMO Value

Regarding the thin-film sample formed on the quartz substrate of 1. (2), the energy gap value (Eg) was measured at an absorption end of a ultraviolet-visible absorption spectrum using a spectrophotometer U-3900 (a product of Hitachi High-Tech Science Co., Ltd.), and then, the LUMO value was calculated according to Equation (3) below. The calculation results are shown in Table 2.

$$LUMO = HOMO + E_g \quad \text{Equation (3)}$$

TABLE 2

HOMO and LUMO values of each compound

| Compound | HOMO (eV) | LUMO (eV) |
|---|---|---|
| 1 | −5.6 | −2.7 |
| 2 | −5.6 | −2.9 |
| 3 | −5.6 | −2.8 |
| 4 | −5.6 | −2.8 |
| 6 | −5.6 | −2.7 |
| 8 | −5.8 | −2.7 |
| 10 | −5.8 | −2.8 |
| 12 | −5.7 | −2.8 |
| 13 | −5.6 | −2.8 |
| 14 | −5.7 | −2.7 |
| 16 | −5.6 | −2.8 |
| 18 | −5.8 | −2.9 |
| 22 | −5.8 | −2.9 |
| 24 | −5.7 | −2.8 |
| 27 | −5.6 | −2.7 |
| 28 | −5.7 | −2.7 |
| 29 | −5.6 | −2.7 |
| 30 | −5.6 | −2.7 |
| 33 | −5.8 | −2.8 |
| 36 | −5.6 | −2.7 |
| 39 | −5.7 | −2.8 |
| 44 | −5.8 | −2.9 |
| 45 | −5.8 | −2.9 |
| 47 | −5.6 | −2.8 |
| 58 | −5.6 | −2.8 |
| 59 | −5.6 | −2.8 |
| 86 | −5.8 | −3.0 |
| 89 | −5.8 | −2.9 |
| 90 | −5.5 | −2.7 |
| 92 | −5.5 | −2.7 |
| 93 | −5.5 | −2.7 |
| 102 | −5.6 | −2.9 |
| 103 | −5.5 | −2.9 |
| 126 | −5.7 | −2.8 |
| 127 | −5.7 | −2.8 |
| 151 | −5.9 | −3.0 |
| 153 | −5.9 | −2.9 |
| 154 | −5.9 | −2.9 |
| 155 | −5.9 | −2.8 |
| 157 | −5.7 | −2.7 |
| 158 | −5.6 | −2.8 |
| 159 | −5.7 | −2.7 |
| 160 | −5.7 | −3.0 |
| 161 | −5.9 | −3.0 |
| 164 | −5.8 | −2.9 |
| 168 | −5.8 | −2.9 |
| C1 | −5.9 | −2.8 |
| C2 | −5.6 | −2.7 |
| C3 | −5.6 | −2.8 |

In addition, the HOMO-LUMO energy gap (energy gap value in Eg) was not particularly limited, 3.0 eV or less was preferable.

Preparation and Evaluation of Organic Electroluminescent Device

Preparation of Organic Electroluminescent Device

Example 1

First, as a first electrode (cathode), an indium tin oxide (ITO) glass substrate on which stripe-type ITO was deposited to form a film form having a thickness of 150 nm was prepared. On the ITO glass substrate, poly(3,4-ethylene dioxythiophene) (PEDOT)/poly(4-styrene sulfonate) (PSS) (a product of Sigma-Aldrich) was applied via spin-coating method to form a dried coating film, i.e., a hole injection layer, having a thickness of 30 nm.

Next, a solution for coating a hole transport layer on the hole injection layer was prepared, the solution containing anisole as a solvent, 3 parts by weight of a hole-transporting polymer (HTP1) having a repeating structure below based on 100 parts by weight of the solvent (weight average molecular weight (Mw)=400,000, PDI (Mw/Mn)=2.7), and 0.6 parts by weight of a low molecular weight compound (AD1) having the following structure based on 100 parts by weight of the solvent. Subsequently, the solution for coating the hole transport layer was applied via spin-coating method to form a dried coating film having a thickness of 125 nm. The dried coating film was heated at a temperature of 230° C. under a vacuum of $10^{-1}$ Pa or less, and cooled to room temperature under a vacuum of $10^{-1}$ Pa or less, so as to form a hole transport layer.

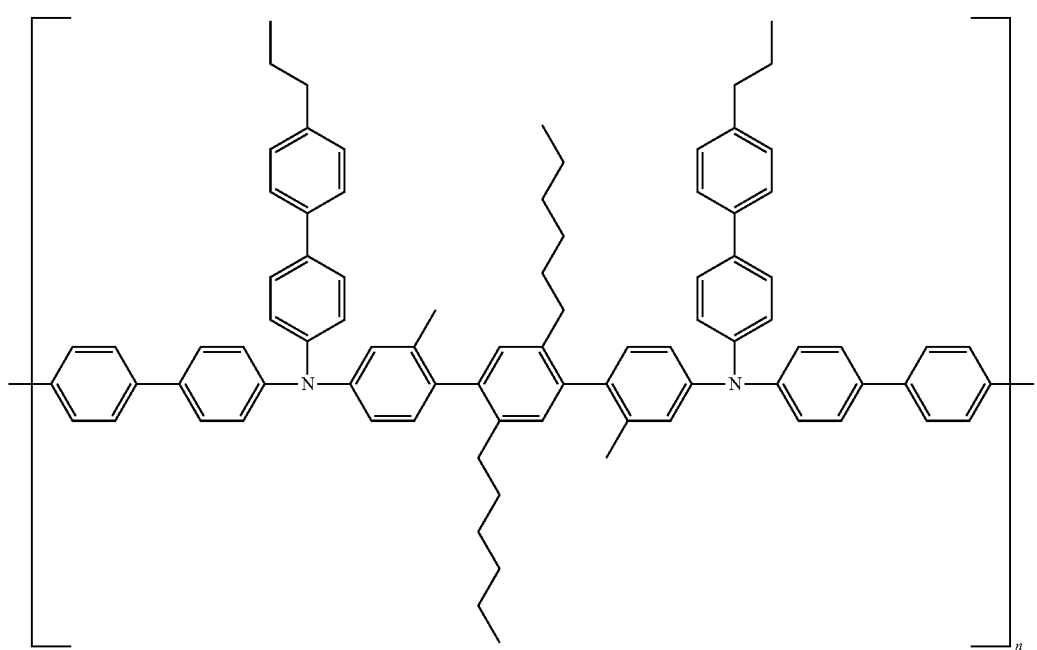

HTP1

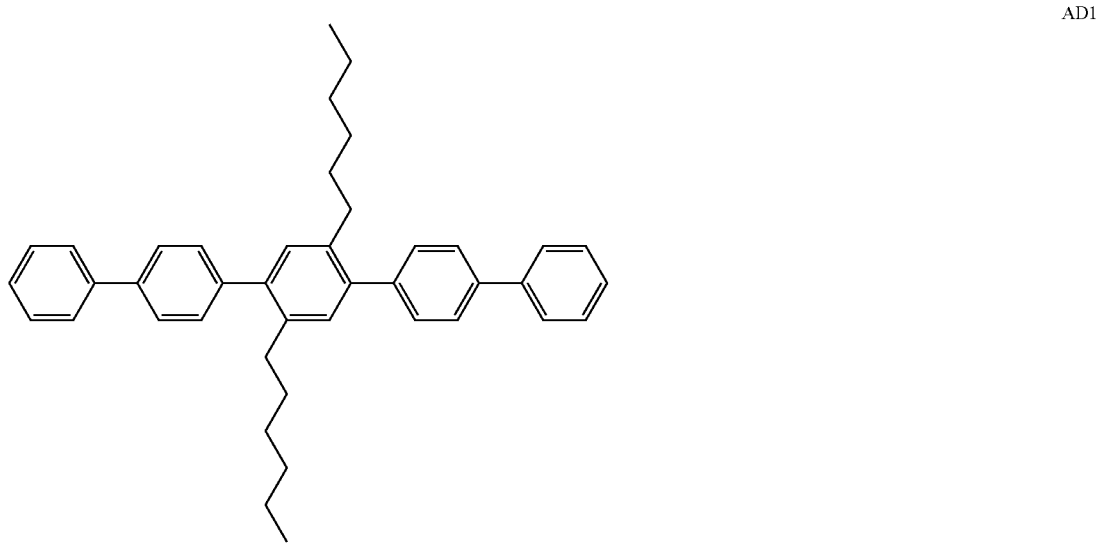

AD1

Next, ink for emission layer which is a liquid composition was applied to the hole transport layer via spin-coating method to form a dried emission layer having a thickness of 55 nm on the hole transport layer. Here, the ink for emission layer was prepared to include, based on 100 parts by weight of methyl benzoate as a solvent, 0.92 parts by weight of Compound W1, 0.92 parts by weight of Compound 2H-34, 2.16 parts by weight of Compound 1 of Example 1, and 0.4 parts by weight of Compound D144 below as solids:

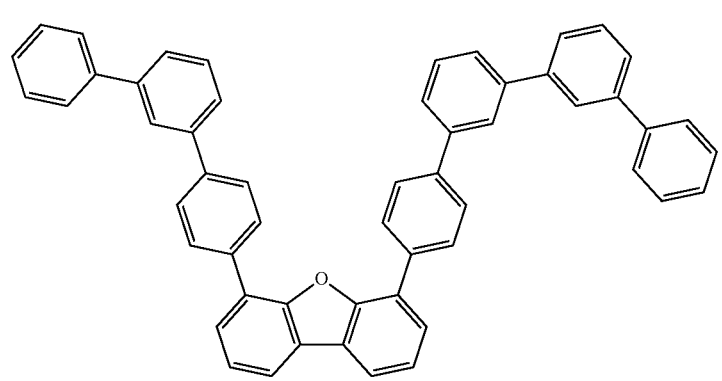

W1

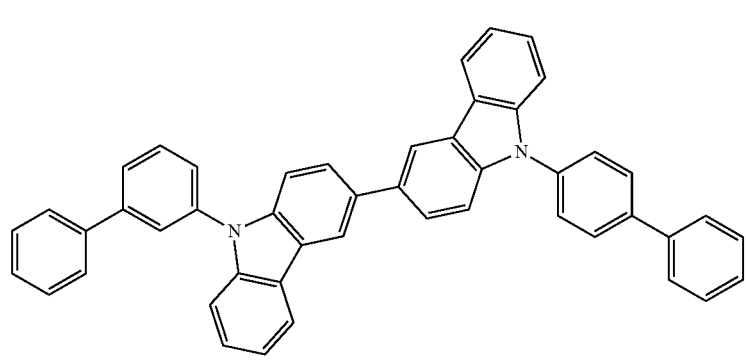

2H-34

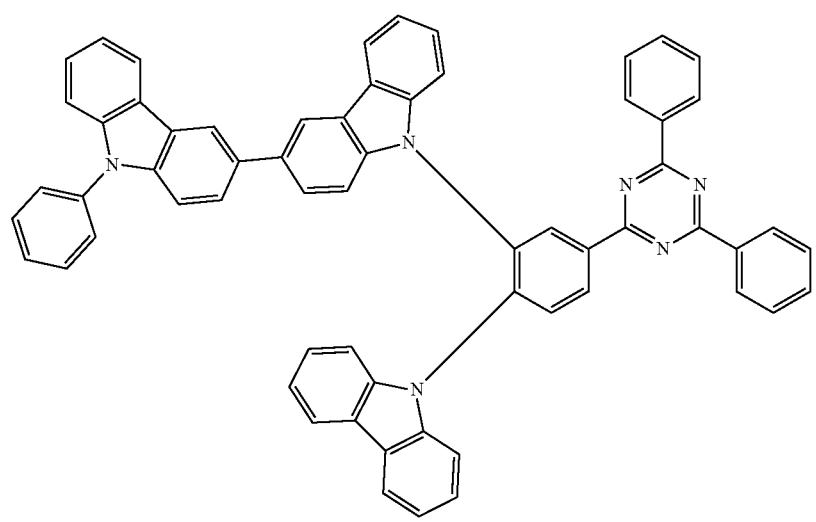

1

D144

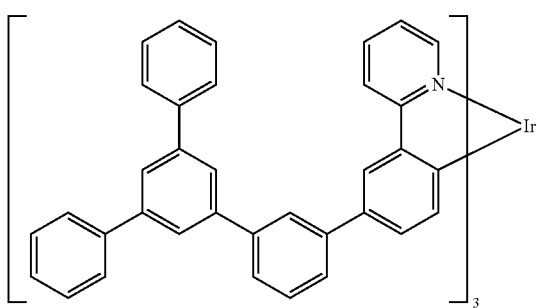

Then, on the emission layer, (8-quinolinato)lithium (Liq) and KLET-03 (manufactured by Chemipro Chemical Corporation) were co-deposited at a weight ratio of 2:8 by using a vacuum deposition apparatus, to form an electron transport layer having a thickness of 20 nm.

Then, on the electron transport layer, Liq was deposited by using a vacuum deposition apparatus to form an electron injection layer having a thickness of 3.5 nm.

Then, on the electron injection layer, aluminum (Al) was deposited by using a vacuum deposition apparatus to form a second electrode (i.e., an anode) having a thickness of 100 nm.

Afterwards, in a glove box under the nitrogen atmosphere with a moisture concentration of 1 ppm or less and an oxygen concentration of 1 ppm or less, the organic electroluminescent device manufactured in the process above was sealed by using a glass sealing tube to which a desiccant was attached and an ultraviolet curable resin.

Synthesis of Compound W1

In addition, Compound W1 was synthesized according to the following procedure.

Synthesis of Compound W1a

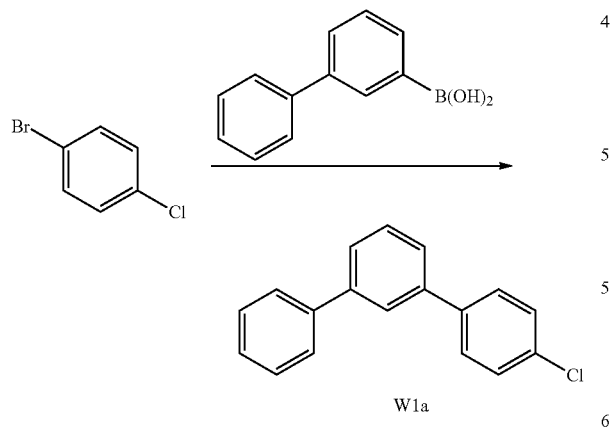

In the nitrogen atmosphere, bromobenzene (220 mmol, 42 g), 3-biphenylboronic acid (1.05 eq., 231 mmol, 45.7 g), toluene (880 ml), and ethanol (EtOH) (110 ml) were added to a three neck-flask, and stirred to prepare a solution. Subsequently, a 2 M aqueous potassium carbonate solution (K$_2$CO$_3$ 2 M Aq)(1.5 eq., 165 ml) was added first to this solution, and tetrakis(triphenylphosphine)palladium(0) (Pd (PPh$_3$)$_4$) (3 mol %, 6.6 mmol, 7.63 g) was added thereto. The mixed solution was stirred at a temperature of 70° C. for 8 hours. Afterwards, the reaction solution was diluted with toluene (500 ml), filtered through Celite, and washed twice using pure water. Then, the resultant solution was dried using anhydrous magnesium sulfate, filtered through a silica gel pad, and then concentrated. The crude thus obtained was subjected to dispersion washing in EtOH (10 ml/1 g) for filtration, and dried in a vacuum condition (50° C., 12 hours), so as to obtain a white target solid (i.e., Compound W1a). Here, Compound W1a had a yield of 57.7 g and a yield rate of 99%.

Synthesis of Compound W1b

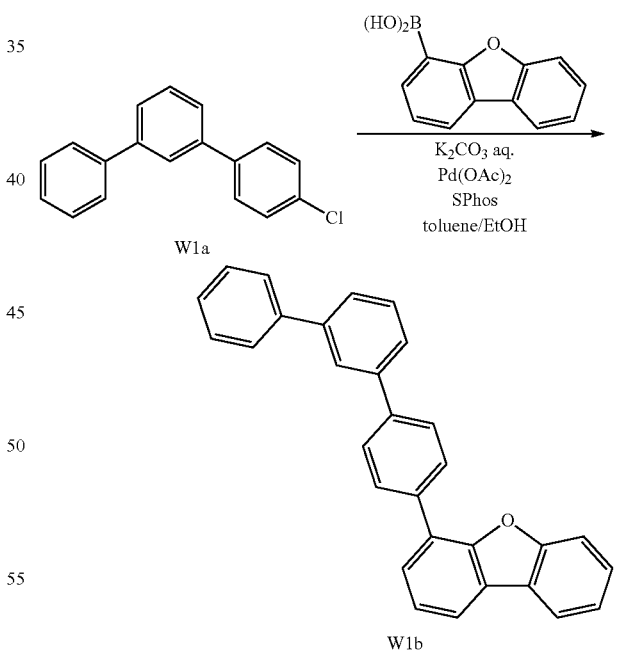

In the nitrogen atmosphere, Compound W1a (255 mmol, 67.4 g), dibenzofuran boronic acid (1.1 eq., 280.5 mmol, 59.5 g), toluene (510 ml), and EtOH (128 ml) were added to a three neck-flask, and stirred to prepare a solution. Subsequently, K$_2$CO$_3$ 2M Aq (191 ml) was added first to this solution, and palladium acetate (3 mol %, 7.65 mmol, 1.71 g) and S-Phos (4.5 mol %, 11.5 mmol, 4.72 g) were added thereto. The mixed solution was stirred at a temperature of 80° C. for 6 hours. After cooling to room temperature, the reaction solution was diluted with methanol (1 L), and ultrasonic irradiation was performed thereon for 30 minutes. Then, the precipitated solid was collected by filtration, and washed with methanol. After washing, the precipitated solid was dried in a vacuum condition (50° C., 12 hours), dissolved in toluene (1 L) by heating, filtered through a silica gel pad, and then concentrated. The crude thus obtained was recrystallized twice using a mixed solvent of toluene and ethanol (toluene:ethanol=6 ml:10 ml/1 g), so as to obtain a white target solid (i.e., Compound W1b). Here, Compound W1b had a yield of 72.8 g and a yield rate of 72%.

Synthesis of Compound W1c

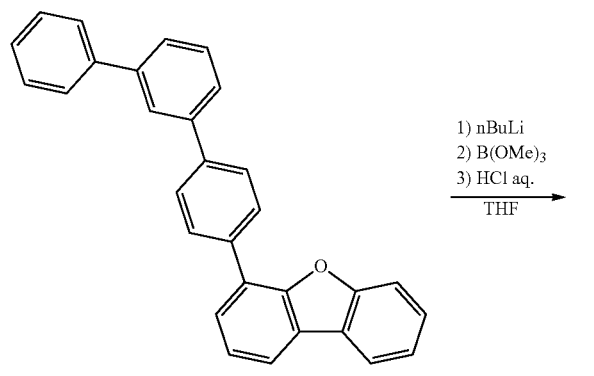

To a three neck-flask, Compound W1b (183 mmol, 72.2 g) and tetrahydrofuran (1,830 ml) were added and stirred to prepare a solution. Subsequently, this solution was cooled to a temperature of 0° C., and an n-butyl lithium/hexane solution (nBuLi hexane solution) (2.65 M, 1.1 eq., 201.3 mmol, 76 ml) was added thereto. As a result, the color of this solution was changed from colorless to dark blue. Then, the resultant solution was stirred at a temperature of 0° C. for 2 hours. Next, trimethyl borate (1.3 eq., 237.9 mmol, 26.6 ml) was added dropwise to the solution. As a result, the color of the solution was changed from dark blue to pale blue. Then, the resultant solution was stirred at room temperature for 5 hours. Next, the reaction system was deactivated with methanol, and pure water was further added thereto. The resultant solution was concentrated to about half and acidified with 1 N aqueous hydrochloric acid solution (HCL Aq.(1 N)) (600 ml). An organic phase was then extracted using ethyl acetate through a separatory funnel, and the extracted organic phase was washed twice with pure water. Then, the extracted solution after washing was dried using anhydrous magnesium sulfate, filtered through a silica gel pad, and then concentrated. The crude thus obtained was dried in a vacuum condition (50° C., 12 hours) and dissolved in toluene (500 ml) by heating. Then, hexane (1 L) was added to the resultant solution to precipitate a solid, and the precipitated solid was subjected to dispersion washing (under reflux for 4 hours). After cooling to room temperature, the precipitated solid was collected by filtration, so as to obtain a white target solid (i.e., Compound W1c). Here, Compound W1c had a yield of 80.6 g and a yield rate of 75%.

Synthesis of Compound W1d

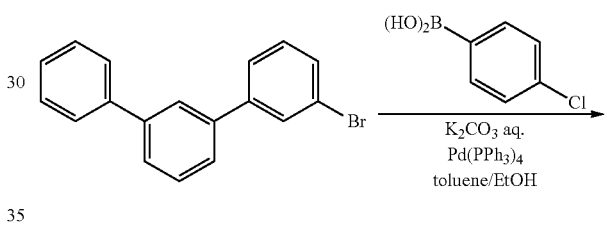

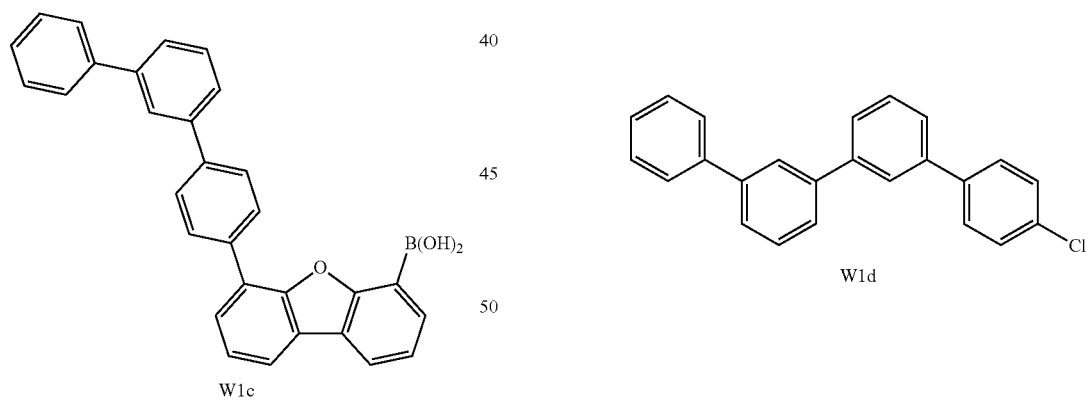

In the nitrogen atmosphere, to a three neck-flask, 3-bromo-1,1': 3'1"-terphenyl (1 mol, 309.2 g), 4-chlorophenyl boronic acid (1.05 eq., 1.05 mol, 164.2 g), toluene (2 L), and EtOH (200 ml) were added and stirred to prepare a solution. Subsequently, K$_2$CO$_3$ 2 M Aq (1.5 eq., 750 ml) was added first to this solution, and Pd(PPh$_3$)$_4$ (3 mol %, 30 mmol, 34.7 g) was added thereto. The mixed solution was stirred at a temperature of 70° C. for 12 hours. After cooling to room temperature, the reaction solution was filtered through Celite and washed twice using pure water. After washing, the resultant solution was dried using anhydrous magnesium sulfate, filtered through a silica gel pad, and then concentrated. The crude thus obtained was recrystallized three times using a mixed solvent of toluene and hexane (toluene:hexane=2 ml:10 ml/1 g), and dried in a vacuum condition (50° C., 12 hours), so as to obtain a white target solid (i.e., Compound W1d). Here, Compound W1d had a yield of 153.7 g and a yield rate of 45%.

(i.e., Compound W1). Here, Compound W1 had a yield of 8.9 g and a yield rate of 85%.

Synthesis of Compound W1

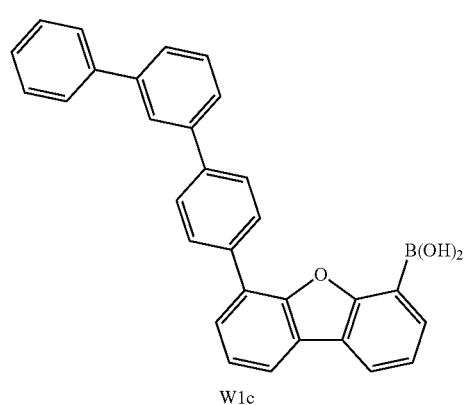

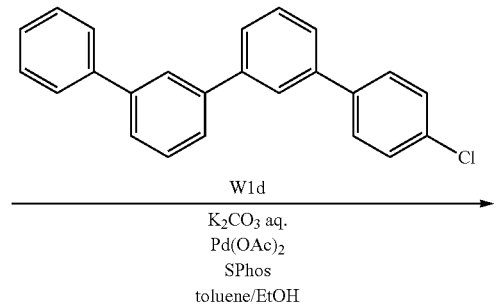

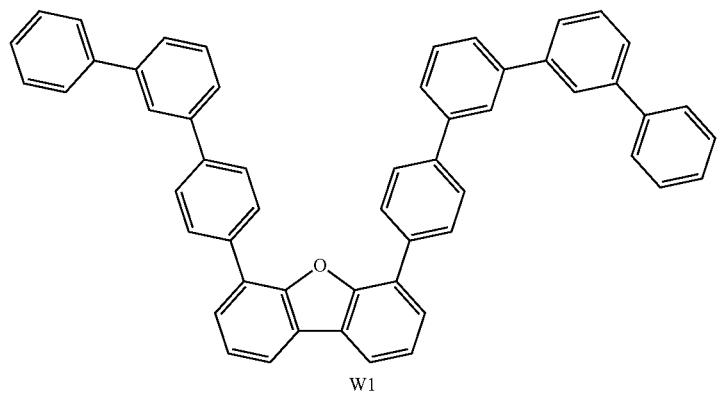

In the nitrogen atmosphere, Compound W1c (15 mmol, 6.6 g), Compound W1d (1.05 eq., 16.5 mmol, 5.6 g), toluene (150 ml), and EtOH (15 ml) were added to a three neck-flask, and stirred to prepare a solution. Subsequently, $K_2CO_3$ 2M Aq (1.5 eq., 11.3 ml) was added first to this solution, and palladium (II) acetate (3 mol %, 0.45 mmol, 101 mg) and S-Phos (4.5 mol %, 0.68 mmol, 279 mg) were added thereto. The mixed solution was stirred at a temperature of 80° C. for 6 hours. After cooling to room temperature, the reaction solution was diluted with methanol (200 ml), and ultrasonic irradiation was performed thereon for 30 minutes to collect a precipitated solid through filtration. The precipitated solid was then washed using methanol. After washing, the precipitated solid was dried in a vacuum condition (50° C., 12 hours), dissolved in toluene (300 ml) by heating, filtered through a silica gel pad, and then concentrated. The crude thus obtained was subjected to dispersion washing three times using a mixed solvent of toluene and ethanol (toluene:ethanol=6 ml:10 ml/1 g), so as to obtain a white target solid Examples 2 to 46 and Comparative Examples 1 to 3

Organic electroluminescent devices were each manufactured in the same manner as in Example 1, except that the ink for emission layer included, based on the same total weight of the solid with respect to 100 parts by weight of methyl benzoate as the solvent, types and ratios of the solid compound were changed as shown in Tables 3 and 4. Here, the content (parts by weight) of Compound D144 as a dopant material was the same as in Example 1.

Examples 47 to 51 and Comparative Examples 4 to 6

Organic electroluminescent devices were each manufactured in the same manner as in Example 1, except that for the composition of the ink for emission layer, based on the same total weight of the solid components with respect to 100 parts by weight of methyl benzoate as the solvent, types and ratios of the solid compound were changed as shown in Table 5. Here, the content (parts by weight) of Compound D144 as a dopant material was the same as in Example 1.

Az27

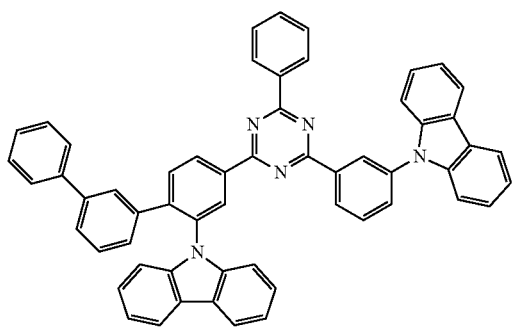

[Evaluation of Organic Electroluminescent Device]

The driving voltage, efficiency, and lifespan (durability) were evaluated according to the following method.

Light was emitted while changing the voltage applied to the organic electroluminescent devices from 0 V to 20 V by using a direct current constant voltage power supply (i.e., a source meter manufactured by Keyence Co., Ltd.), and the brightness at this point was measured using a luminance measuring apparatus (SR-3 manufactured by Topcom).

Here, the current value per unit area (current density) was calculated in the area of the organic electroluminescent device, and the current efficiency (cd/A) was calculated by dividing the luminance (cd/m$^2$) by the current density (A/m$^2$). The driving voltage and current efficiency each indicate a measured value at the luminance of 2,000 cd/m$^2$. Here, when the driving voltage was or less, the driving voltage was determined to be sufficiently low. In this regard, the smaller value was determined to be more preferable. In addition, when the current efficiency was 50 cd/A or more, the efficiency was determined to be high. In this regard, the greater value was determined to be more preferable.

In addition, the luminescence lifespan (durability) was measured as "LT$_{95}$ (h)" as the time until the luminescence brightness which decreased with the elapse of the operating hours became 95% of the initial luminance which was continuously driven at a current value of 10,000 cd/m$^2$. Here, when LT$_{95}$ (h) exceeded 65 hours (h), it was determined that the organic electroluminescent device had a long lifespan. In this regard, it was determined that the longer time was more preferable.

Such evaluation results are shown in Tables 3 to 5.

TABLE 3

Emission layer composition of organic EL device and evaluation results

| | Host material composition in emission layer | Dopant material in emission layer | Driving voltage (V) | Efficiency (Cd/A) | LT$_{95}$ (h) |
|---|---|---|---|---|---|
| Example 1 | W1:2H-34:Compound 1 = 3:3:7 | D114 | 6.2 | 55 | 100 |
| Example 2 | W1:2H-34:Compound 2 = 3:3:7 | D114 | 6.2 | 53 | 110 |
| Example 3 | W1:2H-34:Compound 3 = 3:3:7 | D114 | 6.0 | 61 | 120 |
| Example 4 | W1:2H-34:Compound 4 = 3:3:7 | D114 | 6.1 | 60 | 100 |

TABLE 3-continued

Emission layer composition of organic EL device and evaluation results

| | Host material composition in emission layer | Dopant material in emission layer | Driving voltage (V) | Efficiency (Cd/A) | LT$_{95}$ (h) |
|---|---|---|---|---|---|
| Example 5 | W1:2H-34:Compound 6 = 3:3:7 | D114 | 6.4 | 60 | 80 |
| Example 6 | W1:2H-34:Compound 8 = 3:3:7 | D114 | 6.7 | 56 | 105 |
| Example 7 | W1:2H-34:Compound 10 = 3:3:7 | D114 | 6.6 | 68 | 90 |
| Example 8 | W1:2H-34:Compound 12 = 3:3:7 | D114 | 6.0 | 52 | 105 |
| Example 9 | W1:2H-34:Compound 13 = 3:3:7 | D114 | 5.7 | 53 | 180 |
| Example 10 | W1:2H-34:Compound 14 = 3:3:7 | D114 | 6.1 | 55 | 125 |
| Example 11 | W1:2H-34:Compound 16 = 3:3:7 | D114 | 5.9 | 61 | 140 |
| Example 12 | W1:2H-34:Compound 18 = 3:3:7 | D114 | 6.0 | 60 | 95 |
| Example 13 | W1:2H-34:Compound 22 = 3:3:7 | D114 | 5.9 | 54 | 120 |
| Example 14 | W1:2H-34:Compound 24 = 3:3:7 | D114 | 6.0 | 51 | 90 |
| Example 15 | W1:2H-34:Compound 27 = 3:3:7 | D114 | 5.9 | 56 | 105 |
| Example 16 | W1:2H-34:Compound 28 = 3:3:7 | D114 | 6.1 | 63 | 90 |
| Example 17 | W1:2H-34:Compound 29 = 3:3:7 | D114 | 5.7 | 56 | 80 |
| Example 18 | W1:2H-34:Compound 30 = 3:3:7 | D114 | 5.9 | 57 | 90 |
| Example 19 | W1:2H-34:Compound 33 = 3:3:7 | D114 | 6.4 | 54 | 80 |
| Example 20 | W1:2H-34:Compound 36 = 3:3:7 | D114 | 6.0 | 50 | 120 |
| Example 21 | W1:2H-34:Compound 39 = 3:3:7 | D114 | 6.2 | 52 | 85 |
| Example 22 | W1:2H-34:Compound 44 = 3:3:7 | D114 | 6.5 | 62 | 120 |
| Example 23 | W1:2H-34:Compound 45 = 3:3:7 | D114 | 6.3 | 50 | 75 |
| Example 24 | W1:2H-34:Compound 47 = 3:3:7 | D114 | 6.3 | 51 | 110 |
| Example 25 | W1:2H-34:Compound 58 = 3:3:7 | D114 | 5.9 | 54 | 155 |
| Example 26 | W1:2H-34:Compound 59 = 3:3:7 | D114 | 5.9 | 56 | 130 |

TABLE 4

Emission layer composition of organic EL device and evaluation results

|  | Host material composition in emission layer | Dopant material in emission layer | Driving voltage (V) | Efficiency (Cd/A) | $LT_{95}$ (h) |
|---|---|---|---|---|---|
| Example 27 | W1:2H-34:Compound 86 = 3:3:7 | D114 | 6.5 | 65 | 160 |
| Example 28 | W1:2H-34:Compound 89 = 3:3:7 | D114 | 6.2 | 60 | 100 |
| Example 29 | W1:2H-34:Compound 90 = 3:3:7 | D114 | 5.6 | 68 | 110 |
| Example 30 | W1:2H-34:Compound 92 = 3:3:7 | D114 | 5.5 | 65 | 90 |
| Example 31 | W1:2H-34:Compound 93 = 3:3:7 | D114 | 5.7 | 65 | 85 |
| Example 32 | W1:2H-34:Compound 102 = 3:3:7 | D114 | 5.8 | 66 | 110 |
| Example 33 | W1:2H-34:Compound 103 = 3:3:7 | D114 | 5.6 | 65 | 135 |
| Example 34 | W1:2H-34:Compound 126 = 3:3:7 | D114 | 6.7 | 60 | 90 |
| Example 35 | W1:2H-34:Compound 127 = 3:3:7 | D114 | 6.1 | 64 | 105 |
| Example 36 | W1:2H-34:Compound 151 = 3:3:7 | D114 | 6.6 | 55 | 95 |
| Example 37 | W1:2H-34:Compound 153 = 3:3:7 | D114 | 5.8 | 57 | 135 |
| Example 38 | W1:2H-34:Compound 154 = 3:3:7 | D114 | 5.8 | 58 | 110 |
| Example 39 | W1:2H-34:Compound 155 = 3:3:7 | D114 | 6.0 | 50 | 100 |
| Example 40 | W1:2H-34:Compound 157 = 3:3:7 | D114 | 6.3 | 52 | 90 |
| Example 41 | W1:2H-34:Compound 158 = 3:3:7 | D114 | 6.2 | 54 | 100 |
| Example 42 | W1:2H-34:Compound 159 = 3:3:7 | D114 | 6.4 | 50 | 85 |
| Example 43 | W1:2H-34:Compound 160 = 3:3:7 | D114 | 5.6 | 60 | 165 |
| Example 44 | W1:2H-34:Compound 161 = 3:3:7 | D114 | 6.0 | 57 | 140 |
| Example 45 | W1:2H-34:Compound 164 = 3:3:7 | D114 | 6.5 | 56 | 135 |
| Example 46 | W1:2H-34:Compound 168 = 3:3:7 | D114 | 6.2 | 51 | 135 |
| Comparative Example 1 | W1:2H-34:Compound C1 = 3:3:7 | D114 | 6.5 | 56 | 50 |
| Comparative Example 2 | W1:2H-34:Compound C2 = 3:3:7 | D114 | 6.4 | 45 | 125 |
| Comparative Example 3 | W1:2H-34:Compound C3 = 3:3:7 | D114 | 6.0 | 53 | 60 |

TABLE 5

Emission layer composition of organic EL device and evaluation results

|  | Host material composition in emission layer | Dopant material in emission layer | Driving voltage (V) | Efficiency (Cd/A) | $LT_{95}$ (h) |
|---|---|---|---|---|---|
| Example 47 | W1:Az27:Compound 86 = 1:1:1 | D114 | 5.6 | 56 | 80 |
| Example 48 | W1:Az27:Compound 89 = 1:1:1 | D114 | 5.6 | 53 | 70 |
| Example 49 | W1:Az27:Compound 90 = 1:1:1 | D114 | 5.5 | 53 | 80 |
| Example 50 | W1:Az27:Compound 92 = 1:1:1 | D114 | 5.6 | 54 | 90 |
| Example 51 | W1:Az27:Compound 93 = 1:1:1 | D114 | 5.4 | 55 | 90 |
| Comparative Example 4 | W1:Az27:Compound C1 = 1:1:1 | D114 | 6.5 | 47 | 60 |
| Comparative Example 5 | W1:Az27:Compound C2 = 1:1:1 | D114 | 5.4 | 40 | 75 |
| Comparative Example 6 | W1:Az27:Compound C3 = 1:1:1 | D114 | 5.7 | 44 | 45 |

Referring to Tables 3 to 5, it was confirmed that, in the case of using the compound represented by Formula (1) of the present disclosure, significantly excellent results were exhibited in terms of driving voltage, luminescence efficiency, and luminescence lifespan, compared to the case of using a compound conventionally used as in Comparative Examples.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the FIGURES, it will be understood by those of ordinary skill in the art that various changes in form and details may be made therein without departing from the spirit and scope as defined by the following claims.

What is claimed is:

1. A compound represented by Formula (1):

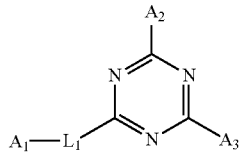

(1)

wherein, in Formula (1), $A_1$ is a substituent represented by Formula (2-1) or (2-2), $A_2$ and $A_3$ are each independently a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, L₁ is a single bond, a substituted or unsubstituted divalent aromatic hydrocarbon group having 6 to 30 carbon atoms or a substituted or unsubstituted divalent aromatic heterocyclic group having 5 to 30 ring-forming atoms,

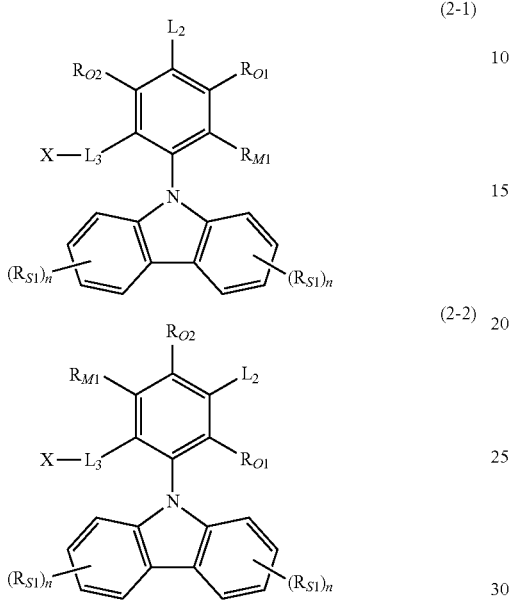

wherein, in Formulae (2-1) and (2-2),

L₂ is a single bond binding to L₁ in Formula (1), a substituted or unsubstituted divalent aromatic hydrocarbon group having 6 to 30 carbon atoms and binding to L₁ in Formula (1), or a substituted or unsubstituted divalent aromatic heterocyclic group having 5 to 30 ring-forming atoms and binding to L₁ in Formula (1), $R_{O1}$ and $R_{O2}$ are each independently a hydrogen atom, a deuterium atom, a fluoro group, a cyano group, or a substituted or unsubstituted monovalent alkyl group having 1 to 20 carbon atoms, $R_{M1}$ is a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of $R_{S1}$ is independently a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of n is independently 0, 1, 2, 3, or 4, L₃ is a single bond, a substituted or unsubstituted divalent aromatic hydrocarbon group having 6 to 30 carbon atoms, or a substituted or unsubstituted divalent aromatic heterocyclic group having 5 to 30 ring-forming atoms and not including a carbazole ring, X is an oligocarbazole group unsubstituted or substituted with a substituent other than a carbazole group; wherein X is re one of Formulae (3a), and (3c) to (3g):

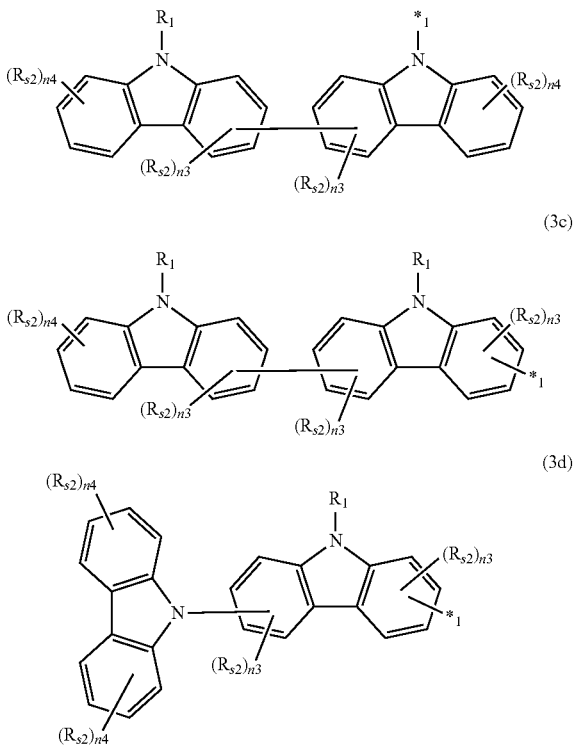

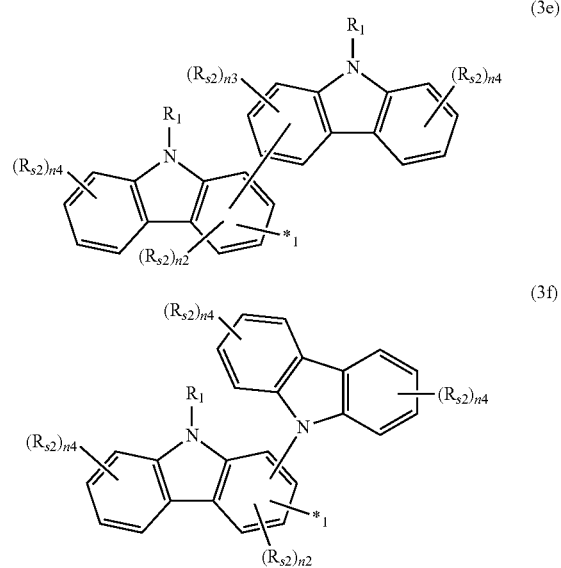

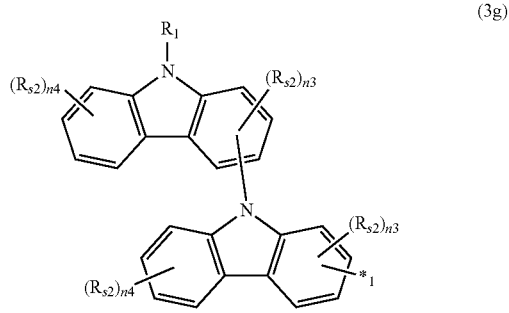

wherein, in Formulae (3a), and (3c) to (3g),

*1 indicates a binding site to $L_3$ in Formula (2-1) or (2-2), each occurrence of $R_1$ is independently a monovalent alkyl group having 1 to 20 carbon atoms and being unsubstituted or substituted with a substituent other than a carbazole group, a monovalent aromatic hydrocarbon group having 6 to 30 carbon atoms and being unsubstituted or substituted with a substituent other than a carbazole group, or a monovalent aromatic heterocyclic group (other than a carbazole group) having 5 to 30 ring-forming atoms and being unsubstituted or substituted with a substituent other than a carbazole group, each occurrence of $R_{32}$ is independently a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms or a substituted or unsubstituted monovalent aromatic heterocyclic group (other than a carbazole group) having 5 to 30 ring-forming atoms, each occurrence of n4 is independently 0, 1, 2, 3, or 4, each occurrence of n3 is independently 0, 1, 2, or 3, and each occurrence of n2 is independently 0, 1, or 2.

2. The compound of claim 1, wherein $L_1$ does not comprise an aromatic hydrocarbon group or an aromatic heterocyclic group at an ortho position in relation to the triazine ring of Formula (1) binding to $L_1$, $L_2$ does not comprise an aromatic hydrocarbon group or an aromatic heterocyclic group at an ortho position in relation to the benzene ring of Formula (2-1) or Formula (2-2) binding to $L_2$, and $L_1$ and $L_2$ do not comprise an aromatic hydrocarbon group or an aromatic heterocyclic group at an ortho position in relation to each other.

3. The compound of claim 1, wherein the oligocarbazole group unsubstituted or substituted with a substituent other than a carbazole group is represented by one of Formulae (3a-1) to (3a-6), (3c-1) to (3c-6), (3d-1), (3d-2), (3g-1), and (3g-2):

(3a-1)

(3a-2)

(3a-3) 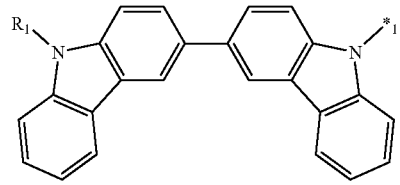 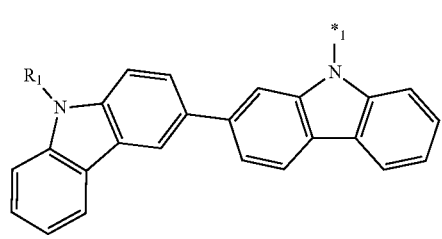 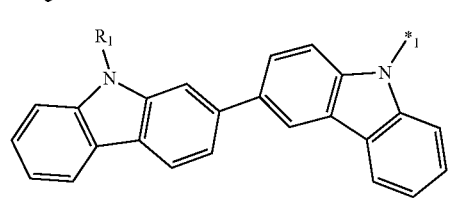 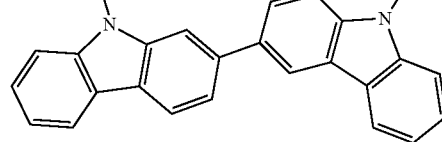

(3a-4) 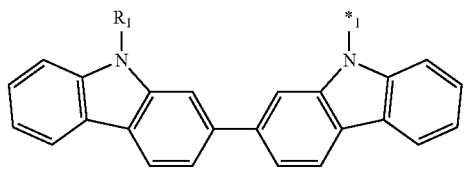

(3a-5) 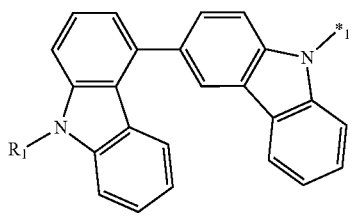

(3a-6) 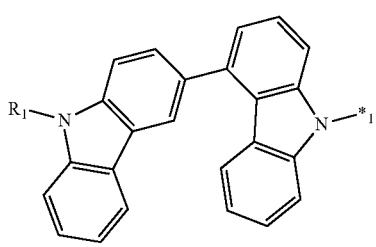

(3c-1) 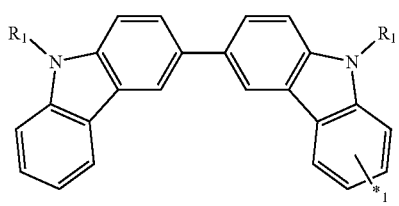

(3c-2) 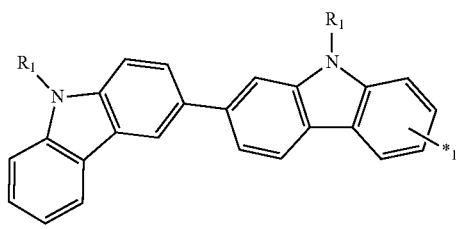

(3c-3) 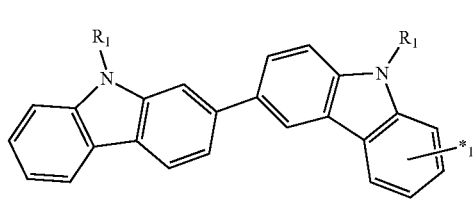

(3c-4) 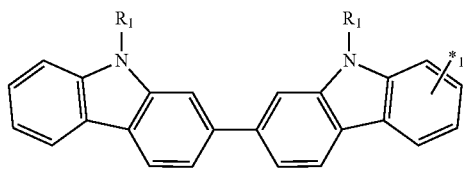

-continued

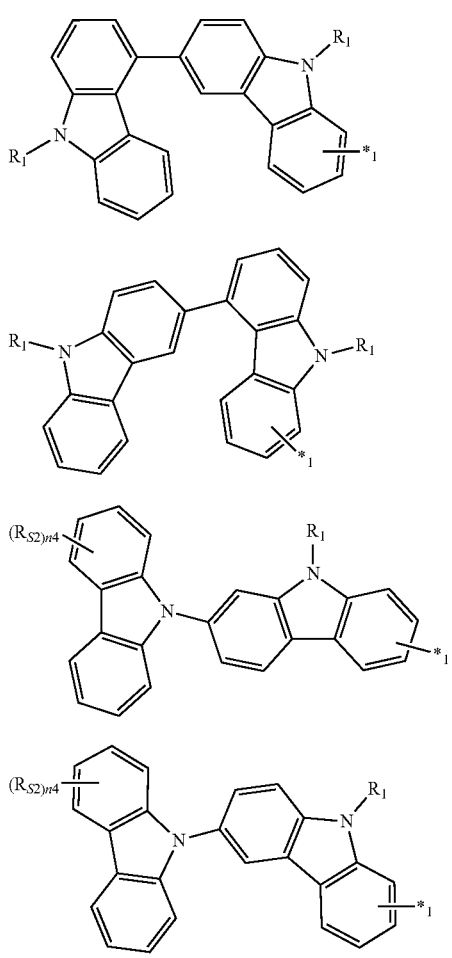

(3c-5)
(3c-6)
(3d-1)
(3d-2)

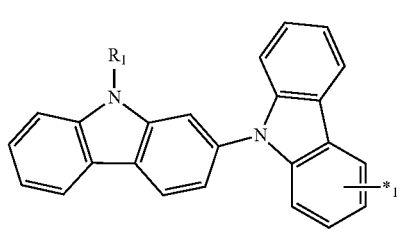

(3g-1)

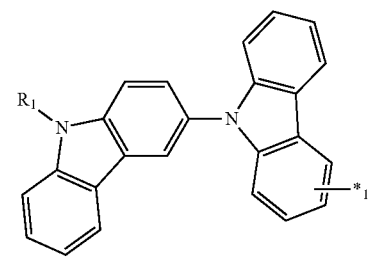

(3g-2)

wherein, in Formulae (3a-1) to (3a-6), (3c-1) to (3c-6), (3d-1), (3d-2), (3g-1), and (3g-2), l, $R_1$ (s), $R_{S2}$ (s), and n4 (s) are each independently the same as described in connection with Formulae (3a), and (3c) to (3g).

4. The compound of claim 1, wherein the oligocarbazole group unsubstituted or substituted with a substituent other than a carbazole group is represented by one of Formulae (4a-1) to (4a-9), (4c-1) to (4c-10), (4d-1) to (4d-6), (4e-1) to (4e-8), (4f-1) to (4f-4), and (4g-1) to (4g-5):

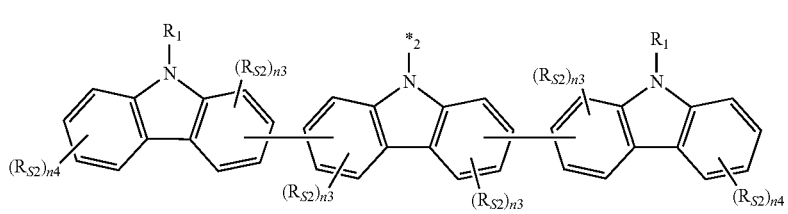

(4a-1)

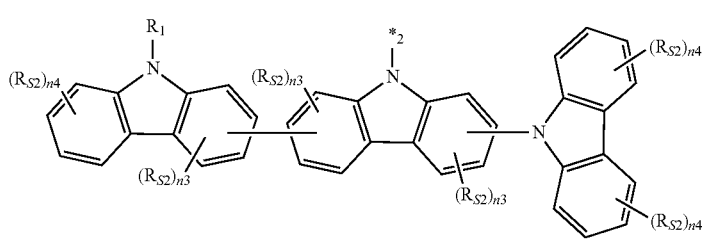

(4a-2)

-continued
(4a-3)
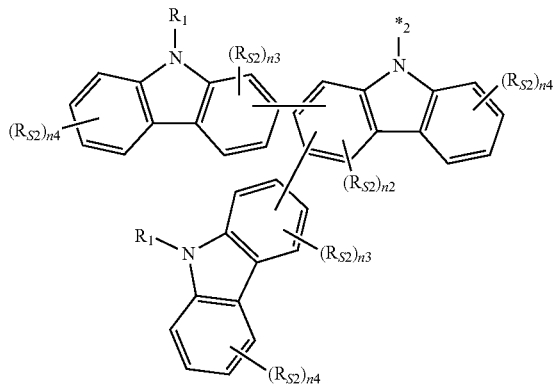
(4a-4)
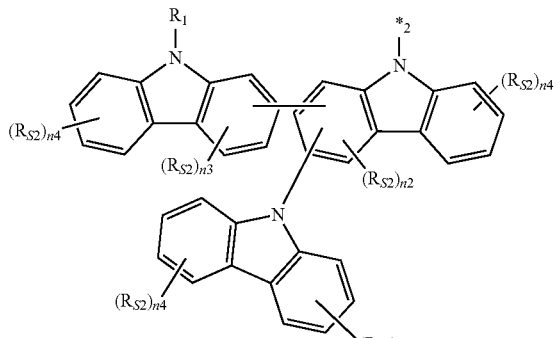
(4a-5)
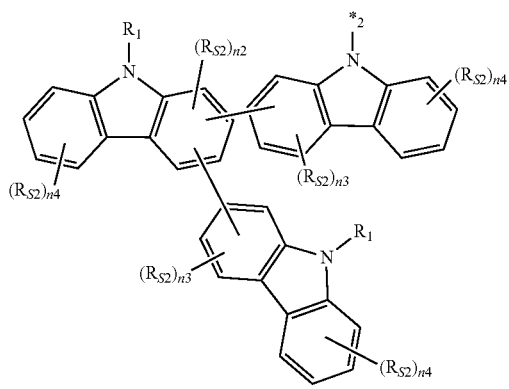
(4a-6)
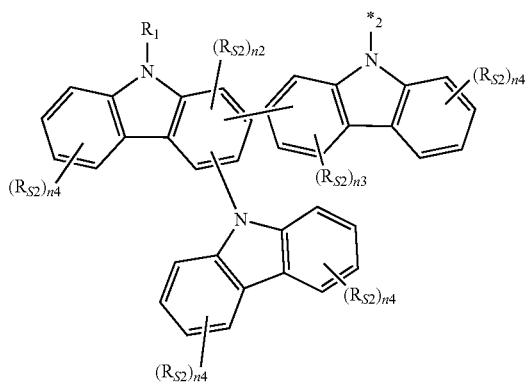
(4a-7)
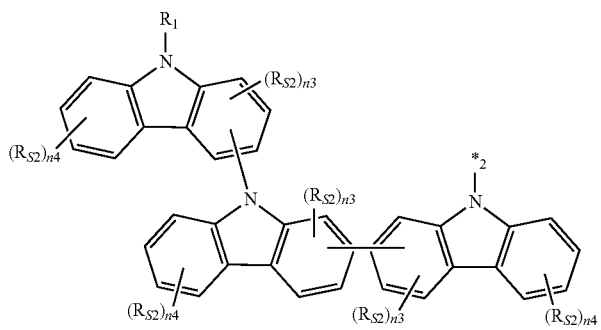
(4a-8)
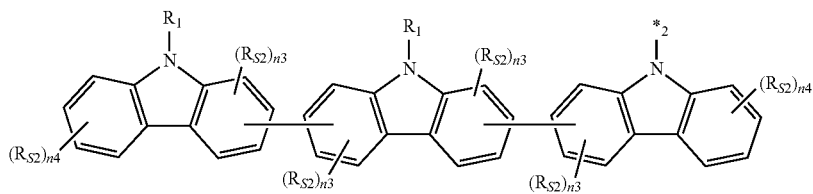
(4a-9)
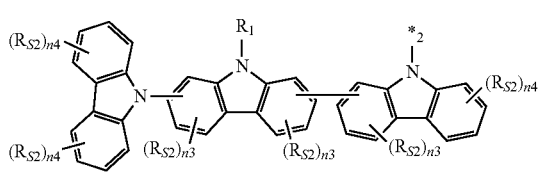

-continued
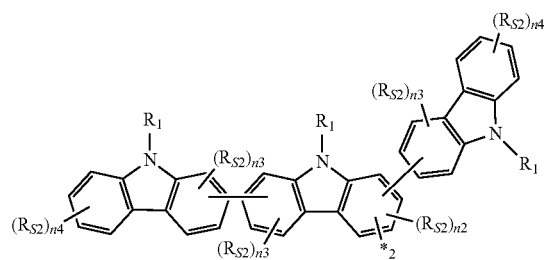
(4c-1)
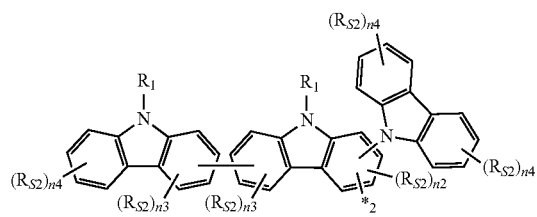
(4c-2)
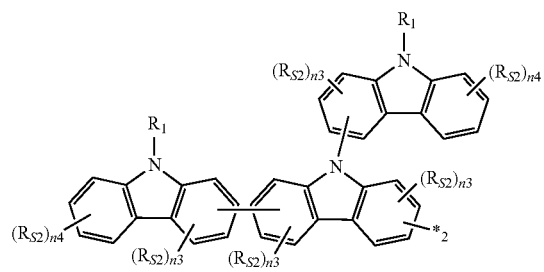
(4c-3)
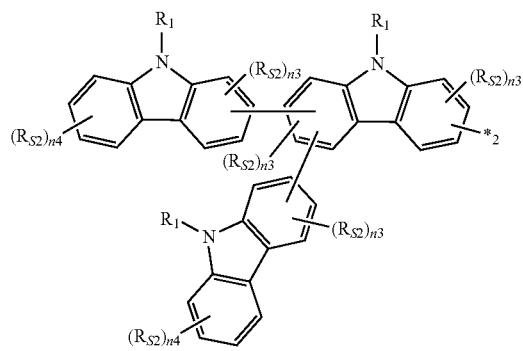
(4c-4)
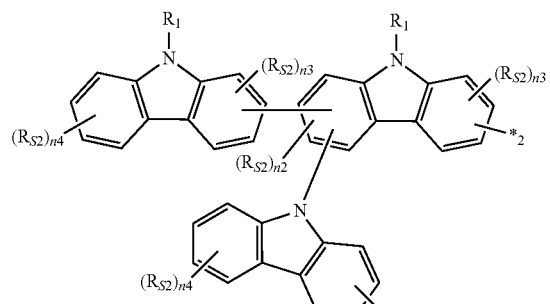
(4c-5)
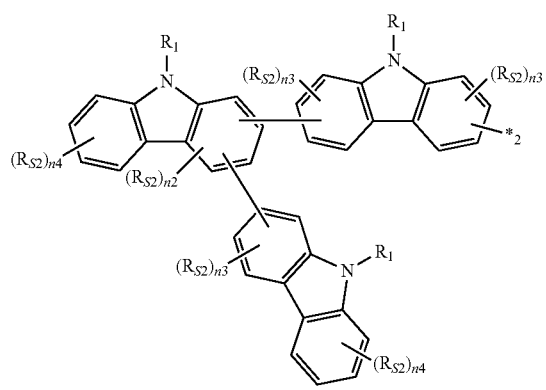
(4c-6)
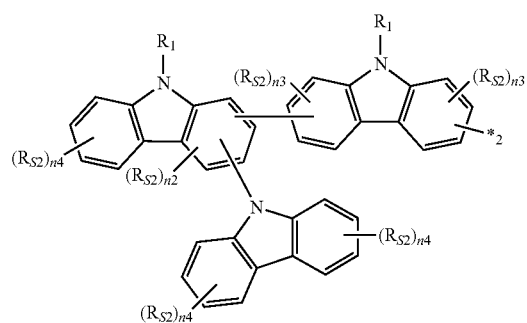
(4c-7)

-continued
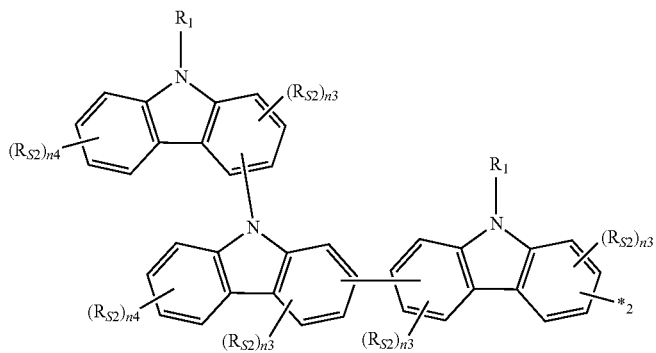
(4c-8)
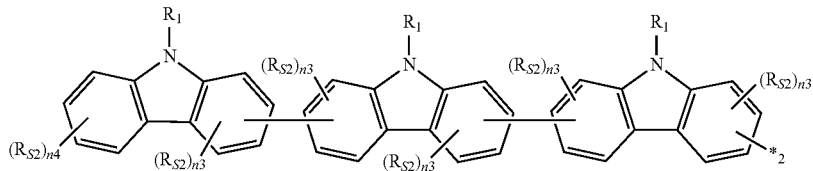
(4c-9)
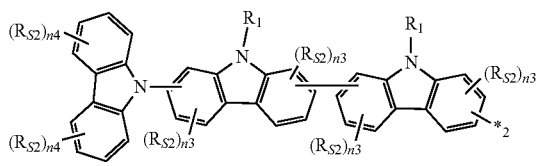
(4c-10)
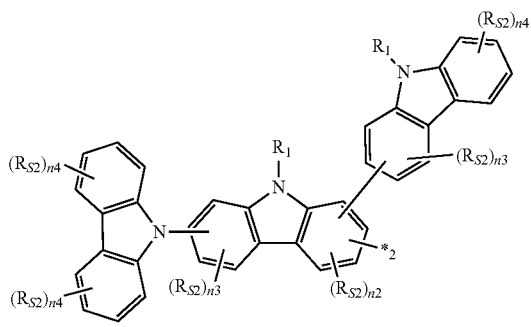
(4d-1)
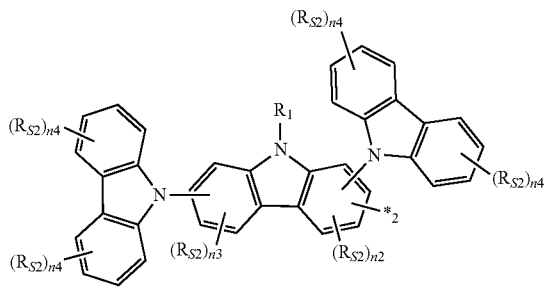
(4d-2)
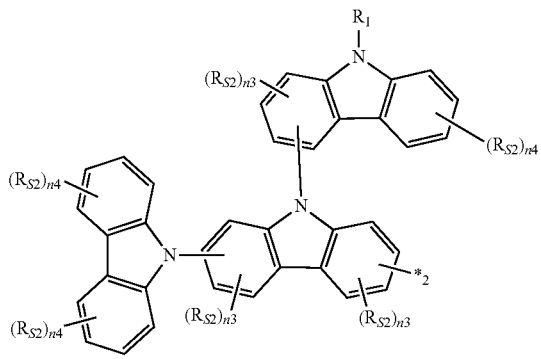
(4d-3)

-continued
(4d-4)
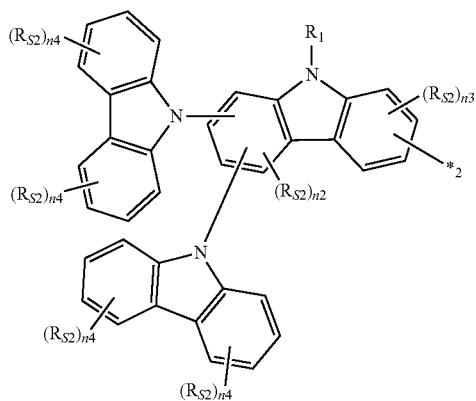
(4d-5)
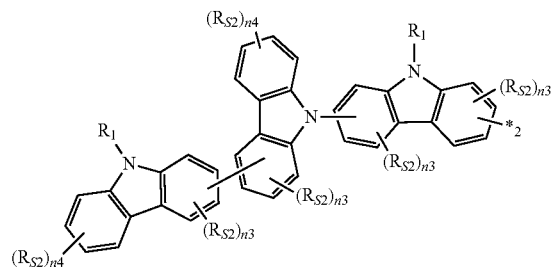
(4d-6)
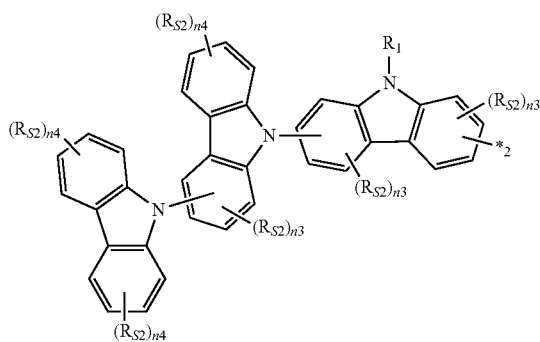
(4e-1)
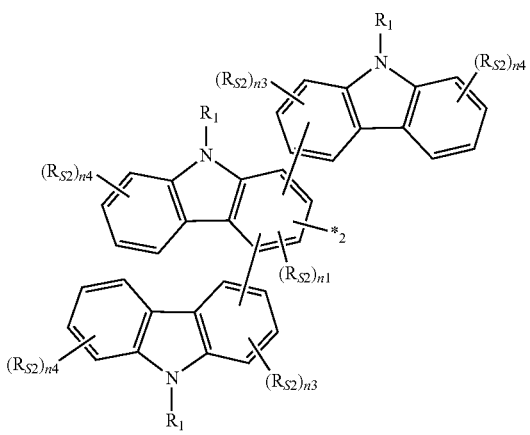
(4e-2)
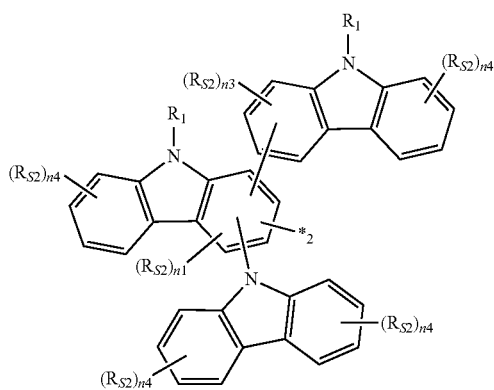
(4e-3)
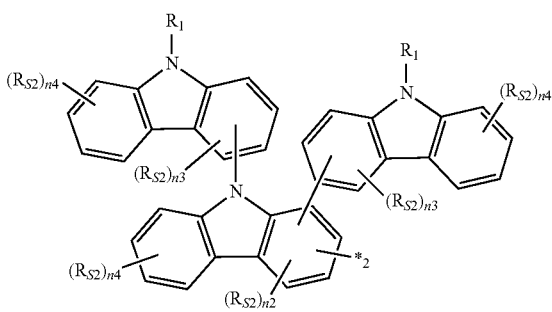

-continued
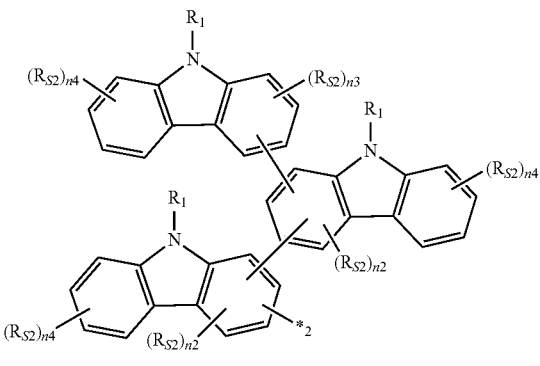
(4e-4)
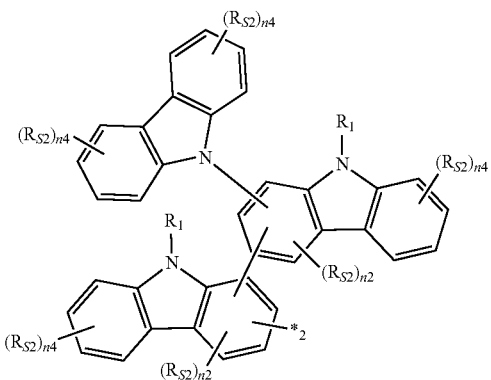
(4e-5)
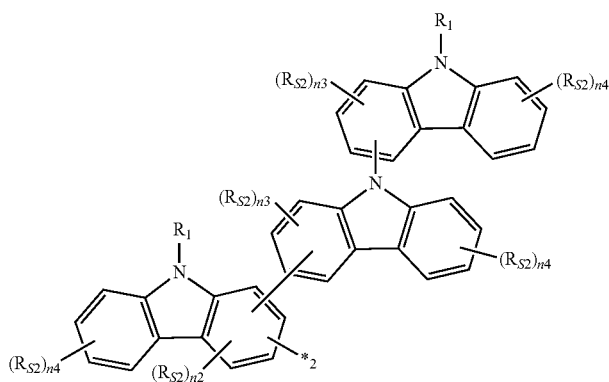
(4e-6)
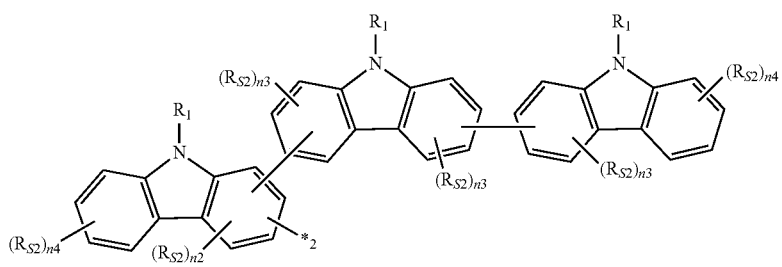
(4e-7)
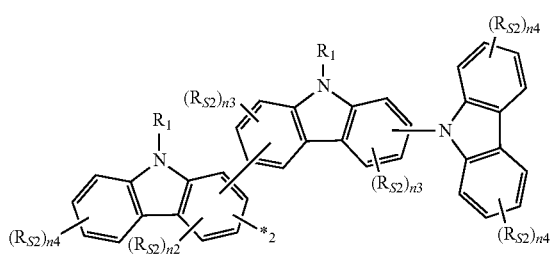
(4e-8)
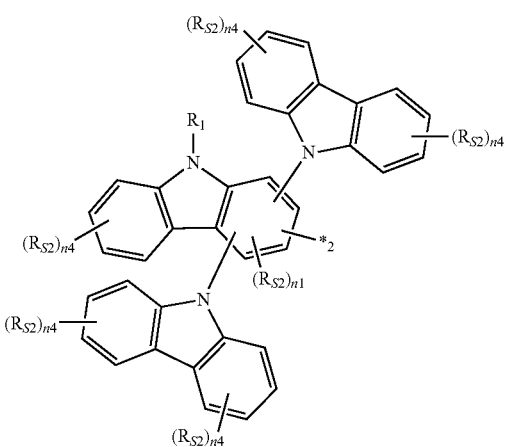
(4f-1)

-continued
(4f-2)
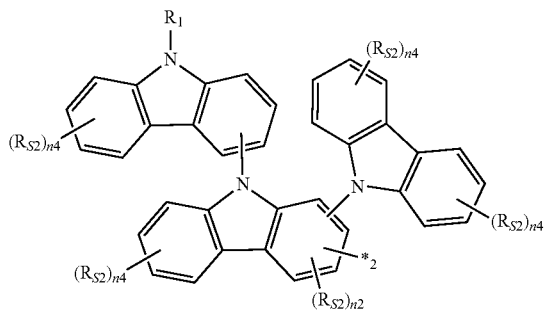
(4f-3)
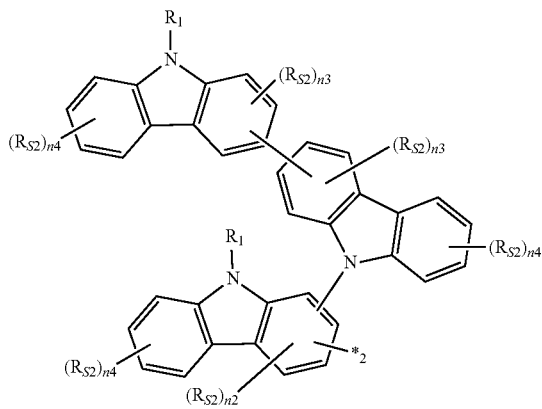
(4f-4)
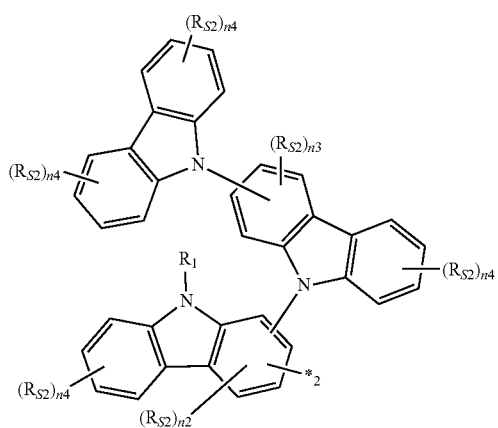
(4g-1)
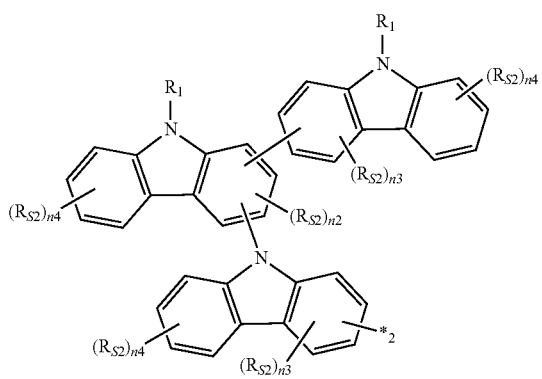
(4g-2)
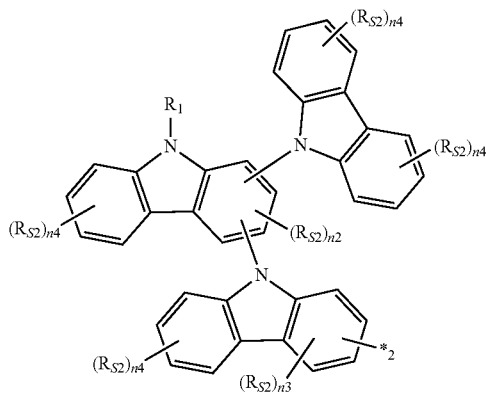
(4g-3)
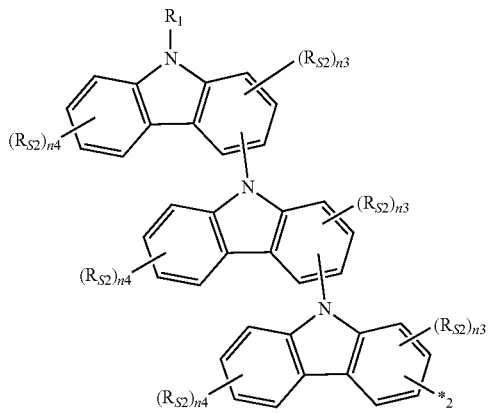
(4g-4)
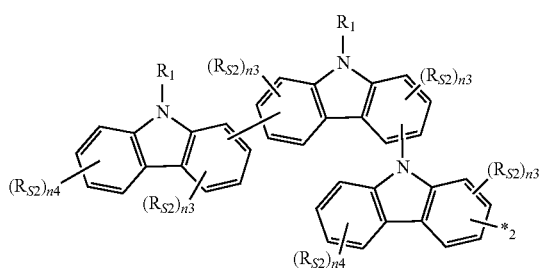
(4g-5)
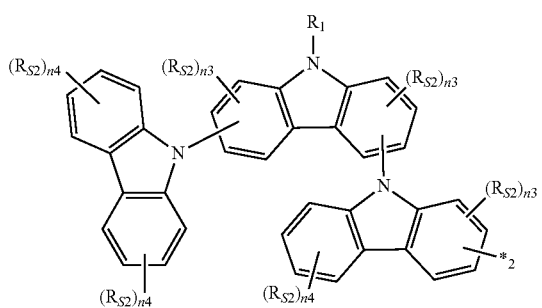

wherein, in Formulae (4a-1) to (4a-9), (4c-1) to (4c-10), (4d-1) to (4d-6), (4e-1) to (4e-8), (4f-1) to (4f-4), and (4g-1) to (4g-5),

*2 indicates a binding site to $L_3$ in Formula (2-1) or (2-2), each occurrence of $R_1$ is independently a monovalent alkyl group having 1 to 20 carbon atoms and being unsubstituted or substituted with a substituent other than a carbazole group, a monovalent aromatic hydrocarbon group having 6 to 30 carbon atoms and being unsubstituted or substituted with a substituent other than a carbazole group, or a monovalent aromatic heterocyclic group (other than a carbazole group) having 5 to 30 ring-forming atoms and being unsubstituted or substituted with a substituent other than a carbazole group, each occurrence of $R_{S2}$ is independently a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group (other than a carbazole group) having 5 to 30 ring-forming atoms, each occurrence of n4 is independently 0, 1, 2, 3, or 4, each occurrence of n3 is independently 0, 1, 2, or 3, each occurrence of n2 is independently 0, 1, or 2, and each occurrence of n1 is independently 0 or 1.

5. The compound of claim 1, wherein the compound is represented by the following formulae:

1

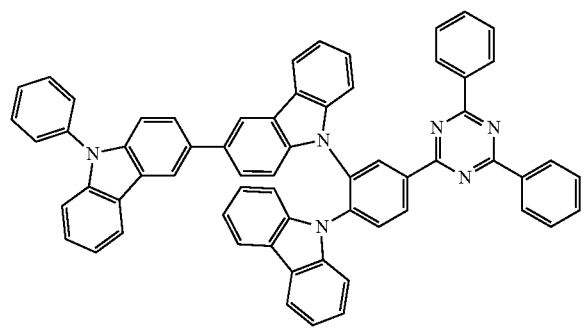

2

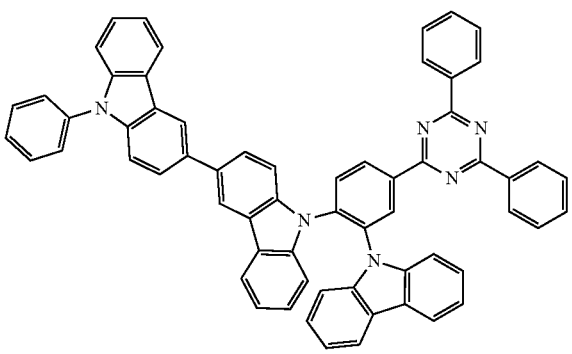

3

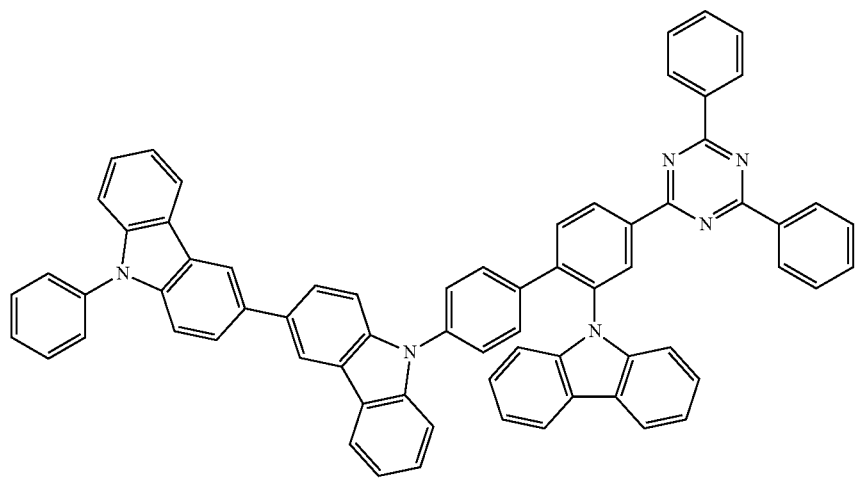

4

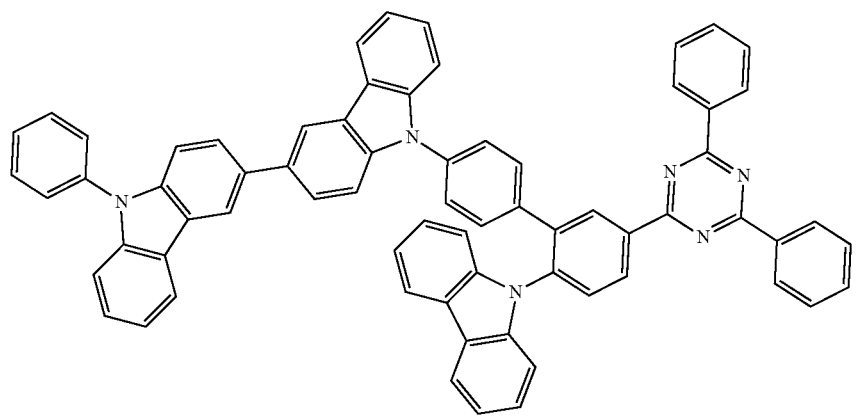

-continued
5
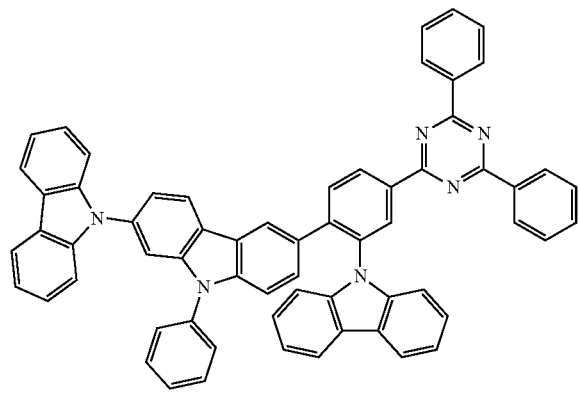
6
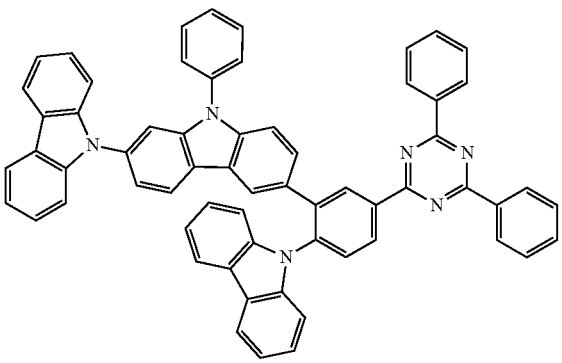
7
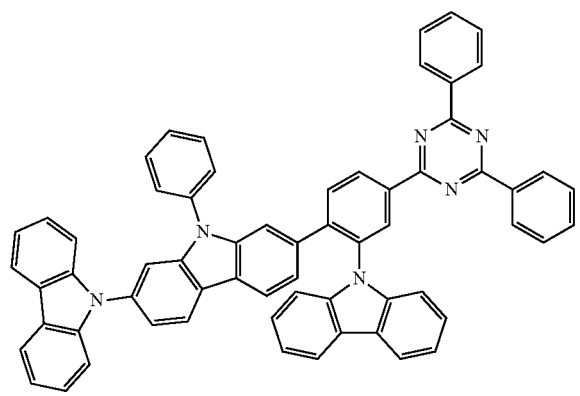
8
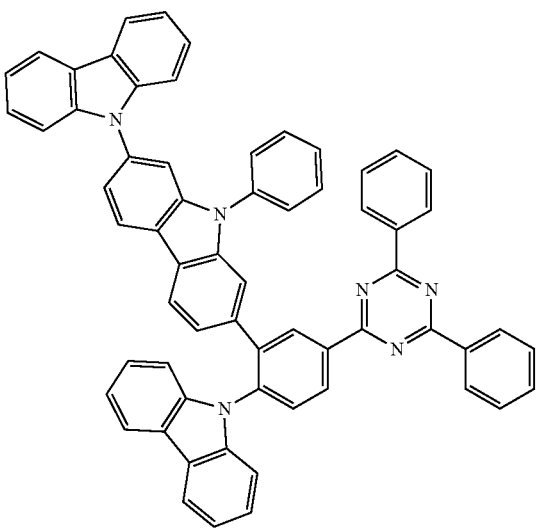
9
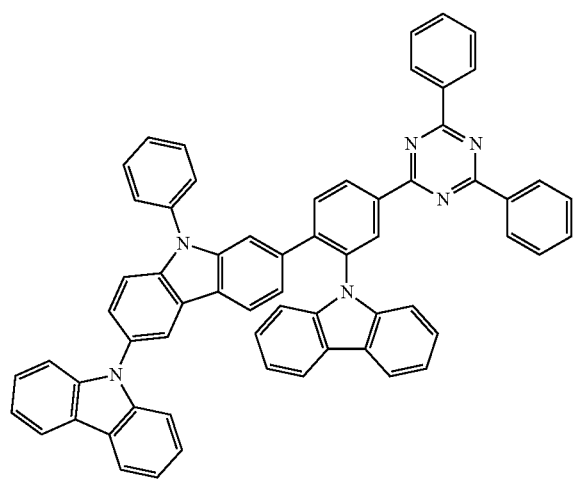
10
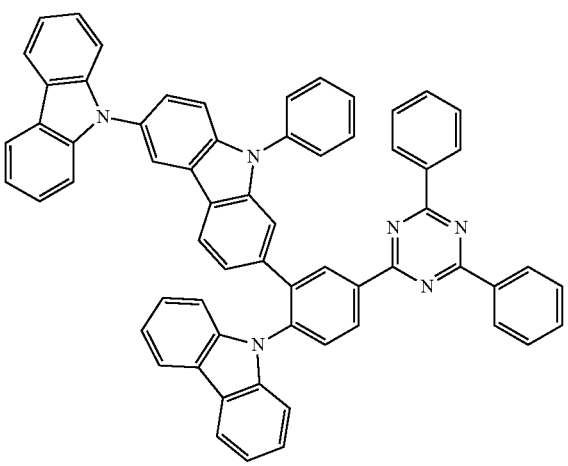

-continued
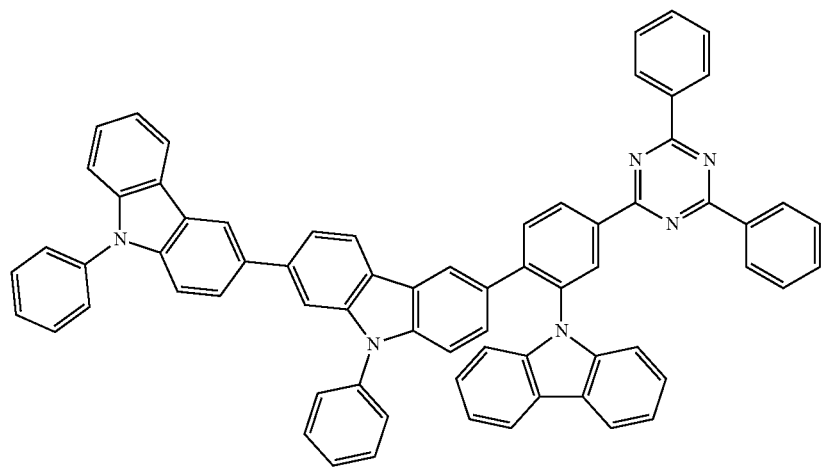
11
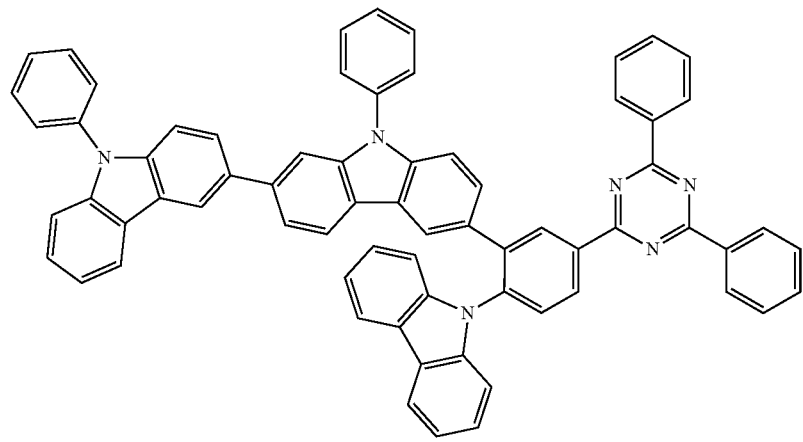
12
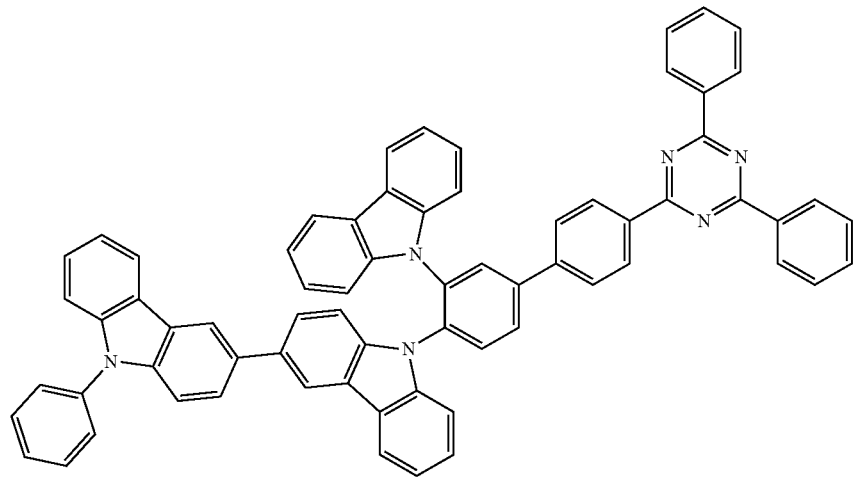
13

14
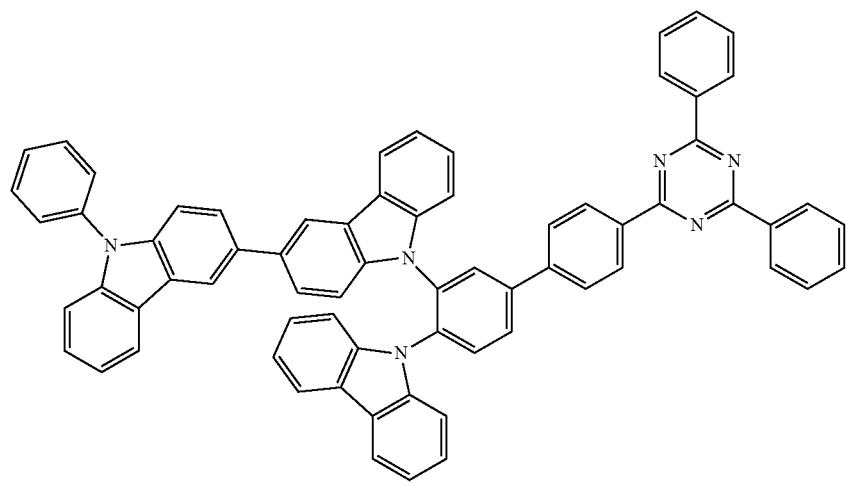
15
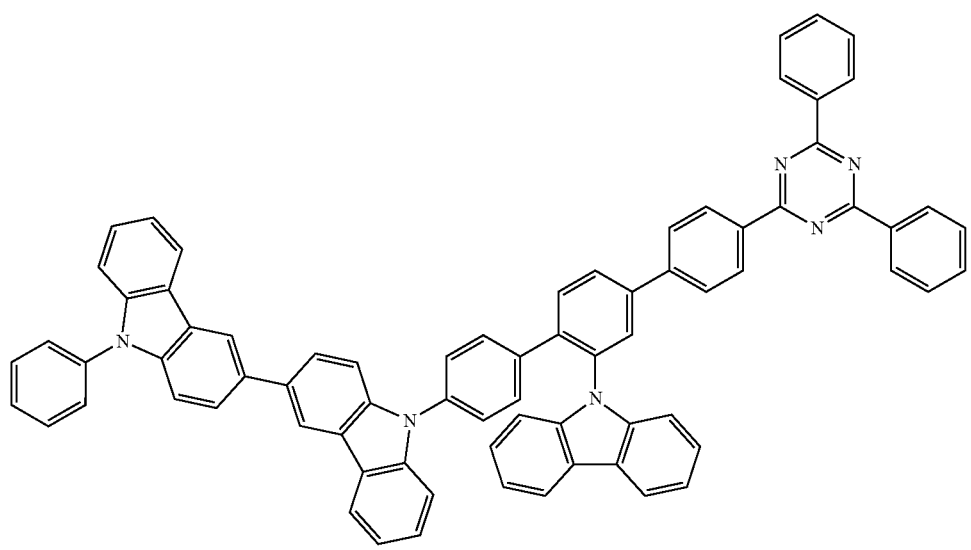
16
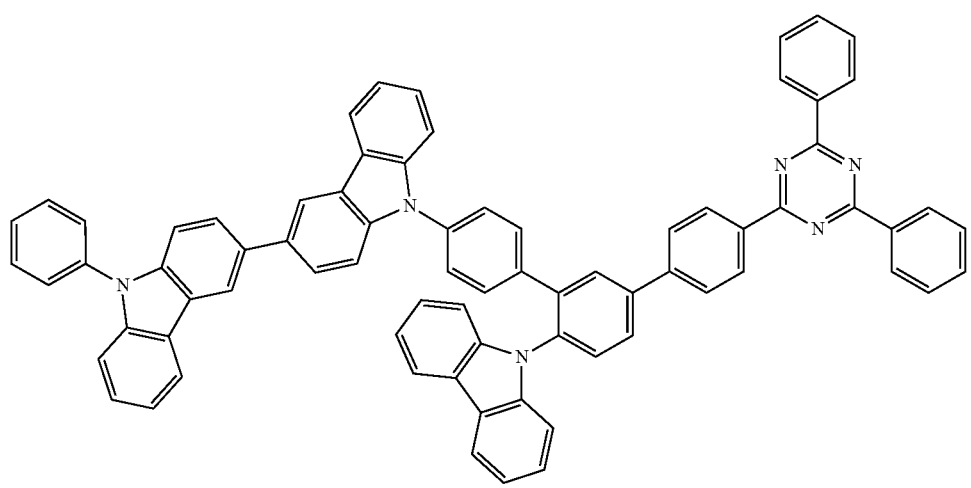

-continued
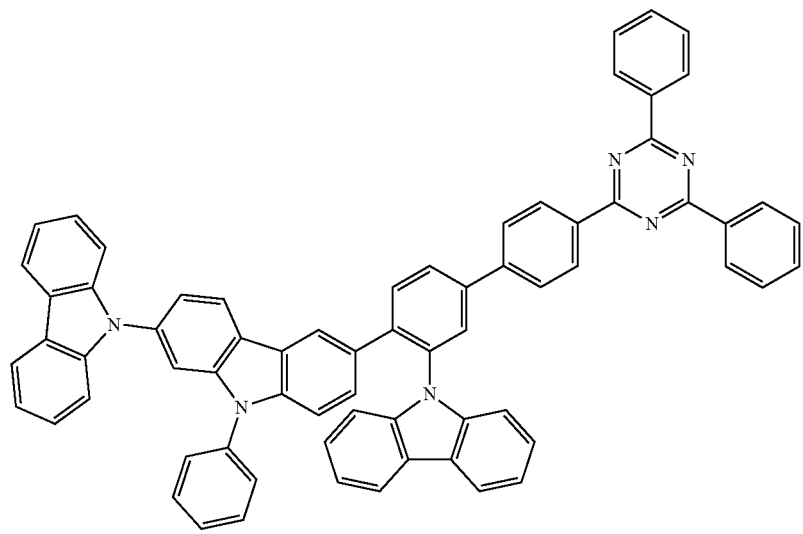
17
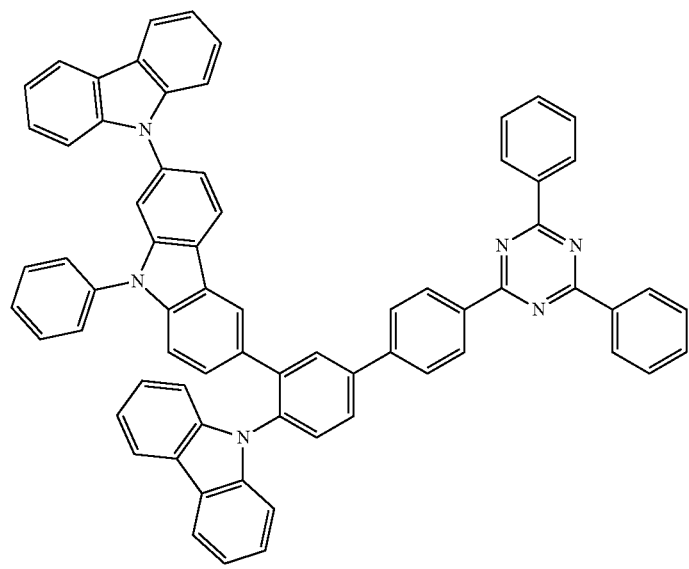
18
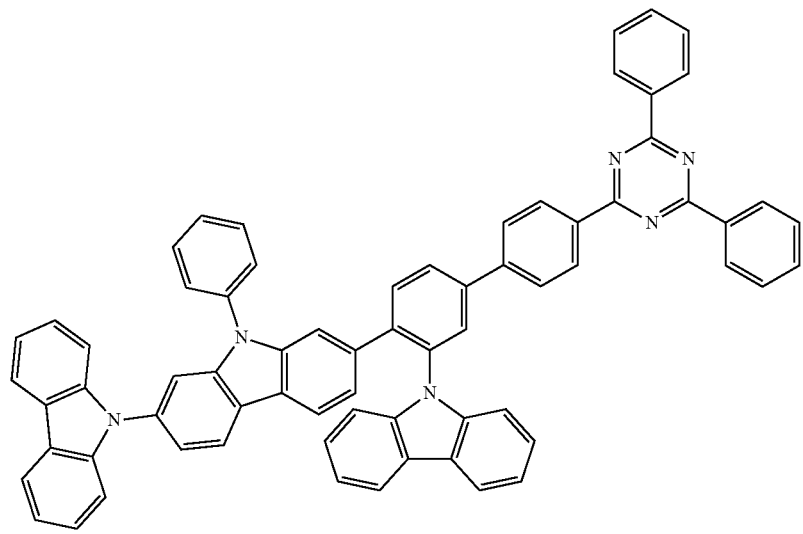
19

20
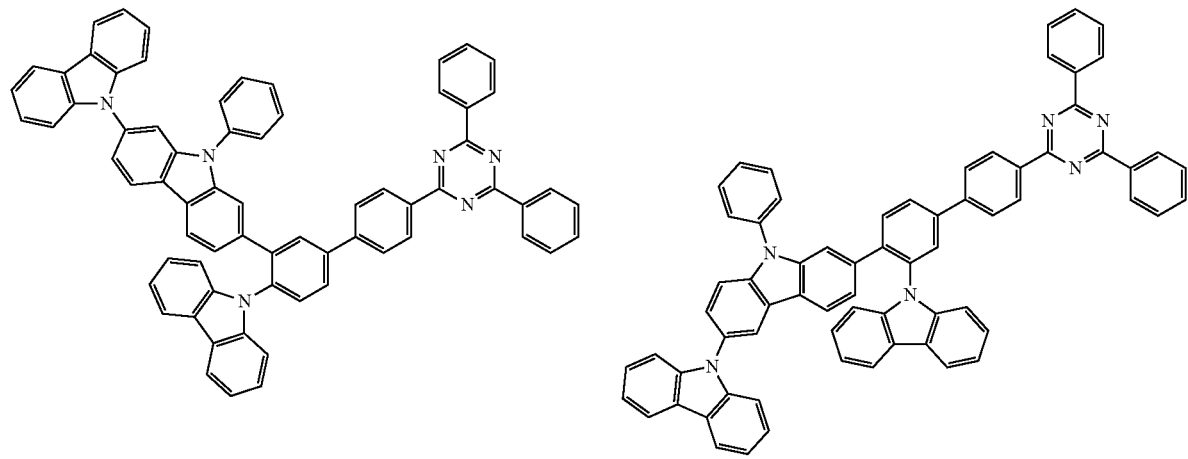
21
22
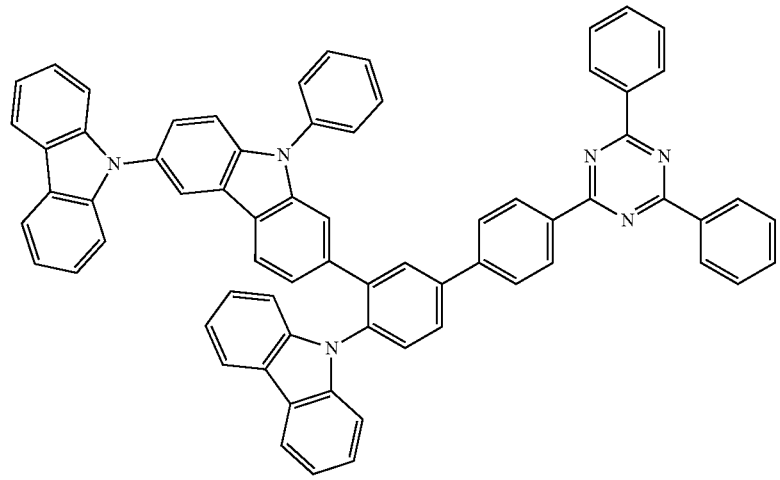
23
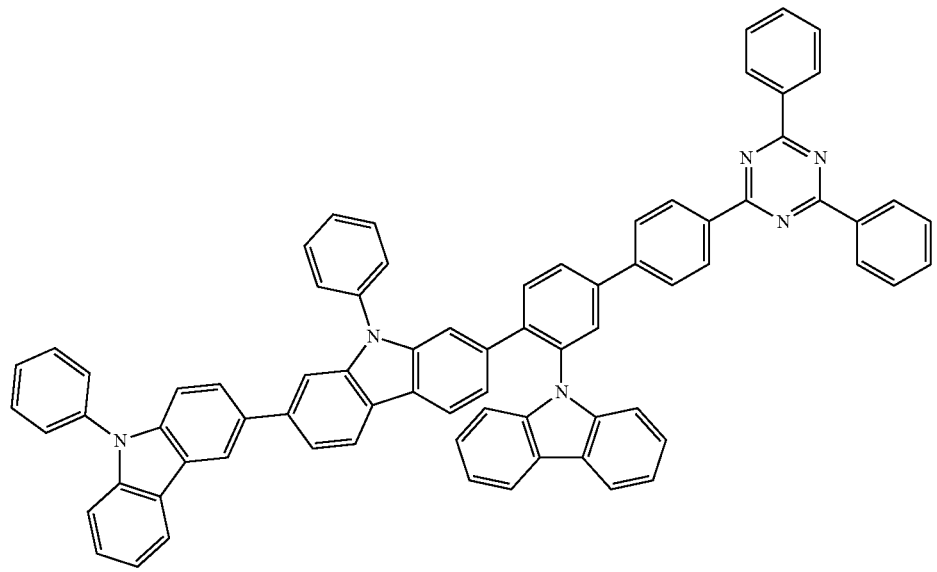

-continued
24
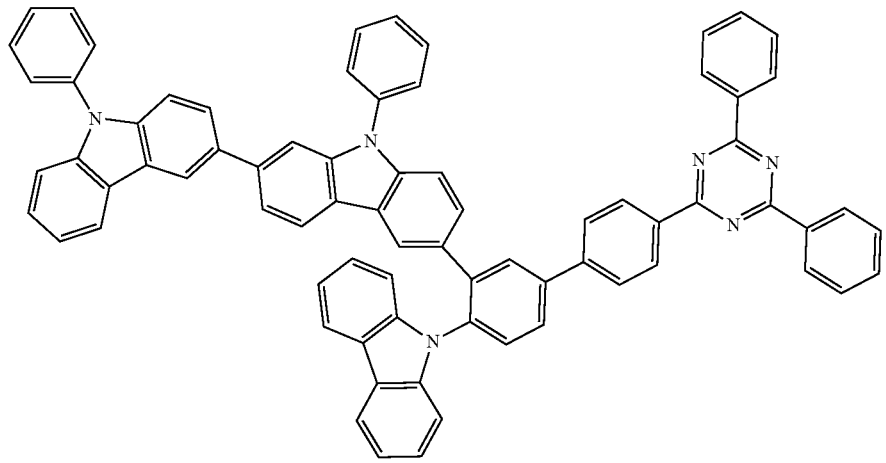
25
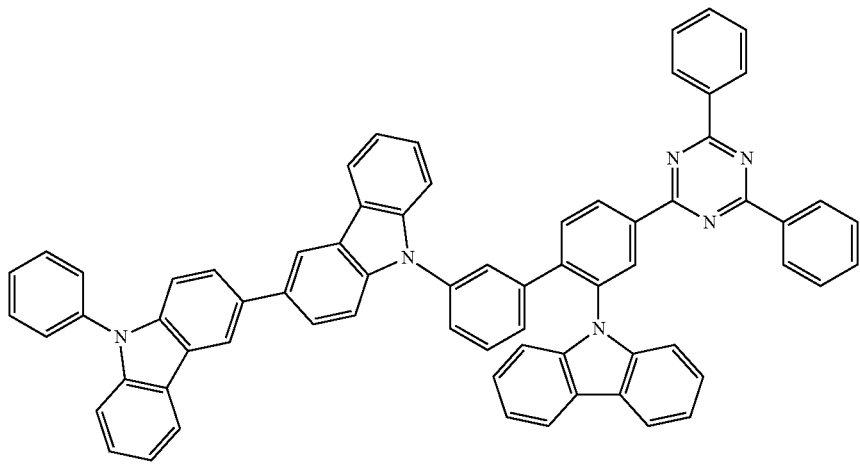
26
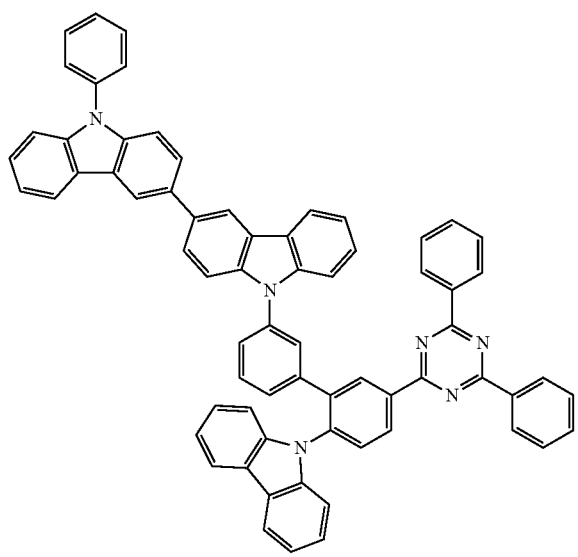
27
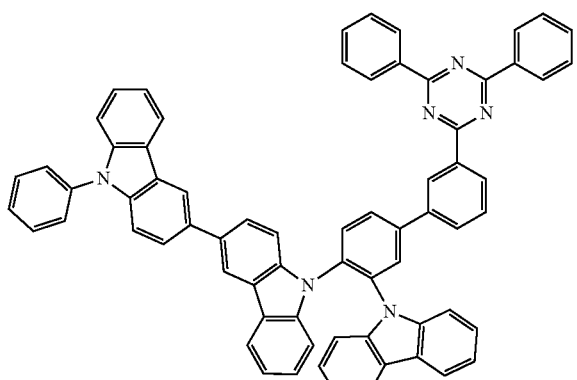

-continued
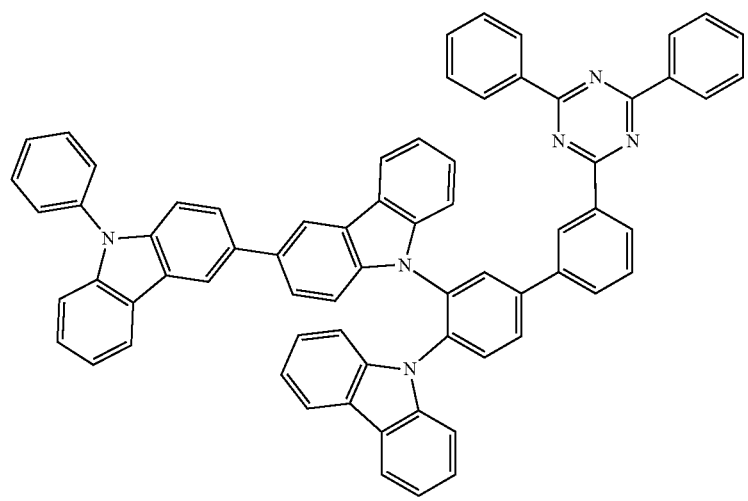
28
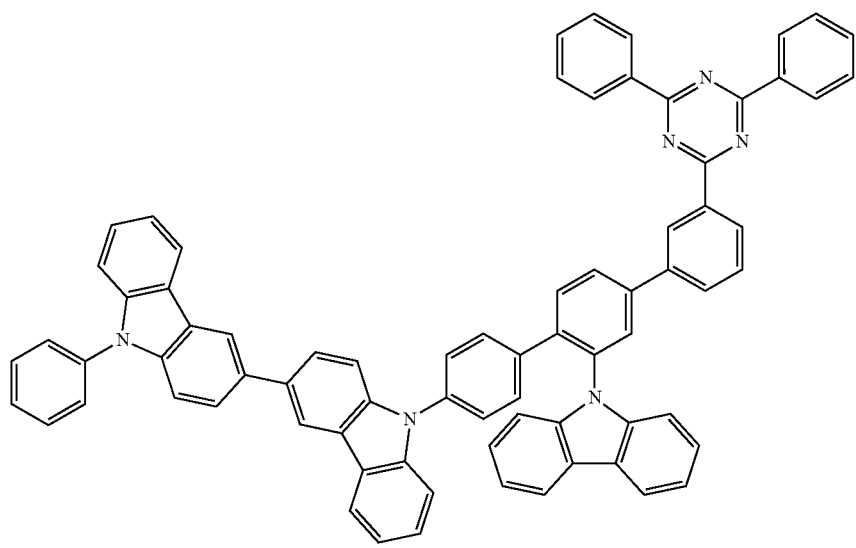
29
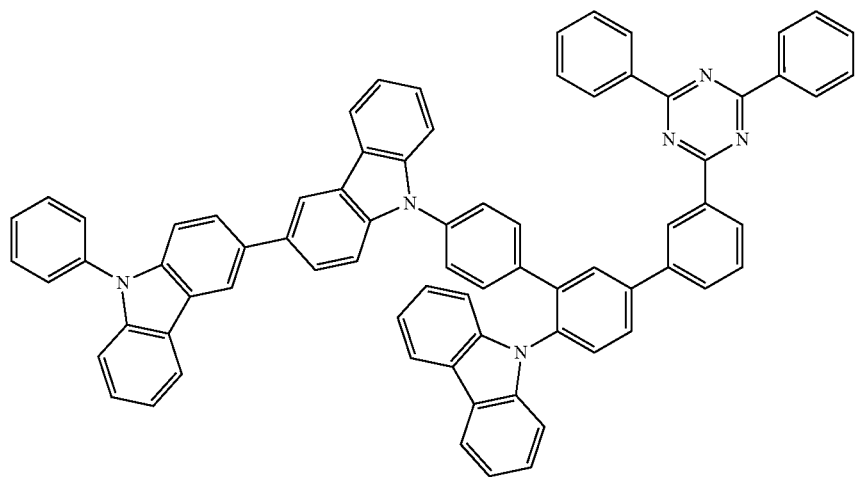
30

-continued
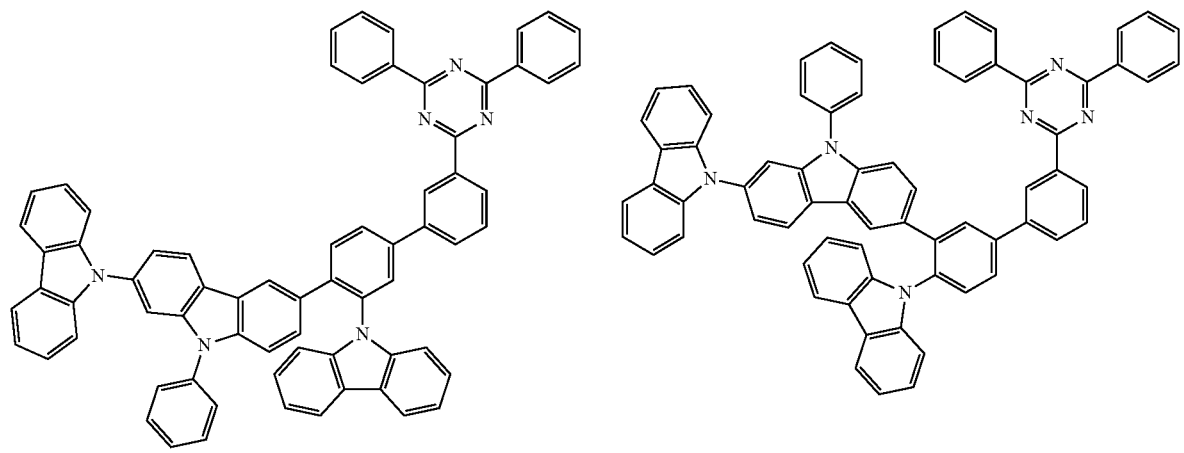
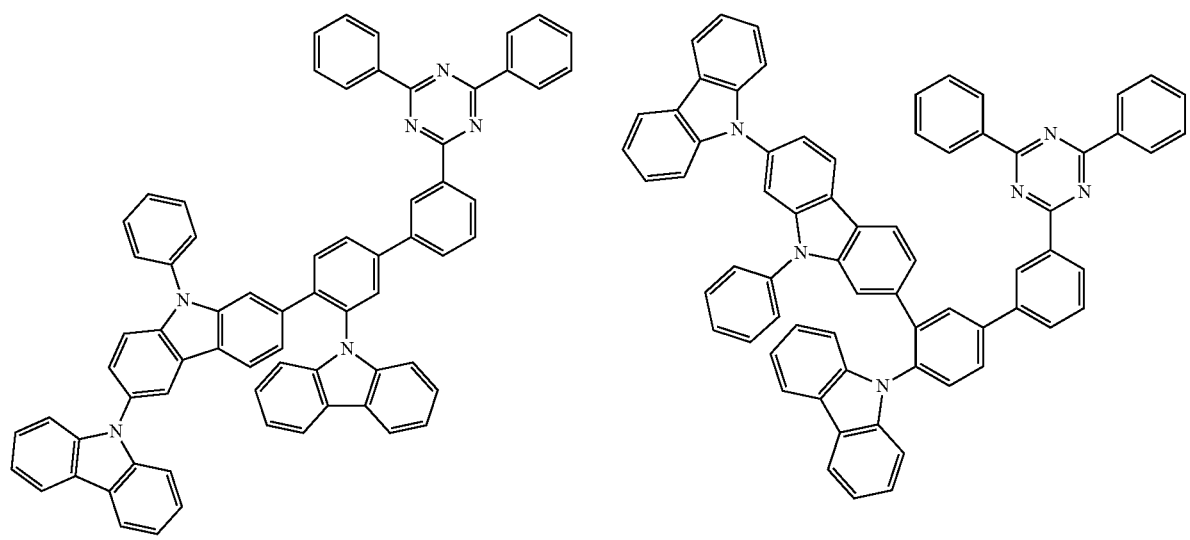
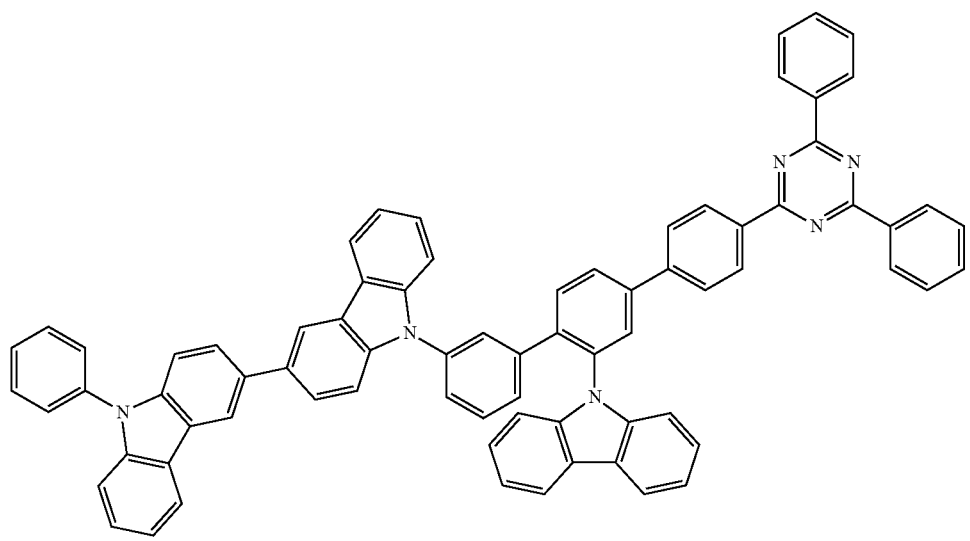

36
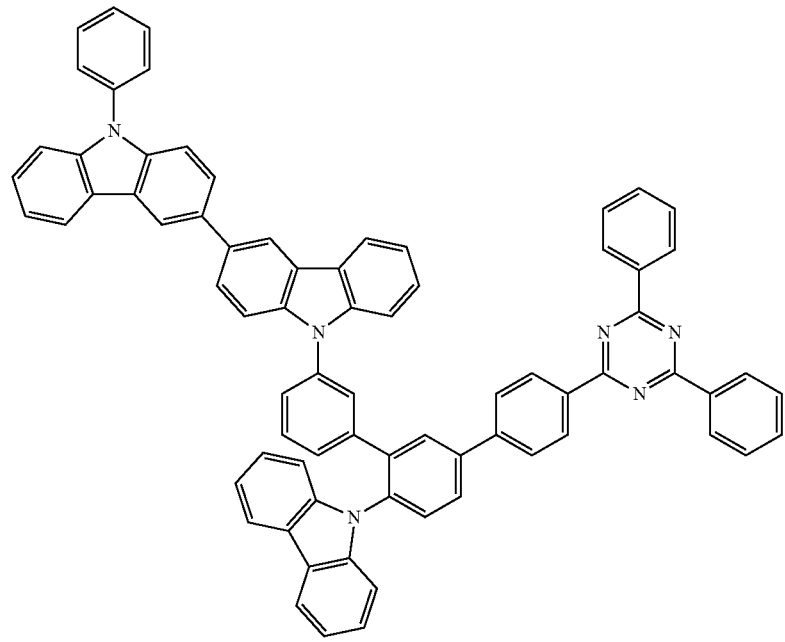
37
38
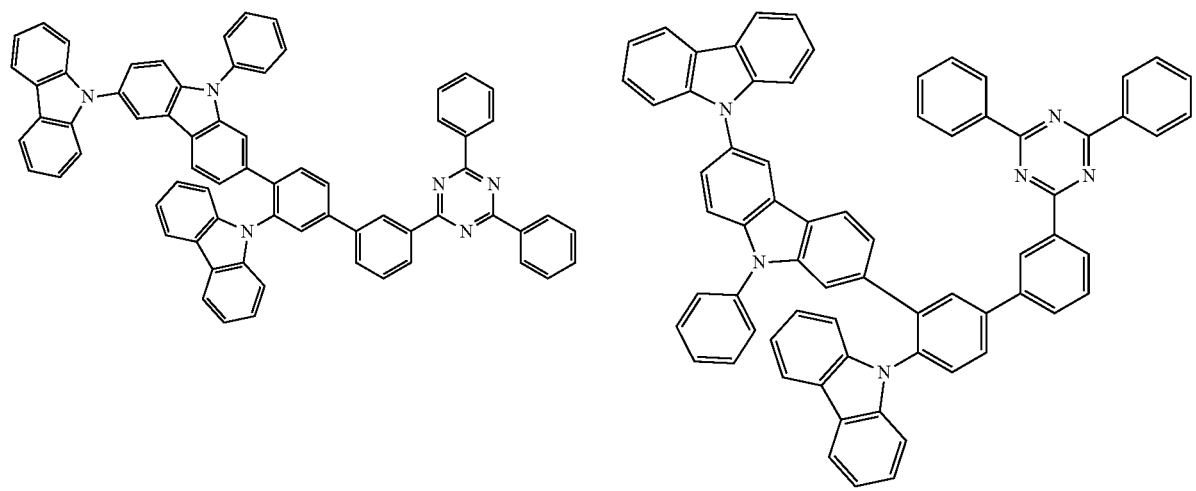
39
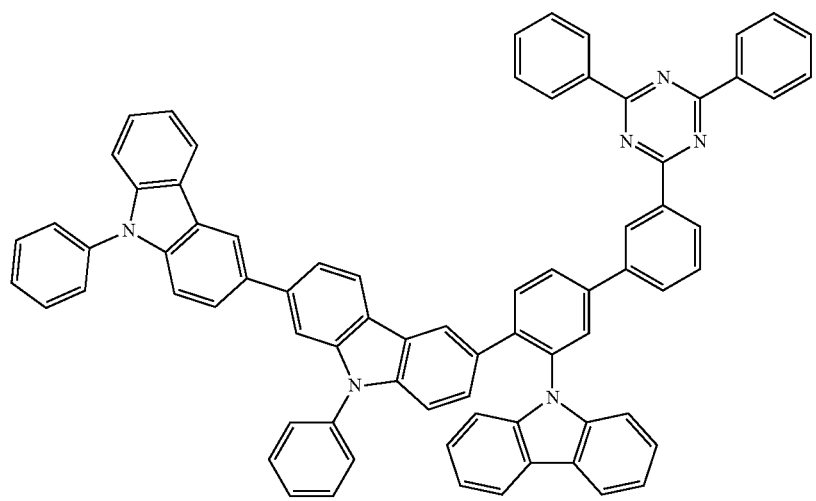

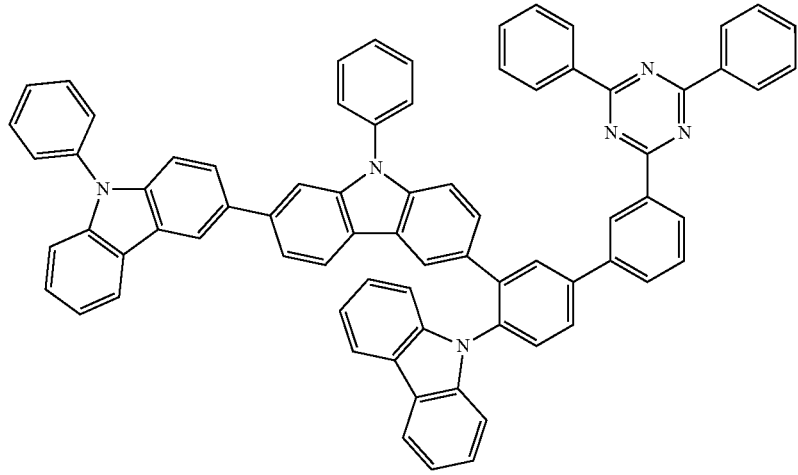
40
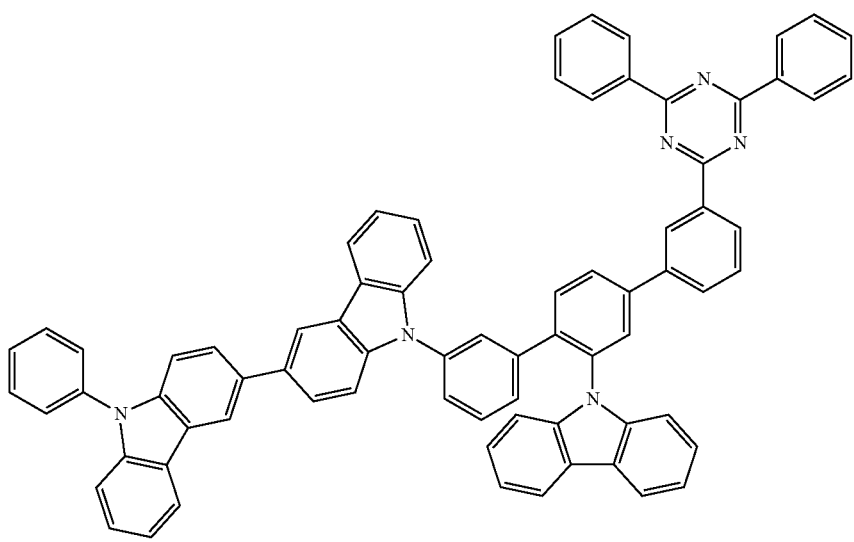
41
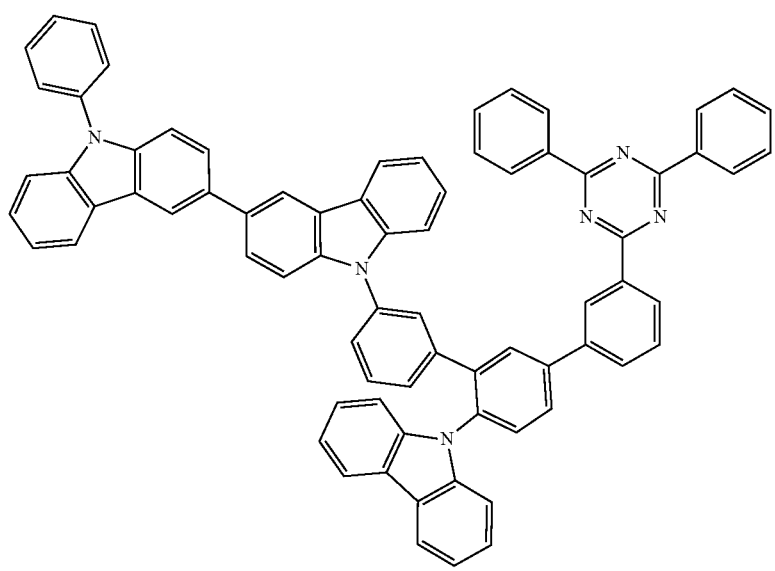
42

46
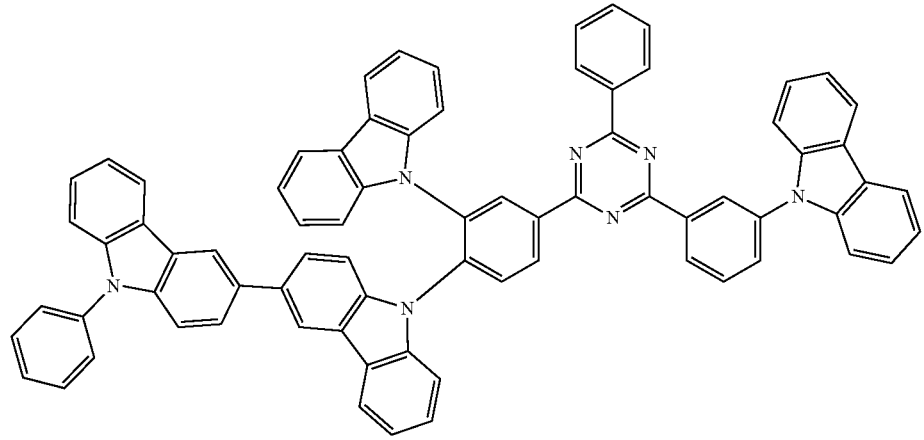
47
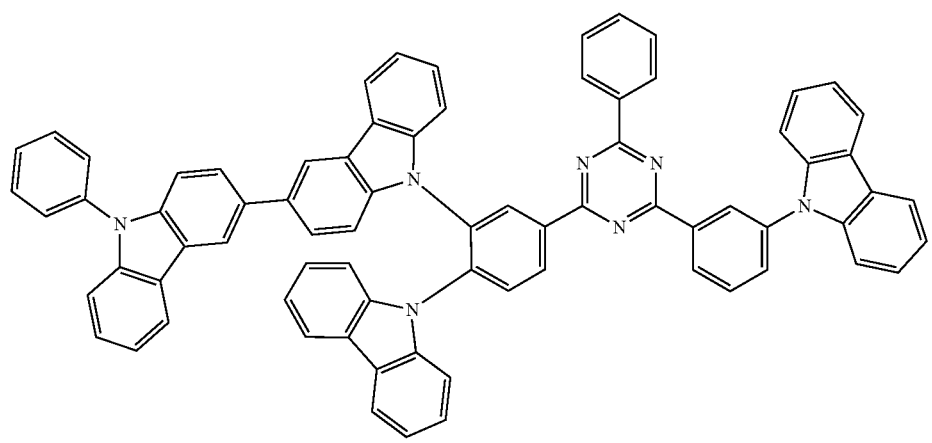
48
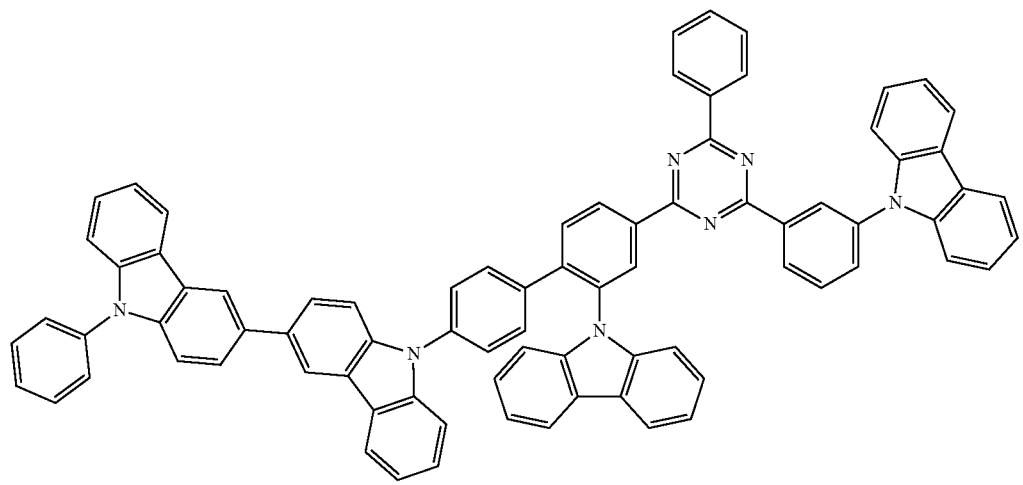

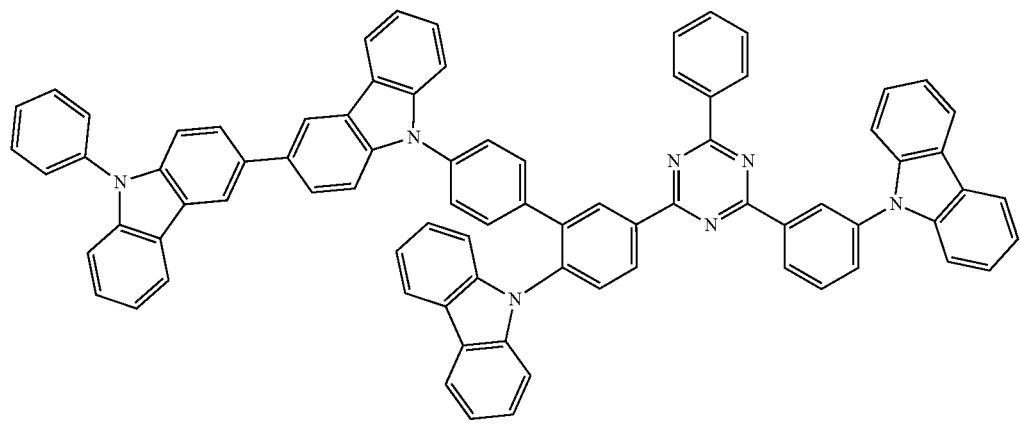
49
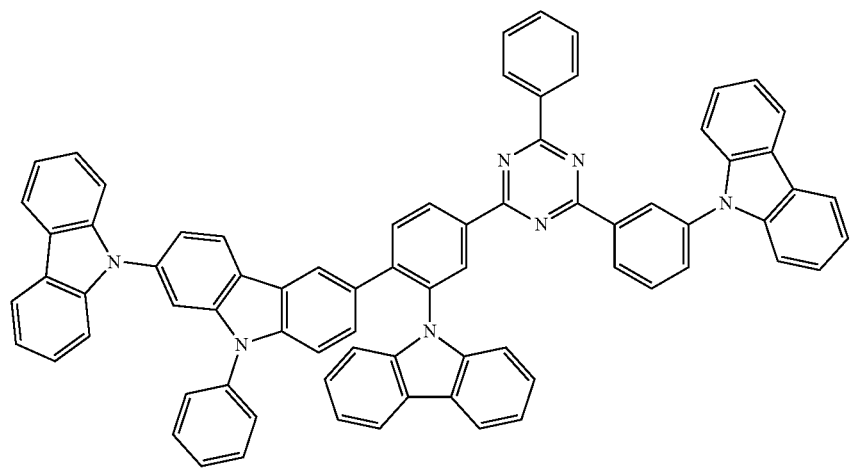
50
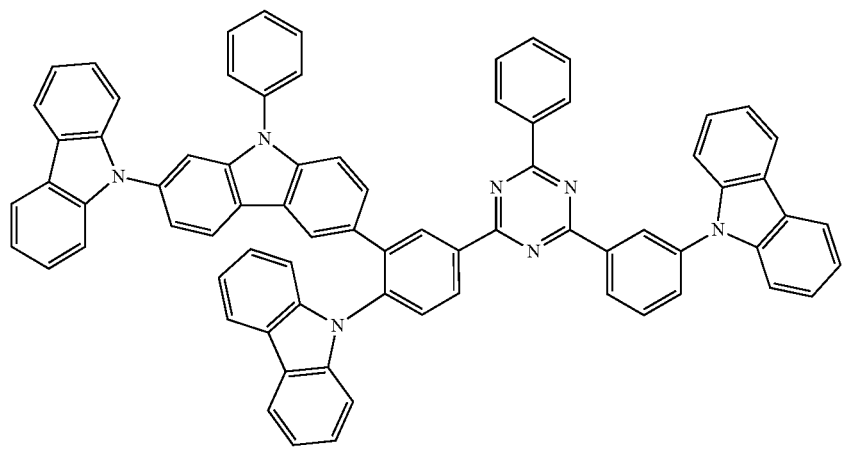
51

52
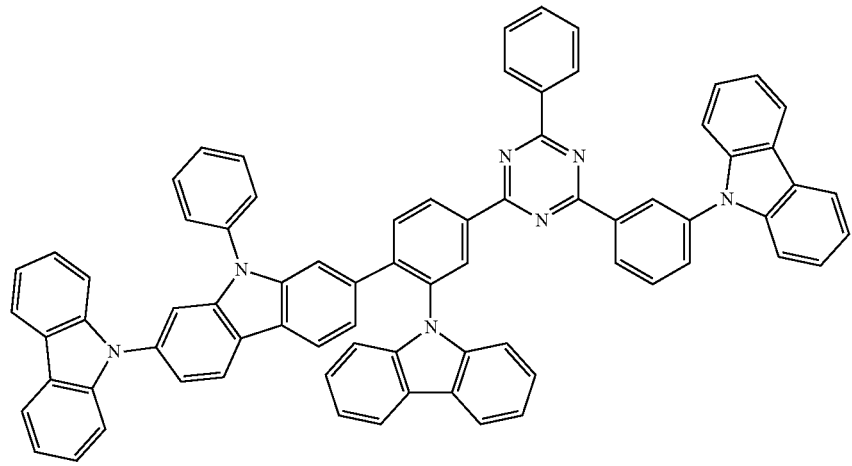
53
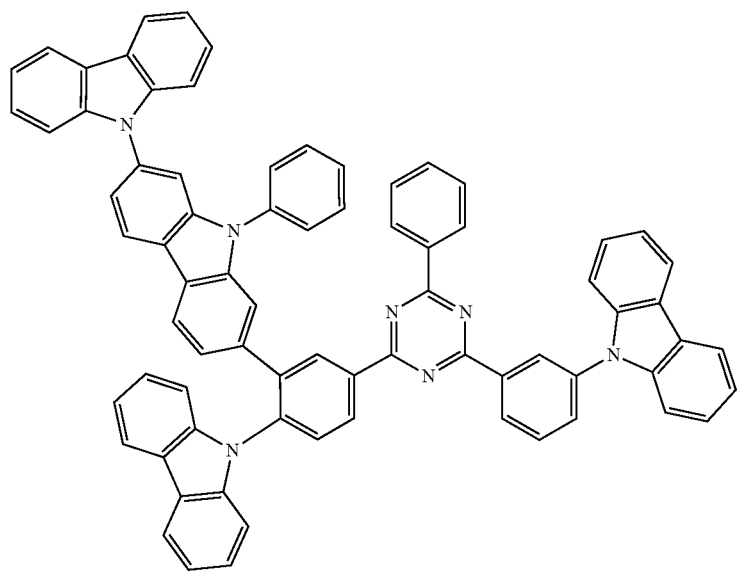
54
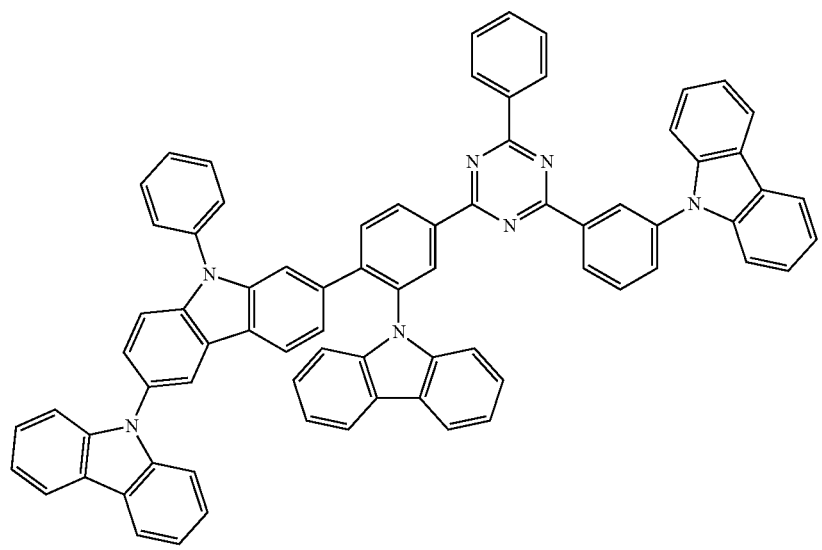

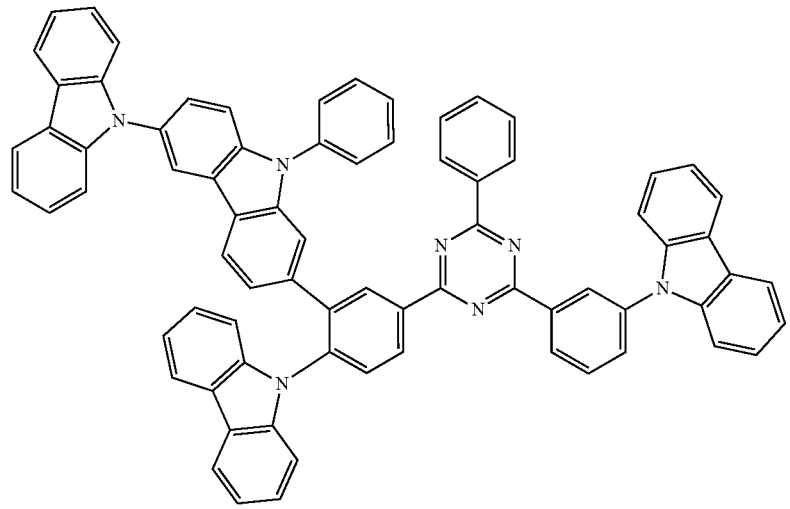
55
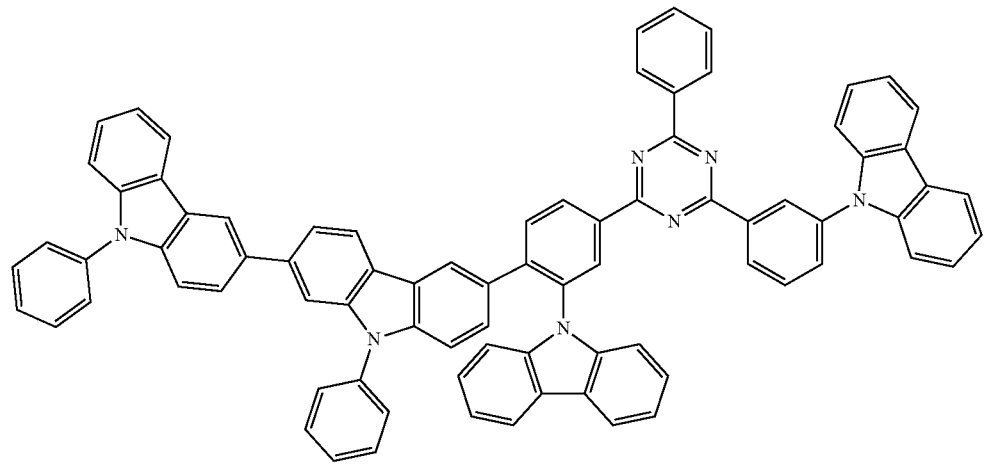
56
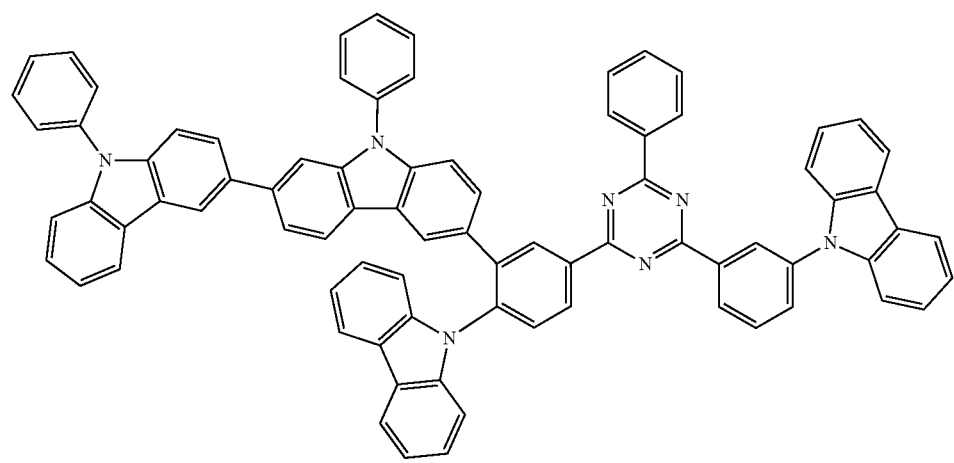
57

58
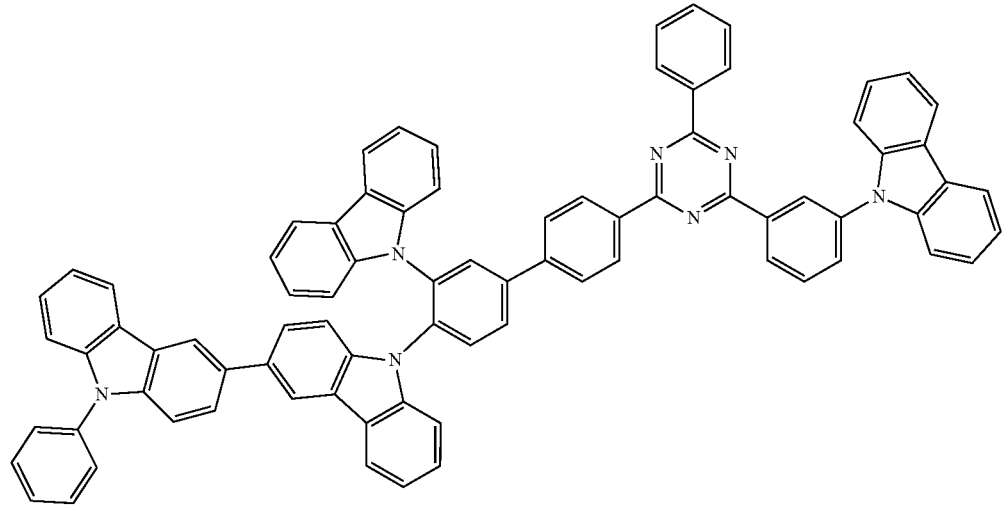
59
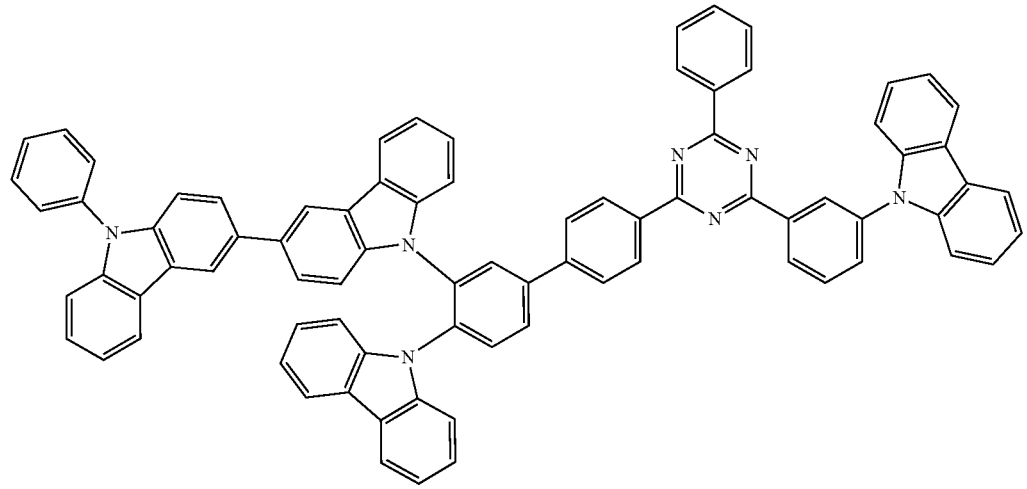
60
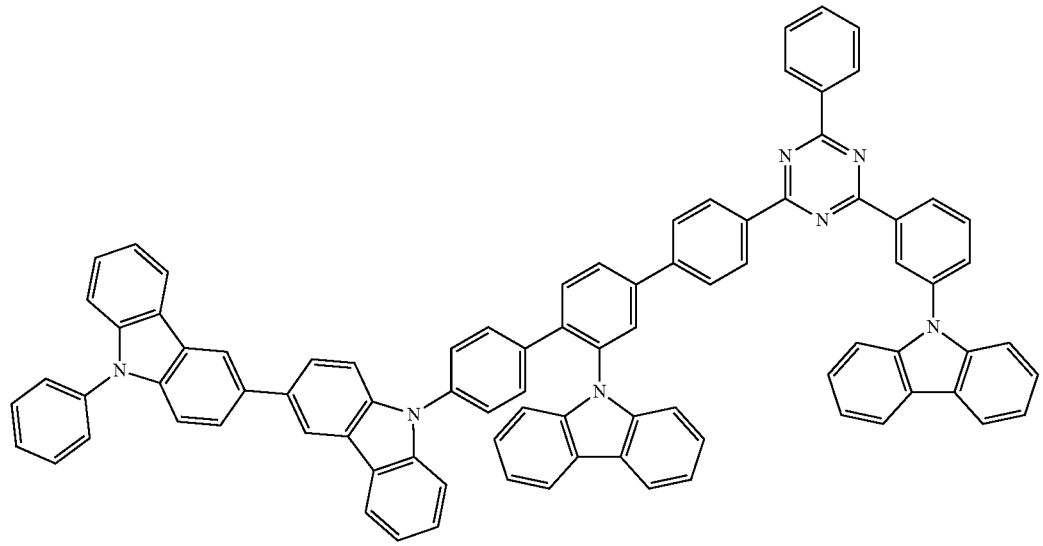

61
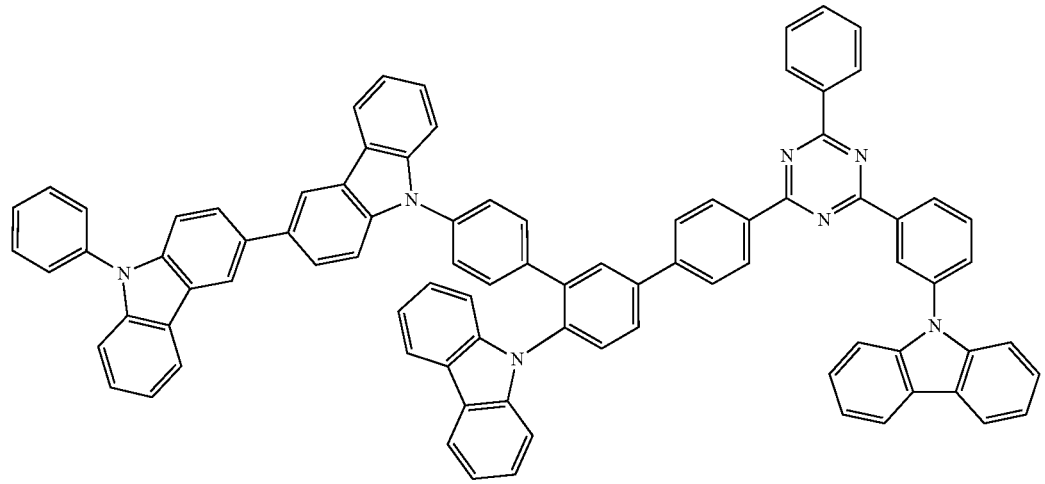
62
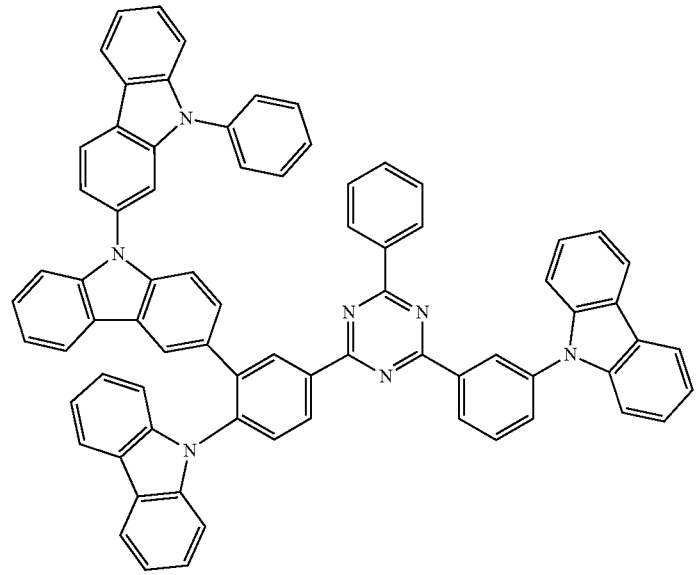
63
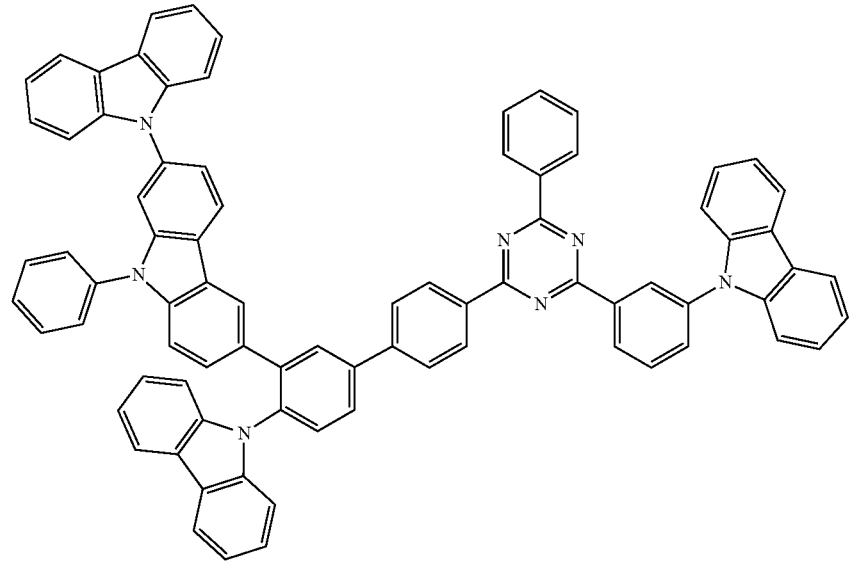

64
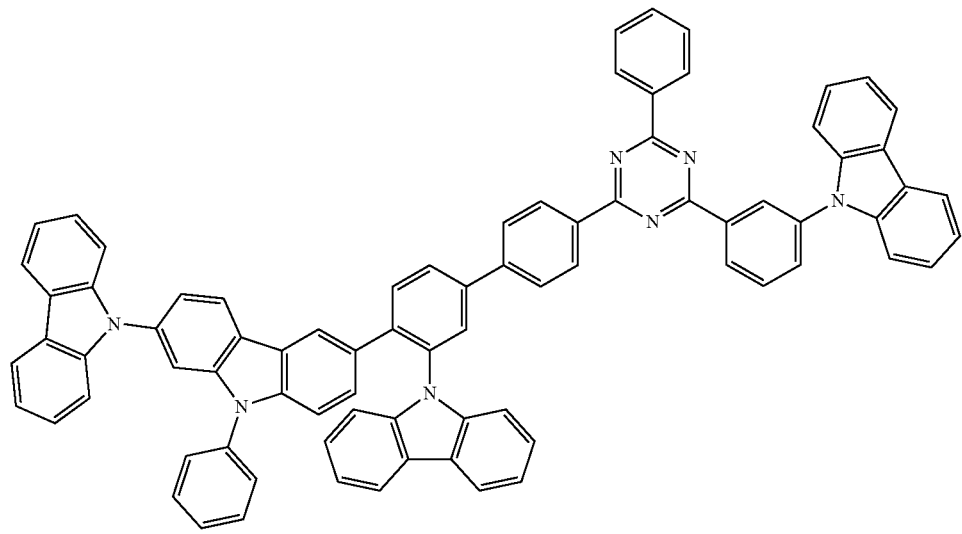
65
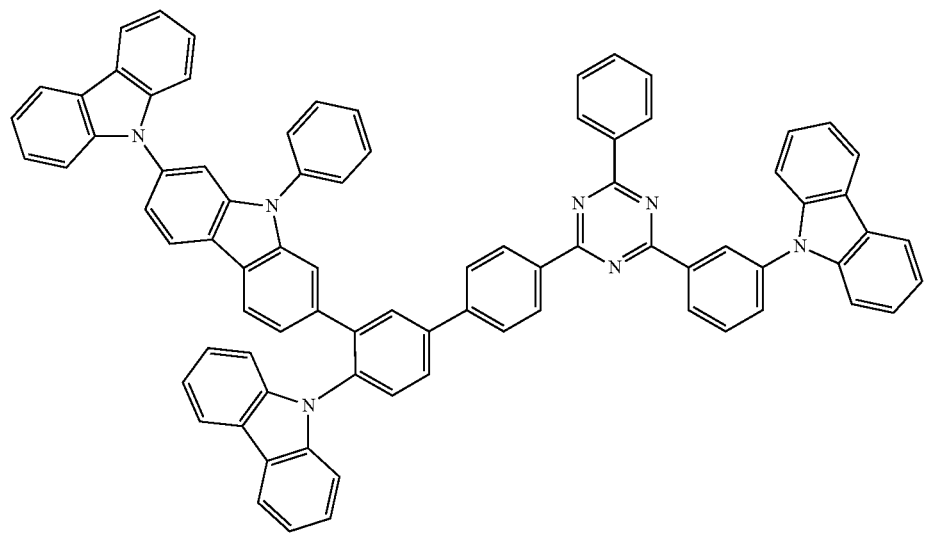
68
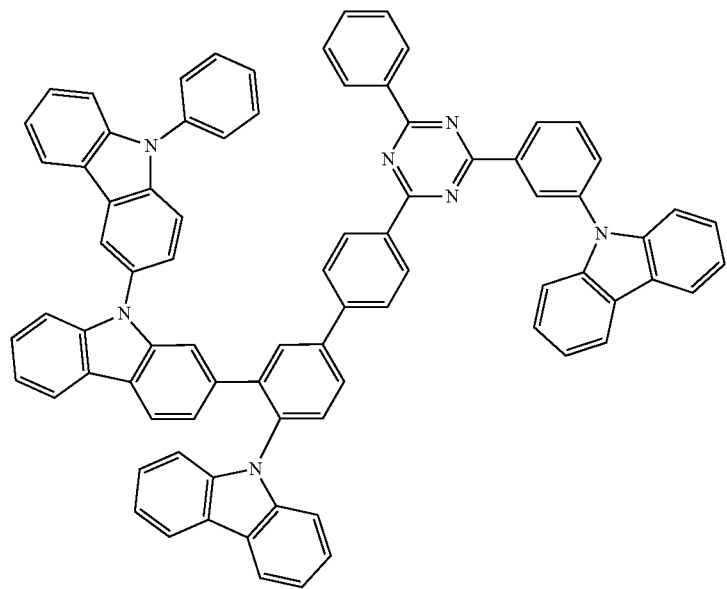

-continued
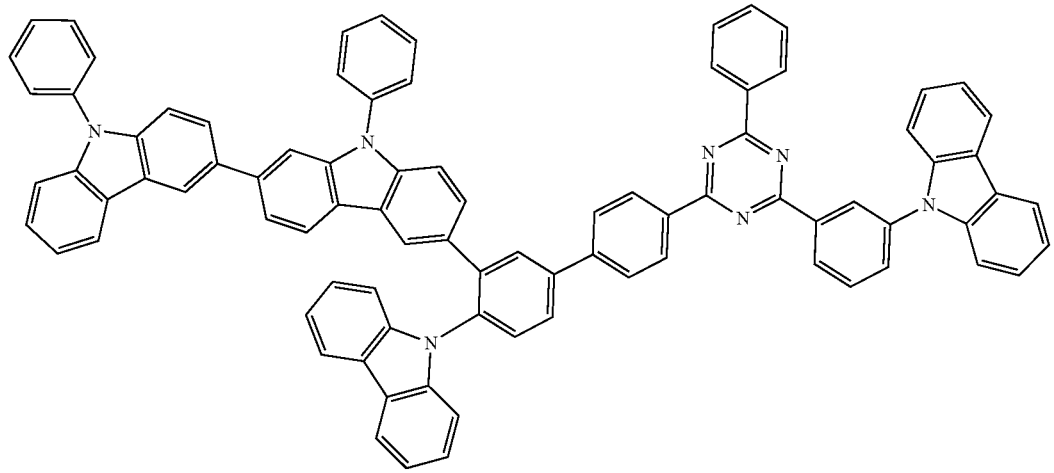
69
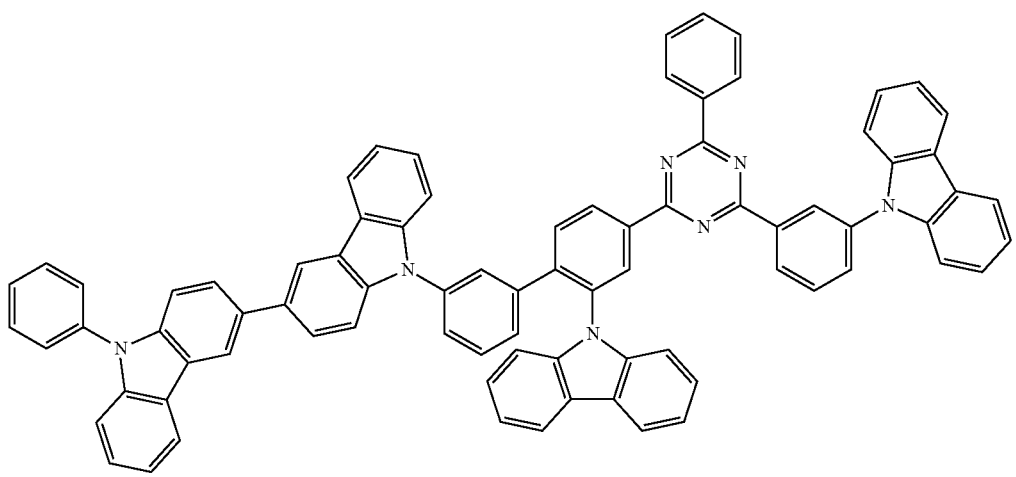
70
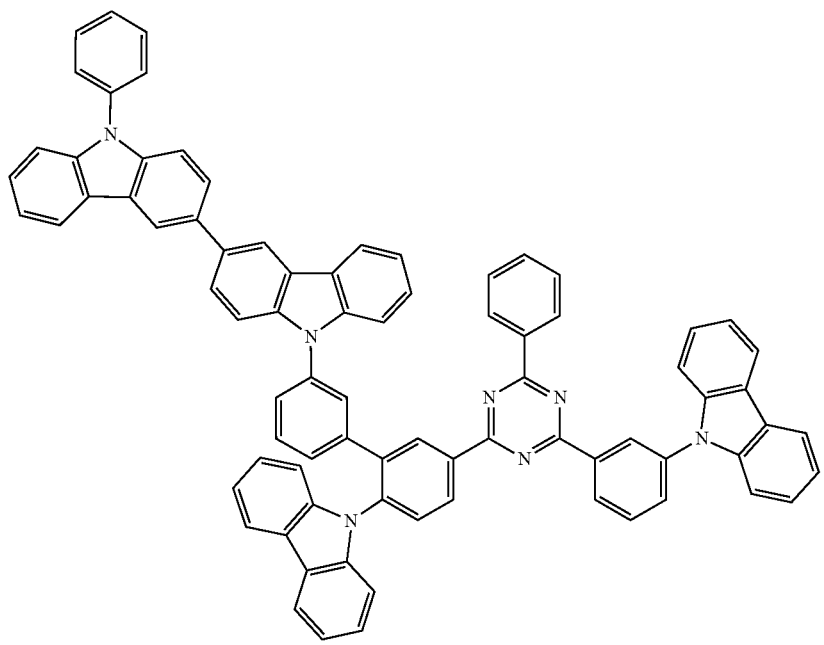
71

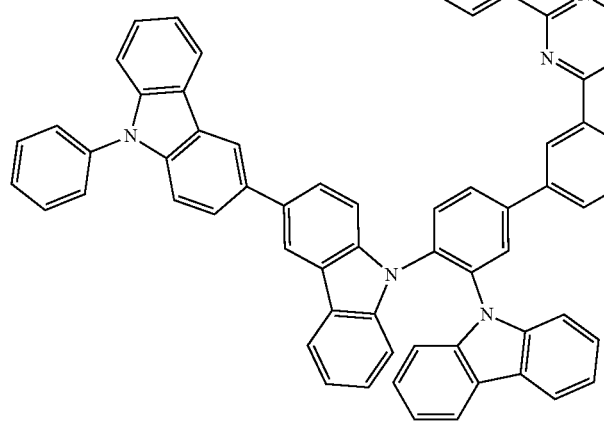
72
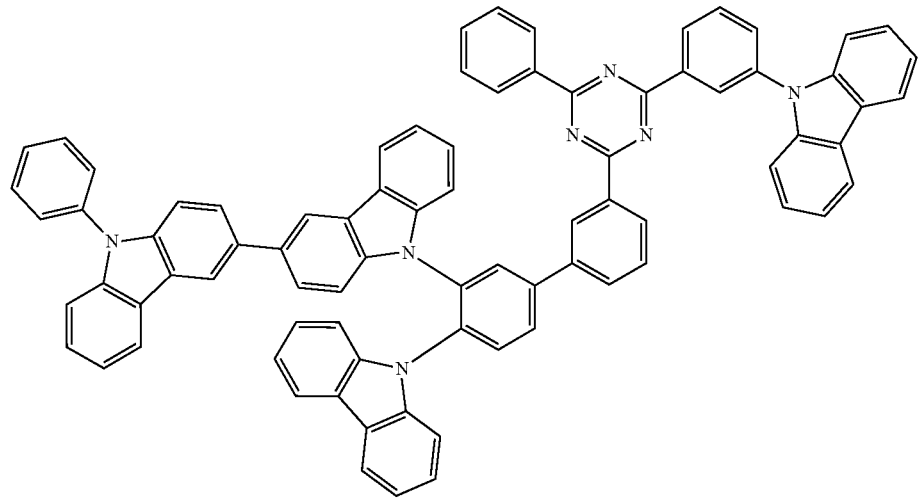
73
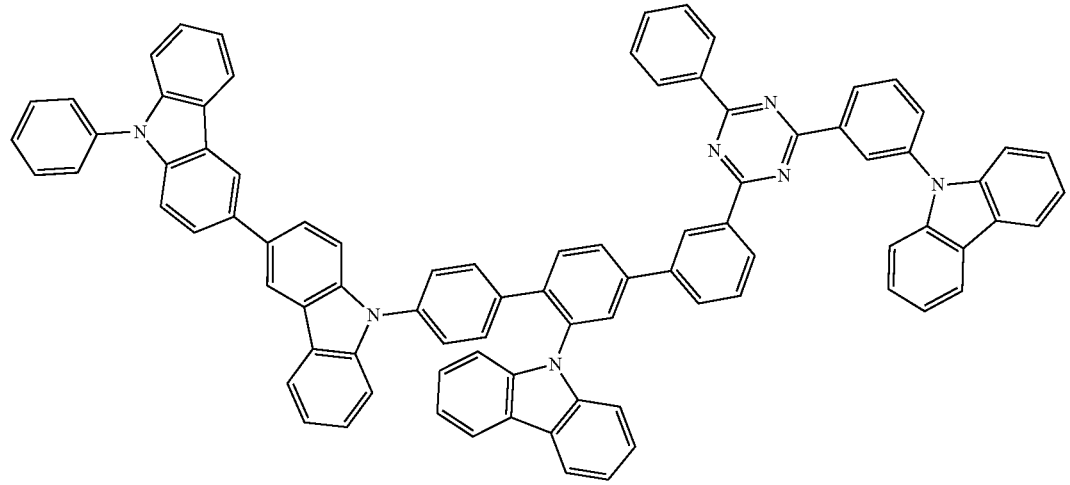
74

75
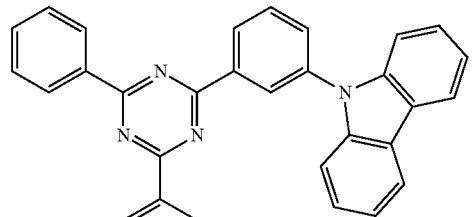
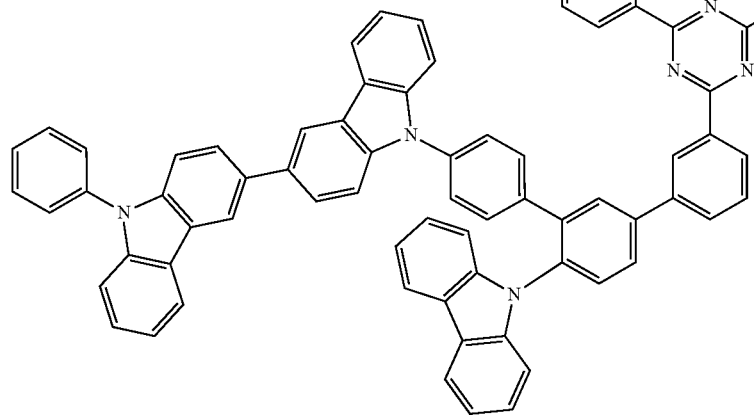
76
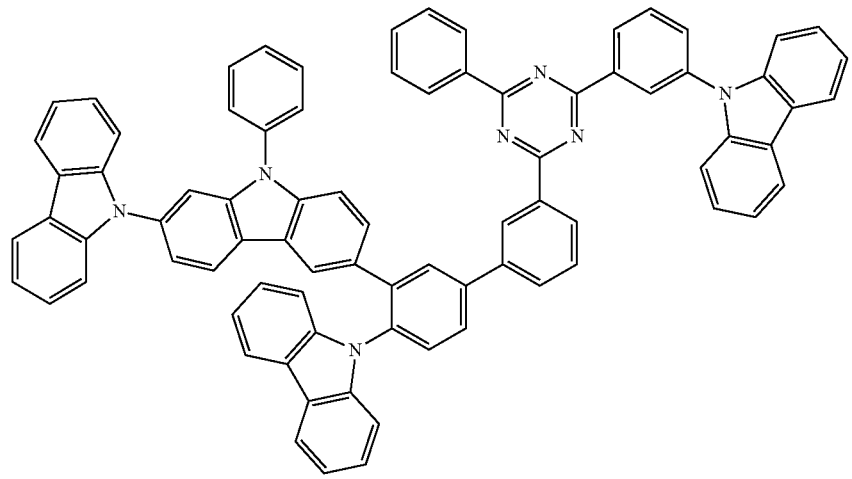
77
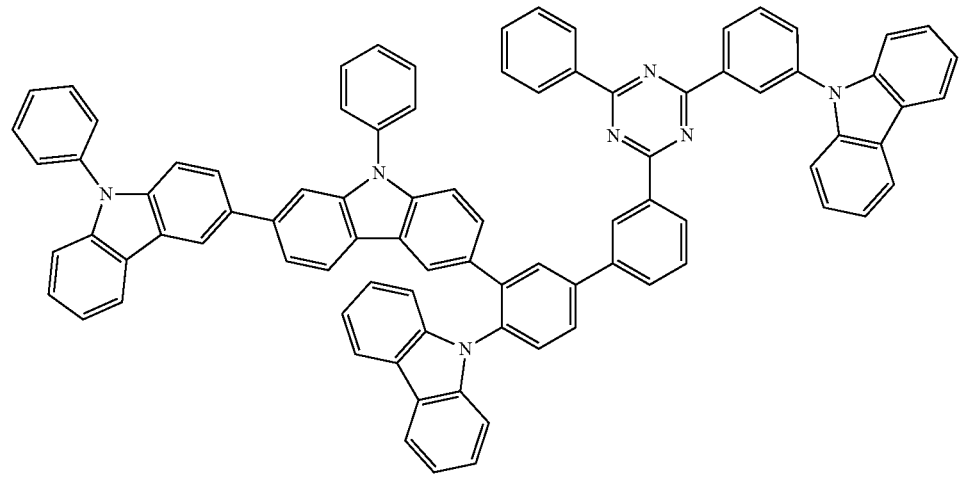

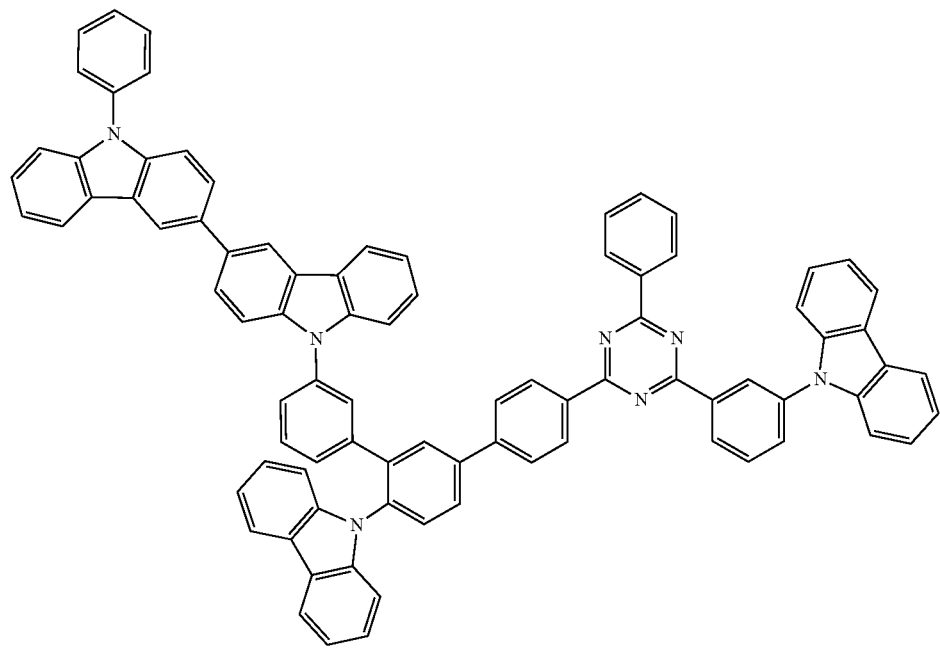
80
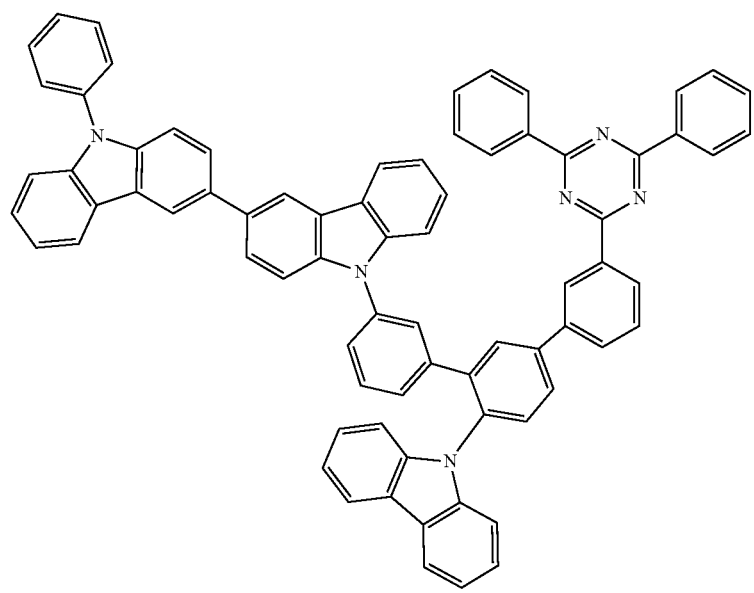
81

82
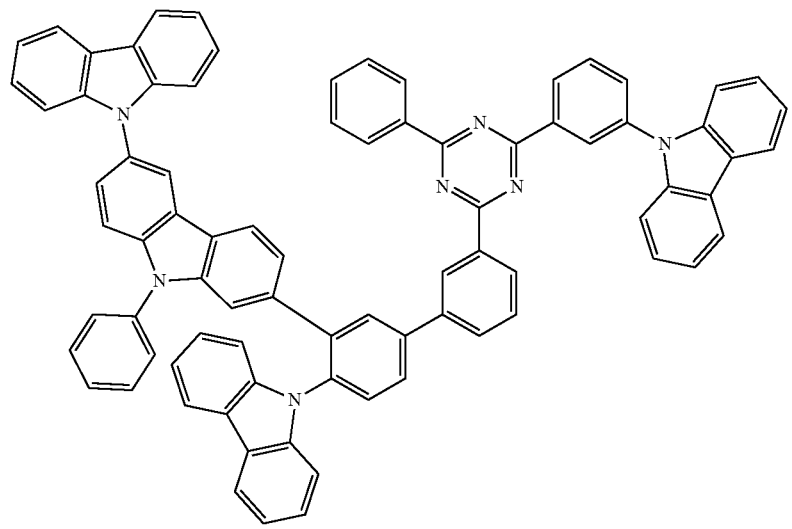
87
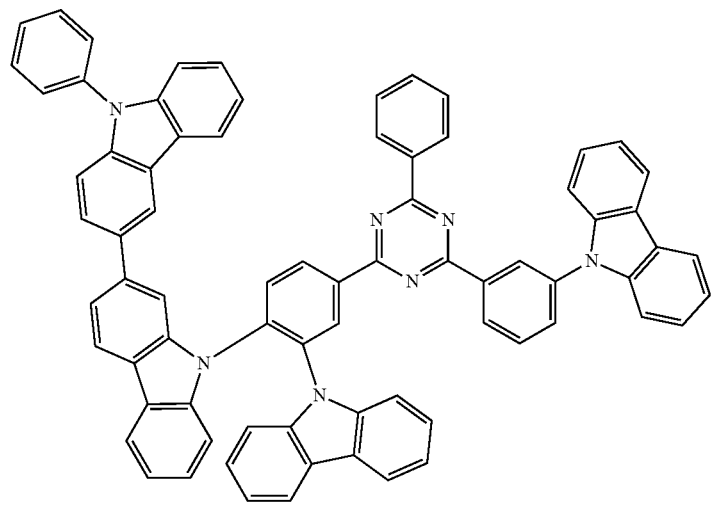
88
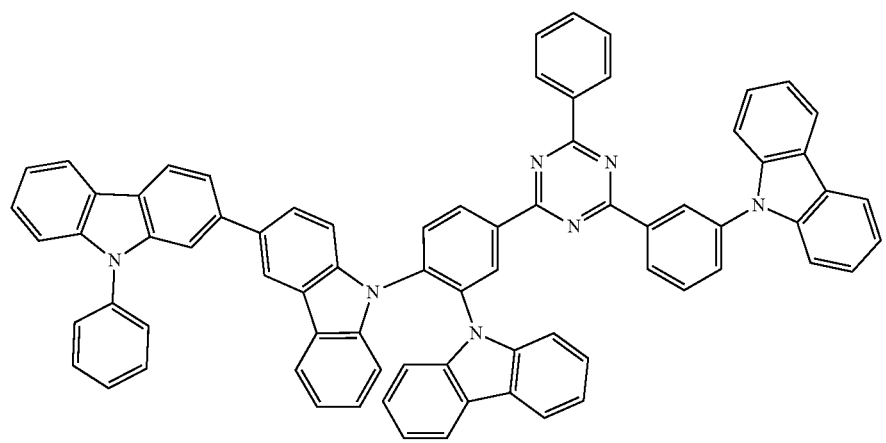

89
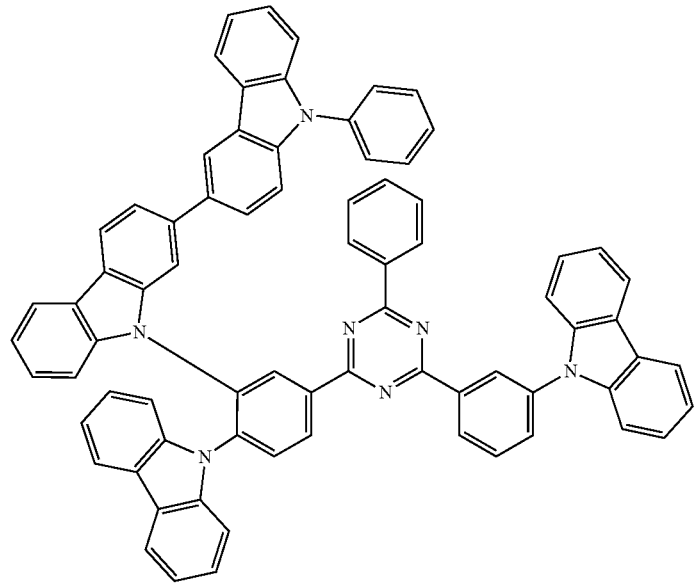
90
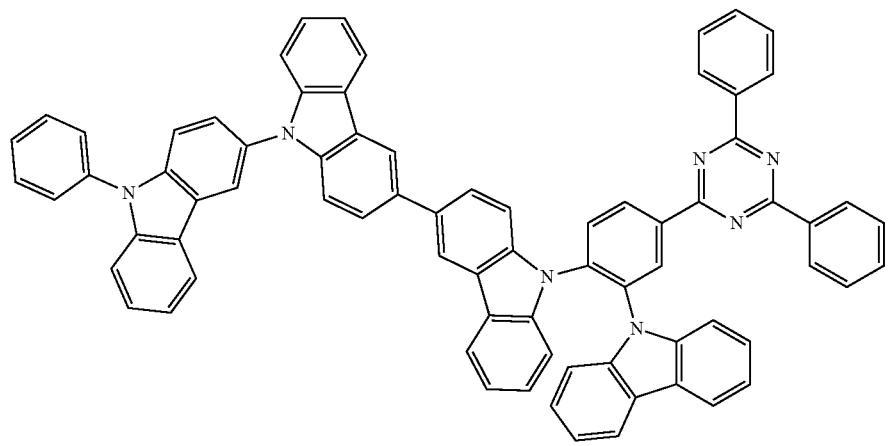
91
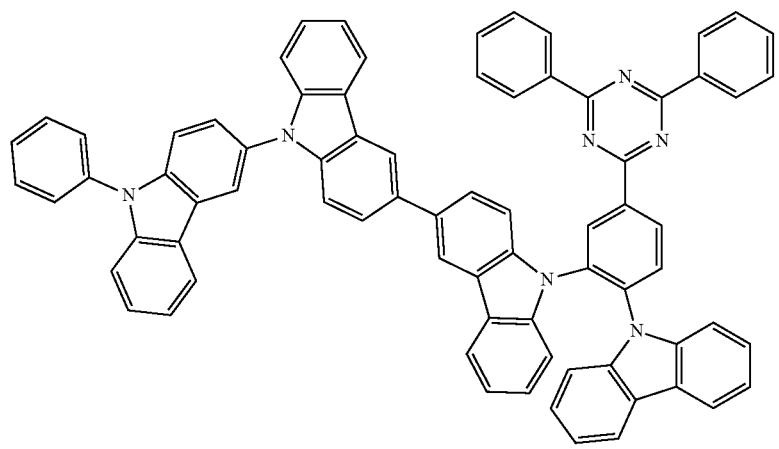

-continued
92
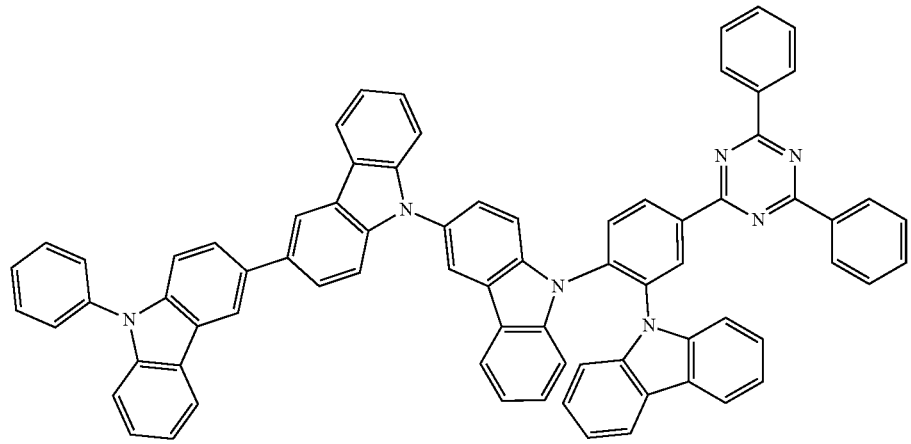
93
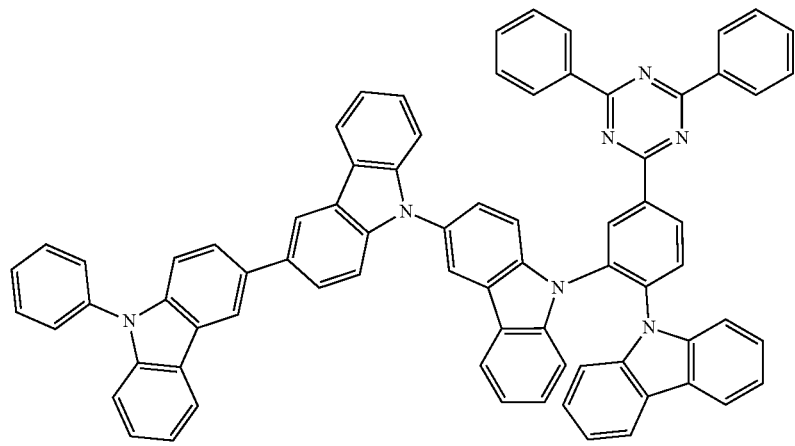
94 95
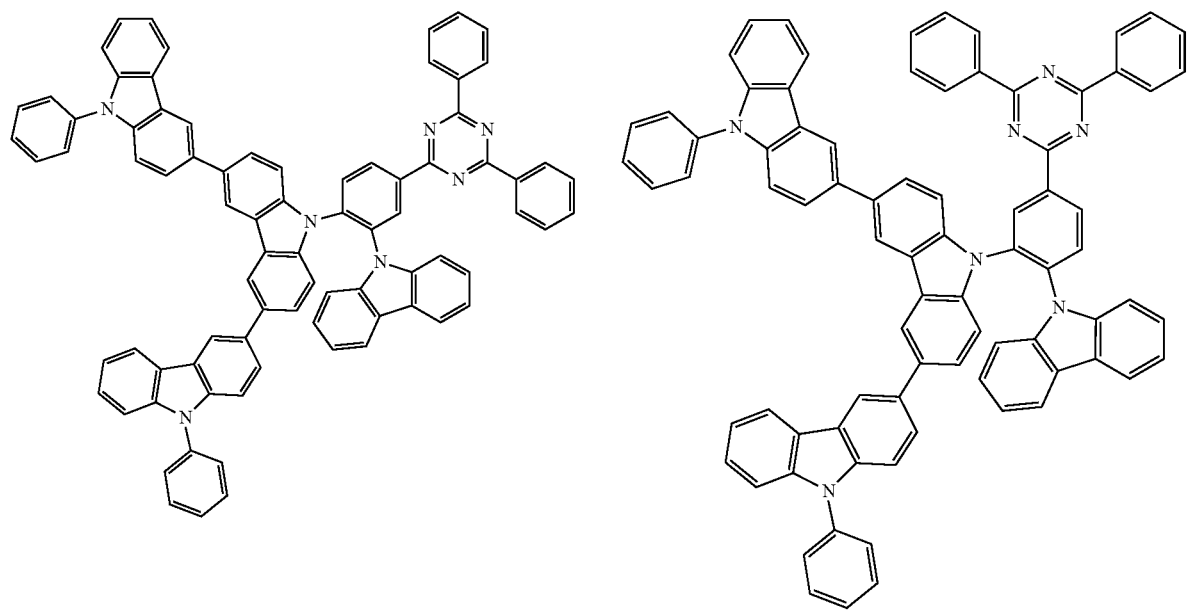

96
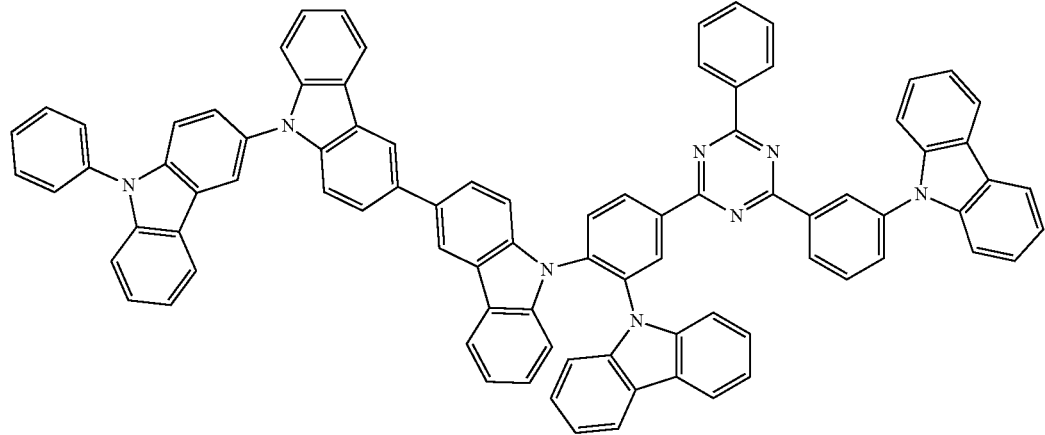
97
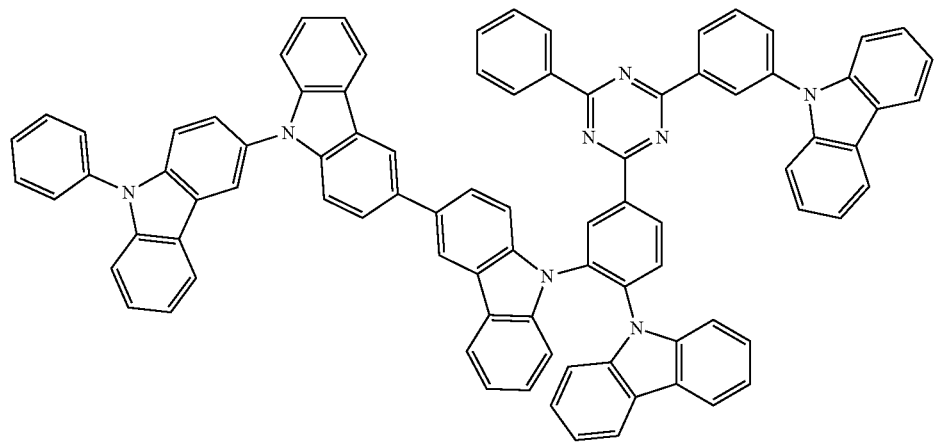
98
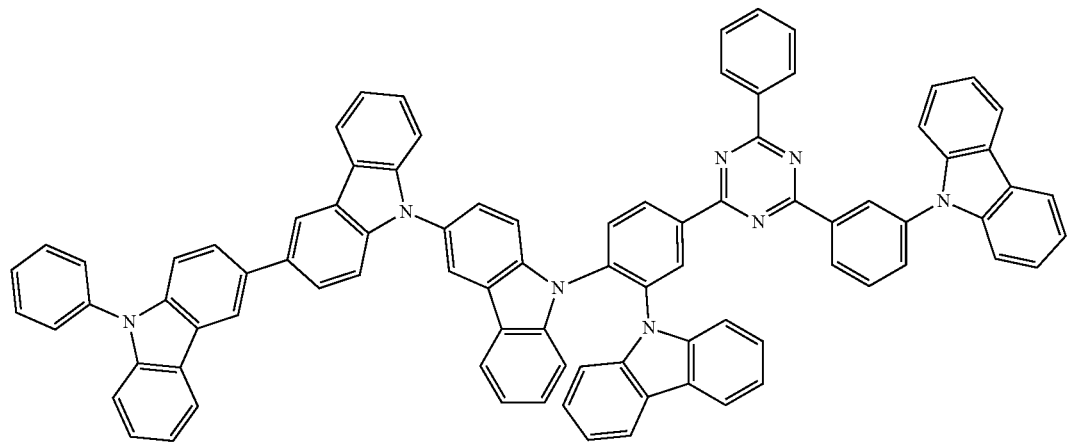

-continued
99
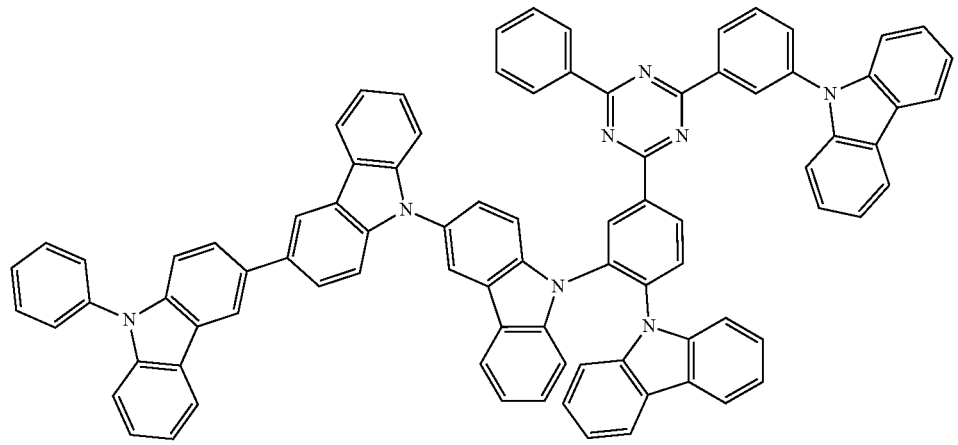
100
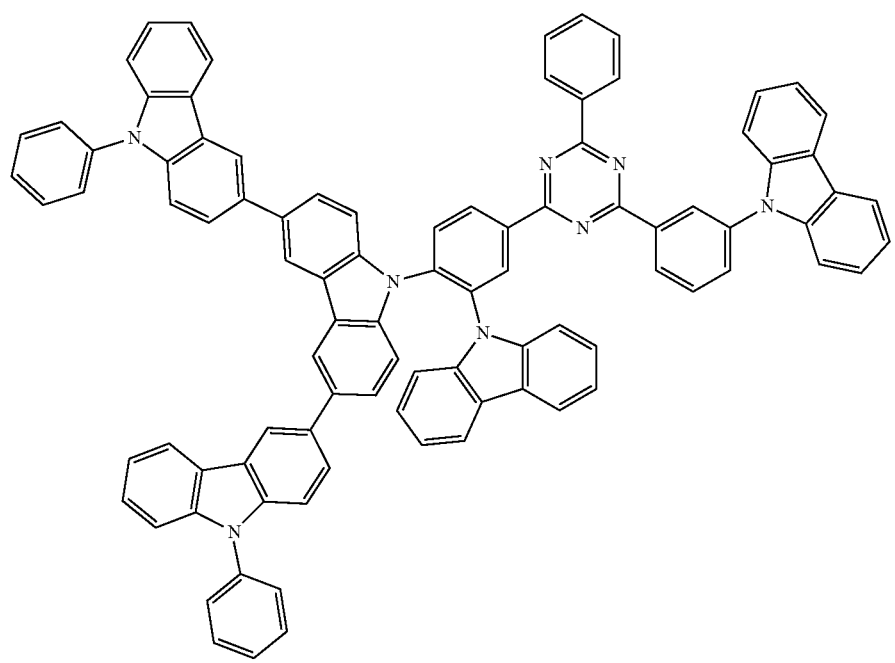

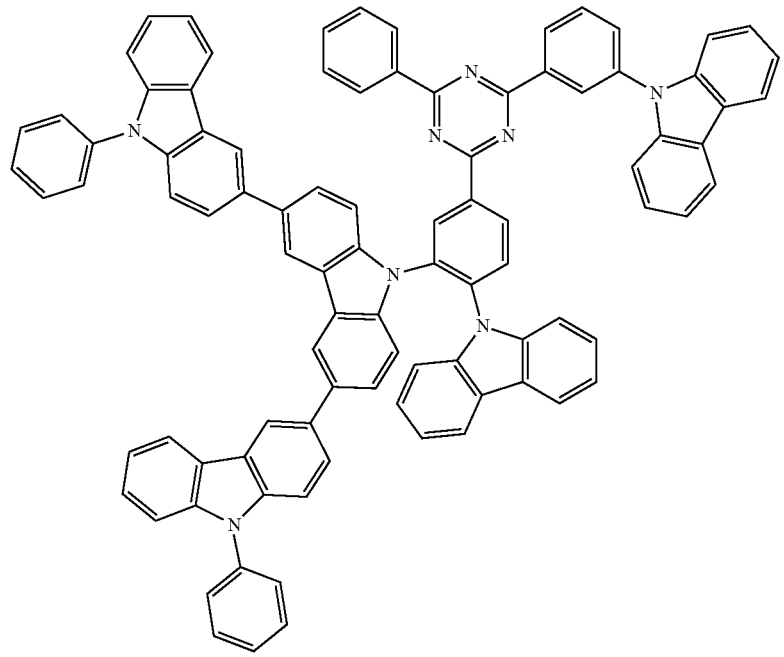
101
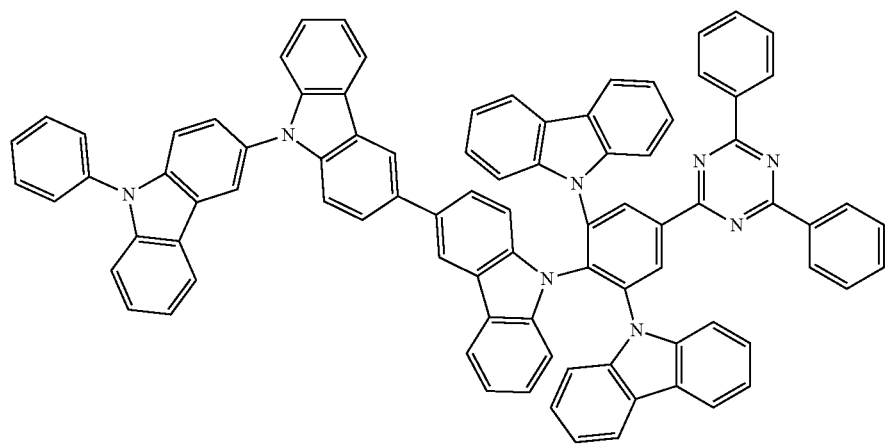
102
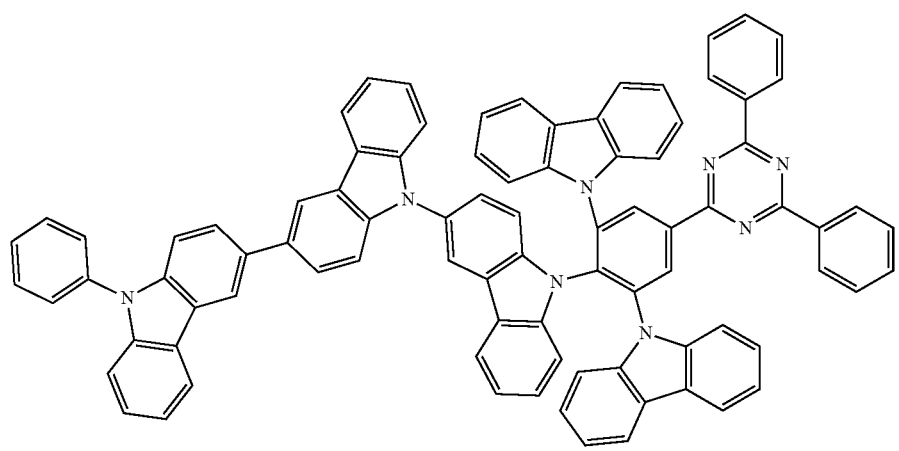
103

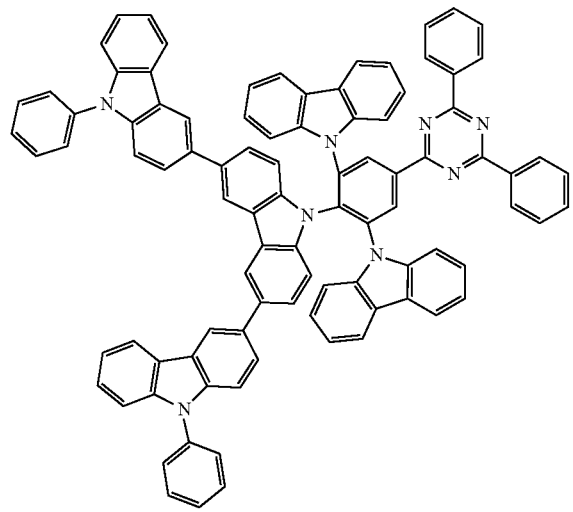
104
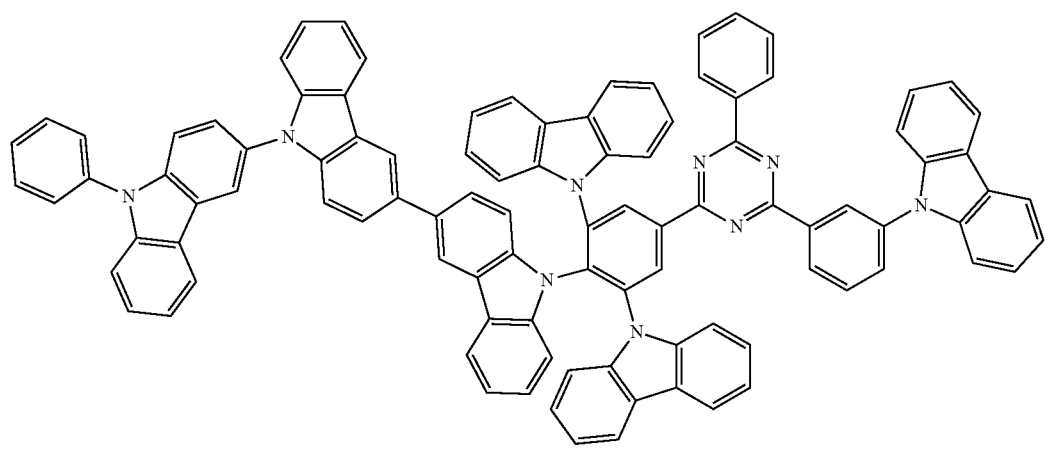
105
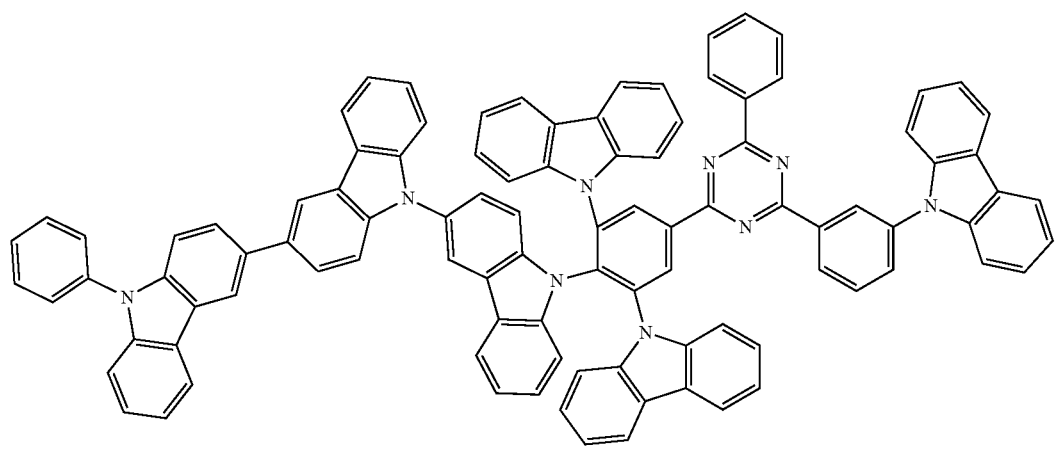
106

107
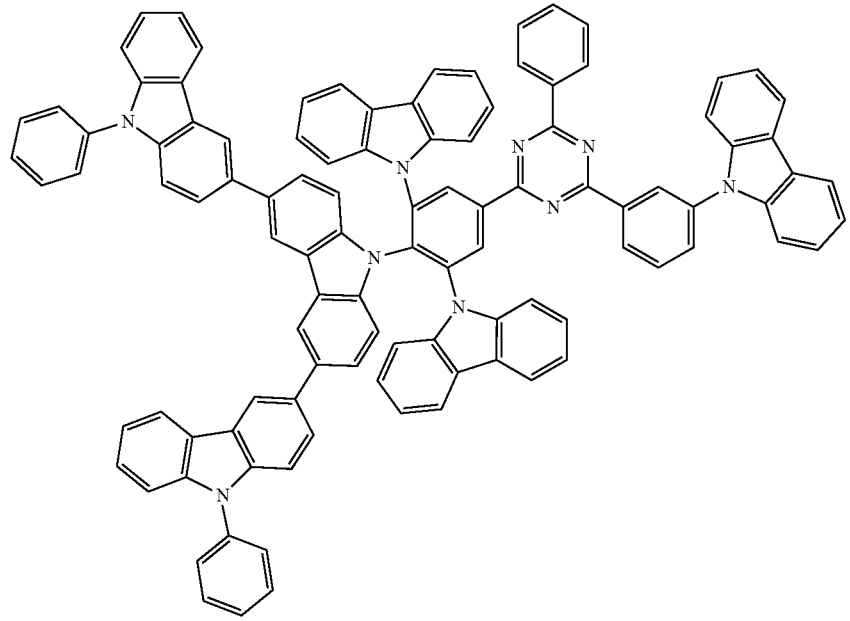
108 109
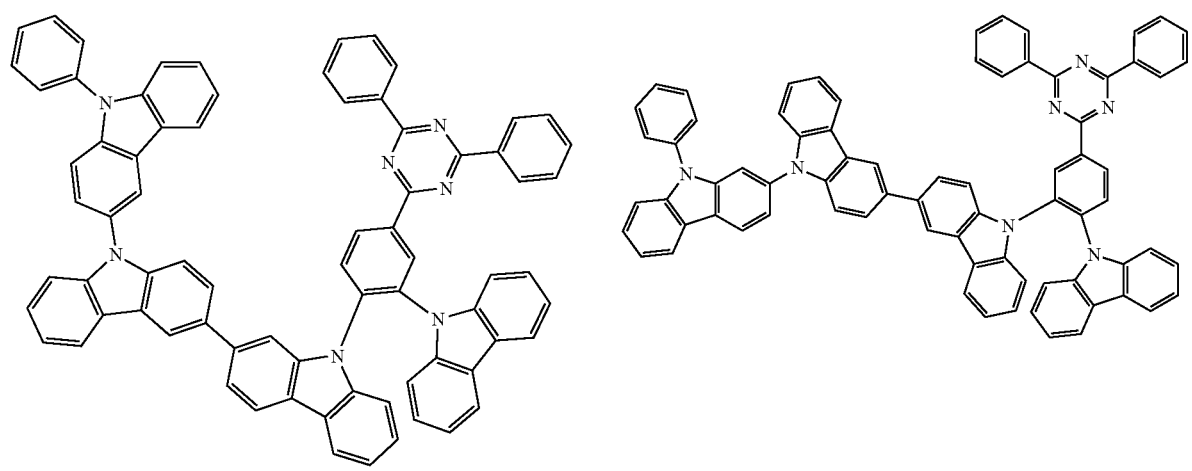
110
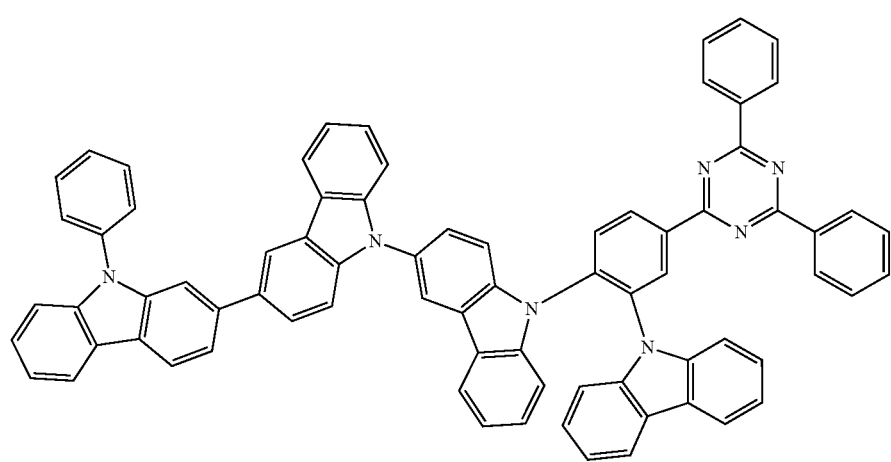

111
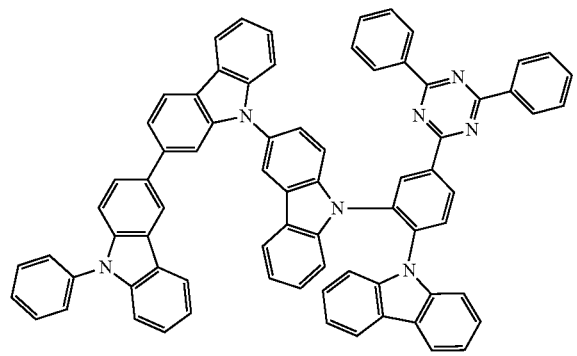
112
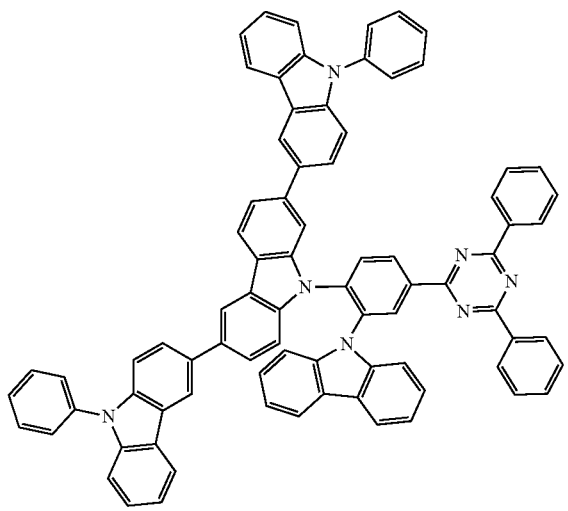
113
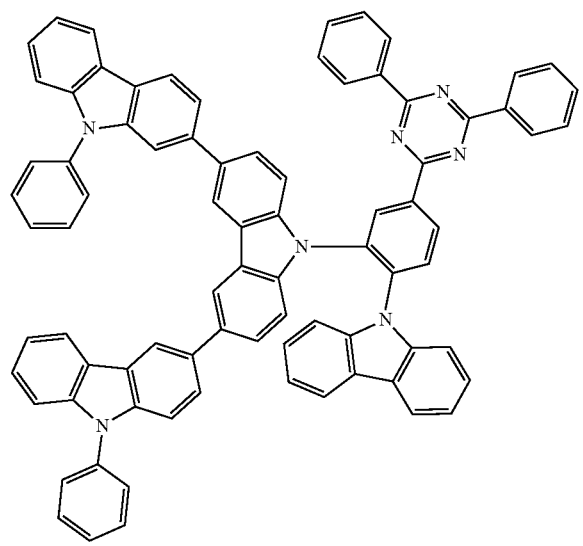
114
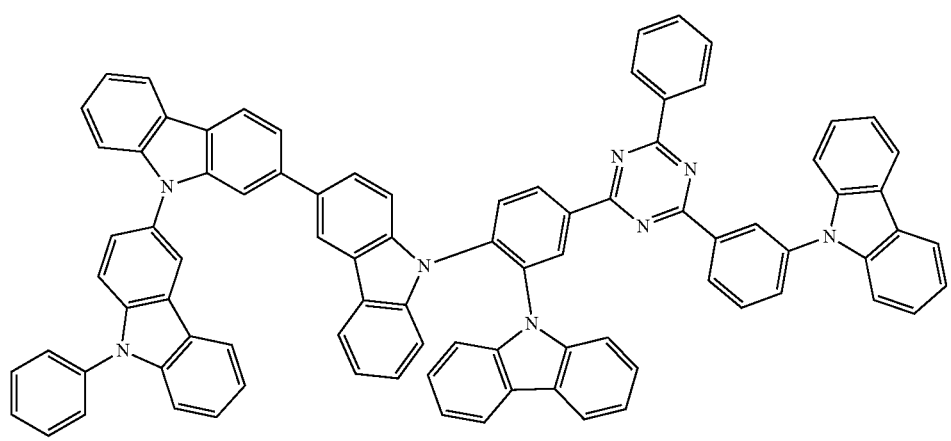

115
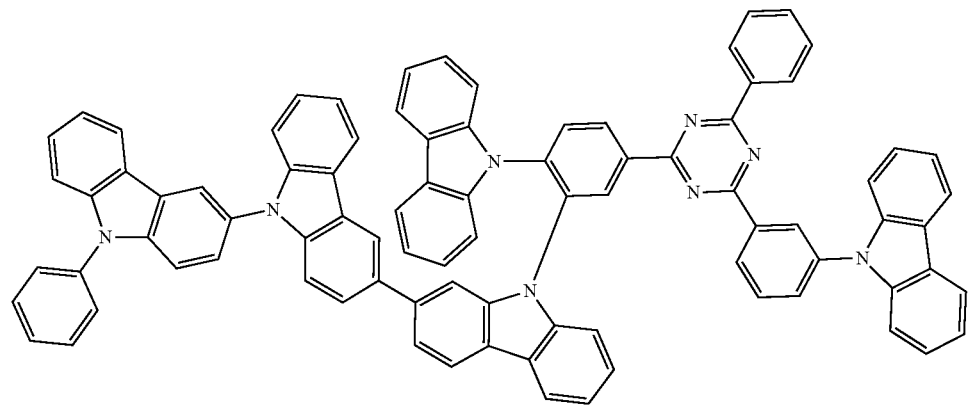
116
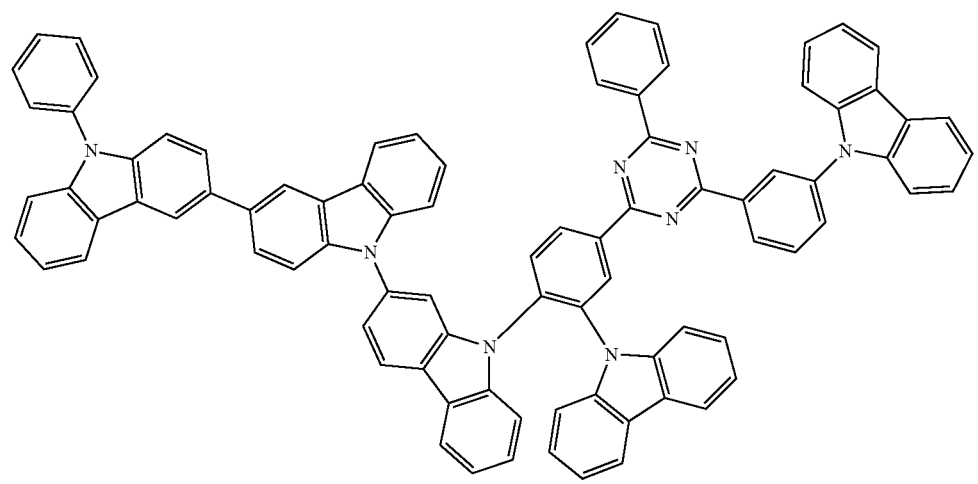
117
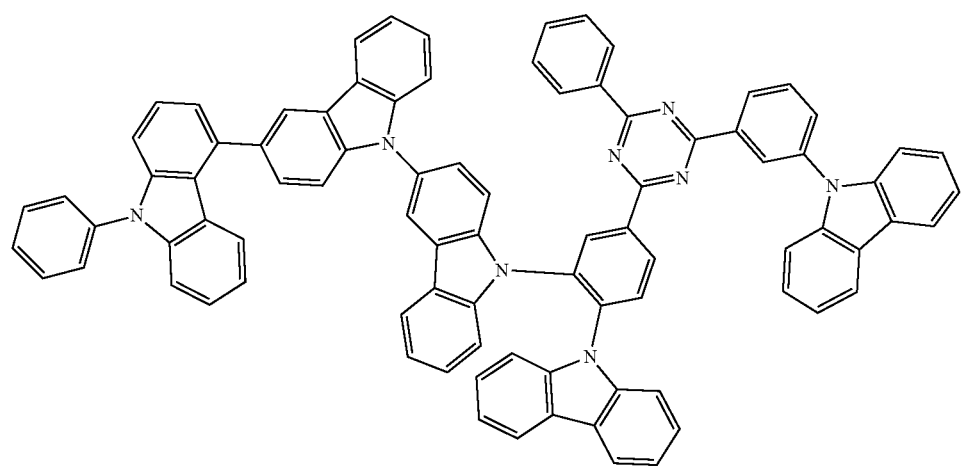

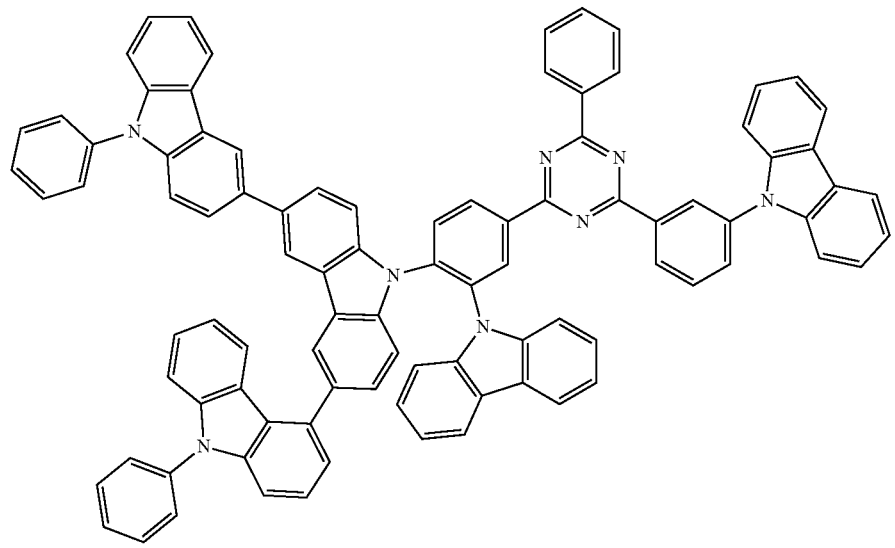
118
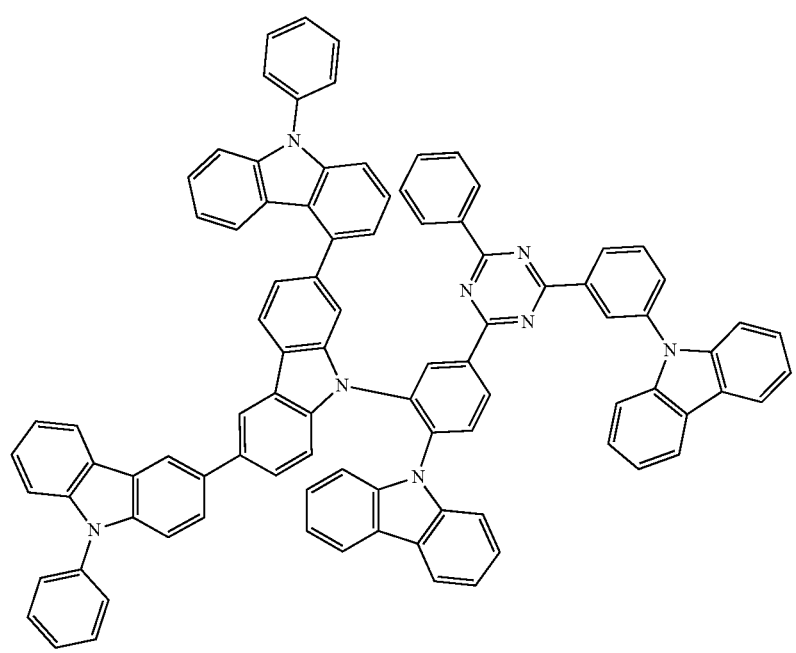
119

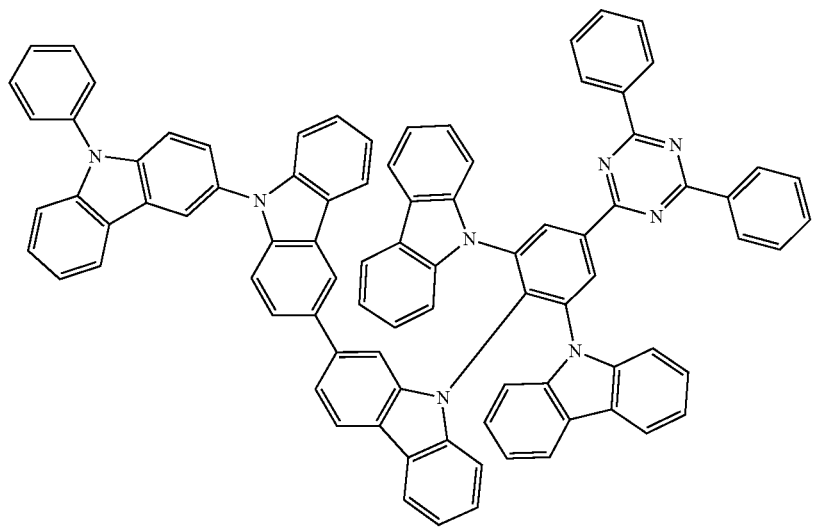
120
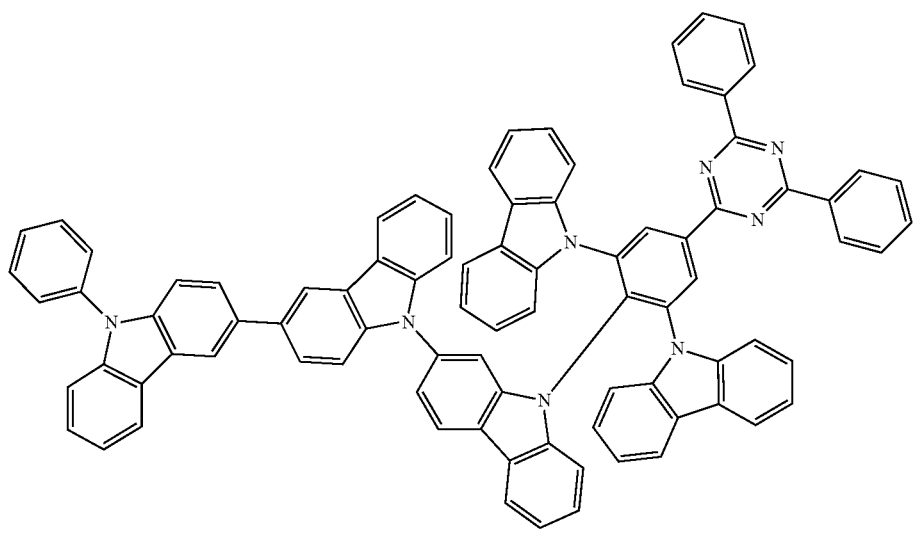
121
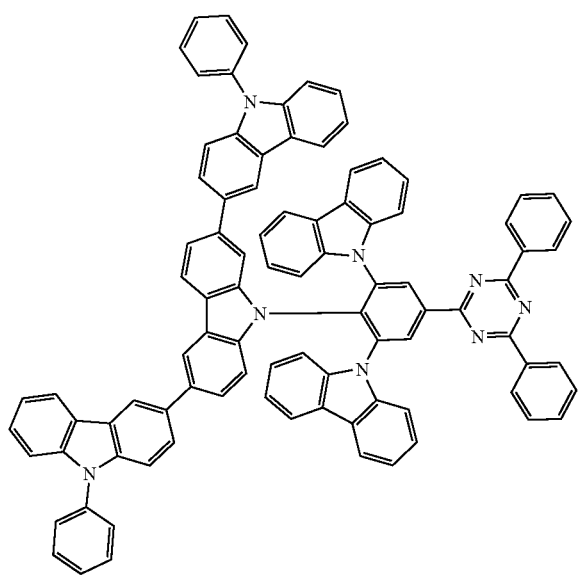
122

123
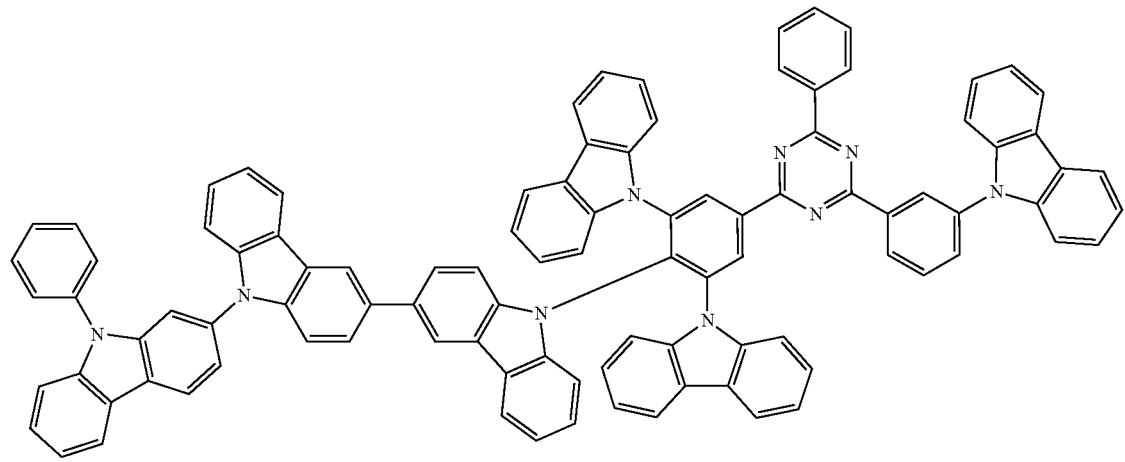
124
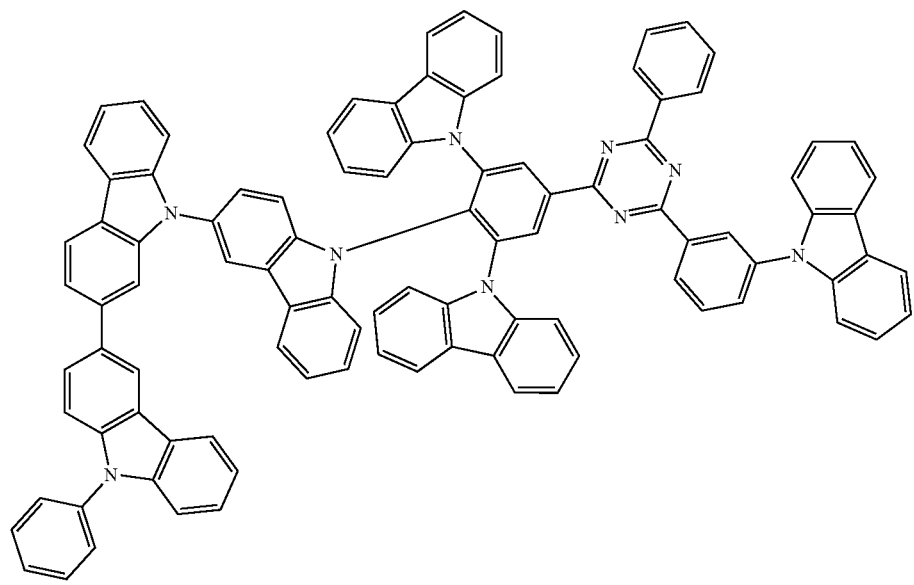
125
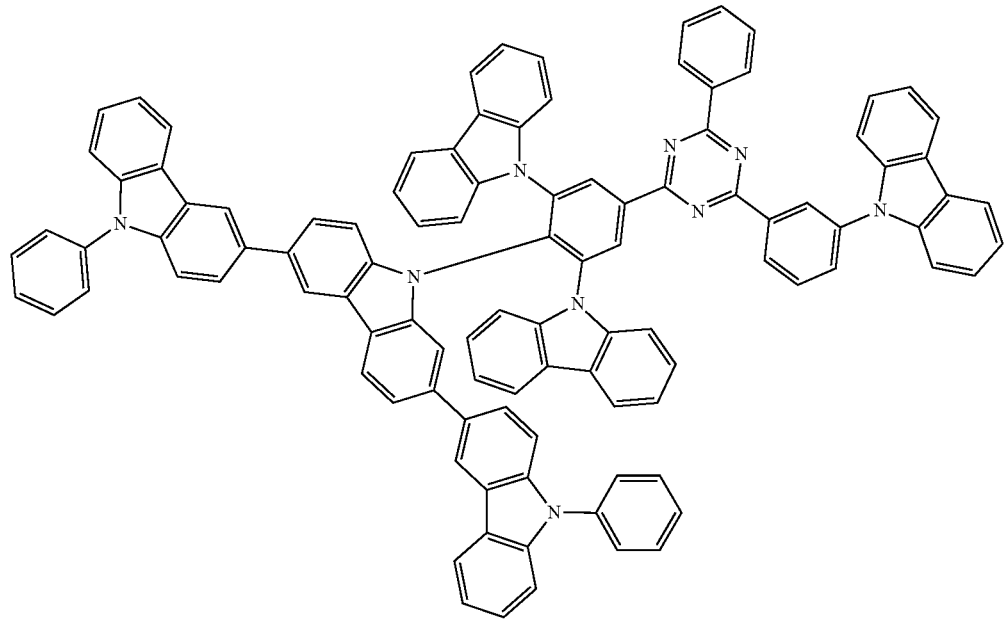

126
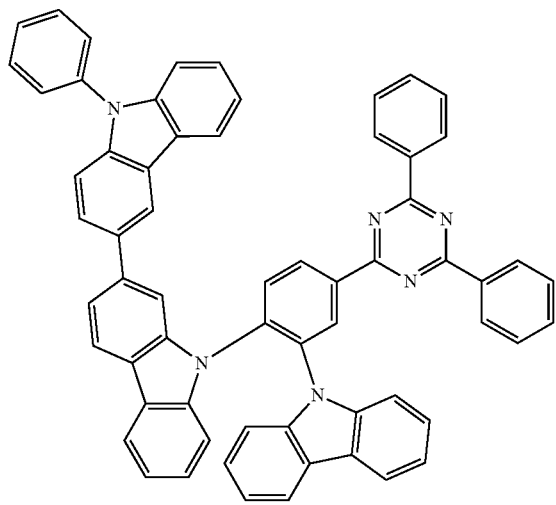
127
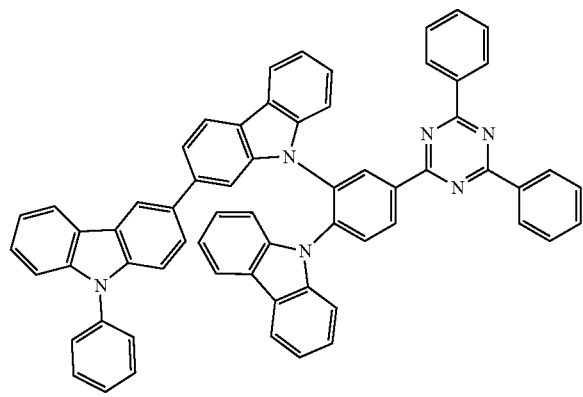
128
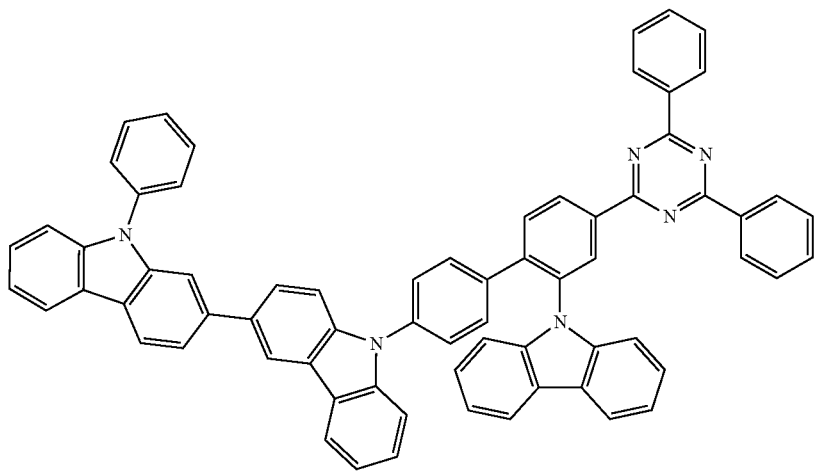
129
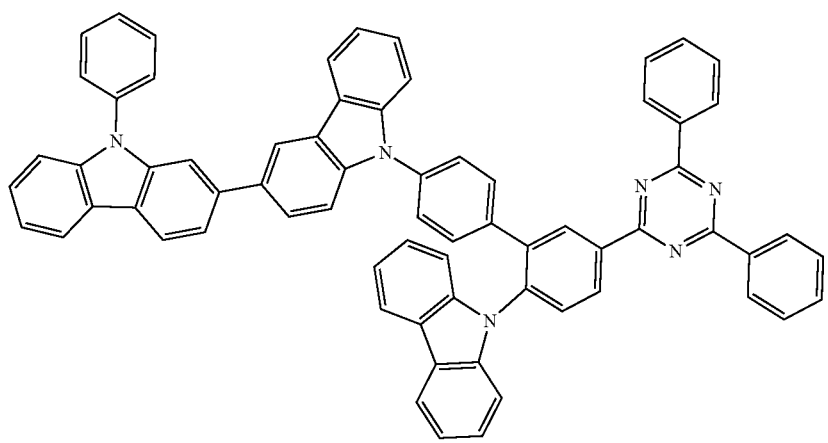

-continued
130
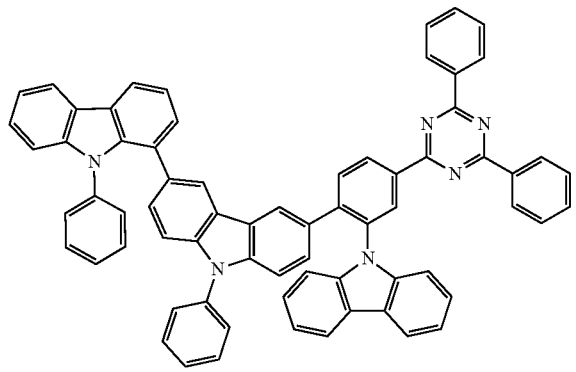
131
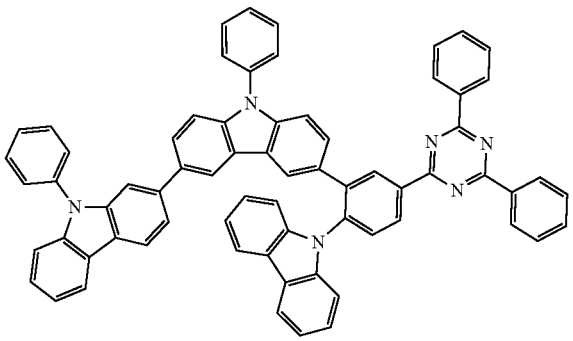
132
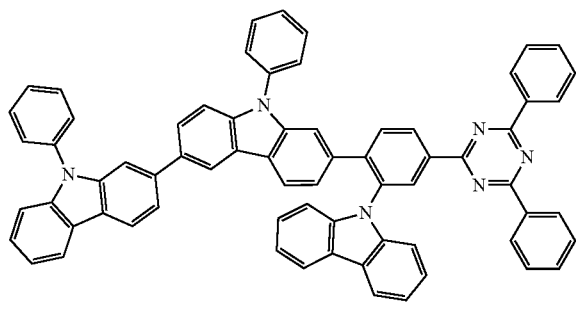
133
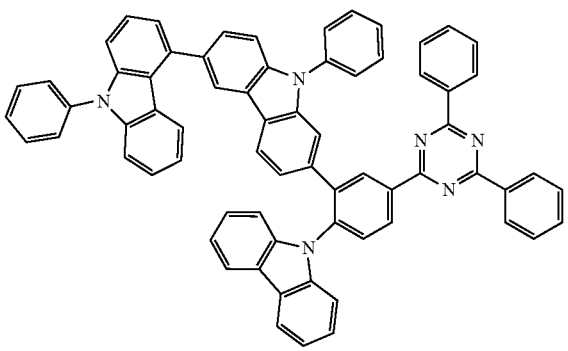
134
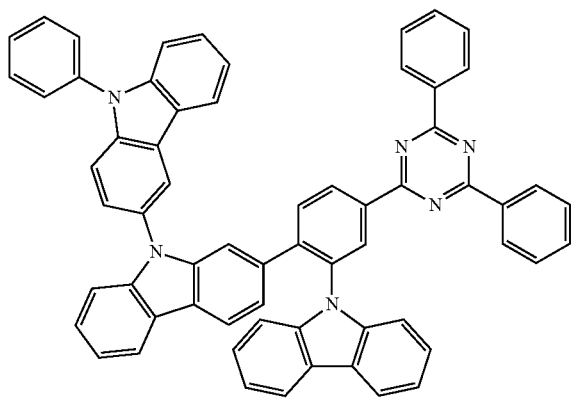
135
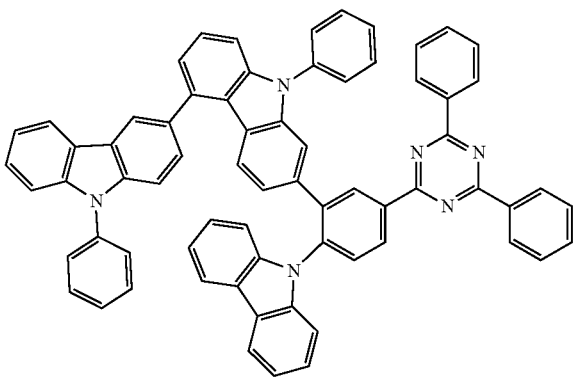
136
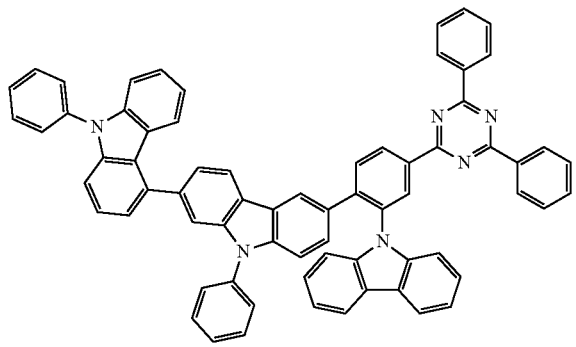
137
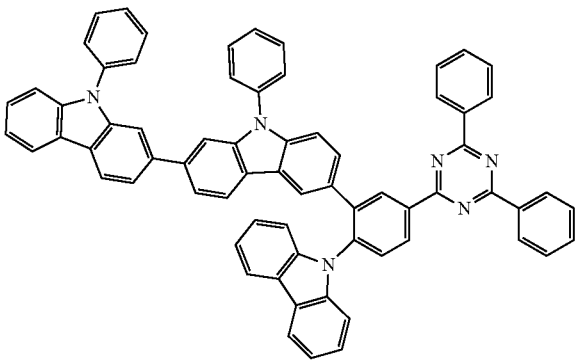

138
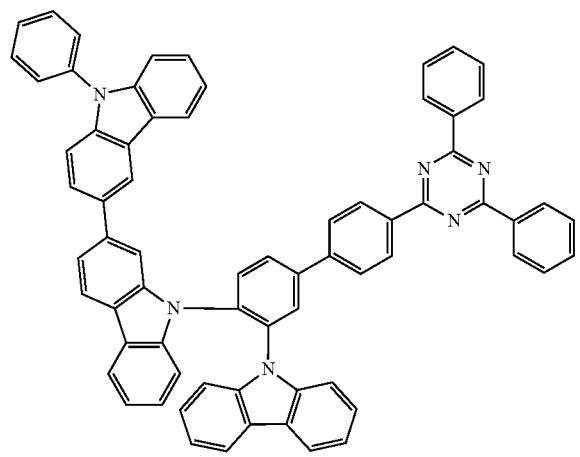
139
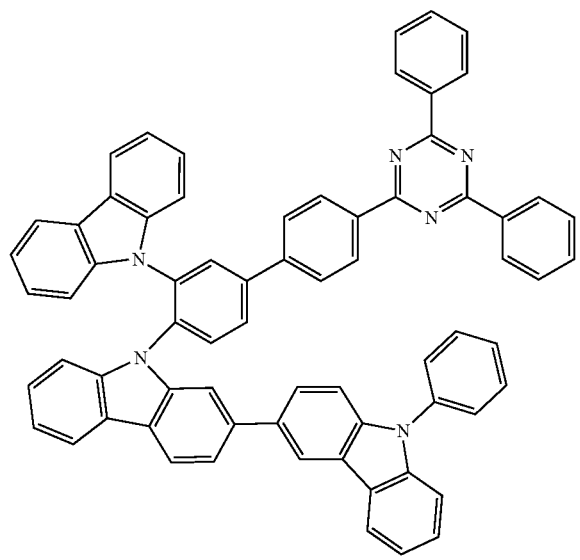
140
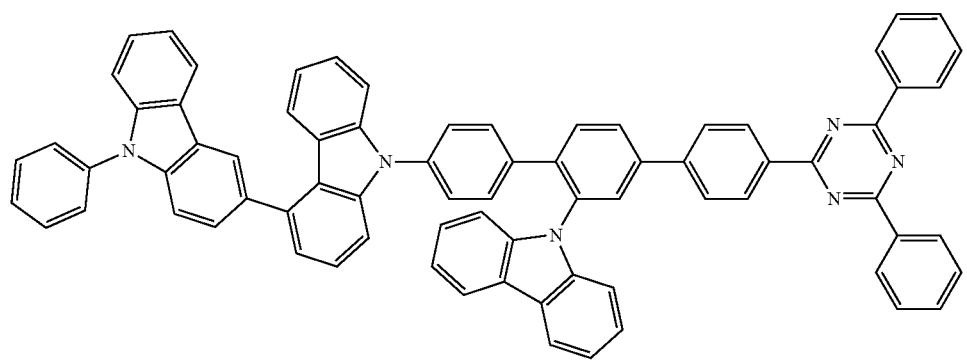
141
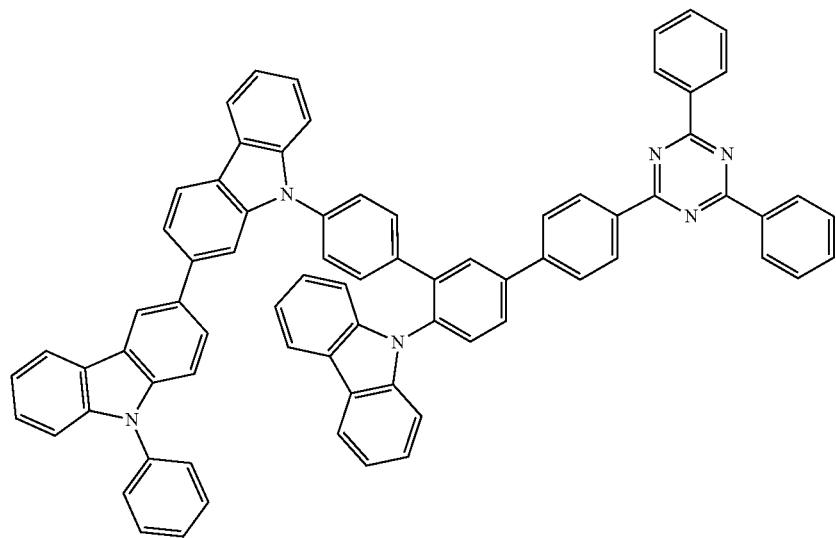

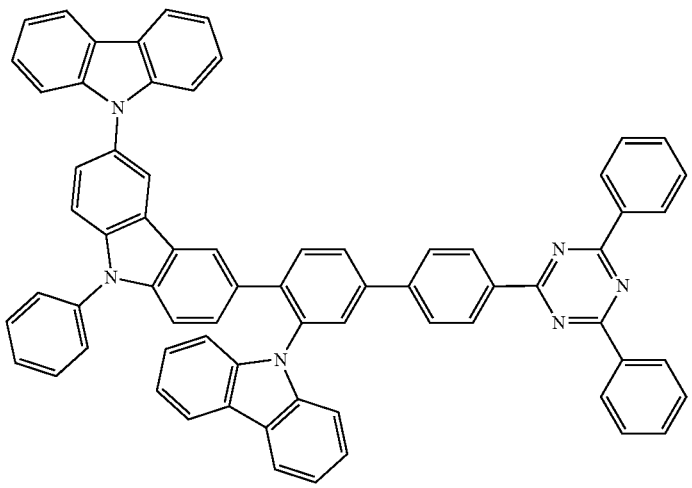
142
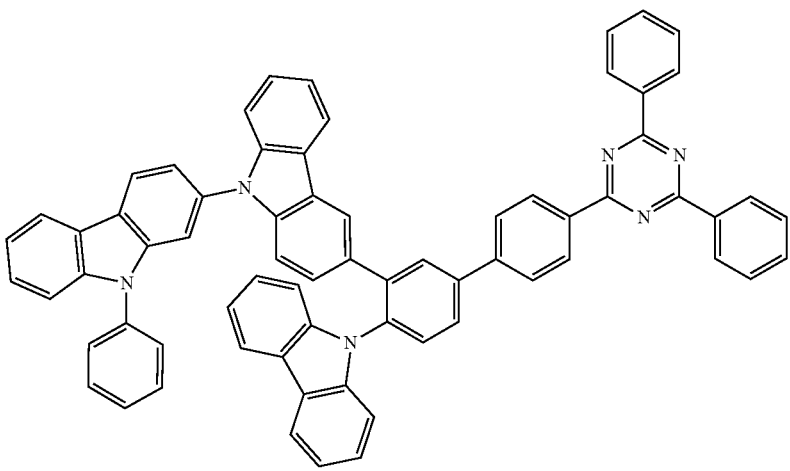
143
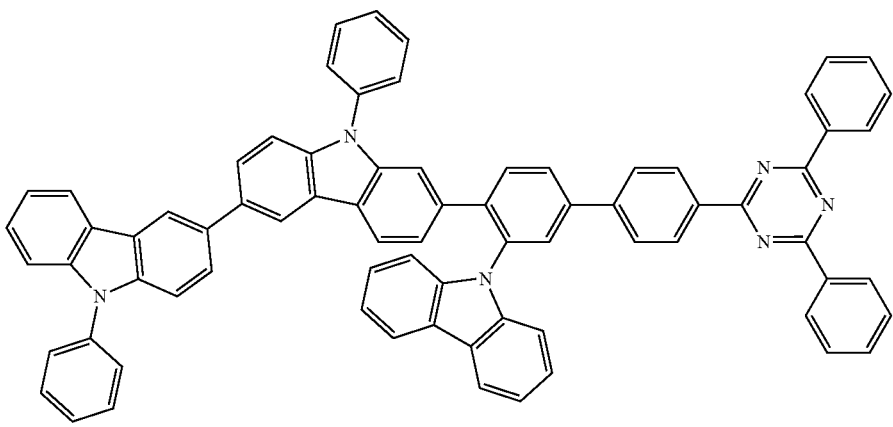
144

145
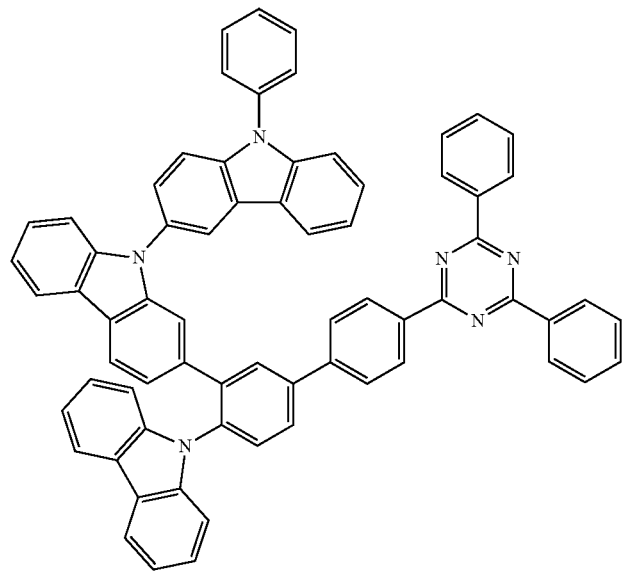
146
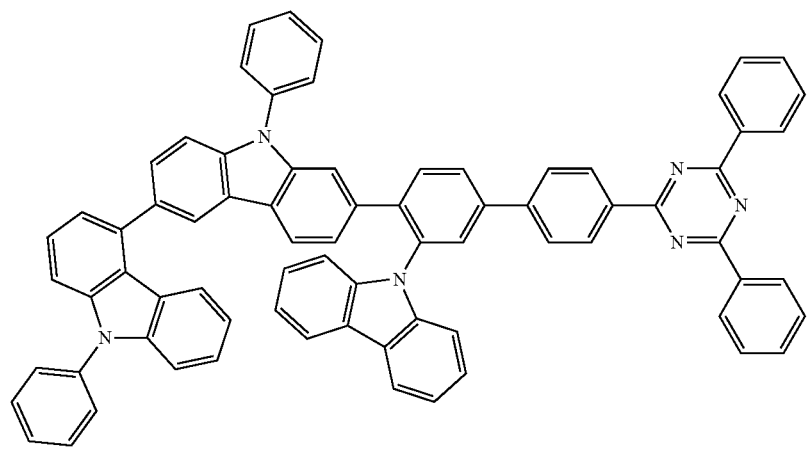
147
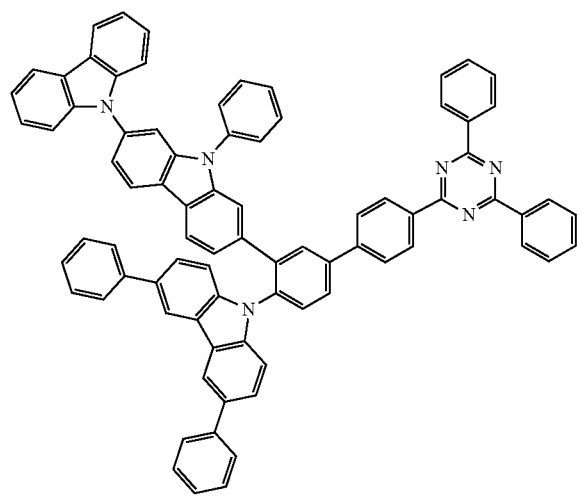
148
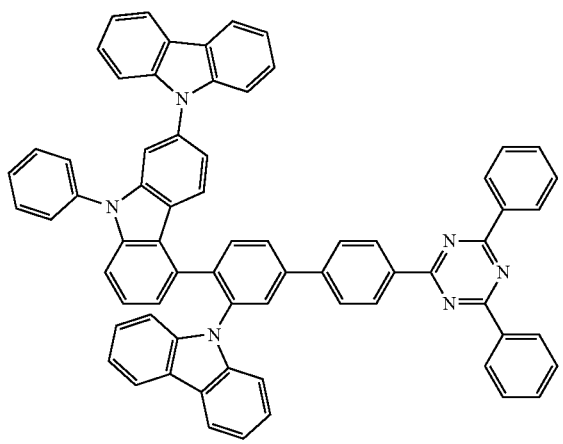

149
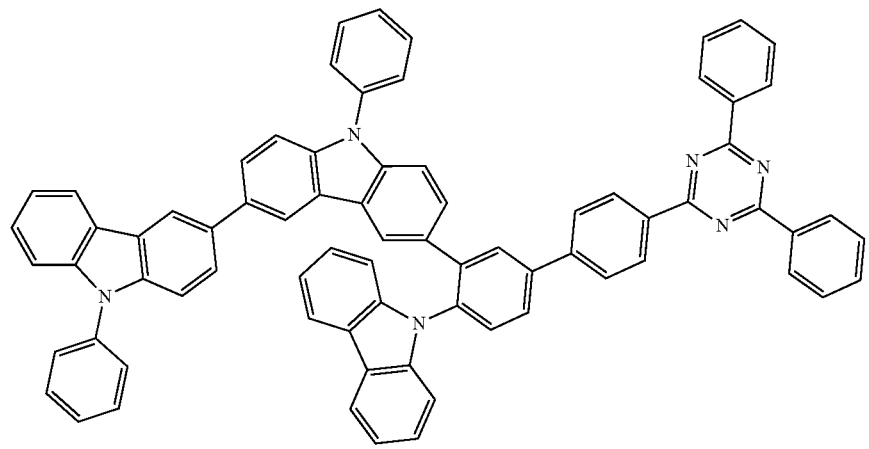
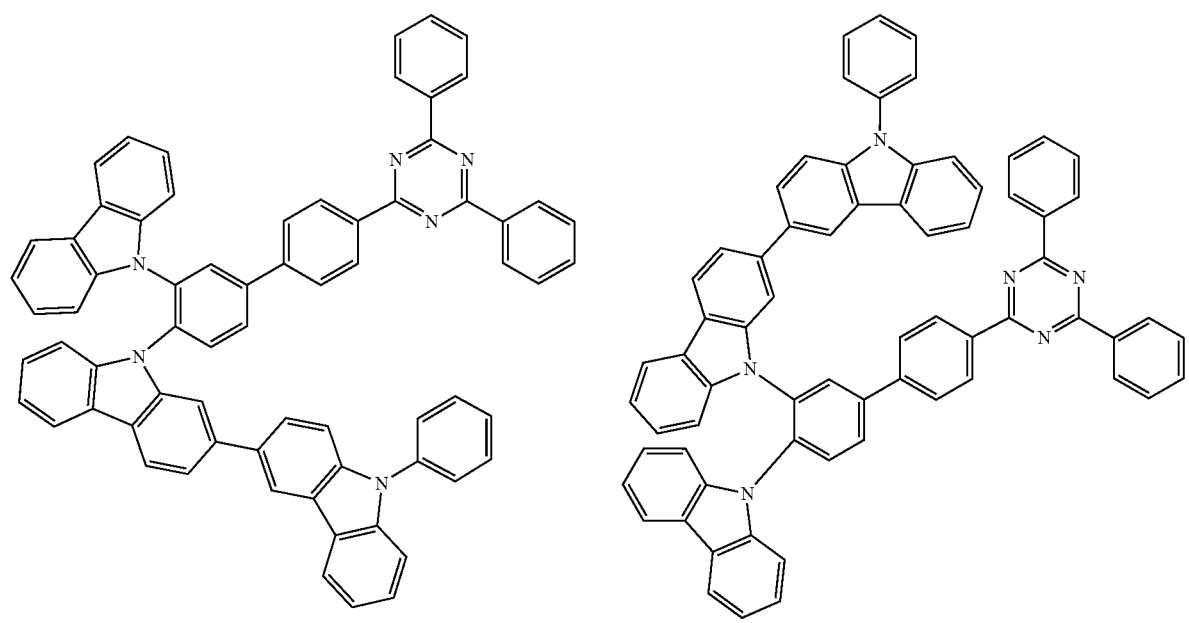

158

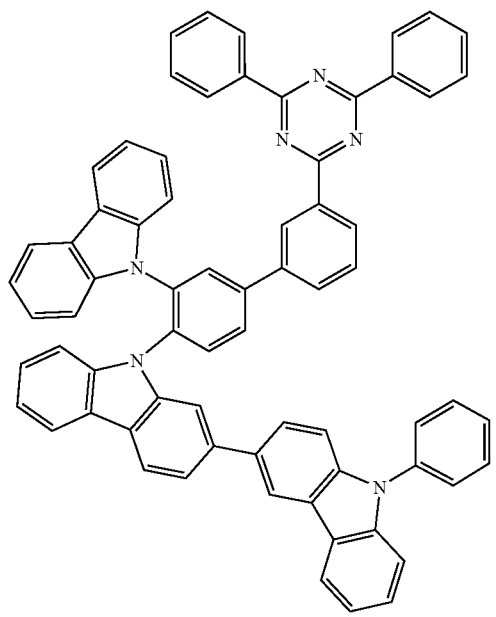

159

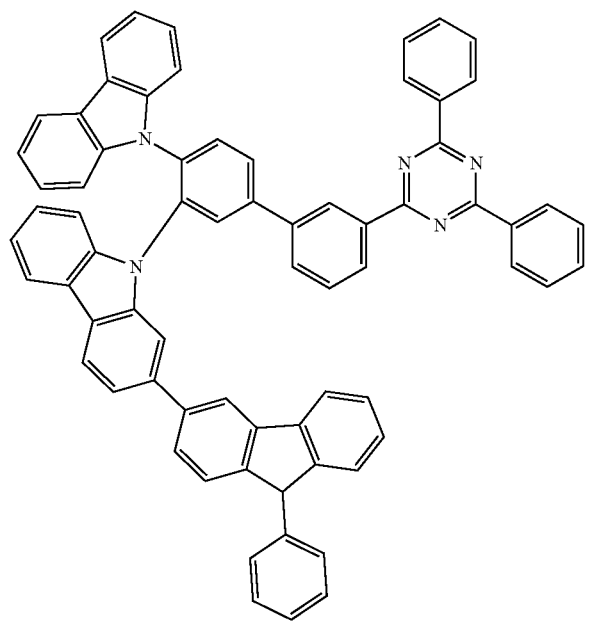

160

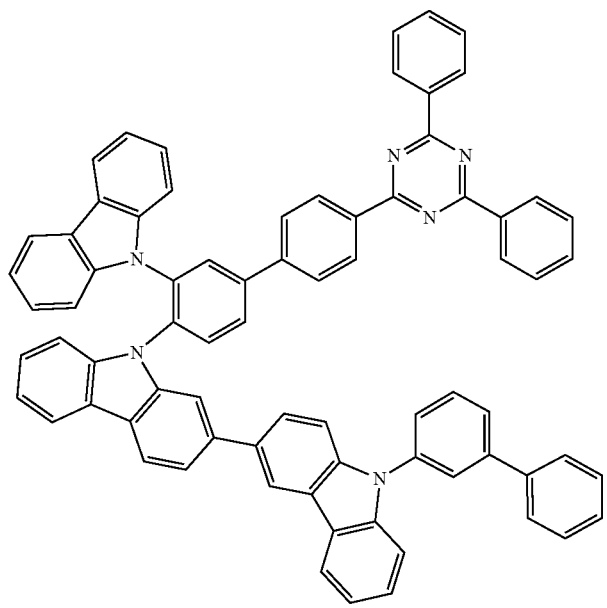

6. The compound of claim 1, wherein a HOMO-LUMO energy gap of the compound is between about 2.4 eV and about 2.9 eV.

7. The compound of claim 1, wherein the HOMO energy level of the compound is between about −5.8 eV and about −5.0 eV.

8. The compound of claim 1, wherein the LUMO energy level of the compound is between about −3.5 eV and about −2.6 eV.

9. A composition comprising:

the compound of claim 1; and at least one of a compound represented by Formula (B1), a carbazole derivative (other than the compound represented by Formula (1)), and an azine ring derivative (other than the compound represented by Formula (1)):

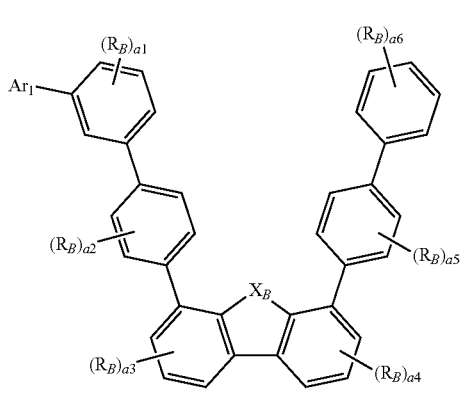

(B1)

wherein, in Formula (B1), $X_B$ is O, S, or Se,

Ar$_1$ is a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), each occurrence of $R_B$ is independently a deuterium atom, a cyano group, a fluoro group, a substituted or unsubstituted alkyl group having 1 to 20 carbon atoms, a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), a1, a2, and a5 are each independently 0, 1, 2, 3, or 4, a3 and a4 are each independently 0, 1, 2, or 3, and a6 is 0, 1, 2, 3, 4, or 5.

10. The composition of claim 9, wherein the compound represented by Formula (B1) is present.

11. The composition of claim 9, wherein:

the carbazole derivative and the azine ring derivative are each present.

12. The composition of claim 9, wherein the carbazole derivative is a compound represented by Formula (C4):

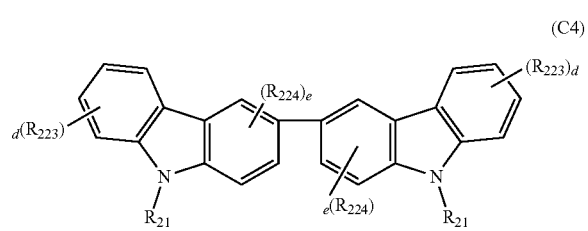

(C4)

wherein, in Formula (C4), each occurrence of $R_{21}$ is independently a monovalent ring derived from an aromatic hydrocarbon ring consisting of at least one substituted or unsubstituted aromatic hydrocarbon ring, a monovalent ring derived from an aromatic hetero ring consisting of at least one substituted or unsubstituted aromatic hetero ring (wherein the monovalent ring does not have an azine ring structure), or a monovalent ring aggregation group consisting of at least one substituted or unsubstituted aromatic hydrocarbon ring and at least one substituted or unsubstituted aromatic hetero ring (wherein the monovalent ring aggregation group does not have an azine ring structure), each occurrence of $R_{223}$ and each occurrence of $R_{224}$ is independently a deuterium atom, a cyano group, a substituted or unsubstituted alkyl group, a substituted or unsubstituted alkoxy group, a substituted or unsubstituted aryloxy group (other than a group having an azine ring structure), a substituted or unsubstituted alkyl amino group, a substituted or unsubstituted aryl amino group (other than a group having an azine ring structure), a monovalent aromatic hydrocarbon group consisting of at least one substituted or unsubstituted aromatic hydrocarbon ring, a monovalent aromatic heterocyclic group consisting of at least one substituted or unsubstituted aromatic hetero ring (wherein the monovalent group does not have an azine ring structure), or a monovalent ring aggregation group consisting of at least one substituted or unsubstituted aromatic hydrocarbon ring and at least one substituted or unsubstituted aromatic hetero ring (wherein the monovalent ring aggregation group does not have an azine ring structure), each occurrence of d is independently 0, 1, 2, 3, or 4, and each occurrence of e is independently 0, 1, 2, or 3.

13. The composition of claim 9, wherein the azine ring derivative is represented by Formula (A3):

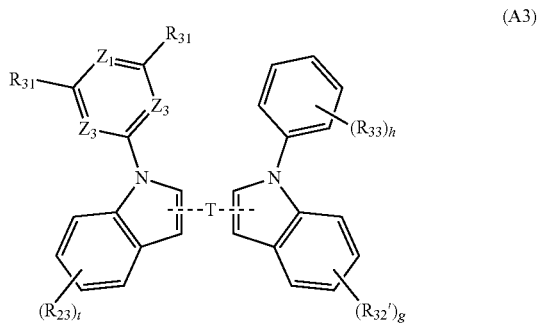

(A3)

wherein, in Formula (A3),

T indicates a ring structure represented by the following formula condensed with each of the indole rings of Formula (A3),

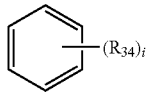

$Z_1$, $Z_3$, and $Z_5$ are each independently CH or N, and at least one of $Z_1$, $Z_3$, and $Z_5$ is N, each occurrence of $R_{31}$ is independently a hydrogen atom, a deuterium atom, or an organic group, each occurrence of each of $R_{32}$, $R_{32}'$, $R_{33}$, and $R_{34}$ is independently a deuterium atom, a cyano group, a substituted or unsubstituted alkyl group, a substituted or unsubstituted alkoxy group, a substituted or unsubstituted aryloxy group, a substituted or unsubstituted alkylamino group, a substituted or unsubstituted arylamino group, a monovalent aromatic hydrocarbon group consisting of at least one substituted or unsubstituted aromatic hydrocarbon ring, a monovalent aromatic heterocyclic group consisting of at least one substituted or unsubstituted aromatic hetero ring, or a monovalent ring aggregation group consisting of at least one substituted or unsubstituted aromatic hydrocarbon ring and at least one substituted or unsubstituted aromatic hetero ring, f and g are each independently 0, 1, 2, 3, or 4, h is 0, 1, 2, 3, 4, or 5, and i is 0, 1, or 2.

14. The composition of claim 9, further comprising:
a phosphorescent platinum family metal complex, wherein the platinum family includes ruthenium (Ru), rhodium (Rh), palladium (Pd), osmium (Os), iridium (Ir), and platinum (Pt).

15. The composition of claim 14, wherein
the phosphorescent platinum family metal complex is an iridium-based metal complex.

16. A liquid composition comprising: the compound of claim 1 or the composition comprising the compound of claim 1; and a solvent having a boiling point between about 100° C. and about 350° C. at atmospheric pressure,
wherein the composition further comprises at least one of a compound represented by Formula (B1), a carbazole derivative (other than the compound represented by Formula (1)), and an azine ring derivative (other than the compound represented by Formula (1)):

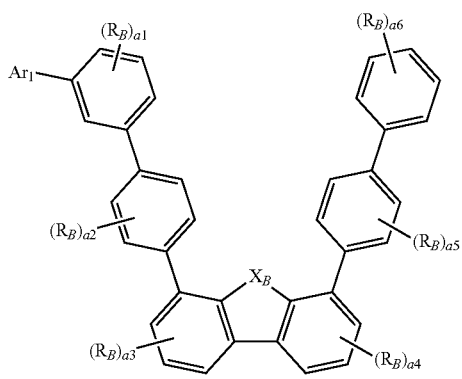

wherein, in Formula (B1), $X_B$ is O, S, or Se, $Ar_1$ is a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), each occurrence of $R_B$ is independently a deuterium atom, a cyano group, a fluoro group, a substituted or unsubstituted alkyl group having 1 to 20 carbon atoms, a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), a1, a2, and a5 are each independently 0, 1, 2, 3, or 4, a3 and a4 are each independently 0, 1, 2, or 3, and a6 is 0, 1, 2, 3, 4, or 5.

17. A material for an organic electroluminescent device comprising: the compound of claim 1 or the composition comprising the compound of claim 1,
wherein the composition further comprises at least one of a compound represented by Formula (B1), a carbazole derivative (other than the compound represented by Formula (1)), and an azine ring derivative (other than the compound represented by Formula (1)):

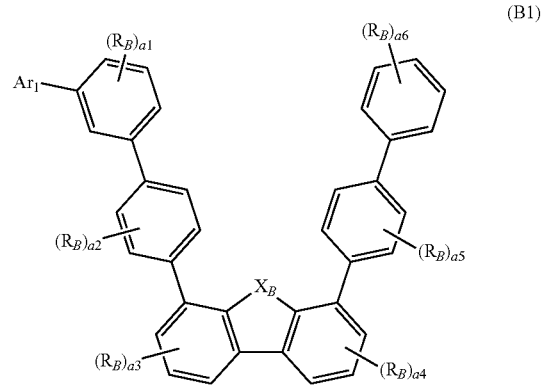

wherein, in Formula (B1), $X_B$ is O, S, or Se, $Ar_1$ is a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), each occurrence of $R_B$ is independently a deuterium atom, a cyano group, a fluoro group, a substituted or unsubstituted alkyl group having 1 to 20 carbon atoms, a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), a1, a2, and a5 are each independently 0, 1, 2, 3, or 4,
a3 and a4 are each independently 0, 1, 2, or 3, and
a6 is 0, 1, 2, 3, 4, or 5.

18. An organic electroluminescent device comprising: a pair of electrodes and an organic layer arranged between the pair of electrodes, wherein the organic layer comprises the compound of claim 1 or the composition comprising the compound of claim 1, wherein the composition further comprises at least one of a compound represented by Formula (B1), a carbazole derivative (other than the compound represented by Formula (1)), and an azine ring derivative (other than the compound represented by Formula (1)):

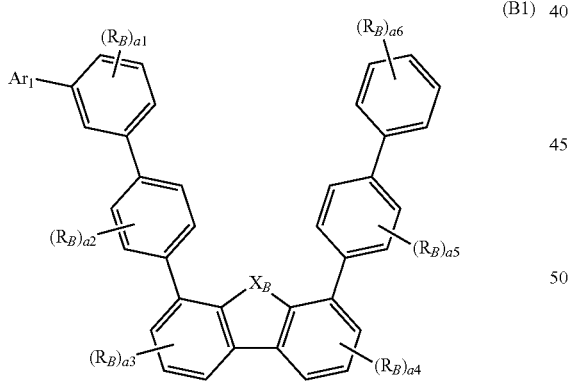

(B1)

wherein, in Formula (B1),
$X_B$ is O, S, or Se,
Ar$_1$ is a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), each occurrence of $R_B$ is independently a deuterium atom, a cyano group, a fluoro group, a substituted or unsubstituted alkyl group having 1 to 20 carbon atoms, a substituted or unsubstituted phenyl group, a substituted or unsubstituted naphthyl group, or a monovalent aromatic hydrocarbon ring aggregation group, wherein the monovalent aromatic hydrocarbon ring aggregation group is two or more substituted or unsubstituted benzene rings directly bonded to each other via a single bond, two or more substituted or unsubstituted naphthalene rings directly bonded to each other via a single bond, or at least one substituted or unsubstituted benzene ring and at least one substituted or unsubstituted naphthalene ring directly bonded to each other via a single bond (wherein a ring is not further condensed in the benzene ring and the naphthalene ring), a1, a2, and a5 are each independently 0, 1, 2, 3, or 4,
a3 and a4 are each independently 0, 1, 2, or 3, and
a6 is 0, 1, 2, 3, 4, or 5.

19. An organic electroluminescent device comprising:
a pair of electrodes and an organic layer arranged between the pair of electrodes, wherein the organic layer comprises a host compound represented by Formula (1):

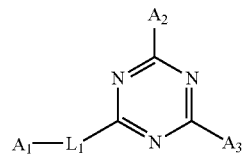

(1)

wherein, in Formula (1),
A$_1$ is a substituent represented by Formula (2-1) or (2-2),
A$_2$ and A$_3$ are each independently a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms,
L$_1$ is a single bond, a substituted or unsubstituted divalent aromatic hydrocarbon group having 6 to 30 carbon atoms or a substituted or unsubstituted divalent aromatic heterocyclic group having 5 to 30 ring-forming atoms,

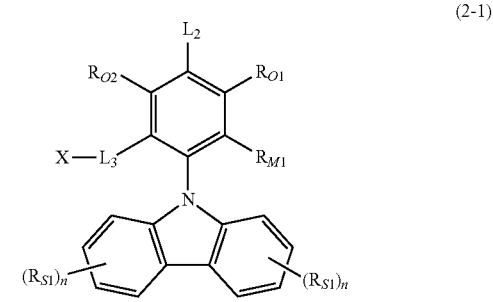

(2-1)

-continued (2-2)

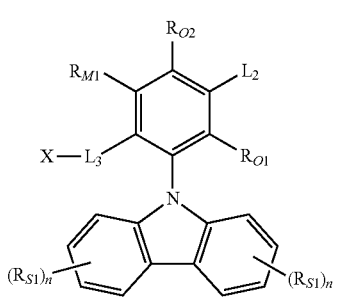

wherein, in Formulae (2-1) and (2-2), $L_2$ is a single bond binding to $L_1$ in Formula (1), a substituted or unsubstituted divalent aromatic hydrocarbon group having 6 to 30 carbon atoms and binding to $L_1$ in Formula (1), or a substituted or unsubstituted divalent aromatic heterocyclic group having 5 to 30 ring-forming atoms and binding to Li in Formula (1), $R_{O1}$ and $R_{O2}$ are each independently a hydrogen atom, a deuterium atom, a fluoro group, a cyano group, or a substituted or unsubstituted monovalent alkyl group having 1 to 20 carbon atoms, $R_{M1}$ is a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of $R_{S1}$ is independently a hydrogen atom, a deuterium atom, a fluoro group, a cyano group, a substituted or unsubstituted monovalent alkyl group having 1 to 20 carbon atoms, a substituted or unsubstituted monovalent aromatic hydrocarbon group having 6 to 30 carbon atoms, or a substituted or unsubstituted monovalent aromatic heterocyclic group having 5 to 30 ring-forming atoms, each occurrence of n is independently 0, 1, 2, 3, or 4, $L_3$ is a single bond, a substituted or unsubstituted divalent aromatic hydrocarbon group having 6 to 30 carbon atoms, or a substituted or unsubstituted divalent aromatic heterocyclic group having 5 to 30 ring-forming atoms and not including a carbazole ring, X is an oligocarbazole group unsubstituted or substituted with a substituent other than a carbazole group, and the oligocarbazole group comprises 2 to 5 carbazole rings that are directly bonded to each other via a single bond, wherein a nitrogen of a carbazole ring of the 2 to 5 carbazole rings binds to $L_3$, a different carbazole ring of the 2 to 5 carbazole rings, an unsubstituted monovalent alkyl group having 1 to 20 carbon atoms, an unsubstituted monovalent aromatic hydrocarbon group having 6 to 30 carbon atoms, or an unsubstituted monovalent aromatic heterocyclic group having 5 to 30 ring-forming atoms (other than a carbazole group).

* * * * *